United States Patent
Hass et al.

(10) Patent No.: US 10,723,795 B2
(45) Date of Patent: Jul. 28, 2020

(54) ANTI-INTERLEUKIN-33 ANTIBODIES AND USES THEREOF

(71) Applicant: Genentech, Inc., South San Francisco, CA (US)

(72) Inventors: Philip E. Hass, Moss Beach, CA (US); Meredith Hazen, Belmont, CA (US); Yi-Chun Hsiao, San Mateo, CA (US); Rajita Khosla, Foster City, CA (US); Gerald R. Nakamura, San Francisco, CA (US); Dhaya Seshasayee, Cupertino, CA (US); Menno Van Lookeren Campagne, San Francisco, CA (US); Hongkang Xi, South San Francisco, CA (US); Wenwu Zhai, Redwood City, CA (US); Jack Bevers, III, San Francisco, CA (US); Nancy Chiang, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 139 days.

(21) Appl. No.: 16/119,667

(22) Filed: Aug. 31, 2018

(65) Prior Publication Data

US 2019/0092852 A1 Mar. 28, 2019

Related U.S. Application Data

(62) Division of application No. 14/937,778, filed on Nov. 10, 2015, now Pat. No. 10,093,730.

(60) Provisional application No. 62/077,876, filed on Nov. 10, 2014, provisional application No. 62/165,732, filed on May 22, 2015.

(51) Int. Cl.
*C07K 16/24* (2006.01)
*C12N 15/63* (2006.01)
*C07K 16/22* (2006.01)
*C07K 16/40* (2006.01)
*A61K 39/395* (2006.01)
*A61K 39/00* (2006.01)

(52) U.S. Cl.
CPC ............ *C07K 16/244* (2013.01); *C07K 16/22* (2013.01); *C07K 16/40* (2013.01); *C12N 15/63* (2013.01); *A61K 2039/507* (2013.01); *C07K 2317/14* (2013.01); *C07K 2317/24* (2013.01); *C07K 2317/31* (2013.01); *C07K 2317/41* (2013.01); *C07K 2317/53* (2013.01); *C07K 2317/54* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,084,083 A | 7/2000 | Levinson |
| 6,156,887 A | 12/2000 | Levinson |
| 6,204,371 B1 | 3/2001 | Levinson |
| 6,288,218 B1 | 9/2001 | Levinson |
| 6,414,117 B1 | 7/2002 | Levinson |
| 6,562,343 B1 | 5/2003 | Levinson |
| 7,172,750 B2 | 2/2007 | Levinson |
| 7,560,530 B1 | 7/2009 | Chackerian et al. |
| 8,187,596 B1 | 5/2012 | Chackerian et al. |
| 9,090,694 B2 | 7/2015 | Duffy et al. |
| 9,212,227 B2 | 12/2015 | Duffy et al. |
| 9,309,319 B2 | 4/2016 | Fertig et al. |
| 9,523,696 B2 | 12/2016 | Snider |
| 2003/0158399 A1 | 8/2003 | Levinson |
| 2007/0042978 A1 | 2/2007 | Girard et al. |
| 2010/0260770 A1 | 10/2010 | Coyle |
| 2011/0045501 A1 | 2/2011 | Bosch et al. |
| 2011/0165063 A1 | 7/2011 | Hsieh et al. |
| 2012/0207752 A1 | 8/2012 | Chackerian et al. |
| 2013/0287777 A1 | 10/2013 | Duffy et al. |
| 2013/0336980 A1 | 12/2013 | Duffy et al. |
| 2014/0105887 A1 | 4/2014 | Chackerian et al. |
| 2016/0145344 A1 | 5/2016 | Akbari |
| 2016/0168640 A1 | 6/2016 | Khosla et al. |
| 2016/0235838 A1 | 8/2016 | Weiner et al. |
| 2017/0066831 A1 | 3/2017 | Duffy et al. |
| 2017/0096483 A1 | 4/2017 | Orengo et al. |
| 2018/0171405 A1 | 6/2018 | Khosla et al. |

FOREIGN PATENT DOCUMENTS

| | | |
|---|---|---|
| EP | 2271672 B1 | 11/2015 |
| EP | 2734222 B1 | 10/2016 |
| JP | 2014-523746 A | 9/2014 |
| WO | WO-96/27603 A1 | 9/1996 |
| WO | WO-01/21641 A1 | 3/2001 |
| WO | WO-01/70817 A1 | 9/2001 |

(Continued)

OTHER PUBLICATIONS

Brown et al., "Tolerance of single, but not multiple, amino acid replacements in antibody $V_H$ CDR2: a means of minimizing B cell wastage from somatic hypermutation?" J Immunol. 156(9):3285-91 (1996).

(Continued)

*Primary Examiner* — Bridget E Bunner
*Assistant Examiner* — Fozia Hamud
(74) *Attorney, Agent, or Firm* — Clark & Elbing LLP; Karen L. Elbing

(57) ABSTRACT

The invention provides interleukin-33 (IL-33) antibodies and methods of using the same.

67 Claims, 110 Drawing Sheets

(48 of 110 Drawing Sheet(s) Filed in Color)

Specification includes a Sequence Listing.

(56) References Cited

FOREIGN PATENT DOCUMENTS

| WO | WO-2005/062967 A2 | 7/2005 |
|---|---|---|
| WO | WO-2005/079844 A2 | 9/2005 |
| WO | WO-2007/127749 A2 | 11/2007 |
| WO | WO-2007/130627 A2 | 11/2007 |
| WO | WO-2007/131031 A2 | 11/2007 |
| WO | WO-2007/140205 A2 | 12/2007 |
| WO | WO-2007/143295 A2 | 12/2007 |
| WO | WO-2008/066443 A1 | 6/2008 |
| WO | WO-2008/132709 A1 | 11/2008 |
| WO | WO-2008/144610 A1 | 11/2008 |
| WO | WO-2009/053098 A1 | 4/2009 |
| WO | WO-2009/120899 A2 | 10/2009 |
| WO | WO-2009/120903 A9 | 10/2009 |
| WO | WO-2010/087972 A2 | 8/2010 |
| WO | WO-2010/102251 A2 | 9/2010 |
| WO | WO-2011/031600 A1 | 3/2011 |
| WO | WO-2011/047266 A1 | 4/2011 |
| WO | WO-2011/143562 A2 | 11/2011 |
| WO | WO-2012/055891 A1 | 5/2012 |
| WO | WO-2012/083132 A2 | 6/2012 |
| WO | WO-2012/088094 A2 | 6/2012 |
| WO | WO-2012/103240 A2 | 8/2012 |
| WO | WO-2012/113927 A1 | 8/2012 |
| WO | WO-2012/145209 A2 | 10/2012 |
| WO | WO-2013/014208 A2 | 1/2013 |
| WO | WO-2013/165894 A2 | 11/2013 |
| WO | WO-2013/173761 A2 | 11/2013 |
| WO | WO-2014/062621 A1 | 4/2014 |
| WO | WO-2014/072446 A1 | 5/2014 |
| WO | WO-2014/090800 A1 | 6/2014 |
| WO | WO-2014/126277 A1 | 8/2014 |
| WO | WO-2014/128254 A1 | 8/2014 |
| WO | WO-2014/152195 A1 | 9/2014 |
| WO | WO-2014/164959 A2 | 10/2014 |
| WO | WO-2014/178392 A1 | 11/2014 |
| WO | WO-2015/042521 A1 | 3/2015 |
| WO | WO-2015/054012 A1 | 4/2015 |
| WO | WO-2015/061441 A1 | 4/2015 |
| WO | WO-2015/077888 A1 | 6/2015 |
| WO | WO-2015/099175 A1 | 7/2015 |
| WO | WO-2015/106080 A2 | 7/2015 |
| WO | WO-2015/132602 A1 | 9/2015 |
| WO | WO-2015/143343 A2 | 9/2015 |
| WO | WO-2015/164354 A1 | 10/2015 |
| WO | WO-2015/179918 A1 | 12/2015 |
| WO | WO-2016/020502 A1 | 2/2016 |
| WO | WO-2016/077366 A1 | 5/2016 |
| WO | WO-2016/077381 A1 | 5/2016 |
| WO | WO-2016/085832 A1 | 6/2016 |
| WO | WO-2016/090250 A1 | 6/2016 |
| WO | WO-2016/122865 A1 | 8/2016 |
| WO | WO-2016/138590 A1 | 9/2016 |
| WO | WO-2016/140921 A1 | 9/2016 |
| WO | WO-2016/149276 A1 | 9/2016 |
| WO | WO-2016/156440 A1 | 10/2016 |
| WO | WO-2016/207304 A2 | 12/2016 |
| WO | WO-2017/009750 A1 | 1/2017 |
| WO | WO-2017/021814 A1 | 2/2017 |

OTHER PUBLICATIONS

Vo et al., "Comparison study of IL-33 gene expression in haplogroup H, J, L, and K cybrids," Invest Ophthalmol Vis Sci. 54(15): 4988 (2013) (Abstract only) (2 pages).
Examination Report for Gulf Cooperation Council Patent Application No. 2015-30359, dated Feb. 14, 2019 (3 pages).
Examination Report for Gulf Cooperation Council Patent Application No. 2015-30359, dated Sep. 3, 2019 (3 pages).
Notice of Reasons for Rejection for Japanese Patent Application No. 2017-525046, dated Dec. 10, 2019 (6 pages).
Office Action for Eurasian Patent Application No. 201791029, dated Jan. 21, 2019 (7 pages).
Substantive Examination Result for Indonesian Patent Application No. PID201703680, dated Jul. 25, 2019 (6 pages).
Akhabir et al., "Lung expression quantitative trait loci data set identifies important functional polymorphisms in the asthma-associated IL1RL1 region," J Allergy Clin Immunol. 134(3):729-31 (2014).
Cairns, "Inhibitors of mast cell tryptase beta as therapeutics for the treatment of asthma and inflammatory disorders," Pulm Pharmacol Ther. 18(1):55-66 (2005).
Casset et al., "A peptide mimetic of an anti-CD4 monoclonal antibody by rational design," Biochem Biophys Res Commun. 307(1):198-205 (2003).
Hamzaoui et al., "Induced sputum levels of IL-33 and soluble ST2 in young asthmatic children," J Asthma. 50(8):803-9 (2013) (7 pages).
Ho et al., "Common genetic variation at the IL1RL1 locus regulates IL-33/ST2 signaling," J Clin Invest. 123(10):4208-18 (2013).
Ito et al., "ST2: the biomarker at the heart of GVHD severity," Blood. 125(1):10-1 (2015).
Jang et al., "Interleukin-33 and Mast Cells Bridge Innate and Adaptive Immunity: From the Allergologist's Perspective," Int Neurourol J. 19(3):142-50 (2015).
Kakkar et al., "The IL-33/ST2 pathway: therapeutic target and novel biomarker," Nat Rev Drug Discov. 7(10):827-40 (2008).
Kim et al., "Anti-IL-33 antibody has a therapeutic effect in a murine model of allergic rhinitis," Allergy. 67(2):183-90 (2012).
Li et al., "IL-33 neutralization suppresses lupus disease in lupus-prone mice," Inflammation. 37(3):824-32 (2014).
Liu et al., "Anti-IL-33 antibody treatment inhibits airway inflammation in a murine model of allergic asthma," Biochem Biophys Res Commun. 386(1):181-5 (2009).
Matsumoto, "Serum periostin: a novel biomarker for asthma management," Allergol Int. 63(2):153-60 (2014).
Nabe, "Interleukin (IL)-33: new therapeutic target for atopic diseases," J Pharmacol Sci. 126(2):85-91 (2014).
Paul, Chapter 9: Structure and Function of Immunoglobulins. *Fundamental Immunology, Third Edition.* Raven Press Ltd., 292-295 (1993).
Qiu et al., "Anti-interleukin-33 inhibits cigarette smoke-induced lung inflammation in mice," Immunology. 138(1):76-82 (2013).
Ramirez-Carrozzi et al., "Functional analysis of protective IL1RL1 variants associated with asthma risk," J Allergy Clin Immunol. 135(4):1080-3.e3 (2015).
Sedhom et al., "Neutralisation of the interleukin-33/ST2 pathway ameliorates experimental colitis through enhancement of mucosal healing in mice," Gut. 62(12):1714-23 (2013).
Yuan et al., "Construction of human nonimmune library and selection of scFvs against IL-33," Appl Biochem Biotechnol. 167(3):498-509 (2012).
International Preliminary Report on Patentability for International Patent Application No. PCT/US2015/059982, dated May 16, 2017 (14 pages).
International Preliminary Report on Patentability for International Patent Application No. PCT/US2015/060008, dated May 16, 2017 (9 pages).
International Search Report and Written Opinion for International Patent Application No. PCT/US2015/059982, dated May 4, 2016 (26 pages).
International Search Report and Written Opinion for International Application No. PCT/US2015/060008, dated Mar. 4, 2016 (15 pages).
Invitation to Pay Additional Fees for International Patent Application No. PCT/US2015/059982, dated Feb. 22, 2016 (11 pages).
Invitation to Respond to Written Opinion for Singaporean Patent Application No. 11201703767X, dated Jun. 19, 2018 (10 pages).
Office Action for U.S. Appl. No. 14/937,721, dated Aug. 16, 2017 (12 pages).
Office Action for U.S. Appl. No. 14/937,778, dated Nov. 2, 2017 (13 pages).
Search Report for Singaporean Patent Application No. 11201703767X, dated Jul. 6, 2018 (3 pages).
Substantive Report for Chilean Patent Application No. 1172-2017, dated Jun. 21, 2018 (25 pages).

Pathway analysis of genes down-regulated in ST2$^{-/-}$ retina after CLE

| GO ID | Biological Function | p-value | Genes Down-regulated |
|---|---|---|---|
| GO:0006886 | Intracellular protein transport | 0.001504 | Bcl3, Egr2, Il1b, Stat3, Tap1, Rtp4, Parp10 |
| GO:0071345 | Cellular response to cytokine stimulus | 0.001569 | Igtp, Il1b, Irf1, Osmr, Ccl2, Stat3, Ifi202b, Irf7, Gbp7 |
| GO:0034124 | MyD88-dependent TLR signaling pathway | 0.002303 | Irf1, Irf7 |
| GO:0060416 | Response to growth hormone | 0.002303 | Irf1, Stat3 |
| GO:0045944 | Transcription from RNA Pol II promoter | 0.004203 | Bcl3, Cebpd, Egr2, Il1b, Irf1, Stat3, Irf7 |
| GO:0006913 | Nucleocytoplasmic transport | 0.005380 | Bcl3, Egr2, Il1b, Stat3, Parp10 |
| GO:0032870 | Cellular response to hormone stimulus | 0.005669 | Egr2, Il1b, Irf1, Stat3 |
| GO:0042089 | Cytokine biosynthetic process | 0.005669 | Bcl3, Il1b, Irf1, Irf7 |
| GO:0070727 | Cellular macromolecule localization | 0.006119 | Bcl3, Egr2, Il1b, Stat3, Tap1, Rtp4, Parp10 |
| GO:0042221 | Response to chemical | 0.006125 | Cp, Egr2, Hsd17b2, Igtp, Il1b, Irf1, Mt2, Mx2, Osmr, Ccl2, Ccl4, Stat3, Ifi202b, Irf7, Irgm2, Rtp4, Gbp7 |
| GO:0031330 | Negative regulation of cellular catabolism | 0.006697 | Stat3, Timp1 |
| GO:0045064 | Th2 cell differentiation | 0.006697 | Bcl3, Irf1 |
| GO:0046688 | Response to copper ion | 0.006697 | Cp, Mt2 |
| GO:1901652 | Response to peptide | 0.007156 | Egr2, Il1b, Irf1, Stat3 |
| GO:0042832 | Defense response to protozoan | 0.007270 | Bcl3, Irgm2, Gbp7 |
| GO:0010557 | Regulation of Macromolecule biosynthesis | 0.007896 | Bcl3, Cebpd, Egr2, Il1b, Irf1, Ccl2, Stat3, Irf7 |
| GO:0034341 | Response to interferon-gamma | 0.008882 | Irf1, Ccl2, Irgm2, Gbp7 |

Figure 20

10C12.38.H6.87Y.58I/IL-13 IgG4 bispecific antibody

| Lot | Human IL-33 | | | Cyno IL-33 | | | Human IL-13 | | |
|---|---|---|---|---|---|---|---|---|---|
| | $k_{on}$ (1/Ms) (x10$^5$) | $k_{off}$ (1/s) (x10$^{-4}$) | $K_D$ (nM) | $k_{on}$ (1/Ms) (x10$^5$) | $k_{off}$ (1/s) (x10$^{-4}$) | $K_D$ (nM) | $k_{on}$ (1/Ms) (x10$^5$) | $k_{off}$ (1/s) (x10$^{-4}$) | KD (nM) |
| 1 | 11.0 | 0.11 | 0.010 | 6.7 | 0.72 | 0.107 | 14.9 | 0.02 | <0.010 |
| 2 | 11.4 | 0.30 | 0.026 | 6.5 | 0.40 | 0.062 | 14.7 | 0.04 | <0.010 |
| 3 | 9.9 | 0.40 | 0.041 | 7.0 | 0.41 | 0.059 | 14.5 | 0.06 | <0.010 |

Figure 21C

| Species | Human | Cyno |
|---|---|---|
| EC50 [M] | 5.5E-12 | 2.1E-11 |
| IL-33 | 10pM hIL-33 | 5pM cIL-33-Nhis |
| Ab | IC50 [M] | IC50 [M] |
| 10C12.38.H6.87Y.58I IgG4 | 2.4E-12 | 4.2E-09 |
| sST2 | 2.7E-11 | 3.0E-11 |
| RG1 | 9.5E-09 | non-blocking |
| RG2 | 1.7E-08 | non-blocking |
| RG3 | 1.1E-10 | 2.9E-08 |
| RG4 | 3.3E-11 | non-blocking |
| RG5 | 3.7E-09 | non-blocking |
| RG6 | 6.1E-10 | non-blocking |
| RG7 | 9.2E-11 | 6.6E-08 |
| RG8 | 3.8E-11 | 4.8E-08 |
| RG9 | 1.5E-10 | 3.4E-08 |
| RG10 | 1.5E-09 | 2.3E-08 |
| RG11 | 1.5E-10 | non-blocking |
| RG12 | 1.1E-09 | 1.1E-08 |
| RG13 | 7.1E-10 | non-blocking |
| RG14 | 1.0E-09 | non-blocking |
| RG15 | 2.6E-09 | non-blocking |
| RG16 | 5.7E-10 | 5.0E-08 |
| RG17 | 9.8E-10 | non-blocking |
| RG18 | 1.1E-11 | 5.7E-08 |
| RG19 | 8.2E-10 | non-blocking |
| RG20 | 1.6E-08 | 6.1E-09 |

Figure 23D

NK assay

| Species | Human |
|---|---|
| EC50 [M] | 3.3E-10 |
| IL-33 | 260pM hIL-33 |
| Ab | IC50 [M] |
| 10C12.38.H6.87Y.58I IgG4 | 3.3E-11 |
| sST2 | 1.5E-10 |
| RG1 | non-blocking |
| RG2 | non-blocking |
| RG3 | non-blocking |
| RG4 | non-blocking |
| RG5 | 4.1E-08 |
| RG6 | 2.4E-09 |
| RG7 | 5.1E-10 |
| RG8 | 2.4E-10 |
| RG9 | 1.2E-09 |
| RG10 | 4.6E-09 |
| RG11 | non-blocking |
| RG12 | non-blocking |
| RG13 | 1.0E-08 |
| RG14 | non-blocking |
| RG15 | non-blocking |
| RG16 | non-blocking |
| RG17 | non-blocking |
| RG18 | 9.7E-11 |
| RG19 | 1.2E-09 |
| RG20 | non-blocking |

Figure 24D

Basophil assay

| Species | Human |
|---|---|
| EC50 [M] | 6.4E-11 |
| IL-33 | 500pM hIL-33 |
| Ab | IC50 [M] |
| 10C12.38.H6.87Y.58I IgG4 | 1.5E-13 |
| sST2 | 7.9E-13 |
| RG1 | non-blocking |
| RG2 | non-blocking |
| RG3 | 4.0E-13 |
| RG4 | 3.6E-13 |
| RG5 | non-blocking |
| RG6 | 3.9E-13 |
| RG7 | 6.7E-13 |
| RG8 | 4.8E-13 |
| RG9 | 2.5E-09 |
| RG10 | partial-blocking |
| RG11 | 1.4E-13 |
| RG12 | 2.4E-09 |
| RG13 | 7.6E-06 |
| RG14 | 2.0E-12 |
| RG15 | 9.4E-03 |
| RG16 | 2.3E-12 |
| RG17 | 5.7E-13 |
| RG18 | 3.5E-13 |
| RG19 | 9.1E-13 |
| RG20 | non-blocking |

SEQUENCE LISTING

<160> NUMBER OF SEQ ID NOS: 371

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Ser Phe Ser Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Thr Ile Ser Gly Gly Lys Thr Phe Thr Asp Tyr Val Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Ala Asn Tyr Gly Asn Trp Phe Phe Glu Val
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Arg Ala Ser Glu Ser Val Ala Lys Tyr Gly Leu Ser Leu Leu Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Ala Ser Asn Arg Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

```
Gln Gln Ser Lys Glu Val Pro Phe Thr
1               5
```

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

```
Ser Phe Ser Leu Ser
1               5
```

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

```
Ser Phe Ser Val Ser
1               5
```

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

```
Thr Ile Ser Gly Gly Lys Thr Phe Thr Asp Tyr Val Asp Ala Val Lys
1               5                   10                  15

Gly
```

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

```
Ala Asn Tyr Gly Asn Phe Phe Phe Glu Val
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

```
Ala Asn Tyr Gly Asp Trp Phe Phe Glu Val
1               5                   10
```

<210> SEQ ID NO 12
<211> LENGTH: 30
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

Trp Val Arg Gln Ala Pro Gly Lys Gly Leu Glu Trp Val Ala
1               5                   10

<210> SEQ ID NO 14
<211> LENGTH: 32
<212> TYPE: PRT
<213> ORGANISM: Artificial Sequence
<220> FEATURE:
<223> OTHER INFORMATION: Synthetic Construct

<400> SEQUENCE: 14

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Trp Gly Gln Gly Thr Leu Val Thr Val Ser Ser
1               5                   10

<210> SEQ ID NO 16
<211> LENGTH: 30
<212> TYPE: PRT
<213> ORGANISM: Artificial Sequence
<220> FEATURE:
<223> OTHER INFORMATION: Synthetic Construct

<400> SEQUENCE: 16

Asp Val Asn Leu Val Glu Ser Gly Gly Gly Ser Val Lys Pro Gly Gly
1               5                   10                  15

Ser Leu Lys Leu Ser Cys Val Ala Ser Gly Phe Thr Phe Ser
            20                  25                  30

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Trp Val Arg Gln Thr Pro Glu Lys Arg Leu Glu Trp Val Ala
1               5                   10

```
<210> SEQ ID NO 18
<211> LENGTH: 32
<212> TYPE: PRT
<213> ORGANISM: Artificial Sequence
<220> FEATURE:
<223> OTHER INFORMATION: Synthetic Construct

<400> SEQUENCE: 18

Arg Phe Thr Ile Ser Arg Asp Asp Ala Lys Asn Thr Leu Tyr Leu Gln
1               5                   10                  15

Met Ser Ser Leu Glu Ser Glu Asp Thr Ala Met Tyr Tyr Cys Thr Arg
            20                  25                  30

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Trp Gly Ala Gly Thr Thr Val Ala Val Ser Ser
1               5                   10

<210> SEQ ID NO 20
<211> LENGTH: 30
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 21
<211> LENGTH: 14
<212> TYPE: PRT
<213> ORGANISM: Artificial Sequence
<220> FEATURE:
<223> OTHER INFORMATION: Synthetic Construct

<400> SEQUENCE: 21

Trp Val Arg Gln Ala Pro Gly Lys Gly Leu Glu Trp Val Ser
1               5                   10

<210> SEQ ID NO 22
<211> LENGTH: 32
<212> TYPE: PRT
<213> ORGANISM: Artificial Sequence
<220> FEATURE:
<223> OTHER INFORMATION: Synthetic Construct

<400> SEQUENCE: 22

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 23
<211> LENGTH: 32
<212> TYPE: PRT
<213> ORGANISM: Artificial Sequence
<220> FEATURE:
```

<223> OTHER INFORMATION: Synthetic Construct

<400> SEQUENCE: 23

Arg Phe Thr Ile Ser Arg Asp Asp Ala Lys Asn Ser Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Synthetic Construct

<400> SEQUENCE: 24

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 25
<211> LENGTH: 23
<212> TYPE: PRT
<213> ORGANISM: Artificial Sequence
<220> FEATURE:
<223> OTHER INFORMATION: Synthetic Construct

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Trp Phe Gln Gln Lys Pro Gly Gln Pro Pro Arg Leu Leu Ile Phe
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 28

Phe Gly Gln Gly Thr Lys Val Glu Ile Lys
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

Asp Ile Val Leu Thr Gln Ser Pro Gly Phe Leu Val Val Ser Leu Gly
1               5                   10                  15

Gln Arg Ala Thr Ile Ser Cys
            20

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp Phe Gln Gln Lys Pro Gly Gln Pro Pro Lys Leu Leu Ile Phe
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Gly Val Pro Ala Arg Phe Ser Gly Ser Gly Ser Gly Thr Asp Phe Ser
1               5                   10                  15

Leu Asn Ile His Pro Met Glu Glu Asp Asp Thr Ala Met Tyr Phe Cys
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Phe Gly Ser Gly Thr Lys Leu Glu Ile Lys
1               5                   10

<210> SEQ ID NO 33
<211> LENGTH: 32
<212> TYPE: PRT
<213> ORGANISM: Artificial Sequence
<220> FEATURE:
<223> OTHER INFORMATION: Synthetic Construct

<400> SEQUENCE: 33

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Phe Cys
            20                  25                  30
```

<210> SEQ ID NO 34
<211> LENGTH: 32
<212> TYPE: PRT
<213> ORGANISM: Artificial Sequence
<220> FEATURE:
<223> OTHER INFORMATION: Synthetic Construct

<400> SEQUENCE: 34

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Synthetic Construct

<400> SEQUENCE: 35

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Phe Cys
            20                  25                  30

<210> SEQ ID NO 36
<211> LENGTH: 119
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
        115

<210> SEQ ID NO 37
<211> LENGTH: 111
<212> TYPE: PRT
<213> ORGANISM: Artificial Sequence
<220> FEATURE:
<223> OTHER INFORMATION: Synthetic Construct

<400> SEQUENCE: 37

Glu Ile Val Leu Thr Gln Ser Pro Ala Thr Leu Ser Leu Ser Pro Gly
1               5                   10                  15

-continued

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 38
<211> LENGTH: 119
<212> TYPE: PRT
<213> ORGANISM: Artificial Sequence
<220> FEATURE:
<223> OTHER INFORMATION: Synthetic Construct

<400> SEQUENCE: 38

Asp Val Asn Leu Val Glu Ser Gly Gly Gly Ser Val Lys Pro Gly Gly
1               5                   10                  15

Ser Leu Lys Leu Ser Cys Val Ala Ser Gly Phe Thr Phe Ser Ser Phe
            20                  25                  30

Ser Met Ser Trp Val Arg Gln Thr Pro Glu Lys Arg Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asp Ala Lys Asn Thr Leu Tyr
65                  70                  75                  80

Leu Gln Met Ser Ser Leu Glu Ser Glu Asp Thr Ala Met Tyr Tyr Cys
                85                  90                  95

Thr Arg Ala Asn Tyr Gly Asn Trp Phe Phe Glu Val Trp Gly Ala Gly
            100                 105                 110

Thr Thr Val Ala Val Ser Ser
        115

<210> SEQ ID NO 39
<211> LENGTH: 111
<212> TYPE: PRT
<213> ORGANISM: Artificial Sequence
<220> FEATURE:
<223> OTHER INFORMATION: Synthetic Construct

<400> SEQUENCE: 39

Asp Ile Val Leu Thr Gln Ser Pro Gly Phe Leu Val Val Ser Leu Gly
1               5                   10                  15

Gln Arg Ala Thr Ile Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Lys Leu Leu Ile Phe Ala Ala Ser Asn Arg Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

-continued

Glu Val Pro Phe Thr Phe Gly Ser Gly Thr Lys Leu Glu Ile Lys
                100                 105                 110

<210> SEQ ID NO 40
<211> LENGTH: 119
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
        115

<210> SEQ ID NO 41
<211> LENGTH: 119
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
        115

<210> SEQ ID NO 42
<211> LENGTH: 119
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Leu Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
            115

<210> SEQ ID NO 43
<211> LENGTH: 119
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Phe Phe Phe Glu Val Trp Gly Gln Gly
            100                 105                 110

Thr Leu Val Thr Val Ser Ser
            115

<210> SEQ ID NO 44
<211> LENGTH: 119
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Val Ser Trp Val Arg Gln Ala Pro Gly Lys Gly Leu Glu Trp Val
        35                  40                  45

```
Ala Thr Ile Ser Gly Gly Lys Thr Phe Thr Asp Tyr Val Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Ala Asn Tyr Gly Asn Trp Phe Phe Glu Val Trp Gly Gln Gly
                100                 105                 110

Thr Leu Val Thr Val Ser Ser
            115

<210> SEQ ID NO 45
<211> LENGTH: 119
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Phe
                 20                  25                  30

Ser Met Ser Trp Val Arg Gln Ala Pro Gly Lys Gly Leu Glu Trp Val
             35                  40                  45

Ala Thr Ile Ser Gly Gly Lys Thr Phe Thr Asp Tyr Val Asp Ser Val
            50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Thr Arg Ala Asn Tyr Gly Asp Trp Phe Phe Glu Val Trp Gly Gln Gly
                100                 105                 110

Thr Leu Val Thr Val Ser Ser
            115

<210> SEQ ID NO 46
<211> LENGTH: 119
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Phe
                 20                  25                  30

Ser Met Ser Trp Val Arg Gln Ala Pro Gly Lys Gly Leu Glu Trp Val
             35                  40                  45

Ser Thr Ile Ser Gly Gly Lys Thr Phe Thr Asp Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Thr Arg Ala Asn Tyr Gly Asp Trp Phe Phe Glu Val Trp Gly Gln Gly
```

Thr Leu Val Thr Val Ser Ser
        115

<210> SEQ ID NO 47
<211> LENGTH: 119
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
        115

<210> SEQ ID NO 49
<211> LENGTH: 119
<212> TYPE: PRT
<213> ORGANISM: Artificial Sequence
<220> FEATURE:

<223> OTHER INFORMATION: Synthetic Construct

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ala Thr Ile Ser Gly Gly Lys Thr Phe Thr Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
            100                 105                 110

Thr Leu Val Thr Val Ser Ser
        115

<210> SEQ ID NO 51
<211> LENGTH: 111
<212> TYPE: PRT
<213> ORGANISM: Artificial Sequence
<220> FEATURE:
<223> OTHER INFORMATION: Synthetic Construct

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro

```
            35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 52
<211> LENGTH: 111
<212> TYPE: PRT
<213> ORGANISM: Artificial Sequence
<220> FEATURE:
<223> OTHER INFORMATION: Synthetic Construct

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 53
<211> LENGTH: 111
<212> TYPE: PRT
<213> ORGANISM: Artificial Sequence
<220> FEATURE:
<223> OTHER INFORMATION: Synthetic Construct

<400> SEQUENCE: 53

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 54
<211> LENGTH: 111
```

```
<212> TYPE: PRT
<213> ORGANISM: Artificial Sequence
<220> FEATURE:
<223> OTHER INFORMATION: Synthetic Construct

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Synthetic Construct

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Synthetic Construct

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
```

```
                50                  55                  60
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Lys
                 85                  90                  95

Glu Val Pro Phe Thr Phe Gly Gln Gly Thr Lys Val Glu Ile Lys
                100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Synthetic Construct

<400> SEQUENCE: 57

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Ala Lys Tyr
                20                  25                  30

Gly Leu Ser Leu Leu Asn Trp Phe Gln Gln Lys Pro Gly Gln Pro Pro
             35                  40                  45

Arg Leu Leu Ile Phe Ala Ala Ser Asn Arg Gly Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Lys
                 85                  90                  95

Glu Val Pro Phe Thr Phe Gly Gln Gly Thr Lys Val Glu Ile Lys
                100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Synthetic Construct

<400> SEQUENCE: 58

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Ala Lys Tyr
                20                  25                  30

Gly Leu Ser Leu Leu Asn Trp Phe Gln Gln Lys Pro Gly Gln Pro Pro
             35                  40                  45

Arg Leu Leu Ile Phe Ala Ala Ser Asn Arg Gly Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Lys
                 85                  90                  95

Glu Val Pro Phe Thr Phe Gly Gln Gly Thr Lys Val Glu Ile Lys
                100                 105                 110

<210> SEQ ID NO 59
<211> LENGTH: 111
<212> TYPE: PRT
<213> ORGANISM: Artificial Sequence
<220> FEATURE:
```

<223> OTHER INFORMATION: Synthetic Construct

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 60
<211> LENGTH: 111
<212> TYPE: PRT
<213> ORGANISM: Artificial Sequence
<220> FEATURE:
<223> OTHER INFORMATION: Synthetic Construct

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys
            100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Synthetic Construct

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser

```
            65                  70                  75                  80
Ser Leu Glu Pro Glu Asp Phe Ala Val Tyr Phe Cys Gln Gln Ser Lys
                    85                  90                  95

Glu Val Pro Phe Thr Phe Gly Gln Gly Thr Lys Val Glu Ile Lys
            100                 105                 110
```

<210> SEQ ID NO 62
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Met, Leu, or Val

<400> SEQUENCE: 62

```
Ser Phe Ser Xaa Ser
1               5
```

<210> SEQ ID NO 63
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (14)..(14)
<223> OTHER INFORMATION: Xaa is Ser or Ala

<400> SEQUENCE: 63

```
Thr Ile Ser Gly Gly Lys Thr Phe Thr Asp Tyr Val Asp Xaa Val Lys
1               5                   10                  15

Gly
```

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Asn or Asp
<220> FEATURE:
<221> NAME/KEY: MOD_RES
<222> LOCATION: (6)..(6)
<223> OTHER INFORMATION: Xaa is Trp or Phe

<400> SEQUENCE: 64

```
Ala Asn Tyr Gly Xaa Xaa Phe Phe Glu Val
1               5                   10
```

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

```
Ser Ser Ile Phe Tyr Trp Gly
1               5
```

```
<210> SEQ ID NO 66
<211> LENGTH: 16
<212> TYPE: PRT
<213> ORGANISM: Artificial Sequence
<220> FEATURE:
<223> OTHER INFORMATION: Synthetic Construct

<400> SEQUENCE: 66

Ser Ile Tyr Tyr Ser Gly Arg Thr Tyr Tyr Asn Pro Ser Leu Lys Ser
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic Construct

<400> SEQUENCE: 67

Ser Ile Tyr Tyr Ser Gly Arg Thr Tyr Tyr Asn Pro Ala Leu Lys Ser
1               5                   10                  15

<210> SEQ ID NO 68
<211> LENGTH: 18
<212> TYPE: PRT
<213> ORGANISM: Artificial Sequence
<220> FEATURE:
<223> OTHER INFORMATION: Synthetic Construct

<400> SEQUENCE: 68

Ala Gly Gly Leu Tyr Asn Trp Asn Asp Glu Ser Phe Ser Phe Tyr Met
1               5                   10                  15

Asp Val

<210> SEQ ID NO 69
<211> LENGTH: 12
<212> TYPE: PRT
<213> ORGANISM: Artificial Sequence
<220> FEATURE:
<223> OTHER INFORMATION: Synthetic Construct

<400> SEQUENCE: 69

Arg Ala Ser Gln Ser Phe Ser Ser Ser Tyr Leu Ala
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Gly Ala Ser Ser Arg Ala Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71

Gln Gln Tyr Asp Arg Ser Pro Leu Thr
1               5
```

<210> SEQ ID NO 72
<211> LENGTH: 30
<212> TYPE: PRT
<213> ORGANISM: Artificial Sequence
<220> FEATURE:
<223> OTHER INFORMATION: Synthetic Construct

<400> SEQUENCE: 72

Glu Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg
            20                  25                  30

<210> SEQ ID NO 73
<211> LENGTH: 14
<212> TYPE: PRT
<213> ORGANISM: Artificial Sequence
<220> FEATURE:
<223> OTHER INFORMATION: Synthetic Construct

<400> SEQUENCE: 73

Trp Ile Arg Gln Pro Pro Gly Lys Gly Leu Glu Trp Ile Gly
1               5                   10

<210> SEQ ID NO 74
<211> LENGTH: 32
<212> TYPE: PRT
<213> ORGANISM: Artificial Sequence
<220> FEATURE:
<223> OTHER INFORMATION: Synthetic Construct

<400> SEQUENCE: 74

Arg Val Thr Ile Ser Val Asp Thr Ser Lys Asn Gln Phe Ser Leu Met
1               5                   10                  15

Leu Thr Ser Val Thr Ala Ala Asp Thr Ala Val Tyr Tyr Cys Ala Arg
            20                  25                  30

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Trp Gly Gln Gly Thr Thr Val Thr Val Ser Ser
1               5                   10

<210> SEQ ID NO 76
<211> LENGTH: 30
<212> TYPE: PRT
<213> ORGANISM: Artificial Sequence
<220> FEATURE:
<223> OTHER INFORMATION: Synthetic Construct

<400> SEQUENCE: 76

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg
            20                  25                  30

<210> SEQ ID NO 77
<211> LENGTH: 30
<212> TYPE: PRT
<213> ORGANISM: Artificial Sequence

```
<220> FEATURE:
<223> OTHER INFORMATION: Synthetic Construct

<400> SEQUENCE: 77

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Arg
            20                  25                  30

<210> SEQ ID NO 78
<211> LENGTH: 11
<212> TYPE: PRT
<213> ORGANISM: Artificial Sequence
<220> FEATURE:
<223> OTHER INFORMATION: Synthetic Construct

<400> SEQUENCE: 78

Trp Gly Asn Gly Thr Thr Val Thr Val Ser Ser
1               5                   10

<210> SEQ ID NO 79
<211> LENGTH: 23
<212> TYPE: PRT
<213> ORGANISM: Artificial Sequence
<220> FEATURE:
<223> OTHER INFORMATION: Synthetic Construct

<400> SEQUENCE: 79

Glu Ile Val Leu Thr Gln Ser Pro Gly Thr Leu Ser Leu Ser Pro Gly
1               5                   10                  15
Glu Arg Ala Thr Leu Ser Cys
            20

<210> SEQ ID NO 80
<211> LENGTH: 15
<212> TYPE: PRT
<213> ORGANISM: Artificial Sequence
<220> FEATURE:
<223> OTHER INFORMATION: Synthetic Construct

<400> SEQUENCE: 80

Trp Tyr Gln Gln Lys Pro Gly Gln Ala Pro Arg Leu Leu Ile Tyr
1               5                   10                  15

<210> SEQ ID NO 81
<211> LENGTH: 32
<212> TYPE: PRT
<213> ORGANISM: Artificial Sequence
<220> FEATURE:
<223> OTHER INFORMATION: Synthetic Construct

<400> SEQUENCE: 81

Gly Ile Pro Asp Arg Phe Ser Gly Ser Gly Ser Gly Thr Asp Phe Thr
1               5                   10                  15
Leu Thr Ile Ser Arg Leu Glu Pro Glu Asp Phe Ala Val Tyr Tyr Cys
            20                  25                  30

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct

<400> SEQUENCE: 82
```

```
Phe Gly Gly Gly Thr Lys Val Glu Ile Lys
 1               5                  10
```

<210> SEQ ID NO 83
<211> LENGTH: 32
<212> TYPE: PRT
<213> ORGANISM: Artificial Sequence
<220> FEATURE:
<223> OTHER INFORMATION: Synthetic Construct

<400> SEQUENCE: 83

```
Gly Ile Pro Asp Arg Phe Ser Gly Ser Gly Ser Gly Thr Asp Phe Thr
 1               5                  10                  15

Leu Thr Ile Ser Arg Leu Glu Pro Lys Asp Phe Ala Val Tyr Tyr Cys
            20                  25                  30
```

<210> SEQ ID NO 84
<211> LENGTH: 128
<212> TYPE: PRT
<213> ORGANISM: Artificial Sequence
<220> FEATURE:
<223> OTHER INFORMATION: Synthetic Construct

<400> SEQUENCE: 84

```
Glu Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
                85                  90                  95

Cys Ala Arg Ala Gly Gly Leu Tyr Asn Trp Asn Asp Glu Ser Phe Ser
            100                 105                 110

Phe Tyr Met Asp Val Trp Gly Gln Gly Thr Thr Val Thr Val Ser Ser
        115                 120                 125
```

<210> SEQ ID NO 85
<211> LENGTH: 108
<212> TYPE: PRT
<213> ORGANISM: Artificial Sequence
<220> FEATURE:
<223> OTHER INFORMATION: Synthetic Construct

<400> SEQUENCE: 85

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
```

-continued

```
                85                  90                  95

Leu Thr Phe Gly Gly Gly Thr Lys Val Glu Ile Lys
            100                 105

<210> SEQ ID NO 86
<211> LENGTH: 128
<212> TYPE: PRT
<213> ORGANISM: Artificial Sequence
<220> FEATURE:
<223> OTHER INFORMATION: Synthetic Construct

<400> SEQUENCE: 86

Glu Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ala
    50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
                85                  90                  95

Cys Ala Arg Ala Gly Gly Leu Tyr Asn Trp Asn Asp Glu Ser Phe Ser
            100                 105                 110

Phe Tyr Met Asp Val Trp Gly Gln Gly Thr Thr Val Thr Val Ser Ser
        115                 120                 125

<210> SEQ ID NO 87
<211> LENGTH: 108
<212> TYPE: PRT
<213> ORGANISM: Artificial Sequence
<220> FEATURE:
<223> OTHER INFORMATION: Synthetic Construct

<400> SEQUENCE: 87

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys
            100                 105

<210> SEQ ID NO 88
<211> LENGTH: 128
<212> TYPE: PRT
<213> ORGANISM: Artificial Sequence
<220> FEATURE:
<223> OTHER INFORMATION: Synthetic Construct

<400> SEQUENCE: 88
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
                85                  90                  95

Cys Ala Arg Ala Gly Gly Leu Tyr Asn Trp Asn Asp Glu Ser Phe Ser
            100                 105                 110

Phe Tyr Met Asp Val Trp Gly Asn Gly Thr Thr Val Thr Val Ser Ser
        115                 120                 125
```

<210> SEQ ID NO 89
<211> LENGTH: 108
<212> TYPE: PRT
<213> ORGANISM: Artificial Sequence
<220> FEATURE:
<223> OTHER INFORMATION: Synthetic Construct

<400> SEQUENCE: 89

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys
            100                 105
```

<210> SEQ ID NO 90
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (13)..(13)
<223> OTHER INFORMATION: Xaa is Ser or Ala

<400> SEQUENCE: 90

```
Ser Ile Tyr Tyr Ser Gly Arg Thr Tyr Tyr Asn Pro Xaa Leu Lys Ser
1               5                   10                  15
```

<210> SEQ ID NO 91
<211> LENGTH: 128
<212> TYPE: PRT
<213> ORGANISM: Artificial Sequence
<220> FEATURE:

<223> OTHER INFORMATION: Synthetic Construct

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
            85                  90                  95

Cys Ala Arg Ala Gly Gly Leu Tyr Asn Trp Asn Asp Glu Ser Phe Ser
            100                 105                 110

Phe Tyr Met Asp Val Trp Gly Asn Gly Thr Thr Val Thr Val Ser Ser
            115                 120                 125

<210> SEQ ID NO 92
<211> LENGTH: 128
<212> TYPE: PRT
<213> ORGANISM: Artificial Sequence
<220> FEATURE:
<223> OTHER INFORMATION: Synthetic Construct

<400> SEQUENCE: 92

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
            85                  90                  95

Cys Ala Arg Ala Gly Gly Leu Tyr Asn Trp Asn Asp Glu Ser Phe Ser
            100                 105                 110

Phe Tyr Met Asp Val Trp Gly Asn Gly Thr Thr Val Thr Val Ser Ser
            115                 120                 125

<210> SEQ ID NO 93
<211> LENGTH: 108
<212> TYPE: PRT
<213> ORGANISM: Artificial Sequence
<220> FEATURE:
<223> OTHER INFORMATION: Synthetic Construct

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu

```
                35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Asp Arg Ser Pro
                 85                  90                  95

Leu Thr Phe Gly Gly Gly Thr Lys Val Glu Ile Lys
                100                 105

<210> SEQ ID NO 94
<211> LENGTH: 108
<212> TYPE: PRT
<213> ORGANISM: Artificial Sequence
<220> FEATURE:
<223> OTHER INFORMATION: Synthetic Construct

<400> SEQUENCE: 94

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Phe Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Asp Arg Ser Pro
                 85                  90                  95

Leu Thr Phe Gly Gly Gly Thr Lys Val Glu Ile Lys
                100                 105

<210> SEQ ID NO 95
<211> LENGTH: 128
<212> TYPE: PRT
<213> ORGANISM: Artificial Sequence
<220> FEATURE:
<223> OTHER INFORMATION: Synthetic Construct

<400> SEQUENCE: 95

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Arg Ser Ser
                 20                  25                  30

Ile Phe Tyr Trp Gly Trp Ile Arg Gln Pro Pro Gly Lys Gly Leu Glu
             35                  40                  45

Trp Ile Gly Ser Ile Tyr Tyr Ser Gly Arg Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Met Leu Thr Ser Val Thr Ala Ala Asp Thr Ala Val Tyr Tyr
                 85                  90                  95

Cys Ala Arg Ala Gly Gly Leu Tyr Asn Trp Asn Asp Glu Ser Phe Ser
                100                 105                 110

Phe Tyr Met Asp Val Trp Gly Asn Gly Thr Thr Val Thr Val Ser Ser
            115                 120                 125
```

<210> SEQ ID NO 96
<211> LENGTH: 108
<212> TYPE: PRT
<213> ORGANISM: Artificial Sequence
<220> FEATURE:
<223> OTHER INFORMATION: Synthetic Construct

<400> SEQUENCE: 96

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Lys Asp Phe Ala Val Tyr Tyr Cys Gln Gln Tyr Asp Arg Ser Pro
                85                  90                  95

Leu Thr Phe Gly Gly Gly Thr Lys Val Glu Ile Lys
            100                 105
```

<210> SEQ ID NO 97
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Trp, Phe, or Tyr

<400> SEQUENCE: 97

```
Asn Tyr Xaa Met Asn
1               5
```

<210> SEQ ID NO 98
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Asn, Asp, Ser, or Ala
<220> FEATURE:
<221> NAME/KEY: MOD_RES
<222> LOCATION: (10)..(10)
<223> OTHER INFORMATION: Xaa is Ser or Ala

<400> SEQUENCE: 98

```
Glu Ile Thr Leu Lys Phe Asn Xaa Tyr Xaa Thr His Tyr Ala Glu Ser
1               5                   10                  15

Val Lys Gly
```

<210> SEQ ID NO 99
<211> LENGTH: 10
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: (5)..(5)
<223> OTHER INFORMATION: Xaa is Asp or Asn
<220> FEATURE:
<221> NAME/KEY: MOD_RES
<222> LOCATION: (6)..(6)
<223> OTHER INFORMATION: Xaa is Trp or Phe

<400> SEQUENCE: 99

Arg Asn Tyr Gly Xaa Xaa Tyr Ile Asn Val
1               5                  10

<210> SEQ ID NO 100
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Met, Val, or Leu

<400> SEQUENCE: 100

Arg Ala Ser Glu Ser Val Asp Lys Phe Gly Xaa Ser Phe Leu Asn
1               5                  10                  15

<210> SEQ ID NO 101
<211> LENGTH: 5
<212> TYPE: PRT
<213> ORGANISM: Artificial Sequence
<220> FEATURE:
<223> OTHER INFORMATION: Synthetic Construct

<400> SEQUENCE: 101

Asn Tyr Trp Met Asn
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic Construct

<400> SEQUENCE: 102

Asn Tyr Phe Met Asn
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic Construct

<400> SEQUENCE: 103

Asn Tyr Tyr Met Asn
1               5

<210> SEQ ID NO 104
<211> LENGTH: 19
<212> TYPE: PRT
<213> ORGANISM: Artificial Sequence
<220> FEATURE:
<223> OTHER INFORMATION: Synthetic Construct

<400> SEQUENCE: 104
```

```
Glu Ile Thr Leu Lys Phe Asn Asn Tyr Ser Thr His Tyr Ala Glu Ser
1               5                   10                  15

Val Lys Gly

<210> SEQ ID NO 105
<211> LENGTH: 19
<212> TYPE: PRT
<213> ORGANISM: Artificial Sequence
<220> FEATURE:
<223> OTHER INFORMATION: Synthetic Construct

<400> SEQUENCE: 105

Glu Ile Thr Leu Lys Phe Asn Asp Tyr Ser Thr His Tyr Ala Glu Ser
1               5                   10                  15

Val Lys Gly

<210> SEQ ID NO 106
<211> LENGTH: 19
<212> TYPE: PRT
<213> ORGANISM: Artificial Sequence
<220> FEATURE:
<223> OTHER INFORMATION: Synthetic Construct

<400> SEQUENCE: 106

Glu Ile Thr Leu Lys Phe Asn Ser Tyr Ser Thr His Tyr Ala Glu Ser
1               5                   10                  15

Val Lys Gly

<210> SEQ ID NO 107
<211> LENGTH: 19
<212> TYPE: PRT
<213> ORGANISM: Artificial Sequence
<220> FEATURE:
<223> OTHER INFORMATION: Synthetic Construct

<400> SEQUENCE: 107

Glu Ile Thr Leu Lys Phe Asn Ala Tyr Ser Thr His Tyr Ala Glu Ser
1               5                   10                  15

Val Lys Gly

<210> SEQ ID NO 108
<211> LENGTH: 19
<212> TYPE: PRT
<213> ORGANISM: Artificial Sequence
<220> FEATURE:
<223> OTHER INFORMATION: Synthetic Construct

<400> SEQUENCE: 108

Glu Ile Thr Leu Lys Phe Asn Asn Tyr Ala Thr His Tyr Ala Glu Ser
1               5                   10                  15

Val Lys Gly

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct

<400> SEQUENCE: 109

Arg Asn Tyr Gly Asp Trp Tyr Ile Asn Val
1               5                   10
```

```
<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Arg Asn Tyr Gly Asn Trp Tyr Ile Asn Val
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic Construct

<400> SEQUENCE: 111

Arg Asn Tyr Gly Asn Phe Tyr Ile Asn Val
1               5                   10

<210> SEQ ID NO 112
<211> LENGTH: 15
<212> TYPE: PRT
<213> ORGANISM: Artificial Sequence
<220> FEATURE:
<223> OTHER INFORMATION: Synthetic Construct

<400> SEQUENCE: 112

Arg Ala Ser Glu Ser Val Asp Lys Phe Gly Met Ser Phe Leu Asn
1               5                   10                  15

<210> SEQ ID NO 113
<211> LENGTH: 7
<212> TYPE: PRT
<213> ORGANISM: Artificial Sequence
<220> FEATURE:
<223> OTHER INFORMATION: Synthetic Construct

<400> SEQUENCE: 113

Val Ala Ser Ser Gln Gly Ser
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Construct

<400> SEQUENCE: 114

Gln Gln Ser Lys Asp Ile Pro Tyr Thr
1               5

<210> SEQ ID NO 115
<211> LENGTH: 15
<212> TYPE: PRT
<213> ORGANISM: Artificial Sequence
<220> FEATURE:
<223> OTHER INFORMATION: Synthetic Construct

<400> SEQUENCE: 115

Arg Ala Ser Glu Ser Val Asp Lys Phe Gly Val Ser Phe Leu Asn
1               5                   10                  15

<210> SEQ ID NO 116
```

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 116

Arg Ala Ser Glu Ser Val Asp Lys Phe Gly Leu Ser Phe Leu Asn
1               5                   10                  15

<210> SEQ ID NO 117
<211> LENGTH: 30
<212> TYPE: PRT
<213> ORGANISM: Artificial Sequence
<220> FEATURE:
<223> OTHER INFORMATION: Synthetic Construct

<400> SEQUENCE: 117

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 119
<211> LENGTH: 14
<212> TYPE: PRT
<213> ORGANISM: Artificial Sequence
<220> FEATURE:
<223> OTHER INFORMATION: Synthetic Construct

<400> SEQUENCE: 119

Trp Val Arg Gln Ser Pro Glu Lys Gly Leu Glu Trp Met Ala
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Synthetic Construct

<400> SEQUENCE: 120

Trp Val Arg Gln Ala Pro Gly Lys Gly Leu Glu Trp Met Ala
1               5                   10

<210> SEQ ID NO 121
<211> LENGTH: 32
<212> TYPE: PRT
<213> ORGANISM: Artificial Sequence
<220> FEATURE:
<223> OTHER INFORMATION: Synthetic Construct

<400> SEQUENCE: 121
```

Arg Phe Ser Ile Ser Arg Asp Asp Ser Lys Ser Thr Val Tyr Leu Gln
1               5                   10                  15

Met Asn Asn Leu Arg Ala Glu Asp Thr Gly Ile Tyr Tyr Cys Ala Arg
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Synthetic Construct

<400> SEQUENCE: 122

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Synthetic Construct

<400> SEQUENCE: 123

Arg Phe Thr Ile Ser Arg Asp Asp Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 124
<211> LENGTH: 11
<212> TYPE: PRT
<213> ORGANISM: Artificial Sequence
<220> FEATURE:
<223> OTHER INFORMATION: Synthetic Construct

<400> SEQUENCE: 124

Trp Gly Ala Gly Thr Thr Val Thr Val Ser Ser
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic Construct

<400> SEQUENCE: 125

Trp Gly Gln Gly Thr Leu Val Thr Val Ser Ser
1               5                   10

<210> SEQ ID NO 126
<211> LENGTH: 23
<212> TYPE: PRT
<213> ORGANISM: Artificial Sequence
<220> FEATURE:
<223> OTHER INFORMATION: Synthetic Construct

<400> SEQUENCE: 126

Asp Ile Val Leu Thr Gln Ser Pro Thr Ser Leu Ala Val Ser Leu Gly
1               5                   10                  15

Gln Arg Ala Thr Ile Ser Cys
            20

```
<210> SEQ ID NO 127
<211> LENGTH: 23
<212> TYPE: PRT
<213> ORGANISM: Artificial Sequence
<220> FEATURE:
<223> OTHER INFORMATION: Synthetic Construct

<400> SEQUENCE: 127

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 128
<211> LENGTH: 15
<212> TYPE: PRT
<213> ORGANISM: Artificial Sequence
<220> FEATURE:
<223> OTHER INFORMATION: Synthetic Construct

<400> SEQUENCE: 128

Trp Phe Gln Gln Lys Pro Gly Gln Pro Pro Lys Leu Leu Ile Phe
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthetic Construct

<400> SEQUENCE: 129

Trp Tyr Gln Gln Lys Pro Gly Gln Pro Pro Lys Leu Leu Ile Phe
1               5                   10                  15

<210> SEQ ID NO 130
<211> LENGTH: 32
<212> TYPE: PRT
<213> ORGANISM: Artificial Sequence
<220> FEATURE:
<223> OTHER INFORMATION: Synthetic Construct

<400> SEQUENCE: 130

Gly Val Pro Ala Arg Phe Ser Gly Ser Gly Ser Gly Thr Asp Phe Ser
1               5                   10                  15

Leu Asn Ile His Pro Val Glu Glu Asp Asp Thr Ala Met Tyr Phe Cys
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Synthetic Construct

<400> SEQUENCE: 131

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 132
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 132

Phe Gly Gly Gly Thr Lys Leu Glu Ile Lys
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Synthetic Construct

<400> SEQUENCE: 133

Phe Gly Gln Gly Thr Lys Val Glu Ile Lys
1               5                   10

<210> SEQ ID NO 134
<211> LENGTH: 121
<212> TYPE: PRT
<213> ORGANISM: Artificial Sequence
<220> FEATURE:
<223> OTHER INFORMATION: Synthetic Construct

<400> SEQUENCE: 134

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Met
        35                  40                  45

Ala Glu Ile Thr Leu Lys Phe Asn Asn Tyr Ser Thr His Tyr Ala Glu
    50                  55                  60

Ser Val Lys Gly Arg Phe Ser Ile Ser Arg Asp Asp Ser Lys Ser Thr
65                  70                  75                  80

Val Tyr Leu Gln Met Asn Asn Leu Arg Ala Glu Asp Thr Gly Ile Tyr
                85                  90                  95

Tyr Cys Ala Arg Arg Asn Tyr Gly Asp Trp Tyr Ile Asn Val Trp Gly
            100                 105                 110

Ala Gly Thr Thr Val Thr Val Ser Ser
        115                 120

<210> SEQ ID NO 135
<211> LENGTH: 111
<212> TYPE: PRT
<213> ORGANISM: Artificial Sequence
<220> FEATURE:
<223> OTHER INFORMATION: Synthetic Construct

<400> SEQUENCE: 135

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Lys Phe
            20                  25                  30

Gly Met Ser Phe Leu Asn Trp Phe Gln Gln Lys Pro Gly Gln Pro Pro
        35                  40                  45

Lys Leu Leu Ile Phe Val Ala Ser Ser Gln Gly Ser Gly Val Pro Ala
    50                  55                  60

Arg Phe Ser Gly Ser Gly Ser Gly Thr Asp Phe Ser Leu Asn Ile His
```

```
                65                  70                  75                  80
Pro Val Glu Glu Asp Asp Thr Ala Met Tyr Phe Cys Gln Gln Ser Lys
                    85                  90                  95

Asp Ile Pro Tyr Thr Phe Gly Gly Gly Thr Lys Leu Glu Ile Lys
                100                 105                 110

<210> SEQ ID NO 136
<211> LENGTH: 121
<212> TYPE: PRT
<213> ORGANISM: Artificial Sequence
<220> FEATURE:
<223> OTHER INFORMATION: Synthetic Construct

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Met
        35                  40                  45

Ala Glu Ile Thr Leu Lys Phe Asn Asn Tyr Ser Thr His Tyr Ala Glu
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Arg Asn Tyr Gly Asn Trp Tyr Ile Asn Val Trp Gly
            100                 105                 110

Gln Gly Thr Leu Val Thr Val Ser Ser
        115                 120

<210> SEQ ID NO 137
<211> LENGTH: 111
<212> TYPE: PRT
<213> ORGANISM: Artificial Sequence
<220> FEATURE:
<223> OTHER INFORMATION: Synthetic Construct

<400> SEQUENCE: 137

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Met Ser Phe Leu Asn Trp Tyr Gln Gln Lys Pro Gly Gln Pro Pro
        35                  40                  45

Lys Leu Leu Ile Phe Val Ala Ser Ser Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
            100                 105                 110

<210> SEQ ID NO 138
<211> LENGTH: 121
<212> TYPE: PRT
<213> ORGANISM: Artificial Sequence
<220> FEATURE:
```

<223> OTHER INFORMATION: Synthetic Construct

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Met
        35                  40                  45

Ala Glu Ile Thr Leu Lys Phe Asn Asp Tyr Ser Thr His Tyr Ala Glu
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Arg Asn Tyr Gly Asn Trp Tyr Ile Asn Val Trp Gly
            100                 105                 110

Gln Gly Thr Leu Val Thr Val Ser Ser
            115                 120

<210> SEQ ID NO 139
<211> LENGTH: 111
<212> TYPE: PRT
<213> ORGANISM: Artificial Sequence
<220> FEATURE:
<223> OTHER INFORMATION: Synthetic Construct

<400> SEQUENCE: 139

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Val Ser Phe Leu Asn Trp Tyr Gln Gln Lys Pro Gly Gln Pro Pro
        35                  40                  45

Lys Leu Leu Ile Phe Val Ala Ser Ser Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
            100                 105                 110

<210> SEQ ID NO 140
<211> LENGTH: 121
<212> TYPE: PRT
<213> ORGANISM: Artificial Sequence
<220> FEATURE:
<223> OTHER INFORMATION: Synthetic Construct

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Met
        35                  40                  45

Ala Glu Ile Thr Leu Lys Phe Asn Asn Tyr Ser Thr His Tyr Ala Glu

```
                    50                  55                  60
Ser Val Lys Gly Arg Phe Thr Ile Ser Arg Asp Asn Ser Lys Asn Thr
 65                  70                  75                  80

Val Tyr Leu Gln Met Asn Ser Leu Arg Ala Glu Asp Thr Ala Val Tyr
                    85                  90                  95

Tyr Cys Ala Arg Arg Asn Tyr Gly Asn Trp Tyr Ile Asn Val Trp Gly
                   100                 105                 110

Gln Gly Thr Leu Val Thr Val Ser Ser
                   115                 120

<210> SEQ ID NO 141
<211> LENGTH: 121
<212> TYPE: PRT
<213> ORGANISM: Artificial Sequence
<220> FEATURE:
<223> OTHER INFORMATION: Synthetic Construct

<400> SEQUENCE: 141

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Trp Met Asn Trp Val Arg Gln Ala Pro Gly Lys Gly Leu Glu Trp Met
             35                  40                  45

Ala Glu Ile Thr Leu Lys Phe Asn Asn Tyr Ser Thr His Tyr Ala Glu
         50                  55                  60

Ser Val Lys Gly Arg Phe Thr Ile Ser Arg Asp Asn Ser Lys Asn Thr
 65                  70                  75                  80

Val Tyr Leu Gln Met Asn Ser Leu Arg Ala Glu Asp Thr Ala Val Tyr
                    85                  90                  95

Tyr Cys Ala Arg Arg Asn Tyr Gly Asn Trp Tyr Ile Asn Val Trp Gly
                   100                 105                 110

Gln Gly Thr Leu Val Thr Val Ser Ser
                   115                 120

<210> SEQ ID NO 142
<211> LENGTH: 121
<212> TYPE: PRT
<213> ORGANISM: Artificial Sequence
<220> FEATURE:
<223> OTHER INFORMATION: Synthetic Construct

<400> SEQUENCE: 142

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Trp Met Asn Trp Val Arg Gln Ala Pro Gly Lys Gly Leu Glu Trp Met
             35                  40                  45

Ala Glu Ile Thr Leu Lys Phe Asn Asp Tyr Ser Thr His Tyr Ala Glu
         50                  55                  60

Ser Val Lys Gly Arg Phe Thr Ile Ser Arg Asp Asn Ser Lys Asn Thr
 65                  70                  75                  80

Val Tyr Leu Gln Met Asn Ser Leu Arg Ala Glu Asp Thr Ala Val Tyr
                    85                  90                  95

Tyr Cys Ala Arg Arg Asn Tyr Gly Asn Trp Tyr Ile Asn Val Trp Gly
                   100                 105                 110
```

Gln Gly Thr Leu Val Thr Val Ser Ser
        115                 120

<210> SEQ ID NO 143
<211> LENGTH: 121
<212> TYPE: PRT
<213> ORGANISM: Artificial Sequence
<220> FEATURE:
<223> OTHER INFORMATION: Synthetic Construct

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Met
        35                  40                  45

Ala Glu Ile Thr Leu Lys Phe Asn Ser Tyr Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Arg Asn Tyr Gly Asn Trp Tyr Ile Asn Val Trp Gly
            100                 105                 110

Gln Gly Thr Leu Val Thr Val Ser Ser
        115                 120

<210> SEQ ID NO 144
<211> LENGTH: 121
<212> TYPE: PRT
<213> ORGANISM: Artificial Sequence
<220> FEATURE:
<223> OTHER INFORMATION: Synthetic Construct

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Met
        35                  40                  45

Ala Glu Ile Thr Leu Lys Phe Asn Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Arg Asn Tyr Gly Asn Trp Tyr Ile Asn Val Trp Gly
            100                 105                 110

Gln Gly Thr Leu Val Thr Val Ser Ser
        115                 120

<210> SEQ ID NO 145
<211> LENGTH: 121
<212> TYPE: PRT
<213> ORGANISM: Artificial Sequence
<220> FEATURE:
<223> OTHER INFORMATION: Synthetic Construct

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Phe Met Asn Trp Val Arg Gln Ala Pro Gly Lys Gly Leu Glu Trp Met
        35                  40                  45

Ala Glu Ile Thr Leu Lys Phe Asn Asn Tyr Ser Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Arg Asn Tyr Gly Asn Trp Tyr Ile Asn Val Trp Gly
            100                 105                 110

Gln Gly Thr Leu Val Thr Val Ser Ser
            115                 120

<210> SEQ ID NO 146
<211> LENGTH: 121
<212> TYPE: PRT
<213> ORGANISM: Artificial Sequence
<220> FEATURE:
<223> OTHER INFORMATION: Synthetic Construct

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Asn Trp Val Arg Gln Ala Pro Gly Lys Gly Leu Glu Trp Met
        35                  40                  45

Ala Glu Ile Thr Leu Lys Phe Asn Asn Tyr Ser Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Arg Asn Tyr Gly Asn Trp Tyr Ile Asn Val Trp Gly
            100                 105                 110

Gln Gly Thr Leu Val Thr Val Ser Ser
            115                 120

<210> SEQ ID NO 147
<211> LENGTH: 121
<212> TYPE: PRT
<213> ORGANISM: Artificial Sequence
<220> FEATURE:
<223> OTHER INFORMATION: Synthetic Construct

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Met
        35                  40                  45

```
Ala Glu Ile Thr Leu Lys Phe Asn Ala Tyr Ser Thr His Tyr Ala Glu
    50                  55                  60

Ser Val Lys Gly Arg Phe Thr Ile Ser Arg Asp Asp Ser Lys Asn Thr
 65                 70                  75                  80

Val Tyr Leu Gln Met Asn Ser Leu Arg Ala Glu Asp Thr Ala Val Tyr
                    85                  90                  95

Tyr Cys Ala Arg Arg Asn Tyr Gly Asn Trp Tyr Ile Asn Val Trp Gly
                100                 105                 110

Gln Gly Thr Leu Val Thr Val Ser Ser
            115                 120
```

<210> SEQ ID NO 148
<211> LENGTH: 121
<212> TYPE: PRT
<213> ORGANISM: Artificial Sequence
<220> FEATURE:
<223> OTHER INFORMATION: Synthetic Construct

<400> SEQUENCE: 148

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Trp Met Asn Trp Val Arg Gln Ala Pro Gly Lys Gly Leu Glu Trp Met
             35                  40                  45

Ala Glu Ile Thr Leu Lys Phe Asn Asn Tyr Ser Thr His Tyr Ala Glu
    50                  55                  60

Ser Val Lys Gly Arg Phe Thr Ile Ser Arg Asp Asp Ser Lys Asn Thr
 65                 70                  75                  80

Val Tyr Leu Gln Met Asn Ser Leu Arg Ala Glu Asp Thr Ala Val Tyr
                    85                  90                  95

Tyr Cys Ala Arg Arg Asn Tyr Gly Asn Tyr Tyr Ile Asn Val Trp Gly
                100                 105                 110

Gln Gly Thr Leu Val Thr Val Ser Ser
            115                 120
```

<210> SEQ ID NO 149
<211> LENGTH: 111
<212> TYPE: PRT
<213> ORGANISM: Artificial Sequence
<220> FEATURE:
<223> OTHER INFORMATION: Synthetic Construct

<400> SEQUENCE: 149

```
Asp Ile Val Met Thr Gln Ser Pro Asp Ser Leu Ala Val Ser Leu Gly
  1               5                  10                  15

Glu Arg Ala Thr Ile Asn Cys Arg Ala Ser Glu Ser Val Asp Lys Phe
             20                  25                  30

Gly Leu Ser Phe Leu Asn Trp Tyr Gln Gln Lys Pro Gly Gln Pro Pro
             35                  40                  45

Lys Leu Leu Ile Phe Val Ala Ser Ser Gln Gly Ser Gly Val Pro Asp
    50                  55                  60

Arg Phe Ser Gly Ser Gly Ser Gly Thr Asp Phe Thr Leu Thr Ile Ser
 65                 70                  75                  80

Ser Leu Gln Ala Glu Asp Val Ala Val Tyr Tyr Cys Gln Gln Ser Lys
                    85                  90                  95

Asp Ile Pro Tyr Thr Phe Gly Gln Gly Thr Lys Val Glu Ile Lys
                100                 105                 110
```

<210> SEQ ID NO 150
<211> LENGTH: 111
<212> TYPE: PRT
<213> ORGANISM: Artificial Sequence
<220> FEATURE:
<223> OTHER INFORMATION: Synthetic Construct

<400> SEQUENCE: 150

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Val Ser Phe Leu Asn Trp Tyr Gln Gln Lys Pro Gly Gln Pro Pro
        35                  40                  45

Lys Leu Leu Ile Phe Val Ala Ser Ser Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
            100                 105                 110

<210> SEQ ID NO 151
<211> LENGTH: 111
<212> TYPE: PRT
<213> ORGANISM: Artificial Sequence
<220> FEATURE:
<223> OTHER INFORMATION: Synthetic Construct

<400> SEQUENCE: 151

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Met Ser Phe Leu Asn Trp Tyr Gln Gln Lys Pro Gly Gln Pro Pro
        35                  40                  45

Lys Leu Leu Ile Phe Val Ala Ser Ser Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
            100                 105                 110

<210> SEQ ID NO 152
<211> LENGTH: 111
<212> TYPE: PRT
<213> ORGANISM: Artificial Sequence
<220> FEATURE:
<223> OTHER INFORMATION: Synthetic Construct

<400> SEQUENCE: 152

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Met Ser Phe Leu Asn Trp Tyr Gln Gln Lys Pro Gly Gln Pro Pro
                35                  40                  45

Lys Leu Leu Ile Phe Val Ala Ser Ser Gln Gly Ser Gly Val Pro Asp
 50                  55                  60

Arg Phe Ser Gly Ser Gly Ser Gly Thr Asp Phe Thr Leu Thr Ile Ser
65                   70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
                100                 105                 110

<210> SEQ ID NO 153
<211> LENGTH: 111
<212> TYPE: PRT
<213> ORGANISM: Artificial Sequence
<220> FEATURE:
<223> OTHER INFORMATION: Synthetic Construct

<400> SEQUENCE: 153

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
                20                  25                  30

Gly Met Ser Phe Leu Asn Trp Tyr Gln Gln Lys Pro Gly Gln Pro Pro
                35                  40                  45

Lys Leu Leu Ile Phe Val Ala Ser Ser Gln Gly Ser Gly Val Pro Asp
 50                  55                  60

Arg Phe Ser Gly Ser Gly Ser Gly Thr Asp Phe Thr Leu Thr Ile Ser
65                   70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
                100                 105                 110

<210> SEQ ID NO 154
<211> LENGTH: 111
<212> TYPE: PRT
<213> ORGANISM: Artificial Sequence
<220> FEATURE:
<223> OTHER INFORMATION: Synthetic Construct

<400> SEQUENCE: 154

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
                20                  25                  30

Gly Met Ser Phe Leu Asn Trp Tyr Gln Gln Lys Pro Gly Gln Pro Pro
                35                  40                  45

Lys Leu Leu Ile Phe Val Ala Ser Ser Gln Gly Ser Gly Val Pro Asp
 50                  55                  60

Arg Phe Ser Gly Ser Gly Ser Gly Thr Asp Phe Thr Leu Thr Ile Ser
65                   70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
                100                 105                 110

<210> SEQ ID NO 155

<211> LENGTH: 111
<212> TYPE: PRT
<213> ORGANISM: Artificial Sequence
<220> FEATURE:
<223> OTHER INFORMATION: Synthetic Construct

<400> SEQUENCE: 155

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Met Ser Phe Leu Asn Trp Tyr Gln Gln Lys Pro Gly Gln Pro Pro
        35                  40                  45

Lys Leu Leu Ile Phe Val Ala Ser Ser Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
            100                 105                 110

<210> SEQ ID NO 156
<211> LENGTH: 111
<212> TYPE: PRT
<213> ORGANISM: Artificial Sequence
<220> FEATURE:
<223> OTHER INFORMATION: Synthetic Construct

<400> SEQUENCE: 156

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Met Ser Phe Leu Asn Trp Tyr Gln Gln Lys Pro Gly Gln Pro Pro
        35                  40                  45

Lys Leu Leu Ile Phe Val Ala Ser Ser Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Asp Ile Pro Tyr Thr Phe Gly Gln Gly Thr Lys Val Glu Ile Lys
            100                 105                 110

<210> SEQ ID NO 157
<211> LENGTH: 111
<212> TYPE: PRT
<213> ORGANISM: Artificial Sequence
<220> FEATURE:
<223> OTHER INFORMATION: Synthetic Construct

<400> SEQUENCE: 157

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Phe
            20                  25                  30

Gly Met Ser Phe Leu Asn Trp Tyr Gln Gln Lys Pro Gly Gln Pro Pro
        35                  40                  45

Lys Leu Leu Ile Phe Val Ala Ser Ser Gln Gly Ser Gly Val Pro Asp
            50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Asp Ile Pro Tyr Thr Phe Gly Gln Gly Thr Lys Val Glu Ile Lys
            100                 105                 110

<210> SEQ ID NO 158
<211> LENGTH: 5
<212> TYPE: PRT
<213> ORGANISM: Artificial Sequence
<220> FEATURE:
<223> OTHER INFORMATION: Synthetic Construct

<400> SEQUENCE: 158

Lys Phe Trp Met Asn
1               5

<210> SEQ ID NO 159
<211> LENGTH: 19
<212> TYPE: PRT
<213> ORGANISM: Artificial Sequence
<220> FEATURE:
<223> OTHER INFORMATION: Synthetic Construct

<400> SEQUENCE: 159

Glu Ile Arg Leu Asn Ser Ile Asn Tyr Val Lys Asp Tyr Ala Glu Ser
1               5                   10                  15

Val Lys Gly

<210> SEQ ID NO 160
<211> LENGTH: 10
<212> TYPE: PRT
<213> ORGANISM: Artificial Sequence
<220> FEATURE:
<223> OTHER INFORMATION: Synthetic Construct

<400> SEQUENCE: 160

Arg Asn Tyr Gly Asn Trp Phe Phe Glu Ile
1               5                   10

<210> SEQ ID NO 161
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Asn or Ser
<220> FEATURE:
<221> NAME/KEY: MOD_RES
<222> LOCATION: (6)..(6)
<223> OTHER INFORMATION: Xaa is Ser or Ala

<400> SEQUENCE: 161

Glu Ile Arg Leu Xaa Xaa Ile Asn Tyr Val Lys Asp Tyr Ala Glu Ser
1               5                   10                  15

Val Lys Gly

<210> SEQ ID NO 162
<211> LENGTH: 19

```
<212> TYPE: PRT
<213> ORGANISM: Artificial Sequence
<220> FEATURE:
<223> OTHER INFORMATION: Synthetic Construct

<400> SEQUENCE: 162

Glu Ile Arg Leu Ser Ser Ile Asn Tyr Val Lys Asp Tyr Ala Glu Ser
1               5                   10                  15

Val Lys Gly

<210> SEQ ID NO 163
<211> LENGTH: 19
<212> TYPE: PRT
<213> ORGANISM: Artificial Sequence
<220> FEATURE:
<223> OTHER INFORMATION: Synthetic Construct

<400> SEQUENCE: 163

Glu Ile Arg Leu Asn Ala Ile Asn Tyr Val Lys Asp Tyr Ala Glu Ser
1               5                   10                  15

Val Lys Gly

<210> SEQ ID NO 164
<211> LENGTH: 15
<212> TYPE: PRT
<213> ORGANISM: Artificial Sequence
<220> FEATURE:
<223> OTHER INFORMATION: Synthetic Construct

<400> SEQUENCE: 164

Arg Ala Ser Glu Ser Val Asp Arg Tyr Gly Ile Ser Phe Met Asn
1               5                   10                  15

<210> SEQ ID NO 165
<211> LENGTH: 7
<212> TYPE: PRT
<213> ORGANISM: Artificial Sequence
<220> FEATURE:
<223> OTHER INFORMATION: Synthetic Construct

<400> SEQUENCE: 165

Ala Ala Ser Asn Gln Gly Ser
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Gln His Ser Lys Glu Val Pro Tyr Thr
1               5

<210> SEQ ID NO 167
<211> LENGTH: 30
<212> TYPE: PRT
<213> ORGANISM: Artificial Sequence
<220> FEATURE:
<223> OTHER INFORMATION: Synthetic Construct

<400> SEQUENCE: 167

Glu Val Lys Leu Glu Glu Ser Gly Gly Gly Leu Val Gln Pro Gly Gly
1               5                   10                  15
```

```
Ser Met Lys Leu Ser Cys Val Ala Ser Gly Phe Thr Phe Asn
            20                  25                  30
```

<210> SEQ ID NO 168
<211> LENGTH: 14
<212> TYPE: PRT
<213> ORGANISM: Artificial Sequence
<220> FEATURE:
<223> OTHER INFORMATION: Synthetic Construct

<400> SEQUENCE: 168

```
Trp Val Arg Gln Ser Pro Glu Lys Gly Leu Glu Trp Val Ala
1               5                   10
```

<210> SEQ ID NO 169
<211> LENGTH: 32
<212> TYPE: PRT
<213> ORGANISM: Artificial Sequence
<220> FEATURE:
<223> OTHER INFORMATION: Synthetic Construct

<400> SEQUENCE: 169

```
Arg Phe Thr Ile Ser Arg Asp Asp Ser Lys Asn Ser Val Tyr Leu Gln
1               5                   10                  15

Met Asn Asn Leu Arg Ala Glu Asp Thr Gly Ile Tyr Tyr Cys Ile Arg
            20                  25                  30
```

<210> SEQ ID NO 170
<211> LENGTH: 11
<212> TYPE: PRT
<213> ORGANISM: Artificial Sequence
<220> FEATURE:
<223> OTHER INFORMATION: Synthetic Construct

<400> SEQUENCE: 170

```
Trp Gly Ala Gly Thr Thr Val Thr Val Ser Ser
1               5                   10
```

<210> SEQ ID NO 171
<211> LENGTH: 30
<212> TYPE: PRT
<213> ORGANISM: Artificial Sequence
<220> FEATURE:
<223> OTHER INFORMATION: Synthetic Construct

<400> SEQUENCE: 171

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn
            20                  25                  30
```

<210> SEQ ID NO 172
<211> LENGTH: 14
<212> TYPE: PRT
<213> ORGANISM: Artificial Sequence
<220> FEATURE:
<223> OTHER INFORMATION: Synthetic Construct

<400> SEQUENCE: 172

```
Trp Val Arg Gln Ala Pro Gly Lys Gly Leu Glu Trp Val Ala
1               5                   10
```

<210> SEQ ID NO 173
<211> LENGTH: 32
<212> TYPE: PRT
<213> ORGANISM: Artificial Sequence

```
<220> FEATURE:
<223> OTHER INFORMATION: Synthetic Construct

<400> SEQUENCE: 173

Arg Phe Thr Ile Ser Arg Asp Asn Ala Lys Asn Ser Val Tyr Leu Gln
1               5                   10                  15

Met Asn Ser Leu Arg Ala Glu Asp Thr Ala Val Tyr Tyr Cys Ile Arg
            20                  25                  30

<210> SEQ ID NO 174
<211> LENGTH: 11
<212> TYPE: PRT
<213> ORGANISM: Artificial Sequence
<220> FEATURE:
<223> OTHER INFORMATION: Synthetic Construct

<400> SEQUENCE: 174

Trp Gly Gln Gly Thr Leu Val Thr Val Ser Ser
1               5                   10

<210> SEQ ID NO 175
<211> LENGTH: 23
<212> TYPE: PRT
<213> ORGANISM: Artificial Sequence
<220> FEATURE:
<223> OTHER INFORMATION: Synthetic Construct

<400> SEQUENCE: 175

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 176
<211> LENGTH: 15
<212> TYPE: PRT
<213> ORGANISM: Artificial Sequence
<220> FEATURE:
<223> OTHER INFORMATION: Synthetic Construct

<400> SEQUENCE: 176

Trp Phe Gln Gln Lys Pro Gly Gln Ser Pro Lys Leu Leu Ile Tyr
1               5                   10                  15

<210> SEQ ID NO 177
<211> LENGTH: 32
<212> TYPE: PRT
<213> ORGANISM: Artificial Sequence
<220> FEATURE:
<223> OTHER INFORMATION: Synthetic Construct

<400> SEQUENCE: 177

Gly Val Pro Ala Arg Phe Ser Gly Ser Gly Ser Gly Thr Asp Phe Ser
1               5                   10                  15

Leu Asn Ile His Pro Leu Glu Glu Asp Asp Ala Ala Met Tyr Phe Cys
            20                  25                  30

<210> SEQ ID NO 178
<211> LENGTH: 10
<212> TYPE: PRT
<213> ORGANISM: Artificial Sequence
<220> FEATURE:
<223> OTHER INFORMATION: Synthetic Construct

<400> SEQUENCE: 178
```

Phe Gly Gly Gly Thr Lys Leu Glu Ile Lys
1               5                   10

<210> SEQ ID NO 179
<211> LENGTH: 23
<212> TYPE: PRT
<213> ORGANISM: Artificial Sequence
<220> FEATURE:
<223> OTHER INFORMATION: Synthetic Construct

<400> SEQUENCE: 179

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 180
<211> LENGTH: 15
<212> TYPE: PRT
<213> ORGANISM: Artificial Sequence
<220> FEATURE:
<223> OTHER INFORMATION: Synthetic Construct

<400> SEQUENCE: 180

Trp Phe Gln Gln Lys Pro Gly Lys Ala Pro Lys Leu Leu Ile Tyr
1               5                   10                  15

<210> SEQ ID NO 181
<211> LENGTH: 32
<212> TYPE: PRT
<213> ORGANISM: Artificial Sequence
<220> FEATURE:
<223> OTHER INFORMATION: Synthetic Construct

<400> SEQUENCE: 181

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 182
<211> LENGTH: 10
<212> TYPE: PRT
<213> ORGANISM: Artificial Sequence
<220> FEATURE:
<223> OTHER INFORMATION: Synthetic Construct

<400> SEQUENCE: 182

Phe Gly Gln Gly Thr Lys Val Glu Ile Lys
1               5                   10

<210> SEQ ID NO 183
<211> LENGTH: 121
<212> TYPE: PRT
<213> ORGANISM: Artificial Sequence
<220> FEATURE:
<223> OTHER INFORMATION: Synthetic Construct

<400> SEQUENCE: 183

Glu Val Lys Leu Glu Glu Ser Gly Gly Gly Leu Val Gln Pro Gly Gly
1               5                   10                  15
Ser Met Lys Leu Ser Cys Val Ala Ser Gly Phe Thr Phe Asn Lys Phe
            20                  25                  30
Trp Met Asn Trp Val Arg Gln Ser Pro Glu Lys Gly Leu Glu Trp Val
        35                  40                  45

```
Ala Glu Ile Arg Leu Asn Ser Ile Asn Tyr Val Lys Asp Tyr Ala Glu
            50                  55                  60

Ser Val Lys Gly Arg Phe Thr Ile Ser Arg Asp Asp Ser Lys Asn Ser
 65                  70                  75                  80

Val Tyr Leu Gln Met Asn Asn Leu Arg Ala Glu Asp Thr Gly Ile Tyr
                    85                  90                  95

Tyr Cys Ile Arg Arg Asn Tyr Gly Asn Trp Phe Phe Glu Ile Trp Gly
                100                 105                 110

Ala Gly Thr Thr Val Thr Val Ser Ser
            115                 120

<210> SEQ ID NO 184
<211> LENGTH: 111
<212> TYPE: PRT
<213> ORGANISM: Artificial Sequence
<220> FEATURE:
<223> OTHER INFORMATION: Synthetic Construct

<400> SEQUENCE: 184

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Arg Tyr
                20                  25                  30

Gly Ile Ser Phe Met Asn Trp Phe Gln Gln Lys Pro Gly Gln Ser Pro
            35                  40                  45

Lys Leu Leu Ile Tyr Ala Ala Ser Asn Gln Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Leu Glu Glu Asp Asp Ala Ala Met Tyr Phe Cys Gln His Ser Lys
                85                  90                  95

Glu Val Pro Tyr Thr Phe Gly Gly Gly Thr Lys Leu Glu Ile Lys
                100                 105                 110

<210> SEQ ID NO 185
<211> LENGTH: 121
<212> TYPE: PRT
<213> ORGANISM: Artificial Sequence
<220> FEATURE:
<223> OTHER INFORMATION: Synthetic Construct

<400> SEQUENCE: 185

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Lys Phe
                20                  25                  30

Trp Met Asn Trp Val Arg Gln Ala Pro Gly Lys Gly Leu Glu Trp Val
            35                  40                  45

Ala Glu Ile Arg Leu Asn Ser Ile Asn Tyr Val Lys Asp Tyr Ala Glu
 50                  55                  60

Ser Val Lys Gly Arg Phe Thr Ile Ser Arg Asp Asn Ala Lys Asn Ser
 65                  70                  75                  80

Val Tyr Leu Gln Met Asn Ser Leu Arg Ala Glu Asp Thr Ala Val Tyr
                85                  90                  95

Tyr Cys Ile Arg Arg Asn Tyr Gly Asn Trp Phe Phe Glu Ile Trp Gly
                100                 105                 110

Gln Gly Thr Leu Val Thr Val Ser Ser
```

```
                115                 120

<210> SEQ ID NO 186
<211> LENGTH: 111
<212> TYPE: PRT
<213> ORGANISM: Artificial Sequence
<220> FEATURE:
<223> OTHER INFORMATION: Synthetic Construct

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Arg Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Lys
                85                  90                  95

Glu Val Pro Tyr Thr Phe Gly Gln Gly Thr Lys Val Glu Ile Lys
            100                 105                 110

<210> SEQ ID NO 187
<211> LENGTH: 121
<212> TYPE: PRT
<213> ORGANISM: Artificial Sequence
<220> FEATURE:
<223> OTHER INFORMATION: Synthetic Construct

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Lys Phe
            20                  25                  30

Trp Met Asn Trp Val Arg Gln Ala Pro Gly Lys Gly Leu Glu Trp Val
        35                  40                  45

Ala Glu Ile Arg Leu Ser Ser Ile Asn Tyr Val Lys Asp Tyr Ala Glu
    50                  55                  60

Ser Val Lys Gly Arg Phe Thr Ile Ser Arg Asp Asn Ala Lys Asn Ser
65                  70                  75                  80

Val Tyr Leu Gln Met Asn Ser Leu Arg Ala Glu Asp Thr Ala Val Tyr
                85                  90                  95

Tyr Cys Ile Arg Arg Asn Tyr Gly Asn Trp Phe Phe Glu Ile Trp Gly
            100                 105                 110

Gln Gly Thr Leu Val Thr Val Ser Ser
        115                 120

<210> SEQ ID NO 188
<211> LENGTH: 111
<212> TYPE: PRT
<213> ORGANISM: Artificial Sequence
<220> FEATURE:
<223> OTHER INFORMATION: Synthetic Construct

<400> SEQUENCE: 188

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Glu Ser Val Asp Arg Tyr
                20                  25                  30

Gly Ile Ser Phe Met Asn Trp Phe Gln Gln Lys Pro Gly Lys Ala Pro
            35                  40                  45

Lys Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Lys
                85                  90                  95

Glu Val Pro Tyr Thr Phe Gly Gln Gly Thr Lys Val Glu Ile Lys
            100                 105                 110

<210> SEQ ID NO 189
<211> LENGTH: 121
<212> TYPE: PRT
<213> ORGANISM: Artificial Sequence
<220> FEATURE:
<223> OTHER INFORMATION: Synthetic Construct

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Lys Phe
                20                  25                  30

Trp Met Asn Trp Val Arg Gln Ala Pro Gly Lys Gly Leu Glu Trp Val
            35                  40                  45

Ala Glu Ile Arg Leu Asn Ala Ile Asn Tyr Val Lys Asp Tyr Ala Glu
 50                  55                  60

Ser Val Lys Gly Arg Phe Thr Ile Ser Arg Asp Asn Ala Lys Asn Ser
65                  70                  75                  80

Val Tyr Leu Gln Met Asn Ser Leu Arg Ala Glu Asp Thr Ala Val Tyr
                85                  90                  95

Tyr Cys Ile Arg Arg Asn Tyr Gly Asn Trp Phe Phe Glu Ile Trp Gly
            100                 105                 110

Gln Gly Thr Leu Val Thr Val Ser Ser
            115                 120

<210> SEQ ID NO 190
<211> LENGTH: 111
<212> TYPE: PRT
<213> ORGANISM: Artificial Sequence
<220> FEATURE:
<223> OTHER INFORMATION: Synthetic Construct

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Arg Tyr
                20                  25                  30

Gly Ile Ser Phe Met Asn Trp Phe Gln Gln Lys Pro Gly Lys Ala Pro
            35                  40                  45

Lys Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Lys 85                  90                  95

Glu Val Pro Tyr Thr Phe Gly Gln Gly Thr Lys Val Glu Ile Lys
            100                 105                 110

<210> SEQ ID NO 191
<211> LENGTH: 5
<212> TYPE: PRT
<213> ORGANISM: Artificial Sequence
<220> FEATURE:
<223> OTHER INFORMATION: Synthetic Construct

<400> SEQUENCE: 191

Asp Tyr Asn Met Asn
1               5

<210> SEQ ID NO 192
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Asn or Ser
<220> FEATURE:
<221> NAME/KEY: MOD_RES
<222> LOCATION: (7)..(7)
<223> OTHER INFORMATION: Xaa is Gly or Ala

<400> SEQUENCE: 192

Asp Ile Asn Pro Lys Xaa Xaa Asp Thr Phe Tyr Asn Gln Asn Phe Lys
1               5                   10                  15

Asp

<210> SEQ ID NO 193
<211> LENGTH: 17
<212> TYPE: PRT
<213> ORGANISM: Artificial Sequence
<220> FEATURE:
<223> OTHER INFORMATION: Synthetic Construct

<400> SEQUENCE: 193

Asp Ile Asn Pro Lys Asn Gly Asp Thr Phe Tyr Asn Gln Asn Phe Lys
1               5                   10                  15

Asp

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct

<400> SEQUENCE: 194

Asp Ile Asn Pro Lys Ser Gly Asp Thr Phe Tyr Asn Gln Asn Phe Lys
1               5                   10                  15

Asp

<210> SEQ ID NO 195
<211> LENGTH: 17
<212> TYPE: PRT
<213> ORGANISM: Artificial Sequence
<220> FEATURE:
<223> OTHER INFORMATION: Synthetic Construct

```
<400> SEQUENCE: 195

Asp Ile Asn Pro Lys Asn Ala Asp Thr Phe Tyr Asn Gln Asn Phe Lys
1               5                   10                  15

Asp

<210> SEQ ID NO 196
<211> LENGTH: 13
<212> TYPE: PRT
<213> ORGANISM: Artificial Sequence
<220> FEATURE:
<223> OTHER INFORMATION: Synthetic Construct

<400> SEQUENCE: 196

His Tyr Tyr Tyr Gly Ser Ser Tyr Gly Gly Phe Val Tyr
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Synthetic Construct

<400> SEQUENCE: 197

His Ala Ser Gln Asn Ile Asn Val Trp Leu Ser
1               5                   10

<210> SEQ ID NO 198
<211> LENGTH: 7
<212> TYPE: PRT
<213> ORGANISM: Artificial Sequence
<220> FEATURE:
<223> OTHER INFORMATION: Synthetic Construct

<400> SEQUENCE: 198

Ala Ala Ser Lys Leu His Thr
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic Construct

<400> SEQUENCE: 199

Gln Gln Gly Gln Ser Tyr Pro Leu Thr
1               5

<210> SEQ ID NO 200
<211> LENGTH: 30
<212> TYPE: PRT
<213> ORGANISM: Artificial Sequence
<220> FEATURE:
<223> OTHER INFORMATION: Synthetic Construct

<400> SEQUENCE: 200

Glu Val Leu Leu Gln Gln Ser Gly Pro Glu Leu Val Lys Pro Gly Ala
1               5                   10                  15

Ser Val Lys Ile Ser Cys Asn Ala Ser Gly Tyr Thr Phe Ser
                20                  25                  30

<210> SEQ ID NO 201
<211> LENGTH: 14
<212> TYPE: PRT
```

```
<213> ORGANISM: Artificial Sequence
<220> FEATURE:
<223> OTHER INFORMATION: Synthetic Construct

<400> SEQUENCE: 201

Trp Val Lys Gln Ser His Gly Lys Ser Leu Glu Ser Ile Gly
1               5                   10

<210> SEQ ID NO 202
<211> LENGTH: 32
<212> TYPE: PRT
<213> ORGANISM: Artificial Sequence
<220> FEATURE:
<223> OTHER INFORMATION: Synthetic Construct

<400> SEQUENCE: 202

Lys Ala Thr Leu Thr Ile Asp Lys Ser Ser Thr Val Tyr Met Glu
1               5                   10                  15

Leu Arg Ser Leu Thr Ser Glu Asp Thr Ala Met Tyr Tyr Cys Ala Arg
                20                  25                  30

<210> SEQ ID NO 203
<211> LENGTH: 11
<212> TYPE: PRT
<213> ORGANISM: Artificial Sequence
<220> FEATURE:
<223> OTHER INFORMATION: Synthetic Construct

<400> SEQUENCE: 203

Trp Gly Gln Gly Thr Leu Val Thr Val Ala Ala
1               5                   10

<210> SEQ ID NO 204
<211> LENGTH: 30
<212> TYPE: PRT
<213> ORGANISM: Artificial Sequence
<220> FEATURE:
<223> OTHER INFORMATION: Synthetic Construct

<400> SEQUENCE: 204

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser
                20                  25                  30

<210> SEQ ID NO 205
<211> LENGTH: 14
<212> TYPE: PRT
<213> ORGANISM: Artificial Sequence
<220> FEATURE:
<223> OTHER INFORMATION: Synthetic Construct

<400> SEQUENCE: 205

Trp Val Arg Gln Ala Pro Gly Gln Gly Leu Glu Ser Ile Gly
1               5                   10

<210> SEQ ID NO 206
<211> LENGTH: 32
<212> TYPE: PRT
<213> ORGANISM: Artificial Sequence
<220> FEATURE:
<223> OTHER INFORMATION: Synthetic Construct

<400> SEQUENCE: 206

Arg Ala Thr Leu Thr Ile Asp Lys Ser Thr Ser Thr Ala Tyr Leu Glu
1               5                   10                  15
```

```
Leu Ser Ser Leu Arg Ser Glu Asp Thr Ala Val Tyr Tyr Cys Ala Arg
            20                  25                  30

<210> SEQ ID NO 207
<211> LENGTH: 11
<212> TYPE: PRT
<213> ORGANISM: Artificial Sequence
<220> FEATURE:
<223> OTHER INFORMATION: Synthetic Construct

<400> SEQUENCE: 207

Trp Gly Gln Gly Thr Leu Val Thr Val Ser Ser
1               5                  10

<210> SEQ ID NO 208
<211> LENGTH: 23
<212> TYPE: PRT
<213> ORGANISM: Artificial Sequence
<220> FEATURE:
<223> OTHER INFORMATION: Synthetic Construct

<400> SEQUENCE: 208

Asp Ile Gln Met Asn Gln Ser Pro Ser Ser Leu Ser Ala Ser Leu Gly
1               5                   10                  15

Asp Thr Ile Thr Ile Thr Cys
            20

<210> SEQ ID NO 209
<211> LENGTH: 15
<212> TYPE: PRT
<213> ORGANISM: Artificial Sequence
<220> FEATURE:
<223> OTHER INFORMATION: Synthetic Construct

<400> SEQUENCE: 209

Trp Tyr Gln Gln Lys Ala Gly Asn Asn Pro Lys Leu Leu Ile Tyr
1               5                   10                  15

<210> SEQ ID NO 210
<211> LENGTH: 32
<212> TYPE: PRT
<213> ORGANISM: Artificial Sequence
<220> FEATURE:
<223> OTHER INFORMATION: Synthetic Construct

<400> SEQUENCE: 210

Gly Val Pro Ser Arg Phe Thr Gly Ser Gly Ser Gly Thr Leu Phe Thr
1               5                   10                  15

Leu Thr Ile Ser Ser Leu Gln Pro Glu Asp Ile Ala Thr Tyr Tyr Cys
            20                  25                  30

<210> SEQ ID NO 211
<211> LENGTH: 10
<212> TYPE: PRT
<213> ORGANISM: Artificial Sequence
<220> FEATURE:
<223> OTHER INFORMATION: Synthetic Construct

<400> SEQUENCE: 211

Phe Gly Ser Gly Thr Asn Leu Glu Leu Lys
1               5                   10

<210> SEQ ID NO 212
<211> LENGTH: 23
<212> TYPE: PRT
```

<213> ORGANISM: Artificial Sequence
<220> FEATURE:
<223> OTHER INFORMATION: Synthetic Construct

<400> SEQUENCE: 212

```
Asp Ile Gln Met Thr Gln Ser Pro Ser Leu Ser Ala Ser Val Gly
1               5                   10                  15

Asp Arg Val Thr Ile Thr Cys
                20
```

<210> SEQ ID NO 213
<211> LENGTH: 15
<212> TYPE: PRT
<213> ORGANISM: Artificial Sequence
<220> FEATURE:
<223> OTHER INFORMATION: Synthetic Construct

<400> SEQUENCE: 213

```
Trp Tyr Gln Gln Lys Pro Gly Lys Asn Pro Lys Leu Leu Ile Tyr
1               5                   10                  15
```

<210> SEQ ID NO 214
<211> LENGTH: 32
<212> TYPE: PRT
<213> ORGANISM: Artificial Sequence
<220> FEATURE:
<223> OTHER INFORMATION: Synthetic Construct

<400> SEQUENCE: 214

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30
```

<210> SEQ ID NO 215
<211> LENGTH: 10
<212> TYPE: PRT
<213> ORGANISM: Artificial Sequence
<220> FEATURE:
<223> OTHER INFORMATION: Synthetic Construct

<400> SEQUENCE: 215

```
Phe Gly Gln Gly Thr Lys Val Glu Ile Lys
1               5                   10
```

<210> SEQ ID NO 216
<211> LENGTH: 122
<212> TYPE: PRT
<213> ORGANISM: Artificial Sequence
<220> FEATURE:
<223> OTHER INFORMATION: Synthetic Construct

<400> SEQUENCE: 216

```
Glu Val Leu Leu Gln Gln Ser Gly Pro Glu Leu Val Lys Pro Gly Ala
1               5                   10                  15

Ser Val Lys Ile Ser Cys Asn Ala Ser Gly Tyr Thr Phe Ser Asp Tyr
                20                  25                  30

Asn Met Asn Trp Val Lys Gln Ser His Gly Lys Ser Leu Glu Ser Ile
            35                  40                  45

Gly Asp Ile Asn Pro Lys Asn Gly Asp Thr Phe Tyr Asn Gln Asn Phe
        50                  55                  60

Lys Asp Lys Ala Thr Leu Thr Ile Asp Lys Ser Ser Ser Thr Val Tyr
65                  70                  75                  80
```

```
Met Glu Leu Arg Ser Leu Thr Ser Glu Asp Thr Ala Met Tyr Tyr Cys
             85                  90                  95

Ala Arg His Tyr Tyr Tyr Gly Ser Ser Tyr Gly Gly Phe Val Tyr Trp
            100                 105                 110

Gly Gln Gly Thr Leu Val Thr Val Ala Ala
        115                 120

<210> SEQ ID NO 217
<211> LENGTH: 107
<212> TYPE: PRT
<213> ORGANISM: Artificial Sequence
<220> FEATURE:
<223> OTHER INFORMATION: Synthetic Construct

<400> SEQUENCE: 217

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Ala Gly Asn Asn Pro Lys Leu Leu Ile
        35                  40                  45

Tyr Ala Ala Ser Lys Leu His Thr Gly Val Pro Ser Arg Phe Thr Gly
    50                  55                  60

Ser Gly Ser Gly Thr Leu Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ser Gly Thr Asn Leu Glu Leu Lys
            100                 105

<210> SEQ ID NO 218
<211> LENGTH: 122
<212> TYPE: PRT
<213> ORGANISM: Artificial Sequence
<220> FEATURE:
<223> OTHER INFORMATION: Synthetic Construct

<400> SEQUENCE: 218

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Asn Met Asn Trp Val Arg Gln Ala Pro Gly Gln Gly Leu Glu Ser Ile
        35                  40                  45

Gly Asp Ile Asn Pro Lys Asn Gly Asp Thr Phe Tyr Asn Gln Asn Phe
    50                  55                  60

Lys Asp Arg Ala Thr Leu Thr Ile Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg His Tyr Tyr Tyr Gly Ser Ser Tyr Gly Gly Phe Val Tyr Trp
            100                 105                 110

Gly Gln Gly Thr Leu Val Thr Val Ser Ser
        115                 120

<210> SEQ ID NO 219
<211> LENGTH: 107
<212> TYPE: PRT
<213> ORGANISM: Artificial Sequence
```

<220> FEATURE:
<223> OTHER INFORMATION: Synthetic Construct

<400> SEQUENCE: 219

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Lys Pro Gly Lys Asn Pro Lys Leu Leu Ile
        35                  40                  45

Tyr Ala Ala Ser Lys Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Leu
                85                  90                  95

Thr Phe Gly Gln Gly Thr Lys Val Glu Ile Lys
            100                 105
```

<210> SEQ ID NO 220
<211> LENGTH: 122
<212> TYPE: PRT
<213> ORGANISM: Artificial Sequence
<220> FEATURE:
<223> OTHER INFORMATION: Synthetic Construct

<400> SEQUENCE: 220

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Asn Met Asn Trp Val Arg Gln Ala Pro Gly Gln Gly Leu Glu Ser Ile
        35                  40                  45

Gly Asp Ile Asn Pro Lys Ser Gly Asp Thr Phe Tyr Asn Gln Asn Phe
    50                  55                  60

Lys Asp Arg Ala Thr Leu Thr Ile Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg His Tyr Tyr Gly Ser Ser Tyr Gly Gly Phe Val Tyr Trp
            100                 105                 110

Gly Gln Gly Thr Leu Val Thr Val Ser Ser
        115                 120
```

<210> SEQ ID NO 221
<211> LENGTH: 122
<212> TYPE: PRT
<213> ORGANISM: Artificial Sequence
<220> FEATURE:
<223> OTHER INFORMATION: Synthetic Construct

<400> SEQUENCE: 221

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Asn Met Asn Trp Val Arg Gln Ala Pro Gly Gln Gly Leu Glu Ser Ile
        35                  40                  45
```

```
Gly Asp Ile Asn Pro Lys Asn Ala Asp Thr Phe Tyr Asn Gln Asn Phe
    50                  55                  60

Lys Asp Arg Ala Thr Leu Thr Ile Asp Lys Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg His Tyr Tyr Tyr Gly Ser Ser Tyr Gly Gly Phe Val Tyr Trp
             100                 105                 110

Gly Gln Gly Thr Leu Val Thr Val Ser Ser
         115                 120
```

<210> SEQ ID NO 222
<211> LENGTH: 5
<212> TYPE: PRT
<213> ORGANISM: Artificial Sequence
<220> FEATURE:
<223> OTHER INFORMATION: Synthetic Construct

<400> SEQUENCE: 222

```
Ser Tyr Trp Ile Asn
 1               5
```

<210> SEQ ID NO 223
<211> LENGTH: 17
<212> TYPE: PRT
<213> ORGANISM: Artificial Sequence
<220> FEATURE:
<223> OTHER INFORMATION: Synthetic Construct

<400> SEQUENCE: 223

```
Arg Ile Ala Pro Gly Ser Gly Phe Ile Ser Tyr Asn Glu Leu Phe Lys
 1               5                  10                  15

Asp
```

<210> SEQ ID NO 224
<211> LENGTH: 13
<212> TYPE: PRT
<213> ORGANISM: Artificial Sequence
<220> FEATURE:
<223> OTHER INFORMATION: Synthetic Construct

<400> SEQUENCE: 224

```
Glu Phe Tyr Tyr Gly Ser Phe Tyr Gly Gly Phe Ala Tyr
 1               5                  10
```

<210> SEQ ID NO 225
<211> LENGTH: 11
<212> TYPE: PRT
<213> ORGANISM: Artificial Sequence
<220> FEATURE:
<223> OTHER INFORMATION: Synthetic Construct

<400> SEQUENCE: 225

```
His Ala Ser Gln Asn Ile His Val Trp Leu Ser
 1               5                  10
```

<210> SEQ ID NO 226
<211> LENGTH: 7
<212> TYPE: PRT
<213> ORGANISM: Artificial Sequence
<220> FEATURE:
<223> OTHER INFORMATION: Synthetic Construct

<400> SEQUENCE: 226

Lys Ala Ser Thr Leu His Thr
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

Gln Gln Gly Gln Ser Ser Pro Leu Thr
1               5

<210> SEQ ID NO 228
<211> LENGTH: 30
<212> TYPE: PRT
<213> ORGANISM: Artificial Sequence
<220> FEATURE:
<223> OTHER INFORMATION: Synthetic Construct

<400> SEQUENCE: 228

Gln Val Gln Leu Gln Gln Ser Gly Asn Asp Leu Val Lys Pro Gly Ala
1               5                   10                  15
Ser Val Lys Leu Ser Cys Lys Ala Ser Gly Tyr Thr Phe Thr
            20                  25                  30

<210> SEQ ID NO 229
<211> LENGTH: 14
<212> TYPE: PRT
<213> ORGANISM: Artificial Sequence
<220> FEATURE:
<223> OTHER INFORMATION: Synthetic Construct

<400> SEQUENCE: 229

Trp Ile Lys Gln Arg Pro Gly Gln Gly Leu Glu Trp Ile Gly
1               5                   10

<210> SEQ ID NO 230
<211> LENGTH: 32
<212> TYPE: PRT
<213> ORGANISM: Artificial Sequence
<220> FEATURE:
<223> OTHER INFORMATION: Synthetic Construct

<400> SEQUENCE: 230

Lys Ala Thr Leu Thr Val Asp Thr Ser Ser Ser Thr Ala Tyr Ile Gln
1               5                   10                  15
Leu Gly Ser Leu Ser Ser Glu Asp Ser Ala Val Tyr Phe Cys Ala Arg
            20                  25                  30

<210> SEQ ID NO 231
<211> LENGTH: 11
<212> TYPE: PRT
<213> ORGANISM: Artificial Sequence
<220> FEATURE:
<223> OTHER INFORMATION: Synthetic Construct

<400> SEQUENCE: 231

Trp Gly Gln Gly Thr Leu Val Thr Val Ser Ala
1               5                   10

<210> SEQ ID NO 232
<211> LENGTH: 23
<212> TYPE: PRT
<213> ORGANISM: Artificial Sequence

```
<220> FEATURE:
<223> OTHER INFORMATION: Synthetic Construct

<400> SEQUENCE: 232

Asp Ile Gln Met Asn Gln Ser Pro Ser Ser Leu Ser Ala Ser Leu Gly
1               5                   10                  15
Asp Thr Ile Thr Ile Thr Cys
            20

<210> SEQ ID NO 233
<211> LENGTH: 15
<212> TYPE: PRT
<213> ORGANISM: Artificial Sequence
<220> FEATURE:
<223> OTHER INFORMATION: Synthetic Construct

<400> SEQUENCE: 233

Trp Tyr Gln Gln Lys Pro Gly Asn Ile Pro Lys Leu Leu Ile Tyr
1               5                   10                  15

<210> SEQ ID NO 234
<211> LENGTH: 32
<212> TYPE: PRT
<213> ORGANISM: Artificial Sequence
<220> FEATURE:
<223> OTHER INFORMATION: Synthetic Construct

<400> SEQUENCE: 234

Gly Val Pro Ser Arg Phe Asn Gly Ser Gly Ser Gly Thr Gly Phe Thr
1               5                   10                  15
Leu Thr Ile Ser Ser Leu Gln Pro Glu Asp Ile Ala Thr Tyr Tyr Cys
            20                  25                  30

<210> SEQ ID NO 235
<211> LENGTH: 10
<212> TYPE: PRT
<213> ORGANISM: Artificial Sequence
<220> FEATURE:
<223> OTHER INFORMATION: Synthetic Construct

<400> SEQUENCE: 235

Phe Gly Ala Gly Thr Lys Leu Glu Val Lys
1               5                   10

<210> SEQ ID NO 236
<211> LENGTH: 122
<212> TYPE: PRT
<213> ORGANISM: Artificial Sequence
<220> FEATURE:
<223> OTHER INFORMATION: Synthetic Construct

<400> SEQUENCE: 236

Gln Val Gln Leu Gln Gln Ser Gly Asn Asp Leu Val Lys Pro Gly Ala
1               5                   10                  15
Ser Val Lys Leu Ser Cys Lys Ala Ser Gly Tyr Thr Phe Thr Ser Tyr
            20                  25                  30
Trp Ile Asn Trp Ile Lys Gln Arg Pro Gly Gln Gly Leu Glu Trp Ile
        35                  40                  45
Gly Arg Ile Ala Pro Gly Ser Gly Phe Ile Ser Tyr Asn Glu Leu Phe
    50                  55                  60
Lys Asp Lys Ala Thr Leu Thr Val Asp Thr Ser Ser Ser Thr Ala Tyr
65                  70                  75                  80
Ile Gln Leu Gly Ser Leu Ser Ser Glu Asp Ser Ala Val Tyr Phe Cys
```

```
                    85                  90                  95
Ala Arg Glu Phe Tyr Tyr Gly Ser Phe Tyr Gly Gly Phe Ala Tyr Trp
            100                 105                 110

Gly Gln Gly Thr Leu Val Thr Val Ser Ala
        115                 120

<210> SEQ ID NO 237
<211> LENGTH: 107
<212> TYPE: PRT
<213> ORGANISM: Artificial Sequence
<220> FEATURE:
<223> OTHER INFORMATION: Synthetic Construct

<400> SEQUENCE: 237

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile His Val Trp
            20                  25                  30

Leu Ser Trp Tyr Gln Gln Lys Pro Gly Asn Ile Pro Lys Leu Leu Ile
        35                  40                  45

Tyr Lys Ala Ser Thr Leu His Thr Gly Val Pro Ser Arg Phe Asn Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Ser Pro Leu
                85                  90                  95

Thr Phe Gly Ala Gly Thr Lys Leu Glu Val Lys
            100                 105

<210> SEQ ID NO 238
<211> LENGTH: 30
<212> TYPE: PRT
<213> ORGANISM: Artificial Sequence
<220> FEATURE:
<223> OTHER INFORMATION: Synthetic Construct

<400> SEQUENCE: 238

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 239
<211> LENGTH: 14
<212> TYPE: PRT
<213> ORGANISM: Artificial Sequence
<220> FEATURE:
<223> OTHER INFORMATION: Synthetic Construct

<400> SEQUENCE: 239

Trp Val Arg Gln Ala Pro Gly Gln Gly Leu Glu Trp Ile Gly
1               5                   10

<210> SEQ ID NO 240
<211> LENGTH: 32
<212> TYPE: PRT
<213> ORGANISM: Artificial Sequence
<220> FEATURE:
<223> OTHER INFORMATION: Synthetic Construct

<400> SEQUENCE: 240

Arg Val Thr Ile Thr Arg Asp Thr Ser Thr Ser Thr Ala Tyr Leu Glu
```

```
                1               5                  10                 15
Leu Ser Ser Leu Arg Ser Glu Asp Thr Ala Val Tyr Tyr Cys Ala Arg
                20                  25                 30
```

<210> SEQ ID NO 241
<211> LENGTH: 11
<212> TYPE: PRT
<213> ORGANISM: Artificial Sequence
<220> FEATURE:
<223> OTHER INFORMATION: Synthetic Construct

<400> SEQUENCE: 241

```
Trp Gly Gln Gly Thr Leu Val Thr Val Ser Ser
1               5                  10
```

<210> SEQ ID NO 242
<211> LENGTH: 23
<212> TYPE: PRT
<213> ORGANISM: Artificial Sequence
<220> FEATURE:
<223> OTHER INFORMATION: Synthetic Construct

<400> SEQUENCE: 242

```
Asp Ile Gln Met Thr Gln Ser Pro Ser Ser Leu Ser Ala Ser Val Gly
1               5                  10                 15
Asp Arg Val Thr Ile Thr Cys
                20
```

<210> SEQ ID NO 243
<211> LENGTH: 15
<212> TYPE: PRT
<213> ORGANISM: Artificial Sequence
<220> FEATURE:
<223> OTHER INFORMATION: Synthetic Construct

<400> SEQUENCE: 243

```
Trp Tyr Gln Gln Lys Pro Gly Lys Ala Pro Lys Leu Leu Ile Tyr
1               5                  10                 15
```

<210> SEQ ID NO 244
<211> LENGTH: 32
<212> TYPE: PRT
<213> ORGANISM: Artificial Sequence
<220> FEATURE:
<223> OTHER INFORMATION: Synthetic Construct

<400> SEQUENCE: 244

```
Gly Val Pro Ser Arg Phe Ser Gly Ser Gly Ser Gly Thr Asp Phe Thr
1               5                  10                 15
Leu Thr Ile Ser Ser Leu Gln Pro Glu Asp Phe Ala Thr Tyr Tyr Cys
                20                  25                 30
```

<210> SEQ ID NO 245
<211> LENGTH: 10
<212> TYPE: PRT
<213> ORGANISM: Artificial Sequence
<220> FEATURE:
<223> OTHER INFORMATION: Synthetic Construct

<400> SEQUENCE: 245

```
Phe Gly Gln Gly Thr Lys Val Glu Ile Lys
1               5                  10
```

<210> SEQ ID NO 246
<211> LENGTH: 122

```
<212> TYPE: PRT
<213> ORGANISM: Artificial Sequence
<220> FEATURE:
<223> OTHER INFORMATION: Synthetic Construct

<400> SEQUENCE: 246
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Arg Ile Ala Pro Gly Ser Gly Phe Ile Ser Tyr Asn Glu Leu Phe
    50                  55                  60

Lys Asp Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Phe Tyr Tyr Gly Ser Phe Tyr Gly Gly Phe Ala Tyr Trp
            100                 105                 110

Gly Gln Gly Thr Leu Val Thr Val Ser Ser
        115                 120

```
<210> SEQ ID NO 247
<211> LENGTH: 107
<212> TYPE: PRT
<213> ORGANISM: Artificial Sequence
<220> FEATURE:
<223> OTHER INFORMATION: Synthetic Construct

<400> SEQUENCE: 247
```

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile His Val Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Ser Pro Leu
                85                  90                  95

Thr Phe Gly Gln Gly Thr Lys Val Glu Ile Lys
            100                 105

```
<210> SEQ ID NO 248
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Met or Ile

<400> SEQUENCE: 248
```

Gly Ser Ala Xaa His
1               5

```
<210> SEQ ID NO 249
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Arg or Lys
<220> FEATURE:
<221> NAME/KEY: MOD_RES
<222> LOCATION: (6)..(6)
<223> OTHER INFORMATION: Xaa is Asn, Thr, or Gly
<220> FEATURE:
<221> NAME/KEY: MOD_RES
<222> LOCATION: (8)..(8)
<223> OTHER INFORMATION: Xaa is Asn or Ser
<220> FEATURE:
<221> NAME/KEY: MOD_RES
<222> LOCATION: (12)..(12)
<223> OTHER INFORMATION: Xaa is Ala or Glu
<220> FEATURE:
<221> NAME/KEY: MOD_RES
<222> LOCATION: (14)..(14)
<223> OTHER INFORMATION: Xaa is Ala or Asp

<400> SEQUENCE: 249

Arg Ile Arg Ser Xaa Xaa Asn Xaa Tyr Ala Thr Xaa Tyr Xaa Ala Ser
1               5                   10                  15

Val Lys Gly

<210> SEQ ID NO 250
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Leu or Gln
<220> FEATURE:
<221> NAME/KEY: MOD_RES
<222> LOCATION: (2)..(2)
<223> OTHER INFORMATION: Xaa is Gln, Gly, or Phe
<220> FEATURE:
<221> NAME/KEY: MOD_RES
<222> LOCATION: (3)..(3)
<223> OTHER INFORMATION: Xaa is Gln or Gly
<220> FEATURE:
<221> NAME/KEY: MOD_RES
<222> LOCATION: (4)..(4)
<223> OTHER INFORMATION: Xaa is Pro or Asp

<400> SEQUENCE: 250

Xaa Xaa Xaa Xaa Pro Phe Asp Tyr
1               5

<210> SEQ ID NO 251
<211> LENGTH: 11
<212> TYPE: PRT
<213> ORGANISM: Artificial Sequence
<220> FEATURE:
<223> OTHER INFORMATION: Synthetic Construct

<400> SEQUENCE: 251

Arg Ala Ser Gln Gly Ile Arg Asn Asp Leu Asp
1               5                   10

<210> SEQ ID NO 252
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 252

Ala Ala Ser Ser Leu Gln Ser
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Asp or Ser
<220> FEATURE:
<221> NAME/KEY: MOD_RES
<222> LOCATION: (5)..(5)
<223> OTHER INFORMATION: Xaa is Ser or Ile
<220> FEATURE:
<221> NAME/KEY: MOD_RES
<222> LOCATION: (8)..(8)
<223> OTHER INFORMATION: Xaa is Leu or Pro

<400> SEQUENCE: 253

Leu Gln His Xaa Xaa Tyr Pro Xaa Thr
1               5

<210> SEQ ID NO 254
<211> LENGTH: 5
<212> TYPE: PRT
<213> ORGANISM: Artificial Sequence
<220> FEATURE:
<223> OTHER INFORMATION: Synthetic Construct

<400> SEQUENCE: 254

Gly Ser Ala Met His
1               5

<210> SEQ ID NO 255
<211> LENGTH: 19
<212> TYPE: PRT
<213> ORGANISM: Artificial Sequence
<220> FEATURE:
<223> OTHER INFORMATION: Synthetic Construct

<400> SEQUENCE: 255

Arg Ile Arg Ser Arg Asn Asn Asn Tyr Ala Thr Ala Tyr Ala Ala Ser
1               5                   10                  15

Val Lys Gly

<210> SEQ ID NO 256
<211> LENGTH: 8
<212> TYPE: PRT
<213> ORGANISM: Artificial Sequence
<220> FEATURE:
<223> OTHER INFORMATION: Synthetic Construct

<400> SEQUENCE: 256

Leu Gln Gln Pro Pro Phe Asp Tyr
1               5

<210> SEQ ID NO 257
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 257

Leu Gln His Asp Ser Tyr Pro Leu Thr
1               5

<210> SEQ ID NO 258
<211> LENGTH: 5
<212> TYPE: PRT
<213> ORGANISM: Artificial Sequence
<220> FEATURE:
<223> OTHER INFORMATION: Synthetic Construct

<400> SEQUENCE: 258

Gly Ser Ala Ile His
1               5

<210> SEQ ID NO 259
<211> LENGTH: 19
<212> TYPE: PRT
<213> ORGANISM: Artificial Sequence
<220> FEATURE:
<223> OTHER INFORMATION: Synthetic Construct

<400> SEQUENCE: 259

Arg Ile Arg Ser Arg Thr Asn Asn Tyr Ala Thr Glu Tyr Asp Ala Ser
1               5                   10                  15

Val Lys Gly

<210> SEQ ID NO 260
<211> LENGTH: 8
<212> TYPE: PRT
<213> ORGANISM: Artificial Sequence
<220> FEATURE:
<223> OTHER INFORMATION: Synthetic Construct

<400> SEQUENCE: 260

Leu Gly Gln Pro Pro Phe Asp Tyr
1               5

<210> SEQ ID NO 261
<211> LENGTH: 9
<212> TYPE: PRT
<213> ORGANISM: Artificial Sequence
<220> FEATURE:
<223> OTHER INFORMATION: Synthetic Construct

<400> SEQUENCE: 261

Leu Gln His Ser Ile Tyr Pro Pro Thr
1               5

<210> SEQ ID NO 262
<211> LENGTH: 19
<212> TYPE: PRT
<213> ORGANISM: Artificial Sequence
<220> FEATURE:
<223> OTHER INFORMATION: Synthetic Construct

<400> SEQUENCE: 262

Arg Ile Arg Ser Lys Gly Asn Ser Tyr Ala Thr Ala Tyr Ala Ala Ser
1               5                   10                  15

Val Lys Gly
```

```
<210> SEQ ID NO 263
<211> LENGTH: 8
<212> TYPE: PRT
<213> ORGANISM: Artificial Sequence
<220> FEATURE:
<223> OTHER INFORMATION: Synthetic Construct

<400> SEQUENCE: 263

Gln Phe Gly Asp Pro Phe Asp Tyr
1               5

<210> SEQ ID NO 264
<211> LENGTH: 30
<212> TYPE: PRT
<213> ORGANISM: Artificial Sequence
<220> FEATURE:
<223> OTHER INFORMATION: Synthetic Construct

<400> SEQUENCE: 264

Gln Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 265
<211> LENGTH: 30
<212> TYPE: PRT
<213> ORGANISM: Artificial Sequence
<220> FEATURE:
<223> OTHER INFORMATION: Synthetic Construct

<400> SEQUENCE: 265

Glu Val Gln Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 266
<211> LENGTH: 30
<212> TYPE: PRT
<213> ORGANISM: Artificial Sequence
<220> FEATURE:
<223> OTHER INFORMATION: Synthetic Construct

<400> SEQUENCE: 266

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 267
<211> LENGTH: 14
<212> TYPE: PRT
<213> ORGANISM: Artificial Sequence
<220> FEATURE:
<223> OTHER INFORMATION: Synthetic Construct

<400> SEQUENCE: 267

Trp Val Arg Gln Ala Ser Gly Lys Gly Leu Glu Trp Val Gly
1               5                   10

<210> SEQ ID NO 268
<211> LENGTH: 14
<212> TYPE: PRT
```

-continued

```
<213> ORGANISM: Artificial Sequence
<220> FEATURE:
<223> OTHER INFORMATION: Synthetic Construct

<400> SEQUENCE: 268

Trp Val Arg Gln Ala Pro Gly Lys Gly Leu Glu Trp Val Gly
1               5                   10

<210> SEQ ID NO 269
<211> LENGTH: 32
<212> TYPE: PRT
<213> ORGANISM: Artificial Sequence
<220> FEATURE:
<223> OTHER INFORMATION: Synthetic Construct

<400> SEQUENCE: 269

Arg Phe Thr Ile Ser Arg Asp Asp Ser Lys Arg Thr Thr Tyr Leu Gln
1               5                   10                  15

Met Asn Ser Leu Lys Thr Glu Asp Thr Ala Val Tyr Tyr Cys Thr Arg
                20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Synthetic Construct

<400> SEQUENCE: 270

Arg Phe Thr Ile Ser Arg Asp Asp Ser Lys Arg Thr Ala Tyr Leu Gln
1               5                   10                  15

Met Asn Ser Leu Lys Thr Glu Asp Thr Ala Val Tyr Tyr Cys Thr Arg
                20                  25                  30

<210> SEQ ID NO 271
<211> LENGTH: 32
<212> TYPE: PRT
<213> ORGANISM: Artificial Sequence
<220> FEATURE:
<223> OTHER INFORMATION: Synthetic Construct

<400> SEQUENCE: 271

Arg Phe Ser Ile Ser Arg Asp Asp Ser Lys Arg Thr Ala Tyr Leu Gln
1               5                   10                  15

Met Ser Ser Leu Lys Thr Glu Asp Ser Ala Val Tyr Tyr Cys Ala Arg
                20                  25                  30

<210> SEQ ID NO 272
<211> LENGTH: 11
<212> TYPE: PRT
<213> ORGANISM: Artificial Sequence
<220> FEATURE:
<223> OTHER INFORMATION: Synthetic Construct

<400> SEQUENCE: 272

Trp Gly Gln Gly Thr Leu Val Thr Val Ser Ser
1               5                   10

<210> SEQ ID NO 273
<211> LENGTH: 23
<212> TYPE: PRT
<213> ORGANISM: Artificial Sequence
<220> FEATURE:
<223> OTHER INFORMATION: Synthetic Construct

<400> SEQUENCE: 273
```

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 274
<211> LENGTH: 23
<212> TYPE: PRT
<213> ORGANISM: Artificial Sequence
<220> FEATURE:
<223> OTHER INFORMATION: Synthetic Construct

<400> SEQUENCE: 274

Ala Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 275
<211> LENGTH: 23
<212> TYPE: PRT
<213> ORGANISM: Artificial Sequence
<220> FEATURE:
<223> OTHER INFORMATION: Synthetic Construct

<400> SEQUENCE: 275

Ala Ile Arg Ile Thr Gln Ser Pro Ser Ser Leu Ser Ala Ser Val Gly
1               5                   10                  15

Asp Arg Val Thr Ile Thr Cys
            20

<210> SEQ ID NO 276
<211> LENGTH: 15
<212> TYPE: PRT
<213> ORGANISM: Artificial Sequence
<220> FEATURE:
<223> OTHER INFORMATION: Synthetic Construct

<400> SEQUENCE: 276

Trp Tyr Gln Gln Lys Pro Gly Lys Ala Pro Lys Arg Leu Ile Tyr
1               5                   10                  15

<210> SEQ ID NO 277
<211> LENGTH: 32
<212> TYPE: PRT
<213> ORGANISM: Artificial Sequence
<220> FEATURE:
<223> OTHER INFORMATION: Synthetic Construct

<400> SEQUENCE: 277

Gly Val Pro Ser Arg Phe Asn Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 278
<211> LENGTH: 32
<212> TYPE: PRT
<213> ORGANISM: Artificial Sequence
<220> FEATURE:
<223> OTHER INFORMATION: Synthetic Construct

<400> SEQUENCE: 278

Gly Val Pro Ser Arg Phe Ser Gly Ser Gly Ser Gly Thr Asp Phe Thr

```
                1               5                  10                  15
Leu Thr Ile Ser Ser Leu Gln Pro Glu Asp Phe Ala Thr Tyr Tyr Cys
                    20                  25                  30
```

<210> SEQ ID NO 279
<211> LENGTH: 32
<212> TYPE: PRT
<213> ORGANISM: Artificial Sequence
<220> FEATURE:
<223> OTHER INFORMATION: Synthetic Construct

<400> SEQUENCE: 279

```
Gly Val Pro Ser Arg Phe Ser Gly Ser Gly Ser Gly Thr Glu Phe Thr
1               5                  10                  15
Leu Thr Ile Ser Ser Leu Gln Pro Glu Asp Phe Ala Thr Tyr Tyr Cys
                    20                  25                  30
```

<210> SEQ ID NO 280
<211> LENGTH: 10
<212> TYPE: PRT
<213> ORGANISM: Artificial Sequence
<220> FEATURE:
<223> OTHER INFORMATION: Synthetic Construct

<400> SEQUENCE: 280

```
Phe Gly Gly Gly Thr Lys Val Glu Ile Lys
1               5                  10
```

<210> SEQ ID NO 281
<211> LENGTH: 10
<212> TYPE: PRT
<213> ORGANISM: Artificial Sequence
<220> FEATURE:
<223> OTHER INFORMATION: Synthetic Construct

<400> SEQUENCE: 281

```
Phe Gly Gln Gly Thr Lys Val Glu Ile Lys
1               5                  10
```

<210> SEQ ID NO 282
<211> LENGTH: 119
<212> TYPE: PRT
<213> ORGANISM: Artificial Sequence
<220> FEATURE:
<223> OTHER INFORMATION: Synthetic Construct

<400> SEQUENCE: 282

```
Gln Val Gln Leu Val Gln Ser Gly Gly Gly Leu Val Gln Pro Gly Gly
1               5                  10                  15
Ser Leu Lys Leu Ser Cys Ala Ala Ser Gly Phe Thr Phe Ser Gly Ser
                    20                  25                  30
Ala Met His Trp Val Arg Gln Ala Ser Gly Lys Gly Leu Glu Trp Val
            35                  40                  45
Gly Arg Ile Arg Ser Arg Asn Asn Asn Tyr Ala Thr Ala Tyr Ala Ala
        50                  55                  60
Ser Val Lys Gly Arg Phe Thr Ile Ser Arg Asp Asp Ser Lys Arg Thr
65                  70                  75                  80
Thr Tyr Leu Gln Met Asn Ser Leu Lys Thr Glu Asp Thr Ala Val Tyr
                85                  90                  95
Tyr Cys Thr Arg Leu Gln Gln Pro Pro Phe Asp Tyr Trp Gly Gln Gly
                    100                 105                 110
Thr Leu Val Thr Val Ser Ser
```

<210> SEQ ID NO 283
<211> LENGTH: 107
<212> TYPE: PRT
<213> ORGANISM: Artificial Sequence
<220> FEATURE:
<223> OTHER INFORMATION: Synthetic Construct

<400> SEQUENCE: 283

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Asp Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Asn Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ser Tyr Pro Leu
                85                  90                  95

Thr Phe Gly Gly Gly Thr Lys Val Glu Ile Lys
            100                 105
```

<210> SEQ ID NO 284
<211> LENGTH: 119
<212> TYPE: PRT
<213> ORGANISM: Artificial Sequence
<220> FEATURE:
<223> OTHER INFORMATION: Synthetic Construct

<400> SEQUENCE: 284

```
Glu Val Gln Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Ile His Trp Val Arg Gln Ala Ser Gly Lys Gly Leu Glu Trp Val
        35                  40                  45

Gly Arg Ile Arg Ser Arg Thr Asn Asn Tyr Ala Thr Glu Tyr Asp Ala
    50                  55                  60

Ser Val Lys Gly Arg Phe Thr Ile Ser Arg Asp Asp Ser Lys Arg Thr
65                  70                  75                  80

Ala Tyr Leu Gln Met Asn Ser Leu Lys Thr Glu Asp Thr Ala Val Tyr
                85                  90                  95

Tyr Cys Thr Arg Leu Gly Gln Pro Pro Phe Asp Tyr Trp Gly Gln Gly
            100                 105                 110

Thr Leu Val Thr Val Ser Ser
        115
```

<210> SEQ ID NO 285
<211> LENGTH: 107
<212> TYPE: PRT
<213> ORGANISM: Artificial Sequence
<220> FEATURE:
<223> OTHER INFORMATION: Synthetic Construct

<400> SEQUENCE: 285

```
Ala Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Arg Asn Asp
            20                  25                  30

Leu Asp Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Ser Ile Tyr Pro Pro
                 85                  90                  95

Thr Phe Gly Gln Gly Thr Lys Val Glu Ile Lys
            100                 105

<210> SEQ ID NO 286
<211> LENGTH: 119
<212> TYPE: PRT
<213> ORGANISM: Artificial Sequence
<220> FEATURE:
<223> OTHER INFORMATION: Synthetic Construct

<400> SEQUENCE: 286

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Ser
            20                  25                  30

Ala Met His Trp Val Arg Gln Ala Pro Gly Lys Gly Leu Glu Trp Val
        35                  40                  45

Gly Arg Ile Arg Ser Lys Gly Asn Ser Tyr Ala Thr Ala Tyr Ala Ala
 50                  55                  60

Ser Val Lys Gly Arg Phe Ser Ile Ser Arg Asp Asp Ser Lys Arg Thr
 65                  70                  75                  80

Ala Tyr Leu Gln Met Ser Ser Leu Lys Thr Glu Asp Ser Ala Val Tyr
                 85                  90                  95

Tyr Cys Ala Arg Gln Phe Gly Asp Pro Phe Asp Tyr Trp Gly Gln Gly
            100                 105                 110

Thr Leu Val Thr Val Ser Ser
        115

<210> SEQ ID NO 287
<211> LENGTH: 107
<212> TYPE: PRT
<213> ORGANISM: Artificial Sequence
<220> FEATURE:
<223> OTHER INFORMATION: Synthetic Construct

<400> SEQUENCE: 287

Ala Ile Arg Ile Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Asp Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asp Ser Tyr Pro Leu
```

```
                    85                  90                  95
Thr Phe Gly Gly Gly Thr Lys Val Glu Ile Lys
                100                 105

<210> SEQ ID NO 288
<211> LENGTH: 445
<212> TYPE: PRT
<213> ORGANISM: Artificial Sequence
<220> FEATURE:
<223> OTHER INFORMATION: Synthetic Construct

<400> SEQUENCE: 288

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
            35                  40                  45

Ala Thr Ile Ser Gly Gly Lys Thr Phe Thr Asp Tyr Val Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Gly Asn Trp Phe Phe Glu Val Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
```

```
                340                 345                 350
Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 289
<211> LENGTH: 218
<212> TYPE: PRT
<213> ORGANISM: Artificial Sequence
<220> FEATURE:
<223> OTHER INFORMATION: Synthetic Construct

<400> SEQUENCE: 289

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 290
<211> LENGTH: 448
<212> TYPE: PRT
<213> ORGANISM: Artificial Sequence
<220> FEATURE:
<223> OTHER INFORMATION: Synthetic Construct
```

<400> SEQUENCE: 290

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Phe
            20                  25                  30
Ser Met Ser Trp Val Arg Gln Ala Pro Gly Lys Gly Leu Glu Trp Val
        35                  40                  45
Ala Thr Ile Ser Gly Gly Lys Thr Phe Thr Asp Tyr Val Asp Ser Val
    50                  55                  60
Lys Gly Arg Phe Thr Ile Ser Arg Asp Asp Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Arg Ala Asn Tyr Gly Asn Trp Phe Phe Glu Val Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
```

-continued

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 291
<211> LENGTH: 218
<212> TYPE: PRT
<213> ORGANISM: Artificial Sequence
<220> FEATURE:
<223> OTHER INFORMATION: Synthetic Construct

<400> SEQUENCE: 291

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 292
<211> LENGTH: 454
<212> TYPE: PRT
<213> ORGANISM: Artificial Sequence
<220> FEATURE:
<223> OTHER INFORMATION: Synthetic Construct

<400> SEQUENCE: 292

Glu Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45
```

```
Trp Ile Gly Ser Ile Tyr Tyr Ser Gly Arg Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
                 85                  90                  95

Cys Ala Arg Ala Gly Gly Leu Tyr Asn Trp Asn Asp Glu Ser Phe Ser
            100                 105                 110

Phe Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly
450
```

```
<210> SEQ ID NO 293
<211> LENGTH: 215
<212> TYPE: PRT
<213> ORGANISM: Artificial Sequence
<220> FEATURE:
<223> OTHER INFORMATION: Synthetic Construct

<400> SEQUENCE: 293

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 294
<211> LENGTH: 457
<212> TYPE: PRT
<213> ORGANISM: Artificial Sequence
<220> FEATURE:
<223> OTHER INFORMATION: Synthetic Construct

<400> SEQUENCE: 294

Glu Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
                85                  90                  95
```

```
Cys Ala Arg Ala Gly Gly Leu Tyr Asn Trp Asn Asp Glu Ser Phe Ser
                100                 105                 110
Phe Tyr Met Asp Val Trp Gly Gln Gly Thr Thr Val Thr Val Ser Ser
            115                 120                 125
Ala Ser Thr Lys Gly Pro Ser Val Phe Pro Leu Ala Pro Ser Ser Lys
        130                 135                 140
Ser Thr Ser Gly Gly Thr Ala Ala Leu Gly Cys Leu Val Lys Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Ser Leu Gly Thr Gln Thr
        195                 200                 205
Tyr Ile Cys Asn Val Asn His Lys Pro Ser Asn Thr Lys Val Asp Lys
210                 215                 220
Lys Val Glu Pro Lys Ser Cys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Glu Glu
        355                 360                 365
Met Thr Lys Asn Gln Val Ser Leu Thr Cys Leu Val Lys Gly Phe Tyr
370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly
450                 455

<210> SEQ ID NO 295
<211> LENGTH: 215
<212> TYPE: PRT
<213> ORGANISM: Artificial Sequence
<220> FEATURE:
<223> OTHER INFORMATION: Synthetic Construct

<400> SEQUENCE: 295
```

-continued

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 296
<211> LENGTH: 5
<212> TYPE: PRT
<213> ORGANISM: Artificial Sequence
<220> FEATURE:
<223> OTHER INFORMATION: Synthetic Construct

<400> SEQUENCE: 296

Ala Tyr Ser Val Asn
1               5

<210> SEQ ID NO 297
<211> LENGTH: 16
<212> TYPE: PRT
<213> ORGANISM: Artificial Sequence
<220> FEATURE:
<223> OTHER INFORMATION: Synthetic Construct

<400> SEQUENCE: 297

Met Ile Trp Gly Asp Gly Lys Ile Val Tyr Asn Ser Ala Leu Lys Ser
1               5                   10                  15

<210> SEQ ID NO 298
<211> LENGTH: 10
<212> TYPE: PRT
<213> ORGANISM: Artificial Sequence
<220> FEATURE:
<223> OTHER INFORMATION: Synthetic Construct

<400> SEQUENCE: 298

Asp Gly Tyr Tyr Pro Tyr Ala Met Asp Asn
```

<210> SEQ ID NO 299
<211> LENGTH: 15
<212> TYPE: PRT
<213> ORGANISM: Artificial Sequence
<220> FEATURE:
<223> OTHER INFORMATION: Synthetic Construct

<400> SEQUENCE: 299

Arg Ala Ser Lys Ser Val Asp Ser Tyr Gly Asn Ser Phe Met His
1               5                   10                  15

<210> SEQ ID NO 300
<211> LENGTH: 7
<212> TYPE: PRT
<213> ORGANISM: Artificial Sequence
<220> FEATURE:
<223> OTHER INFORMATION: Synthetic Construct

<400> SEQUENCE: 300

Leu Ala Ser Asn Leu Glu Ser
1               5

<210> SEQ ID NO 301
<211> LENGTH: 9
<212> TYPE: PRT
<213> ORGANISM: Artificial Sequence
<220> FEATURE:
<223> OTHER INFORMATION: Synthetic Construct

<400> SEQUENCE: 301

Gln Gln Asn Asn Glu Asp Pro Arg Thr
1               5

<210> SEQ ID NO 302
<211> LENGTH: 118
<212> TYPE: PRT
<213> ORGANISM: Artificial Sequence
<220> FEATURE:
<223> OTHER INFORMATION: Synthetic Construct

<400> SEQUENCE: 302

Glu Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
                20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
        50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
                100                 105                 110

Leu Val Thr Val Ser Ser
        115

<210> SEQ ID NO 303
<211> LENGTH: 111
<212> TYPE: PRT

```
<213> ORGANISM: Artificial Sequence
<220> FEATURE:
<223> OTHER INFORMATION: Synthetic Construct

<400> SEQUENCE: 303

Asp Ile Val Leu Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys
            100                 105                 110

<210> SEQ ID NO 304
<211> LENGTH: 444
<212> TYPE: PRT
<213> ORGANISM: Artificial Sequence
<220> FEATURE:
<223> OTHER INFORMATION: Synthetic Construct

<400> SEQUENCE: 304

Glu Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220
```

```
Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Trp Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 305
<211> LENGTH: 218
<212> TYPE: PRT
<213> ORGANISM: Artificial Sequence
<220> FEATURE:
<223> OTHER INFORMATION: Synthetic Construct

<400> SEQUENCE: 305

Asp Ile Val Leu Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 306
<211> LENGTH: 445
<212> TYPE: PRT
<213> ORGANISM: Artificial Sequence
<220> FEATURE:
<223> OTHER INFORMATION: Synthetic Construct

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
            35                  40                  45

Ala Thr Ile Ser Gly Gly Lys Thr Phe Thr Asp Tyr Val Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Arg Ala Asn Tyr Gly Asn Trp Phe Phe Glu Val Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 307
<211> LENGTH: 218
<212> TYPE: PRT
<213> ORGANISM: Artificial Sequence
<220> FEATURE:
<223> OTHER INFORMATION: Synthetic Construct

<400> SEQUENCE: 307

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

```
Val Thr Lys Ser Phe Asn Arg Gly Glu Cys
    210                 215
```

<210> SEQ ID NO 308
<211> LENGTH: 454
<212> TYPE: PRT
<213> ORGANISM: Artificial Sequence
<220> FEATURE:
<223> OTHER INFORMATION: Synthetic Construct

<400> SEQUENCE: 308

```
Glu Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ile Phe Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Met Leu Thr Ser Val Thr Ala Ala Asp Thr Ala Val Tyr Tyr
                85                  90                  95

Cys Ala Arg Ala Gly Gly Leu Tyr Asn Trp Asn Asp Glu Ser Phe Ser
            100                 105                 110

Phe Tyr Met Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350
```

```
Glu Pro Gln Val Tyr Thr Leu Pro Pro Ser Gln Glu Met Thr Lys
            355                 360                 365

Asn Gln Val Ser Leu Ser Cys Ala Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Arg Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Leu Gly
    450

<210> SEQ ID NO 309
<211> LENGTH: 215
<212> TYPE: PRT
<213> ORGANISM: Artificial Sequence
<220> FEATURE:
<223> OTHER INFORMATION: Synthetic Construct

<400> SEQUENCE: 309

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 310
<211> LENGTH: 362
<212> TYPE: PRT
<213> ORGANISM: Artificial Sequence
<220> FEATURE:
```

<223> OTHER INFORMATION: Synthetic Construct

<400> SEQUENCE: 310

```
Ala Lys Phe Ser Lys Gln Ser Trp Gly Leu Glu Asn Glu Ala Leu Ile
1               5                   10                  15

Val Arg Cys Pro Arg Gln Gly Lys Pro Ser Tyr Thr Val Asp Trp Tyr
            20                  25                  30

Tyr Ser Gln Thr Asn Lys Ser Ile Pro Thr Gln Glu Arg Asn Arg Val
        35                  40                  45

Phe Ala Ser Gly Gln Leu Leu Lys Phe Leu Pro Ala Ala Val Ala Asp
    50                  55                  60

Ser Gly Ile Tyr Thr Cys Ile Val Arg Ser Pro Thr Phe Asn Arg Thr
65                  70                  75                  80

Gly Tyr Ala Asn Val Thr Ile Tyr Lys Lys Gln Ser Asp Cys Asn Val
                85                  90                  95

Pro Asp Tyr Leu Met Tyr Ser Thr Val Ser Gly Ser Glu Lys Asn Ser
            100                 105                 110

Lys Ile Tyr Cys Pro Thr Ile Asp Leu Tyr Asn Trp Thr Ala Pro Leu
        115                 120                 125

Glu Trp Phe Lys Asn Cys Gln Ala Leu Gln Gly Ser Arg Tyr Arg Ala
    130                 135                 140

His Lys Ser Phe Leu Val Ile Asp Asn Val Met Thr Glu Asp Ala Gly
145                 150                 155                 160

Asp Tyr Thr Cys Lys Phe Ile His Asn Glu Asn Gly Ala Asn Tyr Ser
                165                 170                 175

Val Thr Ala Thr Arg Ser Phe Thr Val Lys Asp Glu Gln Gly Phe Ser
            180                 185                 190

Leu Phe Pro Val Ile Gly Ala Pro Ala Gln Asn Glu Ile Lys Glu Val
        195                 200                 205

Glu Ile Gly Lys Asn Ala Asn Leu Thr Cys Ser Ala Cys Phe Gly Lys
    210                 215                 220

Gly Thr Gln Phe Leu Ala Ala Val Leu Trp Gln Leu Asn Gly Thr Lys
225                 230                 235                 240

Ile Thr Asp Phe Gly Glu Pro Arg Ile Gln Gln Glu Glu Gly Gln Asn
                245                 250                 255

Gln Ser Phe Ser Asn Gly Leu Ala Cys Leu Asp Met Val Leu Arg Ile
            260                 265                 270

Ala Asp Val Lys Glu Glu Asp Leu Leu Leu Gln Tyr Asp Cys Leu Ala
        275                 280                 285

Leu Asn Leu His Gly Leu Arg Arg His Thr Val Arg Leu Ser Arg Lys
    290                 295                 300

Asn Pro Ile Asp His His Ser Gly Gly Arg Ala Arg Met Lys Gln Leu
305                 310                 315                 320

Glu Asp Lys Val Glu Glu Leu Leu Ser Lys Asn Tyr His Leu Glu Asn
                325                 330                 335

Glu Val Ala Arg Leu Lys Lys Leu Val Gly Glu Arg Asp Tyr Lys Asp
            340                 345                 350

Asp Asp Asp Lys His His His His His His
        355                 360
```

<210> SEQ ID NO 311
<211> LENGTH: 4852
<212> TYPE: DNA
<213> ORGANISM: Artificial Sequence
<220> FEATURE:

<223> OTHER INFORMATION: Synthetic Construct

<400> SEQUENCE: 311

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggtca ccatgggggtt ttggatctta gcaattctca caattctcat    600
gtattccaca gcagcaaagt ttagtaaaca atcatggggc ctggaaaatg aggctttaat    660
tgtaagatgt cctagacaag gaaaacctag ttacaccgtg gattggtatt actcacaaac    720
aaacaaaagt attcccactc aggaaagaaa tcgtgtgttt gcctcaggcc aacttctgaa    780
gtttctacca gctgcagttg ctgattctgg tatttatacc tgtattgtca gaagtcccac    840
attcaatagg actggatatg cgaatgtcac catatataaa aaacaatcag attgcaatgt    900
tccagattat ttgatgtatt caacagtatc tggatcagaa aaaaattcca aaatttattg    960
tcctaccatt gacctctaca actggacagc acctcttgag tggtttaaga attgtcaggc   1020
tcttcaagga tcaaggtaca gggcgcacaa gtcattttg gtcattgata atgtgatgac    1080
tgaggacgca ggtgattaca cctgtaaatt tatacacaat gaaaatggag ccaattatag   1140
tgtgacggcg accaggtcct tcacggtcaa ggatgagcaa ggcttttctc tgtttccagt   1200
aatcggagcc cctgcacaaa atgaaataaa ggaagtggaa attggaaaaa acgcaaacct   1260
aacttgctct gcttgttttg gaaaaggcac tcagttcttg gctgccgtcc tgtggcagct   1320
taatggaaca aaaattacag actttggtga accaagaatt caacaagagg aagggcaaaa   1380
tcaaagtttc agcaatgggc tggcttgtct agacatggtt ttaagaatag ctgacgtgaa   1440
ggaagaggat ttattgctgc agtacgactg tctggccctg aatttgcatg gcttgagaag   1500
gcacaccgta agactaagta ggaaaaatcc aattgatcat catagcatct actgcataat   1560
tgcagtatgt agtgtatttt taatgctaat caatgtcctg gttatcatcc taaaaatgtt   1620
ctggattgag gccactctgc tctggagaga catagctaaa ccttacaaga ctaggaatga   1680
tggaaagctc tatgatgctt atgttgtcta cccacggaac tacaaatcca gtacagatgg   1740
ggccagtcgt gtagagcact tgttcacca gattctgcct gatgttcttg aaaataaatg   1800
tggctatacc ttatgcattt atgggagaga tatgctacct ggagaagatg tagtcactgc   1860
agtggaaacc aacatacgaa agagcaggcg gcacattttc atcctgaccc ctcagatcac   1920
tcacaataag gagtttgcct acgagcagga ggttgccctg cactgtgccc tcatccagaa   1980
cgacgccaag gtgatactta ttgagatgga ggctctgagc gagctggaca tgctgcaggc   2040
tgaggcgctt caggactccc tccagcatct tatgaaagta caggggacca tcaagtggag   2100
ggaggaccac attgccaata aaggtcccct gaattctaaa ttctggaagc acgtgaggta   2160
ccaaatgcct gtgccaagca aaattcccag aaaggcctct agtttgactc ccttggctgc   2220
ccagaagcaa tagagctagc tggccagaca tgataagata cattgatgag tttggacaaa   2280
```

```
ccacaactag aatgcagtga aaaaaatgct ttatttgtga aatttgtgat gctattgctt   2340
tatttgtaac cattataagc tgcaataaac aagttaacaa caacaattgc attcatttta   2400
tgtttcaggt tcaggggggag gtgtgggagg tttttttaaag caagtaaaac ctctacaaat   2460
gtggtatgga attctaaaat acagcatagc aaaactttaa cctccaaatc aagcctctac   2520
ttgaatcctt ttctgaggga tgaataaggc ataggcatca ggggctgttg ccaatgtgca   2580
ttagctgttt gcagcctcac cttctttcat ggagtttaag atatagtgta ttttcccaag   2640
gtttgaacta gctcttcatt tctttatgtt ttaaatgcac tgacctccca cattcccttt   2700
ttagtaaaat attcagaaat aatttaaata catcattgca atgaaaataa atgtttttta   2760
ttaggcagaa tccagatgct caaggccctt cataatatcc cccagtttag tagttggact   2820
tagggaacaa aggaaccttt aatagaaatt ggacagcaag aaagcgagct tctagcttta   2880
gttcctggtg tacttgaggg ggatgagttc ctcaatggtg gttttgacca gcttgccatt   2940
catctcaatg agcacaaagc agtcaggagc atagtcagag atgagctctc tgcacatgcc   3000 acagggctg accaccctga tggatctgtc cacctcatca gagtagggggt gcctgacagc   3060 cacaatggtg tcaaagtcct tctgcccgtt gctcacagca gacccaatgg caatggcttc   3120
agcacagaca gtgaccctgc caatgtaggc ctcaatgtgg acagcagaga tgatctcccc   3180
agtcttggtc ctgatggccg ccccgacatg gtgcttgttg tcctcataga gcatggtgat   3240
cttctcagtg gcgacctcca ccagctccag atcctgctga gagatgttga aggtcttcat   3300
gatggccctc ctatagtgag tcgtattata ctatgccgat atactatgcc gatgattaat   3360
tgtcaaaaca gcgtggatgg cgtctccagc ttatctgacg gttcactaaa cgagctctgc   3420
ttatatagac ctcccaccgt acacgcctac cgcccatttg cgtcaatggg cggagttgt    3480 tacgacattt tggaaagtcc cgttgattta ctagtcaaaa caaactccca ttgacgtcaa   3540
tggggtggag acttggaaat ccccgtgagt caaaccgcta ccacgcccca ttgatgtact   3600
gccaaaaccg catcatcatg gtaatagcga tgactaatac gtagatgtac tgccaagtag   3660
gaaagtccca taaggtcatg tactgggcat aatgccaggc gggccattta ccgtcattga   3720
cgtcaatagg gggcgtactt ggcatatgat acacttgatg tactgccaag tgggcagttt   3780
accgtaaata ctccacccat tgacgtcaat ggaaagtccc tattggcgtt actatgggaa   3840
catacgtcat tattgacgtc aatgggcggg ggtcgttggg cggtcagcca ggcgggccat   3900
ttaccgtaag ttatgtaacg cctgcaggtt aattaagaac atgtgagcaa aaggccagca   3960
aaaggccagg aaccgtaaaa aggccgcgtt gctggcgttt ttccataggc tccgccccc    4020 tgacgagcat cacaaaaatc gacgctcaag tcagaggtgg cgaaacccga caggactata   4080
aagataccag gcgtttcccc ctggaagctc cctcgtgcgc tctcctgttc cgaccctgcc   4140
gcttaccgga tacctgtccg cctttctccc ttcgggaagc gtggcgcttt ctcatagctc   4200
acgctgtagg tatctcagtt cggtgtaggt cgttcgctcc aagctgggct gtgtgcacga   4260
accccccgtt cagcccgacc gctgcgcctt atccggtaac tatcgtcttg agtccaaccc   4320
ggtaagacac gacttatcgc cactggcagc agccactggt aacaggatta gcagagcgag   4380
gtatgtaggc ggtgctacag agttcttgaa gtggtggcct aactacggct acactagaag   4440
aacagtattt ggtatctgcg ctctgctgaa gccagttacc ttcggaaaaa gagttggtag   4500
ctcttgatcc ggcaaacaaa ccaccgctgg tagcggtggt ttttttgttt gcaagcagca   4560
gattacgcgc agaaaaaaag gatctcaaga agatcctttg atcttttcta cggggtctga   4620
```

```
cgctcagtgg aacgaaaact cacgttaagg gattttggtc atggctagtt aattaacatt    4680
taaatcagcg gccgcaataa atatctttta ttttcattac atctgtgtgt tggttttttg    4740
tgtgaatcgt aactaacata cgctctccat caaaacaaaa cgaaacaaaa caaactagca    4800
aaataggctg tccccagtgc aagtgcaggt gccagaacat ttctctatcg aa            4852
```

<210> SEQ ID NO 312
<211> LENGTH: 556
<212> TYPE: PRT
<213> ORGANISM: Homo sapiens

<400> SEQUENCE: 312

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Pro Ser Tyr Thr Val Asp Trp
            35                  40                  45

Tyr Tyr Ser Gln Thr Asn Lys Ser Ile Pro Thr Gln Glu Arg Asn Arg
        50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335
```

```
Ser Val Phe Leu Met Leu Ile Asn Val Leu Val Ile Ile Leu Lys Met
                340                 345                 350

Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Val Tyr Pro
        370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
        435                 440                 445

Thr Pro Gln Ile Thr His Asn Lys Glu Phe Ala Tyr Glu Gln Glu Val
    450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
        515                 520                 525

Lys His Val Arg Tyr Gln Met Pro Val Pro Ser Lys Ile Pro Arg Lys
    530                 535                 540

Ala Ser Ser Leu Thr Pro Leu Ala Ala Gln Lys Gln
545                 550                 555

<210> SEQ ID NO 313
<211> LENGTH: 159
<212> TYPE: PRT
<213> ORGANISM: Homo sapiens

<400> SEQUENCE: 313

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Asp Lys Val
        35                  40                  45

Leu Leu Ser Tyr Tyr Glu Ser Gln His Pro Ser Asn Glu Ser Gly Asp
50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
            85                  90                  95

Cys Glu Lys Pro Leu Pro Asp Gln Ala Phe Phe Val Leu His Asn Met
        100                 105                 110

His Ser Asn Cys Val Ser Phe Glu Cys Lys Thr Asp Pro Gly Val Phe
    115                 120                 125

Ile Gly Val Lys Asp Asn His Leu Ala Leu Ile Lys Val Asp Ser Ser
130                 135                 140

Glu Asn Leu Cys Thr Glu Asn Ile Leu Phe Lys Leu Ser Glu Thr
            150                 155
```

<210> SEQ ID NO 314
<211> LENGTH: 180
<212> TYPE: PRT
<213> ORGANISM: Artificial Sequence
<220> FEATURE:
<223> OTHER INFORMATION: Synthetic Construct

<400> SEQUENCE: 314

Met Gly Ser Ser His His His His His Ser Ser Gly Leu Val Pro
1               5                   10                  15

Arg Gly Ser His Met Ser Ile Thr Gly Ile Ser Pro Ile Thr Glu Tyr
            20                  25                  30

Leu Ala Ser Leu Ser Thr Tyr Asn Asp Gln Ser Ile Thr Phe Ala Leu
        35                  40                  45

Glu Asp Glu Ser Tyr Glu Ile Tyr Val Glu Asp Leu Lys Lys Asp Glu
50                  55                  60

Lys Lys Asp Lys Val Leu Leu Ser Tyr Tyr Glu Ser Gln His Pro Ser
65                  70                  75                  80

Asn Glu Ser Gly Asp Gly Val Asp Gly Lys Met Leu Met Val Thr Leu
                85                  90                  95

Ser Pro Thr Lys Asp Phe Trp Leu His Ala Asn Asn Lys Glu His Ser
            100                 105                 110

Val Glu Leu His Lys Cys Glu Lys Pro Leu Pro Asp Gln Ala Phe Phe
        115                 120                 125

Val Leu His Asn Met His Ser Asn Cys Val Ser Phe Glu Cys Lys Thr
130                 135                 140

Asp Pro Gly Val Phe Ile Gly Val Lys Asp Asn His Leu Ala Leu Ile
145                 150                 155                 160

Lys Val Asp Ser Ser Glu Asn Leu Cys Thr Glu Asn Ile Leu Phe Lys
                165                 170                 175

Leu Ser Glu Thr
            180

<210> SEQ ID NO 315
<211> LENGTH: 194
<212> TYPE: PRT
<213> ORGANISM: Artificial Sequence
<220> FEATURE:
<223> OTHER INFORMATION: Synthetic Construct

<400> SEQUENCE: 315

Met His His His His His His Gly Glu Asn Leu Tyr Phe Gln Gly Ser
1               5                   10                  15

Ile Thr Gly Ile Ser Pro Ile Thr Glu Tyr Leu Ala Ser Leu Ser Thr
            20                  25                  30

Tyr Asn Asp Gln Ser Ile Thr Phe Ala Leu Glu Asp Glu Ser Tyr Glu
        35                  40                  45

Ile Tyr Val Glu Asp Leu Lys Lys Asp Glu Lys Lys Asp Lys Val Leu
    50                  55                  60

Leu Ser Tyr Tyr Glu Ser Gln His Pro Ser Asn Glu Ser Gly Asp Gly
65                  70                  75                  80

Val Asp Gly Lys Met Leu Met Val Thr Leu Ser Pro Thr Lys Asp Phe
                85                  90                  95

Trp Leu His Ala Asn Asn Lys Glu His Ser Val Glu Leu His Lys Cys
            100                 105                 110

Glu Lys Pro Leu Pro Asp Gln Ala Phe Phe Val Leu His Asn Met His

```
                115               120               125
Ser Asn Cys Val Ser Phe Glu Cys Lys Thr Asp Pro Gly Val Phe Ile
    130               135               140
Gly Val Lys Asp Asn His Leu Ala Leu Ile Lys Val Asp Ser Ser Glu
145                 150               155               160
Asn Leu Cys Thr Glu Asn Ile Leu Phe Lys Leu Ser Glu Thr Gly Asn
                165               170               175
Ser Gly Gly Leu Asn Asp Ile Phe Glu Ala Gln Lys Ile Glu Trp
            180               185               190
His Glu

<210> SEQ ID NO 316
<211> LENGTH: 159
<212> TYPE: PRT
<213> ORGANISM: Macaca fascicularis

<400> SEQUENCE: 316

Ser Ile Thr Gly Ile Ser Pro Ile Thr Glu Ser Leu Ala Ser Leu Ser
1               5                   10                  15
Thr Tyr Asn Asp Gln Ser Ile Thr Phe Ala Leu Glu Asp Glu Ser Tyr
            20                  25                  30
Glu Ile Tyr Val Glu Asp Leu Lys Lys Asp Lys Lys Asp Lys Val
        35                  40                  45
Leu Leu Ser Tyr Tyr Glu Ser Gln His Pro Ser Ser Glu Ser Gly Asp
    50                  55                  60
Gly Val Asp Gly Lys Met Leu Met Val Thr Leu Ser Pro Thr Lys Asp
65                  70                  75                  80
Phe Trp Leu Gln Ala Asn Asn Lys Glu His Ser Val Glu Leu His Lys
                85                  90                  95
Cys Glu Lys Pro Leu Pro Asp Gln Ala Phe Phe Val Leu His Asn Arg
            100                 105                 110
Ser Phe Asn Cys Val Ser Phe Glu Cys Lys Thr Asp Pro Gly Val Phe
        115                 120                 125
Ile Gly Val Lys Asp Asn His Leu Ala Leu Ile Lys Val Asp Tyr Ser
    130                 135                 140
Glu Asn Leu Gly Ser Glu Asn Ile Leu Phe Lys Leu Ser Glu Thr
145                 150                 155

<210> SEQ ID NO 317
<211> LENGTH: 180
<212> TYPE: PRT
<213> ORGANISM: Artificial Sequence
<220> FEATURE:
<223> OTHER INFORMATION: Synthetic Construct

<400> SEQUENCE: 317

Met Gly Ser Ser His His His His His His Ser Ser Gly Leu Val Pro
1               5                   10                  15
Arg Gly Ser His Met Ser Ile Thr Gly Ile Ser Pro Ile Thr Glu Ser
            20                  25                  30
Leu Ala Ser Leu Ser Thr Tyr Asn Asp Gln Ser Ile Thr Phe Ala Leu
        35                  40                  45
Glu Asp Glu Ser Tyr Glu Ile Tyr Val Glu Asp Leu Lys Lys Asp Lys
    50                  55                  60
Lys Lys Asp Lys Val Leu Leu Ser Tyr Tyr Glu Ser Gln His Pro Ser
65                  70                  75                  80
```

```
Ser Glu Ser Gly Asp Gly Val Asp Gly Lys Met Leu Met Val Thr Leu
            85                  90                  95

Ser Pro Thr Lys Asp Phe Trp Leu Gln Ala Asn Asn Lys Glu His Ser
            100                 105                 110

Val Glu Leu His Lys Cys Glu Lys Pro Leu Pro Asp Gln Ala Phe Phe
            115                 120                 125

Val Leu His Asn Arg Ser Phe Asn Cys Val Ser Phe Glu Cys Lys Thr
            130                 135                 140

Asp Pro Gly Val Phe Ile Gly Val Lys Asp Asn His Leu Ala Leu Ile
145                 150                 155                 160

Lys Val Asp Tyr Ser Glu Asn Leu Gly Ser Glu Asn Ile Leu Phe Lys
                165                 170                 175

Leu Ser Glu Thr
            180

<210> SEQ ID NO 318
<211> LENGTH: 194
<212> TYPE: PRT
<213> ORGANISM: Artificial Sequence
<220> FEATURE:
<223> OTHER INFORMATION: Synthetic Construct

<400> SEQUENCE: 318

Met His His His His His Gly Glu Asn Leu Tyr Phe Gln Gly Ser
1               5                   10                  15

Ile Thr Gly Ile Ser Pro Ile Thr Glu Ser Leu Ala Ser Leu Ser Thr
                20                  25                  30

Tyr Asn Asp Gln Ser Ile Thr Phe Ala Leu Glu Asp Ser Tyr Glu
            35                  40                  45

Ile Tyr Val Glu Asp Leu Lys Lys Asp Lys Lys Asp Lys Val Leu
        50                  55                  60

Leu Ser Tyr Tyr Glu Ser Gln His Pro Ser Ser Glu Ser Gly Asp Gly
65                  70                  75                  80

Val Asp Gly Lys Met Leu Met Val Thr Leu Ser Pro Thr Lys Asp Phe
            85                  90                  95

Trp Leu Gln Ala Asn Asn Lys Glu His Ser Val Glu Leu His Lys Cys
            100                 105                 110

Glu Lys Pro Leu Pro Asp Gln Ala Phe Phe Val Leu His Asn Arg Ser
            115                 120                 125

Phe Asn Cys Val Ser Phe Glu Cys Lys Thr Asp Pro Gly Val Phe Ile
            130                 135                 140

Gly Val Lys Asp Asn His Leu Ala Leu Ile Lys Val Asp Tyr Ser Glu
145                 150                 155                 160

Asn Leu Gly Ser Glu Asn Ile Leu Phe Lys Leu Ser Glu Thr Gly Asn
                165                 170                 175

Ser Gly Gly Gly Leu Asn Asp Ile Phe Glu Ala Gln Lys Ile Glu Trp
            180                 185                 190

His Glu

<210> SEQ ID NO 319
<211> LENGTH: 379
<212> TYPE: PRT
<213> ORGANISM: Artificial Sequence
<220> FEATURE:
<223> OTHER INFORMATION: Synthetic Construct

<400> SEQUENCE: 319
```

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ile Asp His His Ser Gly Gly Arg Ala Arg Met Lys Gln
                325                 330                 335

Leu Glu Asp Lys Val Glu Glu Leu Leu Ser Lys Asn Tyr His Leu Glu
            340                 345                 350

Asn Glu Val Ala Arg Leu Lys Lys Leu Val Gly Glu Arg Asp Tyr Lys
        355                 360                 365

Asp Asp Asp Asp Lys His His His His His His
    370                 375

<210> SEQ ID NO 320
<211> LENGTH: 23
<212> TYPE: DNA
<213> ORGANISM: Artificial Sequence
<220> FEATURE:
<223> OTHER INFORMATION: Synthetic Construct

<400> SEQUENCE: 320
tttyttgtcc accktggtgc tgc                                          23

<210> SEQ ID NO 321
<211> LENGTH: 19
<212> TYPE: DNA
<213> ORGANISM: Artificial Sequence
<220> FEATURE:
<223> OTHER INFORMATION: Synthetic Construct

<400> SEQUENCE: 321
gtagaagttg ttcaagaag                                               19

<210> SEQ ID NO 322
<211> LENGTH: 21
<212> TYPE: DNA
<213> ORGANISM: Artificial Sequence
<220> FEATURE:
<223> OTHER INFORMATION: Synthetic Construct

<400> SEQUENCE: 322
gtgtagagky cagactscag g                                            21

<210> SEQ ID NO 323
<211> LENGTH: 21
<212> TYPE: DNA
<213> ORGANISM: Artificial Sequence
<220> FEATURE:
<223> OTHER INFORMATION: Synthetic Construct

<400> SEQUENCE: 323
gaggcacctc cagatgttaa c                                            21

<210> SEQ ID NO 324
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (66)..(66)
<223> OTHER INFORMATION: n is a, c, g, or t

<400> SEQUENCE: 324
gattcaaatc tcaattatat aatccgaata tgtttaccgg ctcgctcatg gaccccccccc  60 ccccdn                                                             66

<210> SEQ ID NO 325
<211> LENGTH: 21
<212> TYPE: DNA
<213> ORGANISM: Artificial Sequence
<220> FEATURE:
<223> OTHER INFORMATION: Synthetic Construct

<400> SEQUENCE: 325
caattatata atccgaatat g                                            21

<210> SEQ ID NO 326
<211> LENGTH: 20
<212> TYPE: DNA
<213> ORGANISM: Artificial Sequence
<220> FEATURE:
<223> OTHER INFORMATION: Synthetic Construct

<400> SEQUENCE: 326
gaartarccc ttgaccaggc                                          20

<210> SEQ ID NO 327
<211> LENGTH: 21
<212> TYPE: DNA
<213> ORGANISM: Artificial Sequence
<220> FEATURE:
<223> OTHER INFORMATION: Synthetic Construct

<400> SEQUENCE: 327
gaagatggat acagttggtg c                                        21

<210> SEQ ID NO 328
<211> LENGTH: 118
<212> TYPE: PRT
<213> ORGANISM: Artificial Sequence
<220> FEATURE:
<223> OTHER INFORMATION: Synthetic Construct

<400> SEQUENCE: 328

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 329
<211> LENGTH: 111
<212> TYPE: PRT
<213> ORGANISM: Artificial Sequence
<220> FEATURE:
<223> OTHER INFORMATION: Synthetic Construct

<400> SEQUENCE: 329

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys

<210> SEQ ID NO 330
<211> LENGTH: 444
<212> TYPE: PRT
<213> ORGANISM: Artificial Sequence
<220> FEATURE:
<223> OTHER INFORMATION: Synthetic Construct

<400> SEQUENCE: 330

```
Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
```

```
                  355                 360                 365
Gly Phe Tyr Pro Ser Asp Ile Ala Val Glu Trp Glu Ser Asn Gly Gln
        370                 375                 380

Pro Glu Asn Asn Tyr Lys Thr Thr Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Gly
            435                 440

<210> SEQ ID NO 331
<211> LENGTH: 218
<212> TYPE: PRT
<213> ORGANISM: Artificial Sequence
<220> FEATURE:
<223> OTHER INFORMATION: Synthetic Construct

<400> SEQUENCE: 331

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 332
<211> LENGTH: 1050
<212> TYPE: DNA
<213> ORGANISM: Mus musculus

<400> SEQUENCE: 332
atgattgaca gacagagaat gggactttgg gctttggcaa ttctgacact tcccatgtat      60
```

```
ttgacagtta cggagggcag taaatcgtcc tggggtctgg aaaatgaggc tttaattgtg    120
agatgccccc aaagaggacg ctcgacttat cctgtggaat ggtattactc agatacaaat    180
gaaagtattc ctactcaaaa agaaatcgg atctttgtct caagagatcg tctgaagttt     240
ctaccagcca gagtggaaga ctctgggatt tatgcttgtg ttatcagaag ccccaacttg    300
aataagactg gatacttgaa tgtcaccata cataaaaagc cgccaagctg caatatccct    360
gattatttga tgtactcgac agtacgtgga tcagataaaa atttcaagat aacgtgtcca    420
acaattgacc tgtataattg gacagcacct gttcagtggt ttaagaactg caaagctctc    480
caagagccaa ggttcagggc acacaggtcc tacttgttca ttgacaacgt gactcatgat    540
gatgaaggtg actacacttg tcaattcaca cacgcggaga atggaaccaa ctacatcgtg    600
acggccacca gatcattcac agttgaagaa aaaggctttt ctatgtttcc agtaattaca    660
aatcctccat acaaccacac aatggaagtg gaaataggaa accagcaag tattgcctgt     720
tcagcttgct ttggcaaagg ctctcacttc ttggctgatg tcctgtggca gattaacaaa    780
acagtagttg gaaattttgg tgaagcaaga attcaagaag aggaaggtcg aaatgaaagt    840
tccagcaatg acatggattg tttaacctca gtgttaagga taactggtgt gacagaaaag    900
gacctgtccc tggaatatga ctgtctggcc ctgaaccttc atggcatgat aaggcacacc    960
ataaggctga aaggaaaca accaagtaag gagtgtccct cacacattgc tggcgggcgc    1020
gcccatcatc atcatcatca tcaccactaa                                    1050
```

<210> SEQ ID NO 333
<211> LENGTH: 349
<212> TYPE: PRT
<213> ORGANISM: Mus musculus

<400> SEQUENCE: 333

```
Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
            20                  25                  30

Leu Glu Asn Glu Ala Leu Ile Val Arg Cys Pro Gln Arg Gly Arg Ser
        35                  40                  45

Thr Tyr Pro Val Glu Trp Tyr Tyr Ser Asp Thr Asn Glu Ser Ile Pro
    50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
            100                 105                 110

Lys Pro Pro Ser Cys Asn Ile Pro Asp Tyr Leu Met Tyr Ser Thr Val
        115                 120                 125

Arg Gly Ser Asp Lys Asn Phe Lys Ile Thr Cys Pro Thr Ile Asp Leu
    130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
            180                 185                 190

Glu Asn Gly Thr Asn Tyr Ile Val Thr Ala Thr Arg Ser Phe Thr Val
```

```
                195                 200                 205
Glu Glu Lys Gly Phe Ser Met Phe Pro Val Ile Thr Asn Pro Pro Tyr
210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
                260                 265                 270

Glu Glu Glu Gly Arg Asn Glu Ser Ser Ser Asn Asp Met Asp Cys Leu
275                 280                 285

Thr Ser Val Leu Arg Ile Thr Gly Val Thr Glu Lys Asp Leu Ser Leu
290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ser Lys Glu Cys Pro Ser His Ile
                325                 330                 335

Ala Gly Gly Arg Ala His His His His His His
                340                 345

<210> SEQ ID NO 334
<211> LENGTH: 120
<212> TYPE: PRT
<213> ORGANISM: Artificial Sequence
<220> FEATURE:
<223> OTHER INFORMATION: Synthetic Construct

<400> SEQUENCE: 334

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
                20                  25                  30

Trp Ile His Trp Val Arg Gln Ala Pro Gly Lys Gly Leu Glu Trp Val
            35                  40                  45

Ala Gly Ile Thr Pro Ala Gly Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 335
<211> LENGTH: 107
<212> TYPE: PRT
<213> ORGANISM: Artificial Sequence
<220> FEATURE:
<223> OTHER INFORMATION: Synthetic Construct

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
                100                 105

<210> SEQ ID NO 336
<211> LENGTH: 107
<212> TYPE: PRT
<213> ORGANISM: Artificial Sequence
<220> FEATURE:
<223> OTHER INFORMATION: Synthetic Construct

<400> SEQUENCE: 336

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Asn Pro Phe
                85                  90                  95

Thr Phe Gly Gln Gly Thr Lys Val Glu Ile Lys
                100                 105

<210> SEQ ID NO 337
<211> LENGTH: 121
<212> TYPE: PRT
<213> ORGANISM: Artificial Sequence
<220> FEATURE:
<223> OTHER INFORMATION: Synthetic Construct

<400> SEQUENCE: 337

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Ala Ser
            20                  25                  30

Trp Ile His Trp Val Arg Gln Ala Pro Gly Lys Gly Leu Glu Trp Val
            35                  40                  45

Gly Ala Ile Tyr Pro Tyr Ser Gly Tyr Thr Asn Tyr Ala Asp Ser Val
     50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly His Ser Thr Ser Pro Trp Ala Met Asp Tyr Trp Gly
                100                 105                 110

Gln Gly Thr Leu Val Thr Val Ser Ser
                115                 120

<210> SEQ ID NO 338
<211> LENGTH: 107
<212> TYPE: PRT
<213> ORGANISM: Artificial Sequence
<220> FEATURE:
<223> OTHER INFORMATION: Synthetic Construct

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 339
<211> LENGTH: 107
<212> TYPE: PRT
<213> ORGANISM: Artificial Sequence
<220> FEATURE:
<223> OTHER INFORMATION: Synthetic Construct

<400> SEQUENCE: 339

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Arg Arg Ser
            20                  25                  30

Leu Ala Trp Tyr Gln Gln Lys Pro Gly Lys Ala Pro Lys Leu Leu Ile
        35                  40                  45

Tyr Ala Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Thr Ser Pro Leu
                85                  90                  95

Thr Phe Gly Gln Gly Thr Lys Val Glu Ile Lys
            100                 105

<210> SEQ ID NO 340
<211> LENGTH: 121
<212> TYPE: PRT
<213> ORGANISM: Artificial Sequence
<220> FEATURE:
<223> OTHER INFORMATION: Synthetic Construct

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Ala Ser Gly Phe Ser Ile Asn Gly Ser
            20                  25                  30

-continued

Trp Ile Phe Trp Val Arg Gln Ala Pro Gly Lys Gly Leu Glu Trp Val
                35                  40                  45

Gly Ala Ile Trp Pro Phe Gly Gly Tyr Thr His Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Trp Gly His Ser Thr Ser Pro Trp Ala Met Asp Tyr Trp Gly
                100                 105                 110

Gln Gly Thr Leu Val Thr Val Ser Ser
        115                 120

<210> SEQ ID NO 341
<211> LENGTH: 107
<212> TYPE: PRT
<213> ORGANISM: Artificial Sequence
<220> FEATURE:
<223> OTHER INFORMATION: Synthetic Construct

<400> SEQUENCE: 341

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Val Ile Arg Arg Ser
                20                  25                  30

Leu Ala Trp Tyr Gln Gln Lys Pro Gly Lys Ala Pro Lys Leu Leu Ile
            35                  40                  45

Tyr Ala Ala Ser Asn Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Thr Ser Pro Leu
                 85                  90                  95

Thr Phe Gly Gln Gly Thr Lys Val Glu Ile Lys
            100                 105

<210> SEQ ID NO 342
<211> LENGTH: 23
<212> TYPE: DNA
<213> ORGANISM: Artificial Sequence
<220> FEATURE:
<223> OTHER INFORMATION: Synthetic Construct

<400> SEQUENCE: 342
ttaagaccag ctatctccca tca                                           23

<210> SEQ ID NO 343
<211> LENGTH: 26
<212> TYPE: DNA
<213> ORGANISM: Artificial Sequence
<220> FEATURE:
<223> OTHER INFORMATION: Synthetic Construct

<400> SEQUENCE: 343
acgttacatc ttagagagct taaaca                                        26

<210> SEQ ID NO 344
<211> LENGTH: 122
<212> TYPE: PRT
<213> ORGANISM: Artificial Sequence
<220> FEATURE:

<223> OTHER INFORMATION: Synthetic Construct

<400> SEQUENCE: 344

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Glu Arg Tyr Ile Ser Ser Tyr Tyr Gly Gly Phe Asp Pro Trp
            100                 105                 110

Gly Gln Gly Ala Leu Val Thr Val Ser Ser
        115                 120

<210> SEQ ID NO 345
<211> LENGTH: 107
<212> TYPE: PRT
<213> ORGANISM: Artificial Sequence
<220> FEATURE:
<223> OTHER INFORMATION: Synthetic Construct

<400> SEQUENCE: 345

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Leu Asp Ile Lys
            100                 105

<210> SEQ ID NO 346
<211> LENGTH: 366
<212> TYPE: DNA
<213> ORGANISM: Artificial Sequence
<220> FEATURE:
<223> OTHER INFORMATION: Synthetic Construct

<400> SEQUENCE: 346
caggtgcagc tggtggagtc tgggggaggc gtggtccagc ctggagggtc cctgagactc      60
tcctgtgcag cgtctggatt caccttcagt agttatggca tgcattgggt ccgccaggct     120
ccaggcaagg ggctggagtg ggtggcagtt atatggtatg atggaagaaa taaatactat     180
acagactccg tgaagggccg attcaccatc tccagagaca attccaagaa cacgctgtat     240
ctgcaaatgg acagcctgag agccgaggac acggctgtgt attactgtgc gagagagagg     300

-continued

```
tatatcagca gctattatgg ggggttcgac ccctggggcc agggagccct ggtcaccgtc    360
tcctca                                                              366

<210> SEQ ID NO 347
<211> LENGTH: 321
<212> TYPE: DNA
<213> ORGANISM: Artificial Sequence
<220> FEATURE:
<223> OTHER INFORMATION: Synthetic Construct

<400> SEQUENCE: 347
gacatccaga tgacccagtc tccatcctcc gtgtctgcat ctgtaggaga cagagtcacc     60
atcacttgtc gggcgagtca gggtattagt agttggttag cctggtatca gcagaaacca    120
gggaaagccc ctaaggtcct gatctatgct gcatccagtt tgcaaagtgg gtcccatca     180 aggttcagcg gcagtggatc tgggacagat ttcactctca ccatcagcag cctgcagcct    240
gaagattttg caacttacta ttgtcaacag gctaacagtt tcccattcac tttcggccct    300
gggaccaaac tggatatcaa g                                              321

<210> SEQ ID NO 348
<211> LENGTH: 119
<212> TYPE: PRT
<213> ORGANISM: Artificial Sequence
<220> FEATURE:
<223> OTHER INFORMATION: Synthetic Construct

<400> SEQUENCE: 348

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Ser Thr Asp Tyr Ala Asp Ser Val
    50                  55                  60

Lys Gly Arg Phe Thr Ile Ser Arg Asp Asn Ser Arg Asp Thr Leu His
65                  70                  75                  80

Leu Gln Met Asn Ser Leu Arg Ala Glu Asp Thr Ala Val Tyr Tyr Cys
                85                  90                  95

Ala Lys Thr Phe Tyr Tyr Phe Tyr Gly Leu Asp Val Trp Gly Gln Gly
            100                 105                 110

Thr Thr Val Thr Val Ser Ser
        115

<210> SEQ ID NO 349
<211> LENGTH: 107
<212> TYPE: PRT
<213> ORGANISM: Artificial Sequence
<220> FEATURE:
<223> OTHER INFORMATION: Synthetic Construct

<400> SEQUENCE: 349

Asp Ile Gln Met Thr Gln Ser Pro Ser Ser Leu Ser Ala Ser Leu Arg
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Val Leu Ile
        35                  40                  45
```

Tyr Ala Ala Ser Thr Leu Gln Ser Gly Val Pro Ser Arg Phe Ser Gly
         50                  55                  60

Ser Gly Ser Gly Thr Val Phe Thr Leu Thr Ile Ser Ser Leu Gln Thr
 65                  70                  75                  80

Glu Asp Val Ala Thr Tyr Tyr Cys Gln Lys Tyr Ser Ser Ala Pro Phe
                 85                  90                  95

Thr Phe Gly Pro Gly Thr Lys Val Asp Ile Lys
            100                 105

<210> SEQ ID NO 350
<211> LENGTH: 357
<212> TYPE: DNA
<213> ORGANISM: Artificial Sequence
<220> FEATURE:
<223> OTHER INFORMATION: Synthetic Construct

<400> SEQUENCE: 350
gaggtgcagc tgttggagtc tgggggagac ttggtacagc ctgggggtc cctgagactc      60 tcctgtgcag cctctggatt caccttcagc agctatgcca tgagctgggt ccgccaggct    120
ccagggaagg gctggagtg gtctcagtt attagtggta gtggaagtag cacagactac      180
gcagactccg tgaagggccg gttcaccatt tccagagaca attccaggga cacgctgcat    240
ctgcaaatga acagcctgag agccgaggac acggccgtat attactgtgc gaaaacgttc    300
tactacttct acggtttgga cgtctggggc caagggacca cggtcaccgt ctcctca       357

<210> SEQ ID NO 351
<211> LENGTH: 321
<212> TYPE: DNA
<213> ORGANISM: Artificial Sequence
<220> FEATURE:
<223> OTHER INFORMATION: Synthetic Construct

<400> SEQUENCE: 351
gacatccaga tgacccagtc tccatcctcc ctgtctgcat ctttaagaga cagagtcacc      60
atcacttgcc gggcgagtca gggcattagc aattatttag cctggtatca gcagaaacca    120
gggaaagttc ctaaggtcct aatctatgct gcatccactt tgcaatcagg ggtcccatct    180
cggttcagtg gcagtggatc tgggacagtt ttcactctca ccatcagcag cctgcagact    240
gaagatgttg caacttatta ctgtcaaaag tatagcagtg ccccattcac tttcggccct    300
gggaccaaag tggatatcaa a                                               321

<210> SEQ ID NO 352
<211> LENGTH: 117
<212> TYPE: PRT
<213> ORGANISM: Artificial Sequence
<220> FEATURE:
<223> OTHER INFORMATION: Synthetic Construct

<400> SEQUENCE: 352

Gln Val Leu Leu Val Gln Ser Gly Ala Glu Val Lys Lys Pro Gly Ala
 1               5                   10                  15

Thr Val Lys Val Ser Cys Lys Ala Ser Gly Ser Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Asn Gly Gly Thr Asn Tyr Ala Gln Lys Phe
         50                  55                  60

Gln Gly Arg Val Thr Met Thr Arg Asp Thr Ser Ile Ser Thr Ala Tyr

```
                65                  70                  75                  80
Met Glu Leu Ser Arg Leu Arg Ser Asp Asp Thr Ala Val Tyr Tyr Cys
                    85                  90                  95

Ala Arg Glu Leu Arg Tyr Asn Trp Lys Ser Trp Gly Gln Gly Thr Leu
                100                 105                 110

Val Thr Val Ser Ser
        115

<210> SEQ ID NO 353
<211> LENGTH: 108
<212> TYPE: PRT
<213> ORGANISM: Artificial Sequence
<220> FEATURE:
<223> OTHER INFORMATION: Synthetic Construct

<400> SEQUENCE: 353

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Gly Arg Pro
                20                  25                  30

Tyr Leu Ala Trp Tyr Gln Gln Ile Pro Gly Gln Ala Pro Arg Leu Leu
            35                  40                  45

Ile Tyr Gly Ala Ser Ser Arg Ala Thr Asp Ile Pro Asp Arg Phe Ser
        50                  55                  60

Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Pro
                85                  90                  95

Tyr Thr Phe Gly Gln Gly Thr Arg Leu Glu Ile Lys
                100                 105

<210> SEQ ID NO 354
<211> LENGTH: 351
<212> TYPE: DNA
<213> ORGANISM: Artificial Sequence
<220> FEATURE:
<223> OTHER INFORMATION: Synthetic Construct

<400> SEQUENCE: 354
caggtgcttc tggtacagtc tggggctgag gtgaagaagc ctggggccac agtgaaggtc     60
tcctgcaagg cttctggatc cactttcacc ggctactata tgcactgggt gcgacaggcc    120
cctggacaag gcttgagtg gatgggatgg atcaaccct a caatggtgg cacaaactat     180 gcacagaagt tcagggcag ggtcaccatg accagggaca cgtccatcag cacagcctac    240
atggaattga gcaggctgag atctgacgac acggccgtat attactgtgc gagagagttg    300
cggtataact ggaagtcctg gggccaggga accctggtca ccgtctcctc a             351

<210> SEQ ID NO 355
<211> LENGTH: 324
<212> TYPE: DNA
<213> ORGANISM: Artificial Sequence
<220> FEATURE:
<223> OTHER INFORMATION: Synthetic Construct

<400> SEQUENCE: 355
gaaattgtgt tgacgcagtc tccaggcacc ctgtctttgt ctccagggga aagagtcacc     60
ctctcctgca gggccagtca gagtgttggc aggccctact agcctggta ccaacagata    120 cctggccagg ctcccaggct cctcatctat ggtgcatcca gcagggccac tgacatccca    180
```

```
gacaggttca gtggcaatgg gtctgggaca gacttcactc tcaccatcag tagactggag    240
cctgaagatt ttgcagtgta ttactgtcag cagtatgata attccccctta tactttttggc   300 cagggggacca ggctggagat caaa                                         324
```

<210> SEQ ID NO 356
<211> LENGTH: 122
<212> TYPE: PRT
<213> ORGANISM: Artificial Sequence
<220> FEATURE:
<223> OTHER INFORMATION: Synthetic Construct

<400> SEQUENCE: 356

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Ala Met Ser Trp Val Arg Gln Ala Pro Gly Lys Gly Leu Glu Leu Val
        35                  40                  45

Ser Asp Leu Arg Thr Ser Gly Gly Ser Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Tyr Ser Thr Ser Trp Phe Gly Gly Phe Asp Tyr Trp
            100                 105                 110

Gly Gln Gly Thr Leu Val Thr Val Ser Ser
        115                 120
```

<210> SEQ ID NO 357
<211> LENGTH: 107
<212> TYPE: PRT
<213> ORGANISM: Artificial Sequence
<220> FEATURE:
<223> OTHER INFORMATION: Synthetic Construct

<400> SEQUENCE: 357

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Phe Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Asn Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105
```

<210> SEQ ID NO 358
<211> LENGTH: 366
<212> TYPE: DNA
<213> ORGANISM: Artificial Sequence
<220> FEATURE:
<223> OTHER INFORMATION: Synthetic Construct

<400> SEQUENCE: 358

```
gaggtgcagc tggtggagtc tgggggaggc ttggtacaac ctgggggtc cctgagactc      60
tcctgtgcag cctctggatt cacctttaga agctttgcca tgagctgggt ccgccaggct    120
ccagggaagg gctggaatt ggtctcagat ctcaggacta gtggtggtag tacatactac     180
gcagactccg tgaagggccg gctcaccatc tccagagaca attccaagaa cacgctgtat    240
ctgcaaatga acagcctgag agccgaggac acggccgtat attactgtgc gaaaagccac    300
tatagcacca gctggttcgg ggctttgac tactggggcc agggaaccct ggtcactgtc     360
tcctca                                                                366
```

<210> SEQ ID NO 359
<211> LENGTH: 321
<212> TYPE: DNA
<213> ORGANISM: Artificial Sequence
<220> FEATURE:
<223> OTHER INFORMATION: Synthetic Construct

<400> SEQUENCE: 359

```
gacatccaga tgacccagtc tccatcttcc gtgtctgctt ctgtaggaga cagagtcacc     60
atcacttgtc gggcgagtca gggttttagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcaccaa cctgcagcct    240
gaagattttg caacttacta ttgtcaacag gctaacagtt tccctctcac tttcggcgga    300
gggaccaagg tggagatcaa a                                               321
```

<210> SEQ ID NO 360
<211> LENGTH: 122
<212> TYPE: PRT
<213> ORGANISM: Artificial Sequence
<220> FEATURE:
<223> OTHER INFORMATION: Synthetic Construct

<400> SEQUENCE: 360

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ser Ile Ser Gly Asn Gly Gly Ser Thr Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Glu Met Asn Ser Leu Arg Ala Glu Asp Thr Ala Val Tyr Tyr Cys
                85                  90                  95

Ala Lys Ser Leu Gly Thr Thr Thr Phe Leu Gly Phe Asp Tyr Trp
            100                 105                 110

Gly Gln Gly Thr Leu Val Thr Val Ser Ser
        115                 120
```

<210> SEQ ID NO 361
<211> LENGTH: 107
<212> TYPE: PRT
<213> ORGANISM: Artificial Sequence
<220> FEATURE:

<223> OTHER INFORMATION: Synthetic Construct

<400> SEQUENCE: 361

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 362
<211> LENGTH: 366
<212> TYPE: DNA
<213> ORGANISM: Artificial Sequence
<220> FEATURE:
<223> OTHER INFORMATION: Synthetic Construct

<400> SEQUENCE: 362
gaggtgcagc tggtggagtc tgggggaggc ttggtacagc ctggggggtc cctgagactc    60
tcctgtgcag cctctggatt cacgtttagc agctatgtca tgagctgggt ccgccaggct   120
ccagggaagg gctggagtg gtctcaagt attagtggta atggtggtag cacaaactac    180
gcagactccg tgaagggccg gttcaccatc tccagagaca attccaagaa cacgctgttt   240
ctggaaatga acagcctgag agccgaggac acggccgtat attactgtgc gaaatcactg   300
ggaactacca cgacttttt ggggtttgac tattggggcc agggaaccct ggtcaccgtc   360
tcctca                                                              366

<210> SEQ ID NO 363
<211> LENGTH: 321
<212> TYPE: DNA
<213> ORGANISM: Artificial Sequence
<220> FEATURE:
<223> OTHER INFORMATION: Synthetic Construct

<400> SEQUENCE: 363
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaaactcct gatctatgct gcatccagtt tgcaaagtgg ggtcccatca   180
aggttcagcg gcagtggatc tgggacatat ttcactctca ccatcagcag cctgcagcct   240
gaagattttg caacttacta ttgtcaacag gctaacagtt tccctctcac tttcggcgga   300
gggaccaagg tggagatcaa a                                             321

<210> SEQ ID NO 364
<211> LENGTH: 121
<212> TYPE: PRT
<213> ORGANISM: Artificial Sequence
<220> FEATURE:
<223> OTHER INFORMATION: Synthetic Construct

<400> SEQUENCE: 364

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Leu Ile
        35                  40                  45
Gly Tyr Ile Tyr Tyr Ser Gly Ser Thr Asn Tyr Asn Pro Ser Leu Lys
50                  55                  60
Ser Arg Val Thr Ile Ser Val Asp Thr Ser Lys Asn His Phe Ser Leu
65                  70                  75                  80
Lys Leu Ser Ser Val Thr Ala Ala Asp Thr Ala Val Tyr Tyr Cys Ala
                85                  90                  95
Arg Ser Gln Tyr Thr Ser Ser Trp Tyr Gly Ser Phe Asp Ile Trp Gly
            100                 105                 110
Gln Gly Thr Met Val Thr Val Ser Ser
        115                 120

<210> SEQ ID NO 365
<211> LENGTH: 107
<212> TYPE: PRT
<213> ORGANISM: Artificial Sequence
<220> FEATURE:
<223> OTHER INFORMATION: Synthetic Construct

<400> SEQUENCE: 365

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Thr Trp
            20                  25                  30
Leu Ala Trp Phe Gln Gln Lys Pro Gly Lys Ala Pro Lys Leu Leu Ile
        35                  40                  45
Tyr Ala Ala Ser Thr Leu Gln Gly Gly Val Pro Ser Arg Phe Ser Gly
50                  55                  60
Ser Gly Ser Gly Pro Glu Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Trp
                85                  90                  95
Thr Phe Gly Gln Gly Thr Lys Val Glu Ile Lys
            100                 105

<210> SEQ ID NO 366
<211> LENGTH: 363
<212> TYPE: DNA
<213> ORGANISM: Artificial Sequence
<220> FEATURE:
<223> OTHER INFORMATION: Synthetic Construct

<400> SEQUENCE: 366
caggtgcagc tgcaggagtc gggcccagga ctggtgaagc cttcggagac cctgtccctc      60
acctgcactg tctctggtgg ctccatcagt agttattact ggagctggat ccggcagccc     120
ccagggaagg gactggagtt gattgggtat atttattaca gtgggagcac caattataac     180
ccctccctca agagtcgagt caccatatct gtagacacgt ccaagaacca cttctccctg     240
aagctgagct ctgtgaccgc tgcggacacg gccgtatatt actgtgcgag atcccagtat     300
accagtagtt ggtacggttc ttttgatatc tggggccaag ggacaatggt caccgtctct     360

-continued

```
tca                                                                363
```

<210> SEQ ID NO 367
<211> LENGTH: 321
<212> TYPE: DNA
<213> ORGANISM: Artificial Sequence
<220> FEATURE:
<223> OTHER INFORMATION: Synthetic Construct

<400> SEQUENCE: 367

```
gacatccaga tgacccagtc tccatcttcc gtgtctgcat ctgtaggaga cagagtcacc    60
atcacttgtc gggcgagtca gggtattagc acctggttag cctggtttca gcagaaacca   120
gggaaagccc ctaagctcct gatctatgct gcatccactt tacaaggtgg ggtcccatca   180
aggttcagcg gcagtggatc tgggccagaa ttcactctca ccatcagcag cctgcagcct   240
gaagattttg caacttacta ttgtcaacag gctaacagtt tcccgtggac gttcggccaa   300
gggaccaagg tggaaatcaa a                                             321
```

<210> SEQ ID NO 368
<211> LENGTH: 122
<212> TYPE: PRT
<213> ORGANISM: Artificial Sequence
<220> FEATURE:
<223> OTHER INFORMATION: Synthetic Construct

<400> SEQUENCE: 368

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Gly Ile Ser Trp Val Arg Gln Ala Pro Gly Gln Gly Leu Glu Trp Met
        35                  40                  45

Gly Trp Ile Ser Ser His Asn Gly Asn Ser His Tyr Val Gln Lys Phe
    50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Ser Tyr Thr Thr Ser Trp Tyr Gly Gly Phe Asp Tyr Trp
            100                 105                 110

Gly Gln Gly Thr Leu Val Thr Val Ser Ser
        115                 120
```

<210> SEQ ID NO 369
<211> LENGTH: 107
<212> TYPE: PRT
<213> ORGANISM: Artificial Sequence
<220> FEATURE:
<223> OTHER INFORMATION: Synthetic Construct

<400> SEQUENCE: 369

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Phe Ser Ser Trp
            20                  25                  30

Leu Ala Trp Tyr Gln Gln Lys Pro Gly Lys Ala Pro Gln Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Ser Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105

<210> SEQ ID NO 370
<211> LENGTH: 366
<212> TYPE: DNA
<213> ORGANISM: Artificial Sequence
<220> FEATURE:
<223> OTHER INFORMATION: Synthetic Construct

<400> SEQUENCE: 370
caggttcagc tggtgcagtc tggagctgag gtgaagaagc tggggcctc agtgaaggtc      60 tcctgcaagg cctctggtta ccctttaac agctatggta tcagctgggt gcgacaggcc    120
cctggacaag gcttgagtg gatgggatgg atcagctccc acaatggtaa cagtcactat    180
gtacagaagt tccagggcag agtctccatg accacagaca catccacgag tacagcctac    240
atggaactga ggagccttag atctgacgac acggccgtgt attactgtgc gagacactcg    300
tataccacca gctggtacgg ggttttttgac tattggggcc agggaaccct ggtcaccgtc    360
tcctca                                                                366

<210> SEQ ID NO 371
<211> LENGTH: 321
<212> TYPE: DNA
<213> ORGANISM: Artificial Sequence
<220> FEATURE:
<223> OTHER INFORMATION: Synthetic Construct

<400> SEQUENCE: 371
gacatccaga tgacccagtc tccatcttcc gtgtctgcat ctgtaggaga cagagtcacc      60
atcacttgtc gggcgagtca gggttttagc agctggttag cctggtatca gcagaaacca    120
gggaaagccc ctcagctcct gatctatgct gcatccagtt tgcaaagtgg ggtcccatca    180
aggttcagcg gcagtggatc tgggtcagat ttcactctca ccatcagcag cctgcagcct    240
gaagattttg caacttacta ttgtcaacag gctaacagtt tccctctcac tttcggcgga    300
gggaccaagg tggagatcaa a                                               321
```

ANTI-INTERLEUKIN-33 ANTIBODIES AND USES THEREOF

FIELD OF THE INVENTION

The invention relates to anti-interleukin-33 (IL-33) antibodies, and methods of using the same, including for treatment of IL-33-mediated disorders.

BACKGROUND

Interleukin-33 (IL-33) is a member of the interleukin-1 (IL-1) cytokine family that is encoded by the IL33 gene, and is constitutively expressed in structural cells, such as smooth muscle, epithelial, and endothelial cells. IL-33 can be induced by inflammatory factors in macrophages and dendritic cells. Cellular stress caused by environmental triggers, such as allergens, toxins, and pathogens, can lead to IL-33 release. Bioavailable IL-33 associates with a heterodimeric IL-33 receptor complex composed of suppression of tumorigenicity 2 (ST2) protein and interleukin-1 receptor accessory protein (IL-1RAcP) to activate the AP-1 and NF-κB pathways through the adaptor protein myeloid differentiation primary response 88 (MyD88) and possibly MyD88-adapter-like (Mal) protein. IL-33 stimulates a number of cell types, including innate type II (ILC2) cells, mast cells, basophils, eosinophils, and dendritic cells, to promote Type 2 immunity.

The IL-33 pathway has been suggested to be involved in various diseases, including allergy-related diseases for which there remains a need to develop improved compositions, including therapeutic anti-IL-33 antagonists, and methods for treatment.

SUMMARY

The present invention relates to anti-IL-33 antibodies, including bispecific anti-IL-33/anti-IL-13 antibodies, and methods of using the same.

In one aspect, the invention features an isolated antibody that specifically binds both human and cynomolgus monkey (cyno) interleukin-33 (IL-33) with a $K_D$ of about 500 pM or lower. In some embodiments, the antibody specifically binds human IL-33 with a $K_D$ between about 100 fM and about 500 pM. In some embodiments, the antibody specifically binds human IL-33 with a $K_D$ between about 1 pM and about 200 pM. In some embodiments, the antibody specifically binds human IL-33 with a $K_D$ between about 15 pM and about 180 pM. In some embodiments, the antibody specifically binds human IL-33 with a $K_D$ between about 15 and about 140 pM. In some embodiments, the antibody specifically binds cyno IL-33 with a $K_D$ between about 100 fM and about 500 pM. In some embodiments, the antibody specifically binds cyno IL-33 with a $K_D$ between about 1 pM and about 500 pM. In some embodiments, the antibody specifically binds cyno IL-33 with a $K_D$ between about 100 and about 500 pM. In some embodiments, the antibody specifically binds cyno IL-33 with a $K_D$ between about 125 and about 500 pM. In some embodiments, the antibody the antibody specifically binds both human and cyno IL-33 with a $K_D$ of between about 1 pM and about 500 pM. In some embodiments, the antibody specifically binds human IL-33 with a $K_D$ of between about 1 pM and about 200 pM.

In some embodiments, any one of the preceding antibodies is capable of inhibiting the binding of IL-33 to an IL-33 receptor (e.g., ST2 and/or IL-1RAcP). In some embodiments, the inhibiting is measured using a cell-based blocking assay. In some embodiments, the antibody inhibits the binding of human IL-33 to an IL-33 receptor with a 90% inhibitory concentration (IC90) of between about 0.001 μg/ml and about 0.5 μg/ml. In some embodiments, the IC90 is between about 0.002 μg/ml and about 0.25 μg/ml. In some embodiments, the IC90 is about 0.17 μg/ml. In some embodiments, the IC90 is about 0.004 μg/ml. In some embodiments, the antibody inhibits the binding of human IL-33 to an IL-33 receptor with a 50% inhibitory concentration (IC50) of between about 800 fM and about 10 pM. In some embodiments, the IC50 is between about 1 pM and about 5 pM. In some embodiments, the IC50 is about 2.5 pM. In some embodiments, the antibody inhibits the binding of cyno IL-33 to an IL-33 receptor with an IC50 of between about 1 nM and about 5 nM. In some embodiments, IC50 is about 4 nM. In some embodiments, HEK-BLUE™ IL-33/IL-1β cells are used in the cell-based blocking assay. In some embodiments, the HEK-BLUE™ IL-33/IL-1β cells comprise a nucleic acid comprising the sequence of SEQ ID NO: 311. In some embodiments, the assay comprises treating HEK-BLUE™ IL-33/IL-1β cells with IL-33. In some embodiments, the IL-33 comprises the amino acid sequence of any one of SEQ ID NOs: 313-318. In some embodiments, sST2-LZ is used as a positive control in the cell-based blocking assay. In some embodiments, the sST2-LZ comprises the amino acid sequence of SEQ ID NO: 310.

In some embodiments of the above aspect, the antibody comprises a binding domain comprising: (a) an HVR-H1 comprising the amino acid sequence of SFSMS (SEQ ID NO: 1); (b) an HVR-H2 comprising the amino acid sequence of TISGGKTFTDYVDSVKG (SEQ ID NO: 2); and (c) an HVR-H3 comprising the amino acid sequence of ANYGNWFFEV (SEQ ID NO: 3). In some embodiments, the binding domain further comprises: (a) an FR-H1 comprising the amino acid sequence of EVQLVESGGGLVQPGGSLRLSCAASGFTFS (SEQ ID NO: 12); (b) an FR-H2 comprising the amino acid sequence of WVRQAPGKGLEWVA (SEQ ID NO: 13); (c) an FR-H3 comprising the amino acid sequence of RFTISRDDSKNTLYLQMNSLRAEDTAVYYCTR (SEQ ID NO: 14); and (d) an FR-H4 comprising the amino acid sequence of WGQGTLVTVSS (SEQ ID NO: 15). In some embodiments, the binding domain further comprises: (a) an FR-H1 comprising the amino acid sequence of DVNLVESGGGSVKPGGSLKLSCVASGFTFS (SEQ ID NO: 16); (b) an FR-H2 comprising the amino acid sequence of WVRQTPEKRLEWVA (SEQ ID NO: 17); (c) an FR-H3 comprising the amino acid sequence of RFTISRDDAKNTLYLQMSSLESEDTAMYYCTR (SEQ ID NO: 18); and (d) an FR-H4 comprising the amino acid sequence of WGAGTTVAVSS (SEQ ID NO: 19). In some embodiments, the binding domain further comprises: (a) an FR-H1 comprising the amino acid sequence of EVQLVESGGGLVQPGGSLRLSCAASGFTFS (SEQ ID NO: 12) or EVQLVESGGGLVKPGGSLRLSCAASGFTFS (SEQ ID NO: 20); (b) an FR-H2 comprising the amino acid sequence of WVRQAPGKGLEWVA (SEQ ID NO: 13) or WVRQAPGKGLEWVS (SEQ ID NO: 21); (c) an FR-H3 comprising the amino acid sequence of RFTISRDNSKNTLYLQMNSLRAEDTAVYYCTR (SEQ ID NO: 22), RFTISRDDAKNSLYLQMNSLRAEDTAVYYCTR (SEQ ID NO: 23), RFTISRDNAKNSLYLQMNSLRAEDTAVYYCTR (SEQ ID NO: 24), or RFTISRDDSKNTLYLQMNSLRAEDTAVYYCTR (SEQ ID NO: 14); and (d) an FR-H4 comprising the amino acid sequence of WGQGTLVTVSS (SEQ ID NO: 15). In some embodiments, the binding domain further comprises: (a) an HVR-L1 comprising the amino acid sequence of RASES- VAKYGLSLLN (SEQ ID NO: 4); (b) an HVR-L2 comprising the amino acid sequence of AASNRGS (SEQ ID NO: 5); and (c) an HVR-L3 comprising the amino acid sequence of QQSKEVPFT (SEQ ID NO: 6). In some embodiments, the binding domain further comprises: (a) an FR-L1 comprising the amino acid sequence of EIVLTQSPATLSLSPGERATLSC (SEQ ID NO: 25); (b) an FR-L2 comprising the amino acid sequence of WFQQKPGQPPRLLIF (SEQ ID NO: 26); (c) an FR-L3 comprising the amino acid sequence of GIPARFSGSGSGTDFTLTISSLEPEDFAVYYC (SEQ ID NO: 27); and (d) an FR-L4 comprising the amino acid sequence of FGQGTKVEIK (SEQ ID NO: 28). In some embodiments, the binding domain further comprises: (a) an FR-L1 comprising the amino acid sequence of DIVLTQSPGFLWSLGQRATISC (SEQ ID NO: 29); (b) an FR-L2 comprising the amino acid sequence of WFQQKPGQPPKLLIF (SEQ ID NO: 30); (c) an FR-L3 comprising the amino acid sequence of GVPARFSGSGSGTDFSLNIHPMEEDDTAMYFC (SEQ ID NO: 31): and (d) an FR-L4 comprising the amino acid sequence of FGSGTKLEIK (SEQ ID NO: 32). In some embodiments, the binding domain further comprises: (a) an FR-L1 comprising the amino acid sequence of EIVLTQSPATLSLSPGERATLSC (SEQ ID NO: 25); (b) an FR-L2 comprising the amino acid sequence of WFQQKPGQPPRLLIF (SEQ ID NO: 26); (c) an FR-L3 comprising the amino acid sequence of GIPARFSGSGSGTDFTLTISSLEPEDFAVYYC (SEQ ID NO: 27), GVPARFSGSGSGTDFTLTISSLEPEDFAVYFC (SEQ ID NO: 33), GVPARFSGSGSGTDFTLTISSLEPEDFAVYYC (SEQ ID NO: 34), or GIPARFSGSGSGTDFTLTISSLEPEDFAVYFC (SEQ ID NO: 35); and (d) an FR-L4 comprising the amino acid sequence of FGQGTKVEIK (SEQ ID NO: 28).

In some embodiments of the above aspect, the antibody comprises a binding domain comprising: (a) an HVR-H1 comprising the amino acid sequence of SSIFYWG (SEQ ID NO: 65); (b) an HVR-H2 comprising the amino acid sequence of SIYYSGRTYYNPSLKS (SEQ ID NO: 66) or SIYYSGRTYYNPALKS (SEQ ID NO: 67); and (c) an HVR-H3 comprising the amino acid sequence of AGGLYNWNDESFSFYMDV (SEQ ID NO: 68). In some embodiments, the binding domain further comprises: (a) an FR-H1 comprising the amino acid sequence of ELQLQESGPGLVKPSETLSLTCTVSGGSIR (SEQ ID NO: 72); (b) an FR-H2 comprising the amino acid sequence of WIRQPPGKGLEWIG (SEQ ID NO: 73); (c) an FR-H3 comprising the amino acid sequence of RVTISVDTSKNQFSLMLTSVTAADTAVYYCAR (SEQ ID NO: 74); and (d) an FR-H4 comprising the amino acid sequence of WGQGTTVTVSS (SEQ ID NO: 75). In some embodiments, the binding domain further comprises: (a) an FR-H1 comprising the amino acid sequence of QLQLQESGPGLVKPSETLSLTCTVSGGSIR (SEQ ID NO: 76); (b) an FR-H2 comprising the amino acid sequence of WIRQPPGKGLEWIG (SEQ ID NO: 73); (c) an FR-H3 comprising the amino acid sequence of RVTISVDTSKNQFSLMLTSVTAADTAVYYCAR (SEQ ID NO: 74); and (d) an FR-H4 comprising the amino acid sequence of WGNGTTVTVSS (SEQ ID NO: 78). In some embodiments, the binding domain further comprises: (a) an FR-H1 comprising the amino acid sequence of ELQLQESGPGLVKPSETLSLTCTVSGGSIR (SEQ ID NO: 72), QLQLQESGPGLVKPSETLSLTCTVSGGSIR (SEQ ID NO: 76) or QVQLQESGPGLVKPSETLSLTCTVSGGSIR (SEQ ID NO: 77); (b) an FR-H2 comprising the amino acid sequence of WIRQPPGKGLEWIG (SEQ ID NO: 73); (c) an FR-H3 comprising the amino acid sequence of RVTISVDTSKNQFSLMLTSVTAADTAVYYCAR (SEQ ID NO: 74): and (d) an FR-H4 comprising the amino acid sequence of WGQGTIVTVSS (SEQ ID NO: 75) or WGNGTTVTVSS (SEQ ID NO: 78). In some embodiments, the binding domain further comprises: (a) an HVR-L1 comprising the amino acid sequence of RASQSFSSSYLA (SEQ ID NO: 69); (b) an HVR-L2 comprising the amino acid sequence of GASSRAT (SEQ ID NO: 70); and (c) an HVR-L3 comprising the amino acid sequence of QQYDRSPLT (SEQ ID NO: 71). In some embodiments, the binding domain further comprises: (a) an FR-L1 comprising the amino acid sequence of EIVLTQSPGTLSLSPGERATLSC (SEQ ID NO: 79): (b) an FR-L2 comprising the amino acid sequence of WYQQKPGQAPRLLIY (SEQ ID NO: 80); (c) an FR-L3 comprising the amino acid sequence of GIPDRFSGSGSGTDFTLTISRLEPEDFAVYYC (SEQ ID NO: 81); and (d) an FR-L4 comprising the amino acid sequence of FGGGTKVEIK (SEQ ID NO: 82).

In another aspect, the invention features an isolated antibody that specifically binds IL-33, wherein the antibody comprises a binding domain comprising the following six HVRs: (a) an HVR-H1 comprising the amino acid sequence of SFSX$_1$S (SEQ ID NO: 62), wherein X$_1$ is Met, Leu, or Val; (b) an HVR-H2 comprising the amino acid sequence of TISGGKTFTDYVDX$_1$VKG (SEQ ID NO: 63), wherein X$_1$ is Ser or Ala; (c) an HVR-H3 comprising the amino acid sequence of ANYGX$_1$X$_2$FFEV (SEQ ID NO: 64), wherein X$_1$ is Asn or Asp, and X$_2$ is Trp or Phe; (d) an HVR-L1 comprising the amino acid sequence of RASESVAKYGLSLLN (SEQ ID NO: 4); (e) an HVR-L2 comprising the amino acid sequence of AASNRGS (SEQ ID NO: 5); and (f) an HVR-L3 comprising the amino acid sequence of QQSKEVPFT (SEQ ID NO: 6). In some embodiments, the binding domain comprises the following six HVRs: (a) an HVR-H1 comprising the amino acid sequence of SFSMS (SEQ ID NO: 1); (b) an HVR-H2 comprising the amino acid sequence of TISGGKTFTDYVDSVKG (SEQ ID NO: 2); (c) an HVR-H3 comprising the amino acid sequence of ANYGNWFFEV (SEQ ID NO: 3); (d) an HVR-L1 comprising the amino acid sequence of RASESVAKYGLSLLN (SEQ ID NO: 4); (e) an HVR-L2 comprising the amino acid sequence of AASNRGS (SEQ ID NO: 5); and (f) an HVR-L3 comprising the amino acid sequence of QQSKEVPFT (SEQ ID NO: 6).

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 36; (b) a light chain variable (VL) domain comprising an amino acid sequence having at least 95% sequence identity to the amino acid sequence of SEQ ID NO: 37; or (c) a VH domain as in (a) and a VL domain as in (b). In some embodiments, the VH domain further comprises: (a) an FR-H1 comprising the amino acid sequence of EVQLVESGGGLVQPGGSLRLSCAASGFTFS (SEQ ID NO: 12); (b) an FR-H2 comprising the amino acid sequence of WVRQAPGKGLEWVA (SEQ ID NO: 13); (c) an FR-H3 comprising the amino acid sequence of RFTISRDDSKNTLYLQMNSLRAEDTAVYYCTR (SEQ ID NO: 14); and (d) an FR-H4 comprising the amino acid sequence of WGQGTLVTVSS (SEQ ID NO: 15). In some embodiments, the VH domain comprises the amino acid sequence of SEQ ID NO: 36. In some embodiments, the VL domain further comprises: (a) an FR-L1 comprising the amino acid sequence of EIVLTQSPATLSLSPGERATLSC (SEQ ID NO: 25); (b) an FR-L2 comprising the amino acid sequence of WFQQKPGQPPRLLIF (SEQ ID NO: 26); (c) an FR-L3 comprising the amino acid sequence of GIPARFSGSGSGTDFTLTISSLEPEDFAVYYC (SEQ ID NO: 27); and (d) an FR-L4 comprising the amino acid sequence of FGQGTKVEIK (SEQ ID NO: 28). In some embodiments, the VL domain comprises the amino acid sequence of SEQ ID NO: 37. In some embodiments, the VH domain further comprises: (a) an FR-H1 comprising the amino acid sequence of DVNLVESGGGSVKPGGSLKLSCVASGFTFS (SEQ ID NO: 16); (b) an FR-H2 comprising the amino acid sequence of WVRQTPEKRLEWVA (SEQ ID NO: 17); (c) an FR-H3 comprising the amino acid sequence of RFTISRDDAKNTLYLQMSSLESEDTAMYYCTR (SEQ ID NO: 18); and (d) an FR-H4 comprising the amino acid sequence of WGAGTTVAVSS (SEQ ID NO: 19). In some embodiments, the VH domain comprises the amino acid sequence of SEQ ID NO: 38. In some embodiments, the VL domain further comprises: (a) an FR-L1 comprising the amino acid sequence of DIVLTQSPGFLWSLGQRATISC (SEQ ID NO: 29); (b) an FR-L2 comprising the amino acid sequence of WFQQKPGQPPKLLIF (SEQ ID NO: 30); (c) an FR-L3 comprising the amino acid sequence of GVPARFSGSGSGTDFSLNIHPMEEDDTAMYFC (SEQ ID NO: 31); and (d) an FR-L4 comprising the amino acid sequence of FGSGTKLEIK (SEQ ID NO: 32). In some embodiments, the VL domain comprises the amino acid sequence of SEQ ID NO: 39. In some embodiments, the VH domain further comprises: (a) an FR-H1 comprising the amino acid sequence of EVQLVESGGGLVQPGGSLRLSCAASGFTFS (SEQ ID NO: 12) or EVQLVESGGGLVKPGGSLRLSCAASGFTFS (SEQ ID NO: 20); (b) an FR-H2 comprising the amino acid sequence of WVRQAPGKGLEWVA (SEQ ID NO: 13) or WVRQAPGKGLEWVS (SEQ ID NO: 21); (c) an FR-H3 comprising the amino acid sequence of RFTISRDNSKNTLYLQMNSLRAEDTAVYYCTR (SEQ ID NO: 22), RFTISRDDAKNSLYLQMNSLRAEDTAVYYCTR (SEQ ID NO: 23), RFTISRDNAKNSLYLQMNSLRAEDTAVYYCTR (SEQ ID NO: 24), or RFTISRDDSKNTLYLQMNSLRAEDTAVYYCTR (SEQ ID NO: 14); and (d) an FR-H4 comprising the amino acid sequence of WGQGTLVTVSS (SEQ ID NO: 15). In some embodiments, the VH domain comprises the amino acid sequence of SEQ ID NO: 40. In some embodiments, the VL domain further comprises: (a) an FR-L1 comprising the amino acid sequence of EIVLTQSPATLSLSPGERATLSC (SEQ ID NO: 25); (b) an FR-L2 comprising the amino acid sequence of WFQQKPGQPPRLLIF (SEQ ID NO: 26); (c) an FR-L3 comprising the amino acid sequence of GIPARFSGSGSGTDFTLTISSLEPEDFAVYYC (SEQ ID NO: 27), GVPARFSGSGSGTDFTLTISSLEPEDFAVYFC(SEQ ID NO: 33), GVPARFSGSGSGTDFTLTISSLEPEDFAVYYC (SEQ ID NO: 34), or GIPARFSGSGSGTDFTLTISSLEPEDFAVYFC (SEQ ID NO: 35); and (d) an FR-L4 comprising the amino acid sequence of FGQGTKVEIK (SEQ ID NO: 28). In some embodiments, the VL domain comprises the amino acid sequence of SEQ ID NO: 41.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 36 and (b) a VL domain comprising an amino acid sequence having at least 99% sequence identity to the amino acid sequence of SEQ ID NO: 37.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 38 and (b) a VL domain comprising an amino acid sequence having at least 99% sequence identity to the amino acid sequence of SEQ ID NO: 39.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 40 and (b) a VL domain comprising an amino acid sequence having at least 99% sequence identity to the amino acid sequence of SEQ ID NO: 41.

In another aspect, the invention features an isolated antibody that specifically binds IL-33, wherein the antibody comprises a binding domain comprising the following six HVRs: (a) an HVR-H1 comprising the amino acid sequence of SSIFYWG (SEQ ID NO: 65); (b) an HVR-H2 comprising the amino acid sequence of SIYYSGRTYYNPX$_1$LKS (SEQ ID NO: 90), wherein X$_1$ is Ser or Ala; (c) an HVR-H3 comprising the amino acid sequence of AGGLYNWNDESFSFYMDV (SEQ ID NO: 68); (d) an HVR-L1 comprising the amino acid sequence of RASQSFSSSYLA (SEQ ID NO: 69); (e) an HVR-L2 comprising the amino acid sequence of GASSRAT (SEQ ID NO: 70); and (f) an HVR-L3 comprising the amino acid sequence of QQYDRSPLT (SEQ ID NO: 71). In some embodiments, the binding domain comprises the following six HVRs: (a) an HVR-H1 comprising the amino acid sequence of SSIFYWG (SEQ ID NO: 65); (b) an HVR-H2 comprising the amino acid sequence of SIYYSGRTYYNPSLKS (SEQ ID NO: 66); (c) an HVR-H3 comprising the amino acid sequence of AGGLYNWNDESFSFYMDV (SEQ ID NO: 68); (d) an HVR-L1 comprising the amino acid sequence of RASQSFSSSYLA (SEQ ID NO: 69); (e) an HVR-L2 comprising the amino acid sequence of GASSRAT (SEQ ID NO: 70); and (f) an HVR-L3 comprising the amino acid sequence of QQYDRSPLT (SEQ ID NO: 71). In some embodiments, the binding domain comprises the following six HVRs: (a) an HVR-H1 comprising the amino acid sequence of SSIFYWG (SEQ ID NO: 65); (b) an HVR-H2 comprising the amino acid sequence of SIYYSGRTYYNPALKS (SEQ ID NO: 67); (c) an HVR-H3 comprising the amino acid sequence of AGGLYNWNDESFSFYMDV (SEQ ID NO: 68); (d) an HVR-L1 comprising the amino acid sequence of RASQSFSSSYLA (SEQ ID NO: 69); (e) an HVR-L2 comprising the amino acid sequence of GASSRAT (SEQ ID NO: 70); and (f) an HVR-L3 comprising the amino acid sequence of QQYDRSPLT (SEQ ID NO: 71).

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 84; (b) a light chain variable (VL) domain comprising an amino acid sequence having at least 95% sequence identity to the amino acid sequence of SEQ ID NO: 85; or (c) a VH domain as in (a) and a VL domain as in (b). In some embodiments, the VH domain further comprises: (a) an FR-H1 comprising the amino acid sequence of ELQLQESGPGLVKPSETLSLTCTVSGGSIR (SEQ ID NO: 72); (b) an FR-H2 comprising the amino acid sequence of WIRQPPGKGLEWIG (SEQ ID NO: 73); (c) an FR-H3 comprising the amino acid sequence of RVTISVDTSKNQFSLMLTSVTAADTAVYYCAR (SEQ ID NO: 74); and (d) an FR-H4 comprising the amino acid sequence of WGQGTTVTVSS (SEQ ID NO: 75). In some embodiments, the VH domain comprises the amino acid sequence of SEQ ID NO: 84. In some embodiments, the VL domain further comprises: (a) an FR-L1 comprising the amino acid sequence of EIVLTQSPGTLSLSPGERATLSC (SEQ ID NO: 79); (b) an FR-L2 comprising the amino acid sequence of WYQQKPGQAPRLLIY (SEQ ID NO: 80); (c) an FR-L3 comprising the amino acid sequence of GIPDRFSGSGS-GTDFTLTISRLEPEDFAVYYC (SEQ ID NO: 81); and (d) an FR-L4 comprising the amino acid sequence of FGGGT-KVEIK (SEQ ID NO: 82). In some embodiments, the VL domain comprises the amino acid sequence of SEQ ID NO: 85. In some embodiments, the VH domain comprises the amino acid sequence of SEQ ID NO: 86. In some embodiments, the VL domain further comprises: (a) an FR-L1 comprising the amino acid sequence of EIV-LTQSPGTLSLSPGERATLSC (SEQ ID NO: 79); (b) an FR-L2 comprising the amino acid sequence of WYQQK-PGQAPRLLIY (SEQ ID NO: 80); (c) an FR-L3 comprising the amino acid sequence of GIPDRFSGSGSGTDFTLTISR-LEPEDFAVYYC (SEQ ID NO: 81); and (d) an FR-L4 comprising the amino acid sequence of FGGGTKVEIK (SEQ ID NO: 82). In some embodiments, the VL domain comprises the amino acid sequence of SEQ ID NO: 87. In some embodiments, the VH domain further comprises: (a) an FR-H1 comprising the amino acid sequence of QLQLQESGPGLVKPSETLSLTCTVSGGSIR (SEQ ID NO: 76); (b) an FR-H2 comprising the amino acid sequence of WIRQPPGKGLEWIG (SEQ ID NO: 73); (c) an FR-H3 comprising the amino acid sequence of RVTISVDTSKN-QFSLMLTSVTAADTAVYYCAR (SEQ ID NO: 74); and (d) an FR-H4 comprising the amino acid sequence of WGNGTTVTVSS (SEQ ID NO: 78). In some embodiments, the VH domain comprises the amino acid sequence of SEQ ID NO: 88. In some embodiments, the VL domain further comprises: (a) an FR-L1 comprising the amino acid sequence of EIVLTQSPGTLSLSPGERATLSC (SEQ ID NO: 79); (b) an FR-L2 comprising the amino acid sequence of WYQQKPGQAPRLLIY (SEQ ID NO: 80); (c) an FR-L3 comprising the amino acid sequence of GIPDRFSGSGS-GTDFTLTISRLEPEDFAVYYC (SEQ ID NO: 81); and (d) an FR-L4 comprising the amino acid sequence of FGGGT-KVEIK (SEQ ID NO: 82). In some embodiments, the VL domain comprises the amino acid sequence of SEQ ID NO: 89.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 84 and (b) a VL domain comprising an amino acid sequence having at least 99% sequence identity to the amino acid sequence of SEQ ID NO: 85.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 86 and (b) a VL domain comprising an amino acid sequence having at least 99% sequence identity to the amino acid sequence of SEQ ID NO: 87.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 88 and (b) a VL domain comprising an amino acid sequence having at least 99% sequence identity to the amino acid sequence of SEQ ID NO: 89.

In another aspect, the invention features an isolated antibody that specifically binds IL-33, wherein the antibody comprises a binding domain comprising the following six HVRs: (a) an HVR-H1 comprising the amino acid sequence of NYX$_1$MN (SEQ ID NO: 97), wherein X$_1$ is Trp, Phe, or Tyr; (b) an HVR-H2 comprising the amino acid sequence of EITLKFNX$_1$YX$_2$THYAESVKG (SEQ ID NO: 98), wherein X$_1$ is Asn, Asp, Ser, or Ala, and X$_2$ is Ser or Ala; (c) an HVR-H3 comprising the amino acid sequence of RNYGX$_1$X$_2$YINV (SEQ ID NO: 99), wherein X$_1$ is Asp or Asn, and X$_2$ is Trp or Phe; (d) an HVR-L1 comprising the amino acid sequence of RASESVDKFGX$_1$SFLN (SEQ ID NO: 100), wherein X$_1$ is Met, Val, or Leu; (e) an HVR-L2 comprising the amino acid sequence of VASSQGS (SEQ ID NO: 113); and (f) an HVR-L3 comprising the amino acid sequence of QQSKDIPYT (SEQ ID NO: 114). In some embodiments, the binding domain comprises the following six HVRs: (a) an HVR-H1 comprising the amino acid sequence of NYWMN (SEQ ID NO: 101); (b) an HVR-H2 comprising the amino acid sequence of EITLKFN-NYSTHYAESVKG (SEQ ID NO: 104); (c) an HVR-H3 comprising the amino acid sequence of RNYGDWYINV (SEQ ID NO: 109); (d) an HVR-L1 comprising the amino acid sequence of RASESVDKFGMSFLN (SEQ ID NO: 112); (e) an HVR-L2 comprising the amino acid sequence of VASSQGS (SEQ ID NO: 113); and (f) an HVR-L3 comprising the amino acid sequence of QQSKDIPYT (SEQ ID NO: 114). In some embodiments, the binding domain comprises the following six HVRs: (a) an HVR-H1 comprising the amino acid sequence of NYWMN (SEQ ID NO: 101); (b) an HVR-H2 comprising the amino acid sequence of EITLKFNNYSTHYAESVKG (SEQ ID NO: 104); (c) an HVR-H3 comprising the amino acid sequence of RNYGN-WYINV (SEQ ID NO: 110); (d) an HVR-L1 comprising the amino acid sequence of RASESVDKFGMSFLN (SEQ ID NO: 112); (e) an HVR-L2 comprising the amino acid sequence of VASSQGS (SEQ ID NO: 113); and (f) an HVR-L3 comprising the amino acid sequence of QQSK-DIPYT (SEQ ID NO: 114). In some embodiments, the binding domain comprises the following six HVRs: (a) an HVR-H1 comprising the amino acid sequence of NYWMN (SEQ ID NO: 101); (b) an HVR-H2 comprising the amino acid sequence of EITLKFNDYSTHYAESVKG (SEQ ID NO: 105); (c) an HVR-H3 comprising the amino acid sequence of RNYGNWYINV (SEQ ID NO: 110); (d) an HVR-L1 comprising the amino acid sequence of RASES-VDKFGVSFLN (SEQ ID NO: 115); (e) an HVR-L2 comprising the amino acid sequence of VASSQGS (SEQ ID NO: 113); and (f) an HVR-L3 comprising the amino acid sequence of QQSKDIPYT (SEQ ID NO: 114).

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 134; (b) a light chain variable (VL) domain comprising an amino acid sequence having at least 95% sequence identity to the amino acid sequence of SEQ ID NO: 135; or (c) a VH domain as in (a) and a VL domain as in (b). In some embodiments, the VH domain further comprises: (a) an FR-H1 comprising the amino acid sequence of EVKLEESGGGLVQPGGSMKLSCVAS-GFTFS (SEQ ID NO: 117); (b) an FR-H2 comprising the amino acid sequence of WVRQSPEKGLEWMA (SEQ ID NO: 119); (c) an FR-H3 comprising the amino acid sequence of RFSISRDDSKSTVYLQMNNLRAEDTGIYYCAR (SEQ ID NO: 121); and (d) an FR-H4 comprising the amino acid sequence of WGAGTTVTVSS (SEQ ID NO: 124). In some embodiments, the VH domain comprises the amino acid sequence of SEQ ID NO: 134. In some embodiments, the VL domain further comprises: (a) an FR-L1 comprising the amino acid sequence of DIVLTQSPTSLAVS-LGQRATISC (SEQ ID NO: 126); (b) an FR-L2 comprising the amino acid sequence of WFQQKPGQPPKLLIF (SEQ ID NO: 128); (c) an FR-L3 comprising the amino acid sequence of GVPARFSGSGSGTDFSLNIHPVEEDD-TAMYFC (SEQ ID NO: 130); and (d) an FR-L4 comprising the amino acid sequence of FGGGTKLEIK (SEQ ID NO: 132). In some embodiments, the VL domain comprises the amino acid sequence of SEQ ID NO: 135.

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 136; (b) a light chain variable (VL) domain comprising an amino acid sequence having at least 95% sequence identity to the amino acid sequence of SEQ ID NO: 137; or (c) a VH domain as in (a) and a VL domain as in (b). In some embodiments, the VH domain further comprises: (a) an FR-H1 comprising the amino acid sequence of EVQLVESGGGLVQPGGSLRLSCAAS-GFTFS (SEQ ID NO: 118); (b) an FR-H2 comprising the amino acid sequence of WVRQAPGKGLEWMA (SEQ ID NO: 120); (c) an FR-H3 comprising the amino acid sequence of RFTISRDNSKNTVYLQMNSLRAED-TAVYYCAR (SEQ ID NO: 122) or RFTISRDDSKNT-VYLQMNSLRAEDTAVYYCAR (SEQ ID NO: 123); and (d) an FR-H4 comprising the amino acid sequence of WGQGTLVTVSS (SEQ ID NO: 125). In some embodiments, the VH domain comprises the amino acid sequence of SEQ ID NO: 138. In some embodiments, the VL domain further comprises: (a) an FR-L1 comprising the amino acid sequence of DIVMTQSPDSLAVSLGERATINC (SEQ ID NO: 127); (b) an FR-L2 comprising the amino acid sequence of WYQQKPGQPPKLLIF (SEQ ID NO: 129); (c) an FR-L3 comprising the amino acid sequence of GVPDRF-SGSGSGTDFTLTISSLQAEDVAVYYC (SEQ ID NO: 131); and (d) an FR-L4 comprising the amino acid sequence of FGQGTKVEIK (SEQ ID NO: 133). In some embodiments, the VL domain comprises the amino acid sequence of SEQ ID NO: 139.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 134 and (b) a VL domain comprising an amino acid sequence having at least 99% sequence identity to the amino acid sequence of SEQ ID NO: 135.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 136 and (b) a VL domain comprising an amino acid sequence having at least 99% sequence identity to the amino acid sequence of SEQ ID NO: 137.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 138 and (b) a VL domain comprising an amino acid sequence having at least 99% sequence identity to the amino acid sequence of SEQ ID NO: 139.

In another aspect, the invention features an isolated antibody that specifically binds IL-33, wherein the antibody comprises a binding domain comprising the following six HVRs: (a) an HVR-H1 comprising the amino acid sequence of KFWMN (SEQ ID NO: 158); (b) an HVR-H2 comprising the amino acid sequence of EIRLX$_1$X$_2$INYVKDYAESVKG (SEQ ID NO: 161), wherein X$_1$ is Asn or Ser, and X$_2$ is Ser or Ala; (c) an HVR-H3 comprising the amino acid sequence of RNYGNWFFEI (SEQ ID NO: 160); (d) an HVR-L1 comprising the amino acid sequence of RASESVDRYG-ISFMN (SEQ ID NO: 164); (e) an HVR-L2 comprising the amino acid sequence of AASNQGS (SEQ ID NO: 165); and (f) an HVR-L3 comprising the amino acid sequence of QHSKEVPYT (SEQ ID NO: 166). In some embodiments, the binding domain comprises the following six HVRs: (a) an HVR-H1 comprising the amino acid sequence of KFWMN (SEQ ID NO: 158); (b) an HVR-H2 comprising the amino acid sequence of EIRLNSINYVKDYAESVKG (SEQ ID NO: 159); (c) an HVR-H3 comprising the amino acid sequence of RNYGNWFFEI (SEQ ID NO: 160); (d) an HVR-L1 comprising the amino acid sequence of RASES-VDRYGISFMN (SEQ ID NO: 164); (e) an HVR-L2 comprising the amino acid sequence of AASNQGS (SEQ ID NO: 165); and (t) an HVR-L3 comprising the amino acid sequence of QHSKEVPYT (SEQ ID NO: 166). In some embodiments, the binding domain comprises the following six HVRs: (a) an HVR-H1 comprising the amino acid sequence of KFWMN (SEQ ID NO: 158); (b) an HVR-H2 comprising the amino acid sequence of EIRLSSINYVKDY-AESVKG (SEQ ID NO: 162); (c) an HVR-H3 comprising the amino acid sequence of RNYGNWFFEI (SEQ ID NO: 160); (d) an HVR-L1 comprising the amino acid sequence of RASESVDRYGISFMN (SEQ ID NO: 164); (e) an HVR-L2 comprising the amino acid sequence of AASNQGS (SEQ ID NO: 165); and (f) an HVR-L3 comprising the amino acid sequence of QHSKEVPYT (SEQ ID NO: 166). In some embodiments, the binding domain comprises the following six HVRs: (a) an HVR-H1 comprising the amino acid sequence of KFWMN (SEQ ID NO: 158); (b) an HVR-H2 comprising the amino acid sequence of EIRL-NAINYVKDYAESVKG (SEQ ID NO: 163); (c) an HVR-H3 comprising the amino acid sequence of RNYGNWFFEI (SEQ ID NO: 160); (d) an HVR-L1 comprising the amino acid sequence of RASESVDRYGISFMN (SEQ ID NO: 164); (e) an HVR-L2 comprising the amino acid sequence of AASNQGS (SEQ ID NO: 165); and (f) an HVR-L3 comprising the amino acid sequence of QHSKEVPYT (SEQ ID NO: 166).

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 183; (b) a light chain variable (VL) domain comprising an amino acid sequence having at least 95% sequence identity to the amino acid sequence of SEQ ID NO: 184; or (c) a VH domain as in (a) and a VL domain as in (b). In some embodiments, the VH domain further comprises: (a) an FR-H1 comprising the amino acid sequence of EVKLEESGGGLVQPGGSMKLSCVAS-GFTFN (SEQ ID NO: 167); (b) an FR-H2 comprising the amino acid sequence of WVRQSPEKGLEWVA (SEQ ID NO: 168); (c) an FR-H3 comprising the amino acid sequence of RFTISRDDSKNSVYLQMNNLRAEDTGI-YYCIR (SEQ ID NO: 169); and (d) an FR-H4 comprising the amino acid sequence of WGAGTTVTVSS (SEQ ID NO: 170). In some embodiments, the VH domain comprises the amino acid sequence of SEQ ID NO: 183. In some embodiments, the VL domain further comprises: (a) an FR-L1 comprising the amino acid sequence of DIVLTQS-PASLAVSLGQRATISC (SEQ ID NO: 175); (b) an FR-L2 comprising the amino acid sequence of WFQQKPGQSP-KLLIY (SEQ ID NO: 176); (c) an FR-L3 comprising the amino acid sequence of GVPARFSGSGSGTDFSLNIH-PLEEDDAAMYFC (SEQ ID NO: 177); and (d) an FR-L4 comprising the amino acid sequence of FGGGTKLEIK (SEQ ID NO: 178). In some embodiments, the VL domain comprises the amino acid sequence of SEQ ID NO: 184.

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 185; (b) a light chain variable (VL) domain comprising an amino acid sequence having at least 95% sequence identity to the amino acid sequence of SEQ ID NO: 186; or (c) a VH domain as in (a) and a VL domain as in (b). In some embodiments, VH domain further comprises: (a) an FR-H1 comprising the amino acid sequence of EVQLVESGGGLVQPGGSLRLSCAASGFTFN (SEQ ID NO: 171): (b) an FR-H2 comprising the amino acid sequence of WVRQAPGKGLEWVA (SEQ ID NO: 172); (c) an FR-H3 comprising the amino acid sequence of RFTISRDNAKNSVYLQMNSLRAEDTAVYYCIR (SEQ ID NO: 173); and (d) an FR-H4 comprising the amino acid sequence of WGQGTLVTVSS (SEQ ID NO: 174). In some embodiments, the VH domain comprises the amino acid sequence of SEQ ID NO: 185. In some embodiments, the VL domain further comprises: (a) an FR-L1 comprising the amino acid sequence of DIQMTQSPSSLSASVGDRVTITC (SEQ ID NO: 179); (b) an FR-L2 comprising the amino acid sequence of WFQQKPGKAPKLLIY (SEQ ID NO: 180); (c) an FR-L3 comprising the amino acid sequence of GVPSRF-SGSGSGTDFTLTISSLQPEDFATYYC (SEQ ID NO: 181); and (d) an FR-L4 comprising the amino acid sequence of FGQGTKVEIK (SEQ ID NO: 182). In some embodiments, the VL domain comprises the amino acid sequence of SEQ ID NO: 186. In some embodiments, the VH domain comprises the amino acid sequence of SEQ ID NO: 187. In some embodiments, the VL domain comprises the amino acid sequence of SEQ ID NO: 188. In some embodiments, the VH domain comprises the amino acid sequence of SEQ ID NO: 189. In some embodiments, the VL domain comprises the amino acid sequence of SEQ ID NO: 190.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 183 and (b) a VL domain comprising an amino acid sequence having at least 99% sequence identity to the amino acid sequence of SEQ ID NO: 184.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 185 and (b) a VL domain comprising an amino acid sequence having at least 99% sequence identity to the amino acid sequence of SEQ ID NO: 186.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 187 and (b) a VL domain comprising an amino acid sequence having at least 99% sequence identity to the amino acid sequence of SEQ ID NO: 188.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 189 and (b) a VL domain comprising an amino acid sequence having at least 99% sequence identity to the amino acid sequence of SEQ ID NO: 190.

In another aspect, the invention features an isolated antibody that specifically binds IL-33, wherein the antibody comprises a binding domain comprising the following six HVRs: (a) an HVR-H1 comprising the amino acid sequence of DYNMN (SEQ ID NO: 191); (b) an HVR-H2 comprising the amino acid sequence of DINPKX$_1$X$_2$DTFYNQNFKD (SEQ ID NO: 192), wherein X$_1$ is Asn or Ser, and X$_2$ is Gly or Ala; (c) an HVR-H3 comprising the amino acid sequence of HYYYGSSYGGFVY (SEQ ID NO: 196); (d) an HVR-L1 comprising the amino acid sequence of HASQNIN-VWLS (SEQ ID NO: 197); (e) an HVR-L2 comprising the amino acid sequence of AASKLHT (SEQ ID NO: 198); and (f) an HVR-L3 comprising the amino acid sequence of QQGQSYPLT (SEQ ID NO: 199). In some embodiments, the binding domain comprises the following six HVRs: (a) an HVR-H1 comprising the amino acid sequence of DYNMN (SEQ ID NO: 191); (b) an HVR-H2 comprising the amino acid sequence of DINPKNGDTFYNQNFKD (SEQ ID NO: 193); (c) an HVR-H3 comprising the amino acid sequence of HYYYGSSYGGFVY (SEQ ID NO: 196); (d) an HVR-L1 comprising the amino acid sequence of HASQNINVWLS (SEQ ID NO: 197); (e) an HVR-L2 comprising the amino acid sequence of AASKLHT (SEQ ID NO: 198); and (f) an HVR-L3 comprising the amino acid sequence of QQGQSYPLT (SEQ ID NO: 199). In some embodiments, the binding domain comprises the following six HVRs: (a) an HVR-H1 comprising the amino acid sequence of DYNMN (SEQ ID NO: 191); (b) an HVR-H2 comprising the amino acid sequence of DINPKSGDTFYN-QNFKD (SEQ ID NO: 194) or DINPKNADTFYNQNFKD (SEQ ID NO: 195); (c) an HVR-H3 comprising the amino acid sequence of HYYYGSSYGGFVY (SEQ ID NO: 196); (d) an HVR-L1 comprising the amino acid sequence of HASQNINVWLS (SEQ ID NO: 197); (e) an HVR-L2 comprising the amino acid sequence of AASKLHT (SEQ ID NO: 198); and (f) an HVR-L3 comprising the amino acid sequence of QQGQSYPLT (SEQ ID NO: 199).

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 216; (b) a light chain variable (VL) domain comprising an amino acid sequence having at least 95% sequence identity to the amino acid sequence of SEQ ID NO: 217; or (c) a VH domain as in (a) and a VL domain as in (b). In some embodiments, the VH domain further comprises: (a) an FR-H1 comprising the amino acid sequence of EVLLQQSGPELVKPGASVKISCNAS-GYTFS (SEQ ID NO: 200); (b) an FR-H2 comprising the amino acid sequence of WVKQSHGKSLESIG (SEQ ID NO: 201); (c) an FR-H3 comprising the amino acid sequence of KATLTIDKSSSTVYMELRSLTSEDTAMYYCAR (SEQ ID NO: 202); and (d) an FR-H4 comprising the amino acid sequence of WGQGTLVTVAA (SEQ ID NO: 203). In some embodiments, the VH domain comprises the amino acid sequence of SEQ ID NO: 216. In some embodiments, the VL domain further comprises: (a) an FR-L1 comprising the amino acid sequence of DIQMNQSPSSLSASLGDTITITC (SEQ ID NO: 208); (b) an FR-L2 comprising the amino acid sequence of WYQQKAGNNPKLLIY (SEQ ID NO: 209); (c) an FR-L3 comprising the amino acid sequence of GVPSRFTGSGSGTLFTLTISSLQPEDIATYYC (SEQ ID NO: 210); and (d) an FR-L4 comprising the amino acid sequence of FGSGTNLELK (SEQ ID NO: 211). In some embodiments, the VL domain comprises the amino acid sequence of SEQ ID NO: 217.

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 218; (b) a light chain variable (VL) domain comprising an amino acid sequence having at least 95% sequence identity to the amino acid sequence of SEQ ID NO: 219; or (c) a VH domain as in (a) and a VL domain as in (b). In some embodiments, the VH domain further comprises: (a) an FR-H1 comprising the amino acid sequence of EVQLVQSGAEVKKPGASVKVSCKASGYTFS (SEQ ID NO: 204); (b) an FR-H2 comprising the amino acid sequence of WVRQAPGQGLESIG (SEQ ID NO: 205); (c) an FR-H3 comprising the amino acid sequence of RATLTIDKSTSTAYLELSSLRSEDTAVYYCAR (SEQ ID NO: 206); and (d) an FR-H4 comprising the amino acid sequence of WGQGTLVTVSS (SEQ ID NO: 207). In some embodiments, the VH domain comprises the amino acid sequence of SEQ ID NO: 218. In some embodiments, the VL domain further comprises: (a) an FR-L1 comprising the amino acid sequence of DIQMTQSPSSLSASVGDRVTITC (SEQ ID NO: 212); (b) an FR-L2 comprising the amino acid sequence of WYQQKPGKNPKLLIY (SEQ ID NO: 213); (c) an FR-L3 comprising the amino acid sequence of GVPSRFSGSGSGTDFTLTISSLQPEDFATYYC (SEQ ID NO: 214); and (d) an FR-L4 comprising the amino acid sequence of FGQGTKVEIK (SEQ ID NO: 215). In some embodiments, the VL domain comprises the amino acid sequence of SEQ ID NO: 219.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 216 and (b) a VL domain comprising an amino acid sequence having at least 99% sequence identity to the amino acid sequence of SEQ ID NO: 217. In another embodiment, the VH domain comprises the amino acid sequence of SEQ ID NO: 220. In another embodiment, the VL domain comprises the amino acid sequence of SEQ ID NO: 219.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 218 and (b) a VL domain comprising an amino acid sequence having at least 99% sequence identity to the amino acid sequence of SEQ ID NO: 219.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 220 and (b) a VL domain comprising an amino acid sequence having at least 99% sequence identity to the amino acid sequence of SEQ ID NO: 219.

In another aspect, the invention features an isolated antibody that specifically binds IL-33, wherein the antibody comprises a binding domain comprising the following six HVRs: (a) an HVR-H1 comprising the amino acid sequence of SYWIN (SEQ ID NO: 222); (b) an HVR-H2 comprising the amino acid sequence of RIAPGSGFISYNELFKD (SEQ ID NO: 223); (c) an HVR-H3 comprising the amino acid sequence of EFYYGSFYGGFAY (SEQ ID NO: 224); (d) an HVR-L1 comprising the amino acid sequence of HASQNIHVWLS (SEQ ID NO: 225); (e) an HVR-L2 comprising the amino acid sequence of KASTLHT (SEQ ID NO: 226); and (f) an HVR-L3 comprising the amino acid sequence of QQGQSSPLT (SEQ ID NO: 227).

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 236; (b) a light chain variable (VL) domain comprising an amino acid sequence having at least 95% sequence identity to the amino acid sequence of SEQ ID NO: 237; or (c) a VH domain as in (a) and a VL domain as in (b). In some embodiments, the VH domain further comprises: (a) an FR-H1 comprising the amino acid sequence of QVQLQQSGNDLVKPGASVKLSCKASGYTFT (SEQ ID NO: 228); (b) an FR-H2 comprising the amino acid sequence of WIKQRPGQGLEWIG (SEQ ID NO: 229); (c) an FR-H3 comprising the amino acid sequence of KATLTVDTSSSTAYIQLGSLSSEDSAVYFCAR (SEQ ID NO: 230); and (d) an FR-H4 comprising the amino acid sequence of WGQGTLVTVSA (SEQ ID NO: 231). In some embodiments, the VH domain comprises the amino acid sequence of SEQ ID NO: 236. In some embodiments, the VL domain further comprises: (a) an FR-L1 comprising the amino acid sequence of DIQMNQSPSSLSASLGDTITITC (SEQ ID NO: 232); (b) an FR-L2 comprising the amino acid sequence of WYQQKPGNIPKLLIY (SEQ ID NO: 233); (c) an FR-L3 comprising the amino acid sequence of GVPSRFNGSGSGTGFTLTISSLQPEDIATYYC (SEQ ID NO: 234); and (d) an FR-L4 comprising the amino acid sequence of FGAGTKLEVK (SEQ ID NO: 235). In some embodiments, the VL domain comprises the amino acid sequence of SEQ ID NO: 237.

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 246; (b) a light chain variable (VL) domain comprising an amino acid sequence having at least 95% sequence identity to the amino acid sequence of SEQ ID NO: 247; or (c) a VH domain as in (a) and a VL domain as in (b). In some embodiments, the VH domain further comprises: (a) an FR-H1 comprising the amino acid sequence of EVQLVQSGAEVKKPGASVKVSCKASGYTFT (SEQ ID NO: 238); (b) an FR-H2 comprising the amino acid sequence of WVRQAPGQGLEWIG (SEQ ID NO: 239); (c) an FR-H3 comprising the amino acid sequence of RVTITRDTSTSTAYLELSSLRSEDTAVYY- CAR (SEQ ID NO: 240); and (d) an FR-H4 comprising the amino acid sequence of WGQGTLVTVSS (SEQ ID NO: 241). In some embodiments, the VH domain comprises the amino acid sequence of SEQ ID NO: 246. In some embodiments, the VL domain further comprises: (a) an FR-L1 comprising the amino acid sequence of DIQMTQSPSSLSASVGDRVTITC (SEQ ID NO: 242); (b) an FR-L2 comprising the amino acid sequence of WYQQK-PGKAPKLLIY (SEQ ID NO: 243); (c) an FR-L3 comprising the amino acid sequence of GVPSRFSGSGSGTD-FTLTISSLQPEDFATYYC (SEQ ID NO: 244); and (d) an FR-L4 comprising the amino acid sequence of FGQGTK-VEIK (SEQ ID NO: 245). In some embodiments, the VL domain comprises the amino acid sequence of SEQ ID NO: 247.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 236 and (b) a VL domain comprising an amino acid sequence having at least 99% sequence identity to the amino acid sequence of SEQ ID NO: 237.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 246 and (b) a VL domain comprising an amino acid sequence having at least 99% sequence identity to the amino acid sequence of SEQ ID NO: 247.

In another aspect, the invention features an isolated antibody that specifically binds IL-33, wherein the antibody comprises a binding domain comprising the following six HVRs: (a) an HVR-H1 comprising the amino acid sequence of GSAX$_1$H (SEQ ID NO: 248), wherein X$_1$ is Met or Ile; (b) an HVR-H2 comprising the amino acid sequence of RIRSX$_1$X$_2$NX$_3$YATX$_4$YX$_5$ASVKG (SEQ ID NO: 249), wherein X$_1$ is Arg or Lys, X$_2$ is Asn, Thr, or Gly, X$_3$ is Asn or Ser, X$_4$ is Ala or Glu, and X$_5$ is Ala or Asp; (c) an HVR-H3 comprising the amino acid sequence of X$_1$X$_2$X$_3$X$_4$PFDY (SEQ ID NO: 250), wherein X$_1$ is Leu or Gln, X$_2$ is Gln, Gly, or Phe, X$_3$ is Gln or Gly, and X$_4$ is Pro or Asp; (d) an HVR-L1 comprising the amino acid sequence of RASQGIRNDLD (SEQ ID NO: 251); (e) an HVR-L2 comprising the amino acid sequence of AASSLQS (SEQ ID NO: 252); and (f) an HVR-L3 comprising the amino acid sequence of LQHX$_1$X$_2$YPX$_3$T (SEQ ID NO: 253), wherein X$_1$ is Asp or Ser, X$_2$ is Ser or lie, and X$_3$ is Leu or Pro. In some embodiments, the binding domain comprises the following six HVRs: (a) an HVR-H1 comprising the amino acid sequence of GSAMH (SEQ ID NO: 254); (b) an HVR-H2 comprising the amino acid sequence of RIRSRNNNYATAYAASVKG (SEQ ID NO: 255); (c) an HVR-H3 comprising the amino acid sequence of LQQP-PFDY (SEQ ID NO: 256); (d) an HVR-L1 comprising the amino acid sequence of RASQGIRNDLD (SEQ ID NO: 251); (e) an HVR-L2 comprising the amino acid sequence of AASSLQS (SEQ ID NO: 252); and (f) an HVR-L3 comprising the amino acid sequence of LQHDSYPLT (SEQ ID NO: 257). In some embodiments, the binding domain comprises the following six HVRs: (a) an HVR-H1 comprising the amino acid sequence of GSAIH (SEQ ID NO: 258); (b) an HVR-H2 comprising the amino acid sequence of RIRSRTNNYATEYDASVKG (SEQ ID NO: 259); (c) an HVR-H3 comprising the amino acid sequence of LGQP-PFDY (SEQ ID NO: 260); (d) an HVR-L1 comprising the amino acid sequence of RASQGIRNDLD (SEQ ID NO: 251); (e) an HVR-L2 comprising the amino acid sequence of AASSLQS (SEQ ID NO: 252); and (f) an HVR-L3 comprising the amino acid sequence of LQHSIYPPT (SEQ ID NO: 261). In some embodiments, the binding domain comprises the following six HVRs: (a) an HVR-H11 comprising the amino acid sequence of GSAMH (SEQ ID NO: 254); (b) an HVR-H2 comprising the amino acid sequence of RIR-SKGNSYATAYAASVKG (SEQ ID NO: 262); (c) an HVR-H3 comprising the amino acid sequence of QFGDPFDY (SEQ ID NO: 263); (d) an HVR-L1 comprising the amino acid sequence of RASQGIRNDLD (SEQ ID NO: 251); (e) an HVR-L2 comprising the amino acid sequence of AASS-LQS (SEQ ID NO: 252); and (t) an HVR-L3 comprising the amino acid sequence of LQHDSYPLT (SEQ ID NO: 257).

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 282; (b) a light chain variable (VL) domain comprising an amino acid sequence having at least 95% sequence identity to the amino acid sequence of SEQ ID NO: 283; or (c) a VH domain as in (a) and a VL domain as in (b). In some embodiments, the VH domain further comprises: (a) an FR-H1 comprising the amino acid sequence of QVQLVQSGGGLVQPGGSLKLSCAAS-GFTFS (SEQ ID NO: 264); (b) an FR-H2 comprising the amino acid sequence of WVRQASGKGLEWVG (SEQ ID NO: 267); (c) an FR-H3 comprising the amino acid sequence of RFTISRDDSKRTTYLQMNSLKTED-TAVYYCTR (SEQ ID NO: 269); and (d) an FR-H4 comprising the amino acid sequence of WGQGTLVTVSS (SEQ ID NO: 272). In some embodiments, the VH domain comprises the amino acid sequence of SEQ ID NO: 282. In some embodiments, the VL domain further comprises: (a) an FR-L1 comprising the amino acid sequence of DIQMTQSPSSLSASVGDRVTITC (SEQ ID NO: 273); (b) an FR-L2 comprising the amino acid sequence of WYQQK-PGKAPKRLIY (SEQ ID NO: 276); (c) an FR-L3 comprising the amino acid sequence of GVPSRFNGSGS-GTEFTLTISSLQPEDFATYYC (SEQ ID NO: 277); and (d) an FR-L4 comprising the amino acid sequence of FGGGT-KVEIK (SEQ ID NO: 280). In some embodiments, the VL domain comprises the amino acid sequence of SEQ ID NO: 283.

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 284; (b) a light chain variable (VL) domain comprising an amino acid sequence having at least 95% sequence identity to the amino acid sequence of SEQ ID NO: 285; or (c) a VH domain as in (a) and a VL domain as in (b). In some embodiments, the VH domain further comprises: (a) an FR-H1 comprising the amino acid sequence of EVQLVESGGDLVQPGGSLKLSCAAS-GFTFS (SEQ ID NO: 265); (b) an FR-H2 comprising the amino acid sequence of WVRQASGKGLEWVG (SEQ ID NO: 267); (c) an FR-H3 comprising the amino acid sequence of RFTISRDDSKRTAYLQMNSLKTED-TAVYYCTR (SEQ ID NO: 270); and (d) an FR-H4 comprising the amino acid sequence of WGQGTLVTVSS (SEQ ID NO: 272). In some embodiments, the VH domain comprises the amino acid sequence of SEQ ID NO: 284. In some embodiments, the VL domain further comprises: (a) an FR-L1 comprising the amino acid sequence of AIQMTQSPSSLSASVGDRVTITC (SEQ ID NO: 274); (b) an FR-L2 comprising the amino acid sequence of WYQQKPGKAPKRLIY (SEQ ID NO: 276); (c) an FR-L3 comprising the amino acid sequence of GVPSRFSGSGSGTDFTLTISSLQPEDFATYYC (SEQ ID NO: 278); and (d) an FR-L4 comprising the amino acid sequence of FGQGTKVEIK (SEQ ID NO: 281). In some embodiments, the VL domain comprises the amino acid sequence of SEQ ID NO: 285.

In another aspect, the invention features an isolated antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 286; (b) a light chain variable (VL) domain comprising an amino acid sequence having at least 95% sequence identity to the amino acid sequence of SEQ ID NO: 287; or (c) a VH domain as in (a) and a VL domain as in (b). In some embodiments, the VH domain further comprises: (a) an FR-H1 comprising the amino acid sequence of EVQLVESGGGLVQPGGSLKLSCAASGFTFS (SEQ ID NO: 266); (b) an FR-H2 comprising the amino acid sequence of WVRQAPGKGLEWVG (SEQ ID NO: 268); (c) an FR-H3 comprising the amino acid sequence of RFSISRDDSKRTAYLQMSSLKTEDSAVYYCAR (SEQ ID NO: 271); and (d) an FR-H4 comprising the amino acid sequence of WGQGTLVTVSS (SEQ ID NO: 272). In some embodiments, the VH domain comprises the amino acid sequence of SEQ ID NO: 286. In some embodiments, the VL domain further comprises: (a) an FR-L1 comprising the amino acid sequence of AIRITQSPSSLSASVGDRVTITC (SEQ ID NO: 275); (b) an FR-L2 comprising the amino acid sequence of WYQQKPGKAPKRLIY (SEQ ID NO: 276); (c) an FR-L3 comprising the amino acid sequence of GVPSRFSGSGSGTEFTLTISSLQPEDFATYYC (SEQ ID NO: 279); and (d) an FR-L4 comprising the amino acid sequence of FGGGTKVEIK (SEQ ID NO: 280). In some embodiments, the VL domain comprises the amino acid sequence of SEQ ID NO: 287.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 282 and (b) a VL domain comprising an amino acid sequence having at least 99% sequence identity to the amino acid sequence of SEQ ID NO: 283.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 284 and (b) a VL domain comprising an amino acid sequence having at least 99% sequence identity to the amino acid sequence of SEQ ID NO: 285.

In another aspect, the invention features an isolated antibody that specifically binds IL-33, wherein the antibody comprises a binding domain comprising (a) a VH domain comprising an amino acid sequence having at least 99% sequence identity to the amino acid sequence of SEQ ID NO: 286 and (b) a VL domain comprising an amino acid sequence having at least 99% sequence identity to the amino acid sequence of SEQ ID NO: 287.

In another aspect, the invention features an isolated antibody that specifically binds IL-33, wherein the antibody comprises (a) a heavy chain comprising an amino acid sequence having at least 99% sequence identity to the amino acid sequence of SEQ ID NO: 288 and (b) a light chain comprising an amino acid sequence having at least 99% sequence identity to the amino acid sequence of SEQ ID NO: 289.

In another aspect, the invention features an isolated antibody that specifically binds IL-33, wherein the antibody comprises (a) a heavy chain comprising an amino acid sequence having at least 99% sequence identity to the amino acid sequence of SEQ ID NO: 290 and (b) a light chain comprising an amino acid sequence having at least 99% sequence identity to the amino acid sequence of SEQ ID NO: 291.

In another aspect, the invention features an isolated antibody that specifically binds IL-33, wherein the antibody comprises (a) a heavy chain comprising an amino acid sequence having at least 99% sequence identity to the amino acid sequence of SEQ ID NO: 292 and (b) a light chain comprising an amino acid sequence having at least 99% sequence identity to the amino acid sequence of SEQ ID NO: 293.

In another aspect, the invention features an isolated antibody that specifically binds IL-33, wherein the antibody comprises (a) a heavy chain comprising an amino acid sequence having at least 99% sequence identity to the amino acid sequence of SEQ ID NO: 294 and (b) a light chain comprising an amino acid sequence having at least 99% sequence identity to the amino acid sequence of SEQ ID NO: 295.

In some embodiments of any of the preceding aspects, the antibody specifically binds human or cyno IL-33. In some embodiments, the antibody specifically binds both human and cyno IL-33. In some embodiments, the antibody specifically binds both human and cyno IL-33 with a $K_D$ of about 1 nM or lower. In some embodiments, the antibody specifically binds human IL-33 with a $K_D$ between about 100 fM and about 1 nM. In some embodiments, the antibody specifically binds human IL-33 with a $K_D$ between about 1 pM and about 200 pM. In some embodiments, the antibody specifically binds human IL-33 with a $K_D$ between about 75 pM and about 180 pM. In some embodiments, the antibody specifically binds human IL-33 with a $K_D$ between about 75 and about 140 pM. In some embodiments, the antibody specifically binds cyno IL-33 with a $K_D$ between about 100 fM and about 1 nM. In some embodiments, the antibody specifically binds cyno IL-33 with a $K_D$ between about 1 pM and about 500 pM. In some embodiments, the antibody specifically binds cyno IL-33 with a $K_D$ between about 200 and about 500 pM. In some embodiments, the antibody specifically binds cyno IL-33 with a $K_D$ between about 250 and about 500 pM. In some embodiments, the antibody specifically binds both human and cyno IL-33 with a $K_D$ of between about 1 pM and about 500 pM. In some embodiments, the antibody specifically binds human IL-33 with a $K_D$ of between about 1 pM and about 200 pM.

In some embodiments of any of the preceding aspects, the antibody is capable of inhibiting the binding of IL-33 to an IL-33 receptor. In some embodiments, the inhibiting is measured using a cell-based blocking assay. In some embodiments, the antibody inhibits the binding of human IL-33 to an IL-33 receptor with a 90% inhibitory concentration (IC90) of between about 0.001 µg/ml and about 0.5 µg/ml. In some embodiments, the IC90 is between about 0.002 µg/ml and about 0.25 µg/ml. In some embodiments, the IC90 is about 0.17 µg/ml. In some embodiments, the IC90 is about 0.004 µg/ml.

In some embodiments of any of the preceding aspects, the antibody comprises an aglycosylation site mutation.

In some embodiments of any of the preceding aspects, the antibody is monoclonal, human, humanized, or chimeric.

In some embodiments of any of the preceding aspects, the antibody is an antibody fragment that binds IL-33. In some embodiments, antibody fragment is selected from the group consisting of Fab, Fab'-SH, Fv, scFv, and (Fab')₂ fragments.

In some embodiments of any of the preceding aspects, the antibody is a full-length antibody. In some embodiments, the antibody is an IgG antibody. In some embodiments, the IgG antibody is an IgG1 antibody. In some embodiments, the IgG antibody is an IgG4 antibody. In some embodiments, the IgG4 antibody comprises a mutation in the hinge region. In some embodiments, the mutation is a substitution mutation. In some embodiments, the substitution mutation is at amino acid residue S228 (EU numbering). In some embodiments, the substitution mutation is an S228P mutation.

In some embodiments of any of the preceding aspects, the antibody is a monospecific antibody.

In some embodiments of any of the preceding aspects, the antibody is a multispecific antibody. In some embodiments, the antibody is a bispecific antibody. In some embodiments, the bispecific antibody comprises a second binding domain that binds to a second biological molecule, wherein the second biological molecule is selected from the group consisting of interleukin-13 (IL-13), interleukin-4 (IL-4), interleukin-5 (IL-5), interleukin-17 (IL-17), Factor D, HtrA1, VEGF, and a VEGF receptor. In some embodiments, the second biological molecule is Factor D. In some embodiments, the second biological molecule is HtrA1. In some embodiments, the second biological molecule is VEGF. In some embodiments, the second biological molecule is IL-13. In some embodiments, the second binding domain comprises the following six HVRs: (a) an HVR-H1 comprising the amino acid sequence of AYSVN (SEQ ID NO: 296); (b) an HVR-H2 comprising the amino acid sequence of MIWGDGKIVYNSALKS (SEQ ID NO: 297); (c) an HVR-H3 comprising the amino acid sequence of DGYYPYAMDN (SEQ ID NO: 298); (d) an HVR-L1 comprising the amino acid sequence of RASKSVDSYGNSFMH (SEQ ID NO: 299); (e) an HVR-L2 comprising the amino acid sequence of LASNLES (SEQ ID NO: 300); and (f) an HVR-L3 comprising the amino acid sequence of QQNNEDPRT (SEQ ID NO: 301). In some embodiments, the second binding domain comprises (a) a VH domain comprising an amino acid sequence having at least 95% sequence identity to the amino acid sequence of SEQ ID NO: 302; (b) a VL domain comprising an amino acid sequence having at least 95% sequence identity to the amino acid sequence of SEQ ID NO: 303; or (c) a VH domain as in (a) and a VL domain as in (b). In some embodiments, the VH domain comprises the amino acid sequence of SEQ ID NO: 302. In some embodiments, the VL domain comprises the amino acid sequence of SEQ ID NO: 303.

In another aspect, the invention features an isolated antibody that specifically binds both IL-33 and IL-13, wherein the antibody comprises a first binding domain that specifically binds IL-33 comprising the following six HVRs: (a) an HVR-H1 comprising the amino acid sequence of SFSMS (SEQ ID NO: 1); (b) an HVR-H2 comprising the amino acid sequence of TISGGKTFTDYVDSVKG (SEQ ID NO: 2); (c) an HVR-H3 comprising the amino acid sequence of ANYGNWFFEV (SEQ ID NO: 3); (d) an HVR-L1 comprising the amino acid sequence of RASESVAKYGLSLLN (SEQ ID NO: 4); (e) an HVR-L2 comprising the amino acid sequence of AASNRGS (SEQ ID NO: 5); and (f) an HVR-L3 comprising the amino acid sequence of QQSKEVPFT (SEQ ID NO: 6); and a second binding domain that specifically binds IL-13 comprising the following six HVRs: (a) an HVR-H1 comprising the amino acid sequence of AYSVN (SEQ ID NO: 296); (b) an HVR-H2 comprising the amino acid sequence of MIWGDGKIVYNSALKS (SEQ ID NO: 297); (c) an HVR-H3 comprising the amino acid sequence of DGYYPYAMDN (SEQ ID NO: 298); (d) an HVR-L1 comprising the amino acid sequence of RASKSVDSYGNSFMH (SEQ ID NO: 299); (e) an HVR-L2 comprising the amino acid sequence of LASNLES (SEQ ID NO: 300); and (f) an HVR-L3 comprising the amino acid sequence of QQNNEDPRT (SEQ ID NO: 301).

In another aspect, the invention features an isolated antibody that specifically binds both IL-33 and IL-13, wherein the antibody comprises a first binding domain that specifically binds IL-33 comprising the following six HVRs: (a) an HVR-H1 comprising the amino acid sequence of SSIFYWG (SEQ ID NO: 65); (b) an HVR-H2 comprising the amino acid sequence of SIYYSGRTYYNPSLKS (SEQ ID NO: 66); (c) an HVR-H3 comprising the amino acid sequence of AGGLYNWNDESFSFYMDV (SEQ ID NO: 68); (d) an HVR-L1 comprising the amino acid sequence of RASQSFSSSYLA (SEQ ID NO: 69); (e) an HVR-L2 comprising the amino acid sequence of GASSRAT (SEQ ID NO: 70); and (f) an HVR-L3 comprising the amino acid sequence of QQYDRSPLT (SEQ ID NO: 71); and a second binding domain that specifically binds IL-13 comprising the following six HVRs: (a) an HVR-H1 comprising the amino acid sequence of AYSVN (SEQ ID NO: 296); (b) an HVR-H2 comprising the amino acid sequence of MIWGDGKIVYNSALKS (SEQ ID NO: 297); (c) an HVR-H3 comprising the amino acid sequence of DGYYPYAMDN (SEQ ID NO: 298); (d) an HVR-L1 comprising the amino acid sequence of RASKSVDSYGNSFMH (SEQ ID NO: 299); (e) an HVR-L2 comprising the amino acid sequence of LASNLES (SEQ ID NO: 300); and (f) an HVR-L3 comprising the amino acid sequence of QQNNEDPRT (SEQ ID NO: 301).

In another aspect, the invention features an isolated antibody that specifically binds both IL-33 and IL-13, wherein the antibody comprises a first binding domain that specifically binds IL-33 comprising (a) a VH domain comprising an amino acid sequence having at least 99% sequence identity to the amino acid sequence of SEQ ID NO: 36 and (b) a VL domain comprising an amino acid sequence having at least 99% sequence identity to the amino acid sequence of SEQ ID NO: 37, and a second binding domain that specifically binds IL-13 comprising (a) a VH domain comprising an amino acid sequence having at least 99% sequence identity to the amino acid sequence of SEQ ID NO: 302 and (b) a VL domain comprising an amino acid sequence having at least 99% sequence identity to the amino acid sequence of SEQ ID NO: 303.

In another aspect, the invention features an isolated antibody that specifically binds both IL-33 and IL-13, wherein the antibody comprises a first binding domain that specifically binds IL-33 comprising (a) a VH domain comprising an amino acid sequence having at least 99% sequence identity to the amino acid sequence of SEQ ID NO: 84 and (b) a VL domain comprising an amino acid sequence having at least 99% sequence identity to the amino acid sequence of SEQ ID NO: 85, and a second binding domain that specifically binds IL-13 comprising (a) a VH domain comprising an amino acid sequence having at least 99% sequence identity to the amino acid sequence of SEQ ID NO: 302 and (b) a VL domain comprising an amino acid sequence having at least 99% sequence identity to the amino acid sequence of SEQ ID NO: 303.

In another aspect, the invention features an isolated antibody that specifically binds both IL-33 and IL-13, wherein the antibody comprises: (a) a first heavy chain and a first light chain that specifically bind IL-33, wherein the first heavy chain comprises an amino acid sequence having at least 99% sequence identity to the amino acid sequence of SEQ ID NO: 306 and the first light chain comprises an amino acid sequence having at least 99% sequence identity to the amino acid sequence of SEQ ID NO: 307, and (b) a second heavy chain and a second light chain that specifically bind IL-13, wherein the second heavy chain comprises an amino acid sequence having at least 99% sequence identity to the amino acid sequence of SEQ ID NO: 304 and the second light chain comprising an amino acid sequence having at least 99% sequence identity to the amino acid sequence of SEQ ID NO: 305.

In another aspect, the invention features an isolated antibody that specifically binds both IL-33 and IL-13, wherein the antibody comprises: (a) a first heavy chain and a first light chain that specifically bind IL-33, wherein the first heavy chain comprises an amino acid sequence having at least 99% sequence identity to the amino acid sequence of SEQ ID NO: 308 and the first light chain comprises an amino acid sequence having at least 99% sequence identity to the amino acid sequence of SEQ ID NO: 309, and (b) a second heavy chain and a second light chain that specifically bind IL-13, wherein the second heavy chain comprises an amino acid sequence having at least 99% sequence identity to the amino acid sequence of SEQ ID NO: 304 and the second light chain comprising an amino acid sequence having at least 99% sequence identity to the amino acid sequence of SEQ ID NO: 305.

In some embodiments of any of the preceding aspects, the antibody is an antigen-binding antibody fragment. In some embodiments, the antigen-binding antibody fragment is selected from the group consisting of Fab, Fab'-SH, Fv, scFv, and (Fab')$_2$ fragments. In some embodiments, the antigen-binding antibody fragment is an Fab.

In another aspect, the invention features an isolated nucleic acid encoding any of the antibodies described herein. In another aspect, the invention features a vector (e.g., an expression vector) comprising the isolated nucleic acid for expressing the antibody. In another aspect, the invention features host cells comprising the preceding nucleic acids and/or vectors. In some embodiments, the host cell is a mammalian cell. In some embodiments, the mammalian cell is a Chinese hamster ovary (CHO) cell. In some embodiments, the host cell is a prokaryotic cell. In some embodiments, the prokaryotic cell is E. coli.

In another aspect, the invention features a method of producing any of the antibodies described herein, the method comprising culturing a host cell that comprises any of the preceding vectors (e.g., expression vectors) in a culture medium. In some embodiments, the method further comprises recovering the antibody from the host cell or the culture medium.

In another aspect, the invention features a composition comprising any one of the preceding antibodies. In some embodiments, the composition further comprises a pharmaceutically acceptable carrier, excipient, or diluent. In some embodiments, the composition is a pharmaceutical composition. In some embodiments, the pharmaceutical composition further comprises an ST2 binding antagonist, a Factor D binding antagonist, an HtrA1 antagonist, a VEGF antagonist, a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some embodiments, the pharmaceutical composition comprises a Factor D binding antagonist. In some embodiments, the Factor D binding antagonist is an anti-Factor D antibody or an antigen-binding fragment thereof. In some embodiments, the pharmaceutical composition comprises an HtrA1 antagonist. In some embodiments, the HtrA1 binding antagonist is an anti-HtrA1 antibody or an antigen-binding fragment thereof. In some embodiments, the pharmaceutical composition comprises a VEGF antagonist. In some embodiments, the VEGF antagonist is an anti-VEGF antibody or an antigen-binding fragment thereof.

In some aspects, any one of the preceding antibodies can be used as a medicament.

In some aspects, any one of the preceding antibodies can be used in treating an IL-33-mediated disorder. In some embodiments, the IL-33-mediated disorder is selected from the group consisting of an inflammatory condition, an immune disorder, a fibrotic disorder, an eosinophilic disorder, an infection, pain, a central nervous system disorder, a solid tumor, and an ophthalmologic disorder. In some embodiments, the inflammatory condition is selected from the group consisting of asthma, sepsis, septic shock, atopic dermatitis, allergic rhinitis, rheumatoid arthritis, and chronic obstructive pulmonary disease (COPD). In some embodiments, the immune disorder is selected from the group consisting of asthma, rheumatoid arthritis, allergic rhinitis, psoriasis, inflammatory bowel disease (IBD), Crohn's disease, diabetes, and liver disease. In some embodiments, the fibrotic disease is idiopathic pulmonary fibrosis (IPF). In some embodiments, the eosinophilic disorder is an eosinophil-associated gastrointestinal disorder (EGID). In some embodiments, the EGID is eosinophilic esophagitis. In some embodiments, the infection is a helminth infection, a protozoan infection, or a viral infection. In some embodiments, the protozoan infection is a *Leishmania major* infection. In some embodiments, the viral infection is a respiratory syncytial virus (RSV) infection or an influenza infection. In some embodiments, the pain is inflammatory pain. In some embodiments, the central nervous system disorder is Alzheimer's disease. In some embodiments, the solid tumor is selected from the group consisting of breast tumor, colon tumor, prostate tumor, lung tumor, kidney tumor, liver tumor, pancreas tumor, stomach tumor, intestinal tumor, brain tumor, bone tumor, and skin tumor. In some embodiments, the ophthalmologic disorder is selected from the group consisting of age-related macular degeneration (AMD), retinopathy of the eye, polypoidal choroidal vasculopathy (PCV), diabetic macular edema, dry eye disease, Behcet's disease, retina detachment, glaucoma, uveitis, retinitis pigmentosa, Leber Congenital Amaurosis, Stargardt's disease, traumatic eye injury, and conjunctivitis. In some embodiments, the AMD is wet AMD, dry AMD, or geographic atrophy (GA). In some embodiments, the AMD is intermediate AMD or advanced AMD. In some embodiments, the retinopathy of the eye is diabetic retinopathy (DR) or retinopathy of prematurity (ROP). In some embodiments, the retinopathy of the eye is high-altitude DR. In some embodiments, the conjunctivitis is infectious conjunctivitis or non-infectious conjunctivitis. In some embodiments, the conjunctivitis is allergic conjunctivitis.

In some aspects, any one of the preceding antibodies can be used in the manufacture of a medicament for treating an IL-33-mediated disorder. In some embodiments, the IL-33-mediated disorder is selected from the group consisting of an inflammatory condition, an immune disorder, a fibrotic disorder, an eosinophilic disorder, an infection, pain, a central nervous system disorder, a solid tumor, and an ophthalmologic disorder. In some embodiments, the inflammatory condition is selected from the group consisting of asthma, sepsis, septic shock, atopic dermatitis, allergic rhinitis, rheumatoid arthritis, and chronic obstructive pulmonary disease (COPD). In some embodiments, the immune disorder is selected from the group consisting of asthma, rheumatoid arthritis, allergic rhinitis, psoriasis, inflammatory bowel disease (IBD), Crohn's disease, diabetes, and liver disease. In some embodiments, the fibrotic disease is idiopathic pulmonary fibrosis (IPF). In some embodiments, the eosinophilic disorder is an eosinophil-associated gastrointestinal disorder (EGID). In some embodiments, the EGID is eosinophilic esophagitis. In some embodiments, the infection is a helminth infection, a protozoan infection, or a viral infection. In some embodiments, the protozoan infection is a *Leishmania major* infection. In some embodiments, the viral infection is a respiratory syncytial virus (RSV) infection or an influenza infection. In some embodiments, the pain is inflammatory pain. In some embodiments, the central nervous system disorder is Alzheimer's disease. In some embodiments, the solid tumor is selected from the group consisting of breast tumor, colon tumor, prostate tumor, lung tumor, kidney tumor, liver tumor, pancreas tumor, stomach tumor, intestinal tumor, brain tumor, bone tumor, and skin tumor. In some embodiments, the ophthalmologic disorder is selected from the group consisting of age-related macular degeneration (AMD), retinopathy of the eye, polypoidal choroidal vasculopathy (PCV), diabetic macular edema, dry eye disease, Behcet's disease, retina detachment, glaucoma, uveitis, retinitis pigmentosa, Leber Congenital Amaurosis, Stargardt's disease, traumatic eye injury, and conjunctivitis. In some embodiments, the AMD is wet AMD, dry AMD, or geographic atrophy (GA). In some embodiments, the AMD is intermediate AMD or advanced AMD. In some embodiments, the retinopathy of the eye is diabetic retinopathy (DR) or retinopathy of prematurity (ROP). In some embodiments, the retinopathy of the eye is high-altitude DR. In some embodiments, the conjunctivitis is infectious conjunctivitis or non-infectious conjunctivitis. In some embodiments, the conjunctivitis is allergic conjunctivitis. In some embodiments, the medicament is formulated for use in combination with an ST2 binding antagonist, a Factor D binding antagonist, an HtrA1 binding antagonist, a VEGF antagonist, a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some embodiments, the medicament is formulated for use in combination with a Factor D binding antagonist. In some embodiments, the Factor D binding antagonist is an anti-Factor D antibody or an antigen-binding fragment thereof. In some embodiments, the medicament is formulated for use in combination with an HtrA1 binding antagonist. In some embodiments, the HtrA1 binding antagonist is an anti-HtrA1 antibody or an antigen-binding fragment thereof. In some embodiments, the medicament is formulated for use in combination with a VEGF antagonist. In some embodiments, the VEGF antagonist is an anti-VEGF antibody or an antigen-binding fragment thereof.

In another aspect, the invention provides for the use of a bispecific antibody that specifically binds both IL-33 and Factor D or an antigen-binding antibody fragment thereof in the manufacture of a medicament for treating geographic atrophy (GA). In some embodiments, the antigen-binding antibody fragment is a (Fab')$_2$ fragment.

In another aspect, any one of the preceding antibodies can be used in the manufacture of a medicament for treating geographic atrophy (GA), wherein the medicament is formulated for use in combination with a Factor D binding antagonist. In some embodiments, the Factor D binding antagonist is an anti-Factor D antibody or an antigen-binding fragment thereof.

In another aspect, the invention provides for the use of a bispecific antibody that specifically binds both IL-33 and HtrA1 or an antigen-binding antibody fragment thereof in the manufacture of a medicament for treating geographic atrophy (GA), AMD (wet or dry), DR, PCV, or ROP. In some embodiments, the antigen-binding antibody fragment is a (Fab')$_2$ fragment.

In another aspect, any one of the preceding antibodies can be used in the manufacture of a medicament for treating geographic atrophy (GA), AMD (wet or dry), DR, PCV, or ROP, wherein the medicament is formulated for use in combination with an HtrA1 binding antagonist. In some embodiments, the HtrA1 binding antagonist is an anti-HtrA1 antibody or an antigen-binding fragment thereof.

In another aspect, the invention provides for the use of a bispecific antibody that specifically binds both IL-33 and VEGF or an antigen-binding antibody fragment thereof in the manufacture of a medicament for treating wet AMD. In some embodiments, the antigen-binding antibody fragment is a (Fab')$_2$ fragment.

In another aspect, any one of the preceding antibodies can be used in the manufacture of a medicament for treating wet AMD, wherein the medicament is formulated for use in combination with a VEGF antagonist. In some embodiments, the VEGF antagonist is an anti-VEGF antibody or an antigen-binding fragment thereof.

In another aspect, the invention features a method of treating an IL-33-mediated disorder in a subject in need thereof, the method comprising administering to the subject a therapeutically effective amount of any one of the preceding antibodies. In some embodiments, the IL-33-mediated disorder is selected from the group consisting of an inflammatory condition, an immune disorder, a fibrotic disorder, an eosinophilic disorder, an infection, pain, a central nervous system disorder, a solid tumor, and an ophthalmologic disorder. In some embodiments, the inflammatory condition is selected from the group consisting of asthma, sepsis, septic shock, atopic dermatitis, allergic rhinitis, rheumatoid arthritis, and chronic obstructive pulmonary disease (COPD). In some embodiments, the immune disorder is selected from the group consisting of asthma, rheumatoid arthritis, allergic rhinitis, psoriasis, inflammatory bowel disease (IBD), Crohn's disease, diabetes, and liver disease. In some embodiments, the fibrotic disease is idiopathic pulmonary fibrosis (IPF). In some embodiments, the eosinophilic disorder is an eosinophil-associated gastrointestinal disorder (EGID). In some embodiments, the EGID is eosinophilic esophagitis. In some embodiments, the infection is a helminth infection, a protozoan infection, or a viral infection. In some embodiments, the protozoan infection is a *Leishmania major* infection. In some embodiments, the viral infection is a respiratory syncytial virus (RSV) infection or an influenza infection. In some embodiments, the pain is inflammatory pain. In some embodiments, the central nervous system disorder is Alzheimer's disease. In some embodiments, the solid tumor is selected from the group consisting of breast tumor, colon tumor, prostate tumor, lung tumor, kidney tumor, liver tumor, pancreas tumor, stomach tumor, intestinal tumor, brain tumor, bone tumor, and skin tumor. In some embodiments, the ophthalmologic disorder is selected from the group consisting of age-related macular degeneration (AMD), retinopathy of the eye, polypoidal choroidal vasculopathy (PCV), diabetic macular edema, dry eye disease, Behcet's disease, retina detachment, glaucoma, uveitis, retinitis pigmentosa, Leber Congenital Amaurosis, Stargardt's disease, traumatic eye injury, and conjunctivitis. In some embodiments, the AMD is wet AMD, dry AMD, or geographic atrophy (GA). In some embodiments, the AMD is intermediate AMD or advanced AMD. In some embodiments, the retinopathy of the eye is diabetic retinopathy (DR) or retinopathy of prematurity (ROP). In some embodiments, the retinopathy of the eye is high-altitude DR. In some embodiments, the conjunctivitis is infectious conjunctivitis or non-infectious conjunctivitis. In some embodiments, the conjunctivitis is allergic conjunctivitis. In some embodiments, the method further comprises administering to the subject an ST2 binding antagonist, a Factor D binding antagonist, an HtrA1 binding antagonist, a VEGF antagonist, a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some embodiments, the method further comprises administering to the subject a Factor D binding antagonist. In some embodiments, the Factor D binding antagonist is anti-Factor D antibody or an antigen-binding fragment thereof. In some embodiments, the method further comprises administering to the subject an HtrA1 binding antagonist. In some embodiments, the HtrA1 binding antagonist is anti-HtrA1 antibody or an antigen-binding fragment thereof.

In some embodiments, the method further comprises administering to the subject a VEGF antagonist. In some embodiments, the VEGF antagonist is an anti-VEGF antibody or an antigen-binding fragment thereof.

In another aspect, the invention features a method of treating geographic atrophy (GA) in a subject in need thereof, the method comprising administering to the subject a therapeutically effective amount of a bispecific antibody that specifically binds both IL-33 and Factor D or an antigen-binding antibody fragment thereof. In some embodiments, the antigen-binding antibody fragment is a (Fab')$_2$ fragment.

In another aspect, the invention features a method of treating geographic atrophy (GA) in a subject in need thereof, the method comprising administering to the subject a therapeutically effective amount of any one of the preceding antibodies and a therapeutically effective amount of a Factor D binding antagonist. In some embodiments, the Factor D binding antagonist is an anti-Factor D antibody or an antigen-binding fragment thereof.

In another aspect, the invention features a method of treating geographic atrophy (GA), AMD (wet or dry), DR, PCV, or ROP in a subject in need thereof, the method comprising administering to the subject a therapeutically effective amount of a bispecific antibody that specifically binds both IL-33 and HtrA1 or an antigen-binding antibody fragment thereof. In some embodiments, the antigen-binding antibody fragment is a (Fab')$_2$ fragment.

In another aspect, the invention features a method of treating geographic atrophy (GA), AMD (wet or dry), DR, PCV, or ROP in a subject in need thereof, the method comprising administering to the subject a therapeutically effective amount of any one of the preceding antibodies and a therapeutically effective amount of a HtrA1 binding antagonist. In some embodiments, the HtrA1 binding antagonist is an anti-HtrA1 antibody or an antigen-binding fragment thereof.

In another aspect, the invention features a method of treating wet AMD in a subject in need thereof, the method comprising administering to the subject a therapeutically effective amount of a bispecific antibody that specifically binds both IL-33 and VEGF or an antigen-binding antibody fragment thereof. In some embodiments, the antigen-binding antibody fragment is a (Fab')$_2$ fragment.

In another aspect, the invention features a method of treating wet AMD in a subject in need thereof, the method comprising administering to the subject a therapeutically effective amount of any one of the preceding antibodies and a therapeutically effective amount of a VEGF antagonist. In some embodiments, the VEGF antagonist is an anti-VEGF antibody or an antigen-binding fragment thereof.

In some embodiments of any of the preceding methods, the antibody is administered subcutaneously, intravenously, intramuscularly, topically, orally, transdermally, intraperitoneally, intraorbitally, by implantation, by inhalation, intrathecally, intraventricularly, intranasally, intravitreally, intraocularly, periocularly, conjunctivally, subconjunctivally, subtenonly, intracamerally, subretinally, retrobulbarly, or intracanalicularly. In some embodiments, the subject is a human.

BRIEF DESCRIPTION OF THE DRAWINGS

The application file contains at least one drawing executed in color. Copies of this patent or patent application with color drawings will be provided by the Office upon request and payment of the necessary fee.

FIG. 3 is a table showing the results of cell-based IL-33 blocking assays (IC$_{50}$ and IC$_{90}$) for the indicated parental and humanized anti-IL-33 antibodies.

FIG. 11B is a table showing Gene Ontology (GO) analysis of genes with decreased expression in $ST2^{-/-}$ mice compared to $ST2^{+/+}$ mice (see FIG. 11A). The top 17 enriched GO terms are shown.

FIG. 16C shows the results from ST2$^{+/+}$ (WT) or ST2$^{-/-}$ (KO) mice treated with IgE and IL-33 without DNP-HSA addition. FIG. 16D shows the results from ST2$^{+/+}$ (WT) or ST2$^{-/-}$ (KO) mice treated with IgE and DNP-HSA without IL-33 addition.

The top panel shows a schematic diagram of the experiment. The graphs in the bottom panel show the results from the mast cell cytokine measurements following stimulation with IL-33 and IgE crosslinking for IL-5 (left), IL-13 (middle), and IL-8 (right).

Figure 16A:
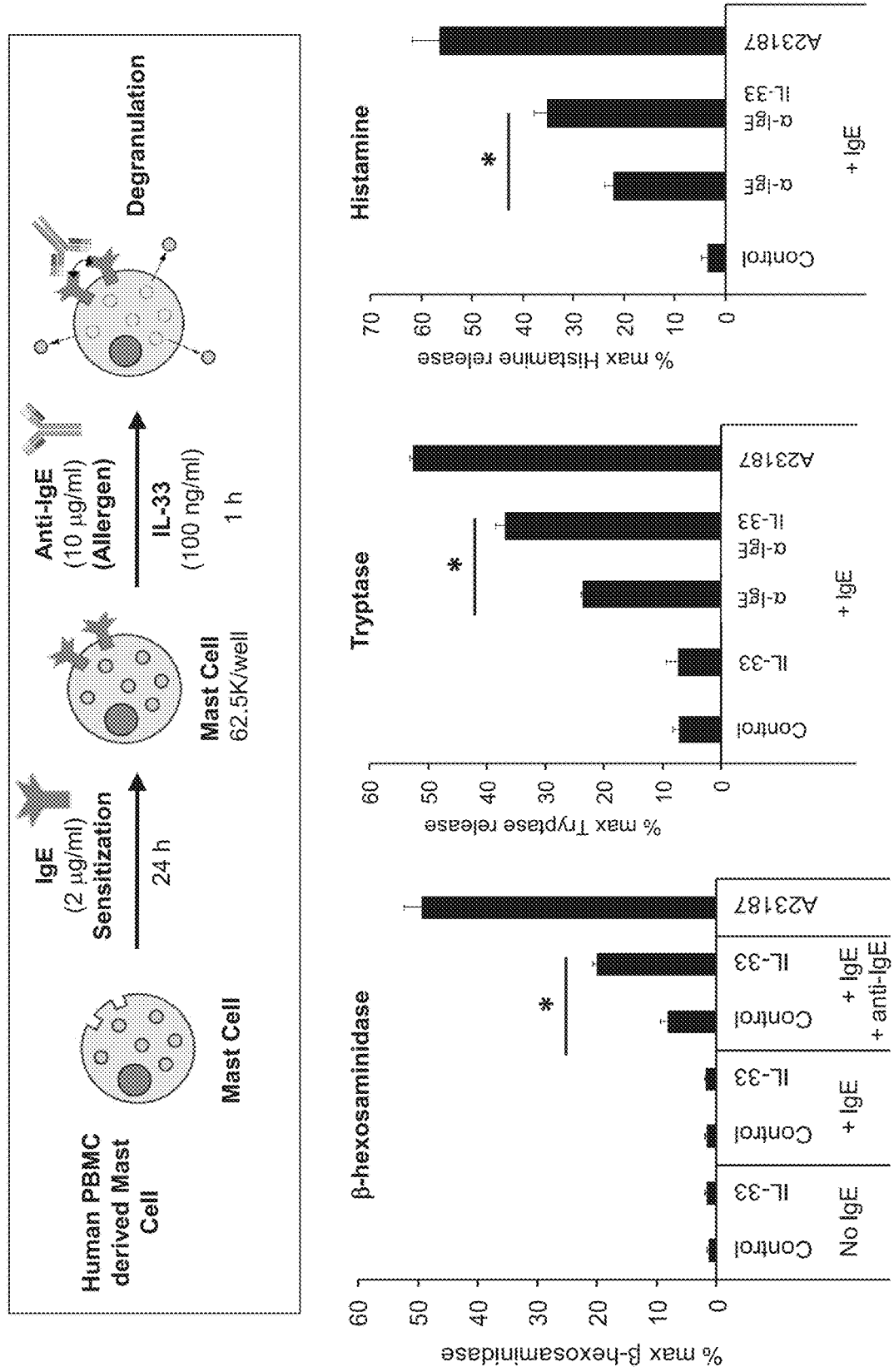
FIG. 16A shows augmentation of mast cell degranulation by IL-33. The top panel shows a schematic diagram of the mast cell degranulation assay, and the bottom panel shows graphs of results from the mast cell degranulation assay for β-hexaminodase (left), tryptase (middle), and histamine (right).
Figure 16B:
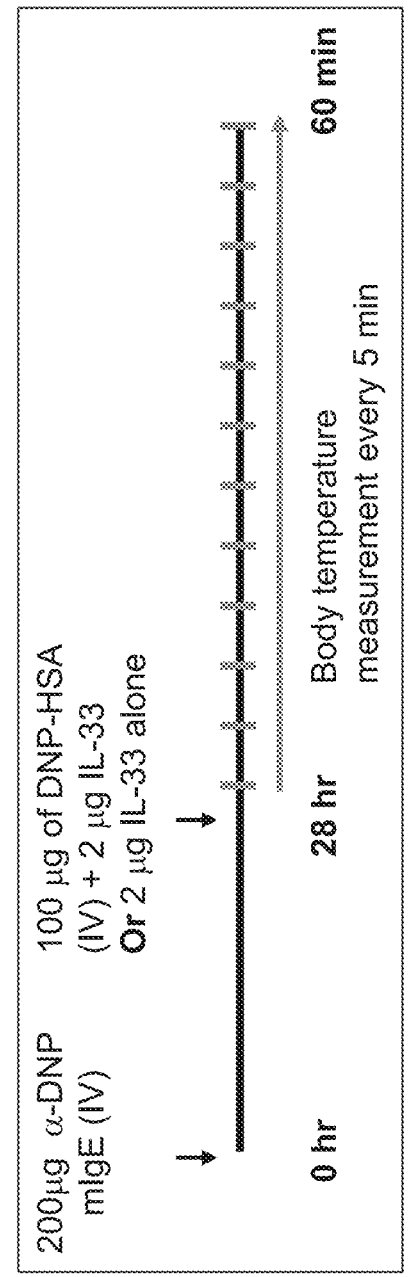
FIG. 16B is a schematic diagram showing the systemic anaphylaxis assay described in Example 5.
Figures 16C, 16D:
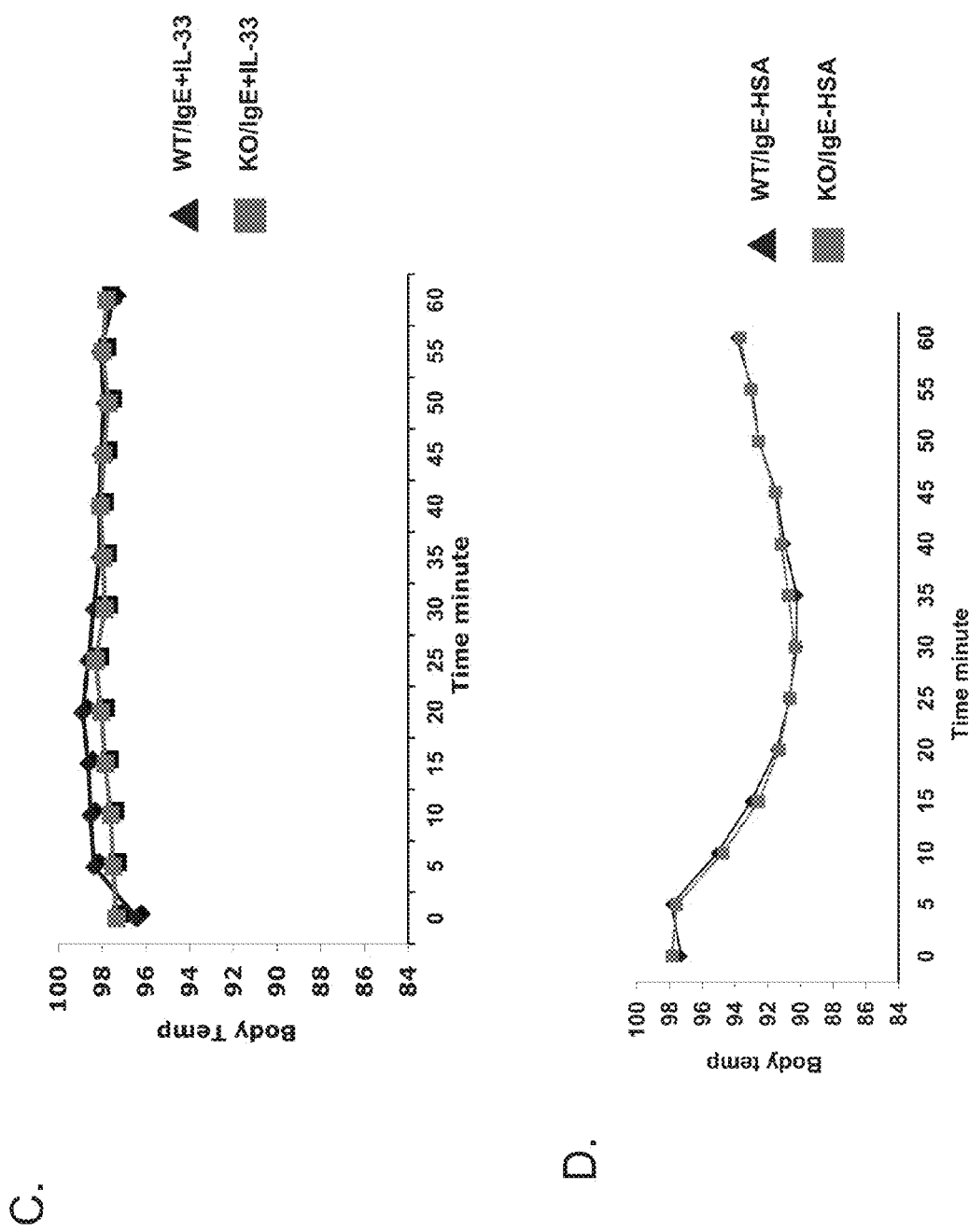
FIGS. 16C and 16D are graphs showing the results from the passive systemic anaphylaxis assay (see, e.g., FIG. 16B).
Figure 16E:
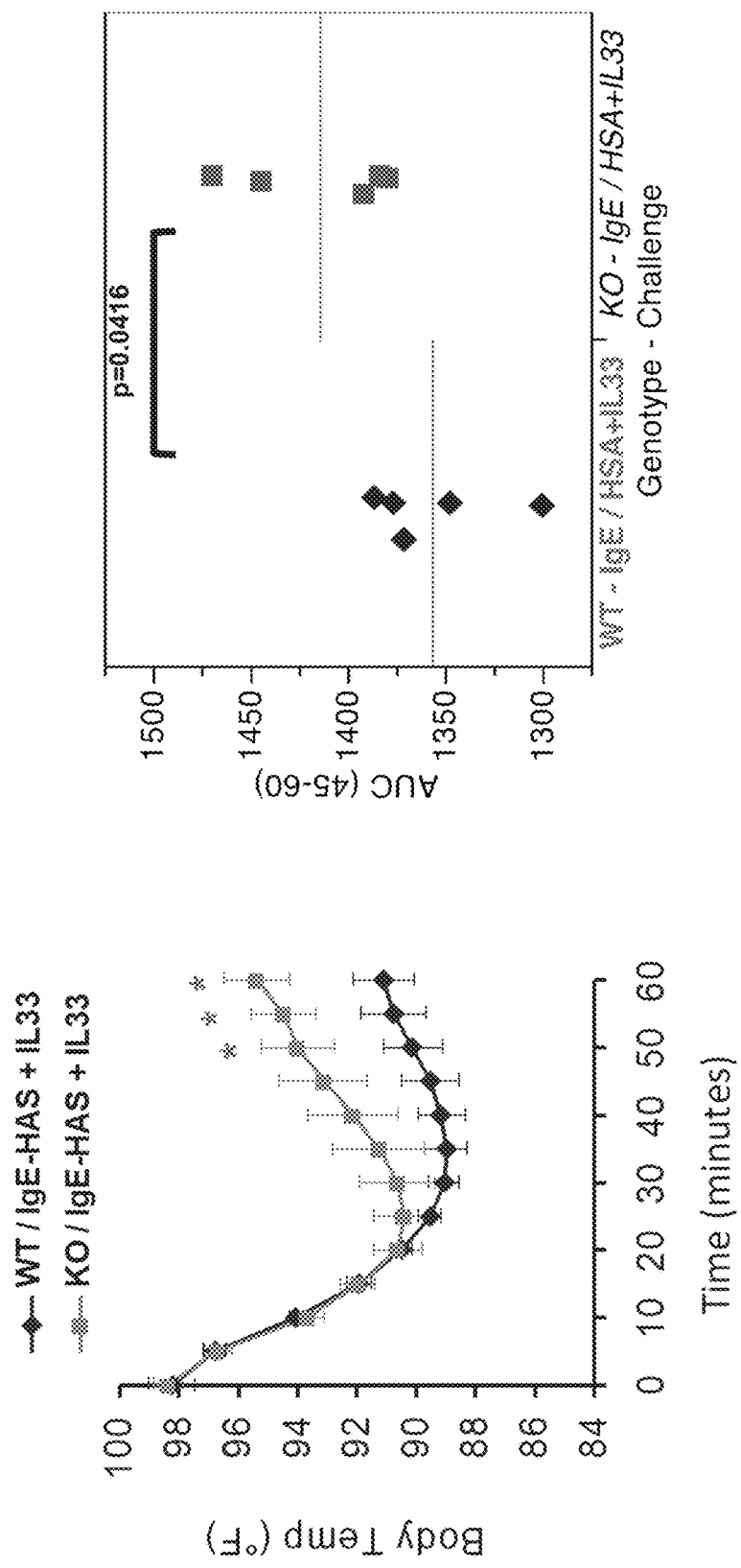
FIG. 16E shows a series of graphs showing the results from the passive systemic anaphylaxis assay. The graph in the left panel shows body temperature (° F.) as a function of time (min) for ST2$^{+/+}$ (WT) or ST2$^{-/-}$ (KO) mice treated with IgE, DNP-HSA, and IL-33. The graph in the right panel shows the area under the curve (AUC) from 45 to 60 min for the indicated genotype and challenge.
Figure 16F:
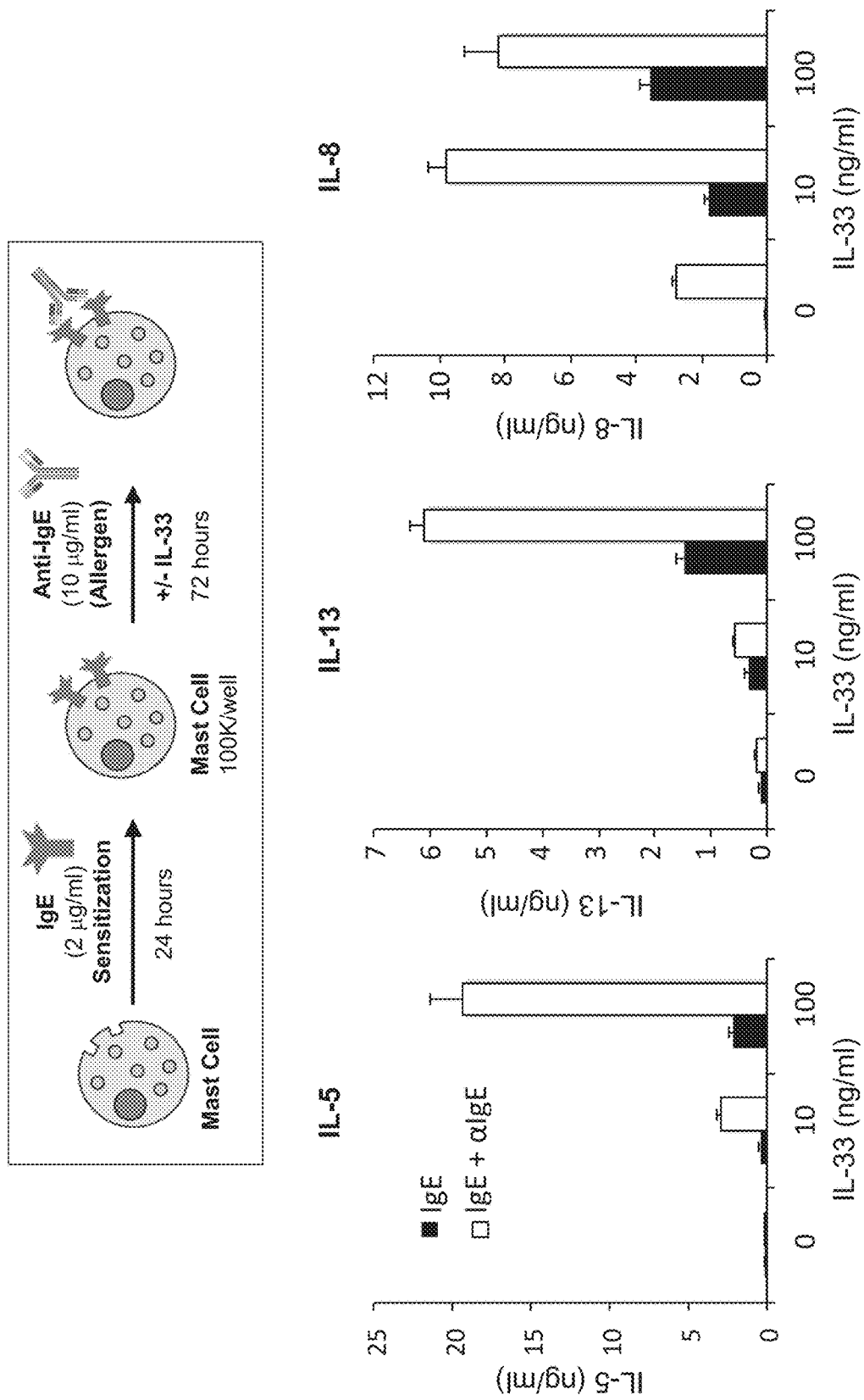
FIG. 16F shows that IL-33 enhances IgE crosslinking-dependent cytokine secretion by human mast cells in vitro.
Figure 16G:
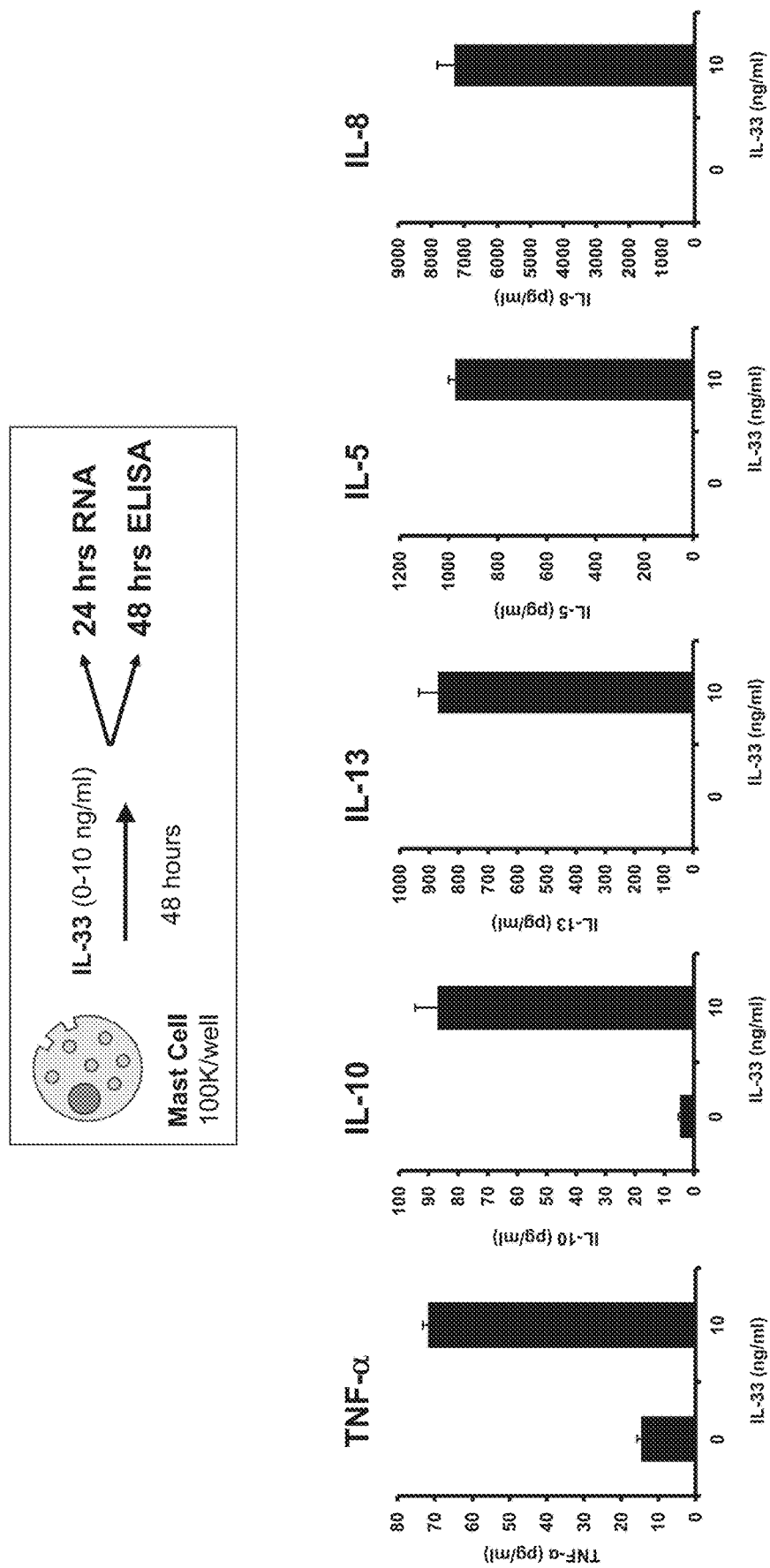

FIG. 16G shows that IL-33 directly stimulates mast cell cytokine secretion independent of IgE or antigen in vitro. The top panel shows a schematic diagram of the experiment. The graphs in the bottom panel show the results of ELISA experiments to determine the expression level of the indicated cytokine (TNF-α, IL-10, IL-13, IL-5, or IL-8) in the absence of IL-33 (0 ng/ml) or in the presence of 10 ng/mL IL-33.

Figure 16H:
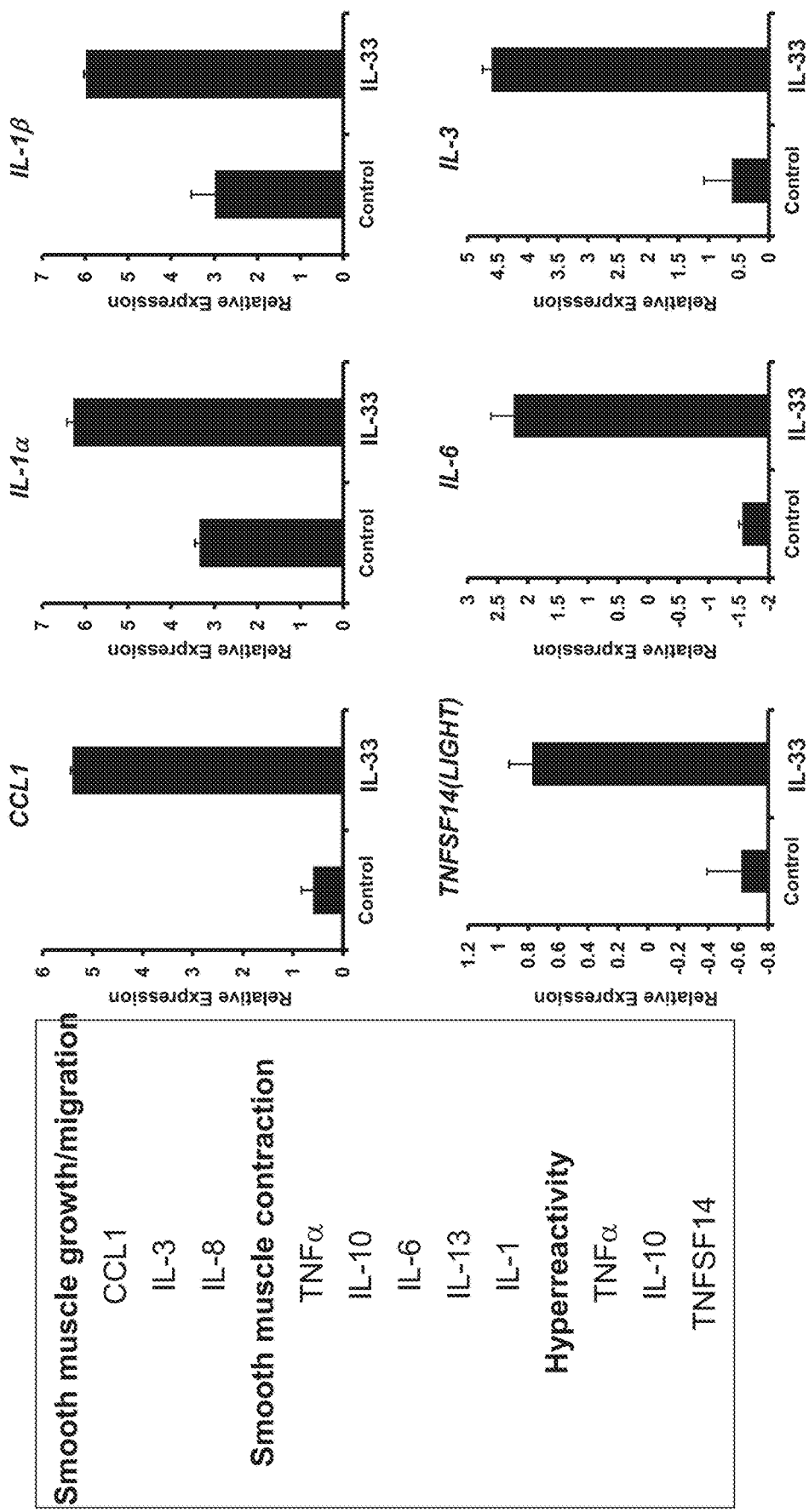

FIG. 16H is a series of graphs showing the relative expression of the indicated genes in mast cells following IL-33 stimulation as determined by microarray analysis. The left panel shows examples of genes that were upregulated following IL-33 stimulation, which included genes involved in smooth muscle growth/migration (e.g., CCL1, IL-3, and IL-8); genes involved in smooth muscle contraction (e.g., TNFα, IL-10, IL-6, IL13, and IL-3); and genes involved in hyperreactivity (e.g., TNFα, IL-10, and TNFSF14).

Figure 17A:
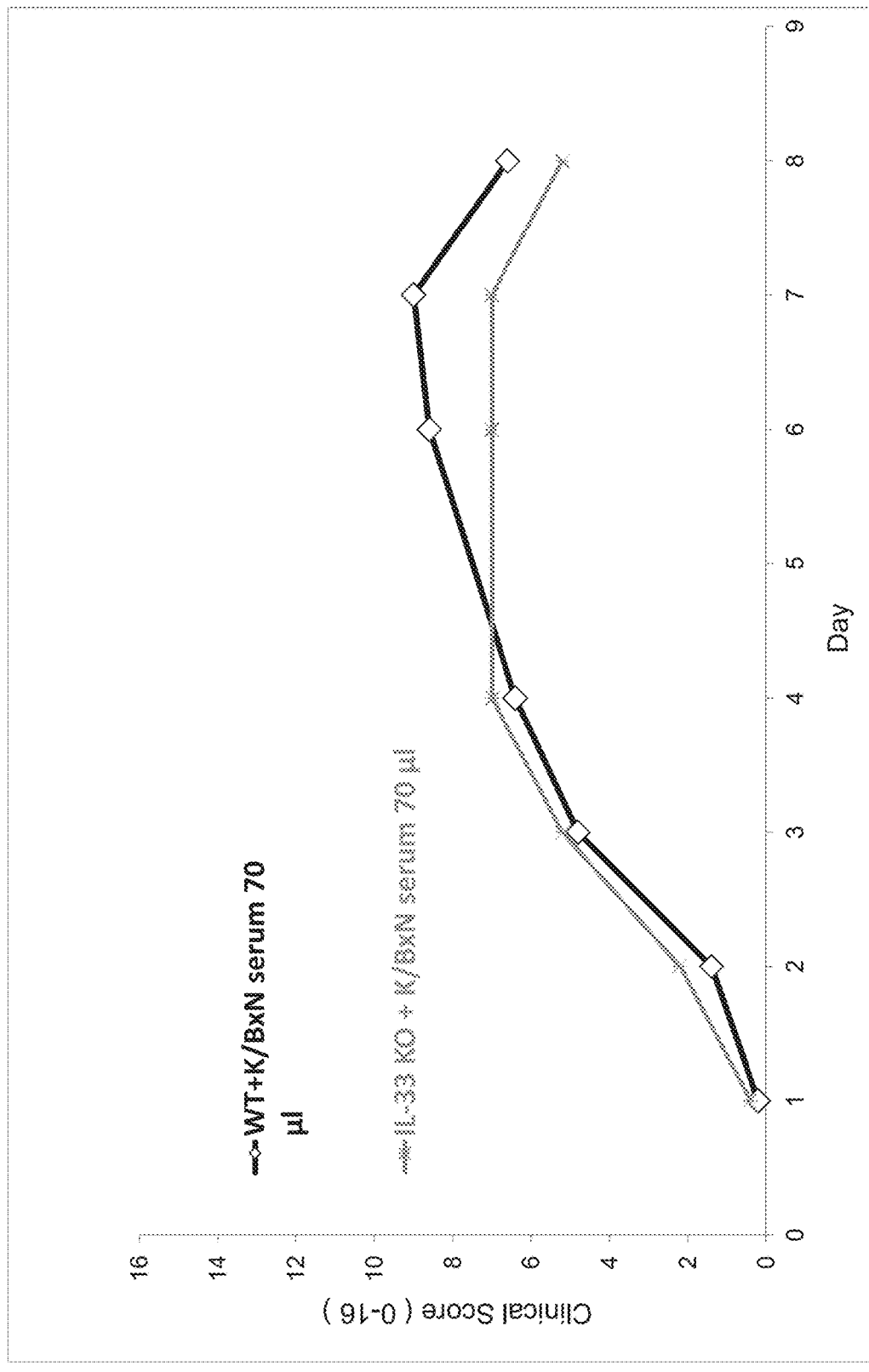

FIG. 17A is a graph showing the arthritic scores from a K/BxN serum transfer experiment as described in Example 6 in IL33$^{-/-}$ mice as compared to an IL33$^{+/+}$ mice. The data represent averages from groups of ST2$^{-/-}$ or ST2$^{+/+}$ mice.

Figure 17B:
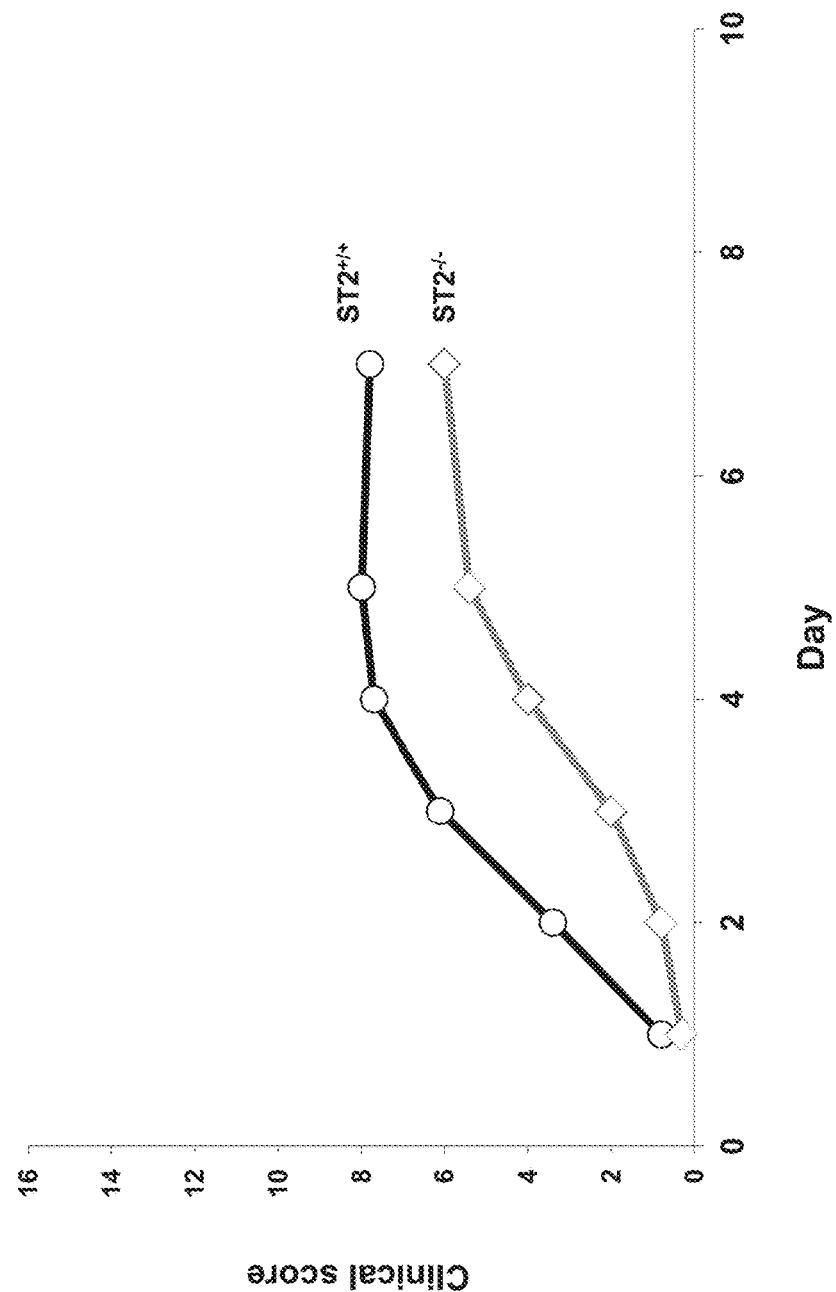

FIG. 17B is a graph showing the arthritic scores from a K/BxN serum transfer experiment as described in Example 6 in ST2$^{-/-}$ mice as compared to wild-type (ST2$^{+/+}$) mice (C57BI/6 background). The data represent averages from groups of ST2$^{-/-}$ or ST2$^{+/+}$ mice. Similar results were obtained using the ST2$^{-/-}$ genotype in the Balb/C background.

Figures 17C, 17D:
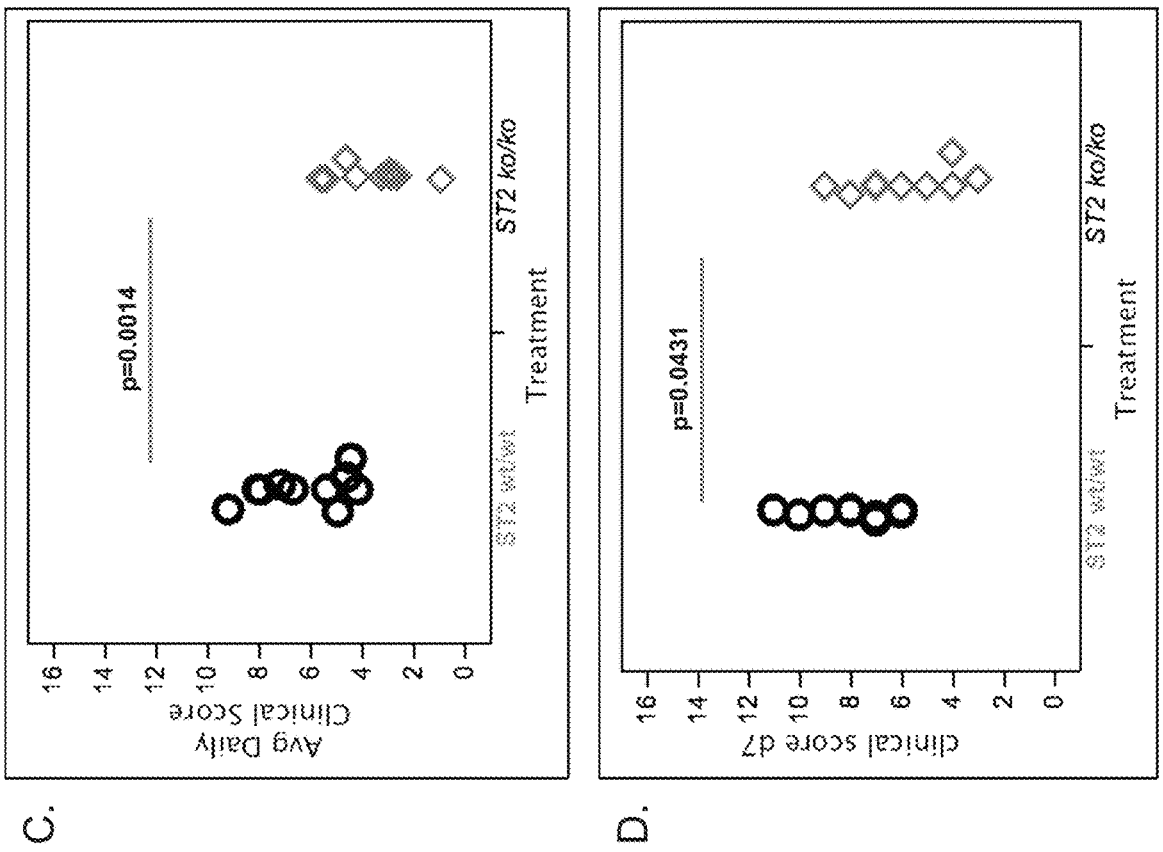

FIGS. 17C-17D are graphs showing the arthritic scores from the K/BxN serum transfer studies in ST2$^{-/-}$ mice compared to wild-type (ST2$^{+/+}$) mice. FIG. 17C shows the average daily clinical score across the entire experiment, while FIG. 17D shows the clinical score at day 7 for individual mice.

Figure 18A:
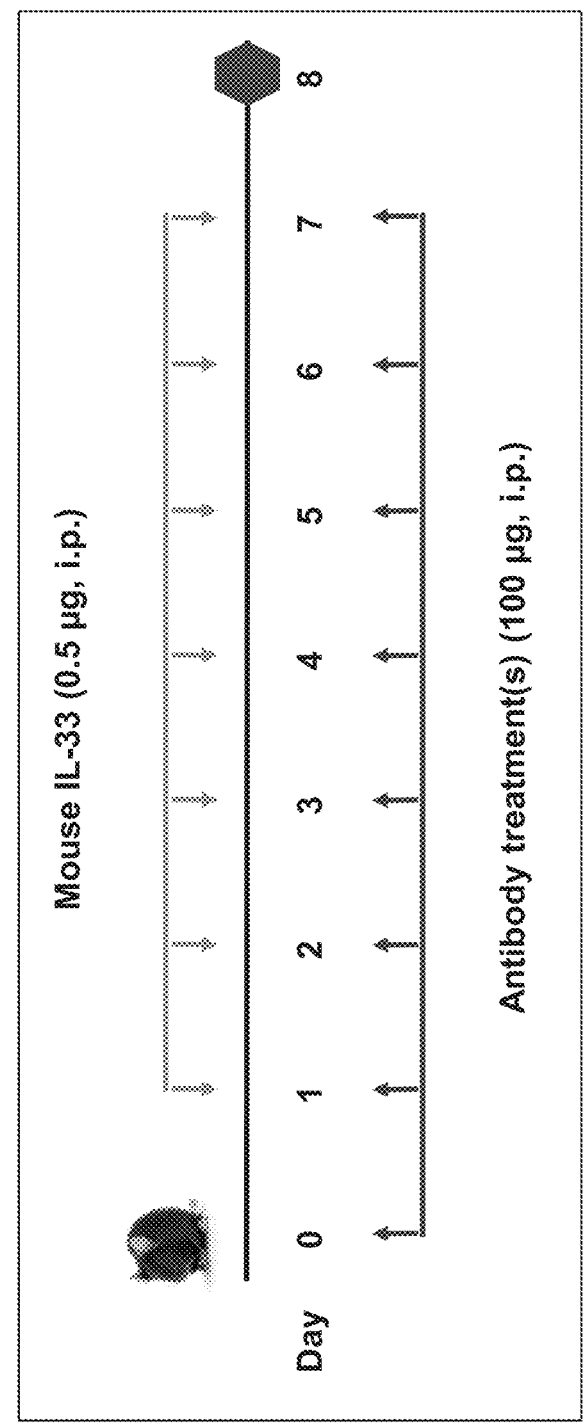

FIG. 18A is schematic diagram of an experiment to determine whether IL-33-induced macrophage recruitment depends on IL-4, IL-5, and IL-13, as described in Example 7.

Figure 18B:
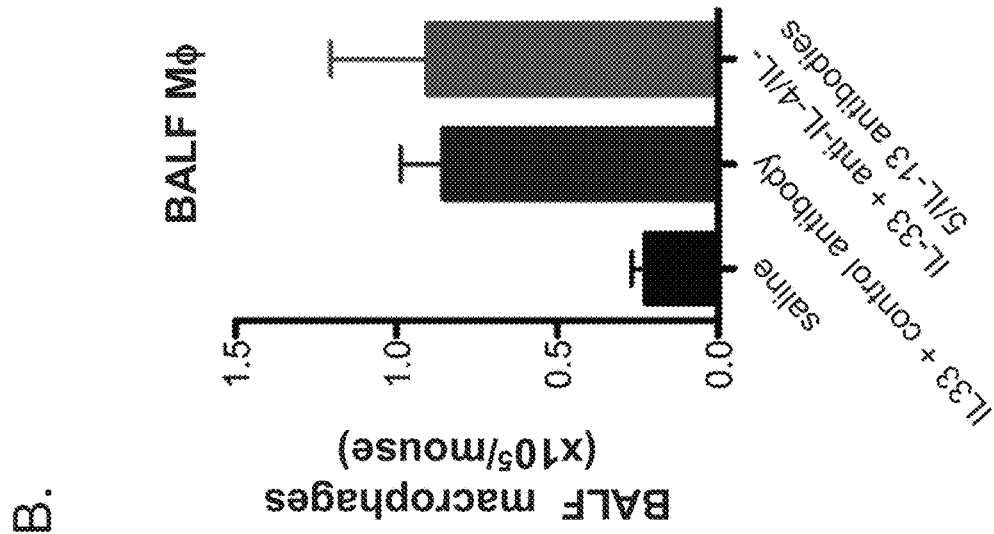
Figure 18C:
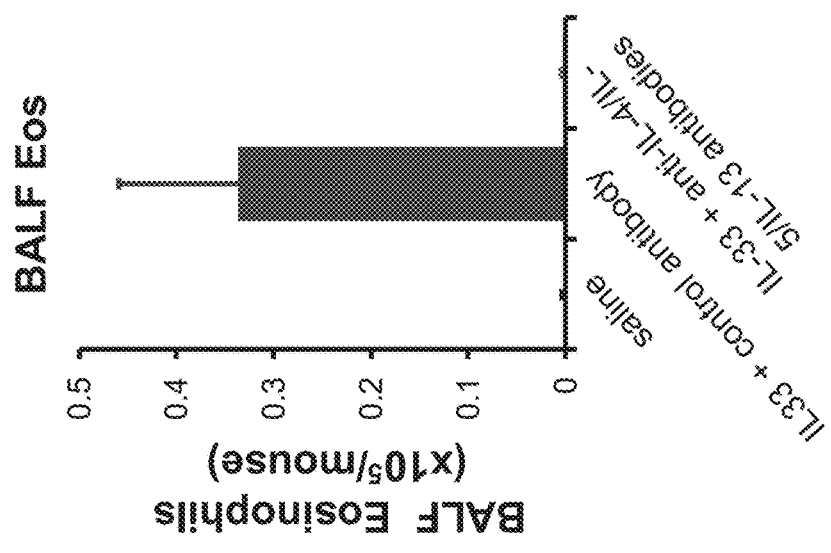

FIGS. 18B and 18C are graphs showing that IL-33-induced macrophage recruitment into the lung is independent of IL-4, IL-5, and IL-13.

Figure 19A:
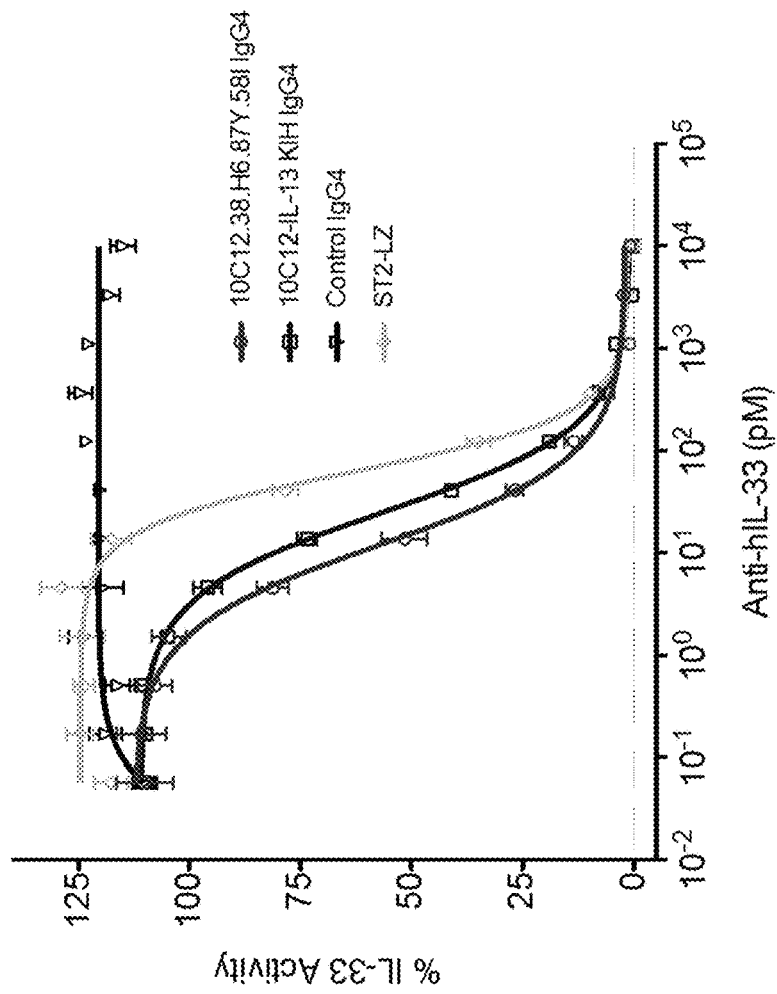

FIG. 19A is a graph showing the results of a cell-based IL-33 blocking assay for human IL-33 using HEK-BLUE™ IL-33 cells as described in Example 8. The concentration of human IL-33 N-His was 15 pM. The cells were stimulated for 20 h. The tables below the graph show the IC90 and IC50 for 10C12.38.H6.87Y.58I IgG4, the anti-IL-33/anti-IL-13 bispecific clone 10C12.38.H6.87Y.58I/IL-13 IgG4 (abbreviated as "10C12-IL-13 KIH IgG4"), a control IgG4 antibody, and ST2-LZ. The values inside parentheses for the IC90 table are the IC90 values in units of μg/ml.

Figure 19B:
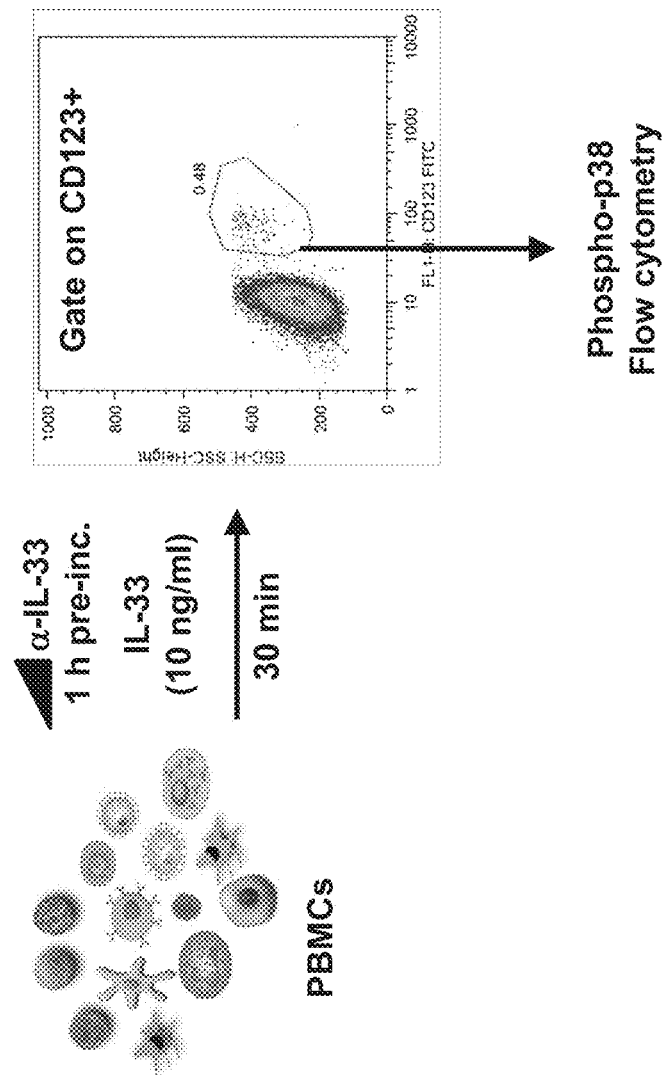

FIG. 19B is a schematic diagram of the basophil IL-33 phospho-p38 assay described in Example 8.

Figure 19C:
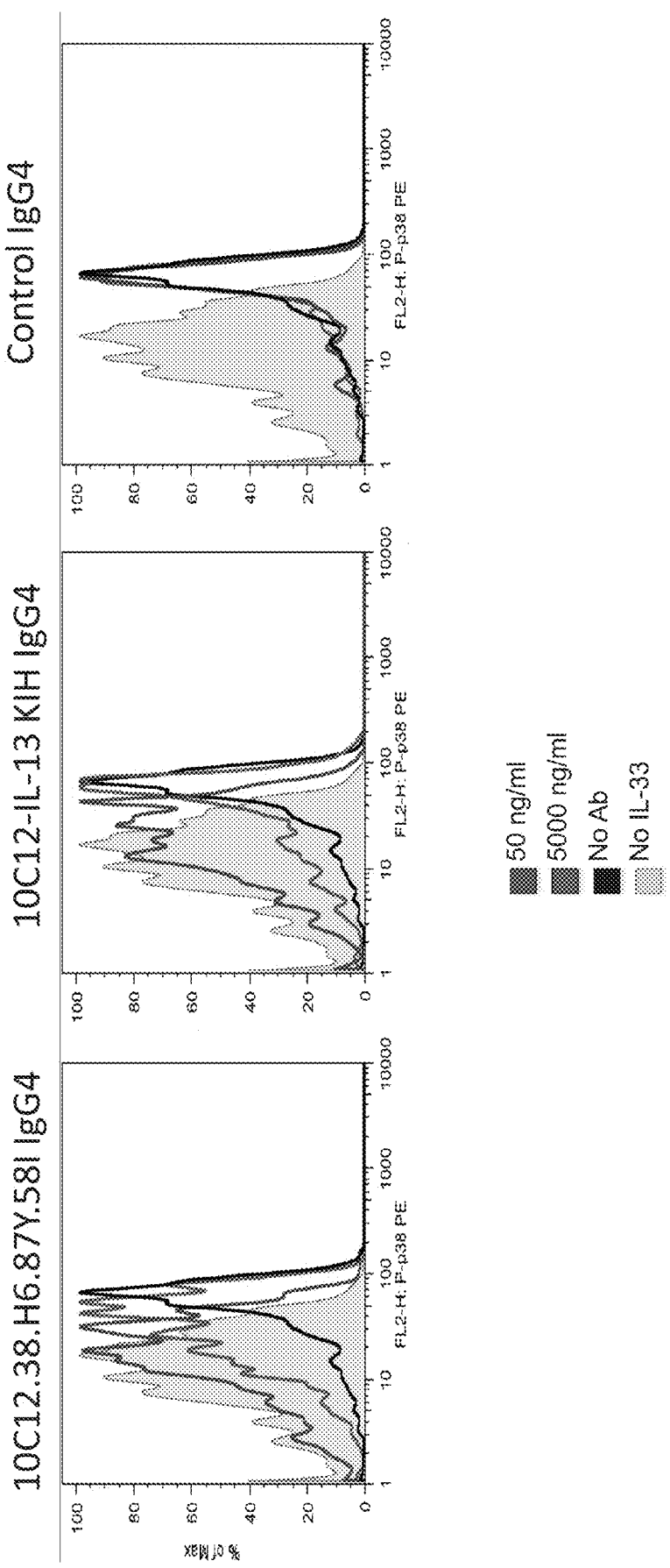

FIG. 19C is a series of graphs showing results from the basophil IL-33 phospho-p38 assay as described in Example 8. The graphs show the percentage of maximum fluorescence intensity as a function of phospho-p38 fluorescence intensity.

Figure 19D:
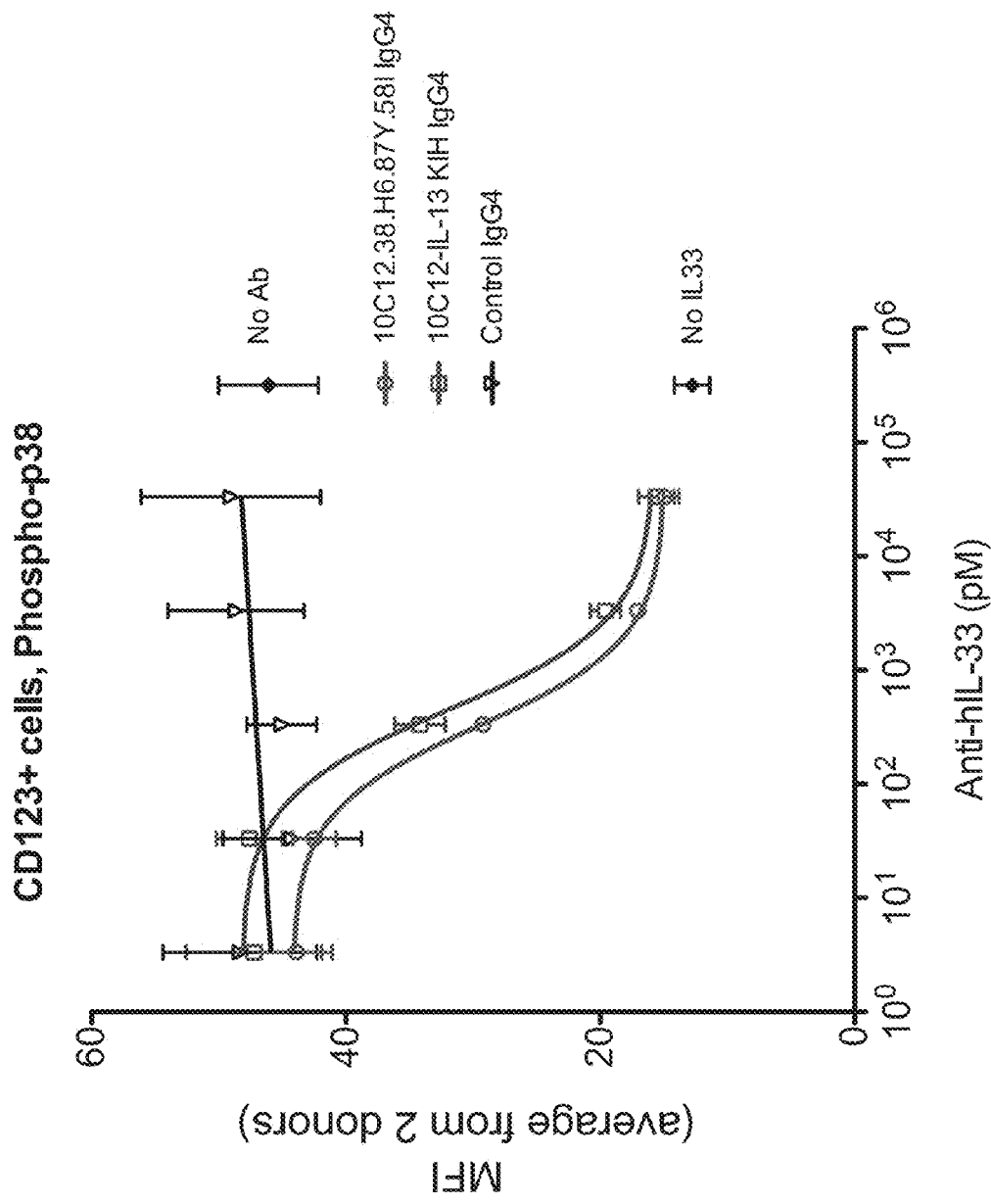

FIG. 19D is a graph showing that the monospecific anti-IL-33 antibody 10C12.38.H6.87Y.58I IgG4 and the bispecific antibody 10C12.38.H6.87Y.58I/IL-13 IgG4 ("10C12-1L13 KIH IgG4") caused a dose-dependent inhibition in IL-33-induced phospho-p38 levels in basophils, as described in Example 8. The graph plots mean fluorescence intensity (MFI) (average from two donors) as a function of antibody concentration. A control IgG4 antibody did not inhibit phospho-p38 levels. The graph also shows the results from control experiments in which no antibody was added ('No Ab') or in which no IL-33 was added ("No IL-33").

FIG. 20 is a table showing the binding kinetics of the 10C12.38.H6.87Y.58I/IL-13 IgG4 bispecific antibody (10C12-IL-13 KIH IgG4) to human IL-33, cyno IL-33, and human IL-13 as assessed by BIACORE® 3000 SPR analysis. The table shows results from three independent antibody preparations (lots).

Figure 21A:
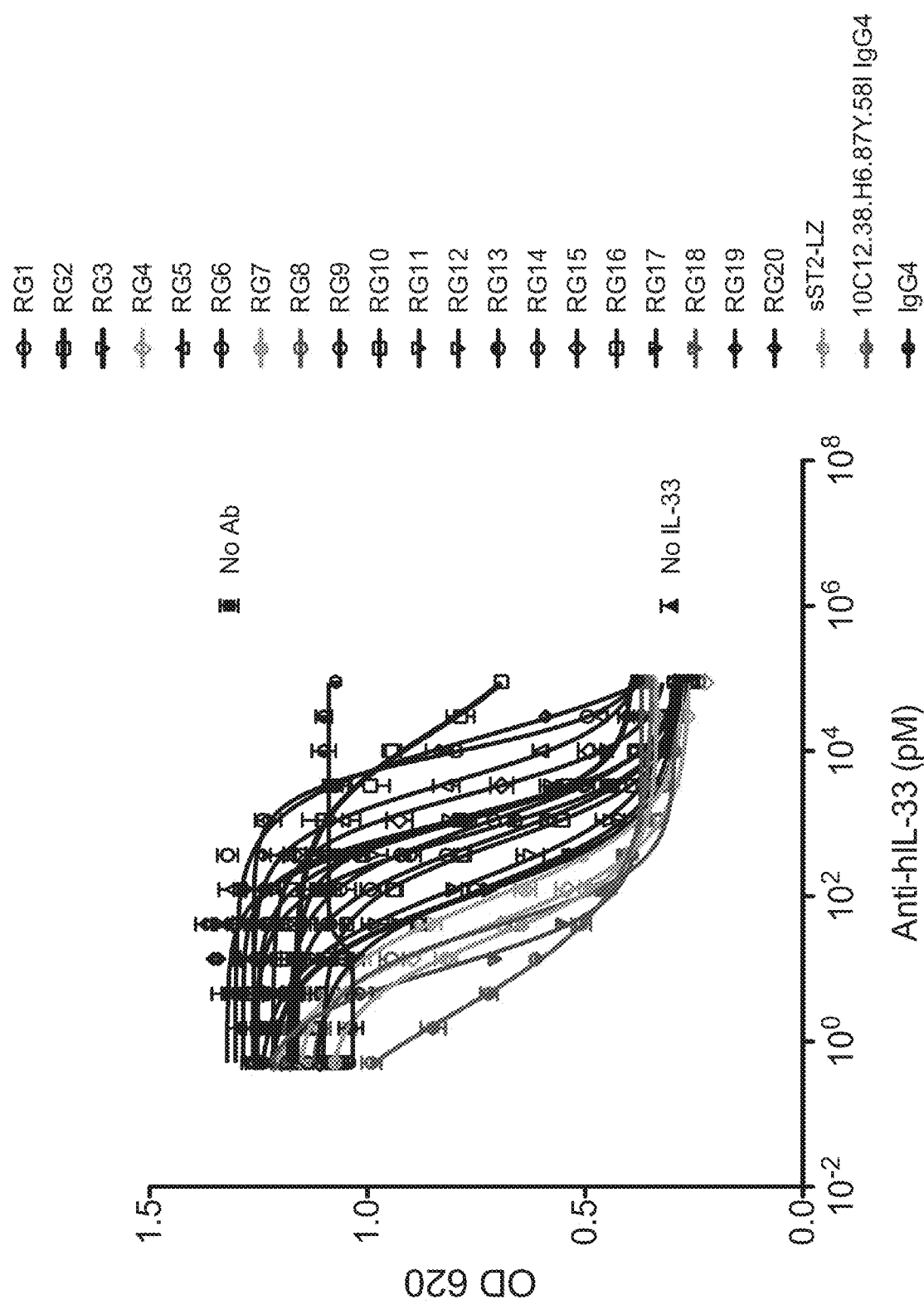

FIG. 21A is a graph showing results of a cell-based human IL-33 blocking using HEK-BLUE™ IL-33/IL-1β reporter cells. Dose-response curves were used to determine the inhibition of 10 pM human IL-33 activity (measured by OD 620) by the indicated anti-IL-33 antibodies (RG1-20 and 10C12.38.H6.87Y.58I IgG4), sST2-LZ, and the isotype control antibody (IgG4). The graph also shows the results from control experiments in which no antibody was added ("No Ab") or in which no IL-33 was added ("No IL-33").

Figure 21B:
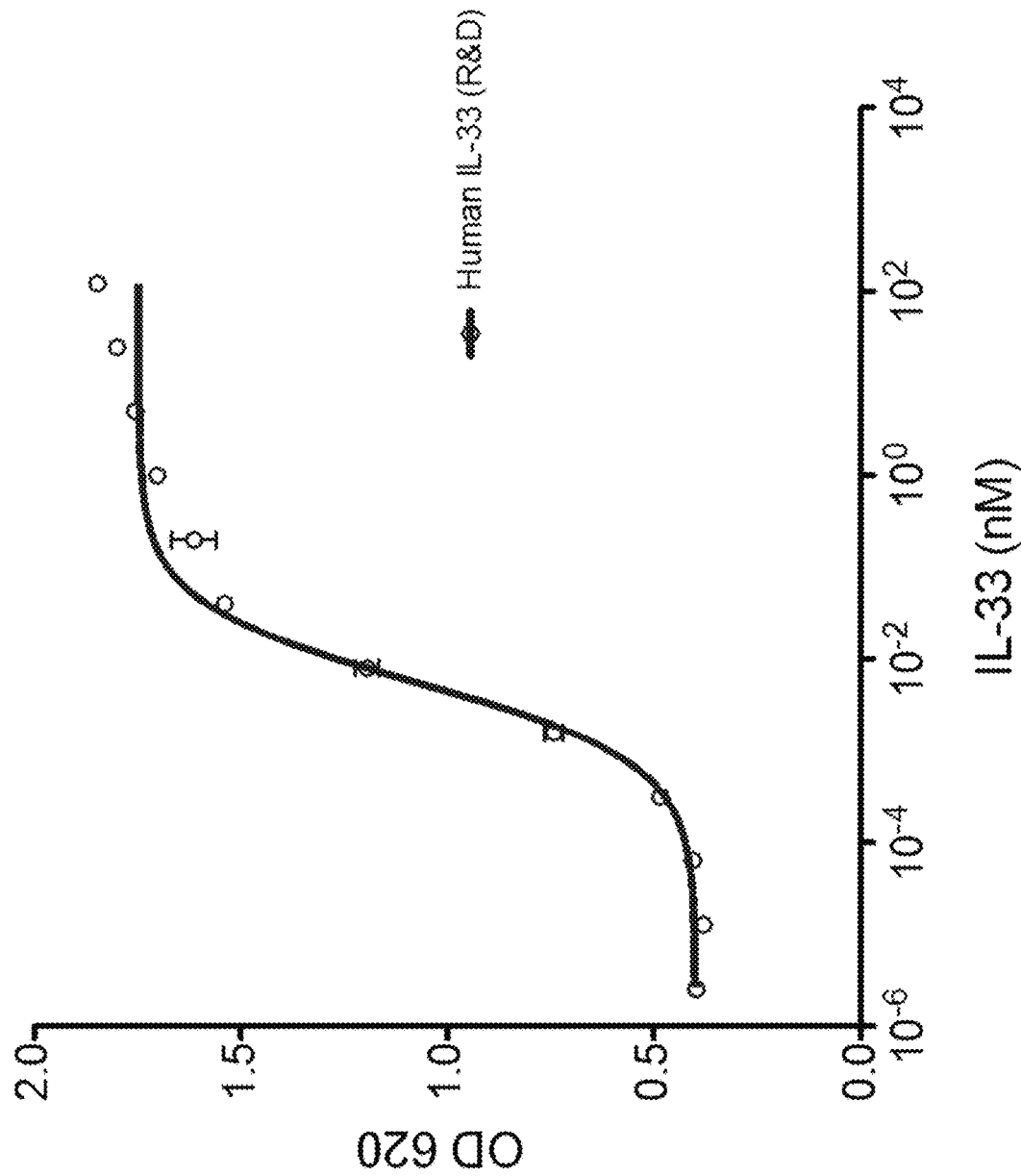

FIG. 21B is a graph showing dose-response of HEK-BLUE™ IL-33/IL-1β reporter cells to human IL-33.

FIG. 21C is a table showing inhibition of human and cynomolgus monkey IL-33 activation of HEK-BLUE™ IL-33/IL-1β reporter cells by the indicated anti-IL-33 antibodies.

Figure 21D:
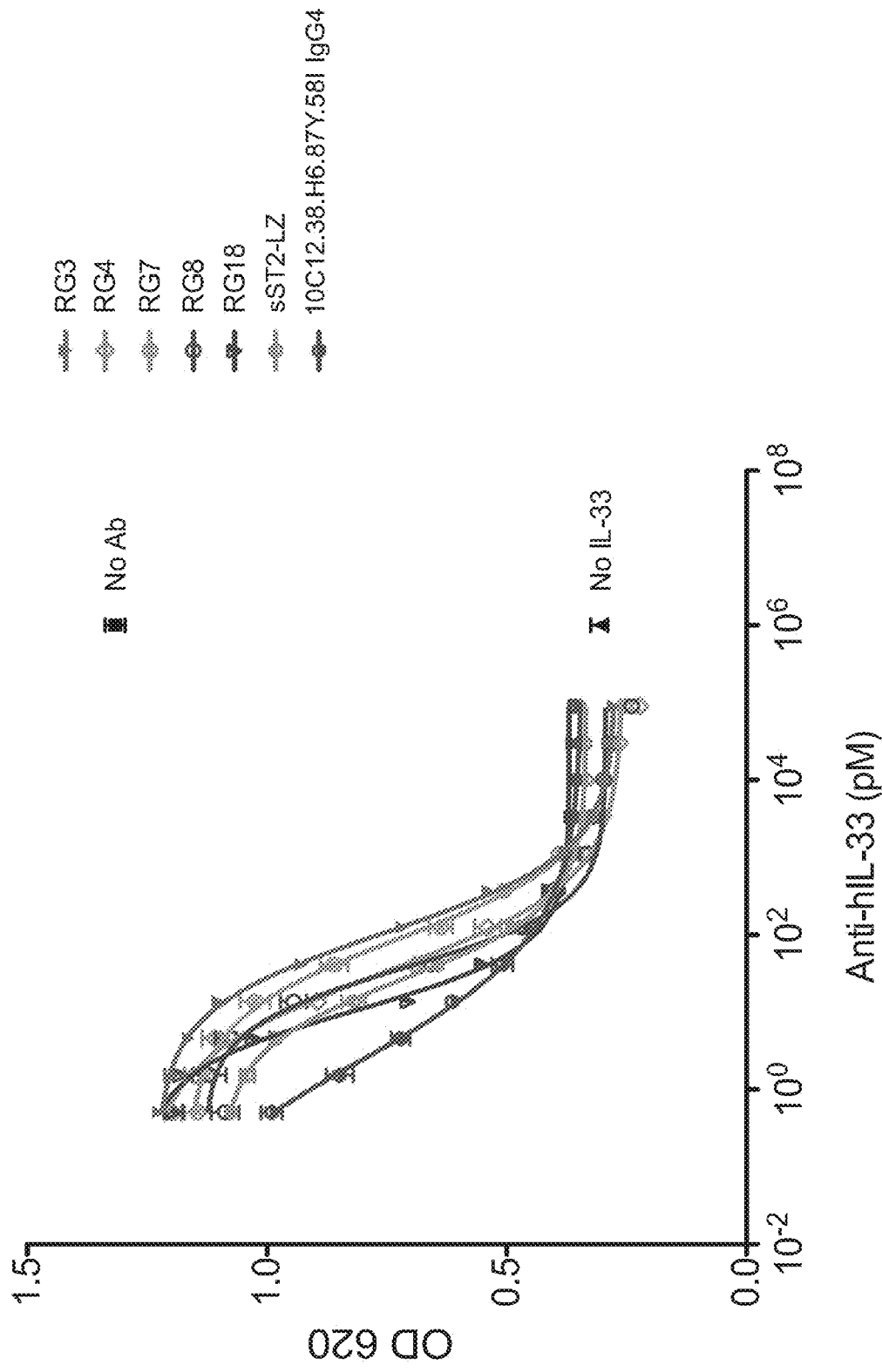

FIG. 21D is a graph showing dose-response curves of the five anti-IL-33 RG antibodies with the highest human IL-33 blocking activity compared to 10C12.38.H6.87Y.58I IgG4 and sST2-LZ. The graph also shows the results from control experiments in which no antibody was added ("No Ab") or in which no IL-33 was added ("No IL-33").

Figure 22A:
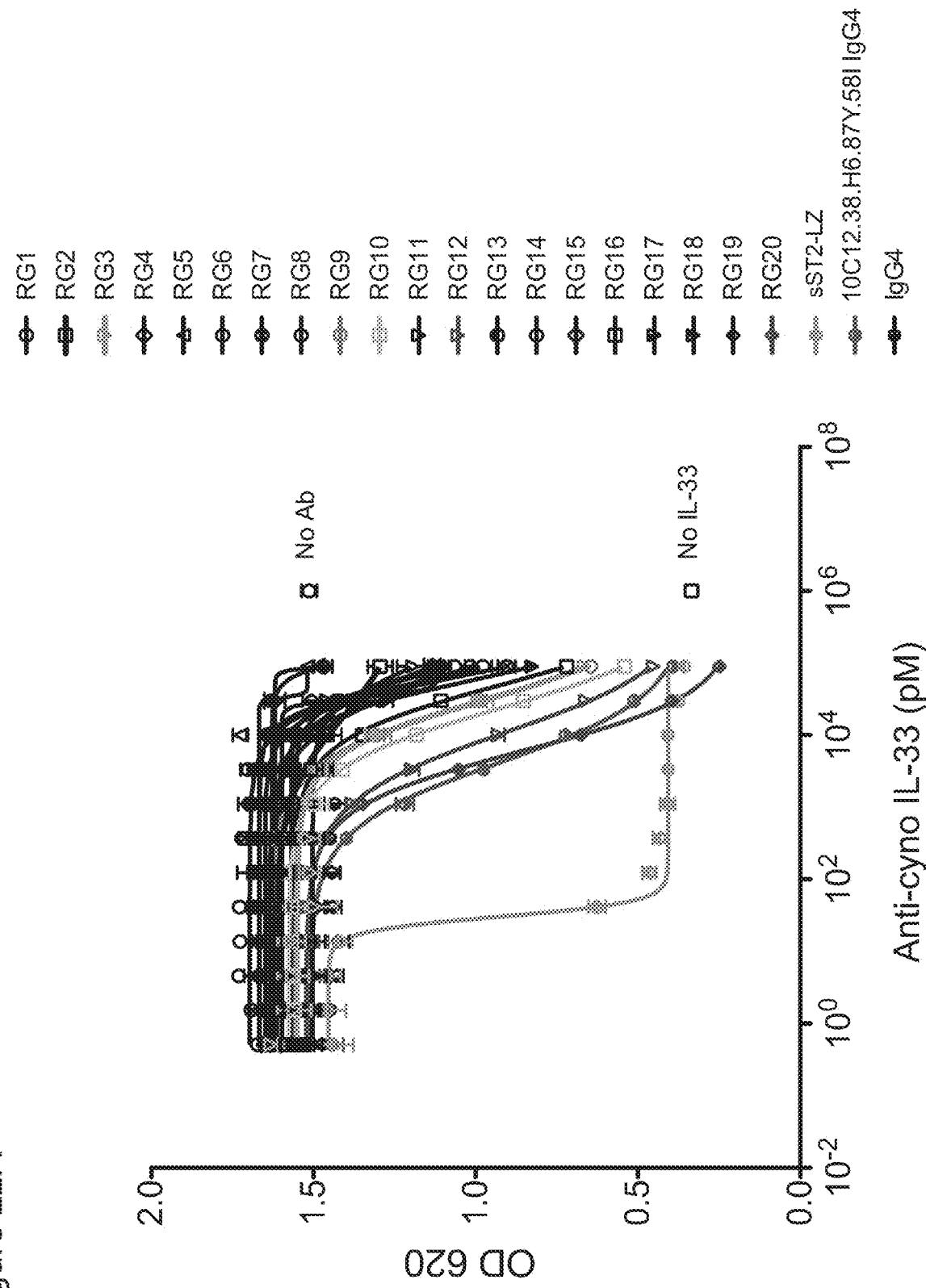

FIG. 22A is a graph showing results of a cell-based cyno IL-33 blocking assay using HEK-BLUE™ IL-33/IL-1β reporter cells. Dose-response curves were used to determine the inhibition of 5 pM cynomolgus monkey IL-33 activity by the indicated anti-IL-33 antibodies (RG1-20 and 10C12.38.H6.87Y.58I IgG4), sST2-LZ, and the isotype control antibody (IgG4).

Figure 22B:
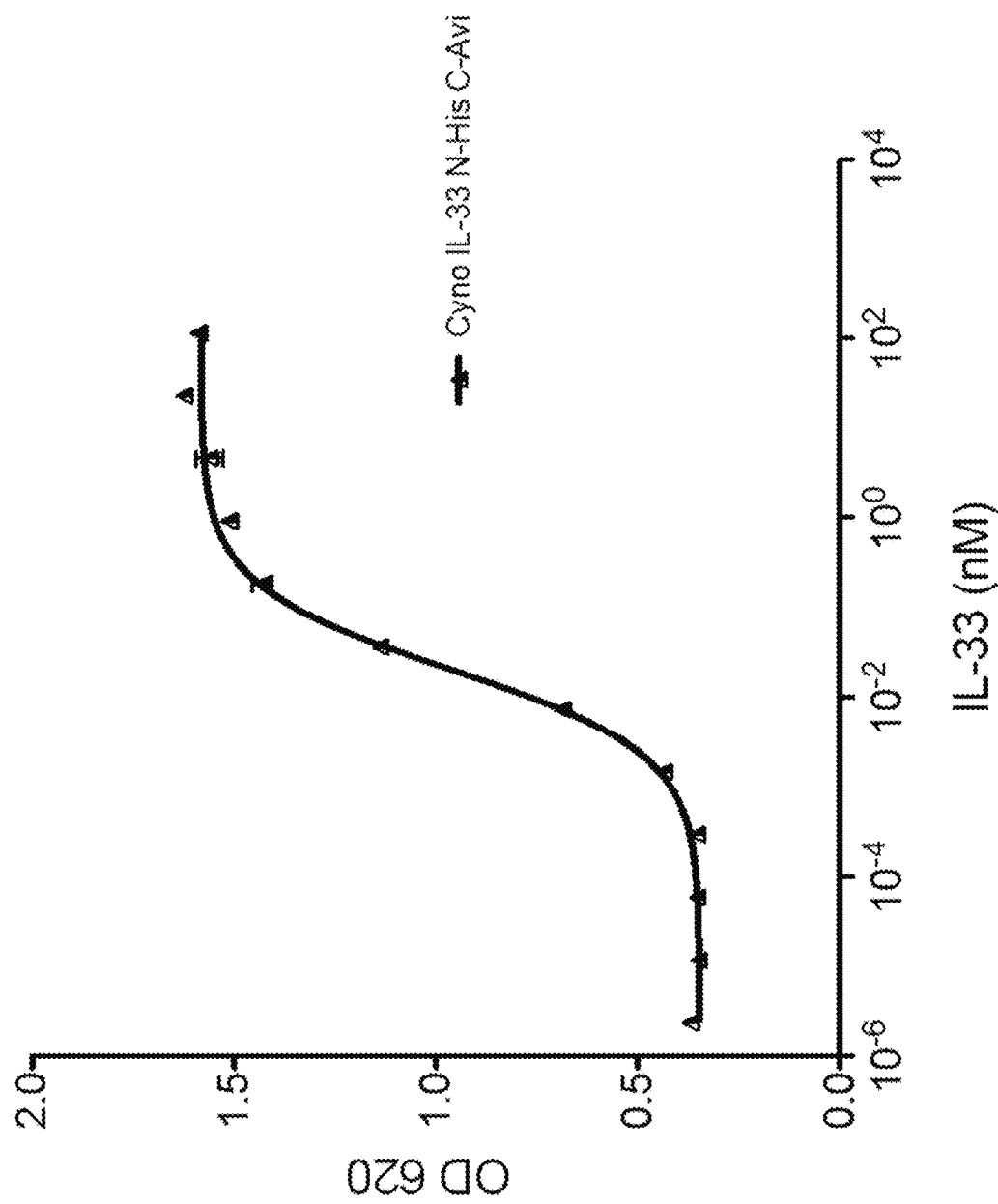

FIG. 22B is a graph showing dose-response of HEK-BLUE™ IL-33/IL-1β reporter cells to cyno IL-33.

Figure 22C:
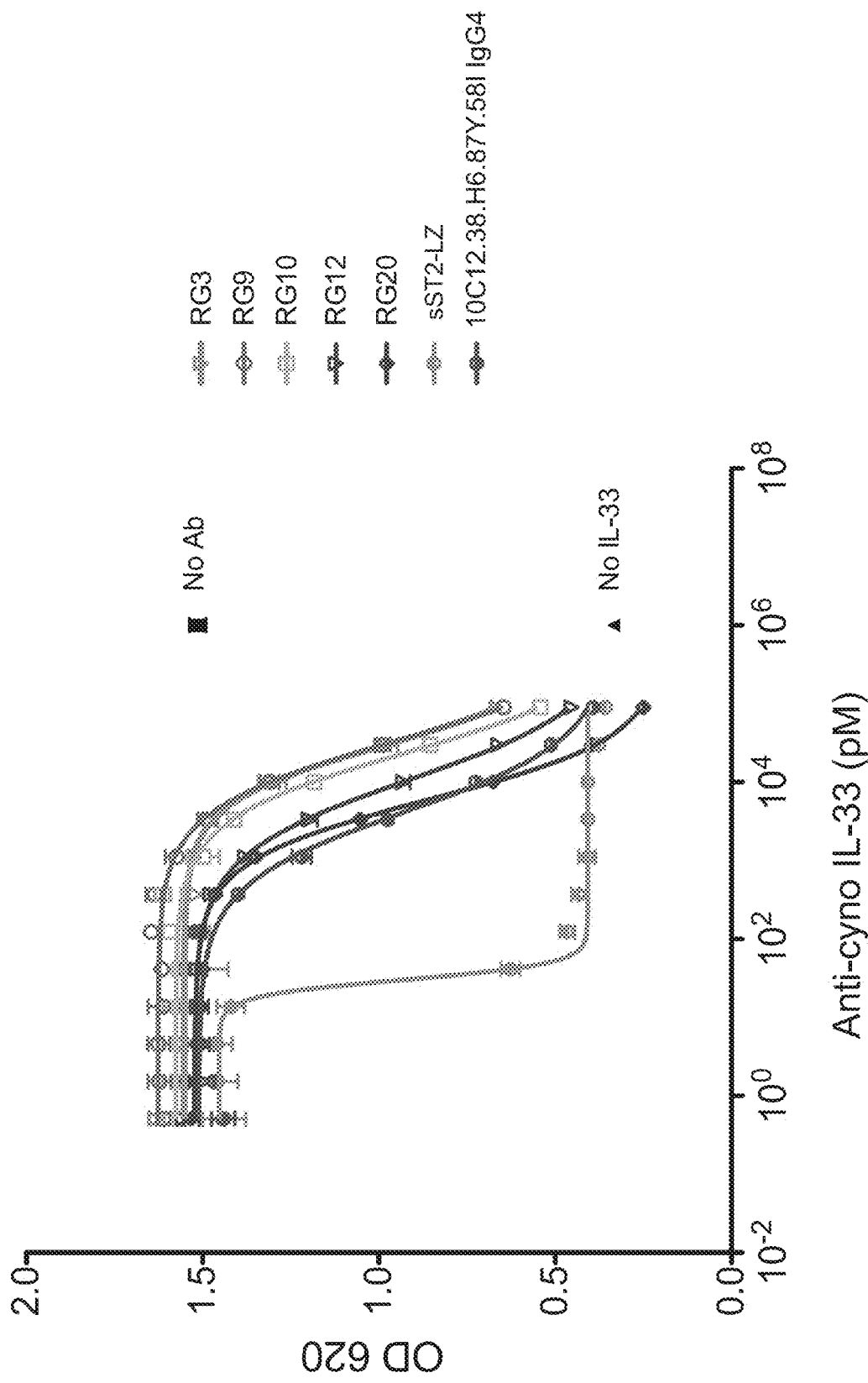

FIG. 22C is a graph showing dose-response curves of the five anti-IL-33 RG antibodies with the highest cynomolgus monkey IL-33 blocking activity relative to 10C12.38.H6.87Y.58I IgG4 and sST2-LZ. The graph also shows the results from control experiments in which no antibody was added ("No Ab") or in which no IL-33 was added ("No IL-33").

Figure 22D:
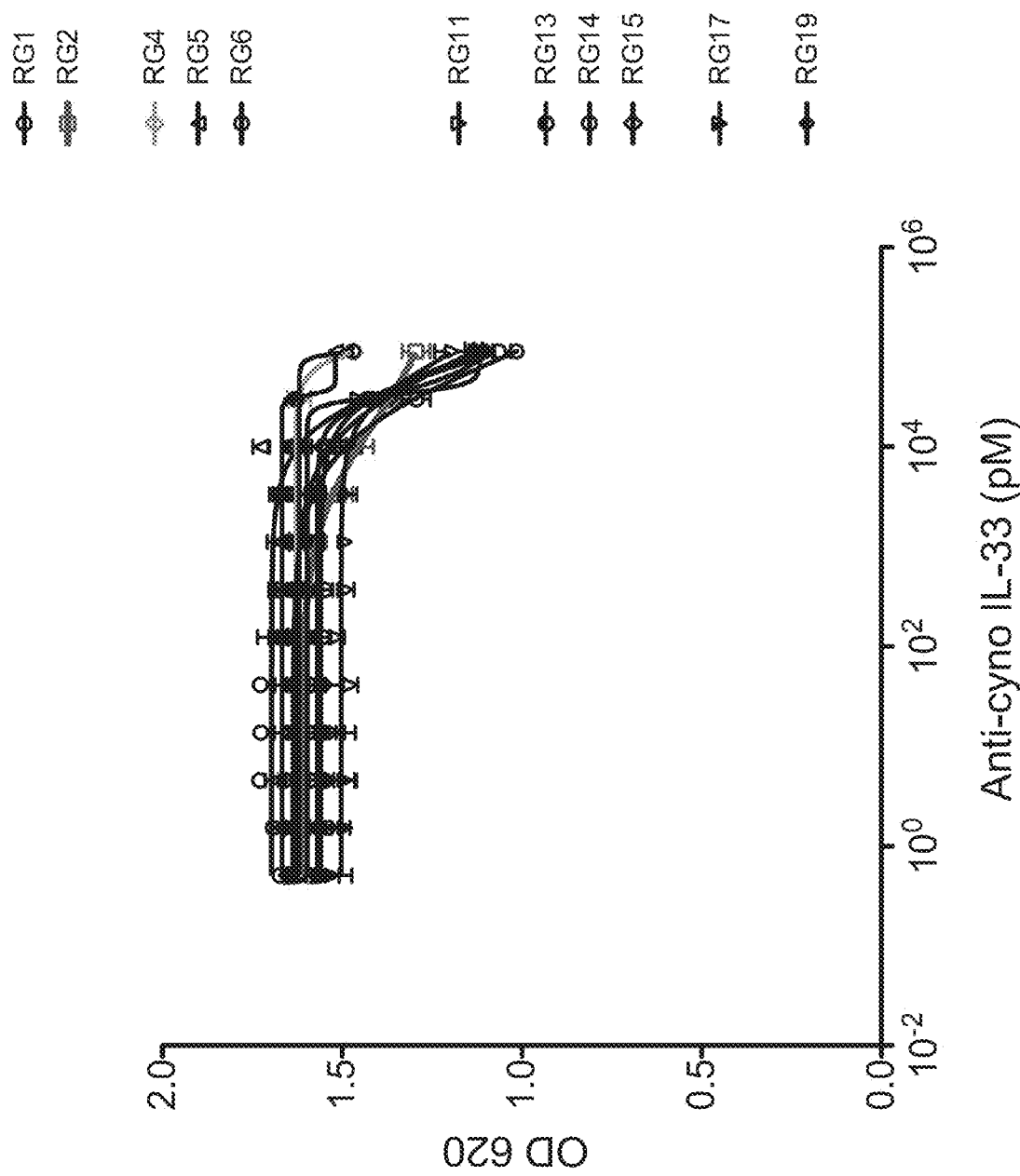

FIG. 22D is a graph showing dose-response curves of anti-IL-33 RG antibodies that were non-blocking for cyno IL-33.

Figure 23A:
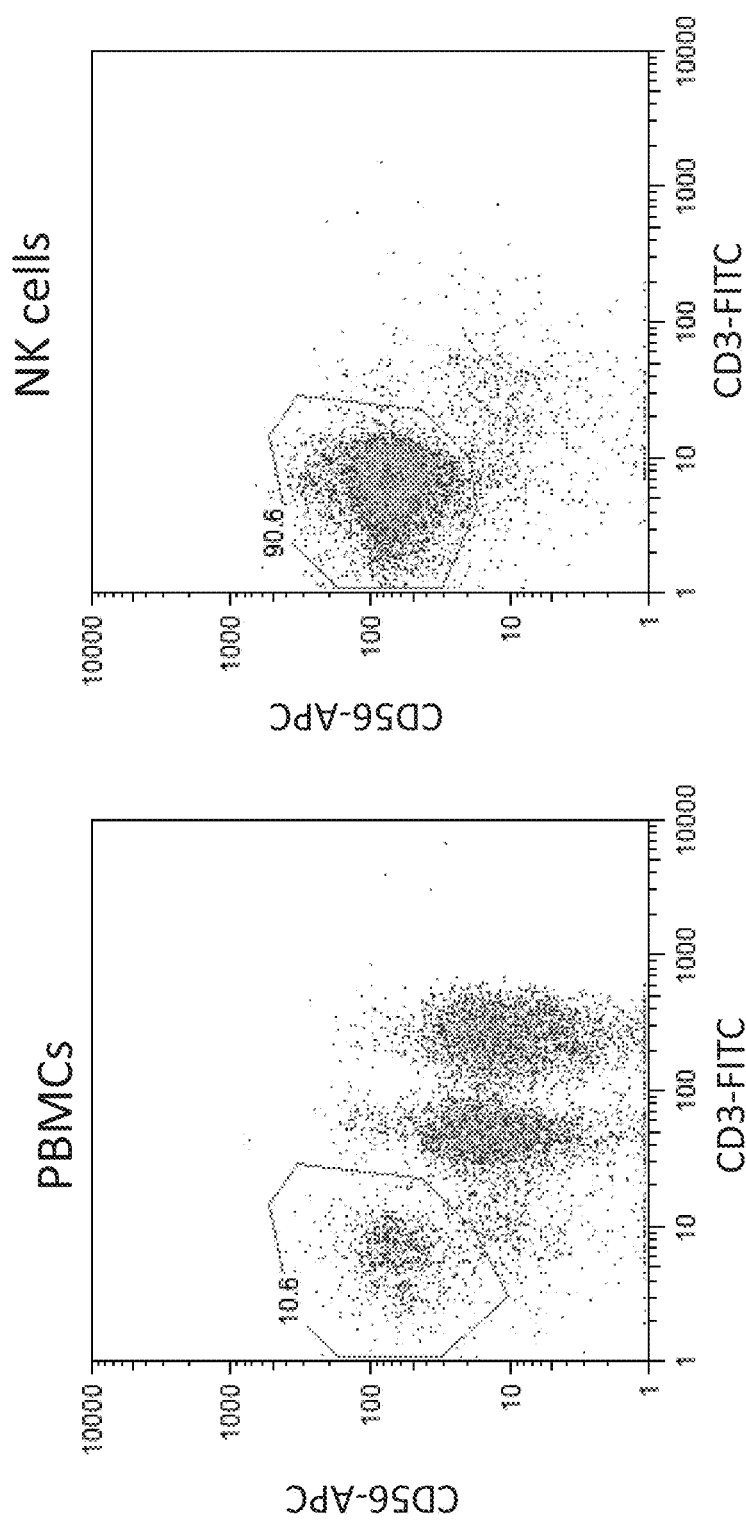

FIG. 23A is a series of graphs showing flow cytometry analysis of the purity of enriched NK cells (CD56$^+$ CD3$^-$) from human PBMCs.

Figure 23B:
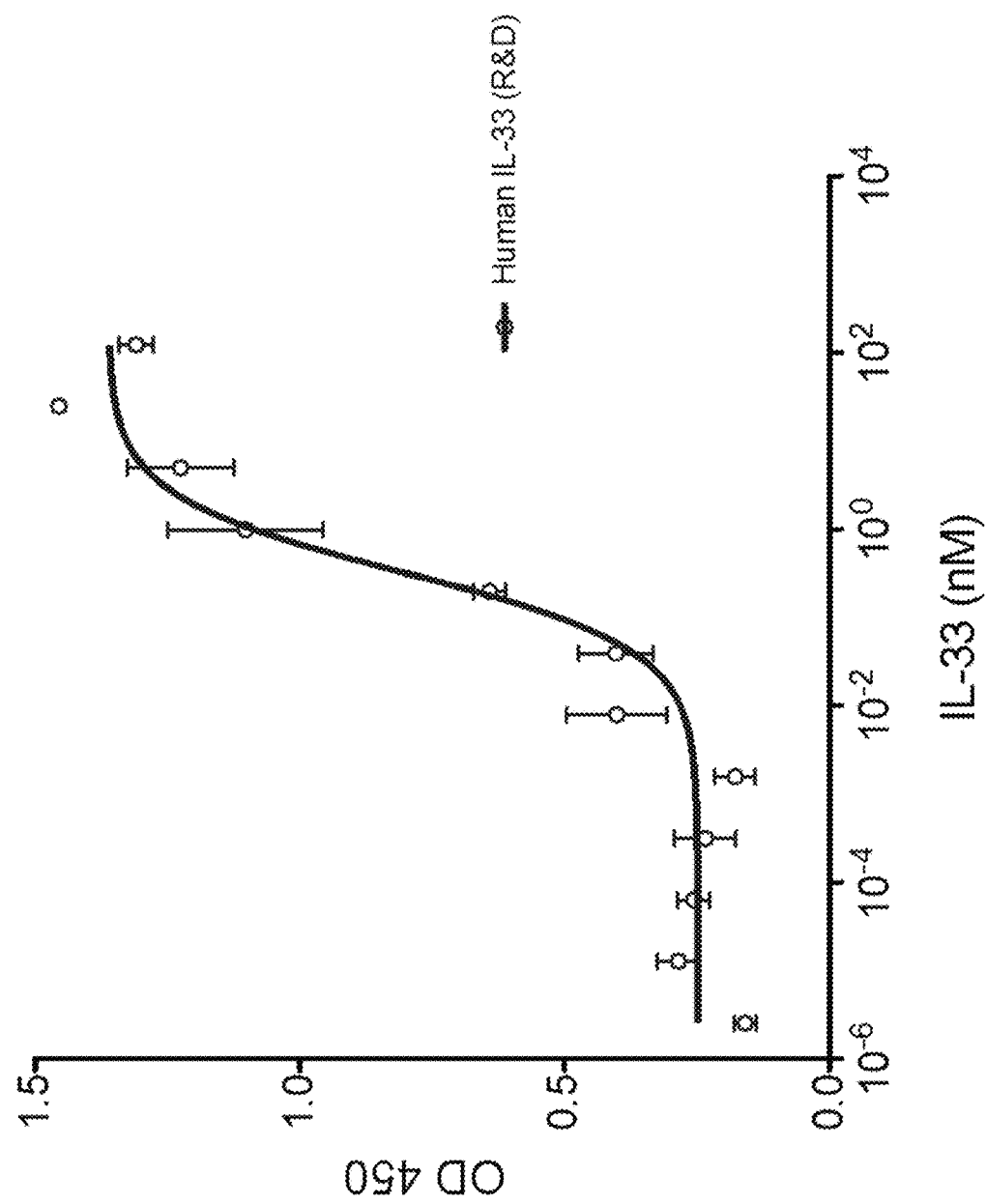

FIG. 23B is a graph showing the results of ELISA analysis of human IFN-γ secretion from primary NK cells in response to human IL-33. Dose-response curves were generated from IFN-γ ELISA OD 450 values.

Figure 23C:
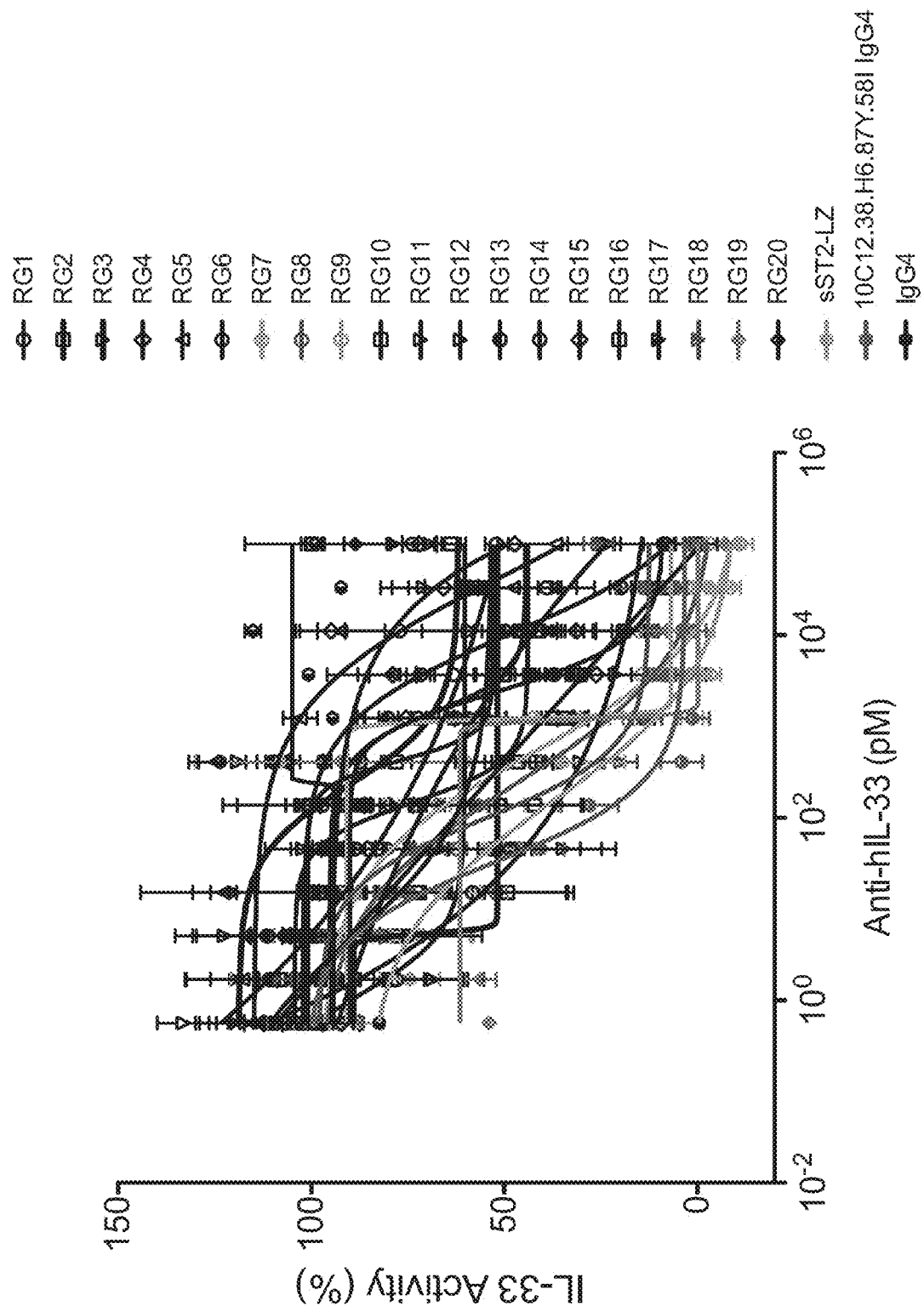

FIG. 23C is a graph showing inhibition of human IL-33 activation of primary NK cells by the indicated anti-IL-33 antibodies. Dose-response curves were used to determine the inhibition of human IL-33 activity in NK cells by the indicated anti-IL-33 antibodies (RG1-RG20 and 10C12.38.H6.87Y.58I IgG4), sST2-LZ, and the isotype control antibody (IgG4).

FIG. 23D is a table showing the inhibition of human IL-33 activation of primary NK cells by the indicated anti-IL-33 antibodies.

Figure 23E:
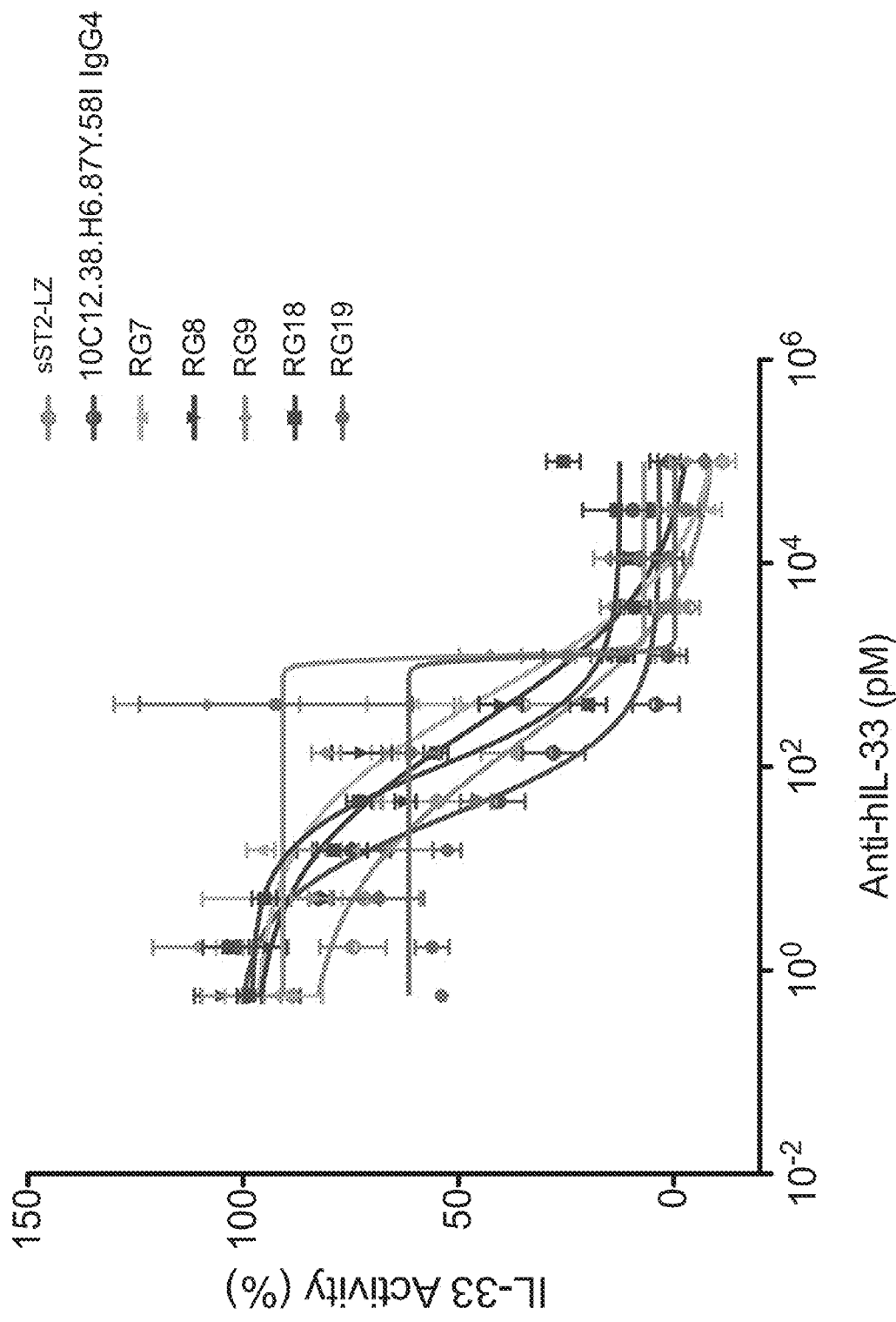

FIG. 23E is a graph showing dose-response curves of the five anti-IL-33 RG antibodies with the highest human IL-33 blocking activity relative to 10C12.38.H6.87Y.58I IgG4 and sST2-LZ.

Figure 23F:
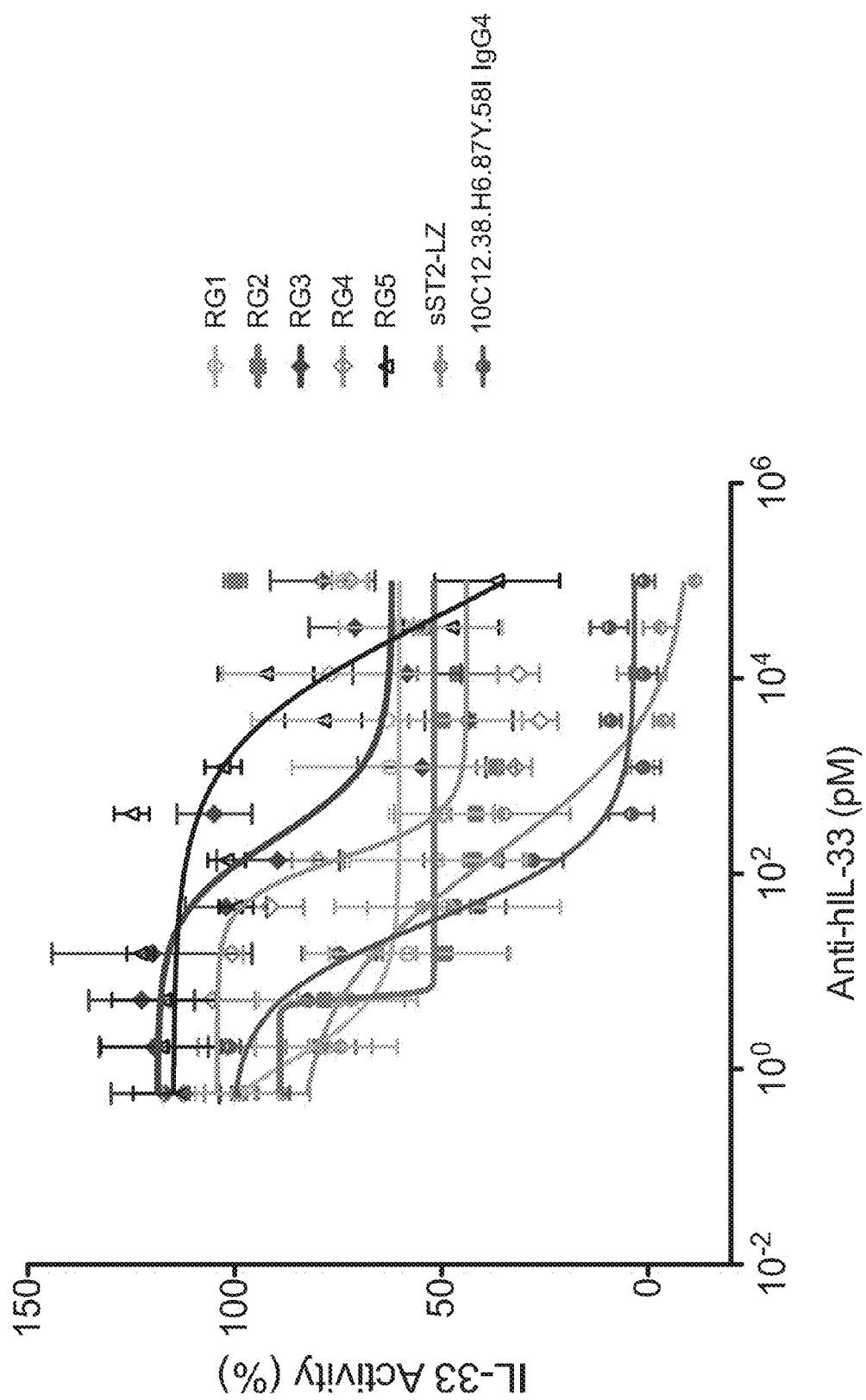

FIG. 23F is a graph showing dose-response curves of anti-IL-33 antibodies RG1-RG5 relative to 10C12.38.H6.87Y.58I IgG4 and sST2-LZ.

Figure 23G:
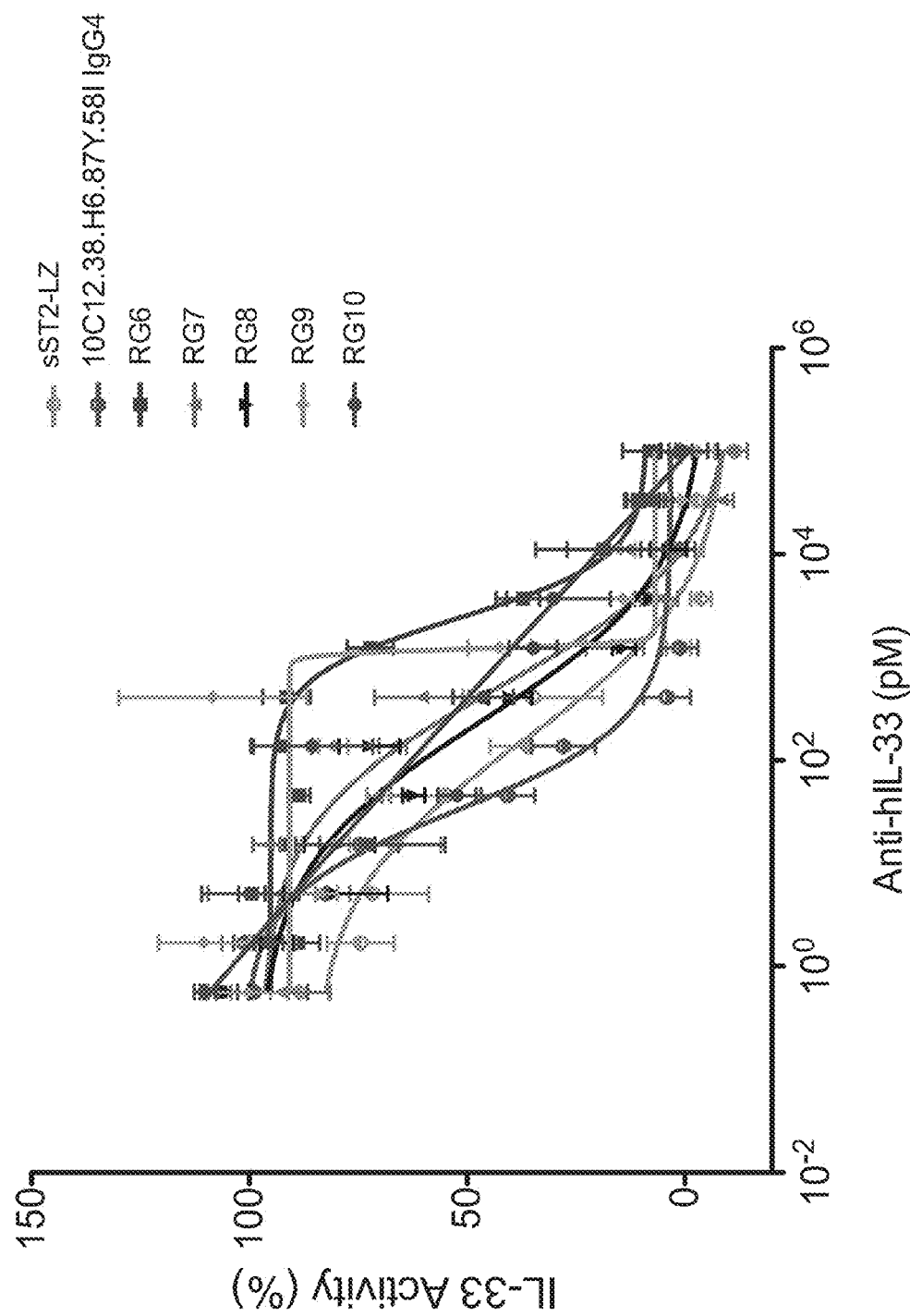

FIG. 23G is a graph showing dose-response curves of anti-IL-33 antibodies RG6-RG10 relative to 10C12.38.H6.87Y.58I IgG4 and sST2-LZ.

Figure 23H:
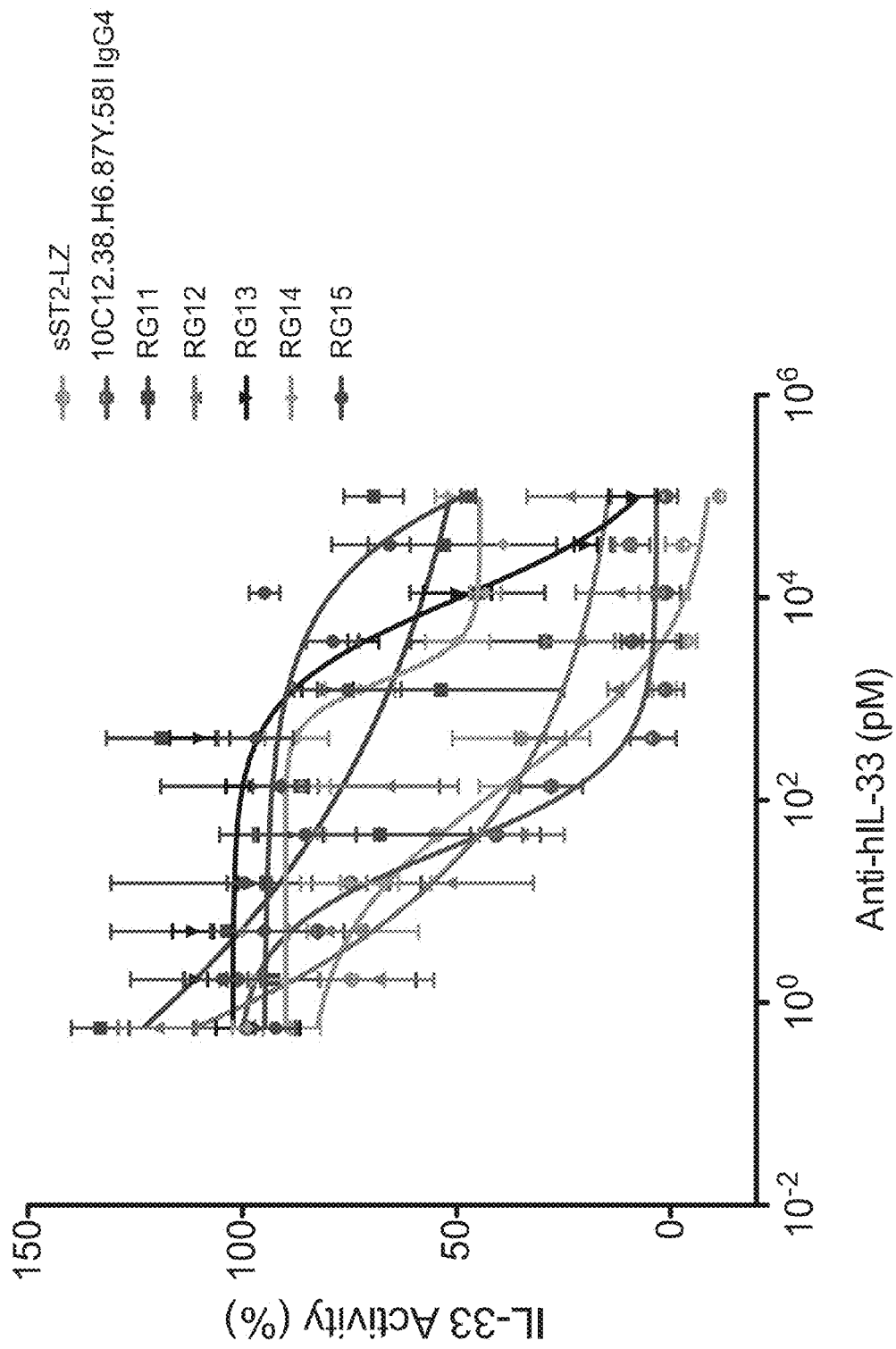

FIG. 23H is a graph showing dose-response curves of anti-IL-33 antibodies RG11-RG15 relative to 10C12.38.H6.87Y.58I IgG4 and sST2-LZ.

Figure 23I:
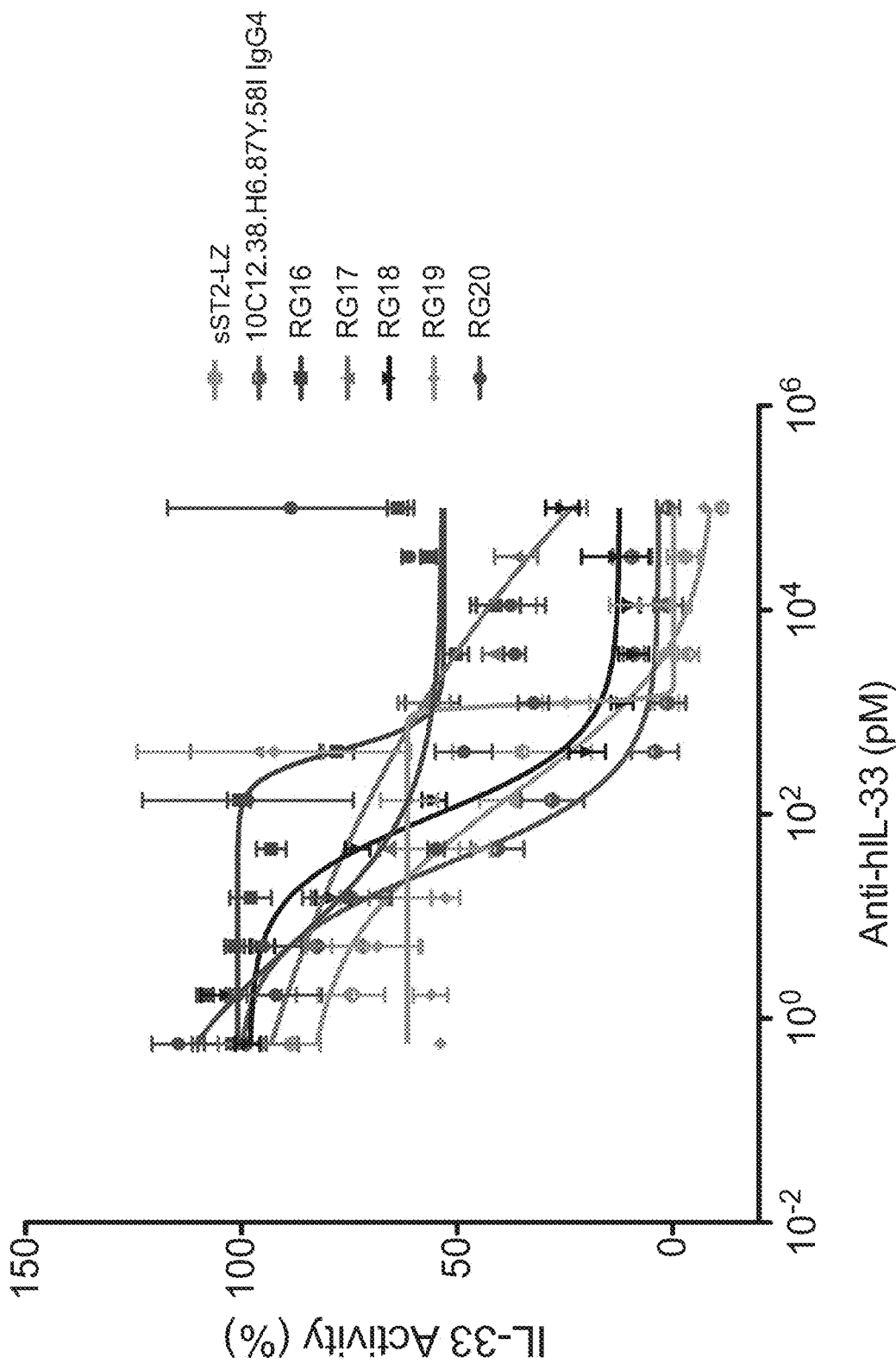

FIG. 23I is a graph showing dose-response curves of anti-IL-33 antibodies RG16-RG20 relative to 10C12.38.H6.87Y.58I IgG4 and sST2-LZ.

Figure 24A:
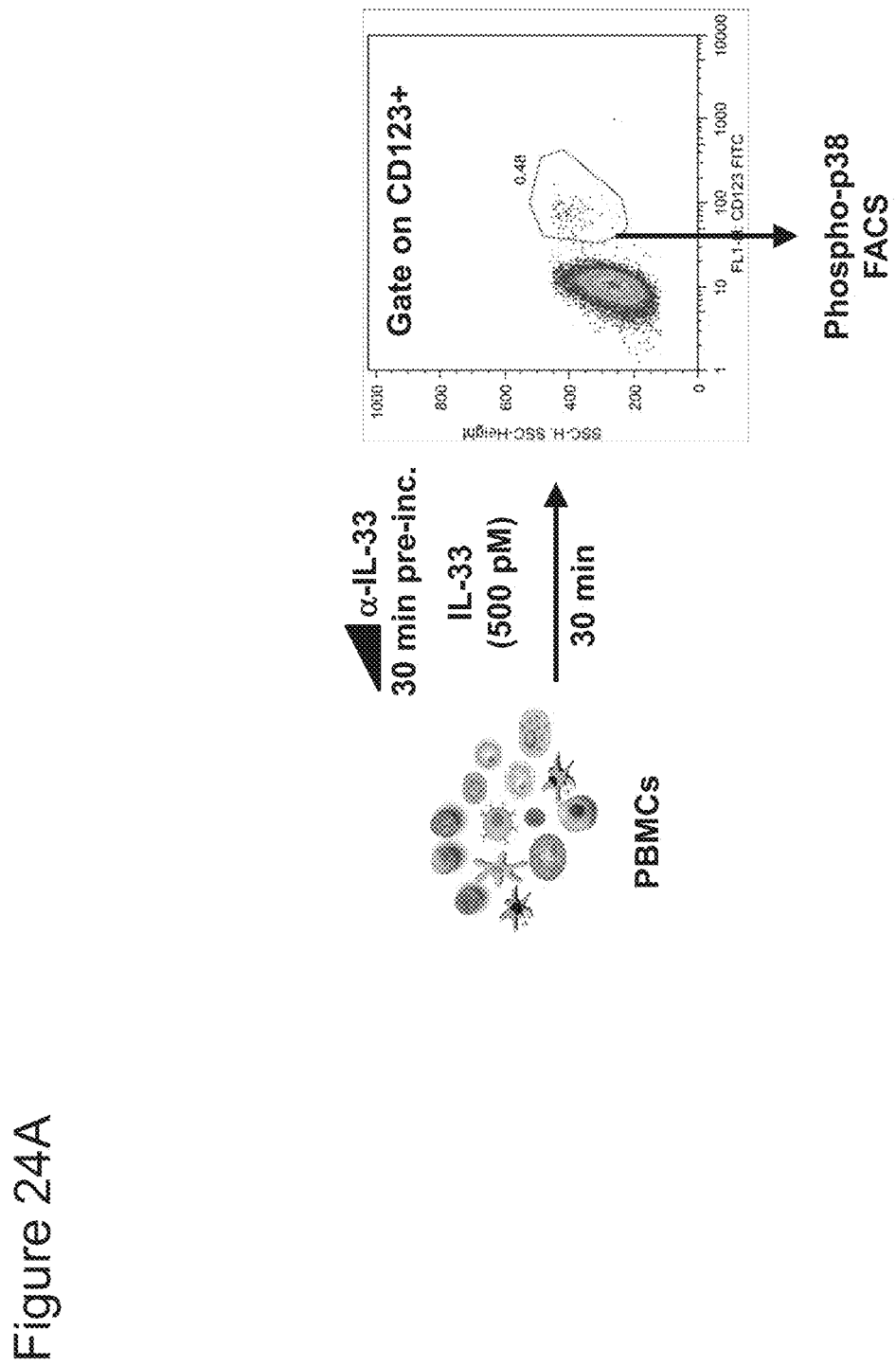

FIG. 24A is a schematic diagram showing the flow cytometry analysis of IL-33-induced p38 MAPK (Thr180/Tyr182) phosphorylation in primary basophils (CD123+) from human PBMCs.

Figure 24B:
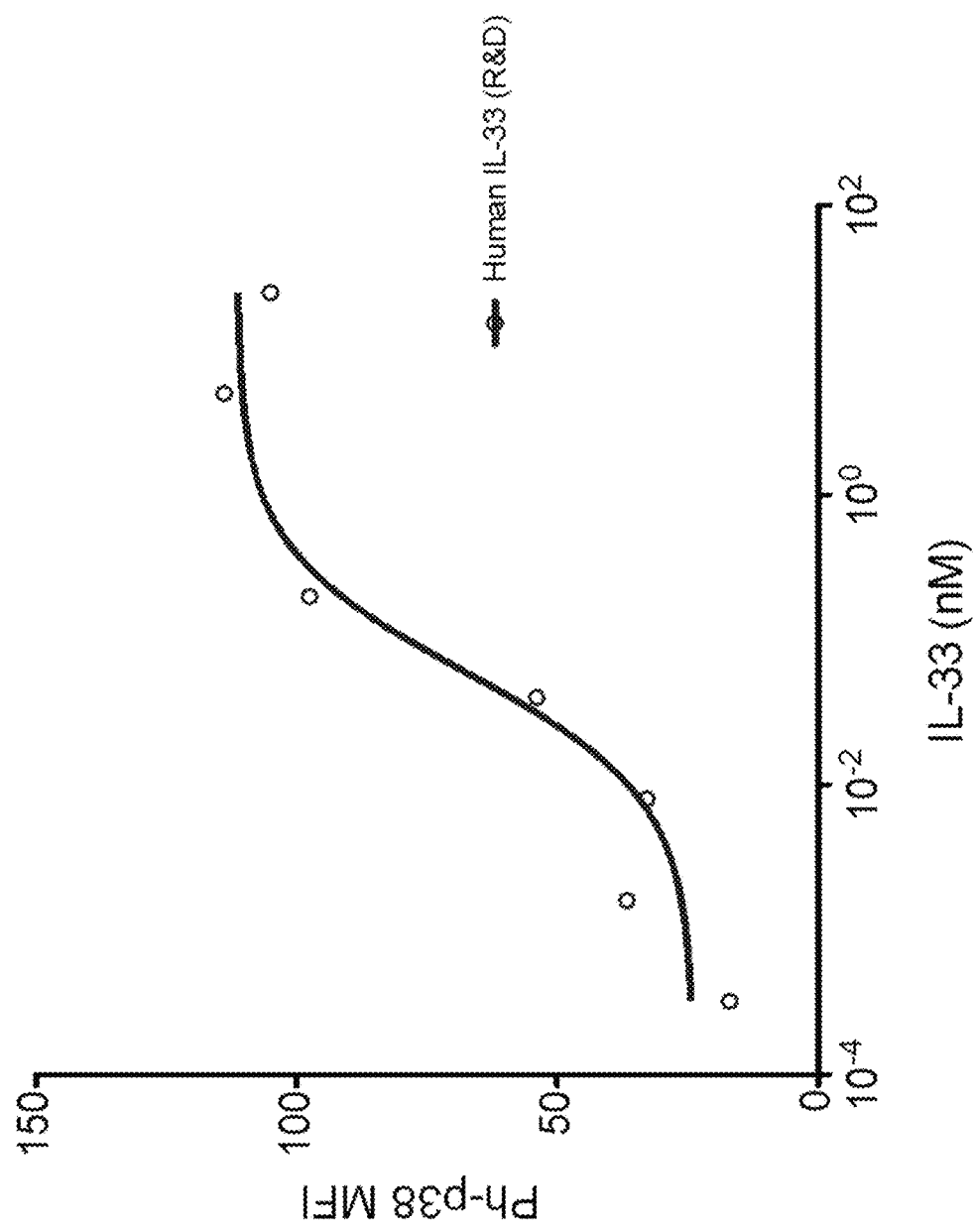

FIG. 24B is a graph showing the mean fluorescence intensity (MFI) of p38 MAPK (Thr180/Tyr182) phosphorylation (ph-p38) from primary basophils in response to increasing doses of human IL-33.

Figure 24C:
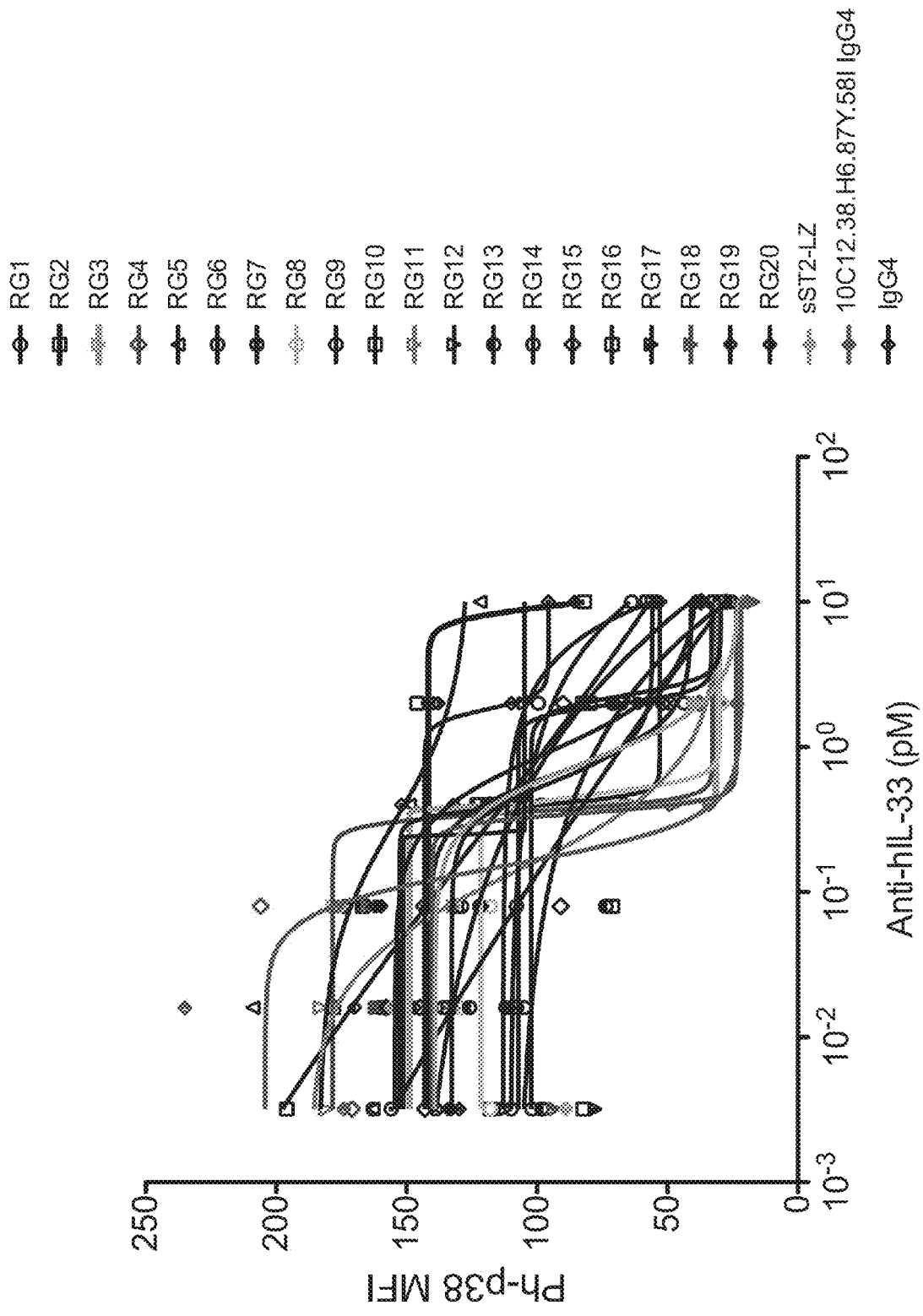

FIG. 24C is a graph showing inhibition of human IL-33 activity in primary basophils by the indicated anti-IL-33 antibodies. Dose-response curves were used to determine the inhibition of human IL-33 activity in basophils by the indicated anti-IL-33 antibodies (RG1-RG20 and 10C12.38.H6.87Y.58I IgG4), sST2-LZ, and the isotype control antibody (IgG4).

FIG. 24D is a table showing inhibition of human IL-33 activation of primary basophils by anti-IL-33 antibodies. "Partial blocking" indicates dose-dependent blocking activity that fails to reach baseline levels at the highest antibody concentrations.

Figure 24E:
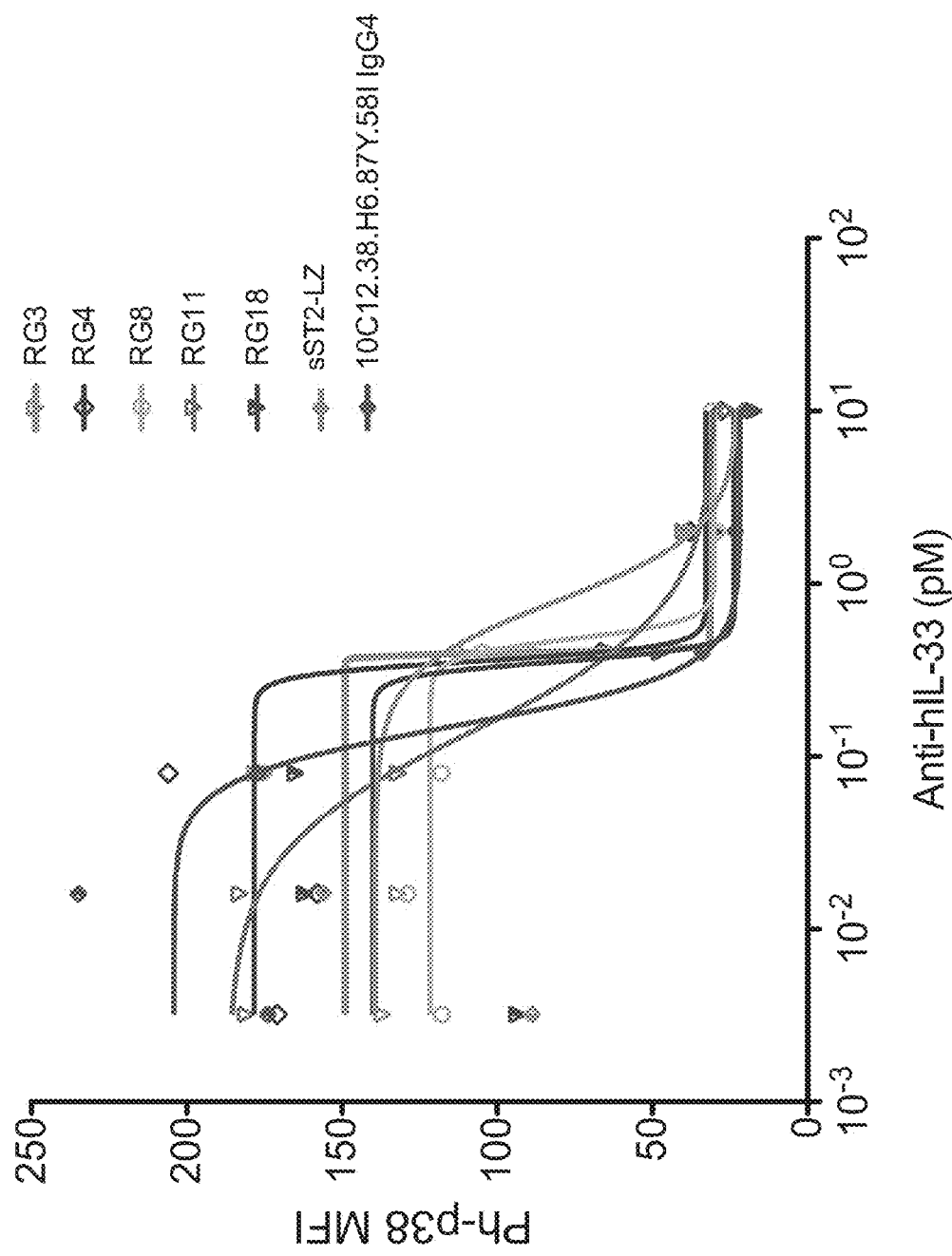

FIG. 24E is a graph showing dose-response curves of the five anti-IL-33 RG antibodies with highest human IL-33 blocking activity relative to 10C12.38.H6.87Y.58I IgG4 and sST2-LZ.

Figure 24F:
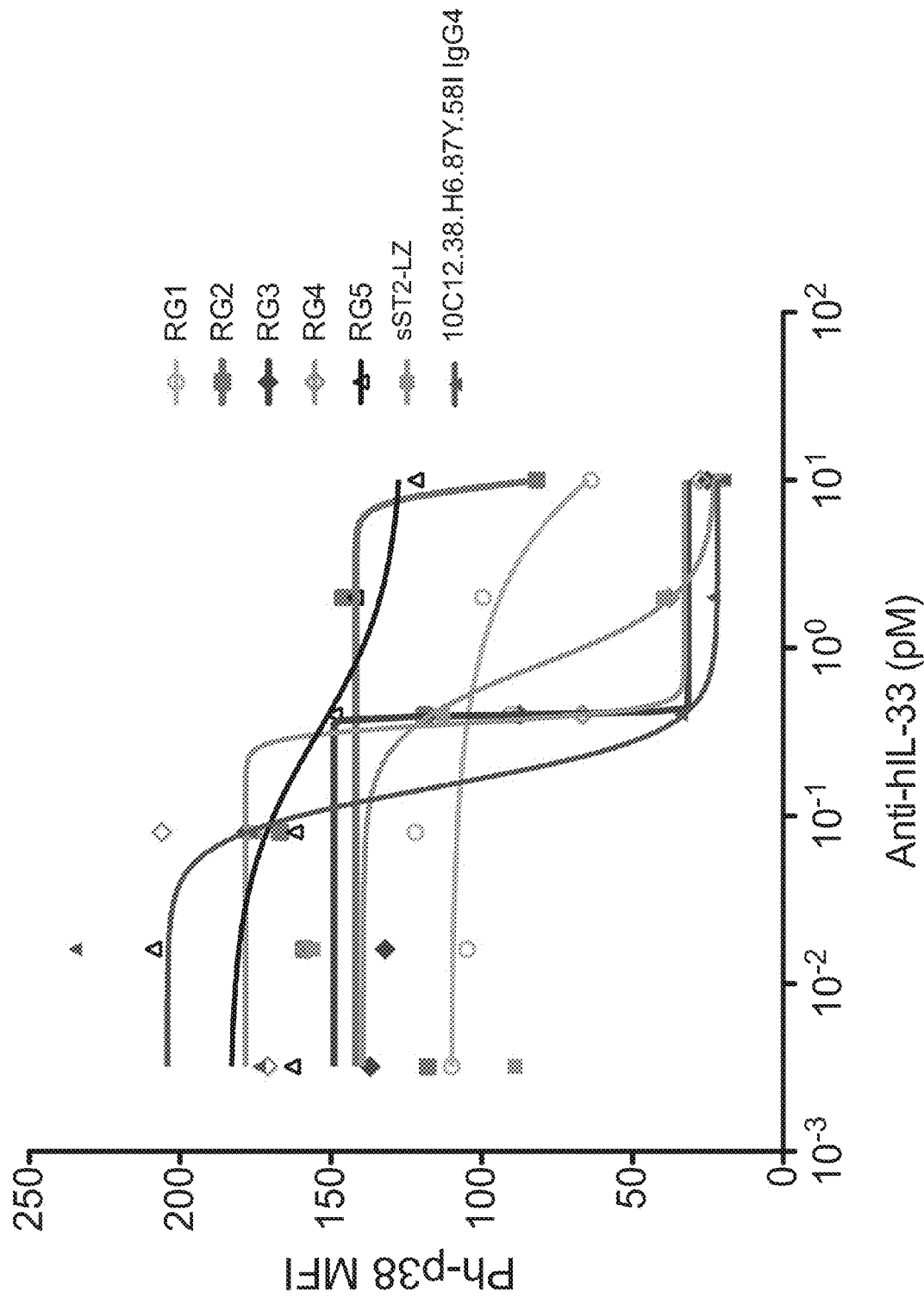

FIG. 24F is a graph showing inhibition of human IL-33 activity in primary basophils. The graph plots dose-response curves of anti-IL-33 antibodies RG1-RG5 relative to 10C12.38.H6.87Y.58I IgG4 and sST2-LZ.

Figure 24G:
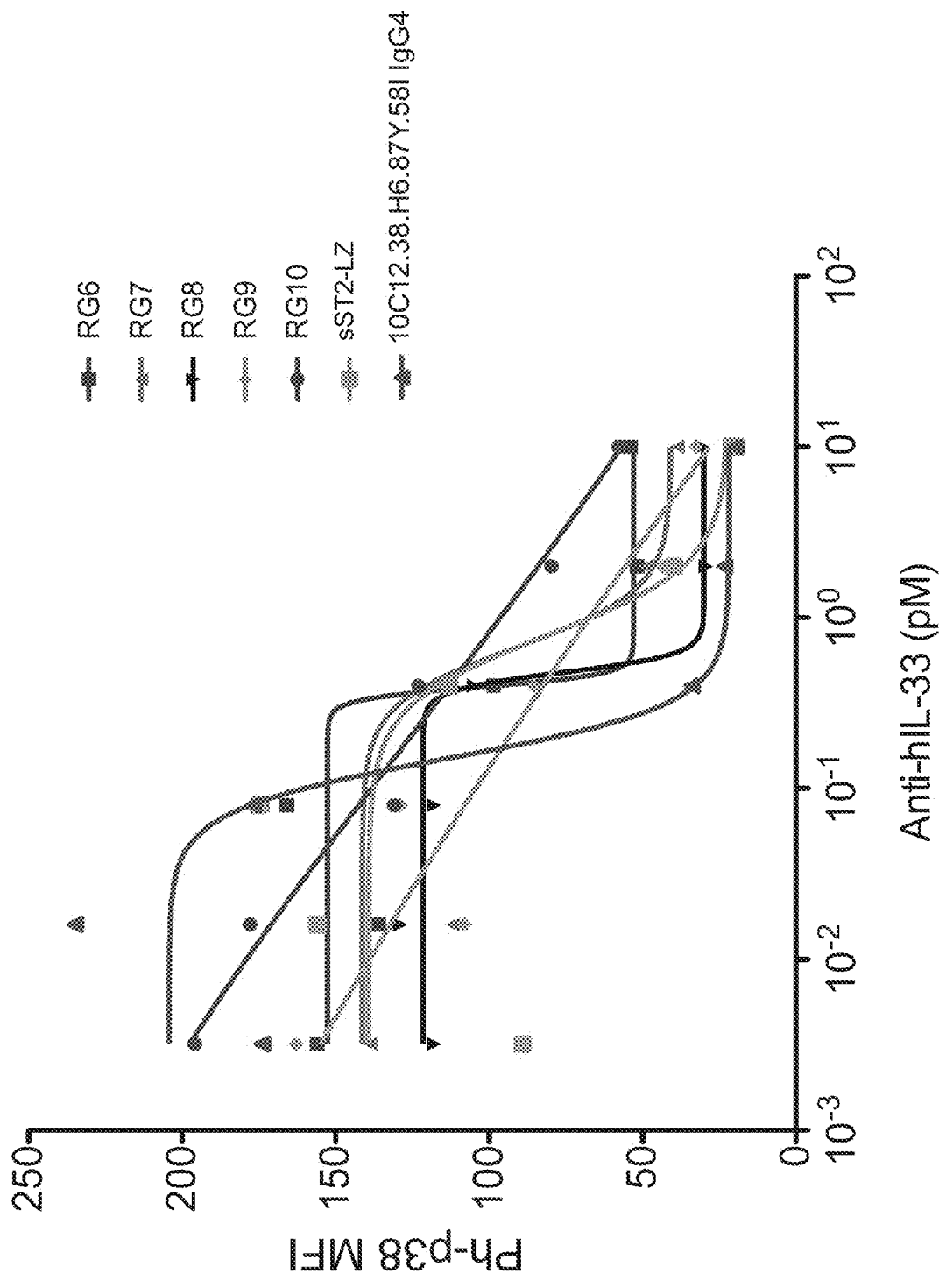

FIG. 24G is a graph showing inhibition of human IL-33 activity in primary basophils. The graph plots dose-response curves of anti-IL-33 antibodies RG6-RG10 relative to 10C12.38.H6.87Y.58I IgG4 and sST2-LZ.

Figure 24H:
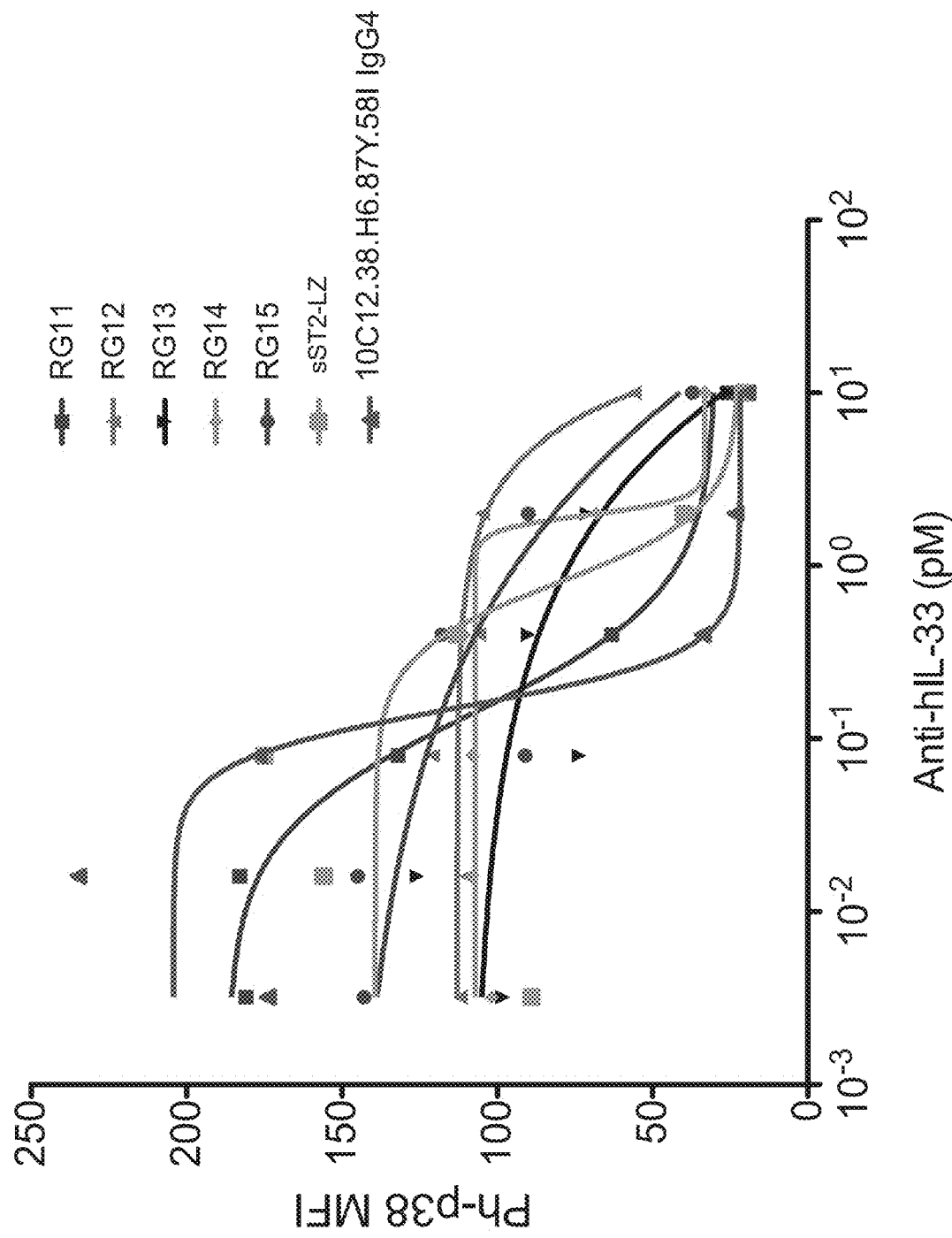

FIG. 24H is a graph showing inhibition of human IL-33 activity in primary basophils. The graph plots dose-response curves of anti-IL-33 antibodies RG11-RG15 relative to 10C12.38.H6.87Y.58I IgG4 and sST2-LZ.

Figure 24I:
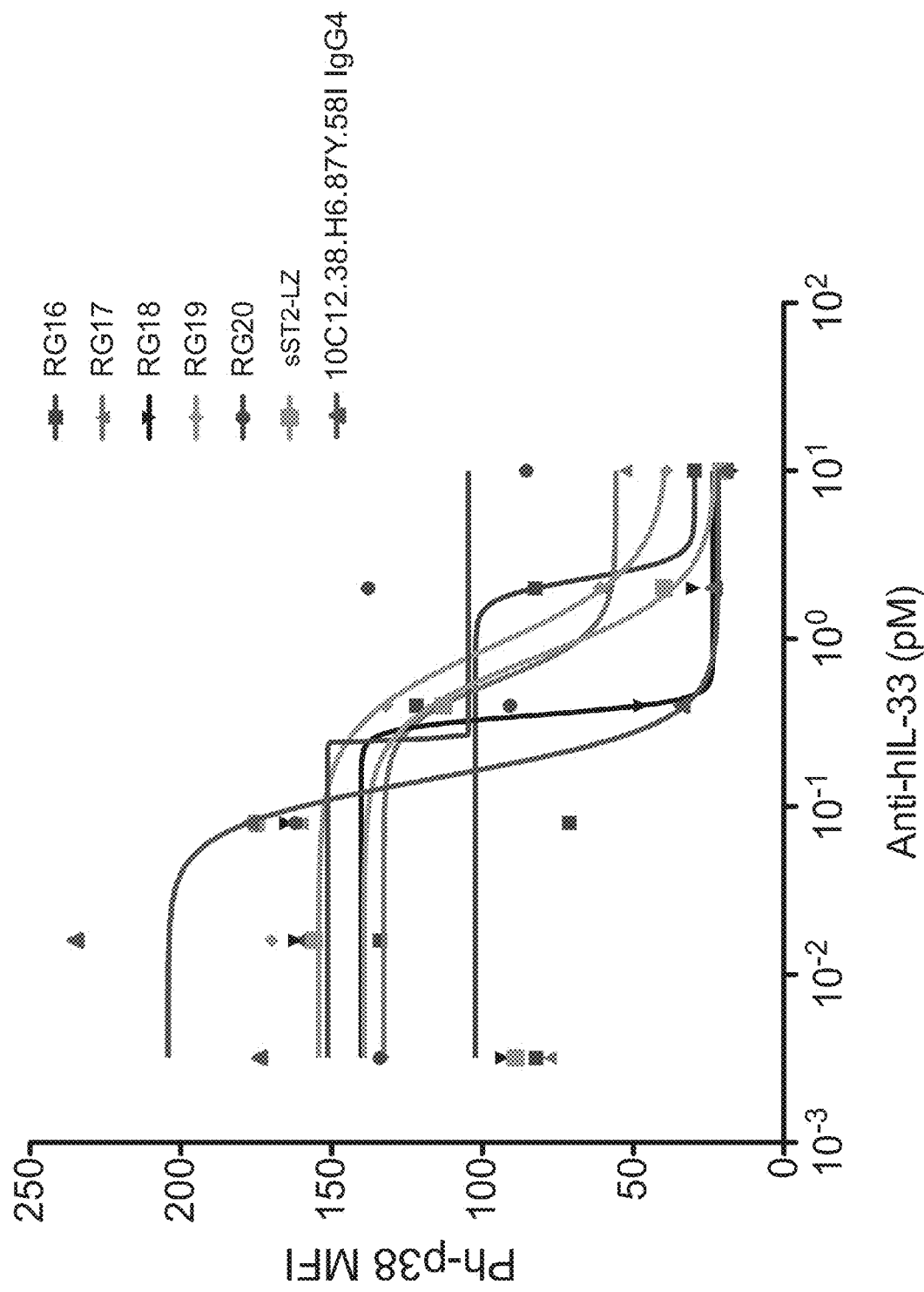

FIG. 24I is a graph showing inhibition of human IL-33 activity in primary basophils. The graph plots dose-response curves of anti-IL-33 antibodies RG16-RG20 relative to 10C12.38.H6.87Y.58I IgG4 and sST2-LZ.

Figure 24J:
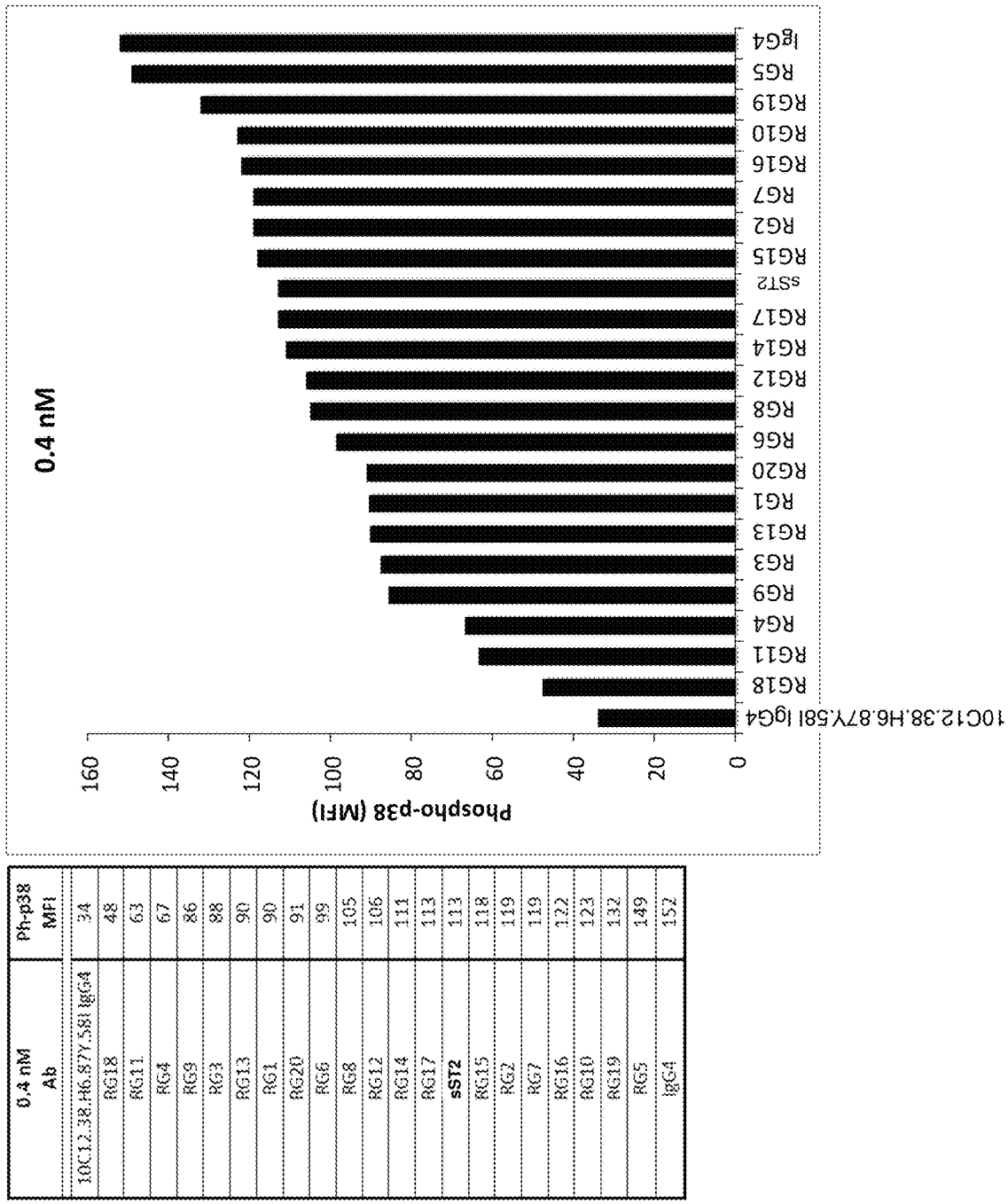
Figure 24K:
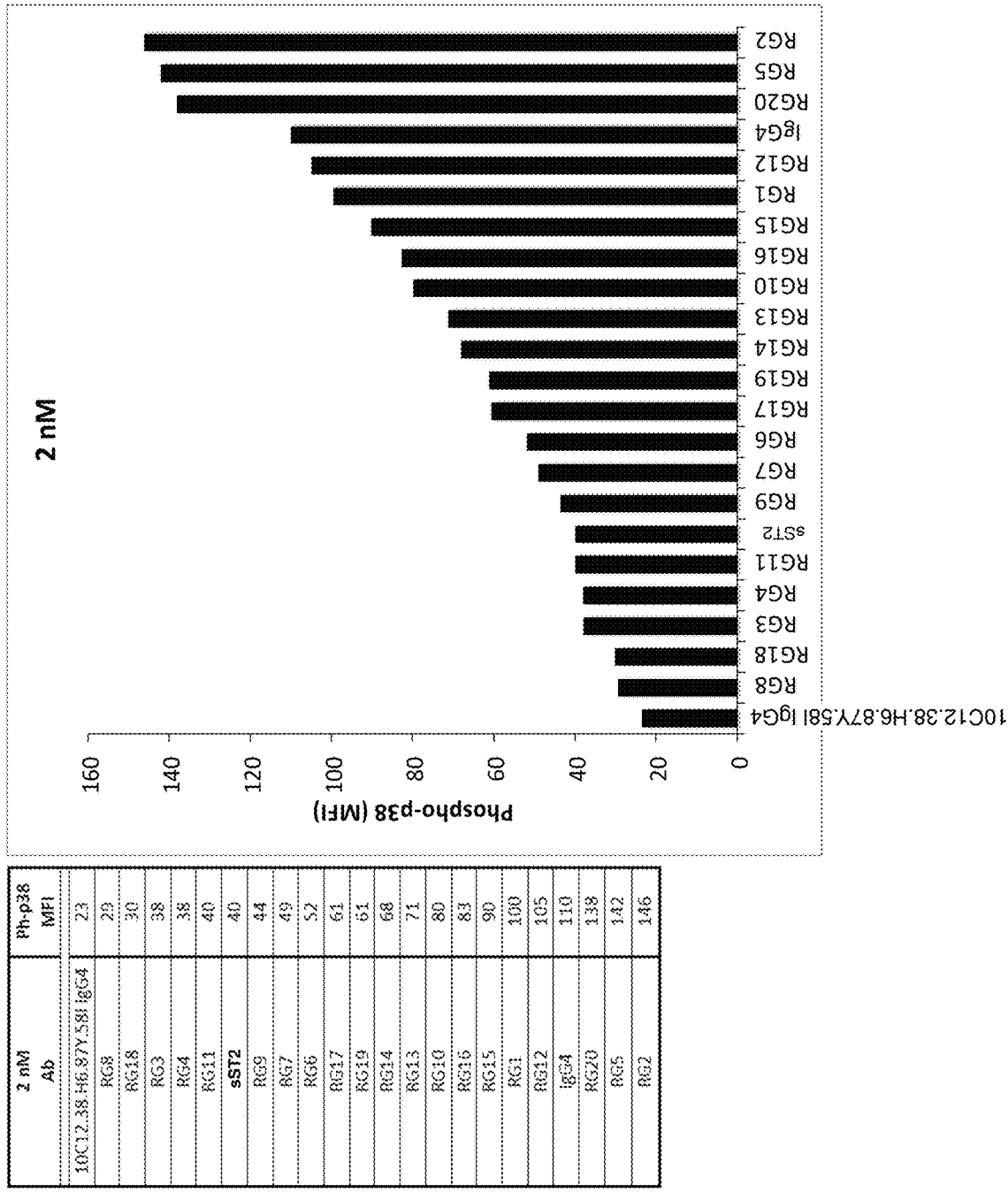

FIGS. 24J and 24K are graphs showing mean fluorescence intensity (MFI) values of p38 MAPK (Thr180/Tyr182) phosphorylation (Ph-p38) used to determine the extent of inhibition of 500 pM human IL-33 activity in basophils by 0.4 nM (FIG. 24J) or 2 nM (FIG. 24K) anti-IL-33 antibodies (RG1-RG20 and 10C12.38.H6.87Y.58I IgG4), sST2-LZ, and the isotype control antibody (IgG4). The table to the left of each graph summarizes the results for the indicated antibodies.

Figure 25A:
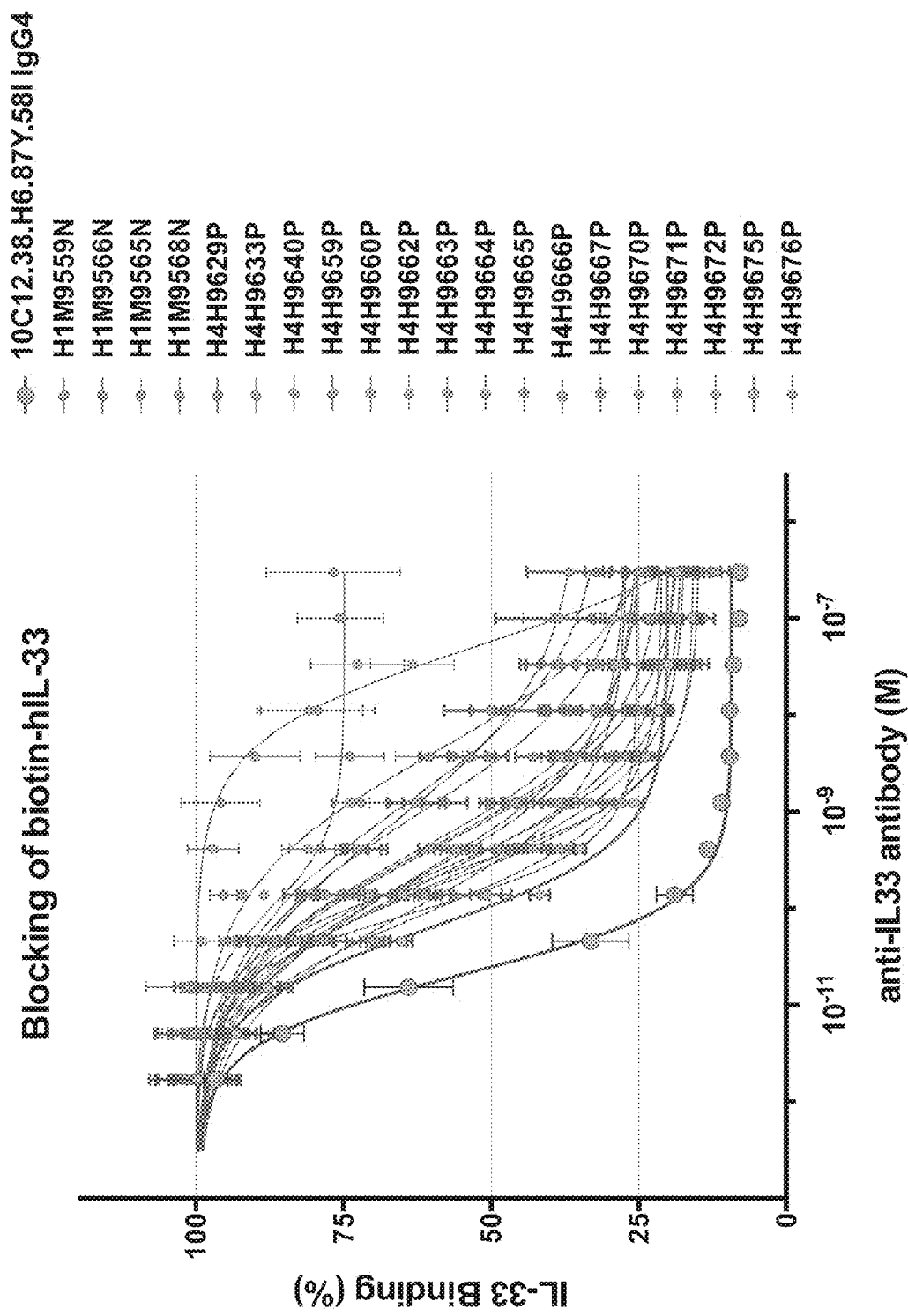
Figure 25B:
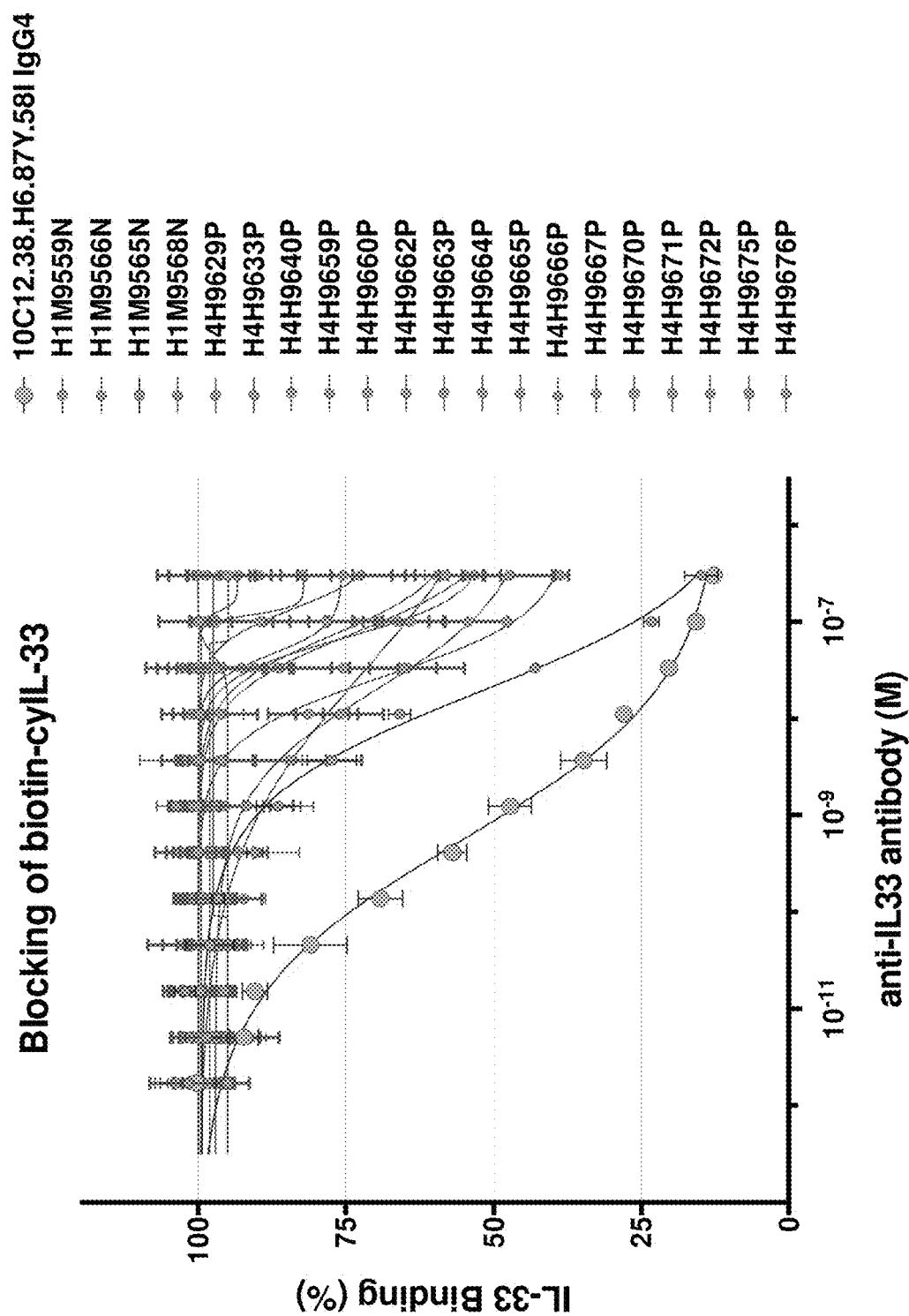

FIGS. 25A and 25B are graphs showing the results of competitive binding ELISA experiments to measure blocking activity of anti-IL-33 antibodies to human (FIG. 25A) or cyno (FIG. 25B) IL-33, as described in Example 9, Section F. The graphs plot % IL-33 binding as a function of anti-IL-33 antibody concentration (M).

DETAILED DESCRIPTION OF EMBODIMENTS OF THE INVENTION

I. Definitions

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity-matured" antibody is one with one or more alterations in one or more HVRs and/or framework regions which result in an improvement in the affinity of the antibody for antigen, compared to a parent antibody which does not possess those alteration(s). Preferred affinity-matured antibodies will have nanomolar or even picomolar affinities for the target antigen. Affinity-matured antibodies are produced by procedures known in the art. For example, Marks et al. *Bio/Technology* 10:779-783, 1992 describes affinity maturation by VH and VL domain shuffling. Random mutagenesis of HVR and/or framework residues is described by: Barbas et al. *Proc. Natl. Acad. Sci. USA* 91:3809-3813, 1994; Schier et al. *Gene* 169:147-155, 1995; Yelton et al. *J. Immunol.* 155:1994-2004, 1995; Jackson et al. *J. Immunol.* 154(7):3310-3319, 1995; and Hawkins et al. *J. Mol. Biol.* 226:889-896, 1992.

The term "antibody" herein is used in the broadest sense and encompasses various antibody structures, including but not limited to monoclonal antibodies, polyclonal antibodies, multispecific antibodies (e.g., bispecific antibodies, including anti-IL-33/anti-IL-13 bispecific antibodies), and antibody fragments so long as they exhibit the desired antigen-binding activity.

The term "interleukin-33 (IL-33)," as used herein, refers to any native IL-33 from any vertebrate source, including mammals such as primates (e.g., humans and cynomoigus monkeys) and rodents (e.g., mice and rats), unless otherwise indicated. IL-33 is also referred to in the art as nuclear factor of high endothelial venules (NF-HEV; see, e.g., Baekkevold et al. *Am. J. Pathol.* 163(1): 69-79, 2003), DVS27, C9orf26, and interleukin-1 family member 11 (IL-1F11). The term encompasses "full-length," unprocessed IL-33, as well as any form of IL-33 that results from processing in the cell. Human full-length, unprocessed IL-33 contains 270 amino acids (a.a.) and may also be referred to as $IL-33_{1-270}$. Processed forms of human IL-33 include, for example, $IL-33_{95-270}$, $IL-33_{99-270}$, $IL-33_{190-270}$, $IL-33_{112-270}$, $IL-33_{1-178}$, and $IL-33_{179-270}$ (Lefrançais et al. *Proc. Natl. Acad. Sci.* 109(5):1673-1678, 2012 and Martin. *Semin. Immunol.* 25: 449-457, 2013). In some embodiments, processed forms of human IL-33, e.g., $IL-33_{95-270}$, $IL-33_{99-270}$, $IL-33_{109-270}$, or other forms processed by proteases such as calpain, proteinase 3, neutrophil elastase, and cathepsin G may have increased biological activity compared to full-length IL-33. The term also encompasses naturally occurring variants of IL-33, for example, splice variants (e.g., the constitutively active splice variant spIL-33 which lacks exon 3, Hong et al. *J. Biol. Chem.* 286(22):20078-20086, 2011) or allelic variants. IL-33 may be present within a cell (e.g., within the nucleus) or as a secreted cytokine form. Full-length IL-33 protein contains a helix-turn-helix DNA-binding motif including nuclear localization sequence (a.a.1-75 of human IL-33), which includes a chromatin binding motif (a.a. 40-58 of human IL-33). Forms of IL-33 that are processed and secreted lack these N-terminal motifs. The amino acid sequence of an exemplary human IL-33 can be found, for example, under UniProtKB accession number O95760.

By "IL-33 axis" is meant a nucleic acid (e.g., a gene or mRNA transcribed from the gene) or polypeptide that is involved in IL-33 signal transduction. For example, the IL-33 axis may include the ligand IL-33, a receptor (e.g., ST2 and/or IL-1RAcP), adaptor molecules (e.g., MyD88), or proteins that associate with receptor molecules and/or adaptor molecules (e.g., kinases, such as interleukin-1 receptor-associated kinase 1 (IRAK1) and interleukin-1 receptor-associated kinase 4 (IRAK4), or E3 ubiquitin ligases, such as TNF receptor associated factor 6 (TRAF6)).

Figure 1A:
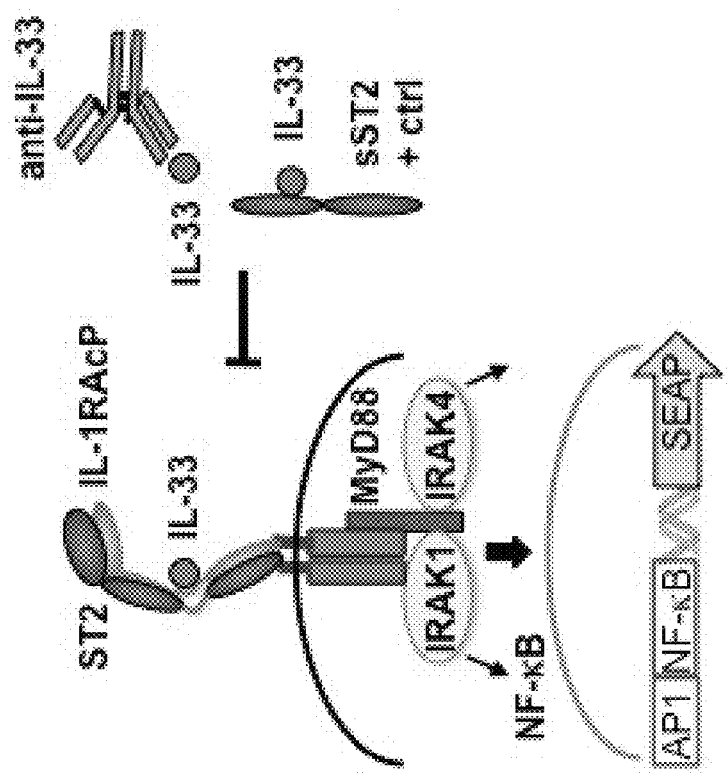
FIG. 1A is a diagram showing a schematic of a cell-based IL-33 blocking assay. SEAP is used as a reporter gene for NF-κB/AP-1 secreted alkaline phosphatase. Soluble ST2 (sST2) is used as a positive control.
Figure 1B:
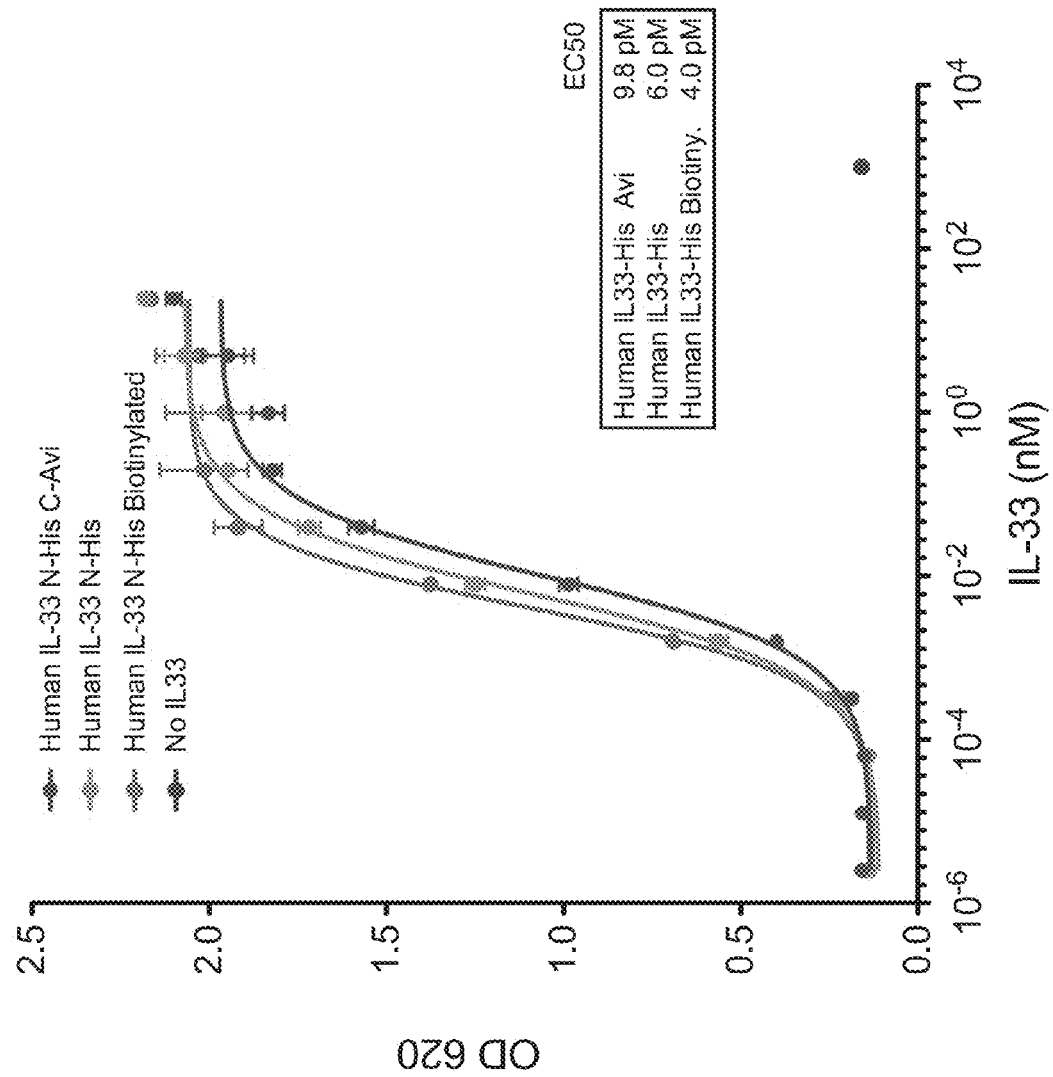
FIG. 1B is a graph showing the results of a cell-based IL-33 blocking assay for human IL-33.
Figure 1C:
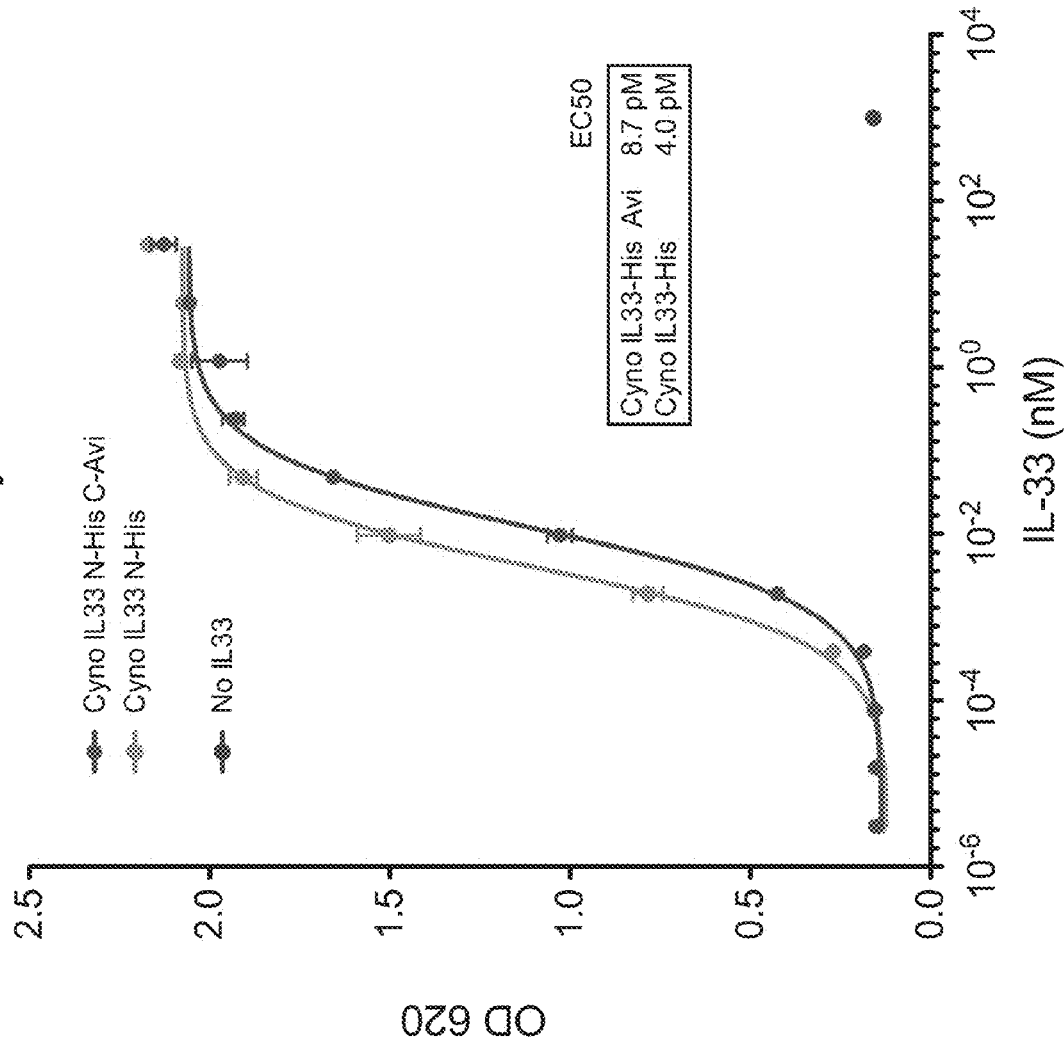
FIG. 1C is a graph showing the results of a cell-based IL-33 blocking assay for cynomolgus monkey (cyno) IL-33.

The terms "interleukin 1 receptor-like 1 (IL1RL1)" and "ST2," used interchangeably herein, refer to any native ST2 from any vertebrate source, including mammals such as primates (e.g., humans) and rodents (e.g., mice and rats), unless otherwise indicated. ST2 is also referred to in the art as DER4, T1, and FIT-1. The term encompasses "full-length," unprocessed ST2, as well as any form of ST2 that results from processing in the cell. At least four isoforms of ST2 are known in the art, including soluble (sST2, also known as IL1RL1-a) and transmembrane (ST2L, also known as IL1RL1-b), which arise from differential mRNA expression from a dual promoter system, and ST2V and ST2LV, which arise from alternative splicing, as described below. The domain structure of ST2L includes three extracellular immunoglobulin-like C2 domains, a transmembrane domain, and a cytoplasmic Toll/Interleukin-1 receptor (TIR) domain, sST2 lacks the transmembrane and cytoplasmic domains contained within ST2L and includes a unique 9 amino acid (a.a.) C-terminal sequence (see, e.g., Kakkar et al. *Nat. Rev. Drug Disc.* 7: 827-840, 2008). sST2 can function as a decoy receptor to inhibit soluble IL-33. The term also encompasses naturally occurring variants of ST2, e.g., splice variants (e.g., ST2V, which lacks the third immunoglobulin motif and has a unique hydrophobic tail, and ST2LV, which lacks the transmembrane domain of ST2L) or allelic variants (e.g., variants that are protective against asthma risk or that confer asthma risk as described herein). The amino acid sequence of an exemplary human ST2 can be found, for example, under UniProtKB accession number Q01638. ST2 is a part of the IL-33 receptor along with the co-receptor protein IL-1RAcP. Binding of IL-33 to ST2 and the co-receptor interleukin-1 receptor accessory protein (IL-1RAcP) forms a 1:1:1 ternary signaling complex to promote downstream signal transduction, as depicted in FIG. 1A (see, e.g., Lingel et al. *Structure* 17(10): 1398-1410, 2009, and Liu et al. *Proc. Natl. Acad. Sci.* 110(37): 14918-14924, 2013).

The terms "anti-IL-33 antibody," an "antibody that binds to IL-33," and "antibody that specifically binds IL-33" refer to an antibody that is capable of binding IL-33 with sufficient affinity such that the antibody is useful as a diagnostic and/or therapeutic agent in targeting IL-33. In one embodiment, the extent of binding of an anti-IL-33 antibody to an unrelated, non-IL-33 protein is less than about 10% of the binding of the antibody to IL-33 as measured, e.g., by a radioimmunoassay (RIA). In certain embodiments, an antibody that binds to IL-33 has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-IL-33 antibody binds to an epitope of IL-33 that is conserved among IL-33 from different species.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al. *Protein Eng.* 8(10):1057-1062, 1995); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain ($C_H1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having an additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest,* 5th Ed. Public Health Service, National Institutes of Health, Bethesda, Md., 1991.

"Fv" consists of a dimer of one heavy- and one light-chain variable region domain in tight, noncovalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three Hs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies,* vol. 113, Rosenburg and Moore eds., Springer-Verlag, New York, pp. 269-315, 1994.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al. *Proc. Natl. Acad. Sci. USA* 90:6444-6448, 1993.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

A "blocking" antibody or an "antagonist" antibody is one which inhibits or reduces biological activity of the antigen it binds. Certain blocking antibodies or antagonist antibodies substantially or completely inhibit the biological activity of the antigen.

A "cell-based blocking assay" refers to an assay in which the ability of an antibody to inhibit or reduce the biological activity of the antigen it binds can be measured. For example, a cell-based assay can be used to measure the concentration of antibody required to inhibit a specific biological or biochemical function. In some embodiments, the half maximal inhibitory concentration (IC50) and/or 90% inhibitory concentration (IC90) of an antibody (e.g., an anti-IL-33 antibody of the invention) is measured using a cell-based blocking assay. In some embodiments, the cell-based blocking assay is used to determine whether an antibody blocks the interaction between a ligand (e.g., IL-33) and its receptor (e.g., ST2 and/or the coreceptor IL-1RAcP). An exemplary cell-based blocking assay for IL-33 is provided herein in Example 2B. Additional exemplary cell-based blocking assays for IL-33 are provided herein, for example, in Example 8, including primary natural killer (NK) cell assays and primary basophil cell assays.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, IgG2, IgG3, IgG4, $IgA_1$, and $IgA_2$. The heavy chain constant domains that correspond to the different classes of immunoglobulins are called α, δ, ε, γ, and μ, respectively.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch et al. *Annu. Rev. Immunol.* 9:457-492, 1991. To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. *Proc. Natl. Acad. Sci. USA* 95:652-656, 1998.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234, 1997). FcRs are reviewed, for example, in Ravetch et al. *Annu. Rev. Immunol.* 9:457-492, 1991; Capel et al. *Immunomethods* 4:25-34, 1994; and de Haas et al. *J. Lab. Clin. Med.* 126:330-41, 1995. Other FcRs, including those to be identified in the future, are encompassed by the term "FcR" herein. The term also includes the neonatal receptor, FcRn, which is responsible for the transfer of maternal IgGs to the fetus (see, e.g., Guyer et al. *J. Immunol.* 117:587, 1976; and Kim et al. *J. Immunol.* 24:249, 1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al. *J. Immunol. Methods* 202:163, 1996, can be performed.

An "epitope" is the portion of the antigen to which the antibody selectively binds. For a polypeptide antigen, the epitope is generally a peptide portion of about 4-15 amino acid residues.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human and/or has been made using any of the techniques for making human antibodies. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. *Sequences of Proteins of Immunological Interest*, Fifth Edition, NIH Publication 91-3242, Bethesda Md., vols. 1-3, 1991. In one embodiment, for the VL, the subgroup is subgroup kappa III or kappa IV as in Kabat et al. supra. In one embodiment, for the VH, the subgroup is subgroup III as in Kabat et al. supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 321:522-525, 1986; Riechmann et al. *Nature* 332:323-329, 1988; and Presta, *Curr. Op. Struct. Biol.* 2:593-596, 1992.

An "immunoconjugate" is an antibody conjugated to one or more heterologous molecule(s), including but not limited to a cytotoxic agent.

The term "isolated" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., sodium dodecyl sulfate polyacrylamide gel electrophoresis (SDS-PAGE), isoelectric focusing (IEF), capillary electrophoresis) or chromatographic (e.g., ion exchange or reverse phase HPLC) methods. For a review of methods for assessment of antibody purity, see, for example, Flatman et al. *J. Chromatogr. B* 848:79-87, 2007. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody comprising a heavy chain variable domain (VH) and a light chain variable domain (VL), where the VHVL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces, or VH/VL interfaces of antibodies (see, e.g., US 2011/0287009, US2007/0178552, WO 96/027011, WO 98/050431, and Zhu et al. *Protein Science* 6:781-788, 1997). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprises different target recognition sequences (e.g., including affibodies, peptibodies, and other Fc fusions).

The term "knob mutation," as used herein, refers to a mutation that introduces a protuberance (knob) into a polypeptide at an interface in which the polypeptide interacts with another polypeptide. In some embodiments, the other polypeptide has a hole mutation (see e.g., U.S. Pat. Nos. 5,731,168; 5,807,706; 5,821,333; 7,695,936; and 8,216,805, which are each incorporated herein by reference in their entirety).

The term "hole mutation," as used herein, refers to a mutation that introduces a cavity (hole) into a polypeptide at an interface in which the polypeptide interacts with another polypeptide. In some embodiments, the other polypeptide has a knob mutation (see e.g., U.S. Pat. Nos. 5,731,168; 5,807,706; 5,821,333; 7,695,936; and 8,216,805, which are each incorporated herein by reference in their entirety).

A "naked antibody" refers to an antibody that is not conjugated to a heterologous moiety (e.g., a cytotoxic moiety) or radiolabel. The naked antibody may be present in a pharmaceutical composition.

With regard to the binding of a antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from e.g., around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al. supra) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia et al. *J. Mol. Biol.* 196:901-917, 1987. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al. supra). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The term "variable domain residue numbering as in Kabat" or "amino acid position numbering as in Kabat," and variations thereof, refers to the numbering system used for heavy chain variable domains or light chain variable domains of the compilation of antibodies in Kabat et al. supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al. supra). The "EU numbering system" or "EU index" is generally used when referring to a residue in an immunoglobulin heavy chain constant region (e.g., the EU index reported in Kabat et al. supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

As used herein, "administering" is meant a method of giving a dosage of a compound (e.g., an anti-IL-33 antibody of the invention or a nucleic acid encoding an anti-IL-33 antibody of the invention) or a composition (e.g., a pharmaceutical composition, e.g., a pharmaceutical composition including an anti-IL-33 antibody of the invention) to a subject. The compositions utilized in the methods described herein can be administered, for example, intravitreally, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, periocularly, conjunctivally, subtenonly, intracamerally, subretinally, retrobulbarly, intracanalicularly, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

The term "asthma" refers herein to a disorder characterized by variable and recurring symptoms, reversible airflow obstruction (e.g., by bronchodilator), and bronchial hyper-responsiveness, which may or may not be associated with underlying inflammation. Asthma may therefore be inflammatory/inflamed asthma or non-inflammatory/non-inflamed asthma. Examples of asthma include allergic asthma, exercise-induced asthma, aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, and other asthmas as mentioned in Bousquet et al. *J. Allergy Clin. Immunol.* 126(5): 926-938, 2010.

A "disorder" or "disease" is any condition that would benefit from treatment with the antibody. For example, a disorder may be an IL-33-mediated disorder. This includes chronic and acute disorders or diseases including those pathological conditions which predispose the mammal to the disorder in question. Examples of disorders to be treated herein include IL-33-mediated disorders (e.g., asthma, allergic rhinitis, atopic dermatitis, and fibrosis (e.g., pulmonary fibrosis, e.g., idiopathic pulmonary fibrosis)).

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including aitretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al. *Angew. Chem Intl. Ed. Engl.,* 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopuine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylomithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifamib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); famesyitransferase inhibitors such as lonafamib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed herein.

An "effective amount" of an agent, e.g., a pharmaceutical formulation, refers to an amount effective, at dosages and for periods of time necessary, to achieve the desired therapeutic or prophylactic result.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn et al. eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "IL-33-mediated disorder," as used herein, refers to any disorder or condition mediated by, or associated with, the IL-33 axis. In some embodiments, IL-33-mediated disorders are associated with excess IL-33 levels or activity in which atypical symptoms may manifest due to the levels or activity of IL-33 locally and/or systemically in the body. Exemplary IL-33-mediated disorders include inflammatory conditions, immune disorders, fibrotic disorders, eosinophilic disorders, infections, pain, central nervous system disorders, solid tumors, and ophthalmologic disorders. IL-33-mediated disorders are described, for example, in Liew et al. *Nature Reviews Immunology* 10: 103-110, 2010, which is incorporated herein by reference in its entirety.

Exemplary inflammatory conditions include asthma (e.g., allergic asthma, exercise-induced asthma, aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, etc.), airway inflammation, airway hyperreactivity, airway hyperresponsiveness, rhinosinusitis, rhinosinusitis with polyps, nasal polyposis, arthritis (e.g., osteoarthritis, rheumatoid arthritis, collagen-induced arthritis, arthritic joints as a result of injury, etc.), eosinophilic inflammation, mast cell-mediated inflammatory diseases, sepsis, septic shock, seronegative enthesopathy and arthropathy (SEA) syndrome, osteoporosis, eosinophilic esophagitis, scleroderma, dermatitis, atopic dermatitis, allergic rhinitis, bullous pemphigoid, chronic urticaria, cartilage inflammation, polymyalgia rheumatic, polyarteritis nodossa, Wegener's granulomatosis, Behcet's disease, myolitis, polymyolitis, dermatomyolitis, dermatomyositis, vasculitis, arteritis, diabetic nephropathy, interstitial cystitis, graft versus host disease (GVHD), gastrointestinal inflammatory conditions (e.g., inflammatory bowel disease (IBD), ulcerative colitis (UC), Crohn's disease (CD), colitis (e.g., colitis caused by environmental insults (e.g., caused by or associated with a therapeutic regimen, such as chemotherapy, radiation therapy, etc.), infectious colitis, ischemic colitis, collagenous or lymphocytic colitis, necrotizing enterocolitis, colitis in conditions such as chronic granulomatous disease or celiac disease, food allergies, gastritis, infectious gastritis or enterocolitis (e.g., *Helicobacter pylori*-infected chronic active gastritis), and other forms of gastrointestinal inflammation caused by an infectious agent), and inflammatory pulmonary conditions (e.g., chronic obstructive pulmonary disease (COPD), eosinophilic pulmonary inflammation, infection-induced pulmonary conditions (including those associated with viral (e.g., influenza, parainfluenza, rotavirus, human metapneumovirus, and respiratory syncytial virus), bacterial, fungal (e.g., *Aspergillus*), parasitic, or prion infection, allergen-induced pulmonary conditions, pollutant-induced pulmonary conditions (e.g., asbestosis, silicosis, or berylliosis), gastric aspiration-induced pulmonary conditions, immune dysregulation, inflammatory conditions with genetic predisposition such as cystic fibrosis, physical trauma-induced pulmonary conditions (e.g., ventilator injury), emphysema, bronchitis, sarcoidosis, histiocytosis, lymphangiomyomatosis, acute lung injury, acute respiratory distress syndrome, chronic lung disease, bronchopulmonary dysplasia, pneumonia (e.g., community-acquired pneumonia, nosocomial pneumonia, ventilator-associated pneumonia, viral pneumonia, bacterial pneumonia, and severe pneumonia), airway exacerbations, and acute respiratory distress syndrome (ARDS)).

Exemplary immune disorders include those mediated at least in part by mast cells, such as asthma (e.g., allergic asthma), eczema, itch, allergy, atopic allergy, anaphylaxis, anaphylactic shock, allergic bronchopulmonary aspergillosis, allergic rhinitis, allergic conjunctivitis, as well as autoimmune disorders including rheumatoid arthritis, juvenile rheumatoid arthritis, psoriatic arthritis, pancreatitis, psoriasis, plaque psoriasis, guttate psoriasis, inverse psoriasis, pustular psoriasis, erythrodermic psoriasis, paraneoplastic autoimmune diseases, autoimmune hepatitis, bullous pemphigoid, myasthenia gravis, inflammatory bowel disease, Crohn's disease, ulcerative colitis, celiac disease, thyroiditis (e.g., Graves' disease), Sjogren's syndrome, Guillain-Barre disease, Raynaud's phenomenon, Addison's disease, liver diseases (e.g., primary biliary cirrhosis, primary sclerosing cholangitis, non-alcoholic fatty liver disease, and non-alcoholic steatohepatitis), and diabetes (e.g., type I diabetes).

As used herein, the terms "fibrotic disorder" or "fibrosis" refer to conditions involving formation of excess fibrous connective tissue in an organ or tissue. Exemplary fibrotic disorders include lung fibrosis, liver fibrosis (e.g., fibrosis associated with cirrhosis (e.g., alcohol-induced cirrhosis, viral-induced cirrhosis, post-hepatitis C cirrhosis, and primary biliary cirrhosis), schistosomiasis, cholangitis (e.g., sclerosing cholangitis), and autoimmune-induced hepatitis), kidney fibrosis (e.g., tubulointerstitial fibrosis, scleroderma, diabetic nephritis, and glomerular nephritis), dermal fibrosis (e.g., scleroderma, hypertrophic and keloid scarring, nephrogenic fibrosing dermatopathy, and burns), myelofibrosis, neurofibromatosis, fibroma, intestinal fibrosis, and fibrotic adhesions resulting from surgical procedures), heart fibrosis (e.g., fibrosis associated with myocardial infarction), vascular fibrosis (e.g., fibrosis associated with postangioplasty arterial restenosis and atherosclerosis), eye fibrosis (e.g., fibrosis associated with post-cataract surgery, proliferative vitreoretinopathy, and retro-orbital fibrosis), and bone marrow fibrosis (e.g., idiopathic myelofibrosis and drug-induced myelofibrosis). The fibrosis can be organ-specific or systemic (e.g., systemic sclerosis and fibrosis associated with GVHD).

Examples of lung fibrosis include, for example, lung or pulmonary fibrosis associated with idiopathic pulmonary fibrosis, fibrosis with collagen vascular disease, Hermansky-Pudlak syndrome, adult respiratory distress syndrome, non-specific interstitial pneumonia, respiratory bronciolitis, sarcoidosis, histiocytosis X, bronchiolitis obliterans, and cryptogenic organizing pneumonia. In one embodiment, the lung fibrosis is idiopathic pulmonary fibrosis.

As used herein, an "eosinophilic disorder" is a disorder associated with excess eosinophil numbers in which atypical symptoms may manifest due to the levels or activity of eosinophils locally or systemically in the body. Eosinophilic disorders include but are not limited to, asthma (including aspirin sensitive asthma, atopic asthma, and severe asthma), eosinophilic inflammation, atopic dermatitis, allergic rhinitis (including seasonal allergic rhinitis), non-allergic rhinitis, chronic eosinophilic pneumonia, allergic bronchopulmonary aspergillosis, celiac disease, Churg-Strauss syndrome (periarteritis nodosa plus atopy), eosinophilic myalgia syndrome, hypereosinophilic syndrome, edematous reactions including episodic angiodema, helminth infections, where eosinophils may have a protective role, onchocercal dermatitis, eosinophil-associated gastrointestinal disorders (EGIDs), including but not limited to, eosinophilic esophagitis, eosinophilic gastritis, eosinophilic gastroenteritis, eosinophilic enteritis and eosinophilic colitis, nasal micropolyposis and polyposis, aspirin intolerance, and obstructive sleep apnea. Eosinophil-derived secretory products have also been associated with the promotion of angiogenesis and connective tissue formation in tumors and the fibrotic responses seen in conditions such as chronic asthma, Crohn's disease, scleroderma and endomyocardial fibrosis (Munitz et al. *Allergy* 59: 268-275, 2004; Adamko et al. *Allergy* 60: 13-22, 2005; Oldhoff et al. *Allergy* 60: 693-696, 2005). Other examples include cancer (e.g., glioblastoma (such as glioblastoma multiforme) and non-Hodgkin's lymphoma (NHL)), atopic dermatitis, allergic rhinitis, inflammatory bowel disease, fibrosis (e.g., pulmonary fibrosis (e.g., idiopathic pulmonary fibrosis (IPF) and pulmonary fibrosis secondary to sclerosis) and hepatic fibrosis), and COPD.

Examples of infection include helminth infection (e.g., nematode infection, such as *Trichuris muris* infection of mice, which is a model for infection by the human parasite *Trichuris trichiura*), protozoan infection (e.g., *Leishmania major* infection), and viral infection (e.g., respiratory syncytial virus infection and influenza virus infection).

Examples of pain include inflammatory pain, hyperalgesia (e.g., mechanical hyperalgesia), allodynia, and hypemociception (e.g., cutaneous and articular hypemociception, which may or may not be antigen-induced).

Examples of central nervous system disorders include subarachnoid hemorrhage, inflammatory diseases of the central nervous system, neurodegenerative diseases (e.g., Alzheimer's disease, experimental autoimmune encephalomyelitis, multiple sclerosis, Parkinson's disease, Huntington's disease), bipolar disorder, and infection of the central nervous system (e.g., viral infection).

Examples of solid tumors include tumors of the colon, breast, prostate, lung, kidney, liver, pancreas, ovary, head and neck, oral cavity, stomach, duodenum, small intestine, large intestine, gastrointestinal tract, anus, gall bladder, labium, nasopharynx, skin, uterus, male genital organ, urinary organs, bladder, and skin. Solid tumors of non-epithelial origin include sarcomas, brain tumors, and bone tumors.

Examples of ophthalmologic disorders include age-related macular degeneration (AMD), including wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retina detachment, glaucoma, uveitis (e.g., infectious and non-infectious uveitis), retinitis pigmentosa, Leber Congenital Amaurosis (also known as Leber's congenital amaurosis), Stargardt's disease, traumatic eye injury, and conjunctivitis (e.g., infectious conjunctivitis, non-infectious conjunctivitis, and allergic conjunctivitis).

In some embodiments, ophthalmologic disorders include AMD (including wet AMD, dry AMD, and GA), retinopathy (e.g., DR and ROP), PCV, diabetic macular edema, dry eye disease, Behcet's disease, allergic conjunctivitis, and retina detachment.

It is to be understood that in other embodiments, ophthalmologic disorders include intermediate AMD, advanced AMD, glaucoma, uveitis (e.g., infectious and non-infectious uveitis), retinitis pigmentosa, Leber Congenital Amaurosis (also known as Leber's congenital amaurosis), Stargardt's disease, high-altitude diabetic retinopathy, traumatic eye injury, and conjunctivitis (e.g., infectious conjunctivitis and non-infectious conjunctivitis).

The above list is not all-inclusive, and it will be understood by the skilled artisan that a disease or disorder may fall within various categories. For example, asthma can be categorized in some instances as both an inflammatory disorder and immune disorder and considered by some clinicians to be an autoimmune disorder.

An "IL-33 axis binding antagonist" refers to a molecule that inhibits the interaction of an IL-33 axis binding partner with one or more of its binding partners. As used herein, an IL-33 axis binding antagonist includes IL-33 binding antagonists, ST2 binding antagonists, and IL1RAcP binding antagonists. Exemplary IL-33 axis binding antagonists include anti-IL-33 antibodies and antigen-binding fragments thereof (e.g., anti-IL-33 antibodies such as ANB-020 (AnaptysBio Inc.) or any of the antibodies described in EP1725261. U.S. Pat. No. 8,187,596, WO2011031600, WO2014164959. WO2015099175 or WO2015106080, which are each incorporated herein by reference in their entirety); polypeptides that bind IL-33 and/or its receptor (ST2 and/or IL-1RAcP) and block ligand-receptor interaction (e.g., ST2-Fc proteins, such as those described in WO 2014/152195, which is herein incorporated by reference in its entirety; immunoadhesins, peptibodies, and soluble ST2, or derivatives thereof); anti-IL-33 receptor antibodies (e.g., anti-ST2 antibodies, for example, AMG-282 (Amgen) or STLM15 (Janssen) or any of the anti-ST2 antibodies described in WO 2013/173761 and WO 2013/165894, which are each incorporated herein in their entirety; or ST2-Fc proteins, such as those described in WO 2013/173761; WO 2013/165894; or WO 2014/152195, which are each incorporated herein by reference in their entirety); and IL-33 receptor antagonists, such as small molecule inhibitors, aptamers that bind IL-33, and nucleic acids that hybridize under stringent conditions to IL-33 axis nucleic acid sequences (e.g., short interfering RNAs (siRNA) or clustered regularly interspaced short palindromic repeat RNAs (CRISPR-RNA or crRNA), including single guide RNAs (sgRNAs) having a crRNA and tracrRNA sequence as described in Mali et al. (*Science*. 339: 823-26, 2013), which is incorporated herein by reference in its entirety).

As used herein, "chemoattractant receptor-homologous molecule expressed on Th2 cells (CRTH2)" refers to any native CRTH2 from any vertebrate source, including mammals such as primates (e.g., humans) and rodents (e.g., mice and rats), unless otherwise indicated. CRTH2 is also referred to as G protein coupled receptor 44 (GPR44), cluster of differentiation 294 (CD294), DL1R, and DP2. The term encompasses "full-length," unprocessed CRTH2, as well as any form of CRTH2 that results from processing in the cell. The amino acid sequence of an exemplary human CRTH2 can be found, for example, under UniProtKB accession number Q9Y5Y4.

The term "CRTH2 binding antagonist" refers to a molecule that decreases, blocks, inhibits, abrogates or interferes with signal transduction resulting from the interaction of CRTH2 with one or more of its binding partners, such as prostaglandin $D_2$. Exemplary CRTH2 binding antagonists known in the art include AMG-853, AP768, AP-761, MLN6095, and ACT129968.

The term "interleukin-5 (IL-5)," as used herein, refers to any native IL-5 from any vertebrate source, including mammals such as primates (e.g. humans) and rodents (e.g., mice and rats), unless otherwise indicated. The term encompasses "full-length," unprocessed IL-5, as well as any form of IL-5 that results from processing in the cell. The term also encompasses naturally occurring variants of IL-5, such as splice variants or allelic variants. The amino acid sequence of an exemplary IL-5 can be found, for example, under UniProtKB accession number P05113.

The term "IL-5 binding antagonist" refers to a molecule that decreases, blocks, inhibits, abrogates or interferes with signal transduction resulting from the interaction of IL-5 with one or more of its binding partners, such as IL-5 receptor, alpha (IL5RA). Exemplary IL-5 binding antagonists that can be used in the methods of the invention include, for example, anti-IL-5 antibodies (e.g., mepolizumab and reslizumab) and anti-IL-5R antibodies.

As used herein, "interleukin-13 (IL-13)" refers to any native IL-13 from any vertebrate source, including mammals such as primates (e.g., humans) and rodents (e.g., mice and rats), unless otherwise indicated. IL-13 is a cytokine secreted by many cell types, including T helper type 2 (Th2) cells. The term encompasses "full-length," unprocessed IL-13, as well as any form of IL-13 that results from processing in the cell. The amino acid sequence of an exemplary human IL-13 can be found, for example, under UniProtKB accession number P35225.

The term "IL-13 binding antagonist" refers to a molecule that decreases, blocks, inhibits, abrogates or interferes with signal transduction resulting from the interaction of IL-13 with one or more of its binding partners, such as IL-4 receptor alpha (IL4Rα), IL-13 receptor alpha1 (IL13RA1) and IL-13 receptor alpha2 (IL13RA2). IL-13 binding antagonists include anti-IL-13 antibodies, for example, lebrikizumab, 228B/C-1, 228A-4, 227-26, and 227-43 (see, for example, U.S. Pat. Nos. 7,674,459; 8,067,199; 8,088,618; 8,318,160; and 8,734,797).

As used herein, "interleukin-17 (IL-17)" refers to any native IL-17 from any vertebrate source, including mammals such as primates (e.g., humans) and rodents (e.g., mice and rats), unless otherwise indicated, and includes family members IL-17A, IL-17B, IL-17C, IL-17D, IL-17E, and IL-17F. The term encompasses "full-length," unprocessed IL-17, as well as any form of IL-17 that results from processing in the cell. The amino acid sequence of an exemplary human IL-17A can be found, for example, under UniProtKB accession number Q16552. The amino acid sequence of an exemplary human IL-17B can be found, for example, under UniProtKB accession number Q9UHF5. The amino acid sequence of an exemplary human IL-17C can be found, for example, under UniProtKB accession number Q9P0M4. The amino acid sequence of an exemplary human IL-17D can be found, for example, under UniProtKB accession number Q8TAD2. The amino acid sequence of an exemplary human IL-17E can be found, for example, under UniProtKB accession number Q9H293. The amino acid sequence of an exemplary human IL-17F can be found, for example, under UniProtKB accession number Q96PD4.

The term "IL-17 binding antagonist" refers to a molecule that decreases, blocks, inhibits, abrogates or interferes with signal transduction resulting from the interaction of IL-17 with one or more of its binding partners, such as interleukin-17 receptor (IL-17R) family member proteins interleukin 17 receptor A (IL17RA), interleukin 17 receptor B (IL17RB), interleukin 17 receptor C (IL17RC), interleukin 17 receptor D (IL17RD), interleukin 17 receptor E (IL17RE), and interleukin 17 receptor E-like (IL17REL). Exemplary IL-17 binding antagonists include, for example, anti-IL-17 antibodies (e.g., ixekizumab (LY2439821) and anti-IL-17R antibodies (e.g., brodalumab (AMG-827)).

The term "Janus kinase 1 (JAK1)," as used herein, refers to any native JAK1 from any vertebrate source, including mammals such as primates (e.g. humans) and rodents (e.g., mice and rats), unless otherwise indicated. The term encompasses "full-length," unprocessed JAK1 as well as any form of JAK1 that results from processing in the cell. The term also encompasses naturally occurring variants of JAK1, e.g., splice variants or allelic variants. The amino acid sequence of an exemplary JAK1 can be found, for example, under UniProtKB accession number P23458.

The term "JAK1 antagonist." as used herein, refers to compounds or agents which inhibit or reduce the biological activity of JAK1. Exemplary JAK1 antagonists include small molecule inhibitors (e.g., ruxolitinib, GLPG0634, and GSK2586184).

The term "ST2 binding antagonist" refers to a molecule that inhibits the interaction of an ST2 with IL-33, IL1RAcP, and/or a second ST2 molecule. The ST2 binding antagonist may be a protein, such as an "ST2-Fc protein" that includes an IL-33-binding domain (e.g., all or a portion of an ST2 or IL1RAcP protein) and a multimerizing domain (e.g., an Fc portion of an immunoglobulin, e.g., an Fc domain of an IgG selected from the isotypes IgG1, IgG2, IgG3, and IgG4, as well as any allotype within each isotype group), which are attached to one another either directly or indirectly through a linker (e.g., a serine-glycine (SG) linker, glycine-glycine (GG) linker, or variant thereof (e.g., a SGG, a GGS, an SGS, or a GSG linker)), and includes, but is not limited to, ST2-Fc proteins and variants thereof described in WO 2013/173761, WO 2013/165894, and WO 2014/152195, which are each incorporated herein by reference in their entirety. In some embodiments, a ST2 binding antagonist may be an anti-ST2 antibody, for example, AMG-282 (Amgen) or STLM15 (Janssen) or any of the anti-ST2 antibodies described in WO 2013/173761 and WO 2013/165894.

As used herein, "tryptase-beta" refers to any native tryptase-beta from any vertebrate source, including mammals such as primates (e.g., humans) and rodents (e.g., mice and rats), unless otherwise indicated. As used herein, the term encompasses tryptase beta-1 (encoded by the TPSAB1 gene, which also encodes tryptase alpha-1) and tryptase beta-2 (encoded by the TPSB2 gene). The term encompasses "full-length," unprocessed tryptase-beta as well as any form of tryptase-beta that results from processing in the cell. The amino acid sequence of an exemplary human tryptase beta-2 can be found, for example, under UniProtKB accession number P20231.

The term "tryptase-beta antagonist," as used herein, refers to compounds or agents which inhibit or reduce the biological activity of tryptase beta.

As used herein, "Factor D" refers to any native Factor D from any vertebrate source, including mammals such as primates (e.g., humans) and rodents (e.g., mice and rats), unless otherwise indicated. Factor D is also referred to as C3 proactivator convertase, properdin factor D esterase, Factor D (complement), Complement Factor D, CFD, and adipsin. The term encompasses "full-length," unprocessed Factor D, as well as any form of Factor D that results from processing in the cell. The amino acid sequence of an exemplary human Factor D can be found, for example, under UniProtKB accession number P00746.

The term "Factor D binding antagonist," as used herein, refers to compounds or agents which inhibit or reduce the biological activity of Factor D. Exemplary Factor D binding antagonists include, for example, small molecule inhibitors and anti-Factor D antibodies, for example, any anti-Factor D antibody described in WO 2007/056227, WO 01/70818, and/or US 2002/0081293, which are each incorporated herein by reference in their entirety. In some embodiments, the anti-Factor D antibody is or is derived from monoclonal antibody 166-32, produced by the hybridoma deposited with the ATCC and designated HB 12476.

The term "High-temperature requirement A serine peptidase 1" or "HtrA1," as used herein, refers to any native HtrA1 from any vertebrate source, including mammals such as primates (e.g., humans) and rodents (e.g., mice and rats), unless otherwise indicated. HtrA1 is also known in the art as HtrA serine peptidase 1, L56, and Serine protease 11. The term encompasses "full-length," unprocessed HtrA1 as well as any form of HtrA1 that results from processing in the cell. The term also encompasses naturally occurring variants of HtrA1, e.g., splice variants or allelic variants. The amino acid sequence of an exemplary human HtrA1 can be found, for example, under UniProtKB accession number Q92743.

The term "HtrA1 binding antagonist" as used herein, refers to compounds or agents which inhibit or reduce the biological activity of HtrA1. Exemplary HtrA1 binding antagonists include, for example, small molecule inhibitors and anti-HtrA1 antibodies, for example, any anti-HtrA1 antibody described in WO 2013/055998, which is incorporated herein by reference in its entirety.

The term "vascular endothelial growth factor" or "VEGF" refers to vascular endothelial growth factor protein A, as exemplified by Swiss Prot Accession Number P15692. The term "VEGF" encompasses the protein having the amino acid sequence exemplified by Swiss Prot Accession Number P15692 as well as homologues and isoforms thereof. The term "VEGF" also encompasses the known isoforms, e.g., splice isoforms of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110-amino acid human vascular endothelial cell growth factor generated by plasmin cleavage of $VEGF_{165}$ as described in Ferrara Mol. Biol. Cell. 21:687 (2010), Leung et al., Science, 246:1306 (1989), and Houck et al., Mol. Endocrin., 5:1806 (1991). The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

The term "VEGF antagonist," as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or $VEGF_{165}$.

As used herein VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP))), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib).

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, for example, by a radioimmunoassay (RIA). In certain embodiments, an antibody that binds to VEGF has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M). In certain embodiments, an anti-VEGF antibody binds to an epitope of VEGF that is conserved among VEGF from different species.

In certain embodiments, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF, or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (1997) *Cancer Res.* 57:4593-4599, including but not limited to the antibody known as bevacizumab (BV; AVASTIN®).

The anti-VEGF antibody "bevacizumab (BV)," also known as "rhuMAb VEGF" or "AVASTIN®," is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879 issued Feb. 26, 2005, the entire disclosure of which is expressly incorporated herein by reference. Additional preferred antibodies include the G6 or B20 series antibodies (e.g., G6-31, B20-4.1), as described in PCT Application Publication Nos. WO 2005/012359 and WO 2005/044853, which are each incorporated herein by reference in their entirety. For additional preferred antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004). Other preferred antibodies include those that bind to a functional epitope on human VEGF comprising of residues F17, M18, D19, Y21, Y25, Q89, I91, K101, E103, and C104 or, alternatively, comprising residues F17, Y21, Q22, Y25, D63, I83, and Q89. Additional anti-VEGF antibodies include anti-VEGF antibodies described in PCT Application Publication No. WO 2009/155724.

The anti-VEGF antibody "ranibizumab" also known as "LUCENTIS®" or "rhuFab V2" is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of ~48,000 daltons. See WO 98/45331 and US 2003/0190317.

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The amino acid sequences described herein are contiguous amino acid sequences unless otherwise specified.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al. "Prodrugs: A Chemical Approach to Targeted Drug Delivery," *Directed Drug Delivery*, Borchardt et al. (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, 3-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor.

A "subject" is a vertebrate, preferably a mammal, more preferably a human. Mammals include, but are not limited to, farm animals (such as cows, and sheep), sport animals, pets (such as cats, dogs and horses), primates (e.g., humans and non-human primates such as monkeys), and rodents (e.g., mice and rats).

The term "therapeutically effective amount" refers to an amount of an antibody or antibody fragment to treat a disease or disorder in a subject. In the case of an IL-33-mediated disorder, the therapeutically effective amount of the antibody or antibody fragment (e.g., an anti-IL-33 antibody, including bispecific anti-IL-33 antibodies that bind to IL-33 and a second biological molecule, e.g., IL-13, e.g., bispecific anti-IL-33/anti-IL-13 antibodies) may ameliorate or treat the disease, or prevent, reduce, ameliorate, or treat symptoms associated with the disease. In the case of a proliferative disease (e.g., a solid tumor), the therapeutically effective amount of the antibody or antibody fragment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), duration of disease free survival (DFS), duration of progression free survival (PFS), the response rates (RR), duration of response, and/or quality of life.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease. A patient may be successfully "treated" for asthma if, for example, after receiving an asthma therapy, the patient shows observable and/or measurable reduction in or absence of one or more of the following: recurrent wheezing, coughing, trouble breathing, chest tightness, symptoms that occur or worsen at night, symptoms that are triggered by cold air, exercise or exposure to allergens.

"Tumor", as used herein, refers to all neoplastic cell growth and proliferation, whether malignant or benign, and all pre-cancerous and cancerous cells and tissues.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors" or "expression vectors"). In general, expression vectors of utility in recombinant DNA techniques are often in the form of plasmids. In the present specification, "plasmid" and "vector" may be used interchangeably.

II. Compositions and Methods

In one aspect, the invention is based, in part, on novel antibodies that bind to IL-33. Antibodies of the invention are useful, e.g., for the diagnosis and/or treatment of IL-33-mediated disorders.

A. Exemplary Anti-IL-33 Antibodies

The invention provides isolated antibodies that bind to IL-33. In certain embodiments, an anti-IL-33 antibody of the invention specifically binds both human and cynomolgus monkey (cyno) IL-33 with a $K_D$ of 100 nM or lower (e.g., 100 nM or lower, 10 nM or lower, 1 nM or lower, 100 pM or lower, 10 pM or lower, 1 pM or lower, or 0.1 pM or lower). In some instances, the antibody specifically binds human IL-33 with a $K_D$ of 1 nM or lower (e.g., 1 nm or lower, 100 pM or lower, 10 pM or lower, 1 pM or lower, or 0.1 pM or lower). For example, in some instances, the antibody specifically binds human IL-33 with a $K_D$ between 100 fM and 1 nM. In some instances, the antibody specifically binds cyno IL-33 with a $K_D$ of 1 nM or lower (e.g., 1 nm or lower, 100 pM or lower, 10 pM or lower, 1 pM or lower, or 0.1 pM or lower). For example, in some instances, the antibody specifically binds cyno IL-33 with a $K_D$ between 100 fM and 1 nM. In certain instances, the antibody specifically binds both human and cyno IL-33 with a $K_D$ of 1 nM or lower (e.g., 1 nm or lower, 100 pM or lower, 10 pM or lower, 1 pM or lower, or 0.1 pM or lower). For example, in some instances, the antibody specifically binds both human and cyno IL-33 with a $K_D$ of between 1 pM and 500 pM. In some instances, the antibody specifically binds human IL-33 with a $K_D$ of between 1 pM and 10 pM. In some instances, the antibody does not specifically bind to murine IL-33.

For example, in some instances, the antibody specifically binds human IL-33 with a $K_D$ of between about 1 pM and about 1 nM (e.g., between about 1 pM and about 900 pM, between about 1 pM and about 800 pM, between about 1 pM and about 700 pM, between about 1 pM and about 600 pM, between about 1 pM and about 500 pM, between about 1 pM and about 400 pM, between about 1 pM and about 300 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 20 pM, or between about 1 pM and about 10 pM). In some instances, the antibody specifically binds human IL-33 with a $K_D$ of between about 1 pM and about 250 pM (e.g., between about 1 pM and about 250 pM, between about 1 pM and about 225 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 20 pM, or between about 1 pM and about 10 pM). In some instances, the antibody specifically binds human IL-33 with a $K_D$ of between about 50 pM and about 180 pM (e.g., about 50 pM, about 60 pM, about 70 pM, about 80 pM, about 90 pM, about 100 pM, about 110 pM, about 120 pM, about 130 pM, about 140 pM, about 150 pM, about 160 pM, or about 180 pM). In some embodiments, any of the preceding $K_D$ values may be determined by surface plasmon resonance, for example, as described herein (see, e.g., the Examples, including Example 2, Section D and Example 8, Section E).

In some instances, the antibody specifically binds human IL-33 with a $K_D$ of about 400 pM or lower at 25° C. For example, in some instances, the antibody specifically binds human IL-33 with a $K_D$ of about 390 pM or lower, about 380 pM or lower, about 375 pM or lower, about 350 pM or lower, about 325 pM or lower, about 300 pM or lower, about 275 pM or lower, about 250 pM or lower, about 250 pM or lower, about 225 pM or lower, about 200 pM or lower, about 175 pM or lower, about 150 pM or lower, about 130 pM or lower, about 125 pM or lower, about 100 pM or lower, about 75 pM or lower, about 50 pM or lower, or about 25 pM or lower at 25° C. In some instances, the antibody specifically binds human IL-33 with a $K_D$ of about 20 pM to about 150 pM (e.g., about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, or about 150 pM) at 25° C. In some instances, the antibody specifically binds human IL-33 with a $K_D$ of about 130 pM at 25° C. In some embodiments, any of the preceding $K_D$ values may be determined by surface plasmon resonance, for example, as described herein (see, e.g., the Examples, including Example 2, Section D and Example 8. Section E).

In some instances, the antibody specifically binds human IL-33 with a $K_D$ of about 200 pM or lower at 37° C. For example, in some instances, the antibody specifically binds human IL-33 with a $K_D$ of about 190 pM or lower, about 180 pM or lower, about 175 pM or lower, about 150 pM or lower, about 130 pM or lower, about 125 pM or lower, about 100 pM or lower, about 90 pM or lower, about 80 pM or lower, about 75 pM or lower, about 50 pM or lower, or about 25 pM or lower at 37° C. In some instances, the antibody specifically binds human IL-33 with a $K_D$ of about 20 pM to about 100 pM (e.g., about 20 pM, about 30 pM, about 40 pM, about 50 pM, about 60 pM, about 70 pM, about 80 pM, about 90 pM, or about 100 pM) at 37° C. In some instances, the antibody specifically binds human IL-33 with a $K_D$ of about 90 pM at 37° C. In some embodiments, any of the preceding $K_D$ values may be determined by surface plasmon resonance, for example, as described herein (see, e.g., the Examples, including Example 2, Section D and Example 8, Section E).

In some instances, the antibody specifically binds cyno IL-33 with a $K_D$ of between about 1 pM and about 1 nM (e.g., between about 1 pM and about 900 pM, between about 1 pM and about 800 pM, between about 1 pM and about 700 pM, between about 1 pM and about 600 pM, between about 1 pM and about 500 pM, between about 1 pM and about 400 pM, between about 1 pM and about 300 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 20 pM, or between about 1 pM and about 10 pM). In some instances, the antibody specifically binds cyno IL-33 with a $K_D$ of between about 100 pM and about 750 pM (e.g., between about 100 pM and about 750 pM, between about 200 pM and about 750 pM, between about 225 pM and about 750 pM, between about 250 pM and about 750 pM, between about 265 pM and about 750 pM, between about 275 pM and about 750 pM, between about 300 pM and about 750 pM, between about 325 pM and about 750 pM, between about 350 pM and about 750 pM, between about 375 pM and about 750 pM, between about 400 pM and about 750 pM, between about 425 pM and about 750 pM, between about 450 pM and about 750 pM, between about 475 pM and about 750 pM, between about 500 pM and about 750 pM, between about 525 pM and about 750 pM, between about 550 pM and about 750 pM, between about 575 pM and about 750 pM, between about 600 pM and about 750 pM, between about 650 pM and about 750 pM, or between about 250 pM and about 650 pM). In some embodiments, any of the preceding $K_D$ values may be determined by surface plasmon resonance, for example, as described herein (see, e.g., the Examples, including Example 2, Section D and Example 8, Section E).

For example, in some instances, the antibody specifically binds cyno IL-33 with a $K_D$ of about 650 pM or lower at 25° C. For example, in some instances, the antibody specifically binds cyno IL-33 with a $K_D$ of about 650 pM or lower, about 625 pM or lower, about 600 pM or lower, about 575 pM or lower, about 550 pM or lower, about 525 pM or lower, about 500 pM or lower, about 475 pM or lower, about 450 pM or lower, about 425 pM or lower, about 400 pM or lower, about 375 pM or lower, about 350 pM or lower, about 325 pM or lower, about 300 pM or lower, about 275 pM or lower, about 265 pM or lower, about 250 pM or lower, about 225 pM or lower, about 200 pM or lower, about 175 pM or lower, about 150 pM or lower, about 125 pM or lower, about 100 pM or lower, about 75 pM or lower, about 50 pM or lower, or about 25 pM or lower at 25° C. In some instances, the antibody specifically binds cyno IL-33 with a $K_D$ of about 150 pM to about 500 pM (e.g., about 150 pM, about 175 pM, about 200 pM, about 225 pM, about 250 pM, about 265 pM, about 275 pM, about 300 pM, about 325 pM, about 350 pM, about 375 pM, about 400 pM, about 425 pM, about 450 pM, about 475 pM or about 500 pM) at 25° C. In some instances, the antibody specifically binds cyno IL-33 with a $K_D$ of about 265 pM at 25° C. In some embodiments, any of the preceding $K_D$ values may be determined by surface plasmon resonance, for example, as described herein (see, e.g., the Examples, including Example 2, Section D and Example 8, Section E).

In other instances, the antibody specifically binds cyno IL-33 with a $K_D$ of about 1 nM or lower at 37° C. For example, in some instances, the antibody specifically binds cyno IL-33 with a $K_D$ of about 1 nM or lower, about 950 pM or lower, about 900 pM or lower, about 850 pM or lower, about 800 pM or lower, about 750 pM or lower, about 700 pM or lower, about 650 pM or lower, about 600 pM or lower, about 550 pM or lower, about 525 pM or lower, about 500 pM or lower, about 475 pM or lower, about 450 pM or lower, about 425 pM or lower, about 400 pM or lower, about 350 pM or lower, about 300 pM or lower, about 250 pM or lower, about 200 pM or lower, about 150 pM or lower, about 100 pM or lower, or about 50 pM or lower at 37° C. In some instances, the antibody specifically binds cyno IL-33 with a $K_D$ of about 250 pM to about 750 pM (e.g., about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, or about 750 pM) at 37° C. In some instances, the antibody specifically binds cyno IL-33 with a $K_D$ of about 475 pM at 37° C. In some embodiments, any of the preceding $K_D$ values may be determined by surface plasmon resonance, for example, as described herein (see, e.g., the Examples, including Example 2, Section D and Example 8, Section E). In some embodiments, an anti-IL-33 antibody of the invention is capable of inhibiting the binding of IL-33 to an IL-33 receptor. In some embodiments, the inhibiting is measured using a cell-based blocking assay. In some instances, the antibody inhibits the binding of human IL-33 to an IL-33 receptor with a 90% inhibitory concentration (IC90) of between about 0.0001 μg/ml to about 1 μg/ml (e.g., about 0.001 μg/ml to about 0.5 μg/ml). In some embodiments, the IC90 is between about 0.002 μg/ml to about 0.25 μg/ml. In some embodiments, the IC90 is about 0.17 μg/ml. In some embodiments, the IC90 is about 0.004 μg/ml. In some embodiments, IC90 is about 0.003 μg/ml. In some embodiments, IC90 is about 0.002 μg/ml. In some embodiments, IC90 is about 0.001 μg/ml.

In some instances, the antibody inhibits the binding of human IL-33 to an IL-33 receptor with a half-maximal inhibitory concentration (IC50) of between about 750 fM and about 250 pM (e.g., between about 750 fM and about 250 pM, between about 1 pM and about 250 pM, between about 1 pM and about 100 pM, between about 1 pM and about 50 pM, between about 1 pM and about 10 pM, or between about 1 pM and about 5 pM). In some instances, the antibody inhibits the binding of human IL-33 to an IL-33 receptor with an IC50 of about 10 pM or below (e.g., about 10 pM or below, about 9 pM or below, about 8 pM or below, about 7 pM or below, about 6 pM or below, about 5 pM or below, about 4 pM or below, about 3 pM or below, about 2.5 pM or below, about 2 pM or below, about 1 pM or below, about 900 fM or below, about 800 fM or below, or about 750 fM or below). In some instances, the antibody inhibits the binding of human IL-33 to an IL-33 receptor with an IC50 of about 2.4 pM. In some instances, the inhibiting is measured using a cell-based blocking assay using HEK-BLUE™ cells, for example, as described in Example 8, Section B.

In some instances, the antibody inhibits the binding of cyno IL-33 to an IL-33 receptor with an IC50 of between about 1 nM and about 10 nM. (e.g., between about 1 nM and about 10 nM, between about 1 nM and about 9 nM, between about 1 nM and about 8 nM, between about 1 nM and about 7 nM, between about 1 nM and about 6 nM, between about 1 nM and about 5 nM, between about 1 nM and about 4 nM, or between about 1 nM and about 3 nM). In some instances, the antibody inhibits the binding of cyno IL-33 to an IL-33 receptor with an IC50 of about 4.2 nM. In some instances, the inhibiting is measured using a cell-based blocking assay using HEK-BLUE™ cells, for example, as described in Example 8, Section B.

In some instances, the antibody inhibits human IL-33- and IL-12-mediated induction of TNF-α from human natural killer (NK) cells. For example, in some instances, the antibody inhibits human IL-33- and IL-12-mediated induction of TNF-α from human NK cells with an IC50 of between about 1 pM and about 200 pM (e.g., between about 1 pM and about 200 pM, between about 1 pM and about 175 pM, between about 1 pM and about 150 pM, between about 1 pM and about 125 pM, between about 1 pM and about 100 pM, between about 1 pM and about 75 pM, between about 1 pM and about 50 pM, between about 1 pM and about 30 pM, or between about 1 pM and about 25 pM). In some instances, the antibody inhibits human IL-33- and IL-12-mediated induction of TNF-α from human NK cells with an IC50 of about 100 pM or below, e.g., 100 pM or below, 75 pM or below, 50 pM or below, 30 pM or below, or 25 pM or below. In some instances, the antibody inhibits human IL-33- and IL-12-mediated induction of TNF-α from human NK cells with an IC50 of about 30 pM. In some instances, the inhibiting is measured using an NK primary cell assay, for example, as described in Example 8, Section C.

In some instances, the antibody inhibits human IL-33-mediated induction of p38 MAPK (Thr180/Tyr182) phosphorylation in human basophils. For example, in some instances, the antibody inhibits human IL-33-mediated induction of p38 MAPK (Thr180/Tyr182) phosphorylation in human basophils with an IC50 of about 1 pM or below (e.g., 1 pM or below, 0.75 pM or below, 0.5 pM or below, 0.25 pM or below, 0.15 pM or below, 0.1 pM or below, or 0.05 pM or below). In some instances, the antibody inhibits human IL-33-mediated induction of p38 MAPK (Thr180/Tyr182) phosphorylation in human basophils with an IC50 of about 0.15 pM. In some instances, the inhibiting is measured using a basophil primary cell assay, for example, as described in Example 8, Section D.

In some instances, the antibody inhibits the binding of human IL-33 to an IL-33 receptor in a competitive binding ELISA assay. In some instances, the antibody inhibits the binding of human IL-33 to an IL-33 receptor in a competitive binding ELISA assay with an IC50 of between about 1 pM and about 200 pM (e.g., between about 1 pM and about 200 pM, between about 1 pM and about 175 pM, between about 1 pM and about 150 pM, between about 1 pM and about 125 pM, between about 1 pM and about 100 pM, between about 1 pM and about 75 pM, between about 1 pM and about 60 pM, between about 1 pM and about 50 pM, between about 1 pM and about 25 pM, between about 10 pM and about 60 pM, between about 10 pM and about 50 pM, or between about 20 pM and about 50 pM). In some instances, the antibody inhibits the binding of human IL-33 to an IL-33 receptor in a competitive binding ELISA assay with an IC50 of about 21 pM. In some instances, the inhibiting is measured using a competitive binding ELISA, for example, as described in Example 8, Section F.

In some instances, the antibody inhibits the binding of cyno IL-33 to an IL-33 receptor in a competitive binding ELISA assay. In some instances, the antibody inhibits the binding of cyno IL-33 to an IL-33 receptor in a competitive binding ELISA assay with an IC50 of between about 1 pM and about 20 nM (e.g., between about 1 pM and about 20 nM, between about 1 pM and about 15 nM, between about 1 pM and about 10 nM, between about 1 pM and about 5 nM, between about 1 pM and about 1 nM, between about 1 pM and about 800 pM, between about 1 pM and about 600 pM, between about 1 pM and about 500 pM, between about 1 nM and about 400 pM, between about 1 nM and about 300 pM, between about 200 pM and about 1 nM, between about 200 pM and about 800 pM, between about 200 pM and about 600 pM, between about 200 pM and about 500 pM, between about 300 pM and about 600 pM, or between about 300 pM and about 500 pM). In some instances, the antibody inhibits the binding of cyno IL-33 to an IL-33 receptor in a competitive binding ELISA assay with an IC50 of about 1 nM or below, e.g., about 1 nM or below, about 800 pM or below, about 600 pM or below, about 500 pM or below, about 430 pM or below, about 400 pM or below, or about 300 pM or below. In some instances, the antibody inhibits the binding of cyno IL-33 to an IL-33 receptor in a competitive binding ELISA assay with an IC50 of about 430 pM. In some instances, the inhibiting is measured using a competitive binding ELISA, for example, as described in Example 8, Section F.

In some instances, any of the anti-IL-33 antibodies described herein (e.g., described above or below) may have one or more (e.g., 1, 2, 3, 4, 5, 6, 7, or 8) of the following features: (i) the antibody specifically binds human IL-33 with a $K_D$ of between about 1 pM and about 1 nM; (ii) the antibody specifically binds cyno IL-33 with a $K_D$ of between about 1 pM and about 1 nM; (iii) the antibody inhibits the binding of human IL-33 to an IL-33 receptor (e.g., ST2 and/or IL-1RAcP) with an IC50 of between about 750 fM and about 250 pM, for example, in a cell-based blocking assay using HEK-BLUE™ cells; (iv) the antibody inhibits the binding of cyno IL-33 to an IL-33 receptor (e.g., ST2 and/or IL-1RAcP) with an IC50 of between about 1 nM and about 10 nM, for example, in a cell-based blocking assay using HEK-BLUE™ cells; (v) the antibody inhibits human IL-33- and IL-12-mediated induction of TNF-α from human NK cells with an IC50 of between about 1 pM and about 200 pM; (vi) the antibody inhibits human IL-33-mediated induction of p38 MAPK (Thr180/Tyr182) phosphorylation in human basophils with an IC50 of about 1 pM or below; (vii) the antibody inhibits the binding of human IL-33 to an IL-33 receptor (e.g., ST2 and/or IL-1RAcP) in a competitive binding ELISA assay with an IC50 of between about 1 pM and about 200 pM; and/or (viii) the antibody inhibits the binding of cyno IL-33 to an IL-33 receptor (e.g., ST2 and/or IL-1RAcP) in a competitive binding ELISA assay with an IC50 of between about 1 pM and about 20 nM. In some embodiments, any of the anti-IL-33 antibodies described herein may have one of the preceding features. In some embodiments, any of the anti-IL-33 antibodies described herein may have two of the preceding features. In some embodiments, any of the anti-IL-33 antibodies described herein may have three of the preceding features. In some embodiments, any of the anti-IL-33 antibodies described herein may have four of the preceding features. In some embodiments, any of the anti-IL-33 antibodies described herein may have five of the preceding features. In some embodiments, any of the anti-IL-33 antibodies described herein may have six of the preceding features. In some embodiments, any of the anti-IL-33 antibodies described herein may have seven of the preceding features. In some embodiments, any of the anti-IL-33 antibodies described herein may have eight of the preceding features.

For example, in some embodiments, any of the anti-IL-33 antibodies described herein may have the following features: (i) the antibody specifically binds human IL-33 with a $K_D$ of between about 1 pM and about 1 nM (e.g., between about 15 pM and about 180 pM); and (ii) the antibody specifically binds cyno IL-33 with a $K_D$ of between about 1 pM and about 1 nM (e.g., between about 100 pM and about 500 pM).

In another example, in some embodiments, any of the anti-IL-33 antibodies described herein may have the following features: (i) the antibody specifically binds human IL-33 with a $K_D$ of between about 1 pM and about 1 nM (e.g., between about 15 pM and about 180 pM); and (ii) the antibody inhibits the binding of human IL-33 to an IL-33 receptor with an IC50 of between about 750 fM and about 250 pM (e.g., between about 800 fM and about 10 pM), for example, in a cell-based blocking assay using HEK-BLUE™ cells.

In another example, in some embodiments, any of the anti-IL-33 antibodies described herein may have the following features: (i) the antibody specifically binds human IL-33 with a $K_D$ of between about 1 pM and about 1 nM (e.g., between about 15 pM and about 180 pM); and (ii) the antibody inhibits the binding of cyno IL-33 to an IL-33 receptor with an IC50 of between about 1 nM and about 10 nM (e.g., between about 1 nM and about 5 nM), for example, in a cell-based blocking assay using HEK-BLUE™ cells.

In yet another example, in some embodiments, any of the anti-IL-33 antibodies described herein may have the following features: (i) the antibody specifically binds human IL-33 with a $K_D$ of between about 1 pM and about 1 nM (e.g., between about 15 pM and about 180 pM); and (ii) the antibody inhibits human IL-33- and IL-12-mediated induction of TNF-α from human NK cells with an IC50 of between about 1 pM and about 200 pM (e.g., between about 1 pM and about 80 pM).

In a further example, in some embodiments, any of the anti-IL-33 antibodies described herein may have the following features: (i) the antibody specifically binds human IL-33 with a $K_D$ of between about 1 pM and about 1 nM (e.g., between about 15 pM and about 180 pM); and (ii) the antibody inhibits human IL-33-mediated induction of p38 MAPK (Thr180/Tyr182) phosphorylation in human basophils with an IC50 of about 1 pM or below (e.g., between about 0.05 pM to about 0.5 pM).

In a still further example, in some embodiments, any of the anti-IL-33 antibodies described herein may have the following features: (i) the antibody specifically binds human IL-33 with a $K_D$ of between about 1 pM and about 1 nM (e.g., between about 15 pM and about 180 pM); and (ii) the antibody inhibits the binding of human IL-33 to an IL-33 receptor in a competitive binding ELISA assay with an IC50 of between about 1 pM and about 200 pM (e.g., between about 1 pM to about 50 pM).

In another embodiment, any of the anti-IL-33 antibodies described herein may have the following features: (i) the antibody specifically binds human IL-33 with a $K_D$ of between about 1 pM and about 1 nM (e.g., between about 15 pM and about 180 pM); and (ii) the antibody inhibits the binding of cyno IL-33 to an IL-33 receptor in a competitive binding ELISA assay with an IC50 of between about 1 pM and about 20 nM (e.g., between about 200 pM to about 1 nM).

In another example, in some embodiments, any of the anti-IL-33 antibodies described herein may have the following features: (i) the antibody specifically binds cyno IL-33 with a $K_D$ of between about 1 pM and about 1 nM (e.g., between about 100 pM and about 500 pM); and (ii) the antibody inhibits the binding of human IL-33 to an IL-33 receptor with an IC50 of between about 750 fM and about 250 pM (e.g., between about 800 fM and about 10 pM), for example, in a cell-based blocking assay using HEK-BLUE™ cells.

In yet another example, in some embodiments, any of the anti-IL-33 antibodies described herein may have the following features: (i) the antibody specifically binds cyno IL-33 with a $K_D$ of between about 1 pM and about 1 nM (e.g., between about 100 pM and about 500 pM); and (ii) the antibody inhibits the binding of cyno IL-33 to an IL-33 receptor with an IC50 of between about 1 nM and about 10 nM (e.g., between about 1 nM and about 5 nM), for example, in a cell-based blocking assay using HEK-BLUE™ cells. In another example, in some embodiments, any of the anti-IL-33 antibodies described herein may have the following features: (i) the antibody specifically binds cyno IL-33 with a $K_D$ of between about 1 pM and about 1 nM (e.g., between about 100 pM and about 500 pM); and (ii) the antibody inhibits human IL-33- and IL-12-mediated induction of TNF-α from human NK cells with an IC50 of between about 1 pM and about 200 pM (e.g., between about 1 pM and about 80 pM).

In a further example, in some embodiments, any of the anti-IL-33 antibodies described herein may have the following features: (i) the antibody specifically binds cyno IL-33 with a $K_D$ of between about 1 pM and about 1 nM (e.g., between about 100 pM and about 500 pM); and (ii) the antibody inhibits human IL-33-mediated induction of p38 MAPK (Thr180/Tyr182) phosphorylation in human basophils with an IC50 of about 1 pM or below (e.g., between about 0.05 pM to about 0.5 pM).

In yet another example, in some embodiments, any of the anti-IL-33 antibodies described herein may have the following features: (i) the antibody specifically binds cyno IL-33 with a $K_D$ of between about 1 pM and about 1 nM (e.g., between about 100 pM and about 500 pM); and (ii) the antibody inhibits the binding of human IL-33 to an IL-33 receptor in a competitive binding ELISA assay with an IC50 of between about 1 pM and about 200 pM (e.g., between about 1 pM to about 50 pM).

In another embodiment, any of the anti-IL-33 antibodies described herein may have the following features: (i) the antibody specifically binds cyno IL-33 with a $K_D$ of between about 1 pM and about 1 nM (e.g., between about 100 pM and about 500 pM); and (ii) the antibody inhibits the binding of cyno IL-33 to an IL-33 receptor in a competitive binding ELISA assay with an IC50 of between about 1 pM and about 20 nM (e.g., between about 200 pM to about 1 nM).

In a further example, in some embodiments, any of the anti-IL-33 antibodies described herein may have the following features: (i) the antibody inhibits the binding of human IL-33 to an IL-33 receptor with an IC50 of between about 750 fM and about 250 pM (e.g., between about 800 fM and about 10 pM), for example, in a cell-based blocking assay using HEK-BLUE™ cells; and (ii) the antibody inhibits the binding of cyno IL-33 to an IL-33 receptor with an IC50 of between about 1 nM and about 10 nM (e.g., between about 1 nM and about 5 nM), for example, in a cell-based blocking assay using HEK-BLUE™ cells.

In a still further example, in some embodiments, any of the anti-IL-33 antibodies described herein may have the following features: (i) the antibody inhibits the binding of human IL-33 to an IL-33 receptor with an IC50 of between about 750 fM and about 250 pM (e.g., between about 800 fM and about 10 pM), for example, in a cell-based blocking assay using HEK-BLUE™ cells; and (ii) the antibody inhibits human IL-33- and IL-12-mediated induction of TNF-α from human NK cells with an IC50 of between about 1 pM and about 200 pM (e.g., between about 1 pM and about 80 pM).

In another example, in some embodiments, any of the anti-IL-33 antibodies described herein may have the following features: (i) the antibody inhibits the binding of human IL-33 to an IL-33 receptor with an IC50 of between about 750 fM and about 250 pM (e.g., between about 800 fM and about 10 pM), for example, in a cell-based blocking assay using HEK-BLUE™ cells; and (ii) the antibody inhibits human IL-33-mediated induction of p38 MAPK (Thr80/Tyr182) phosphorylation in human basophils with an IC50 of about 1 pM or below (e.g., between about 0.05 pM to about 0.5 pM).

In yet another example, in some embodiments, any of the anti-IL-33 antibodies described herein may have the following features: (i) the antibody inhibits the binding of human IL-33 to an IL-33 receptor with an IC50 of between about 750 fM and about 250 pM (e.g., between about 800 fM and about 10 pM), for example, in a cell-based blocking assay using HEK-BLUE™ cells; and (ii) the antibody inhibits the binding of human IL-33 to an IL-33 receptor in a competitive binding ELISA assay with an IC50 of between about 1 pM and about 200 pM (e.g., between about 1 pM to about 50 pM).

In another embodiment, any of the anti-IL-33 antibodies described herein may have the following features: (i) the antibody inhibits the binding of human IL-33 to an IL-33 receptor with an IC50 of between about 750 fM and about 250 pM (e.g., between about 800 fM and about 10 pM), for example, in a cell-based blocking assay using HEK-BLUE™ cells); and (ii) the antibody inhibits the binding of cyno IL-33 to an IL-33 receptor in a competitive binding ELISA assay with an IC50 of between about 1 pM and about 20 nM (e.g., between about 200 pM to about 1 nM).

In a further example, in some embodiments, any of the anti-IL-33 antibodies described herein may have the following features: (i) the antibody inhibits the binding of cyno IL-33 to an IL-33 receptor with an IC50 of between about 1 nM and about 10 nM (e.g., between about 1 nM and about 5 nM), for example, in a cell-based blocking assay using HEK-BLUE™ cells; and (ii) the antibody inhibits human IL-33- and IL-12-mediated induction of TNF-α from human NK cells with an IC50 of between about 1 pM and about 200 pM (e.g., between about 1 pM and about 80 pM).

In a still further example, in some embodiments, any of the anti-IL-33 antibodies described herein may have the following features: (i) the antibody inhibits the binding of cyno IL-33 to an IL-33 receptor with an IC50 of between about 1 nM and about 10 nM (e.g., between about 1 nM and about 5 nM), for example, in a cell-based blocking assay using HEK-BLUE™ cells; and (ii) the antibody inhibits human IL-33-mediated induction of p38 MAPK (Thr80/Tyr182) phosphorylation in human basophils with an IC50 of about 1 pM or below (e.g., between about 0.05 pM to about 0.5 pM).

In another example, in some embodiments, any of the anti-IL-33 antibodies described herein may have the following features: (i) the antibody inhibits the binding of cyno IL-33 to an IL-33 receptor with an IC50 of between about 1 nM and about 10 nM (e.g., between about 1 nM and about 5 nM), for example, in a cell-based blocking assay using HEK-BLUE™ cells; and (ii) the antibody inhibits the binding of human IL-33 to an IL-33 receptor in a competitive binding ELISA assay with an IC50 of between about 1 pM and about 200 pM (e.g., between about 1 pM to about 50 pM).

In another embodiment, any of the anti-IL-33 antibodies described herein may have the following features: (i) the antibody inhibits the binding of cyno IL-33 to an IL-33 receptor with an IC50 of between about 1 nM and about 10 nM (e.g., between about 1 nM and about 5 nM), for example, in a cell-based blocking assay using HEK-BLUE™ cells); and (ii) the antibody inhibits the binding of cyno IL-33 to an IL-33 receptor in a competitive binding ELISA assay with an IC50 of between about 1 pM and about 20 nM (e.g., between about 200 pM to about 1 nM).

In yet another example, in some embodiments, any of the anti-IL-33 antibodies described herein may have the following features: (i) the antibody inhibits human IL-33- and IL-12-mediated induction of TNF-α from human NK cells with an IC50 of between about 1 pM and about 200 pM (e.g., between about 1 pM and about 80 pM); and (ii) the antibody inhibits human IL-33-mediated induction of p38 MAPK (Thr180/Tyr182) phosphorylation in human basophils with an IC50 of about 1 pM or below (e.g., between about 0.05 pM to about 0.5 pM).

In another example, in some embodiments, any of the anti-IL-33 antibodies described herein may have the following features: (i) the antibody inhibits human IL-33- and IL-12-mediated induction of TNF-α from human NK cells with an IC50 of between about 1 pM and about 200 pM (e.g., between about 1 pM and about 80 pM); and (ii) the antibody inhibits the binding of human IL-33 to an IL-33 receptor in a competitive binding ELISA assay with an IC50 of between about 1 pM and about 200 pM (e.g., between about 1 pM to about 50 pM).

In another example, in some embodiments, any of the anti-IL-33 antibodies described herein may have the following features: (i) the antibody inhibits human IL-33- and IL-12-mediated induction of TNF-α from human NK cells with an IC50 of between about 1 pM and about 200 pM (e.g., between about 1 pM and about 80 pM); and (ii) the antibody inhibits the binding of cyno IL-33 to an IL-33 receptor in a competitive binding ELISA assay with an IC50 of between about 1 pM and about 20 nM (e.g., between about 200 pM to about 1 nM).

In another example, in some embodiments, any of the anti-IL-33 antibodies described herein may have the following features: (i) the antibody inhibits human IL-33-mediated induction of p38 MAPK (Thr180/Tyr182) phosphorylation in human basophils with an IC50 of about 1 pM or below (e.g., between about 0.05 pM to about 0.5 pM); and (ii) the antibody inhibits the binding of human IL-33 to an IL-33 receptor in a competitive binding ELISA assay with an IC50 of between about 1 pM and about 200 pM (e.g., between about 1 pM to about 50 pM).

In another example, in some embodiments, any of the anti-IL-33 antibodies described herein may have the following features: (i) the antibody inhibits human IL-33-mediated induction of p38 MAPK (Thr180/Tyr182) phosphorylation in human basophils with an IC50 of about 1 pM or below (e.g., between about 0.05 pM to about 0.5 pM); and (i) the antibody inhibits the binding of cyno IL-33 to an IL-33 receptor in a competitive binding ELISA assay with an IC50 of between about 1 pM and about 20 nM (e.g., between about 200 pM to about 1 nM).

In another example, in some embodiments, any of the anti-IL-33 antibodies described herein may have the following features: (i) the antibody inhibits the binding of human IL-33 to an IL-33 receptor in a competitive binding ELISA assay with an IC50 of between about 1 pM and about 200 pM (e.g., between about 1 pM to about 50 pM); and/or (ii) the antibody inhibits the binding of cyno IL-33 to an IL-33 receptor in a competitive binding ELISA assay with an IC50 of between about 1 pM and about 20 nM (e.g., between about 200 pM to about 1 nM).

In some instances, the anti-IL-33 antibody may include at least one, two, three, four, five, or six HVRs selected from: (a) HVR-H1 comprising the amino acid sequence of SFSX$_1$S (SEQ ID NO: 62), wherein X$_1$ is Met, Leu, or Val; (b) HVR-H2 comprising the amino acid sequence of TISGGKTFTDYVDX$_1$VKG (SEQ ID NO: 63), wherein X$_1$ is Ser or Ala; (c) HVR-H3 comprising the amino acid sequence of ANYGX$_1$X$_2$FFEV (SEQ ID NO: 64), wherein X$_1$ is Asn or Asp, and X$_2$ is Trp or Phe; (d) HVR-L1 comprising the amino acid sequence of RASESVAKYGLSLLN (SEQ ID NO: 4); (e) HVR-L2 comprising the amino acid sequence of AASNRGS (SEQ ID NO: 5); and (f) HVR-L3 comprising the amino acid sequence of QQSKEVPFT (SEQ ID NO: 6), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 4-6 or 62-64.

For instance, the anti-IL-33 antibody may include at least one, two, three, four, five, or six HVRs selected from: (a) HVR-H1 comprising the amino acid sequence of SFSMS (SEQ ID NO: 1), SFSLS (SEQ ID NO: 7), or SFSVS (SEQ ID NO: 8); (b) HVR-H2 comprising the amino acid sequence of TISGGKTFTDYVDSVKG (SEQ ID NO: 2) or TISGGKTFTDYVDAVKG (SEQ ID NO: 9); (c) HVR-H3 comprising the amino acid sequence of ANYGNWFFEV (SEQ ID NO: 3), ANYGNFFFEV (SEQ ID NO: 10), or ANYGDWFFEV (SEQ ID NO: 11); (d) HVR-L1 comprising the amino acid sequence of RASESVAKYGLSLLN (SEQ ID NO: 4); (e) HVR-L2 comprising the amino acid sequence of AASNRGS (SEQ ID NO: 5); and (f) HVR-L3 comprising the amino acid sequence of QQSKEVPFT (SEQ ID NO: 6), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-11.

In some instances, the anti-IL-33 antibody may includes one, two, three, or four of the following heavy chain framework regions: an FR-H1 comprising the amino acid sequence of EVQLVESGGGLVQPGGSLRLSCAASGFTFS (SEQ ID NO: 12), DVNLVESGGGSVKPGGSLKLSCVASGFTFS (SEQ ID NO: 16), or EVQLVESGGGLVKPGGSLRLSCAASGFTFS (SEQ ID NO: 20); an FR-H2 comprising the amino acid sequence of WVRQAPGKGLEWVA (SEQ ID NO: 13), WVRQTPEKRLEWVA (SEQ ID NO: 17), or WVRQAPGKGLEWVS (SEQ ID NO: 21); an FR-H3 comprising the amino acid sequence of RFTISRDDSKNTLYLQMNSLRAEDTAVYYCTR (SEQ ID NO: 14), RFTISRDNSKNTLYLQMNSLRAEDTAVYYCTR (SEQ ID NO: 22), RFTISRDDAKNTLYLQMSSLESEDTAMYYCTR (SEQ ID NO: 18), RFTISRDDAKNSLYLQMNSLRAEDTAVYYCTR (SEQ ID NO: 23), RFTISRDNAKNSLYLQMNSLRAEDTAVYYCTR (SEQ ID NO: 24), or RFTISRDDSKNTLYLQMNSLRAEDTAVYYCTR (SEQ ID NO: 14); and an FR-H4 comprising the amino acid sequence of WGQGTLVTVSS (SEQ ID NO: 15) or WGAGTTVAVSS (SEQ ID NO: 19).

In some instances, the anti-IL-33 antibody may include one, two, three, or four of the following light chain framework regions: an FR-L1 comprising the amino acid sequence of EIVLTQSPATLSLSPGERATLSC (SEQ ID NO: 25) or DIVLTQSPGFLWSLGQRATISC (SEQ ID NO: 29); an FR-L2 comprising the amino acid sequence of WFQQKPGQPPRLLIF (SEQ ID NO: 26) or WFQQKPGQPPKLLIF (SEQ ID NO: 30); an FR-L3 comprising the amino acid sequence of GIPARFSGSGSGTDFTLTISSLEPEDFAVYYC (SEQ ID NO: 27), GVPARFSGSGSGTDFSLNIHPMEEDDTAMYFC (SEQ ID NO: 31), GVPARFSGSGSGTDFTLTISSLEPEDFAVYFC (SEQ ID NO: 33), GVPARFSGSGSGTDFTLTISSLEPEDFAVYYC (SEQ ID NO: 34), or GIPARFSGSGSGTDFTLTISSLEPEDFAVYFC (SEQ ID NO: 35); and an FR-L4 comprising the amino acid sequence of FGQGTKVEIK (SEQ ID NO: 28) or FGSGTKLEIK (SEQ ID NO: 32).

In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 36, 38, or 40-50; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 37, 39, or 51-61; or (c) a VH domain as in (a) and a VL domain as in (b). For example, in some instances, the antibody comprises a binding domain comprising a VH domain comprising the amino acid sequence of SEQ ID NO: 36 and a VL domain comprising the amino acid sequence of SEQ ID NO: 37. In some instances, the antibody comprises a binding domain comprising a VH domain comprising the amino acid sequence of SEQ ID NO: 38 and a VL domain comprising the amino acid sequence of SEQ ID NO: 39. In some instances, the antibody comprises a binding domain comprising a VH domain comprising the amino acid sequence of SEQ ID NO: 40 and a VL domain comprising the amino acid sequence of SEQ ID NO: 51. In some instances, the antibody comprises a binding domain comprising a VH domain comprising the amino acid sequence of SEQ ID NO: 41 and a VL domain comprising the amino acid sequence of SEQ ID NO: 52. In some instances, the antibody comprises a binding domain comprising a VH domain comprising the amino acid sequence of SEQ ID NO: 42 and a VL domain comprising the amino acid sequence of SEQ ID NO: 53. In some instances, the antibody comprises a binding domain comprising a VH domain comprising the amino acid sequence of SEQ ID NO: 43 and a VL domain comprising the amino acid sequence of SEQ ID NO: 54. In some instances, the antibody comprises a binding domain comprising a VH domain comprising the amino acid sequence of SEQ ID NO: 44 and a VL domain comprising the amino acid sequence of SEQ ID NO: 55. In some instances, the antibody comprises a binding domain comprising a VH domain comprising the amino acid sequence of SEQ ID NO: 45 and a VL domain comprising the amino acid sequence of SEQ ID NO: 56. In some instances, the antibody comprises a binding domain comprising a VH domain comprising the amino acid sequence of SEQ ID NO: 46 and a VL domain comprising the amino acid sequence of SEQ ID NO: 57. In some instances, the antibody comprises a binding domain comprising a VH domain comprising the amino acid sequence of SEQ ID NO: 47 and a VL domain comprising the amino acid sequence of SEQ ID NO: 58. In some instances, the antibody comprises a binding domain comprising a VH domain comprising the amino acid sequence of SEQ ID NO: 48 and a VL domain comprising the amino acid sequence of SEQ ID NO: 59. In some instances, the antibody comprises a binding domain comprising a VH domain comprising the amino acid sequence of SEQ ID NO: 49 and a VL domain comprising the amino acid sequence of SEQ ID NO: 60. In some instances, the antibody comprises a binding domain comprising a VH domain comprising the amino acid sequence of SEQ ID NO: 50 and a VL domain comprising the amino acid sequence of SEQ ID NO: 61.

For instance, the anti-IL-33 antibody may include (a) HVR-H1 comprising the amino acid sequence of SFSMS (SEQ ID NO: 1); (b) HVR-H2 comprising the amino acid sequence of TISGGKTFTDYVDSVKG (SEQ ID NO: 2); (c) HVR-H3 comprising the amino acid sequence of ANYGNWFFEV (SEQ ID NO: 3); (d) HVR-L1 comprising the amino acid sequence of RASESVAKYGLSLLN (SEQ ID NO: 4); (e) HVR-L2 comprising the amino acid sequence of AASNRGS (SEQ ID NO: 5); and (f) HVR-L3 comprising the amino acid sequence of QQSKEVPFT (SEQ ID NO: 6). In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 36; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 37; or (c) a VH domain as in (a) and a VL domain as in (b). In some instances, the anti-IL-33 antibody includes the following heavy chain framework regions: FR-H1 comprising the amino acid sequence of EVQLVESGGGLVQPGGSLRLSCAASGFTFS (SEQ ID NO: 12); FR-H2 comprising the amino acid sequence of WVRQAPGKGLEWVA (SEQ ID NO: 13); FR-H3 comprising the amino acid sequence of RFTISRDDSKNTLYLQMNSLRAEDTAVYYCTR (SEQ ID NO: 14); and FR-H4 comprising the amino acid sequence of WGQGTLVTVSS (SEQ ID NO: 15). In some instances, the anti-IL-33 antibody includes the following light chain framework regions: FR-L1 comprising the amino acid sequence of EIVLTQSPATLSLSPGERATLSC (SEQ ID NO: 25); FR-L2 comprising the amino acid sequence of WFQQKPGQPPRLLIF (SEQ ID NO: 26); FR-L3 comprising the amino acid sequence of GIPARFSGSGSGTDFTLTISSLEPEDFAVYYC (SEQ ID NO: 27); and FR-L4 comprising the amino acid sequence of FGQGTKVEIK (SEQ ID NO: 28). In some instances, the anti-IL-33 antibody includes a binding domain comprising (a) a VH domain comprising an amino acid sequence of SEQ ID NO: 36 and (b) a VL domain comprising an amino acid sequence of SEQ ID NO: 37. In some instances, the exemplary anti-IL-33 antibody is 10C12.38.H6.87Y.58I.

In other instances, the anti-IL-33 antibody may include at least one, two, three, four, five, or six HVRs selected from: (a) HVR-H1 comprising the amino acid sequence of SSIFYWG (SEQ ID NO: 65); (b) HVR-H2 comprising the amino acid sequence of SIYYSGRTYYNPX$_1$LKS (SEQ ID NO: 90), wherein X$_1$ is Ser or Ala; (c) HVR-H3 comprising the amino acid sequence of AGGLYNWNDESFSFYMDV (SEQ ID NO: 68); (d) HVR-L1 comprising the amino acid sequence of RASQSFSSSYLA (SEQ ID NO: 69); (e) HVR-L2 comprising the amino acid sequence of GASSRAT (SEQ ID NO: 70); and (f) HVR-L3 comprising the amino acid sequence of QQYDRSPLT (SEQ ID NO: 71), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 65, 68-71, or 90.

For instance, the anti-IL-33 antibody may include at least one, two, three, four, five, or six HVRs selected from: (a) HVR-H1 comprising the amino acid sequence of SSIFYWG (SEQ ID NO: 65); (b) HVR-H2 comprising the amino acid sequence of SIYYSGRTYYNPSLKS (SEQ ID NO: 66) or SIYYSGRTYYNPALKS (SEQ ID NO: 67); (c) HVR-H3 comprising the amino acid sequence of AGGLYNWNDESFSFYMDV (SEQ ID NO: 68); (d) HVR-L1 comprising the amino acid sequence of RASQSFSSSYLA (SEQ ID NO: 69); (e) HVR-L2 comprising the amino acid sequence of GASSRAT (SEQ ID NO: 70); and (f) HVR-L3 comprising the amino acid sequence of QQYDRSPLT (SEQ ID NO: 71), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 65-71.

In some instances, the anti-IL-33 antibody may include one, two, three, or four of the following heavy chain framework regions: an FR-H1 comprising the amino acid sequence of ELQLQESGPGLVKPSETLSLTCTVSGGSIR (SEQ ID NO: 72), QVQLQESGPGLVKPSETLSLTCTVSGGSIR (SEQ ID NO: 77), or QLQLQESGPGLVKPSETLSLTCTVSGGSIR (SEQ ID NO: 76); an FR-H2 comprising the amino acid sequence of WIRQPPGKGLEWIG (SEQ ID NO: 73); an FR-H3 comprising the amino acid sequence of RVTISVDTSKNQFSLMLTSVTAADTAVYYCAR (SEQ ID NO: 74); and an FR-H4 comprising the amino acid sequence of WGQGTTVTVSS (SEQ ID NO: 75) or WGNGTTVTVSS (SEQ ID NO: 78).

In some instances, the anti-IL-33 antibody may include one, two, three, or four of the following light chain framework regions: an FR-L1 comprising the amino acid sequence of EIVLTQSPGTLSLSPGERATLSC (SEQ ID NO: 79); an FR-L2 comprising the amino acid sequence of WYQQKPGQAPRLLIY (SEQ ID NO: 80); an FR-L3 comprising the amino acid sequence of GIPDRFSGSGSGTDFTLTISRLEPEDFAVYYC (SEQ ID NO: 81) or GIPDRFSGSGSGTDFTLTISRLEPKDFAVYYC (SEQ ID NO: 83); and an FR-L4 comprising the amino acid sequence of FGGGTKVEIK (SEQ ID NO: 82).

In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 84, 86, 88, 91, 92, or 95; (b) a light chain variable (VL)

domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 85, 87, 89, 93, 94, or 96; or (c) a VH domain as in (a) and a VL domain as in (b). For example, some instances, the antibody comprises a binding domain comprising a VH domain comprising the amino acid sequence of SEQ ID NO: 84 and a VL domain comprising the amino acid sequence of SEQ ID NO: 85. In some instances, the antibody comprises a binding domain comprising a VH domain comprising the amino acid sequence of SEQ ID NO: 86 and a VL domain comprising the amino acid sequence of SEQ ID NO: 87. In some instances, the antibody comprises a binding domain comprising a VH domain comprising the amino acid sequence of SEQ ID NO: 88 and a VL domain comprising the amino acid sequence of SEQ ID NO: 89. In some instances, the antibody comprises a binding domain comprising a VH domain comprising the amino acid sequence of SEQ ID NO: 91 and a VL domain comprising the amino acid sequence of SEQ ID NO: 93.

In some instances, the antibody comprises a binding domain comprising a VH domain comprising the amino acid sequence of SEQ ID NO: 92 and a VL domain comprising the amino acid sequence of SEQ ID NO: 94. In some instances, the antibody comprises a binding domain comprising a VH domain comprising the amino acid sequence of SEQ ID NO: 95 and a VL domain comprising the amino acid sequence of SEQ ID NO: 96.

For instance, the anti-IL-33 antibody may include (a) HVR-H1 comprising the amino acid sequence of SSIFYWG (SEQ ID NO: 65); (b) HVR-H2 comprising the amino acid sequence of SIYYSGRTYYNPSLKS (SEQ ID NO: 66); (c) HVR-H3 comprising the amino acid sequence of AGGLYNWNDESFSFYMDV (SEQ ID NO: 68); (d) HVR-L1 comprising the amino acid sequence of RASQSFSSSYLA (SEQ ID NO: 69); (e) HVR-L2 comprising the amino acid sequence of GASSRAT (SEQ ID NO: 70); and (f) HVR-L3 comprising the amino acid sequence of QQYDRSPLT (SEQ ID NO: 71). In some instances, the antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 84; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 85; or (c) a VH domain as in (a) and a VL domain as in (b). In some instances, the anti-IL-33 antibody includes the following heavy chain framework regions: FR-H1 comprising the amino acid sequence of ELQLQESGPGLVKPSETLSLTCTVSGGSIR (SEQ ID NO: 72); FR-H2 comprising the amino acid sequence of WIRQPPGKGLEWIG (SEQ ID NO: 73); FR-H3 comprising the amino acid sequence of RVTISVDTSKNQFSLMLTSVTAADTAVYYCAR (SEQ ID NO: 74); and FR-H4 comprising the amino acid sequence of WGQGTTVTVSS (SEQ ID NO: 75). In some instances, the anti-IL-33 antibody includes the following light chain framework regions: FR-L1 comprising the amino acid sequence of EIVLTQSPGTLSLSPGERATLSC (SEQ ID NO: 79); FR-L2 comprising the amino acid sequence of WYQQKPGQAPRLLIY (SEQ ID NO: 80); FR-L3 comprising the amino acid sequence of GIPDRFSGSGSGTDFTLTISRLEPEDFAVYYC (SEQ ID NO: 81); and FR-L4 comprising the amino acid sequence of FGGGTKVEIK (SEQ ID NO: 82). In some instances, the anti-IL-33 antibody includes a binding domain comprising (a) a VH domain comprising an amino acid sequence of SEQ ID NO: 84 and (b) a VL domain comprising an amino acid sequence of SEQ ID NO: 85. In some instances, the exemplary anti-IL-33 antibody is 4G12.FW4.

In some instances, the anti-IL-33 antibody may include at least one, two, three, four, five, or six HVRs selected from: (a) HVR-H1 comprising the amino acid sequence of NYX$_1$MN (SEQ ID NO: 97), wherein X$_1$ is Trp, Phe, or Tyr; (b) HVR-H2 comprising the amino acid sequence of EITLKFNX$_1$YX$_2$THYAESVKG (SEQ ID NO: 98), wherein X$_1$ is Asn, Asp, Ser, or Ala, and X$_2$ is Ser or Ala; (c) HVR-H3 comprising the amino acid sequence of RNYGX$_1$X$_2$YINV (SEQ ID NO: 99), wherein X$_1$ is Asp or Asn, and X$_2$ is Trp or Tyr; (d) HVR-L1 comprising the amino acid sequence of RASESVDKFGX$_1$SFLN (SEQ ID NO: 100), wherein X$_1$ is Met, Val, or Leu; (e) HVR-L2 comprising the amino acid sequence of VASSQGS (SEQ ID NO: 113); and (f) HVR-L3 comprising the amino acid sequence of QQSKDIPYT (SEQ ID NO: 114), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 97-100, 113, or 114. In some embodiments, any of the preceding antibodies does not comprise an HVR-H1 comprising the amino acid sequence NYWMN (SEQ ID NO: 101).

For instance, the anti-IL-33 antibody may include at least one, two, three, four, five, or six HVRs selected from: (a) HVR-H1 comprising the amino acid sequence of NYWMN (SEQ ID NO: 101), NYFMN (SEQ ID NO: 102), or NYYMN (SEQ ID NO: 103); (b) HVR-H2 comprising the amino acid sequence of EITLKFNNYSTHYAESVKG (SEQ ID NO: 104), EITLKFNDYSTHYAESVKG (SEQ ID NO: 105). EITLKFNSYSTHYAESVKG (SEQ ID NO: 106), EITLKFNAYSTHYAESVKG (SEQ ID NO: 107), or EITLKFNNYATHYAESVKG (SEQ ID NO: 108); (c) HVR-H3 comprising the amino acid sequence of RNYGDWYINV (SEQ ID NO: 109), RNYGNWYINV (SEQ ID NO: 110), or RNYGNFYINV (SEQ ID NO: 111); (d) HVR-L1 comprising the amino acid sequence of RASESVDKFGMSFLN (SEQ ID NO: 112), RASESVDKFGVSFLN (SEQ ID NO: 115), or RASESVDKFGLSFLN (SEQ ID NO: 116); (e) HVR-L2 comprising the amino acid sequence of VASSQGS (SEQ ID NO: 113); and (f) HVR-L3 comprising the amino acid sequence of QQSKDIPYT (SEQ ID NO: 114), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 101-116. In some embodiments, any of the preceding antibodies does not comprise an HVR-H1 comprising the amino acid sequence NYWMN (SEQ ID NO: 101).

In some instances, the anti-IL-33 antibody may include one, two, three, or four of the following heavy chain framework regions: an FR-H1 comprising the amino acid sequence of EVKLEESGGGLVQPGGSMKLSCVASGFTFS (SEQ ID NO: 117) or EVQLVESGGGLVQPGGSLRLSCAASGFTFS (SEQ ID NO: 118); an FR-H2 comprising the amino acid sequence of WVRQSPEKGLEWMA (SEQ ID NO: 119) or WVRQAPGKGLEWMA (SEQ ID NO: 120); an FR-H3 comprising the amino acid sequence of RFSISRDDSKSTVYLQMNNLRAEDTGIYYCAR (SEQ ID NO: 121), RFTISRDNSKNTVYLQMNSLRAEDTAVYYCAR (SEQ ID NO: 122), or RFTISRDDSKNT- VYLQMNSLRAEDTAVYYCAR (SEQ ID NO: 123); and an FR-H4 comprising the amino acid sequence of WGAGTTVTVSS (SEQ ID NO: 124) or WGQGTLVTVSS (SEQ ID NO: 125). In some embodiments, any of the preceding antibodies does not comprise an HVR-H1 comprising the amino acid sequence NYWMN (SEQ ID NO: 101).

In some instances, the anti-IL-33 antibody may include one, two, three, or four of the following light chain framework regions: an FR-L1 comprising the amino acid sequence of DIVLTQSPTSLAVSLGQRATISC (SEQ ID NO: 126) or DIVMTQSPDSLAVSLGERATINC (SEQ ID NO: 127); an FR-L2 comprising the amino acid sequence of WFQQKPGQPPKLLIF (SEQ ID NO: 128) or WYQQKPGQPPKLLIF (SEQ ID NO: 129); an FR-L3 comprising the amino acid sequence of GVPARFSGSGSGTDFSLNIHPVEEDDTAMYFC (SEQ ID NO: 130) or GVPDRFSGSGSGTDFTLTISSLQAEDVAVYYC (SEQ ID NO: 131); and an FR-L4 comprising the amino acid sequence of FGGGTKLEIK (SEQ ID NO: 132) or FGQGTKVEIK (SEQ ID NO: 133). In some embodiments, any of the preceding antibodies does not comprise an HVR-H1 comprising the amino acid sequence NYWMN (SEQ ID NO: 101).

In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 134, 136, 138, or 140-148; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 135, 137, 139, or 149-157; or (c) a VH domain as in (a) and a VL domain as in (b). For example, in some instances, the antibody comprises a binding domain comprising a VH domain comprising an amino acid sequence of SEQ ID NO: 134 and a VL domain comprising an amino acid sequence of SEQ ID NO: 135. In some instances, the antibody comprises a binding domain comprising a VH domain comprising an amino acid sequence of SEQ ID NO: 136 and a VL domain comprising an amino acid sequence of SEQ ID NO: 137. In some instances, the antibody comprises a binding domain comprising a VH domain comprising an amino acid sequence of SEQ ID NO: 138 and a VL domain comprising an amino acid sequence of SEQ ID NO: 139. In some instances, the antibody comprises a binding domain comprising a VH domain comprising an amino acid sequence of SEQ ID NO: 140 and a VL domain comprising an amino acid sequence of SEQ ID NO: 149. In some instances, the antibody comprises a binding domain comprising a VH domain comprising an amino acid sequence of SEQ ID NO: 141 and a VL domain comprising an amino acid sequence of SEQ ID NO: 150. In some instances, the antibody comprises a binding domain comprising a VH domain comprising an amino acid sequence of SEQ ID NO: 142 and a VL domain comprising an amino acid sequence of SEQ ID NO: 151. In some instances, the antibody comprises a binding domain comprising a VH domain comprising an amino acid sequence of SEQ ID NO: 143 and a VL domain comprising an amino acid sequence of SEQ ID NO: 152. In some instances, the antibody comprises a binding domain comprising a VH domain comprising an amino acid sequence of SEQ ID NO: 144 and a VL domain comprising an amino acid sequence of SEQ ID NO: 153. In some instances, the antibody comprises a binding domain comprising a VH domain comprising an amino acid sequence of SEQ ID NO: 145 and a VL domain comprising an amino acid sequence of SEQ ID NO: 154. In some instances, the antibody comprises a binding domain comprising a VH domain comprising an amino acid sequence of SEQ ID NO: 146 and a VL domain comprising an amino acid sequence of SEQ ID NO: 155. In some instances, the antibody comprises a binding domain comprising a VH domain comprising an amino acid sequence of SEQ ID NO: 147 and a VL domain comprising an amino acid sequence of SEQ ID NO: 156. In some instances, the antibody comprises a binding domain comprising a VH domain comprising an amino acid sequence of SEQ ID NO: 148 and a VL domain comprising an amino acid sequence of SEQ ID NO: 157. In some embodiments, any of the preceding antibodies does not comprise an HVR-H1 comprising the amino acid sequence NYWMN (SEQ ID NO: 101).

For instance, the anti-IL-33 antibody may include (a) HVR-H1 comprising the amino acid sequence of NYWMN (SEQ ID NO: 101); (b) HVR-H2 comprising the amino acid sequence of EITLKFNNYSTHYAESVKG (SEQ ID NO: 104); (c) HVR-H3 comprising the amino acid sequence of RNYGDWYINV (SEQ ID NO: 109); (d) HVR-L1 comprising the amino acid sequence of RASESVDKFGMSFLN (SEQ ID NO: 112); (e) HVR-L2 comprising the amino acid sequence of VASSQGS (SEQ ID NO: 113); and (f) HVR-L3 comprising the amino acid sequence of QQSKDIPYT (SEQ ID NO: 114). In some instances, the antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 134; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 135; or (c) a VH domain as in (a) and a VL domain as in (b). In some instances, the anti-IL-33 antibody includes the following heavy chain framework regions: FR-H1 comprising the amino acid sequence of EVKLEESGGGLVQPGGSMKLSCVASGFTFS (SEQ ID NO: 117); FR-H2 comprising the amino acid sequence of WVRQSPEKGLEWMA (SEQ ID NO: 119); FR-H3 comprising the amino acid sequence of RFSISRDDSKSTVYLQMNNLRAEDTGIYYCAR (SEQ ID NO: 121); and FR-H4 comprising the amino acid sequence of WGAGTTVTVSS (SEQ ID NO: 124). In some instances, the anti-IL-33 antibody includes the following light chain framework regions: FR-L1 comprising the amino acid sequence of DIVLTQSPTSLAVSLGQRATISC (SEQ ID NO: 126); FR-L2 comprising the amino acid sequence of WFQQKPGQPPKLLIF (SEQ ID NO: 128); FR-L3 comprising the amino acid sequence of GVPARFSGSGSGTDFSLNIHPVEEDDTAMYFC (SEQ ID NO: 130); and FR-L4 comprising the amino acid sequence of FGGGTKLEIK (SEQ ID NO: 132). In some instances, the anti-IL-33 antibody includes a binding domain comprising (a) a VH domain comprising an amino acid sequence of SEQ ID NO: 134 and (b) a VL domain comprising an amino acid sequence of SEQ ID NO: 135. In some instances, the exemplary anti-IL-33 antibody is 10H2.

In some instances, the anti-IL-33 antibody may include at least one, two, three, four, five, or six HVRs selected from: (a) HVR-H1 comprising the amino acid sequence of KFWMN (SEQ ID NO: 158); (b) HVR-H2 comprising the amino acid sequence of EIRLX$_1$X$_2$INYVKDYAESVKG (SEQ ID NO: 161), wherein X$_1$ is Asn or Ser, and X$_2$ is Ser or Ala, wherein X$_1$ is Asn, Asp, Ser, or Ala, and X$_2$ is Ser or Ala; (c) HVR-H3 comprising the amino acid sequence of RNYGNWFFEI (SEQ ID NO: 160); (d) HVR-L1 comprising the amino acid sequence of RASESVDRYGISFMN (SEQ ID NO: 164); (e) HVR-L2 comprising the amino acid sequence of AASNQGS (SEQ ID NO: 165); and (f) HVR-L3 comprising the amino acid sequence of QHSKEVPYT (SEQ ID NO: 166), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 158, 160, 161, or 164-166.

For instance, the anti-IL-33 antibody may include at least one, two, three, four, five, or six HVRs selected from: (a) HVR-H1 comprising the amino acid sequence of KFWMN (SEQ ID NO: 158); (b) HVR-H2 comprising the amino acid sequence of EIRLNSINYVKDYAESVKG (SEQ ID NO: 159), EIRLSSINYVKDYAESVKG (SEQ ID NO: 162), or EIRLNAINYVKDYAESVKG (SEQ ID NO: 163); (c) HVR-H3 comprising the amino acid sequence of RNYGNWFFEI (SEQ ID NO: 160); (d) HVR-L1 comprising the amino acid sequence of RASESVDRYGISFMN (SEQ ID NO: 164); (e) HVR-L2 comprising the amino acid sequence of AASNQGS (SEQ ID NO: 165); and (t) HVR-L3 comprising the amino acid sequence of QHSKEVPYT (SEQ ID NO: 166), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 158-160, or 162-166.

In some instances, the anti-IL-33 antibody may include one, two, three, or four of the following heavy chain framework regions: an FR-H1 comprising the amino acid sequence of EVKLEESGGGLVQPGGSMKLSCVASGFTFN (SEQ ID NO: 167) or EVQLVESGGGLVQPGGSLRLSCAASGFTFN (SEQ ID NO: 171); an FR-H2 comprising the amino acid sequence of WVRQSPEKGLEWVA (SEQ ID NO: 168) or WVRQAPGKGLEWVA (SEQ ID NO: 172); an FR-H3 comprising the amino acid sequence of RFTISRDDSKNSVYLQMNNLRAEDTGIYYCIR (SEQ ID NO: 169) or RFTISRDNAKNSVYLQMNSLRAEDTAVYYCIR (SEQ ID NO: 173); and an FR-H4 comprising the amino acid sequence of WGAGTTVTVSS (SEQ ID NO: 170) or WGQGTLVTVSS (SEQ ID NO: 174).

In some instances, the anti-IL-33 antibody may include one, two, three, or four of the following light chain framework regions: an FR-L1 comprising the amino acid sequence of DIVLTQSPASLAVSLGQRATISC (SEQ ID NO: 175) or DIQMTQSPSSLSASVGDRVTITC (SEQ ID NO: 179); an FR-L2 comprising the amino acid sequence of WFQQKPGQSPKLLIY (SEQ ID NO: 176) or WFQQKPGKAPKLLIY (SEQ ID NO: 180); an FR-L3 comprising the amino acid sequence of GVPARFSGSGSGTDFSLNIHPLEEDDAAMYFC (SEQ ID NO: 177) or GVPSRFSGSGSGTDFTLTISSLQPEDFATYYC (SEQ ID NO: 181); and an FR-L4 comprising the amino acid sequence of FGGGTKLEIK (SEQ ID NO: 178) or FGQGTKVEIK (SEQ ID NO: 182).

In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 183, 185, 187, or 189; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 184, 186, 188, 190; or (c) a VH domain as in (a) and a VL domain as in (b). For example, in some instances, the antibody comprises a binding domain comprising a VH domain comprising the amino acid sequence of SEQ ID NO: 183 and a VL domain comprising the amino acid sequence of SEQ ID NO: 184. In some instances, the antibody comprises a binding domain comprising a VH domain comprising the amino acid sequence of SEQ ID NO: 185 and a VL domain comprising the amino acid sequence of SEQ ID NO: 186. In some instances, the antibody comprises a binding domain comprising a VH domain comprising the amino acid sequence of SEQ ID NO: 187 and a VL domain comprising the amino acid sequence of SEQ ID NO: 188. In some instances, the antibody comprises a binding domain comprising a VH domain comprising the amino acid sequence of SEQ ID NO: 189 and a VL domain comprising the amino acid sequence of SEQ ID NO: 190.

For instance, the anti-IL-33 antibody may include (a) HVR-H1 comprising the amino acid sequence of KFWMN (SEQ ID NO: 158); (b) HVR-H2 comprising the amino acid sequence of EIRLNSINYVKDYAESVKG (SEQ ID NO: 159); (c) HVR-H3 comprising the amino acid sequence of RNYGNWFFEI (SEQ ID NO: 160); (d) HVR-L1 comprising the amino acid sequence of RASESVDRYGISFMN (SEQ ID NO: 164); (e) HVR-L2 comprising the amino acid sequence of AASNQGS (SEQ ID NO: 165); and (f) HVR-L3 comprising the amino acid sequence of QHSKEVPYT (SEQ ID NO: 166). In some instances, the antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 183; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 184; or (c) a VH domain as in (a) and a VL domain as in (b). In some instances, the anti-IL-33 antibody includes the following heavy chain framework regions: FR-H1 comprising the amino acid sequence of EVKLEESGGGLVQPGGSMKLSCVASGFTFN (SEQ ID NO: 167); FR-H2 comprising the amino acid sequence of WVRQSPEKGLEWVA (SEQ ID NO: 168); FR-H3 comprising the amino acid sequence of RFTISRDDSKNSVYLQMNNLRAEDTGIYYCIR (SEQ ID NO: 169); and FR-H4 comprising the amino acid sequence of WGAGTTVTVSS (SEQ ID NO: 170). In some instances, the anti-IL-33 antibody includes the following light chain framework regions: FR-L1 comprising the amino acid sequence of DIVLTQSPASLAVSLGQRATISC (SEQ ID NO: 175); FR-L2 comprising the amino acid sequence of WFQQKPGQSPKLLIY (SEQ ID NO: 176); FR-L3 comprising the amino acid sequence of GVPARFSGSGSGTDFSLNIHPLEEDDAAMYFC (SEQ ID NO: 177); and FR-L4 comprising the amino acid sequence of FGGGTKLEIK (SEQ ID NO: 178). In some instances, the anti-IL-33 antibody includes a binding domain comprising (a) a VH domain comprising an amino acid sequence of SEQ ID NO: 183 and (b) a VL domain comprising an amino acid sequence of SEQ ID NO: 184. In some instances, the exemplary anti-IL-33 antibody is 6C11.

In other instances, the anti-IL-33 antibody may include at least one, two, three, four, five, or six HVRs selected from: (a) HVR-H1 comprising the amino acid sequence of DYNMN (SEQ ID NO: 191); (b) HVR-H2 comprising the amino acid sequence of DINPKX$_1$X$_2$DTFYNQNFKD (SEQ ID NO: 192), wherein X$_1$ is Asn or Ser, and X$_2$ is Gly or Ala; (c) HVR-H3 comprising the amino acid sequence of HYYYGSSYGGFVY (SEQ ID NO: 196); (d) HVR-L1 comprising the amino acid sequence of HASQNINVWLS (SEQ ID NO: 197); (e) HVR-L2 comprising the amino acid sequence of AASKLHT (SEQ ID NO: 198); and (f) HVR-L3 comprising the amino acid sequence of QQGQSYPLT (SEQ ID NO: 199), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 191, 192, or 196-199.

For instance, the anti-IL-33 antibody may include at least one, two, three, four, five, or six HVRs selected from: (a) HVR-H1 comprising the amino acid sequence of DYNMN (SEQ ID NO: 191); (b) HVR-H2 comprising the amino acid sequence of DINPKNGDTFYNQNFKD (SEQ ID NO: 193), DINPKSGDTFYNQNFKD (SEQ ID NO: 194), or DINPKNADTFYNQNFKD (SEQ ID NO: 195); (c) HVR-H3 comprising the amino acid sequence of HYYYGSSYG-GFVY (SEQ ID NO: 196); (d) HVR-L1 comprising the amino acid sequence of HASQNINVWLS (SEQ ID NO: 197); (e) HVR-L2 comprising the amino acid sequence of AASKLHT (SEQ ID NO: 198); and (f) HVR-L3 comprising the amino acid sequence of QQGQSYPLT (SEQ ID NO: 199), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 191 or 193-199.

In some instances, the anti-IL-33 antibody may include one, two, three, or four of the following heavy chain framework regions: an FR-H1 comprising the amino acid sequence of EVLLQQSGPELVKPGASVKISCNAS-GYTFS (SEQ ID NO: 200) or EVQLVQSGAEVKKPGAS-VKVSCKASGYTFS (SEQ ID NO: 204); an FR-H2 comprising the amino acid sequence of WVKQSHGKSLESIG (SEQ ID NO: 201) or WVRQAPGQGLESIG (SEQ ID NO: 205); an FR-H3 comprising the amino acid sequence of KATLTIDKSSSTVYMELRSLTSEDTAMYYCAR (SEQ ID NO: 202) or RATLTIDKSTSTAYLELSSLRSED-TAVYYCAR (SEQ ID NO: 206); and an FR-H4 comprising the amino acid sequence of WGQGTLVTVAA (SEQ ID NO: 203) or WGQGTLVTVSS (SEQ ID NO: 207).

In some instances, the anti-IL-33 antibody may include one, two, three, or four of the following light chain framework regions: an FR-L1 comprising the amino acid sequence of DIQMNQSPSSLSASLGDTITITC (SEQ ID NO: 208) or DIQMTQSPSSLSASVGDRVTITC (SEQ ID NO:212); an FR-L2 comprising the amino acid sequence of WYQQKAGNNPKLLIY (SEQ ID NO: 209) or WYQQK-PGKNPKLLIY (SEQ ID NO: 213); an FR-L3 comprising the amino acid sequence of GVPSRFTGSGSGTLFTLTISS-LQPEDIATYYC (SEQ ID NO: 210) or GVPSRFSGSGS-GTDFTLTISSLQPEDFATYYC (SEQ ID NO: 214); and an FR-L4 comprising the amino acid sequence of FGSGTN-LELK (SEQ ID NO: 211) or FGQGTKVEIK (SEQ ID NO: 215).

In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 216, 218, 220, or 221; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 217 or SEQ ID NO: 219; or (c) a VH domain as in (a) and a VL domain as in (b). For example, in some instances, the antibody comprises a binding domain comprising a VH domain comprising the amino acid sequence of SEQ ID NO: 216 and a VL domain comprising the amino acid sequence of SEQ ID NO: 217. In some instances, the antibody comprises a binding domain comprising a VH domain comprising the amino acid sequence of SEQ ID NO: 218 and a VL domain comprising the amino acid sequence of SEQ ID NO: 219. In some instances, the antibody comprises a binding domain comprising a VH domain comprising the amino acid sequence of SEQ ID NO: 220 and a VL domain comprising the amino acid sequence of SEQ ID NO: 219. In some instances, the antibody comprises a binding domain comprising a VH domain comprising the amino acid sequence of SEQ ID NO: 221 and a VL domain comprising the amino acid sequence of SEQ ID NO: 219.

For instance, the anti-IL-33 antibody may include (a) HVR-H1 comprising the amino acid sequence of DYNMN (SEQ ID NO: 191); (b) HVR-H2 comprising the amino acid sequence of DINPKNGDTFYNQNFKD (SEQ ID NO: 193); (c) HVR-H3 comprising the amino acid sequence of HYYYGSSYGGFVY (SEQ ID NO: 196); (d) HVR-L1 comprising the amino acid sequence of HASQNINVWLS (SEQ ID NO: 197); (e) HVR-L2 comprising the amino acid sequence of AASKLHT (SEQ ID NO: 198); and (f) HVR-L3 comprising the amino acid sequence of QQGQSYPLT (SEQ ID NO: 199). In some instances, the antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 216; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 217; or (c) a VH domain as in (a) and a VL domain as in (b). In some instances, the anti-IL-33 antibody includes the following heavy chain framework regions: FR-H1 comprising the amino acid sequence of EVLLQQSGPELVKPGASVKISC-NASGYTFS (SEQ ID NO: 200); FR-H2 comprising the amino acid sequence of WVKQSHGKSLESIG (SEQ ID NO: 201); FR-H3 comprising the amino acid sequence of KATLTIDKSSSTVYMELRSLTSEDTAMYYCAR (SEQ ID NO: 202); and FR-H4 comprising the amino acid sequence of WGQGTLVTVAA (SEQ ID NO: 203). In some instances, the anti-IL-33 antibody includes the following light chain framework regions: FR-L1 comprising the amino acid sequence of DIQMNQSPSSLSASLGDTITITC (SEQ ID NO: 208); FR-L2 comprising the amino acid sequence of WYQQKAGNNPKLLIY (SEQ ID NO: 209); FR-L3 comprising the amino acid sequence of GVPSRFTGSGS-GTLFTLTISSLQPEDIATYYC (SEQ ID NO: 210); and FR-L4 comprising the amino acid sequence of FGSGTN-LELK (SEQ ID NO: 211). In some instances, the anti-IL-33 antibody includes a binding domain comprising (a) a VH domain comprising an amino acid sequence of SEQ ID NO: 216 and (b) a VL domain comprising an amino acid sequence of SEQ ID NO: 217. In some instances, the exemplary anti-IL-33 antibody is 2B6.

For instance, the anti-IL-33 antibody may include at least one, two, three, four, five, or six HVRs selected from: (a) HVR-H1 comprising the amino acid sequence of SYWIN (SEQ ID NO: 222); (b) HVR-H2 comprising the amino acid sequence of RIAPGSGFISYNELFKD (SEQ ID NO: 223); (c) HVR-H3 comprising the amino acid sequence of EFYYGSFYGGFAY (SEQ ID NO: 224); (d) HVR-L1 comprising the amino acid sequence of HASQNIHVWLS (SEQ ID NO: 225); (e) HVR-L2 comprising the amino acid sequence of KASTLHT (SEQ ID NO: 226); and (f) HVR-L3 comprising the amino acid sequence of QQGQSSPLT (SEQ ID NO: 227), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 222-227.

In some instances, the anti-IL-33 antibody may include one, two, three, or four of the following heavy chain framework regions: an FR-H1 comprising the amino acid sequence of QVQLQQSGNDLVKPGASVKLSCKAS-GYTFT (SEQ ID NO: 228) or EVQLVQSGAEVKKPGAS-VKVSCKASGYTFT (SEQ ID NO: 238); an FR-H2 comprising the amino acid sequence of WIKQRPGQGLEWIG (SEQ ID NO: 229) or WVRQAPGQGLEWIG (SEQ ID NO: 239); an FR-H3 comprising the amino acid sequence of KATLTVDTSSSTAYIQLGSLSSEDSAVYFCAR (SEQ ID NO: 230) or RVTITRDTSTSTAYLELSSLRSEDTAVYY-CAR (SEQ ID NO: 240); and an FR-H4 comprising the amino acid sequence of WGQGTLVTVSA (SEQ ID NO: 231) or WGQGTLVTVSS (SEQ ID NO: 241).

In some instances, the anti-IL-33 antibody may include one, two, three, or four of the following light chain framework regions: an FR-L1 comprising the amino acid sequence of DIQMNQSPSSLSASLGDTITITC (SEQ ID NO: 232) or DIQMTQSPSSLSASVGDRVTITC (SEQ ID NO: 242); an FR-L2 comprising the amino acid sequence of WYQQKPGNIPKLLIY (SEQ ID NO: 233) or WYQQK-PGKAPKLLIY (SEQ ID NO: 243); an FR-L3 comprising the amino acid sequence of GVPSRFNGSGSGTG-FTLTISSLQPEDIATYYC (SEQ ID NO: 234) or GVPSRF-SGSGSGTDFTLTISSLQPEDFATYYC (SEQ ID NO: 244); and an FR-L4 comprising the amino acid sequence of FGAGTKLEVK (SEQ ID NO: 235) or FGQGTKVEIK (SEQ ID NO: 245).

In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 236 or SEQ ID NO: 246; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 237 or SEQ ID NO: 247; or (c) a VH domain as in (a) and a VL domain as in (b).

For instance, the anti-IL-33 antibody may include (a) HVR-H1 comprising the amino acid sequence of SYWIN (SEQ ID NO: 222); (b) HVR-H2 comprising the amino acid sequence of RIAPGSGFISYNELFKD (SEQ ID NO: 223); (c) HVR-H3 comprising the amino acid sequence of EFYYGSFYGGFAY (SEQ ID NO: 224); (d) HVR-L1 comprising the amino acid sequence of HASQNIHVWLS (SEQ ID NO: 225); (e) HVR-L2 comprising the amino acid sequence of KASTLHT (SEQ ID NO: 226); and (f) HVR-L3 comprising the amino acid sequence of QQGQSSPLT (SEQ ID NO: 227). In some instances, the antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 236; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 237; or (c) a VH domain as in (a) and a VL domain as in (b). In some instances, the anti-IL-33 antibody includes the following heavy chain framework regions: FR-H1 comprising the amino acid sequence of QVQLQQSGNDLVKPGAS-VKLSCKASGYTFT (SEQ ID NO: 228); FR-H2 comprising the amino acid sequence of WIKQRPGQGLEWIG (SEQ ID NO: 229); FR-H3 comprising the amino acid sequence of KATLTVDTSSSTAYIQLGSLSSEDSAVYF-CAR (SEQ ID NO: 230); and FR-H4 comprising the amino acid sequence of WGQGTLVTVSA (SEQ ID NO: 231). In some instances, the anti-IL-33 antibody includes the following light chain framework regions: FR-L1 comprising the amino acid sequence of DIQMNQSPSSLSASLGDTITITC (SEQ ID NO: 232); FR-L2 comprising the amino acid sequence of WYQQKPGNIPKLLIY (SEQ ID NO: 233); FR-L3 comprising the amino acid sequence of GVPSRF-NGSGSGTGFTLTISSLQPEDIATYYC (SEQ ID NO: 234); and FR-L4 comprising the amino acid sequence of FGAGT-KLEVK (SEQ ID NO: 235). In some instances, the anti-IL-33 antibody includes a binding domain comprising (a) a VH domain comprising an amino acid sequence of SEQ ID NO: 236 and (b) a VL domain comprising an amino acid sequence of SEQ ID NO: 237. In some instances, the exemplary anti-IL-33 antibody is 9F6.

In other instances, the anti-IL-33 antibody may include at least one, two, three, four, five, or six HVRs selected from: (a) HVR-H1 comprising the amino acid sequence of GSAX$_1$H (SEQ ID NO: 248), wherein X$_1$ is Met or Ile; (b) HVR-H2 comprising the amino acid sequence of RIRSX$_1$X$_2$NX$_3$YATX$_4$YX$_5$ASVKG (SEQ ID NO: 249), wherein X$_1$ is Arg or Lys, X$_2$ is Asn, Thr, or Gly, X$_3$ is Asn or Ser, X$_4$ is Ala or Glu, and X$_5$ is Ala or Asp; (c) comprising the amino acid sequence of X$_1$X$_2$X$_3$X$_4$PFDY (SEQ ID NO: 250), wherein X$_1$ is Leu or Gln, X$_2$ is Gln, Gly, or Phe, X$_3$ is Gln or Gly, and X$_4$ is Pro or Asp; (d) HVR-L1 comprising the amino acid sequence of RASQGIRNDLD (SEQ ID NO: 251); (e) HVR-L2 comprising the amino acid sequence of AASSLQS (SEQ ID NO: 252); and (f) HVR-L3 comprising the amino acid sequence of LQHX$_1$X$_2$YPX$_3$T (SEQ ID NO: 253), wherein X$_1$ is Asp or Ser, X$_2$ is Ser or Ile, and X$_3$ is Leu or Pro, or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 248-253.

For instance, the anti-IL-33 antibody may include at least one, two, three, four, five, or six HVRs selected from: (a) HVR-H1 comprising the amino acid sequence of GSAMH (SEQ ID NO: 254) or GSAIH (SEQ ID NO: 258); (b) HVR-H2 comprising the amino acid sequence of RIRSRNNNYATAYAASVKG (SEQ ID NO: 255), RIRSRTNNYATEYDASVKG (SEQ ID NO: 259) or RIR-SKGNSYATAYAASVKG (SEQ ID NO: 262); (c) HVR-H3 comprising the amino acid sequence of LQQPPFDY (SEQ ID NO: 256), LGQPPFDY (SEQ ID NO: 260), or QFGD-PFDY (SEQ ID NO: 263); (d) HVR-L1 comprising the amino acid sequence of RASQGIRNDLD (SEQ ID NO: 251); (e) HVR-L2 comprising the amino acid sequence of AASSLQS (SEQ ID NO: 252); and (f) HVR-L3 comprising the amino acid sequence of LQHDSYPLT (SEQ ID NO: 257) or LQHSIYPPT (SEQ ID NO: 261), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 251, 252, or 254-263.

In some instances, the anti-IL-33 antibody may include one, two, three, or four of the following heavy chain framework regions: an FR-H1 comprising the amino acid sequence of QVQLVQSGGGLVQPGGSLKLSCAAS-GFTFS (SEQ ID NO: 264), EVQLVESGGDLVQPGG-SLKLSCAASGFTFS (SEQ ID NO: 265), or EVQLVES-GGGLVQPGGSLKLSCAASGFTFS (SEQ ID NO: 266); an FR-H2 comprising the amino acid sequence of WVRQAS-GKGLEWVG (SEQ ID NO: 267) or WVRQAPGK-GLEWVG (SEQ ID NO: 268); an FR-H3 comprising the amino acid sequence of RFTISRDDSKRTTYLQMNSLK-TEDTAVYYCTR (SEQ ID NO: 269), RFTISRDDSKRTAYLQMNSLKTEDTAVYYCTR (SEQ ID NO: 270), or RFSISRDDSKRTAYLQMSSLKTED-SAVYYCAR (SEQ ID NO: 271); and an FR-H4 comprising the amino acid sequence of WGQGTLVTVSS (SEQ ID NO: 272).

In some instances, the anti-IL-33 antibody may include one, two, three, or four of the following light chain framework regions: an FR-L1 comprising the amino acid sequence of DIQMTQSPSSLSASVGDRVTITC (SEQ ID NO: 273), AIQMTQSPSSLSASVGDRVTITC (SEQ ID NO: 274), or AIRITQSPSSLSASVGDRVTITC (SEQ ID NO: 275); an FR-L2 comprising the amino acid sequence of WYQQKPGKAPKRLIY (SEQ ID NO: 276); an FR-L3 comprising the amino acid sequence of GVPSRFNGSGS-GTEFTLTISSLQPEDFATYYC (SEQ ID NO: 277), GVPSRFSGSGSGTDFTLTISSLQPEDFATYYC (SEQ ID NO: 278), or GVPSRFSGSGSGTEFTLTISSLQPEDFA-TYYC (SEQ ID NO: 279); and an FR-L4 comprising the amino acid sequence of FGGGTKVEIK (SEQ ID NO: 280) or FGQGTKVEIK (SEQ ID NO: 281).

In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 282, 284, or 286; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 283, 285, or 287; or (c) a VH domain as in (a) and a VL domain as in (b). In some instances, the antibody comprises a binding domain comprising a VH domain comprising the amino acid sequence of SEQ ID NO: 282 and a VL domain comprising the amino acid sequence of SEQ ID NO: 283. In some instances, the antibody comprises a binding domain comprising a VH domain comprising the amino acid sequence of SEQ ID NO: 284 and a VL domain comprising the amino acid sequence of SEQ ID NO: 285. In some instances, the antibody comprises a binding domain comprising a VH domain comprising the amino acid sequence of SEQ ID NO: 286 and a VL domain comprising the amino acid sequence of SEQ ID NO: 287.

For instance, the anti-IL-33 antibody may include (a) HVR-H1 comprising the amino acid sequence of GSAMH (SEQ ID NO: 254); (b) HVR-H2 comprising the amino acid sequence of RIRSRNNNYATAYAASVKG (SEQ ID NO: 255); (c) HVR-H3 comprising the amino acid sequence of LQQPPFDY (SEQ ID NO: 256); (d) HVR-L1 comprising the amino acid sequence of RASQGIRNDLD (SEQ ID NO: 251); (e) HVR-L2 comprising the amino acid sequence of AASSLQS (SEQ ID NO: 252); and (f) HVR-L3 comprising the amino acid sequence of LQHDSYPLT (SEQ ID NO: 257). In some instances, the antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 282; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 283; or (c) a VH domain as in (a) and a VL domain as in (b). In some instances, the anti-IL-33 antibody includes the following heavy chain framework regions: FR-H1 comprising the amino acid sequence of QVQLVQSGGGLVQPGGSLKLS-CAASGFTFS (SEQ ID NO: 264); FR-H2 comprising the amino acid sequence of WVRQASGKGLEWVG (SEQ ID NO: 267); FR-H3 comprising the amino acid sequence of RFTISRDDSKRTTYLQMNSLKTEDTAVYYCTR (SEQ ID NO: 269); and FR-H4 comprising the amino acid sequence of WGQGTLVTVSS (SEQ ID NO: 272). In some instances, the anti-IL-33 antibody includes the following light chain framework regions: FR-L1 comprising the amino acid sequence of DIQMTQSPSSLSASVGDRVTITC (SEQ ID NO: 273); FR-L2 comprising the amino acid sequence of WYQQKPGKAPKRLIY (SEQ ID NO: 276); FR-L3 comprising the amino acid sequence of GVPSRFNGSGS-GTEFTLTISSLQPEDFATYYC (SEQ ID NO: 277); and FR-L4 comprising the amino acid sequence of FGGGTK-VEIK (SEQ ID NO: 280). In some instances, the anti-IL-33 antibody includes a binding domain comprising (a) a VH domain comprising an amino acid sequence of SEQ ID NO: 282 and (b) a VL domain comprising an amino acid sequence of SEQ ID NO: 283. In some instances, the exemplary anti-IL-33 antibody is 101.B11.

In some instances, the invention provides an antibody comprising (a) a heavy chain comprising the amino acid sequence of SEQ ID NO: 288 and/or (b) a light chain comprising the amino acid sequence of SEQ ID NO: 289. In certain embodiments, the antibody is 10C12.38.H6.87Y.58I expressed in IgG4.S228P format.

In some instances, the invention provides an antibody comprising (a) a heavy chain comprising the amino acid sequence of SEQ ID NO: 292 and/or (b) a light chain comprising the amino acid sequence of SEQ ID NO: 293. In certain embodiments, the antibody is 4G12.FW4 expressed in IgG4.S228P format.

In some instances, the invention provides an antibody comprising (a) a heavy chain comprising the amino acid sequence of SEQ ID NO: 290 and/or (b) a light chain comprising the amino acid sequence of SEQ ID NO: 291. In certain embodiments, the antibody is 10C12.38.H6.87Y.58I expressed in IgG1 format.

In some instances, the invention provides an antibody comprising (a) a heavy chain comprising the amino acid sequence of SEQ ID NO: 294 and/or (b) a light chain comprising the amino acid sequence of SEQ ID NO: 295. In certain embodiments, the antibody is 4G12.FW4 expressed in IgG1 format.

In a further aspect, the invention provides an antibody that binds to the same epitope as an anti-IL-33 antibody provided herein. For example, in certain embodiments, an antibody is provided that binds to the same epitope as 10C12.38.H6.87Y.58I or 4G12.FW4.

In a further aspect of the invention, an anti-IL-33 antibody according to any of the above embodiments is a monoclonal antibody, including a chimeric, humanized or human antibody. In one embodiment, an anti-IL-33 antibody is an antibody fragment, e.g., a Fv, Fab, Fab', scFv, diabody, or F(ab')2 fragment. In another embodiment, the antibody is a full length antibody, e.g., an intact IgG1 antibody, an intact IgG4 antibody, or other antibody class or isotype as defined herein. In some instances, the antibody is an IgG4 antibody that comprises a mutation in the hinge region. In some instances, the mutation is a substitution mutation. In some instances, the substitution mutation is at amino acid residue S228 (EU numbering). In some instances, the substitution mutation is an S228P mutation.

In a further aspect, an anti-IL-33 antibody according to any of the above embodiments may incorporate any of the features, singly or in combination, as described in Sections 1-7 below:

1. Antibody Affinity

In certain embodiments, an antibody provided herein has a dissociation constant ($K_D$) of ≤1 µM, ≤100 nM, ≤10 nM, ≤1 nM, ≤0.1 nM, ≤0.01 nM, ≤1 pM, or ≤0.1 pM (e.g., 106 M or less, e.g., from 10. M to $10^{-9}$ M or less, e.g., from $10^{-9}$ M to $10^{-13}$ M or less).

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. *J. Mol. Biol.* 293:865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57:4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN®-20) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in phosphate buffered saline (PBS) with 0.05% polysorbate 20 (TWEEN®-20) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al. (*J. Mol. Biol.* 293: 865-881, 1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134, 2003; and Hollinger et al. *Proc. Natl. Acad. Sci. USA* 90: 6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci USA*, 81:6851-6855, 1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:1619-1633, 2008, and are further described, e.g., in Riechmann et al. *Nature* 332:323-329, 1988; Queen et al. *Proc. Natl. Acad. Sci. USA* 86:10029-10033, 1989; U.S. Pat. Nos. 5,821,337, 7,527,791, 6,982,321, and 7,087,409; Kashmiri et al. *Methods* 36:25-34, 2005 (describing specificity determining region (SDR) grafting); Padlan, *Mol. Immunol.* 28:489-498, 1991 (describing "resurfacing"); Dall'Acqua et al. *Methods* 36:43-60, 2005 (describing "FR shuffling"); and Osbourn et al. *Methods* 36:61-68, 2005 and Klimka et al. *Br. J. Cancer,* 83:252-260, 2000 (describing the "guided selection" approach to FR shuffling).

Human framework regions that may be used for humanization include but are not limited to: framework regions selected using the "best-fit" method (see, e.g., Sims et al. *J. Immunol.* 151:2296, 1993); framework regions derived from the consensus sequence of human antibodies of a particular subgroup of light or heavy chain variable regions (see, e.g., Carter et al. *Proc. Natl. Acad. Sci. USA,* 89:4285, 1992; and Presta et al. *J. Immunol.,* 151:2623, 1993); human mature (somatically mutated) framework regions or human germline framework regions (see, e.g., Almagro et al. *Front. Biosci.* 13:1619-1633, 2008); and framework regions derived from screening FR libraries (see, e.g., Baca et al. *J. Biol. Chem.* 272:10678-10684, 1997 and Rosok et al. *J. Biol. Chem.* 271:22611-22618, 1996).

4. Human Antibodies

In certain embodiments, an antibody provided herein is a human antibody. Human antibodies can be produced using various techniques known in the art. Human antibodies are described generally in van Dijk et al. *Curr. Opin. Pharmacol.* 5:368-74, 2001 and Lonberg, *Curr. Opin. Immunol.* 20:450-459, 2008.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125, 2005. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001, 1984; Brodeur et al. *Monoclonal Antibody Production Techniques and Applications,* pp. 51-63 (Marcel Dekker, Inc., New York, 1987); and Boemer et al. *J. Immunol.* 147: 86, 1991). Human antibodies generated via human B-cell hybridoma technology are also described in Li et al. *Proc. Natl. Acad. Sci. USA,* 103:3557-3562, 2006. Additional methods include those described, for example, in U.S. Pat. No. 7,189,826 (describing production of monoclonal human IgM antibodies from hybridoma cell lines) and Ni, Xiandai Mianyixue, 26(4):265-268, 2006 (describing human-human hybridomas). Human hybridoma technology (Trioma technology) is also described in Vollmers et al. *Histology and Histopathology* 20(3):927-937, 2005 and Vollmers et al. *Methods and Findings in Experimental and Clinical Pharmacology* 27(3):185-91, 2005.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al. *Nature* 348:552-554, 1990; Clackson et al. *Nature* 352: 624-628, 1991; Marks et al. *J. Mol. Biol.* 222: 581-597, 1992; Marks et al. in *Methods in Molecular Biology* 248:161-175 (Lo, ed., Human Press, Totowa, N.J., 2003); Sidhu et al. *J. Mol. Biol.* 338(2): 299-310, 2004; Lee et al. *J. Mol Biol.* 340(5): 1073-1093, 2004; Fellouse, *Proc. Natl. Acad. Sci. USA* 101(34):12467-12472, 2004; and Lee et al. *J. Immunol. Methods* 284(1-2): 119-132, 2004.

In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.,* 12: 433-455, 1994. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. *EMBO J.* 12: 725-734, 1993. Finally, naive libraries can also be made synthetically by cloning unrearranged V-gene segments from stem cells, and using PCR primers containing random sequence to encode the highly variable HVR3 regions and to accomplish rearrangement in vitro, as described by Hoogenboom et al. *J. Mol. Biol.,* 227: 381-388, 1992. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, bispecific antibodies may bind to two different epitopes of IL-33. In certain embodiments, one of the binding specificities is for IL-33 and the other is for any other antigen (e.g., a second biological molecule, e.g., IL-13, IL-4, IL-5, IL-17, Factor D, HtrA1, VEGF, or a VEGF receptor). Accordingly, the bispecific antibody may have binding specificity for IL-33 and IL-13; IL-33 and IL-4; IL-33 and IL-5; IL-33 and IL-17; IL-33 and Factor D; IL-33 and HtrA1; IL-33 and VEGF; or IL-33 and a VEGF receptor (e.g., VEGFR1, VEGFR2, VEGFR3, membrane-bound VEGF receptor (mbVEGFR), or soluble VEGF receptor (sVEGFR)). In some instances, the bispecific antibody may have binding specificity for IL-33 and Factor D. In other instances, the bispecific antibody may have binding specificity for IL-33 and HtrA1. In yet other instances, the bispecific antibody may have binding specificity for IL-33 and VEGF. In other instances, the bispecific antibody may have binding specificity for IL-33 and a VEGF receptor. In particular, the bispecific antibody may have binding specificity for IL-33 and IL-13. Bispecific antibodies can be prepared as full length antibodies or antibody fragments.

For example, in some instances, a bispecific anti-IL-33 antibody comprising a first binding domain that specifically binds IL-33 comprising at least one, two, three, four, five, or six HVRs selected from: (a) HVR-H1 comprising the amino acid sequence of SFSX$_1$S (SEQ ID NO: 62), wherein X$_1$ is Met, Leu, or Val; (b) HVR-H2 comprising the amino acid sequence of TISGGKTFTDYVDX$_1$VKG (SEQ ID NO: 63), wherein X$_1$ is Ser or Ala; (c) HVR-H3 comprising the amino acid sequence of ANYGX$_1$X$_2$FFEV (SEQ ID NO: 64), wherein X$_1$ is Asn or Asp, and X$_2$ is Trp or Phe; (d) HVR-L1 comprising the amino acid sequence of RASESVAKYGLSLLN (SEQ ID NO: 4); (e) HVR-L2 comprising the amino acid sequence of AASNRGS (SEQ ID NO: 5); and (f) HVR-L3 comprising the amino acid sequence of QQSKEVPFT (SEQ ID NO: 6), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 4-6 or 62-64, may have a second binding domain that binds to IL-13. The second binding domain that specifically binds to IL-13 may, for example, include at least one, two, three, four, five, or six HVRs selected from (a) HVR-H1 comprising the amino acid sequence of AYSVN (SEQ ID NO: 296); (b) HVR-H2 comprising the amino acid sequence of MIWGDGKIVYNSALKS (SEQ ID NO: 297); (c) HVR-H3 comprising the amino acid sequence of DGYYPYAMDN (SEQ ID NO: 298); (d) HVR-L1 comprising the amino acid sequence of RASKSVDSYGNSFMH (SEQ ID NO: 299); (e) HVR-L2 comprising the amino acid sequence of LASNLES (SEQ ID NO: 300); and (f) HVR-L3 comprising the amino acid sequence of QQNNEDPRT (SEQ ID NO: 301), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 296-301. In some embodiments, the second binding domain comprises one, two, three, four, five, or six HVRs of the anti-IL-13 antibody lebrikizumab.

For example, in some instances, a bispecific anti-IL-33 antibody comprising a first binding domain that specifically binds IL-33 comprising at least one, two, three, four, five, or six hypervariable regions (HVRs) selected from (a) HVR-H1 comprising the amino acid sequence of SFSMS (SEQ ID NO: 1); (b) HVR-H2 comprising the amino acid sequence of TISGGKTFTDYVDSVKG (SEQ ID NO: 2); (c) HVR-H3 comprising the amino acid sequence of ANYGNWFFEV (SEQ ID NO: 3); (d) HVR-L1 comprising the amino acid sequence of RASESVAKYGLSLLN (SEQ ID NO: 4); (e) HVR-L2 comprising the amino acid sequence of AASNRGS (SEQ ID NO: 5); and (f) HVR-L3 comprising the amino acid sequence of QQSKEVPFT (SEQ ID NO: 6), such as 10C12.38.H6.87Y.58I, has a second binding domain that binds to IL-13. The second binding domain that specifically binds to IL-13 may, for example, comprise at least one, two, three, four, five, or six HVRs selected from (a) HVR-H1 comprising the amino acid sequence of AYSVN (SEQ ID NO: 296); (b) HVR-H2 comprising the amino acid sequence of MIWGDGKIVYNSALKS (SEQ ID NO: 297); (c) HVR-H3 comprising the amino acid sequence of DGYYPYAMDN (SEQ ID NO: 298); (d) HVR-L1 comprising the amino acid sequence of RASKSVDSYGNSFMH (SEQ ID NO: 299); (e) HVR-L2 comprising the amino acid sequence of LASNLES (SEQ ID NO: 300); and (f) HVR-L3 comprising the amino acid sequence of QQNNEDPRT (SEQ ID NO: 301). In some embodiments, the second binding domain comprises one, two, three, four, five, or six HVRs of the anti-IL-13 antibody lebrikizumab.

In some instances, a bispecific anti-IL-33 antibody comprises a first binding domain that specifically binds IL-33 comprising (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 36; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 37; or (c) a VH domain as in (a) and a VL domain as in (b), such as 10C12.38.H6.87Y.58I, may have a second binding domain that binds to IL-13. The second binding domain that specifically binds to IL-13 may, for example, comprise (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 302; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 303; or (c) a VH domain as in (a) and a VL domain as in (b). In some instances, the second binding domain that specifically binds to IL-13 may comprise (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 328; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 329; or (c) a VH domain as in (a) and a VL domain as in (b). In some instances, the second binding domain that specifically binds to IL-13 may comprise (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the anti-IL-13 antibody lebrikizumab; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the anti-IL-13 antibody lebrikizumab; or (c) a VH domain as in (a) and a VL domain as in (b).

In other instances, a bispecific anti-IL-33 antibody comprising a first binding domain that specifically binds IL-33 including at least one, two, three, four, five, or six HVRs selected from: (a) HVR-H1 comprising the amino acid sequence of SSIFYWG (SEQ ID NO: 65); (b) HVR-H2 comprising the amino acid sequence of SIYYSGRTYYNPX$_1$LKS (SEQ ID NO: 90), wherein X$_1$ is Ser or Ala; (c) HVR-H3 comprising the amino acid sequence of AGGLYNWNDESFSFYMDV (SEQ ID NO: 68); (d) HVR-L1 comprising the amino acid sequence of RASQSFSSSYLA (SEQ ID NO: 69); (e) HVR-L2 comprising the amino acid sequence of GASSRAT (SEQ ID NO: 70); and (f) HVR-L3 comprising the amino acid sequence of QQYDRSPLT (SEQ ID NO: 71), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 65, 68-71, or 90, may have a second binding domain that binds to IL-13. The second binding domain that specifically binds to IL-13 may, for example, include at least one, two, three, four, five, or six HVRs selected from (a) HVR-H1 comprising the amino acid sequence of AYSVN (SEQ ID NO: 296); (b) HVR-H2 comprising the amino acid sequence of MIWGDGKIVYNSALKS (SEQ ID NO: 297); (c) HVR-H3 comprising the amino acid sequence of DGYYPYAMDN (SEQ ID NO: 298); (d) HVR-L1 comprising the amino acid sequence of RASKSVDSYGNSFMH (SEQ ID NO: 299); (e) HVR-L2 comprising the amino acid sequence of LASNLES (SEQ ID NO: 300); and (f) HVR-L3 comprising the amino acid sequence of QQNNEDPRT (SEQ ID NO: 301), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 296-301. In some embodiments, the second binding domain comprises one, two, three, four, five, or six HVRs of the anti-IL-13 antibody lebrikizumab.

For example, in some instances, a bispecific anti-IL-33 antibody comprising a first binding domain that specifically binds IL-33 comprising at least one, two, three, four, five, or six hypervariable regions (HVRs) selected from (a) HVR-H1 comprising the amino acid sequence of SSIFYWG (SEQ ID NO: 65); (b) HVR-H2 comprising the amino acid sequence of SIYYSGRTYYNPSLKS (SEQ ID NO: 66); (c) HVR-H3 comprising the amino acid sequence of AGGLYNWNDESFSFYMDV (SEQ ID NO: 68); (d) HVR-L1 comprising the amino acid sequence of RASQSFSSSYLA (SEQ ID NO: 69); (e) HVR-L2 comprising the amino acid sequence of GASSRAT (SEQ ID NO: 70); and (f) HVR-L3 comprising the amino acid sequence of QQYDRSPLT (SEQ ID NO: 71), such as 4G12.FW4, may have a second binding domain that binds to IL-13. The second binding domain that specifically binds to IL-13 may, for example, comprise at least one, two, three, four, five, or six HVRs selected from (a) HVR-H1 comprising the amino acid sequence of AYSVN (SEQ ID NO: 296); (b) HVR-H2 comprising the amino acid sequence of MIWGDGKIVYNSALKS (SEQ ID NO: 297); (c) HVR-H3 comprising the amino acid sequence of DGYYPYAMDN (SEQ ID NO: 298); (d) HVR-L1 comprising the amino acid sequence of RASKSVDSYGNSFMH (SEQ ID NO: 299); (e) HVR-L2 comprising the amino acid sequence of LASNLES (SEQ ID NO: 300); and (f) HVR-L3 comprising the amino acid sequence of QQNNEDPRT (SEQ ID NO: 301). In some embodiments, the second binding domain comprises one, two, three, four, five, or six HVRs of the anti-IL-13 antibody lebrikizumab.

In some instances, a bispecific anti-IL-33 antibody comprising a first binding domain that specifically binds IL-33 comprising (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 84; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 85; or (c) a VH domain as in (a) and a VL domain as in (b), such as 4G12.FW4, may have a second binding domain that binds to IL-13. The second binding domain that specifically binds to IL-13 may, for example, comprise (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 302; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 303; or (c) a VH domain as in (a) and a VL domain as in (b). In some instances, the second binding domain that specifically binds to IL-13 may comprise (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 328; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 329; or (c) a VH domain as in (a) and a VL domain as in (b). In some instances, the second binding domain that specifically binds to IL-13 may comprise (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the anti-IL-13 antibody lebrikizumab; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the anti-IL-13 antibody lebrikizumab; or (c) a VH domain as in (a) and a VL domain as in (b).

In some instances, a bispecific anti-IL-33 antibody may comprise (a) a first heavy chain and a first light chain that specifically bind IL-33, wherein the first heavy chain comprises an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 306 and the first light chain comprises an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 307, and (b) a second heavy chain and a second light chain that specifically bind IL-13, wherein the second heavy chain comprises an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 304 or 330 and the second light chain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 305 or 331. In some embodiments, the second heavy chain and second light chain that specifically bind IL-13 are the heavy and light chain of the anti-IL-13 antibody lebrikizumab.

In some instances, a bispecific anti-IL-33 antibody may comprise (a) a first heavy chain and a first light chain that specifically bind IL-33, wherein the first heavy chain comprises an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 308 and the first light chain comprises an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 309, and (b) a second heavy chain and a second light chain that specifically bind IL-13, wherein the second heavy chain comprises an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 304 or 330 and the second light chain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 305 or 331. In some embodiments, the second heavy chain and second light chain that specifically bind IL-13 are the heavy and light chain of the anti-IL-13 antibody lebrikizumab.

Any of the preceding bispecific antibodies may specifically bind both human and cynomolgus monkey (cyno) IL-33 with a $K_D$ of about 1 nM or lower. Any of the preceding bispecific antibodies may specifically bind human IL-33 with a $K_D$ of about 1 nM or lower. For example, in some instances, the bispecific antibody specifically binds human IL-33 with a $K_D$ of between about 1 pM and about 1 nM (e.g., between about 1 pM and about 900 pM, between about 1 pM and about 800 pM, between about 1 pM and about 700 pM, between about 1 pM and about 600 pM, between about 1 pM and about 500 pM, between about 1 pM and about 400 pM, between about 1 pM and about 300 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 25 pM, between about 1 pM and about 20 pM, or between about 1 pM and about 10 pM). In some instances, the bispecific antibody specifically binds human IL-33 with a $K_D$ of between about 1 pM and about 250 pM (e.g., between about 1 pM and about 250 pM, between about 1 pM and about 225 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 25 pM, between about 1 pM and about 20 pM, or between about 1 pM and about 10 pM). In some embodiments, the bispecific antibody specifically binds human IL-33 with a $K_D$ of about 25 pM.

Any of the preceding bispecific antibodies may specifically bind human IL-13 with a $K_D$ of about 1 nM or lower. For example, in some instances, the bispecific antibody specifically binds human IL-13 with a $K_D$ of between about 1 pM and about 1 nM (e.g., between about 1 pM and about 900 pM, between about 1 pM and about 800 pM, between about 1 pM and about 700 pM, between about 1 pM and about 600 pM, between about 1 pM and about 500 pM, between about 1 pM and about 400 pM, between about 1 pM and about 300 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 25 pM, between about 1 pM and about 20 pM, or between about 1 pM and about 10 pM). In some instances, the bispecific antibody specifically binds human IL-13 with a $K_D$ of between about 1 pM and about 250 pM (e.g., between about 1 pM and about 250 pM, between about 1 pM and about 225 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 25 pM, between about 1 pM and about 20 pM, or between about 1 pM and about 10 pM). In some embodiments, the bispecific antibody specifically binds human IL-13 with a $K_D$ of about 10 pM or below. In some embodiments, the bispecific antibody specifically binds human IL-13 with a $K_D$ of about 1 pM to about 10 pM (e.g., about 1 pM, about 2 pM, about 3 pM, about 4 pM, about 5 pM, about 6 pM, about 7 pM, about 8 pM, about 9 pM or about 10 pM.

Techniques for making multispecific antibodies include, but are not limited to, recombinant co-expression of two immunoglobulin heavy chain-light chain pairs having different specificities (see Milstein et al. *Nature* 305: 537, 1983; WO 93/08829; and Traunecker et al. *EMBO J.* 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al. *Science,* 229: 81, 1985); using leucine zippers to produce bispecific antibodies (see, e.g., Kostelny et al. *J. Immunol.,* 148(5):1547-1553, 1992); using "diabody" technology for making bispecific antibody fragments (see, e.g., Hollinger et al. *Proc. Natl. Acad. Sci. USA* 90:6444-6448, 1993); and using single-chain Fv (scFv) dimers (see, e.g. Gruber et al. *J. Immunol.* 152:5368, 1994); and preparing trispecific antibodies as described, e.g., in Tutt et al. *J. Immunol.* 147: 60, 1991.

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to IL-33 as well as another, different antigen (see, US 2008/0069820, for example).

Knobs-into-Holes

The use of knobs-into-holes as a method of producing multispecific antibodies is described, e.g., in U.S. Pat. No. 5,731,168, WO2009/089004, US2009/0182127, US2011/0287009, Marvin and Zhu, *Acta Pharmacol. Sin.* (2005) 26(6):649-658, and Kontermann (2005) *Acta Pharmacol. Sin.,* 26:1-9. A brief nonlimiting discussion is provided below.

A "protuberance" refers to at least one amino acid side chain which projects from the interface of a first polypeptide and is therefore positionable in a compensatory cavity in the adjacent interface (i.e., the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, a nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US 2011/0287009 or Table 1 of U.S. Pat. No. 7,642,228.

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiments, the original residue for the formation of the protuberance has a small side chain volume, such as alanine, asparagine, aspartic acid, glycine, serine, threonine, or valine. See, for example, U.S. Pat. No. 7,642,228.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g., by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T), and valine (V). In some embodiments, an import residue is serine, alanine, or threonine. In some embodiments, the original residue for the formation of the cavity has a large side chain volume, such as tyrosine, arginine, phenylalanine, or tryptophan.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe, and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely-accepted techniques in the art.

In some embodiments, a knob mutation in an IgG1 constant region is T366W. In some embodiments, a hole mutation in an IgG1 constant region comprises one or more mutations selected from T366S, L368A, and Y407V. In some embodiments, a hole mutation in an IgG1 constant region comprises T366S, L368A, and Y407V.

In some embodiments, a knob mutation in an IgG4 constant region is T366W. In some embodiments, a hole mutation in an IgG4 constant region comprises one or more mutations selected from T366S, L368A, and Y407V. In some embodiments, a hole mutation in an IgG4 constant region comprises T366S, L368A, and Y407V.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity. e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, lie;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr. Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol* 207:179-196, 2008), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al. ed., Human Press, Totowa, N.J., 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. *Science* 244:1081-1085, 1989. In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al. *TIBTECH* 15:26-32, 1997. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. 2003/0157108 and 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al. *J. Mol. Biol.* 336:1239-1249, 2004; Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem. Biophys.* 249:533-545, 1986; US 2003/0157108; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda et al. *Biotechnol. Bioeng.* 94(4):680-688, 2006; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example. Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch et al. *Annu. Rev. Immunol.* 9:457-492, 1991. Non-limiting examples of in vitro assays to assess ADCC activity of a molecule of interest is described in U.S. Pat. No. 5,500,362 (see, e.g. Hellstrom et al. *Proc. Natl. Acad. Sci. USA* 83:7059-7063, 1986 and Hellstrom et al. *Poc. Natl. Acad. Sci. USA* 82:1499-1502, 1985; U.S. Pat. No. 5,821,337 (see Bruggemann et al. *J. Exp. Med.* 166:1351-1361, 1987). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al. *Proc. Natl. Acad. Sci. USA* 95:652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods* 202:163, 1996; Cragg et al. *Blood* 101:1045-1052, 2003; and Cragg et al. *Blood* 103:2738-2743, 2004). FcRn binding and in vivo clearance/half life determinations can also be performed using methods known in the art (see, e.g., Petkova et al. *Intl. Immunol.* 18(12):1759-1769, 2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312; and Shields et al. *J. Biol. Chem.* 9(2): 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), for example, as described in U.S. Pat. No. 6,194,551, WO 99/51642, and Idusogie et al. *J. Immunol.* 164: 4178-4184, 2000.

Antibodies with increased half lives and improved binding to the neonatal Fc receptor (FcRn), which is responsible for the transfer of maternal IgGs to the fetus (Guyer et al. *J. Immunol.* 117:587, 1976 and Kim et al. *J. Immunol.* 24:249, 1994), are described in US2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan et al. *Nature* 322:738-40, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, for example, "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, for example, as described in U.S. Pat. No. 4,816,567. In one embodiment, isolated nucleic acid encoding an anti-IL-33 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell, 293 cell, or lymphoid cell (e.g., Y0, NS0, Sp20 cell). In one embodiment, a method of making an anti-IL-33 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-IL-33 antibody, nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross *Nat. Biotech.* 22:1409-1414, 2004 and Li et al. *Nat. Biotech.* 24:210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59, 1977); baby hamster kidney cells (BHK); mouse sertoli cells (TM4 cells as described, e.g., in Mather *Biol. Reprod.* 23:243-251, 1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68, 1982; MRC 5 cells; and FS4 cells. Other useful mammalian host cell lines include Chinese hamster ovary (CHO) cells, including DHFR$^-$ CHO cells (Urlaub et al. *Proc. Natl. Acad. Sci. USA* 77:4216, 1980); and myeloma cell lines such as Y0, NS0 and Sp2/0. For a review of certain mammalian host cell lines suitable for antibody production, see, e.g., Yazaki et al. *Methods in Molecular Biology*, Vol. 248 (B. K. C. Lo, ed., Humana Press. Totowa, N.J.), pp. 255-268, 2003.

C. Assays

Anti-IL-33 antibodies provided herein may be identified, screened for, or characterized for their physical/chemical properties and/or biological activities by various assays known in the art.

1. Binding Assays and Other Assays

In one aspect, an anti-IL-33 antibody of the invention is tested for its antigen-binding activity, for example, by known methods such as ELISA, Western blot, etc.

In another aspect, competition assays may be used to identify an antibody that competes with an anti-IL-33 antibody of the invention for binding to IL-33. In certain embodiments, such a competing antibody binds to the same epitope (e.g., a linear or a conformational epitope) that is bound by an anti-IL-33 antibody of the invention. Detailed exemplary methods for mapping an epitope to which an antibody binds are provided in Morris "Epitope Mapping Protocols," in *Methods in Molecular Biology* Vol. 66 (Humana Press, Totowa, N.J.), 1996.

In an exemplary competition assay, immobilized IL-33 is incubated in a solution comprising a first labeled antibody that binds to IL-33 and a second unlabeled antibody that is being tested for its ability to compete with the first antibody for binding to IL-33. The second antibody may be present in a hybridoma supernatant. As a control, immobilized IL-33 is incubated in a solution comprising the first labeled antibody but not the second unlabeled antibody. After incubation under conditions permissive for binding of the first antibody to IL-33, excess unbound antibody is removed, and the amount of label associated with immobilized IL-33 is measured. If the amount of label associated with immobilized IL-33 is substantially reduced in the test sample relative to the control sample, then that indicates that the second antibody is competing with the first antibody for binding to IL-33. See Harlow et al. *Antibodies: A Laboratory Manual* Ch. 14 (Cold Spring Harbor Laboratory, Cold Spring Harbor, N.Y.), 1988.

2. Activity Assays

In one aspect, assays are provided for identifying anti-IL-33 antibodies thereof having biological activity. Biological activity may include, for example, binding to IL-33 (e.g., IL-33 in the blood stream), or a peptide fragment thereof, either in vivo, in vitro, or ex vivo. In other embodiments, biological activity may include blocking or neutralizing IL-33, or preventing IL-33 from binding to a ligand, for example, a receptor (e.g., the IL-33 receptor ST2 and/or IL-1RAcP). In some embodiments, biological activity may include binding to site 1 on IL-33 and blocking of binding to the IL-33 receptor (i.e., ST2 and/or IL-1RAcP). Antibodies having such biological activity in vivo and/or in vitro are also provided. In certain embodiments, an antibody of the invention is tested for such biological activity. In some embodiments, an anti-IL-33 antibody of the invention is tested for inhibition in a cell-based IL-33 blocking assay. In some embodiments, an anti-IL-33 antibody of the invention is tested for inhibition of IL-33-induced reporter activity in a cell-based blocking assay (e.g., an IL-33 HEK-BLUE™ cell-based assay as described herein (see, e.g., Example 2 and Example 8, Section B)). In some embodiments, an antibody of the invention is tested for inhibition of an IL-33 activity in primary cells, for example, in a primary NK cell assay (see, e.g., Example 8, Section C) or a primary basophil assay (see, e.g., Example 8, Section D). In some embodiments, an antibody of the invention is tested for inhibiting the binding of IL-33 to an IL-33 receptor in a competitive binding ELISA (see, e.g., Example 8, Section F).

D. Immunoconjugates

The invention also provides immunoconjugates comprising an anti-IL-33 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al. *Cancer Res.* 53:3336-3342, 1993; and Lode et al. *Cancer Res.* 58:2925-2928, 1998); an anthracycline such daunomycin or doxorubicin (see Kratz et al. *Current Med. Chem.* 13:477-523, 2006; Jeffrey et al. *Bioorganic & Med. Chem. Letters* 16:358-362, 2006; Torgov et al. *Bioconj. Chem.* 16:717-721, 2005; Nagy et al. *Proc. Natl. Acad. Sci. USA* 97:829-834, 2000; Dubowchik et al. *Bioorg. & Med. Chem. Letters* 12:1529-1532, 2002; King et al. *J. Med. Chem.* 45:4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example technetium-99m (tc99m) or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. *Science* 238:1098, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (see, e.g., Chad et al. *Cancer Res.* 52:127-131, 1992; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-IL-33 antibodies provided herein is useful for detecting the presence of IL-33 in a biological sample. The term "detecting" as used herein encompasses quantitative or qualitative detection. In certain embodiments, a biological sample comprises a cell or tissue, such as smooth muscle, epithelial cells, endothelial cells, blood, blood cells (e.g., macrophages, innate type II (ILC2) cells, mast cells, basophils, eosinophils, and dendritic cells), central nervous system cells (e.g., glia cells), or eye cells (e.g., retinal cells (e.g., Müller cells or retinal pigment epithelium (RPE) cells) and vascular endothelial cells of the eye).

In one embodiment, an anti-IL-33 antibody for use in a method of diagnosis or detection is provided. In a further aspect, a method of detecting the presence of IL-33 in a biological sample is provided. In certain embodiments, the method comprises contacting the biological sample with an anti-IL-33 antibody as described herein under conditions permissive for binding of the anti-IL-33 antibody to IL-33, and detecting whether a complex is formed between the anti-IL-33 antibody and IL-33. Such method may be an in vitro or in vivo method. In one embodiment, an anti-IL-33 antibody is used to select subjects eligible for therapy with an anti-IL-33 antibody, for example, where IL-33 is a biomarker for selection of patients.

Exemplary disorders that may be diagnosed using an antibody of the invention include IL-33-mediated disorders, including, for example, inflammatory conditions (e.g., asthma, sepsis, septic shock, atopic dermatitis, allergic rhinitis, rheumatoid arthritis, and chronic obstructive pulmonary disease (COPD)), immune disorders (e.g., asthma, rheumatoid arthritis, allergy, atopic allergy, anaphylaxis, anaphylactic shock, allergic rhinitis, psoriasis, inflammatory bowel disease (IBD), Crohn's disease, diabetes, and liver disease), fibrotic disorders (e.g., pulmonary fibrosis (e.g., idiopathic pulmonary fibrosis), eosinophilic disorders (e.g., eosinophil-associated gastrointestinal disorders (EGIDs) including eosinophilic esophagitis), infections (e.g., helminth infections, protozoan infections, and viral infections), pain (e.g., inflammatory pain), central nervous system disorders (e.g., Alzheimer's disease), solid tumors (e.g., breast, colon, prostate, lung, kidney, liver, pancreas, stomach, intestinal, brain, bone, and skin tumors), and ophthalmologic disorders (e.g., age-related macular degeneration (AMD) or retinopathy of the eye). In some instances, the ophthalmologic disorder that may be diagnosed using an antibody of the invention includes AMD (e.g., wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retina detachment, glaucoma, uveitis (e.g., infectious and non-infectious uveitis), retinitis pigmentosa, Leber Congenital Amaurosis, Stargardt's disease, traumatic eye injury, and conjunctivitis (e.g., infectious conjunctivitis, non-infectious conjunctivitis, and allergic conjunctivitis).

In some instances, the ophthalmologic disorder includes AMD (including wet AMD, dry AMD, and GA), retinopathy (e.g., DR and ROP), PCV, diabetic macular edema, dry eye disease, Behcet's disease, allergic conjunctivitis, and retina detachment.

In other instances, the ophthalmologic disorder includes intermediate AMD, advanced AMD, glaucoma, uveitis (e.g., infectious and non-infectious uveitis), retinitis pigmentosa, Leber Congenital Amaurosis, Stargardt's disease, high-altitude diabetic retinopathy, traumatic eye injury, and conjunctivitis (e.g., infectious conjunctivitis and non-infectious conjunctivitis).

In certain embodiments, labeled anti-IL-33 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^3$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-IL-33 antibody of the invention are prepared by mixing such antibody having the desired degree of purity with one or more optional pharmaceutically acceptable carriers (see, e.g., *Remington's Pharmaceutical Sciences* 16th edition, Osol, A. Ed., 1980), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an ST2 binding antagonist, a complement pathway inhibitor (e.g., a Factor D binding antagonist), an HtrA1 binding antagonist, a VEGF antagonist, a tryptase-beta binding antagonist, a chemoat-tractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some instances, the complement pathway inhibitor is a Factor D binding antagonist. In some instances, the Factor D binding antagonist is an anti-Factor D antibody or an antigen-binding fragment thereof, for example, as described below in Section G, "Therapeutic Methods and Compositions." In some instances, the HtrA1 binding antagonist is an anti-HtrA1 antibody or an antigen-binding fragment thereof, for example, as described below in Section G, "Therapeutic Methods and Compositions." In some instances, the anti-HtrA1 antibody fragment is an Fab, Fab'-SH, Fv, scFv, or an (Fab')$_2$ fragment. In some instances, the anti-Factor D antibody fragment is an Fab, Fab'-SH, Fv, scFv, or an (Fab')$_2$ fragment. In some instances, the VEGF antagonist is an anti-VEGF antibody or an antigen-binding fragment thereof, for example, as described below in Section G, "Therapeutic Methods and Compositions." In some instances, the anti-VEGF antibody fragment is an Fab, Fab'-SH, Fv, scFv, or an (Fab')$_2$ fragment. In some instances, the VEGF antagonist is an anti-VEGF receptor antibody or an antigen-binding fragment thereof. In some instances, the anti-VEGF receptor antibody fragment is an Fab, Fab'-SH, Fv, scFv, or an (Fab')$_2$ fragment. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the antibody, which matrices are in the form of shaped articles, e.g., films, or microcapsules.

For delivery to the eye (ophthalmic delivery), an antibody of the invention may be combined, for example, with ophthalmologically acceptable preservatives, co-solvents, surfactants, viscosity enhancers, penetration enhancers, buffers, sodium chloride, and/or water. Preservatives may be included, for example, to inhibit microbial contamination during use. Suitable preservatives include: edetate disodium, methyl paraben, propyl paraben, sorbic acid, phenylethyl alcohol, chlorobutanol, polyquaternium-1, or other agents known in the art. Such preservatives are typically employed at a level of from 0.001 to 1.0% w/v. In some instances, a pharmaceutical formulation of the invention does not include a preservative. In certain instances, compositions intended to be administered topically to the eye may be formulated as eye drops or eye ointments. In some instances, the total amount of antibody will be about 0.001 to 1.0% (w/w), for example, about 0.01 to about 1.0% (w/w), of such a formulation.

The formulations to be used for in vivo administration are generally sterile. Sterility may be readily accomplished, for example, by filtration through sterile filtration membranes.

G. Therapeutic Methods and Compositions

Any of the anti-IL-33 antibodies of the invention may be used in therapeutic methods.

The invention provides an IL-33 axis binding antagonist for use as a medicament. In one aspect, an anti-IL-33 antibody for use as a medicament is provided. In further aspects, an anti-IL-33 antibody for use in treating IL-33-mediated disorders is provided. In certain embodiments, an anti-IL-33 antibody for use in a method of treatment is provided. In certain embodiments, the invention provides an anti-IL-33 antibody for use in a method of treating an individual having an IL-33-mediated disorder comprising administering to the individual an effective amount of the anti-IL-33 antibody. In one such embodiment, the method further comprises administering to the individual an effective amount of at least one additional therapeutic agent, for example, as described below. An "individual" according to any of the above embodiments is preferably a human.

The invention provides an IL-33 axis binding antagonist in the manufacture or preparation of a medicament. In a further aspect, the invention provides for the use of an anti-IL-33 antibody in the manufacture or preparation of a medicament. In one embodiment, the medicament is for treatment of an IL-33-mediated disorder. In a further embodiment, the medicament is for use in a method of treating IL-33-mediated disorder comprising administering to an individual having IL-33-mediated disorder an effective amount of the medicament. In one such embodiment, the method further comprises administering to the individual an effective amount of at least one additional therapeutic agent, e.g., as described below. An "individual" according to any of the above embodiments may be a human.

In another aspect, the invention provides for the use of a bispecific antibody that specifically binds both IL-33 and IL-13 or an antigen-binding antibody fragment thereof in the manufacture of a medicament for an inflammatory disorder, such as, for example, asthma, airway hyperresponsiveness, airway inflammation, sepsis, septic shock, atopic dermatitis, allergic rhinitis, rheumatoid arthritis, or chronic obstructive pulmonary disease (COPD), or a fibrotic disorder, such as, for example, idiopathic pulmonary fibrosis (IPF). In an exemplary embodiment, the invention provides for the use of a bispecific antibody that specifically binds both IL-33 and IL-13 or an antigen-binding antibody fragment thereof in the manufacture of a medicament for treatment of asthma. The bispecific antibody may comprise a binding domain that specifically binds IL-33 that is derived from any of the anti-IL-33 antibodies described herein. The bispecific antibody may comprise a binding domain that specifically binds IL-13 as described herein. In an exemplary embodiment, the bispecific antibody that specifically binds both IL-33 and IL-13 comprises a first binding domain that specifically binds IL-33 comprising the following six HVRs: an HVR-H1 comprising the amino acid sequence of SFSMS (SEQ ID NO: 1); an HVR-H2 comprising the amino acid sequence of TISGGKTFTDYVDSVKG (SEQ ID NO: 2); an HVR-H3 comprising the amino acid sequence of ANYGNWFFEV (SEQ ID NO: 3); an HVR-L1 comprising the amino acid sequence of RASESVAKYGLSLLN (SEQ ID NO: 4); an HVR-L2 comprising the amino acid sequence of AASNRGS (SEQ ID NO: 5); and an HVR-L3 comprising the amino acid sequence of QQSKEVPFT (SEQ ID NO: 6); and a second binding domain that specifically binds IL-13 comprising the following six HVRs: an HVR-H1 comprising the amino acid sequence of AYSVN (SEQ ID NO: 296); an HVR-H2 comprising the amino acid sequence of MIWGDGKIVYN-SALKS (SEQ ID NO: 297); an HVR-H3 comprising the amino acid sequence of DGYYPYAMDN (SEQ ID NO: 298); an HVR-L1 comprising the amino acid sequence of RASKSVDSYGNSFMH (SEQ ID NO: 299); an HVR-L2 comprising the amino acid sequence of LASNLES (SEQ ID NO: 300); and an HVR-L3 comprising the amino acid sequence of QQNNEDPRT (SEQ ID NO: 301). In another embodiment, the bispecific antibody that specifically binds both IL-33 and IL-13 comprises a first binding domain that specifically binds IL-33 comprising (a) a VH domain comprising an amino acid sequence having at least 99% sequence identity to the amino acid sequence of SEQ ID NO: 36 and (b) a VL domain comprising an amino acid sequence having at least 99% sequence identity to the amino acid sequence of SEQ ID NO: 37, and a second binding domain that specifically binds IL-13 comprising (a) a VH domain comprising an amino acid sequence having at least 99% sequence identity to the amino acid sequence of SEQ ID NO: 302 and (b) a VL domain comprising an amino acid sequence having at least 99% sequence identity to the amino acid sequence of SEQ ID NO: 303. In another embodiment, the bispecific antibody that specifically binds both IL-33 and IL-13 comprises a first binding domain that specifically binds IL-33 comprising (a) a VH domain comprising the amino acid sequence of SEQ ID NO: 36 and (b) a VL domain comprising the amino acid sequence of SEQ ID NO: 37, and a second binding domain that specifically binds IL-13 comprising (a) a VH domain comprising the amino acid sequence of SEQ ID NO: 302 and (b) a VL domain comprising the amino acid sequence of SEQ ID NO: 303. In another embodiment, the bispecific antibody that specifically binds both IL-33 and IL-13 comprises: (a) a first heavy chain and a first light chain that specifically bind IL-33, wherein the first heavy chain comprises an amino acid sequence having at least 99% sequence identity to the amino acid sequence of SEQ ID NO: 308 and the first light chain comprises an amino acid sequence having at least 99% sequence identity to the amino acid sequence of SEQ ID NO: 309, and (b) a second heavy chain and a second light chain that specifically bind IL-13, wherein the second heavy chain comprises an amino acid sequence having at least 99% sequence identity to the amino acid sequence of SEQ ID NO: 304 and the second light chain comprising an amino acid sequence having at least 99% sequence identity to the amino acid sequence of SEQ ID NO: 305. In another embodiment, the bispecific antibody that specifically binds both IL-33 and IL-13 comprises: (a) a first heavy chain and a first light chain that specifically bind IL-33, wherein the first heavy chain comprises the amino acid sequence of SEQ ID NO: 308 and the first light chain comprises the amino acid sequence of SEQ ID NO: 309, and (b) a second heavy chain and a second light chain that specifically bind IL-13, wherein the second heavy chain comprises the amino acid sequence of SEQ ID NO: 304 and the second light chain comprising amino acid sequence of SEQ ID NO: 305.

In another aspect, the invention provides for the use of a bispecific antibody that specifically binds both IL-33 and Factor D or an antigen-binding antibody fragment thereof in the manufacture of a medicament for treating geographic atrophy (GA). The bispecific antibody may comprise a binding domain that specifically binds IL-33 that is derived from any of the anti-IL-33 antibodies described herein. The bispecific antibody may comprise a binding domain that specifically binds Factor D that is derived from any of the anti-Factor D antibodies described below. In some embodiments, the antigen-binding antibody fragment is a (Fab')$_2$ fragment.

In another aspect, the invention provides for the use of a bispecific antibody that specifically binds both IL-33 and HtrA1 or an antigen-binding antibody fragment thereof in the manufacture of a medicament for treating geographic atrophy (GA), AMD (wet or dry), DR, PCV, or ROP. The bispecific antibody may comprise a binding domain that specifically binds IL-33 that is derived from any of the anti-IL-33 antibodies described herein. The bispecific antibody may comprise a binding domain that specifically binds HtrA1 that is derived from any of the anti-HtrA1 antibodies described herein. In some embodiments, the antigen-binding antibody fragment is a (Fab')$_2$ fragment.

In yet another aspect, the invention provides for the use of a bispecific antibody that specifically binds both IL-33 and VEGF or an antigen-binding antibody fragment thereof in the manufacture of a medicament for treating wet AMD. The bispecific antibody may comprise a binding domain that specifically binds IL-33 that is derived from any of the anti-IL-33 antibodies described herein. The bispecific antibody may comprise a binding domain that specifically binds VEGF that is derived from any of the anti-VEGF antibodies described below. In some embodiments, the antigen-binding antibody fragment is a (Fab')$_2$ fragment.

In a further aspect, the invention provides a method for treating an IL-33-mediated disorder. In some instances, the method comprises administering the individual having such an IL-33-mediated disorder an effective amount of an IL-33 axis binding antagonist. In one embodiment, the method comprises administering to an individual having such IL-33-mediated disorder an effective amount of an anti-IL-33 antibody. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the anti-IL-33 antibodies provided herein, e.g., for use in any of the above therapeutic methods. In one embodiment, a pharmaceutical formulation comprises any of the anti-IL-33 antibodies provided herein and a pharmaceutically acceptable carrier. In another embodiment, a pharmaceutical formulation comprises any of the anti-IL-33 antibodies provided herein and at least one additional therapeutic agent, for example, as described below.

In any of the preceding aspects, the IL-33 mediated disorder may be an inflammatory condition, an immune disorder, a fibrotic disorder, an eosinophilic disorder, an infection, pain, a central nervous system disorder, a solid tumor, or an ophthalmologic disorder. For example, in some instances, an inflammatory condition may be asthma, airway hyperresponsiveness, airway inflammation, sepsis, septic shock, atopic dermatitis, allergic rhinitis, rheumatoid arthritis, or chronic obstructive pulmonary disease (COPD). In some instances, an immune disorder may be asthma, rheumatoid arthritis, allergy, atopic allergy, anaphylaxis, anaphylactic shock, allergic rhinitis, psoriasis, inflammatory bowel disease (IBD), Crohn's disease, diabetes, or liver disease. In some instances, the fibrotic disease may be idiopathic pulmonary fibrosis (IPF). In some instances, the eosinophilic disorder may be an eosinophil-associated gastrointestinal disorder (EGID). In some instances, the EGID may be eosinophilic esophagitis. In some instances, the infection may be a helminth infection, a protozoan infection, or a viral infection. In some instances, the protozoan infection may be *Leishmania major* infection. In some instances, the viral infection may be respiratory syncytial virus (RSV) infection or influenza infection. In some instances, the pain may be inflammatory pain. In some instances, the central nervous system disorder may be Alzheimer's disease. In some instances, the solid tumor may be a breast tumor, colon tumor, prostate tumor, lung tumor, kidney tumor, liver tumor, pancreas tumor, stomach tumor, intestinal tumor, brain tumor, bone tumor, or skin tumor. In particular instances, the IL-33-mediated disorder may be asthma, allergic rhinitis, atopic dermatitis, COPD, eosinophilic esophagitis, or pulmonary fibrosis (e.g., IPF). For example, in some instances, the IL-33-mediated disorder is asthma. In other instances, the IL-33-mediated disorder is pulmonary fibrosis (e.g., IPF).

In some instances of any of the preceding aspects, the IL-33-mediated disorder may be an opthamologic disorder, including but not limited to age-related macular degeneration (AMD), including wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retina detachment, glaucoma, uveitis (e.g., infectious and non-infectious uveitis), retinitis pigmentosa, Leber Congenital Amaurosis, Stargardt's disease, traumatic eye injury, and conjunctivitis (e.g., infectious conjunctivitis, non-infectious conjunctivitis, and allergic conjunctivitis).

In some instances, the ophthalmologic disorder includes AMD (including wet AMD, dry AMD, and GA), retinopathy (e.g., DR and ROP), PCV, diabetic macular edema, dry eye disease, Behcet's disease, allergic conjunctivitis, and retina detachment.

In other instances, the ophthalmologic disorder includes intermediate AMD, advanced AMD, glaucoma, uveitis (e.g., infectious and non-infectious uveitis), retinitis pigmentosa, Leber Congenital Amaurosis. Stargardt's disease, high-altitude diabetic retinopathy, traumatic eye injury, and conjunctivitis (e.g., infectious conjunctivitis and non-infectious conjunctivitis).

For example, the invention provides a method of treating an ophthalmologic disorder in a subject in need thereof, the method comprising administering to the subject a therapeutically effective amount of an IL-33 axis binding antagonist. In some instances, the IL-33 axis binding antagonist is an anti-IL-33 antibody, for example, an anti-IL-33 antibody of the invention. In some instances, the IL-33 axis binding antagonist is anti-IL-33 antibody such as ANB-020 (AnaptyxBio Inc.) or any of the antibodies described in WO2014164959, EP1725261, U.S. Pat. No. 8,187,569, WO2011031600, WO2015099175 or WO2015106080 (which are each incorporated herein by reference in their entirety); an anti-ST2 antibody such as AMG-282 (Amgen) or STLM15 (Janssen), or any of the antibodies described in WO2013173761 or WO2013165894 (which are each incorporated herein by reference in their entirety); or a ST2-Fc protein and variants thereof such as those described in WO 2013/173761, WO 2013/165894, or WO 2014/152195 (which are each incorporated herein by reference in their entirety). In some instances, the opthamologic disorder may be selected from the group consisting of age-related macular degeneration (AMD), including wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retina detachment, glaucoma, uveitis (e.g., infectious and non-infectious uveitis), retinitis pigmentosa, Leber Congenital Amaurosis (also known as Leber's congenital amaurosis), Stargardt's disease, traumatic eye injury, and conjunctivitis (e.g., infectious conjunctivitis, non-infectious conjunctivitis, and allergic conjunctivitis). In some instances, the ophthalmologic disorder includes AMD (including wet AMD, dry AMD, and GA), retinopathy (e.g., DR and ROP), PCV, diabetic macular edema, dry eye disease, Behcet's disease, allergic conjunctivitis, and retina detachment. In other instances, the ophthalmologic disorder includes intermediate AMD, advanced AMD, glaucoma, uveitis (e.g., infectious and non-infectious uveitis), retinitis pigmentosa, Leber Congenital Amaurosis, Stargardt's disease, high-altitude diabetic retinopathy, traumatic eye injury, and conjunctivitis (e.g., infectious conjunctivitis and non-infectious conjunctivitis).

IL-33 axis binding antagonists (e.g., anti-IL-33 antibodies of the invention) can be used either alone or in combination with other agents in a therapy. For instance, an IL-33 axis binding antagonist (e.g., an anti-IL-33 antibody of the invention) may be co-administered with at least one additional therapeutic agent. In certain embodiments, an additional therapeutic agent is an ST2 binding antagonist, a complement pathway inhibitor (e.g., a Factor D binding antagonist), an HtrA1 binding antagonist, a VEGF antagonist, a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some embodiments, an additional therapeutic agent is a chemotherapeutic agent, an anti-hormonal agent, a cytotoxic agent, a growth inhibitory agent, or combinations thereof.

For example, an IL-33 axis binding antagonist (e.g., an anti-IL-33 antibody of the invention) may be co-administered with an anti-IL-13 antibody, e.g., for the treatment of an inflammatory disorder, such as, for example, asthma, airway hyperresponsiveness, airway inflammation, sepsis, septic shock, atopic dermatitis, allergic rhinitis, rheumatoid arthritis, or chronic obstructive pulmonary disease (COPD), or a fibrotic disorder, such as, for example, idiopathic pulmonary fibrosis (IPF). In an exemplary embodiment, an IL-33 axis binding antagonist (e.g., an anti-IL-33 antibody of the invention) may be co-administered with an anti-IL-13 antibody for treatment of asthma. Any of the anti-IL-13 antibodies described herein may be administered in combination with an anti-IL-33 axis binding antagonist. In one embodiment, an anti-IL-33 antibody is administered in combination with an anti-IL-13 antibody. In an exemplary embodiment, the anti-IL-33 antibody comprises the following six HVRs: an HVR-H1 comprising the amino acid sequence of SFSMS (SEQ ID NO: 1); an HVR-H2 comprising the amino acid sequence of TISGGKTFTDYVDS-VKG (SEQ ID NO: 2); an HVR-H3 comprising the amino acid sequence of ANYGNWFFEV (SEQ ID NO: 3); an HVR-L1 comprising the amino acid sequence of RASES-VAKYGLSLLN (SEQ ID NO: 4); an HVR-L2 comprising the amino acid sequence of AASNRGS (SEQ ID NO: 5); and an HVR-L3 comprising the amino acid sequence of QQSKEVPFT (SEQ ID NO: 6); and the anti-IL-13 antibody comprises the following six HVRs: an HVR-H1 comprising the amino acid sequence of AYSVN (SEQ ID NO: 296); an HVR-H2 comprising the amino acid sequence of MIWGDGKIVYNSALKS (SEQ ID NO: 297); an HVR-H3 comprising the amino acid sequence of DGYYPYAMDN (SEQ ID NO: 298); an HVR-L1 comprising the amino acid sequence of RASKSVDSYGNSFMH (SEQ ID NO: 299); an HVR-L2 comprising the amino acid sequence of LASN-LES (SEQ ID NO: 300); and an HVR-L3 comprising the amino acid sequence of QQNNEDPRT (SEQ ID NO: 301). In another embodiment, the anti-IL-33 antibody comprises (a) a VH domain comprising an amino acid sequence having at least 99% sequence identity to the amino acid sequence of SEQ ID NO: 36 and (b) a VL domain comprising an amino acid sequence having at least 99% sequence identity to the amino acid sequence of SEQ ID NO: 37, and the anti-IL-13 antibody comprises (a) a VH domain comprising an amino acid sequence having at least 99% sequence identity to the amino acid sequence of SEQ ID NO: 302 and (b) a VL domain comprising an amino acid sequence having at least 99% sequence identity to the amino acid sequence of SEQ ID NO: 303. In another embodiment, the anti-IL-33 antibody comprises (a) a VH domain comprising the amino acid sequence of SEQ ID NO: 36 and (b) a VL domain comprising the amino acid sequence of SEQ ID NO: 37, and the anti-IL-13 antibody comprises (a) a VH domain comprising the amino acid sequence of SEQ ID NO: 302 and (b) a VL domain comprising the amino acid sequence of SEQ ID NO: 303. In another embodiment, the anti-IL-33 comprises a heavy chain comprising an amino acid sequence having at least 99% sequence identity to the amino acid sequence of SEQ ID NO: 308 and a light chain comprising an amino acid sequence having at least 99% sequence identity to the amino acid sequence of SEQ ID NO: 309, and the anti-IL-13 antibody comprises a heavy chain comprising an amino acid sequence having at least 99% sequence identity to the amino acid sequence of SEQ ID NO: 304 and a light chain comprising an amino acid sequence having at least 99% sequence identity to the amino acid sequence of SEQ ID NO: 305. In another embodiment, the anti-IL-33 comprises a heavy chain comprising the amino acid sequence of SEQ ID NO: 308 and a light chain comprising the amino acid sequence of SEQ ID NO: 309, and the anti-IL-13 antibody comprises a heavy chain comprising the amino acid sequence of SEQ ID NO: 304 and a light chain comprising amino acid sequence of SEQ ID NO: 305.

In another example, an IL-33 axis binding antagonist (e.g., an anti-IL-33 antibody of the invention) may be co-administered with a complement pathway inhibitor. In some instances, a complement pathway inhibitor may be an inhibitor of the alternative complement pathway (e.g., Factor D, properdin, Factor B, Factor Ba, and Factor Bb) or the classical complement pathway (e.g., C3a, C5, C5a, C5b, C6, C7, C8, C9, and C5b-9). In some instances, the complement pathway inhibitor may be any complement pathway inhibitor described in WO 2007/056227, which is incorporated herein by reference in its entirety. In some instances, the complement pathway inhibitor may be a Factor D binding antagonist. In particular instances, a Factor D binding antagonist may an anti-Factor D antibody or an antigen-binding fragment thereof, for example, any Factor D antibody described in WO 2007/056227, WO 01/70818, and/or US 2002/0081293, which are each incorporated herein by reference in their entirety. As a non-limiting example, in some instances, the anti-Factor D antibody may comprise an amino acid sequence having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the monoclonal antibody 166-32 produced from the hybridoma deposited with the American Type Culture Collection (ATCC) and designated HB12476. In some instances, the anti-Factor D antibody is a humanized derivative of monoclonal antibody 166-32. In some embodiments, the anti-Factor D antibody binds to the same epitope as monoclonal antibody 166-32. In some instances, the anti-Factor D antibody is an antibody fragment derived from monoclonal antibody 166-32. In some instances, the antibody fragment derived from monoclonal antibody 166-32 is an Fab, Fab'-SH, Fv, scFv, or an (Fab')$_2$ fragment. In some embodiments, the antibody fragment derived from monoclonal antibody 166-32 is an Fab.

In another example, an IL-33 axis binding antagonist (e.g., an anti-IL-33 antibody of the invention) may be co-administered with an HtrA1 binding antagonist. In some instances, the HtrA1 binding antagonist may be an anti-HtrA1 antibody or an antigen-binding fragment thereof. Any of the anti-HtrA1 antibodies or antigen-binding fragments thereof known in the art and/or described herein may be used. For example, in some instances, the anti-HtrA1 antibody is an anti-HtrA1 antibody described in WO 2013/055998. In some instances, the anti-HtrA1 antibody fragment is an Fab, Fab'-SH, Fv, scFv, or an (Fab')$_2$ fragment. In some embodiments, the anti-HtrA1 antibody fragment is an Fab.

In another example, an IL-33 axis binding antagonist (e.g., an anti-IL-33 antibody of the invention) may be co-administered with a VEGF antagonist. In some instances, the VEGF antagonist may be an anti-VEGF antibody or an antigen-binding fragment thereof. Any of the anti-VEGF antibodies or antigen-binding fragments thereof known in the art and/or described herein may be used. For example, in some instances, the anti-VEGF antibody is bevacizumab (AVASTIN®) or ranibizumab (LUCENTIS®). In some instances, the anti-VEGF antibody fragment is an Fab, Fab'-SH, Fv, scFv, or an (Fab')$_2$ fragment. In some embodiments, the anti-VEGF antibody fragment is an Fab.

In some instances, the anti-VEGF antibody or antigen-binding fragment thereof is or is derived from any anti-VEGF antibody described in WO 2005/044853, which is incorporated herein by reference in its entirety. For example, in some instances, the anti-VEGF antibody is or is derived from a G6 series antibody (e.g., G6, G6-8, G6-23, G6-23.1, G6-23.2, or G6-31) or a B20 series antibody (e.g., B20, B20-4, or B20-4.1). For example, in some instances, the anti-VEGF antibody comprises (a) a heavy chain variable (VH) domain comprising an amino acid sequence having at least 80% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, any one of SEQ ID NOs: 334, 337, or 340; (b) a light chain variable (VL) domain comprising an amino acid sequence having at least 80% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, any one of SEQ ID NOs: 335, 336, 338, 339, or 341; or (c) a VH domain as in (a) and a VL domain as in (b). For example, in some instances, the anti-VEGF antibody comprises a VH domain comprising the amino acid sequence of SEQ ID NO: 334 and a VL domain comprising the amino acid sequence of SEQ ID NO: 335 (such as the anti-VEGF antibody G6). In some instances, the anti-VEGF antibody comprises a VH domain comprising the amino acid sequence of SEQ ID NO: 334 and a VL domain comprising the amino acid sequence of SEQ ID NO: 336 (such as the anti-VEGF antibody G6.31). In some instances, the anti-VEGF antibody comprises a VH domain comprising the amino acid sequence of SEQ ID NO: 337 and a VL domain comprising the amino acid sequence of SEQ ID NO: 338 (such as the anti-VEGF antibody B20). In other instances, the anti-VEGF antibody comprises a VH domain comprising the amino acid sequence of SEQ ID NO: 337 and a VL domain comprising the amino acid sequence of SEQ ID NO: 339 (such as the anti-VEGF antibody B20-4). In yet other instances, the anti-VEGF antibody comprises a VH domain comprising the amino acid sequence of SEQ ID NO: 340 and a VL domain comprising the amino acid sequence of SEQ ID NO: 341 (such as the anti-VEGF antibody B20-4.1). In some embodiments, the anti-VEGF antibody is a humanized derivative of any of the preceding antibodies. In some embodiments, the anti-VEGF antibody is an antibody fragment derived from any of the preceding antibodies. In some embodiments, the antibody fragment is an Fab, Fab'-SH, Fv, scFv, or an (Fab')$_2$ fragment. In some embodiments, the antibody fragment is an Fab.

In one aspect, the invention provides a method of treating an inflammatory disorder, such as, for example, asthma, airway hyperresponsiveness, airway inflammation, sepsis, septic shock, atopic dermatitis, allergic rhinitis, rheumatoid arthritis, or chronic obstructive pulmonary disease (COPD), or a fibrotic disorder, such as, for example, idiopathic pulmonary fibrosis (IPF) in a subject in need thereof, the method comprising administering to the subject a therapeutically effective amount of an IL-33 axis binding antagonist (e.g., an anti-IL-33 antibody of the invention) and a therapeutically effective amount of an anti-IL-13 antibody. In an exemplary embodiment, the invention provides a method of treating asthma in a subject in need thereof, the method comprising administering to the subject a therapeutically effective amount of an IL-33 axis binding antagonist (e.g., an anti-IL-33 antibody of the invention) and a therapeutically effective amount of an anti-IL-13 antibody. Any of the anti-IL-13 antibodies described herein may be administered in combination with an anti-IL-33 axis binding antagonist. In one embodiment, an anti-IL-33 antibody is administered in combination with an anti-IL-13 antibody. In an exemplary embodiment, the anti-IL-33 antibody comprises the following six HVRs: an HVR-H1 comprising the amino acid sequence of SFSMS (SEQ ID NO: 1); an HVR-H2 comprising the amino acid sequence of TISGGKTFTDYVDS-VKG (SEQ ID NO: 2); an HVR-H3 comprising the amino acid sequence of ANYGNWFFEV (SEQ ID NO: 3); an HVR-L1 comprising the amino acid sequence of RASES-VAKYGLSLLN (SEQ ID NO: 4); an HVR-L2 comprising the amino acid sequence of AASNRGS (SEQ ID NO: 5); and an HVR-L3 comprising the amino acid sequence of QQSKEVPFT (SEQ ID NO: 6); and the anti-IL-13 antibody comprises the following six HVRs: an HVR-H1 comprising the amino acid sequence of AYSVN (SEQ ID NO: 296); an HVR-H2 comprising the amino acid sequence of MIWGDGKIVYNSALKS (SEQ ID NO: 297); an HVR-H3 comprising the amino acid sequence of DGYYPYAMDN (SEQ ID NO: 298); an HVR-L1 comprising the amino acid sequence of RASKSVDSYGNSFMH (SEQ ID NO: 299); an HVR-L2 comprising the amino acid sequence of LASN-LES (SEQ ID NO: 300); and an HVR-L3 comprising the amino acid sequence of QQNNEDPRT (SEQ ID NO: 301). In another embodiment, the anti-IL-33 antibody comprises (a) a VH domain comprising an amino acid sequence having at least 99% sequence identity to the amino acid sequence of SEQ ID NO: 36 and (b) a VL domain comprising an amino acid sequence having at least 99% sequence identity to the amino acid sequence of SEQ ID NO: 37, and the anti-IL-13 antibody comprises (a) a VH domain comprising an amino acid sequence having at least 99% sequence identity to the amino acid sequence of SEQ ID NO: 302 and (b) a VL domain comprising an amino acid sequence having at least 99% sequence identity to the amino acid sequence of SEQ ID NO: 303. In another embodiment, the anti-IL-33 antibody comprises (a) a VH domain comprising the amino acid sequence of SEQ ID NO: 36 and (b) a VL domain comprising the amino acid sequence of SEQ ID NO: 37, and the anti-IL-13 antibody comprises (a) a VH domain comprising the amino acid sequence of SEQ ID NO: 302 and (b) a VL domain comprising the amino acid sequence of SEQ ID NO: 303. In another embodiment, the anti-IL-33 comprises a heavy chain comprising an amino acid sequence having at least 99% sequence identity to the amino acid sequence of SEQ ID NO: 308 and a light chain comprising an amino acid sequence having at least 99% sequence identity to the amino acid sequence of SEQ ID NO: 309, and the anti-IL-13 antibody comprises a heavy chain comprising an amino acid sequence having at least 99% sequence identity to the amino acid sequence of SEQ ID NO: 304 and a light chain comprising an amino acid sequence having at least 99% sequence identity to the amino acid sequence of SEQ ID NO: 305. In another embodiment, the anti-IL-33 comprises a heavy chain comprising the amino acid sequence of SEQ ID NO: 308 and a light chain comprising the amino acid sequence of SEQ ID NO: 309, and the anti-IL-13 antibody comprises a heavy chain comprising the amino acid sequence of SEQ ID NO: 304 and a light chain comprising amino acid sequence of SEQ ID NO: 305.

In another aspect, the invention provides a method of treating an inflammatory disorder, such as, for example, asthma, airway hyperresponsiveness, airway inflammation, sepsis, septic shock, atopic dermatitis, allergic rhinitis, rheumatoid arthritis, or chronic obstructive pulmonary disease (COPD), or a fibrotic disorder, such as, for example, idiopathic pulmonary fibrosis (IPF) in a subject in need thereof, the method comprising administering to the subject a therapeutically effective amount of a bispecific antibody that specifically binds both IL-33 and IL-13 or an antigen-binding antibody fragment thereof. In an exemplary embodiment, the invention provides a method of treating asthma in a subject in need thereof, the method comprising administering to the subject a therapeutically effective amount of a bispecific antibody that specifically binds both IL-33 and IL-13 or an antigen-binding antibody fragment thereof. The bispecific antibody may comprise a binding domain that specifically binds IL-33 that is derived from any of the anti-IL-33 antibodies described herein. The bispecific antibody may comprise a binding domain that specifically binds IL-13 as described herein. In an exemplary embodiment, the bispecific antibody that specifically binds both IL-33 and IL-13 comprises a first binding domain that specifically binds IL-33 comprising the following six HVRs: an HVR-H1 comprising the amino acid sequence of SFSMS (SEQ ID NO: 1); an HVR-H2 comprising the amino acid sequence of TISGGKTFTDYVDSVKG (SEQ ID NO: 2); an HVR-H3 comprising the amino acid sequence of ANYGNWFFEV (SEQ ID NO: 3); an HVR-L1 comprising the amino acid sequence of RASESVAKYGLSLLN (SEQ ID NO: 4); an HVR-L2 comprising the amino acid sequence of AASNRGS (SEQ ID NO: 5); and an HVR-L3 comprising the amino acid sequence of QQSKEVPFT (SEQ ID NO: 6); and a second binding domain that specifically binds IL-13 comprising the following six HVRs: an HVR-H1 comprising the amino acid sequence of AYSVN (SEQ ID NO: 296); an HVR-H2 comprising the amino acid sequence of MIWGDGKIVYNSALKS (SEQ ID NO: 297); an HVR-H3 comprising the amino acid sequence of DGYYPYAMDN (SEQ ID NO: 298); an HVR-L1 comprising the amino acid sequence of RASKSVDSYGNSFMH (SEQ ID NO: 299); an HVR-L2 comprising the amino acid sequence of LASNLES (SEQ ID NO: 300); and an HVR-L3 comprising the amino acid sequence of QQNNEDPRT (SEQ ID NO: 301). In another embodiment, the bispecific antibody that specifically binds both IL-33 and IL-13 comprises a first binding domain that specifically binds IL-33 comprising (a) a VH domain comprising an amino acid sequence having at least 99% sequence identity to the amino acid sequence of SEQ ID NO: 36 and (b) a VL domain comprising an amino acid sequence having at least 99% sequence identity to the amino acid sequence of SEQ ID NO: 37, and a second binding domain that specifically binds IL-13 comprising (a) a VH domain comprising an amino acid sequence having at least 99% sequence identity to the amino acid sequence of SEQ ID NO: 302 and (b) a VL domain comprising an amino acid sequence having at least 99% sequence identity to the amino acid sequence of SEQ ID NO: 303. In another embodiment, the bispecific antibody that specifically binds both IL-33 and IL-13 comprises a first binding domain that specifically binds IL-33 comprising (a) a VH domain comprising the amino acid sequence of SEQ ID NO: 36 and (b) a VL domain comprising the amino acid sequence of SEQ ID NO: 37, and a second binding domain that specifically binds IL-13 comprising (a) a VH domain comprising the amino acid sequence of SEQ ID NO: 302 and (b) a VL domain comprising the amino acid sequence of SEQ ID NO: 303. In another embodiment, the bispecific antibody that specifically binds both IL-33 and IL-13 comprises: (a) a first heavy chain and a first light chain that specifically bind IL-33, wherein the first heavy chain comprises an amino acid sequence having at least 99% sequence identity to the amino acid sequence of SEQ ID NO: 308 and the first light chain comprises an amino acid sequence having at least 99% sequence identity to the amino acid sequence of SEQ ID NO: 309, and (b) a second heavy chain and a second light chain that specifically bind IL-13, wherein the second heavy chain comprises an amino acid sequence having at least 99% sequence identity to the amino acid sequence of SEQ ID NO: 304 and the second light chain comprising an amino acid sequence having at least 99% sequence identity to the amino acid sequence of SEQ ID NO: 305. In another embodiment, the bispecific antibody that specifically binds both IL-33 and IL-13, comprises: (a) a first heavy chain and a first light chain that specifically bind IL-33, wherein the first heavy chain comprises the amino acid sequence of SEQ ID NO: 308 and the first light chain comprises the amino acid sequence of SEQ ID NO: 309, and (b) a second heavy chain and a second light chain that specifically bind IL-13, wherein the second heavy chain comprises the amino acid sequence of SEQ ID NO: 304 and the second light chain comprising amino acid sequence of SEQ ID NO: 305.

In another aspect, the invention provides a method of treating geographic atrophy in a subject in need thereof, the method comprising administering to the subject a therapeutically effective amount of an IL-33 axis binding antagonist (e.g., an anti-IL-33 antibody of the invention) and a therapeutically effective amount of a Factor D binding antagonist. In some instances, the Factor D binding antagonist may be an anti-Factor D antibody or an antigen-binding fragment thereof, for example, any Factor D antibody described in WO 2007/056227, WO 01/70818, and/or US 2002/0081293. For example, in some instances, the anti-Factor D antibody may comprise an amino acid sequence having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the monoclonal antibody 166-32 produced from the hybridoma deposited with the American Type Culture Collection (ATCC) and designated HB12476. In some instances, the anti-Factor D antibody is a humanized derivative of monoclonal antibody 166-32. In some embodiments, the anti-Factor D antibody binds to the same epitope as monoclonal antibody 166-32. In some instances, the anti-Factor D antibody is an antibody fragment derived from monoclonal antibody 166-32. In some instances, the antibody fragment derived from monoclonal antibody 166-32 is an Fab, Fab'-SH, Fv, scFv, or an (Fab')$_2$ fragment. In some embodiments, the antibody fragment derived from monoclonal antibody 166-32 is an Fab.

In another aspect, the invention features a method of treating geographic atrophy (GA) in a subject in need thereof, the method comprising administering to the subject a therapeutically effective amount of a bispecific antibody that specifically binds both IL-33 and Factor D or an antigen-binding antibody fragment thereof. The bispecific antibody may comprise a binding domain that specifically binds IL-33 that is derived from any of the anti-IL-33 antibodies described herein. The bispecific antibody may comprise a binding domain that specifically binds Factor D that is derived from any of the anti-Factor D antibodies described above. In some embodiments, the antigen-binding antibody fragment is a (Fab')$_2$ fragment.

In another aspect, the invention provides a method of treating GA, AMD (wet or dry), DR, PCV, or ROP in a subject in need thereof, the method comprising administering to the subject a therapeutically effective amount of an IL-33 axis binding antagonist (e.g., an anti-IL-33 antibody of the invention) and a therapeutically effective amount of a HtrA1 binding antagonist. In some instances, the HtrA1 binding antagonist may be an anti-HtrA1 antibody or an antigen-binding fragment thereof, for example, any HtrA1 antibody described in WO 2013/055998. In some instances, the anti-HtrA1 antibody is an antibody fragment. In some instances, the antibody fragment is an Fab, Fab'-SH, Fv, scFv, or an (Fab')$_2$ fragment. In some embodiments, the antibody fragment derived is an Fab.

In another aspect, the invention features a method of treating geographic atrophy (GA), AMD (wet or dry), DR, PCV, or ROP in a subject in need thereof, the method comprising administering to the subject a therapeutically effective amount of a bispecific antibody that specifically binds both IL-33 and HtrA1 or an antigen-binding antibody fragment thereof. The bispecific antibody may comprise a binding domain that specifically binds IL-33 that is derived from any of the anti-IL-33 antibodies described herein. The bispecific antibody may comprise a binding domain that specifically binds HtrA1 that is derived from any of the anti-HtrA1 antibodies described above. In some embodiments, the antigen-binding antibody fragment is a (Fab')$_2$ fragment.

In another aspect, the invention provides a method of treating wet AMD in a subject in need thereof, the method comprising administering to the subject a therapeutically effective amount of an IL-33 axis binding antagonist (e.g., an anti-IL-33 antibody of the invention) and a therapeutically effective amount of a VEGF antagonist. In some instances, the VEGF antagonist may be an anti-VEGF antibody or an antigen-binding fragment thereof. Any of the anti-VEGF antibodies or antigen-binding fragments thereof known in the art and/or described herein may be used. In some instances, the anti-VEGF antibody or antigen-binding fragment thereof is or is derived from an anti-VEGF antibody described in WO 2005/044853, which is incorporated herein by reference in its entirety. For example, in some instances, the anti-VEGF antibody is or is derived from a G6 series antibody (G6, G6-8, G6-23, G6-23.1, G6-23.2, or G6-31) or a B20 series antibody (e.g., B20, B20-4, or B20-4.1). For example, in some instances, the anti-VEGF antibody comprises (a) a heavy chain variable (VH) domain comprising an amino acid sequence having at least 80% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, any one of SEQ ID NOs: 334, 337, or 340; (b) a light chain variable (VL) domain comprising an amino acid sequence having at least 80% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, any one of SEQ ID NOs: 335, 336, 338, 339, or 341; or (c) a VH domain as in (a) and a VL domain as in (b). For example, in some instances, the anti-VEGF antibody comprises a VH domain comprising the amino acid sequence of SEQ ID NO: 334 and a VL domain comprising the amino acid sequence of SEQ ID NO: 335 (such as the anti-VEGF antibody G6). In some instances, the anti-VEGF antibody comprises a VH domain comprising the amino acid sequence of SEQ ID NO: 334 and a VL domain comprising the amino acid sequence of SEQ ID NO: 336 (such as the anti-VEGF antibody G6.31). In some instances, the anti-VEGF antibody comprises a VH domain comprising the amino acid sequence of SEQ ID NO: 337 and a VL domain comprising the amino acid sequence of SEQ ID NO: 338 (such as the anti-VEGF antibody B20). In other instances, the anti-VEGF antibody comprises a VH domain comprising the amino acid sequence of SEQ ID NO: 337 and a VL domain comprising the amino acid sequence of SEQ ID NO: 339 (such as the anti-VEGF antibody B20-4). In yet other instances, the anti-VEGF antibody comprises a VH domain comprising the amino acid sequence of SEQ ID NO: 340 and a VL domain comprising the amino acid sequence of SEQ ID NO: 341 (such as the anti-VEGF antibody B20-4.1). In some embodiments, the anti-VEGF antibody is a humanized derivative of any of the preceding antibodies. In some embodiments, the anti-VEGF antibody is an antibody fragment derived from any of the preceding antibodies. In some embodiments, the antibody fragment is an Fab, Fab'-SH, Fv, scFv. or an (Fab')$_2$ fragment. In some embodiments, the antibody fragment is an Fab.

In another aspect, the invention features a method of treating wet AMD in a subject in need thereof, the method comprising administering to the subject a therapeutically effective amount of a bispecific antibody that specifically binds both IL-33 and VEGF or an antigen-binding antibody fragment thereof. The bispecific antibody may comprise a binding domain that specifically binds IL-33 that is derived from any of the anti-IL-33 antibodies described herein. The bispecific antibody may comprise a binding domain that specifically binds VEGF that is derived from any of the anti-VEGF antibodies described above. In some embodiments, the antigen-binding antibody fragment is a (Fab')$_2$ fragment.

In yet another aspect, the invention provides a method of treating uveitis (e.g., infectious or non-infectious uveitis) in a subject in need thereof, the method comprising administering to the subject a therapeutically effective amount of an IL-33 axis binding antagonist (e.g., an anti-IL-33 antibody of the invention). In some embodiments, the IL-33 axis binding antagonist may be administered as a monotherapy.

In a still further aspect, the invention provides a method of treating conjunctivitis (e.g., infectious conjunctivitis, non-infectious conjunctivitis, or allergic conjunctivitis) in a subject in need thereof, the method comprising administering to the subject a therapeutically effective amount of an IL-33 axis binding antagonist (e.g., an anti-IL-33 antibody of the invention). In some embodiments, the IL-33 axis binding antagonist may be administered as a monotherapy.

In some embodiments, an additional therapeutic agent is an asthma therapy, as described below. Moderate asthma is currently treated with a daily inhaled anti-inflammatory-corticosteroid or mast cell inhibitor such as cromolyn sodium or nedocromil plus an inhaled beta2-agonist as needed (3-4 times per day) to relieve breakthrough symptoms or allergen- or exercise-induced asthma. Exemplary inhaled corticosteroids include QVAR®, PULMICORT®, SYMBICORT®, AEROBID®, FLOVENT®, FLONASE®, ADVAIR®, and AZMACORT®. Additional asthma therapies include long acting bronchial dilators (LABD). In certain embodiments, the LABD is a long-acting beta-2 agonist (LABA), leukotriene receptor antagonist (LTRA), long-acting muscarinic antagonist (LAMA), theophylline, or oral corticosteroids (OCS). Exemplary LABDs include SYMBICORT®, ADVAIR®, BROVANA®, FORADIL®, PERFOROMIST™ and SEREVENT®.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-IL-33 antibody and administration of an additional therapeutic agent occur within about one month, or within about one, two or three weeks, or within about one, two, three, four, five, or six days, of each other. Antibodies of the invention can also be used in combination with radiation therapy.

An IL-33 axis binding antagonist, for example, an anti-IL-33 antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some instances, a IL-33 axis binding antagonist, for example, an anti-IL-33 antibody of the invention may be administered intravitreally, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, periocularly, conjunctivally, subtenonly, intracamerally, subretinally, retrobulbary, intracanalicularly, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

In some instances, an IL-33 axis binding antagonist (e.g., an anti-IL-33 antibody of the invention) may be administered directly to the eye by ocular tissue injection, for example, using intravitreal, intraocular, periocular, conjunctival, subconjunctival, subtenon, intracameral, subretinal, retrobulbar, or intracanalicular injections; by direct application to the eye, for example, using a catheter or other placement device (e.g., a retinal pellet, intraocular insert, suppository or an implant comprising a porous, non-porous, or gelatinous material); by topical ocular drops or ointments; or by a slow-release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg to 10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week, every two weeks, every three weeks, or every four weeks (e.g., such that the patient receives from about two to about twenty, or e.g., about six doses of the antibody). For example, a dose may be administered once per month, (e.g., by subcutaneous injection). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-IL-33 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-IL-33 antibody.

III. EXAMPLES

The following are examples of methods and compositions of the invention. It is understood that various other embodiments may be practiced, given the general description provided above.

Example 1. Generation of Anti-IL-33 Antibodies

Several strategies were pursued to develop therapeutic anti-IL-33 antibodies, as described below. Desired characteristics for a candidate anti-IL-33 antibody included specific binding to human IL-33, cross-reactivity with cynomolgus monkey (cyno) IL-33, inhibition of IL-33 activity (as measured, for example, in a cell-based IL-33 reporter assay), and/or blocking of binding to the IL-33 receptor (ST2 and IL-1RAcP).

A. Development and Characterization of Mouse Monoclonal Anti-Human IL-33 Hybridoma Antibodies BALB/c mice (Charles River, Hollister, Calif.) or IL33 knockout (ko) mice (Genentech, Inc.) were immunized intraperitoneally twice weekly with 2 μg each of human (hu) IL-33 and cynomolgus (cyno) monkey IL-33 protein (Genentech, Inc.) mixed with monophosphoryl-lipid A and trehalose dicorynomycolate (MPL®+TDM) adjuvant (Sigma-Aldrich, St. Louis, Mo.) or a combination of the Toll-like receptor (TLR) agonists MPL® (Sigma-Aldrich, St. Louis, Mo.), polyinosinic-polycytidylic acid (PolyI:C: InvivoGen, San Diego, Calif.), R848 (InvivoGen), and CpG oligodeoxynucleotides (InvivoGen). Spleens and bone marrow were harvested three days after the last immunization. Splenocytes from these mice were fused with P3X63-Ag8U.1 mouse myeloma cells (American Type Culture Collection. Rockville, Md.) via electrofusion (Harvard Apparatus, Holliston, Mass.). Fused cells were incubated at 37° C., 7% $CO_2$, overnight in CLONACELL™-HY Medium C (StemCell Technologies, Vancouver, BC, Canada), before resuspension in semi-solid CLONACELL™-HY Medium D (StemCell Technologies) with anti-species IgG-FITC (Jackson Immunoresearch, West Grove, Pa.) and plating into OMNIWELL™ trays (Thermo Fisher Scientific, Rochester, N.Y.). Seven days after plating, fluorescent colonies were selected and transferred into 96-well plates containing CLONACELL™-HY Medium E (StemCell Technologies) using a CLONEPIX™ FL (Genetix, New Milton, Hampshire, UK). Supernatants were screened by enzyme-linked immunosorbant assay (ELISA) against human IL-33 protein seven days after picking, as described below. Hybridoma cell lines that showed human IL-33 binding were expanded and retested by ELISA; supernatant from cell lines demonstrating binding to both human and cynomoigus IL-33 by ELISA were harvested and purified by protein A (MABSELECT™ SURE™, GE Healthcare, Pittsburgh, Pa.). Purified IgG was evaluated for ability to block binding of IL-33 to ST2 using a HEK-BLUE™ cell reporter kit (InvivoGen), as described below. Using a high-throughput system of IgG purification from a large panel of hybridomas allowed for early and efficient selection of potential blocking clones. RNA was extracted from strong blocking hybridoma cell lines using the RNEASY® kit (Qiagen, Hilden, Germany), and cDNA was generated and amplified for sequence determination, as described below. Variable region genes of heavy and light chains were inserted into pRK plasmid vectors (Genentech, Inc.) for expression. Plasmid DNA from unique clones demonstrating the highest IL-33 blocking activity and affinity were expressed recombinantly in 293 cells. Supernatants were then purified by Protein A affinity chromatography.

B. Generation of Anti-IL-33 Monoclonal Antibodies from Single B Cell Cloning

Transgenic mice were immunized with human and cynomolgus IL-33 as described above. Following the initial immunization and seven boosts, serum from the immunized transgenic mice was tested for binding to IL-33. Mice with significantly high titers to human and cynomolgus IL-33 were identified and then tested for serum inhibition of IL-33 binding to ST-2 in the HEK-BLUE™ assay. Splenic, lymph nodal, and bone marrow tissues were isolated from the mice that demonstrated IL-33 blocking activity. The tissues were mechanically reduced to single cell suspensions, premixed with IL-33 antigen (human and cynomolgus) and implanted intrasplenically into muSCID mice. 7-8 days later, the spleens were removed and resuspended as single cells. Splenic cells were stained with fluorophore-conjugated markers to identify CD138-positive plasmablast and IgM-positive populations. Plasmablast populations that were IgM-negative and able to bind both human and cynomogus IL-33 were sorted singly into 96-well plates by FACS™ flow cytometry. The immunoglobulin variable regions of the sorted cells were molecularly cloned and reformatted into human IgG1 mammalian expression vectors. Each reformatted monoclonal antibody was expressed transiently in mammalian cells and purified. A general method is described in Lin et al. (*Nature Protocols* 9:1563-1577, 2014).

C. Generation of Anti-IL-33 Monoclonal Antibodies from Immunized Phage Derived Libraries Single chain Fv libraries displayed on phage were constructed from RNA isolated from transgenic mice that were immunized with human and cynomolgus IL-33. The ScFv phage display libraries were panned for several rounds against human and cynomoigus IL-33. Individual phage clones were propagated and assayed by ELISA for binding to human and cynomogus IL-33. Positive binding clones were reformatted for expression in IgG format and transiently expressed. IgG was purified from the transiently-expressing cultures and tested for binding to IL-33 and for inhibition of IL-33 binding to HEK-BLUE™ cells.

Example 2. Screening and Sequencing of Anti-IL-33 Antibodies

A. ELISA Screening for Anti-Human/Cyno IL-33 Antibodies

Hybridoma clones generated as described above were screened for production of monoclonal antibodies that bind to human and cyno IL-33 in an ELISA format. To screen the 1921 hybridoma cell lines generated, ELISA was performed generally as described in Baker et al. (*Trends Biotechnol.* 20:149-156, 2002). Briefly, 96-well MAXISORPP flat bottom plates (Nalge Nunc International, Rochester, N.Y.) were coated with 50 µl of soluble IL-33 (Genentech) at a concentration of 2 µg/ml in coating buffer (0.05 M carbonate buffer, pH 9.6), sealed, and stored overnight at 4° C. After removing the coating solution, 200 µl of assay/blocking solution containing 0.5% bovine serum albumin (BSA) and 0.05% TWEEN®-20 in phosphate buffered saline (PBS) pH 7.4 (ELISA diluent) was added to each well and incubated at room temperature for one hour with agitation. Wells were then washed three times with 300 µl of 0.05% TWEEN®-20 in PBS (wash buffer).

After the washing step, 100 µl of culture supernatant from individual hybridoma clones was added to individual wells. Plates were incubated at room temperature for one hour with agitation, and the wells were washed three times with wash buffer as before.

After washing, 50 µl of a 1:1000 dilution of sheep anti-mouse IgG coupled to horseradish peroxidase (no cross-reactivity to human IgG (MP Biomedicals. Solon, Ohio)) in ELISA diluent was added to each well. Plates were incubated at room temperature for one hour with agitation, washed three times with wash buffer as before, and patted dry. Wells were developed by adding 50 µl of tetramethyl-benzidine (TMB) microwell peroxidase substrate (BioFX Laboratories, Owing Mills, Md., catalog #TMBW-0100-01) to each well and incubating at room temperature for 5-10 minutes or until color change was observed. Enzymatic color development was stopped by adding 50 µl of TMB Stop Solution (BioFX Laboratories catalog #BSTP-0100-01) to each well. Plates were analyzed with a SUNRISE™ plate reader (Tecan US, Inc., Research Triangle Park, N.C.) at 650 nm.

Pre-immune sera collected before the first immunization was used as a negative control. Immune sera collected after seven immunizations was used as a positive control.

Clones 2B6, 6C11, 9F6, 10C12, and 10H2 were positive for human IL-33 and cynomolgus IL-13 binding.

B. Cell-Based IL-33 Blocking Assay

The IL-33 neutralizing activities of anti-IL-33 antibodies obtained using the methods described above were determined by a cell-based blocking assay, in which IL-33 stimulates HEK-BLUE™ IL-33/IL-10 cells (InvivoGen) and activates the NF-κB and AP-1 pathways, triggering the production of secreted alkaline phosphatase (SEAP) (FIG. 1A). HEK-BLUE™ IL-33/IL-1β cells are human HEK293 cells which have been stably transfected with a human ST2 construct (pUNO1-hIL01RL1a; SEQ ID NO: 311), and contain a SEAP reporter gene under the control of the IFN-β minimal promoter fused to five NF-κB and five AP-1 binding sites (InvivoGen). The pUNO1-hIL01 RL1a plasmid encodes ST2L protein having an amino acid sequence of SEQ ID NO: 312. HEK293 cells express endogenous IL-1RAcP. The amino acid sequences of IL-33 used in cell-based blocking assays were as follows: mature human IL-33 (S112-T270), SEQ ID NO:313; human IL-33 N-His, SEQ ID NO: 314; human IL-33 N-His C-Avi, SEQ ID NO: 315; mature cyno IL-33 (S112-T270), SEQ ID NO: 316; cyno IL-33 N-His, SEQ ID NO: 317; and cyno IL-33 N-His C-Avi, SEQ ID NO: 318.

Briefly, IL-33 ligand and pre-diluted anti-IL-33 antibodies were mixed and incubated for 1 hour at room temperature. The antibody and ligand mixture were transferred to HEK-BLUE™ IL-33/IL-1β cells. After incubation at 37° C. for 20 hours in a $CO_2$ incubator, the SEAP activities in cell culture supernatants were measured by recording the OD values at 630 nm after incubating with the substrate of alkaline phosphatase (QUANTI-BLUE™, InvivoGen). The full-length amino acid sequence of sST2-LZ (sST2 (M1-F328) C-terminal leucine zipper (LZ)-Flag-His), which was used in the cell-based blocking assay as a positive control (see, e.g., FIG. 2), can be found in SEQ ID NO: 319. The mature form of sST2-LZ in which the signal peptide has been removed is shown in SEQ ID NO: 310.

Figure 2:
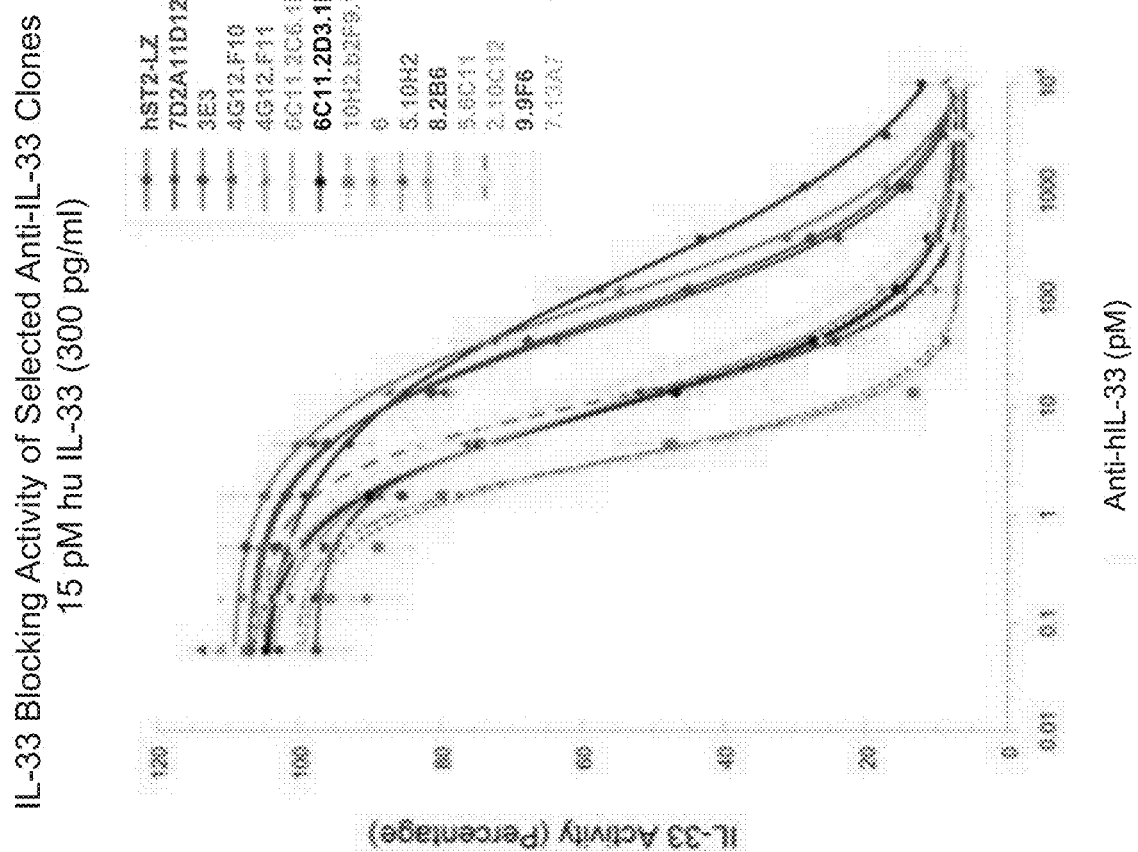
FIG. 2 is a graph showing the results of a cell-based IL-33 blocking assay for the indicated anti-IL-33 antibody clones.

When expressed in IgG format, the purified anti-IL-33 antibodies showed complete inhibition of IL-33 at concentrations less than 1 nM (FIG. 2). In contrast, no inhibition was observed with a negative control monoclonal antibody specific for IL-13 (not shown).

C. Hybridoma Molecular Cloning and Sequencing

The antibody expressed by each hybridoma cell line was cloned directly from cells without RNA purification. Variable heavy and light immunoglobulin regions were cloned using a modified 5' RACE (rapid amplification of cDNA ends) protocol (Qzawa et al. *BioTechniques* 40(4):469-478, 2006). First strand cDNA was generated directly from the hybridoma cells using SUPERSCRIPT® III (Invitrogen, Carlsbad, Calif.) reverse transcriptase with oligonudeotide primers specific for murine heavy (5'-TTTYTTGTCCAC-CKTGGTGCTGC-3', SEQ ID NO: 320) and light constant (5'-GTAGAAGTTGTTCAAGAAG-3'; SEQ ID NO: 321) regions at 55° C. for 1 hour. Degenerate primers were designed to allow priming across the various murine heavy chain isotypes. The 3' end of the reverse transcriptase product was poly-G tailed using terminal deoxynucleotidyl transferase (Promega, San Luis Obispo, Calif.) and dGTP (Roche Diagnostics, Indianapolis, Ind.) for 1 h at 37° C. Amplification of the variable heavy and light chain cDNA was performed separately by touchdown PCR (ADVANTAGE®-GC 2, Clontech, Mountain View, Calif.) using nested heavy chain constant region primer (5'-GTGTA-GAGKYCAGACTSCAGG-3'; SEQ ID NO: 322) and light constant region primer (5'-GAGGCACCTCCAGATGT-TAAC-3'; SEQ ID NO: 323), and a poly-C containing N-terminal primer (5'-GATTCAAATCTCAAT-TATATAATCCGAATATGTTTACCGGCTCGCTCATG-GACCCCCCCCCCCCDN-3'; SEQ ID NO: 324). A second nested touchdown PCR set was performed using N-terminal primer (5'-CAATTATATAATCCGAATATG-3'; SEQ ID NO: 325), heavy chain constant region primer (5'-GAARTARC-CCTTGACCAGGC-3'; SEQ ID NO: 326) and light chain constant region primer (5'-GAAGATGGATACAGTTG-GTGC-3'; SEQ ID NO: 327).

PCR products were ligated into a pCR2.1®-TOPO® cloning vector (TOPO® TA cloning Kit, Invitrogen, Carlsbad, Calif.) and transformed into ONESHOT® TOP10 Competent cells. Transformed *Escherichia coli* (*E. coli*) colonies were isolated and cultured for DNA plasmid isolation. The plasmids were sequenced to determine DNA sequences of the VH and VL for each cell line. Following the sequence determination, variable heavy and light chains regions were amplified by PCR using primers containing endonuclease restriction sites (EcoRI and XhoI) to allow subcloning into murine IgG2a and kappa constant region encoding mammalian IgG and IgK expression vectors respectively.

Prior to subcloning of the hybridoma cells, the parental clones were molecularly cloned to determine the sequence of the variable heavy and light domains. The cloning was performed prior to subcloning to capture the sequence in event that the hybridoma clones were lost due to instability during the subcloning process. Based on the molecular cloning sequence data, 17C4, 17H2, and 19C11 were determined to be sibling clones based on alignment of CDR and framework sequences. This agreed with the assay data generated for the three clones.

D. Humanization of Murine Hybridoma-Derived Clones

Murine hybridomas expressing antibodies that bind to IL-33 with high affinity and that block cytokine binding to its receptor ST2 were selected for humanization. Variable sequences for the antibodies obtained from cloning the hybridomas were aligned to the closest matching human variable consensus sequences. The hypervariable regions (HVRs) from the murine hybridoma antibodies were grafted into the corresponding human variable consensus sequences using Kunkel mutagenesis (see, e.g., Kunkel et al. *Methods Enzymol.* 154: 367-382, 1987). Additional variants for each clone were generated by mutating residues in both the light chain and heavy chain at key Vernier positions back to murine as well as sites of framework/HVR interactions and variable heavy and variable light interactions. For instance, the cloned HVR sequences for hybridoma clone 10C12 were grafted into a consensus kappa III light chain and a consensus VHIII heavy chain to generate humanized variants. The cloned HVR sequences for hybridoma clone 10H2 were grafted into a consensus kappa IV light chain and a consensus VH III heavy chain to generate humanized variants. The cloned HVR sequences for 6C11, 2B6, and 9F6 were humanized in a similar format to 10C12 and 10H2. Humanized variants were expressed transiently in 293 cells and then tested for binding and function.

Figure 3:
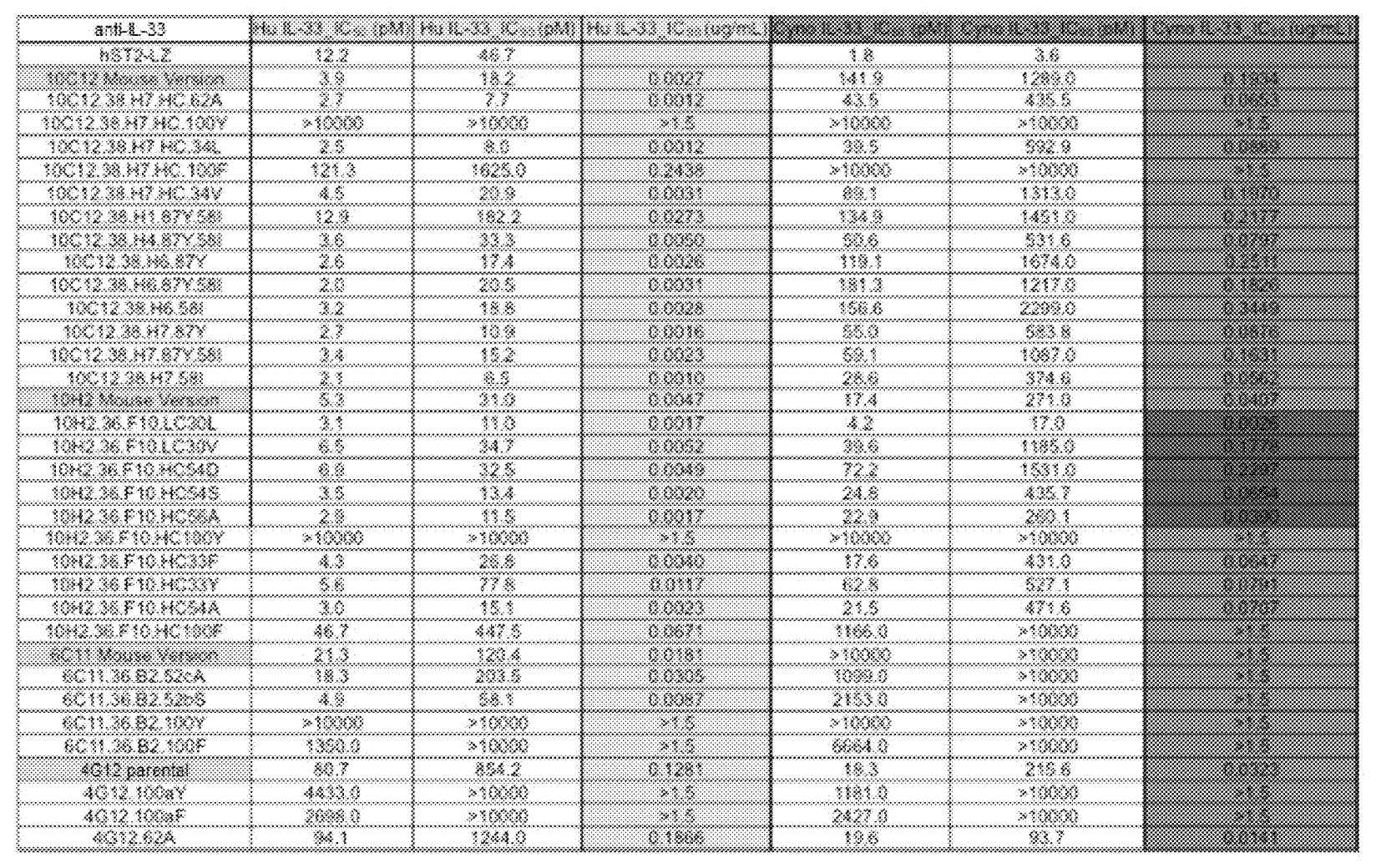

The binding kinetics of the humanized variants of the hybridoma-derived clones 10C12, 10H2, 6C11, 2B6, and 9F6 to IL-33 were measured using surface plasmon resonance (SPR) on a Biacore 3000 or T200 instrument (GE Healthcare). Anti-human Fc (GE Healthcare) was immobilized on a CM5 sensor chip via amine-based coupling according to the manufacturer's protocol. The humanized variant anti-IL-33 antibody was captured at a level of 500-600 resonance units (RU). Antibody binding was measured to human IL-33 (Genentech, huIL33.his). Two-fold concentration series of humanIL-33 with a range of 0.78 to 50 nM was used for the experiments. Sensograms for binding of IL-33 were recorded using an injection time of 2 minutes with a flow rate of 30 µl/min, at a temperature of 25C, and with a running buffer of 10 mM HEPES, pH 7.4, 150 mM NaCl, 3 mM EDTA, and 0.005% TWEEN®-20. After injection, disassociation of the ligand from the antibody was monitored for 600 seconds in running buffer. The surface was regenerated between binding cycles with a 40 µl injection of 3M magnesium chloride. After subtraction of a blank which contained running buffer only, sensograms observed for IL-33 binding to humanized anti-IL-33 antibodies were analyzed using a 1:1 Langmuir binding model with software supplied by the manufacturer to calculate the kinetics and binding constants, including the dissociation constant ($K_D$). Anti-IL-33 10C12 humanized variants retained high affinity binding to human IL-33 after humanization as measured by Biacore (see FIG. 3 and Table 2). Table 2 also shows kinetic data for selected antibody clones derived from B cell cloning and phage display.

To test the function of the humanized anti-IL-33 antibodies, as well as antibodies obtained from single B cell cloning (e.g., 4G12 and derivatives and 3E3) and phage display, their activity in cell-based receptor-blocking assays was measured, as described above. Antibodies were tested for blocking of both human and cynomolgus IL-33 binding to ST2. The results of receptor-blocking assays for a selected group of antibodies are shown in Table 3.

TABLE 2

Kinetic Data for selected anti-IL-33 antibody clones

| Clone | Type | Source | $K_D$ (hu) | $K_D$ (cyno) |
|---|---|---|---|---|
| 10C12 | Murine | IL33 KO | ≤7 pM | 70 pM |
| 10C12.38.H6.87Y.58I | Humanized | | 15 pM | 37 pM |
| 10C12.38.H7.87Y.58I | Humanized | | 177 pM | |
| 10H2 | Murine | Balb/C | 60 pM | 90 pM |
| 10H2.36.F10 | Humanized | | 220 pM | |
| 10H2.36.F10.30V.54D | Humanized | | 220 pM | |
| 4G12 | B cell cloning | | 96 pM | 60 pM |
| 4G12.62A | Humanized | | 84 pM | 73 pM |
| 4G12.FW4 | Humanized | | 38 pM | 70 pM |
| 4G12.F10.F6 | B cell cloning | | 110 pM | 60 pM |
| 4G12.F11.F8 | B cell cloning | | 100 pM | 40 pM |
| 3E3 | B cell cloning | | 260 pM | 40 pM |
| 6C11 | Murine | Balb/C | 60 pM | 790 pM |
| 6C11.34.B2 | Humanized | | 225 pM | |
| 6C11.34.B2.52bS | Humanized | | 310 pM | |
| 6C11.HC.G.2.52CA | Humanized | | 152 pM | |
| 2B6 | Murine | Balb/C | 30 pM | 330 pM |
| 2B6.35.D1 | Humanized | | 312 nM | |
| 2B6.54S | Humanized | | 336 nM | |
| 2B6.55A (NA) | Humanized | | 363 pM | |
| 9F6 | Murine | Balb/C | 70 pM | 910 pM |
| 9F6.34.E10 | Humanized | | 795 pM | |
| 101.B11 | Transgenic mouse/phage display | | 527 pM | 783 pM |
| 101.E11 | Transgenic mouse/phage display | | 420 pM | 467 pM |
| 101.D9 | Transgenic mouse/phage display | | 361 pM | 576 pM |

TABLE 3

Receptor-blocking data for selected anti-IL-33 antibody clones

| Clone | Cell assay (hu) IC$_{90}$ (µg/mL) | Cell assay (hu) IC$_{90}$ (nM) | Cell assay (cy) IC$_{90}$ (µg/mL) | Cell assay (cy) IC$_{90}$ (nM) |
|---|---|---|---|---|
| 10C12 | 0.002 | 0.013 | 0.193 | 1.27 |
| 10C12.38.H6.87Y.58I | 0.004 | 0.026 | 0.185 | 1.22 |
| 10C12.38.H7.87Y.58I | 0.003 | 0.02 | 0.09 | 0.594 |
| 10H2 | 0.003 | 0.02 | 0.041 | 0.27 |
| 10H2.36.F10 | 0.17 | 1.12 | 0.025 | 0.165 |
| 10H2.36.F10.30V.54D | 0.344 | 2.27 | >1.5 | >9.9 |
| 4G12 | 0.128 | 0.845 | 0.032 | 0.211 |
| 4G12.62A | 0.187 | 1.23 | 0.014 | 0.092 |
| 4G12.FW4 | 0.17 | 1.12 | 0.034 | 0.224 |
| 4G12.F10.F6 | 0.16 | | | |
| 4G12.F11.F8 | 0.31 | | | |
| 3E3 | 0.21 | | | |
| 6C11 | 0.021 | 0.14 | >1.5 | >9.9 |
| 6C11.34.B2 | 0.017 | 0.112 | >1.5 | >9.9 |
| 6C11.34.B2.52bS | 0.0087 | 0.057 | >1.5 | >9.9 |
| 6C11.HC.G.2.52CA | 0.0305 | 0.201 | >1.5 | >9.9 |
| 2B6 | 0.02 | 0.13 | 0.526 | 3.47 |
| 2B6.35.D1 | 0.0093 | 0.061 | 0.184 | 1.21 |
| 2B6.54S | ND | ND | ND | ND |
| 2B6.55A (NA) | ND | ND | ND | ND |
| 9F6 | 0.011 | 0.73 | >1.5 | >9.9 |
| 9F6.34.E10 | 0.0128 | 0.84 | >1.5 | >9.9 |
| 101.B11 | 0.3 | | | |
| 101.E11 | 0.1 | | | |
| 101.D9 | 0.3 | | | |

Example 3. Role of IL-33 in Inflammation in Ophthalmologic Disorders Including Age-Related Macular Degeneration (AMD)

Inflammation is typically considered a defense response triggered by infection or injury. Inflammation can also be induced by tissue stress and malfunction in the absence of infection or overt tissue damage. Examples of such sterile inflammatory responses are found at immune-privileged areas in the central nervous system, including the retina. In AMD, lifelong exposure of the retina and the underlining retinal pigment epithelium (RPE) cells to various stimuli (e.g., light, oxidative stress, and proteolytic enzymes) can lead to aberrant neovascularization, RPE cell death, and photoreceptor loss. Neural retina loss is often associated with a sterile inflammatory response, which is in part characterized by accumulation of mononuclear phagocytes in the photoreceptor and photoreceptor outer-segment layers. The factors that initiate recruitment of mononuclear phagocytes remain largely unknown.

A. IL-33 Expression in Müller Cells of the Human Macula is Increased in AMD

Figure 4A:
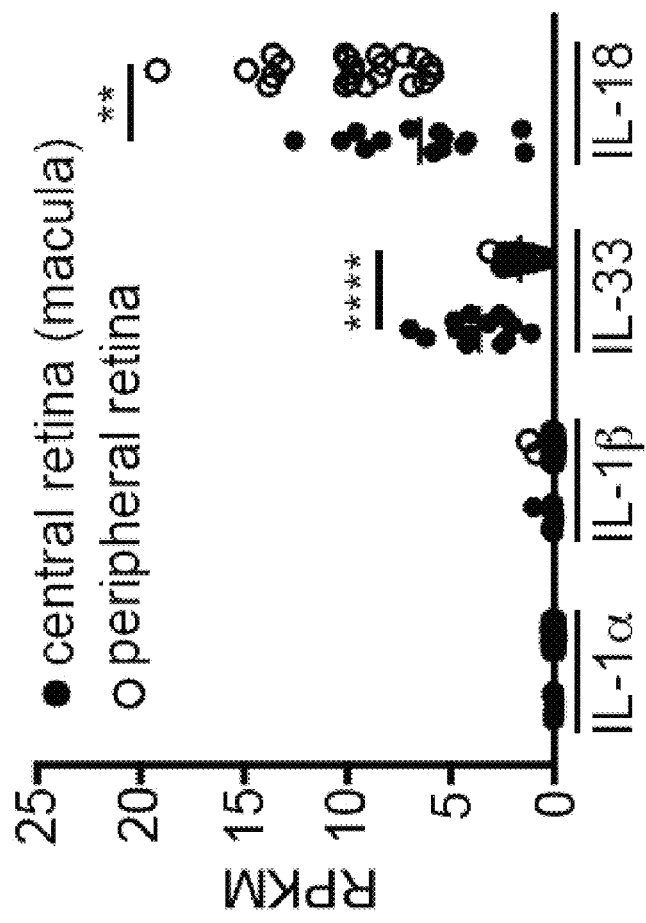
FIG. 4A is an image showing the macular and peripheral retina dissected for RNA-seq analysis. The macular area between the superior and inferior temporal vascular arcades was separated from the peripheral fundus using dissecting scissors. RNA was isolated from both macular and peripheral retina tissues for RNA-seq. The dashed outline indicates the area of the macula, and the solid circle indicates the area of the fovea. The arrow indicates the location of the optic disc.
Figure 4B:
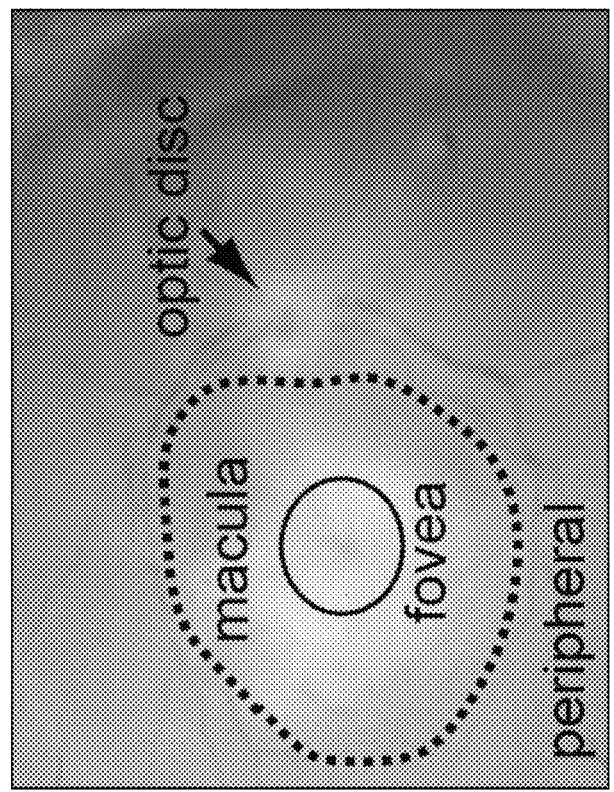
FIG. 4B is a graph showing expression of IL-1α, IL-1β, IL-33, and IL-18 in macular and peripheral retina of healthy donor eyes. Macula (n=14) and peripheral (n=22) retina of normal donor eyes were isolated and RNA was analyzed by RNA-seq. The data are presented as reads per kilobase per million total reads (RPKM). Horizontal bars represent means. , $P<0.01$; **, $P<0.0001$; unpaired two-tailed Student's t test.

The macula, an area near the center of the human retina, is critical for high-acuity vision. Reduced viability of RPE and photoreceptor cells in the macula due to lifelong exposure to oxidative stress or exposure to toxic by-products of the visual cycle can have important consequences for visual function. To determine whether IL-33 expression is different in the macula compared with the peripheral retina, dissected post-mortem human retinas (FIG. 4A) were analyzed by RNA sequencing (RNA-seq). IL-33 transcripts were significantly increased in the macula compared to the peripheral retina of normal donors, while expression levels of other interleukin 1 (IL-1) family cytokines, IL-1α, IL-1β, and IL-18, were either similar or increased in the peripheral retina compared to the macula (FIG. 4B).

Figure 5A:
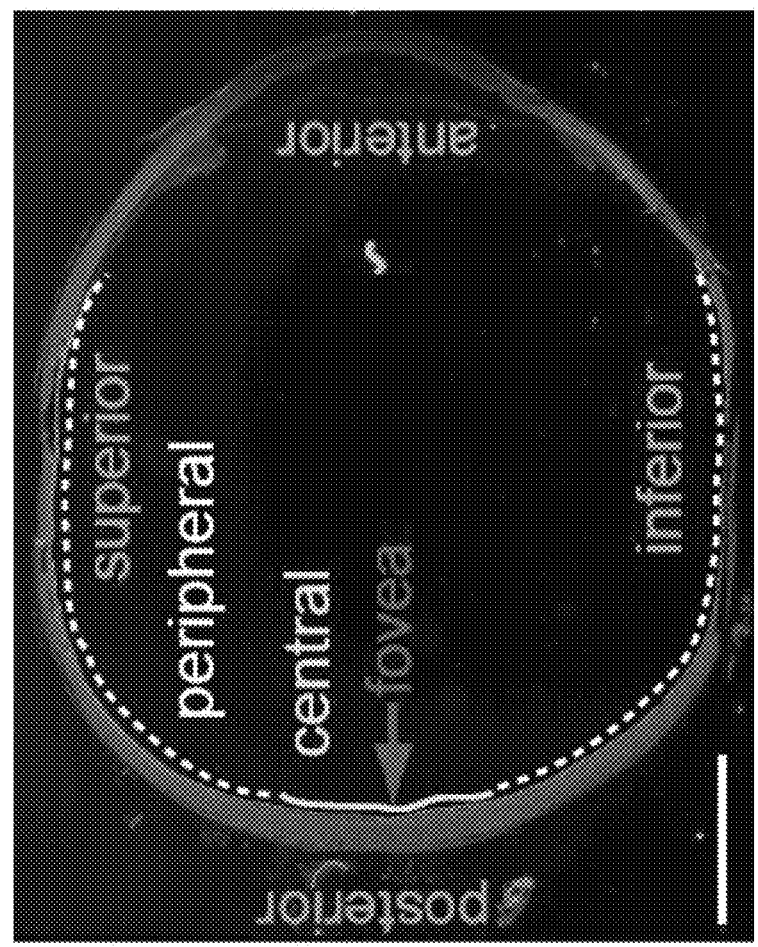
FIG. 5A is an image showing a representative cross-section of an eye with central and peripheral areas studied by quantitative analysis (see FIG. 5B) indicated by the solid and dashed lines, respectively. Arrows indicate the fovea and the ciliary bodies. Bar, 5 mm.
Figures 5B, 5C:
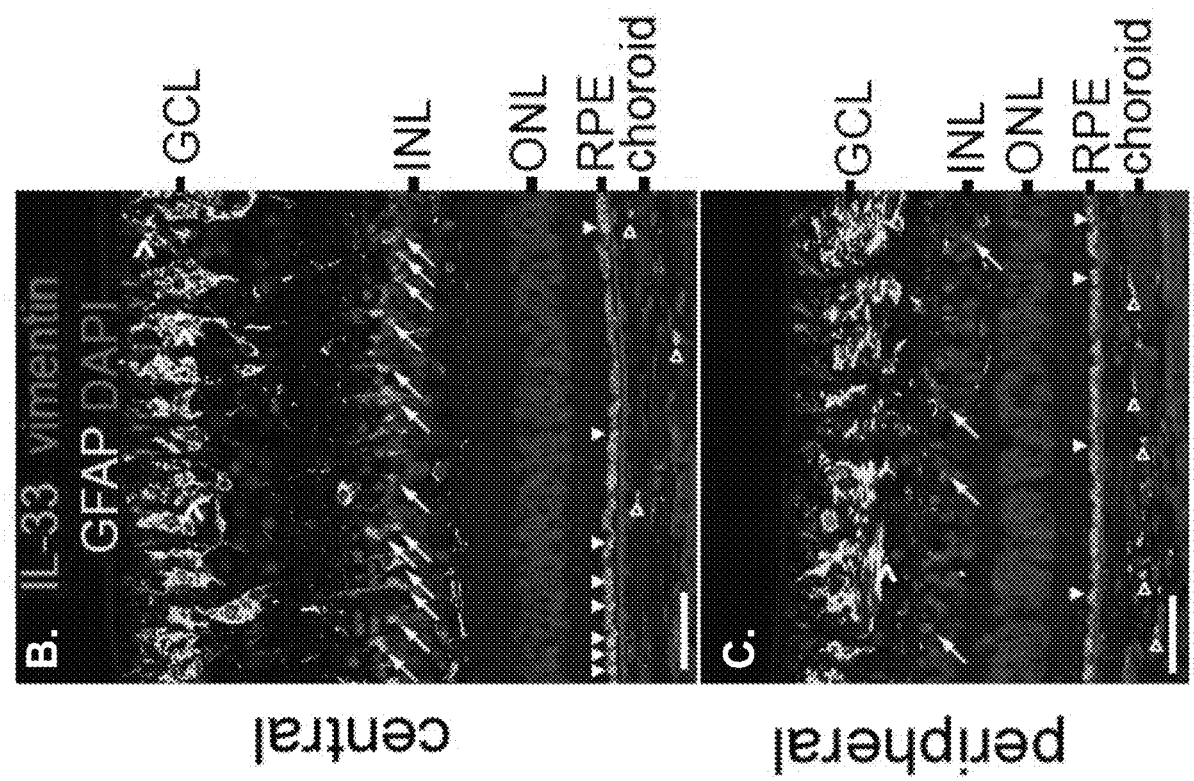
FIGS. 5B and 5C are images showing immunohistochemical triple staining of IL-33 (green), vimentin (red), and GFAP (yellow) in the central (FIG. 5B) and peripheral (FIG. 5C) retina of a control eye from an 84-year-old male donor. 4',6-Diamidino-2-Phenylindole (DAPI) staining is shown in blue. Arrows indicate IL-33$^+$ Müller cells in the inner nuclear layer (INL); closed arrowheads indicate IL-33$^+$ cells in the retinal pigment epithelium (RPE); open arrowheads indicate IL-33$^+$ cells in the choroidal vasculature; and angle brackets indicate IL-33$^+$ astrocytes in the ganglion cell layer (GCL). Bars, 50 µm.
Figure 5D:
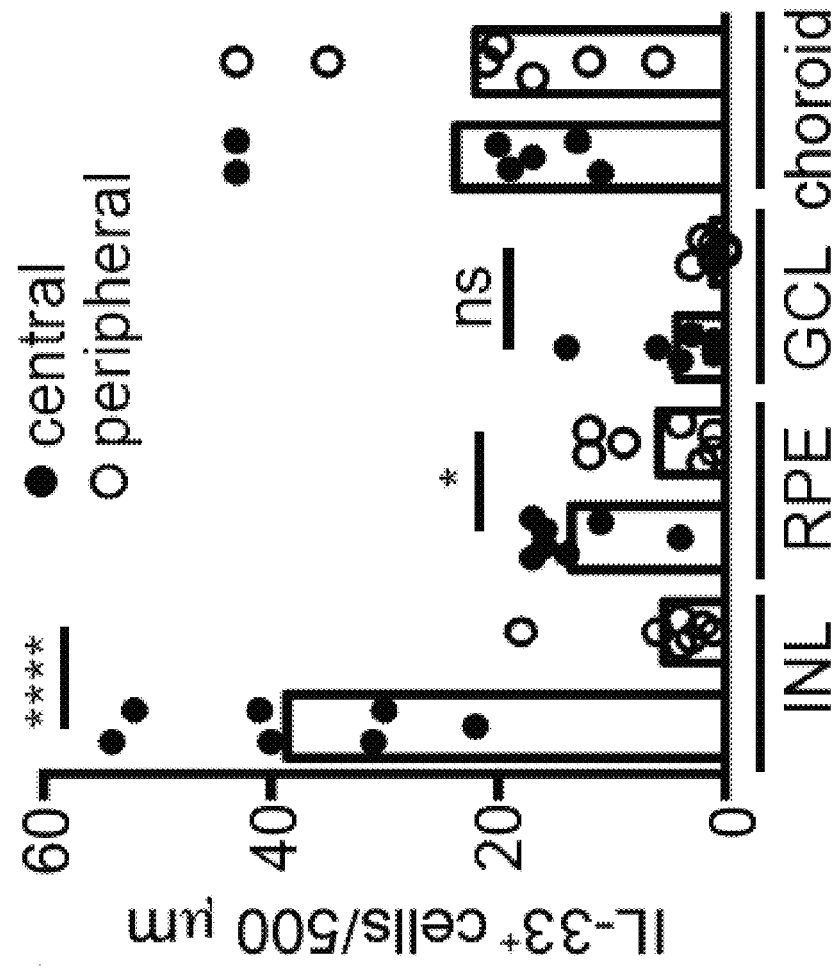
FIG. 5D is a graph showing quantification of IL-33$^+$ cells in each retinal layer of central and peripheral areas. IL-33$^+$ cells were quantified along an approximately 500 µm section within the central and peripheral areas from 7 eyes from normal human donors whose ages ranged from 67-89 years (median age 84, 5 males and 2 females). The number of IL-33$^+$ cells in the inner nuclear layer (INL) and retinal pigment epithelium (RPE) were higher in the central retina compared to the peripheral retina. GCL, ganglion cell layer; ONL, outer nuclear layer. *, $P<0.05$; ****, $P<0.0001$; ns, non-significant; unpaired two-tailed Student's t test.
Figure 5E:
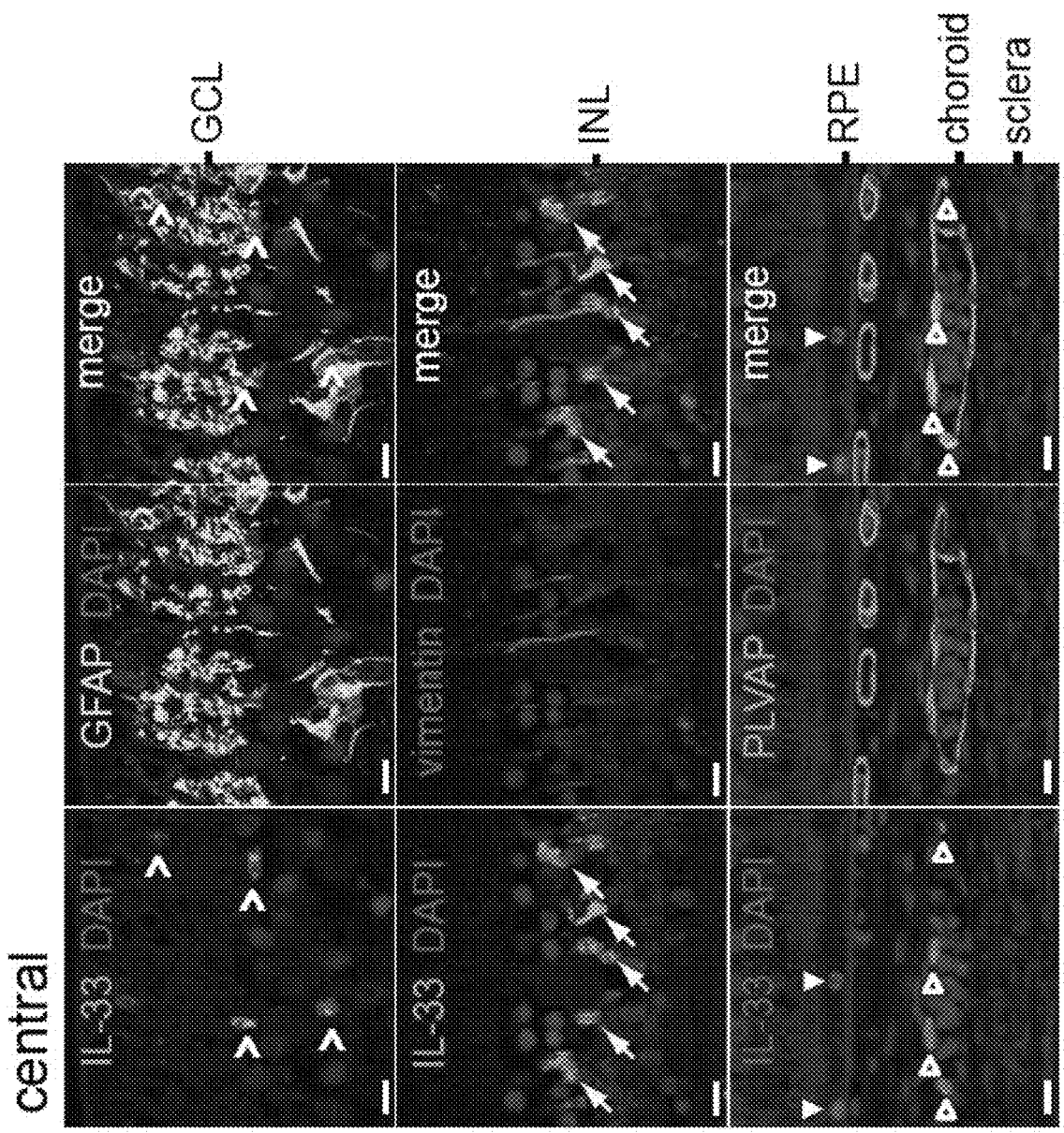
FIG. 5E is a series of representative high-magnification images of IL-33$^+$ cells in GCL, INL, RPE, and choroid in the central area of a control donor eye. IL-33 (green), vimentin (red), and GFAP (yellow) co-staining showed IL-33$^+$ astrocytes (GFAP$^+$, angle brackets) and IL-33$^+$ Müller cells (vimentin$^+$, arrows). IL-33+ endothelial cells (open arrowheads) of the choroid vasculature are shown by IL-33 (red) and PLVAP (green) co-staining. Closed arrowheads, IL-33$^+$ RPE. DAPI staining is shown in blue. Bars, 10 µm.

To further determine the cellular source of IL-33 in the normal human retina, 7 eyes from human donors with no history of ocular disease were processed for immunohistochemistry. IL-33 was predominantly present in the nuclei of vimentin-positive Müller cells of the central retina, with significantly lower numbers of IL-33-positive (IL-33$^+$) Müller cells in the peripheral retina (FIGS. 5A-5E) in line with the RNA-sequencing results. IL-33 was also expressed in the nucleus of a sub-population of RPE cells, with slightly higher expression in the central retina compared to peripheral retina (FIGS. 5B, 5C, and 5D). The number of IL-33$^+$ astrocytes (glial fibrillary acidic protein-positive (GFAP$^+$)) in the retinal ganglion cell layer and IL-33$^+$ endothelial cells (plasmalemma vesicle associated protein-positive (PLVAP$^+$)) of the choroid were not different in the central retina compared with the peripheral retina.

Figure 6A:
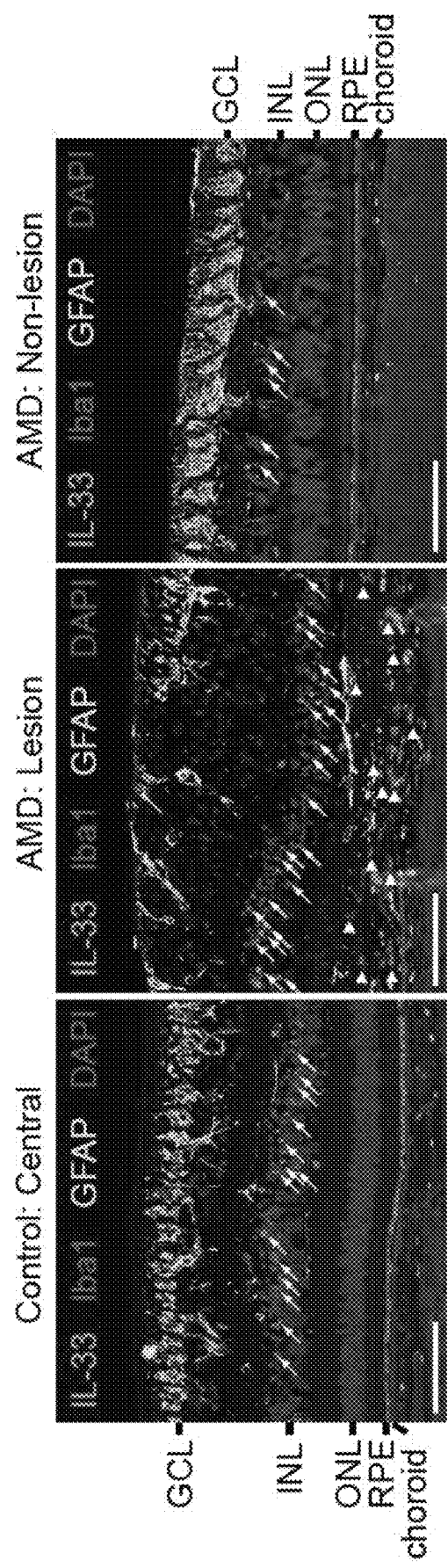
FIG. 6A is a series of representative images showing fluorescence immunohistochemical triple staining for IL-33 (green), Iba1 (red), and GFAP (yellow) in the central retina of a control human donor eye from an 84-year-old male with no history of ocular diseases, and from an eye of an 82-year-old female donor diagnosed with AMD. Numbers of IL-33$^+$ Muller cells and mononuclear phagocytic cells (Iba1$^+$ cells) were significantly increased in areas of retina degeneration (AMD: Lesion) compared with adjacent areas of the same donors that did not exhibit retina degeneration (AMD: Non-lesion), or compared with the central retina of control donor eyes (Control: Central). Arrows, IL-33$^+$ Müller cells; arrowheads, Iba1$^+$ cells in the subretinal space. DAPI (blue), nuclear stain. Bars, 100 µm.
Figure 6B:
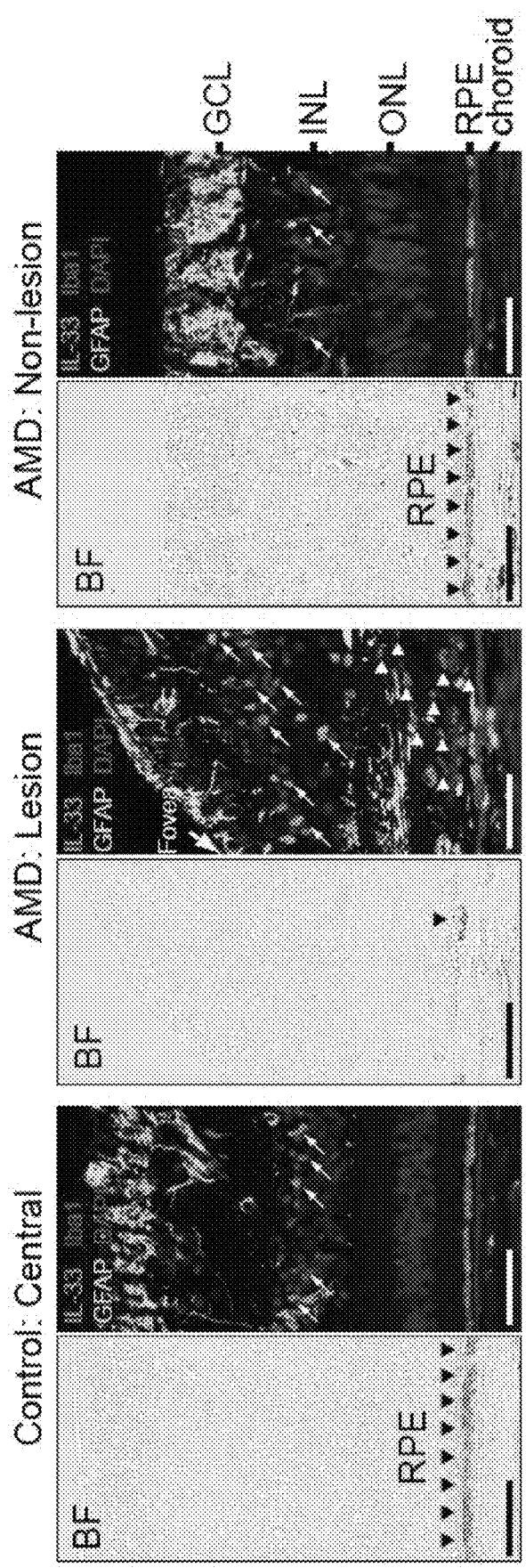
FIG. 6B is a series of representative high-magnification images showing immunohistochemistry of IL-33 (green), Iba1 (red), and GFAP (yellow) in the central retina of a control eye and lesion and non-lesion areas of an AMD eye. The bright field (BF) images show RPE loss in the AMD lesion site. Bars, 50 µm.
Figures 6C, 6D:
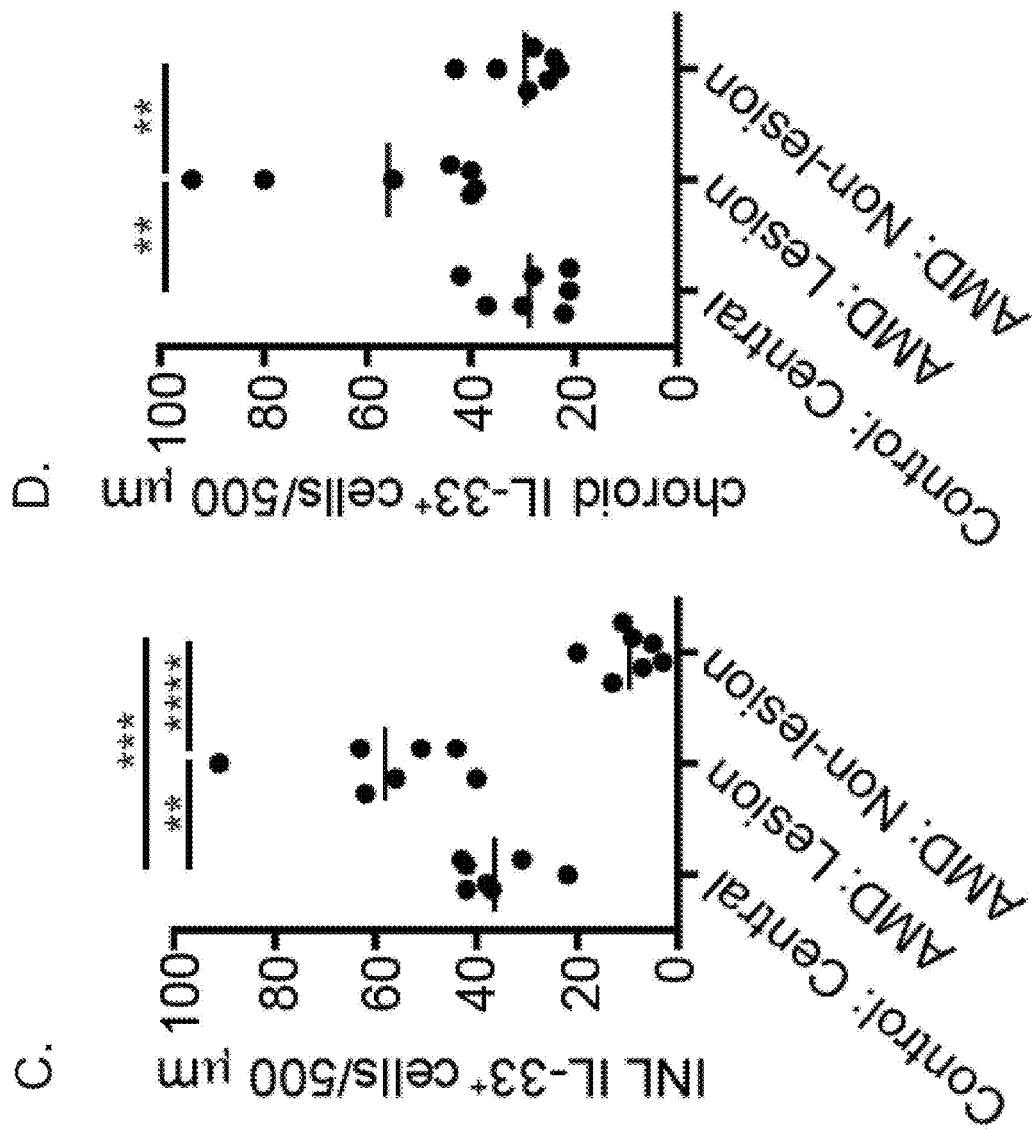
FIGS. 6C-6E are graphs showing quantification of IL-33$^+$ Müller cells in the INL (FIG. 6C), IL-33$^+$ cells in the choroid (FIG. 6D), and Iba1$^+$ cells in the retina (FIG. 6E) counted along an approximately 500 µm-long section within the central retina of 7 control human donors aged 67-89 years (median age 84) and lesion and non-lesion areas of eyes from 7 AMD donors aged 82-92 years (median age 86). , $P<0.01$; *, $P<0.001$, ****, $P<0.0001$; one-way ANOVA with Tukey's post-test. Horizontal bars represent means.
Figures 6E, 6F:
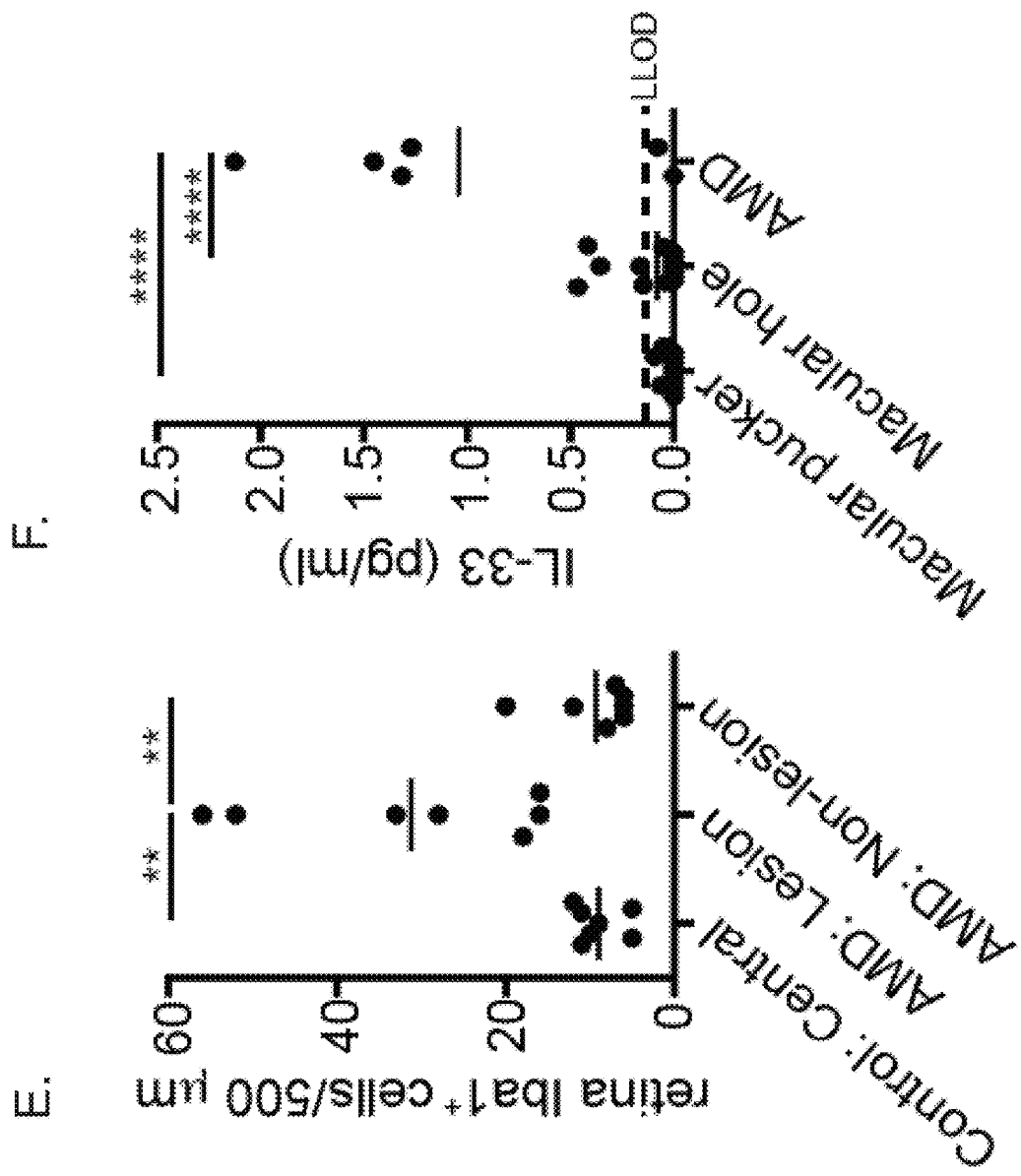
FIG. 6F is a graph showing increased IL-33 levels in the vitreous from human AMD patients. IL-33 concentration was determined in vitreous samples obtained from AMD patients (n=6, 1 male and 5 females, age 68-91, median age 79), control patients with macular pucker (n=12, 3 males and 9 females, age 56-79, median age 72), and control patients with macular hole (n=21, 5 males and 16 females, age 46-75, median age 65) by ELISA. ****, $P<0.0001$; one-way ANOVA with Tukey's post-test. Horizontal bars represent means.

In donors with a history of AMD, areas of RPE and photoreceptor cell loss, reminiscent of advanced dry AMD or geographic atrophy, were observed in the macula (FIGS. 6A and 6B). Using multi-marker fluorescence immunohistochemistry, an increased number of IL-33$^+$ Müller cells and myeloid cells was observed in areas of RPE and photoreceptor atrophy (FIGS. 6A-6E). The number of IL-33$^+$ Müller cells in the AMD non-lesion area was significantly lower than those in the central retina of controls (FIG. 6C). Without wishing to be bound by theory, this could be due to the fact that the non-lesion areas are typically located in the peripheral retina, where IL-33$^+$ Müller cells are less abundant than in the central retina of non-AMD eyes (FIG. 5D). Increased IL-33$^+$ cells were also observed in the choroid of AMD lesion areas relative to controls or non-lesion areas (FIG. 6D). None of the Iba1$^+$ myeloid cells were positive for IL-33 (FIG. 6E). In the vitreous of a subpopulation of AMD patients, IL-33 levels were significantly increased compared to normal controls (patients with macular hole or macular pucker) (FIG. 6F).

Figure 7A:
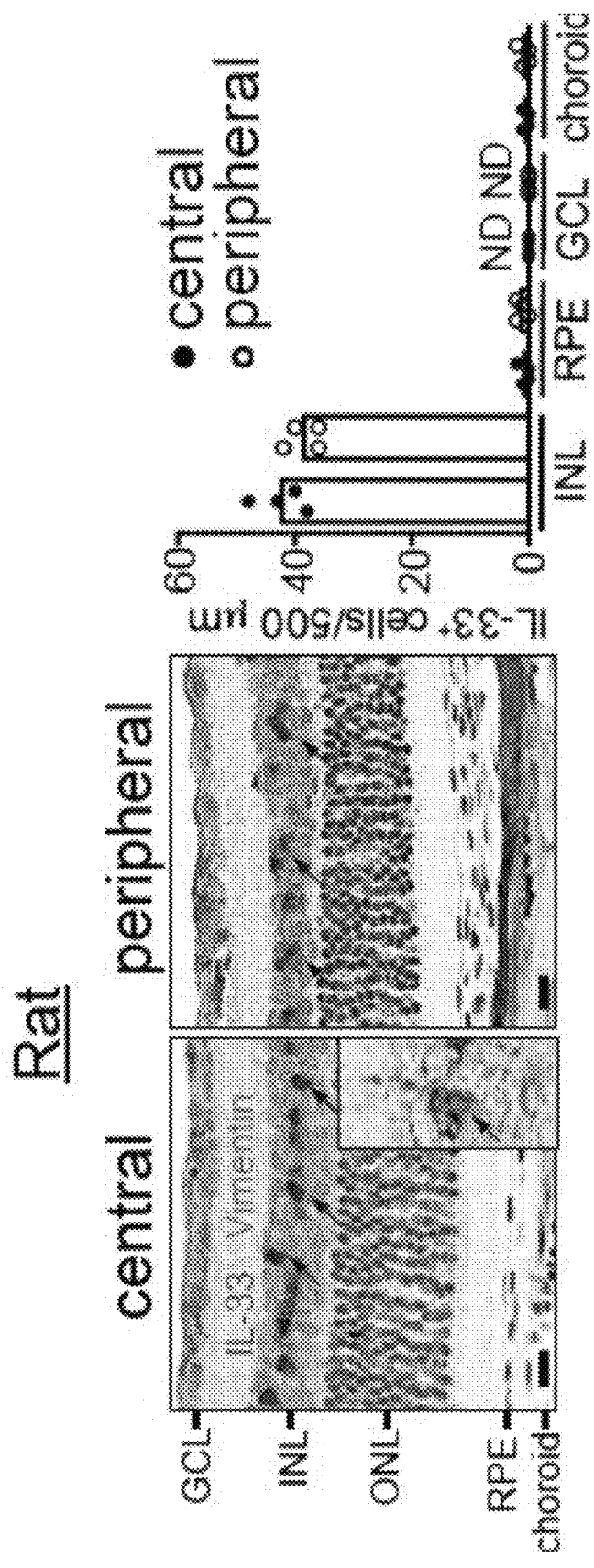
FIG. 7A shows the results of immunohistochemical staining of IL-33 (brown) and vimentin (red) in Sprague-Dawley (SD) rat retina. Arrows in the images in the left panel indicate IL-33$^+$ Müller cells. The inset in the left panel shows an IL-33$^+$ Müller cell (vimentin$^+$). IL-33$^+$ cells in INL, RPE, GCL, and choroid in the central and peripheral retina were counted along a ~500 µm long section. The results of this quantification are shown in the right panel. Bar, 10 µm. ND, not detected.
Figure 7B:
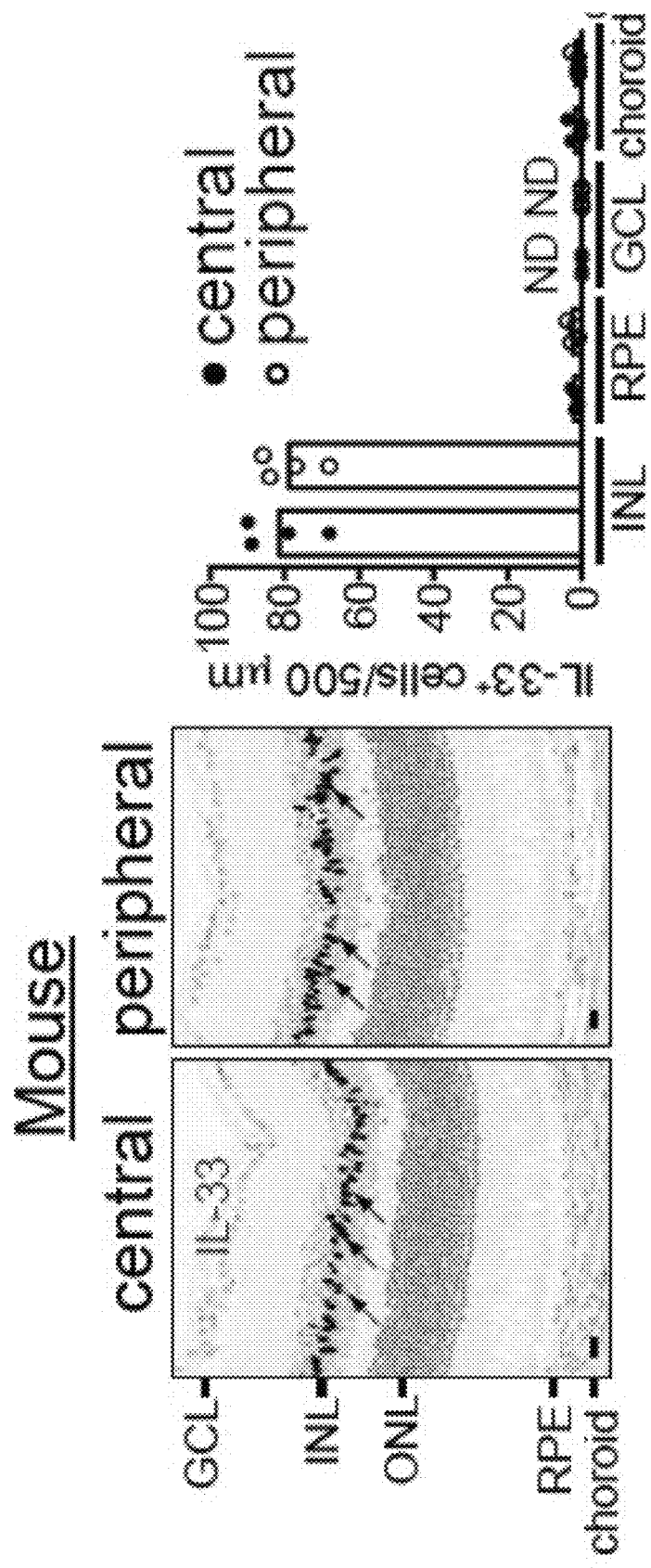
FIG. 7B shows the results of immunohistochemical staining of IL-33 (brown) in BALB/c mice. Arrows in the images in the left panel indicate IL-33$^+$ Müller cells. IL-33$^+$ cells in INL, RPE, GCL, and choroid in the central and peripheral retina were counted along a ~500 µm long section. The results of this quantification are shown in the right panel. Bar, 10 µm.
Figure 7C:
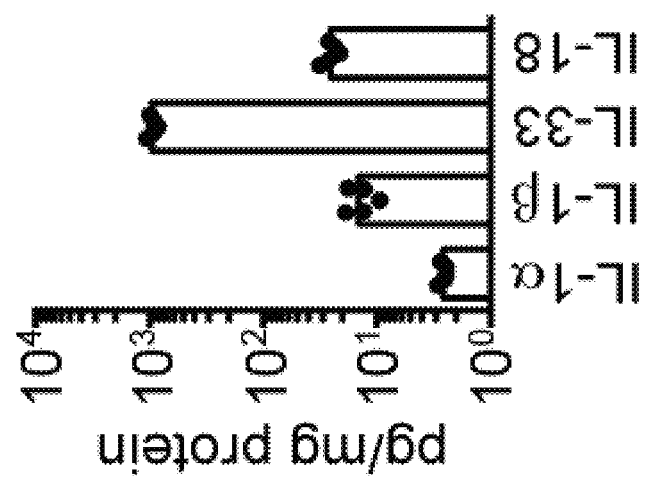
FIG. 7C is a graph showing expression of IL-1 family genes (IL-1α, IL-1β, IL-33, and IL-18) in the retina of BALB/c mice as determined by ELISA. Each data point represents an individual mouse (n=5). The data represent at least two experiments with similar results.
Figure 7D:
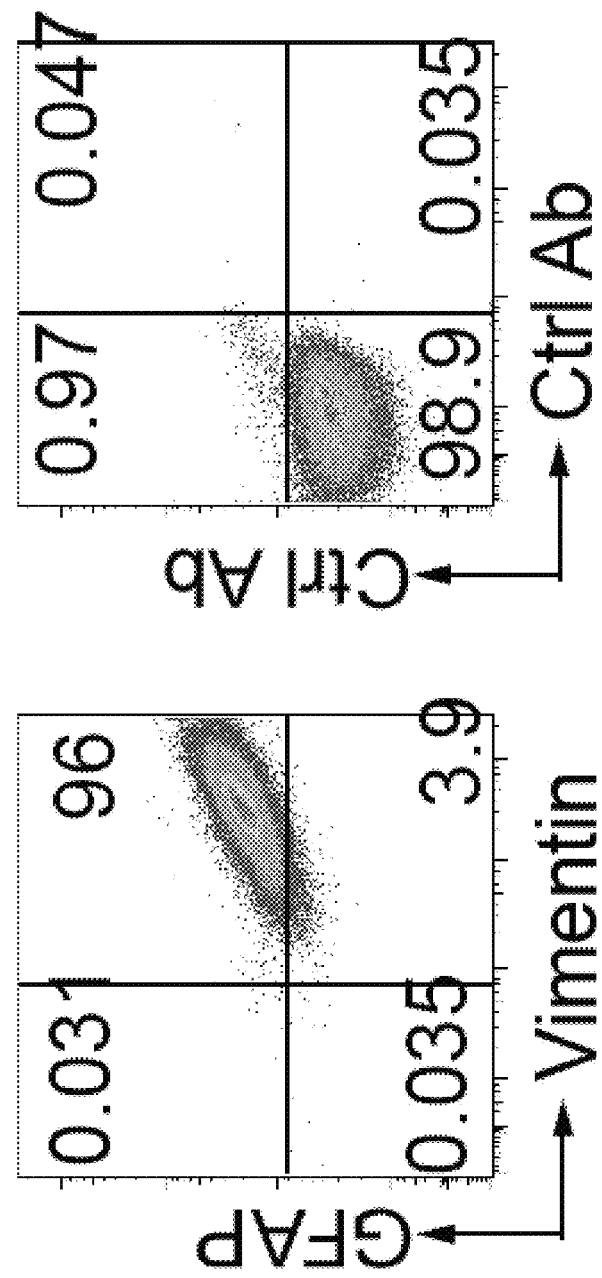
FIG. 7D is a series of graphs showing expression of GFAP and vimentin in rMC-1 cells measured by intracellular staining using GFAP- and vimentin-specific antibodies or control antibodies followed by flow cytometry. Activated Müller cells are GFAP$^+$.
Figure 7E:
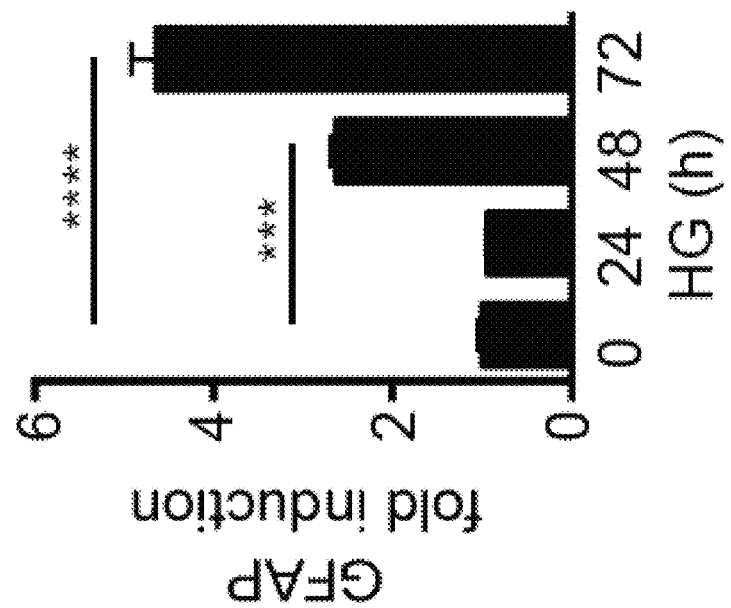
FIG. 7E is a Western blot showing IL-33 expression in the nuclear ("nucl") and cytoplasmic ("cyto") fractions of rMC-1 cells. Full-length (IL-33p30) and a processed form (IL-33p19) of IL-33 were detected in the nucleus, but only IL-33p19 was present in the cytoplasm. The data represent at least two experiments with similar results.
Figure 7F:
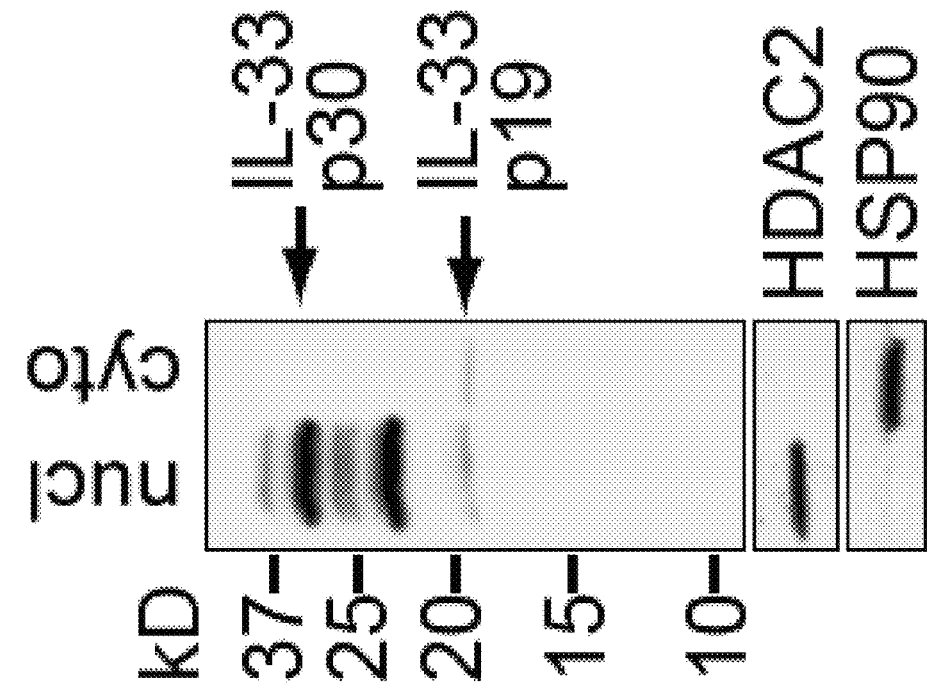
FIG. 7F is a graph showing results of a time course analysis of GFAP expression in rMC-1 cells cultured in high-glucose medium ("HG") by qPCR. GFAP mRNA was normalized to β-actin mRNA. GFAP expression at 0 h was set as 1. Data represents mean±SEM of triplicate experiments. *, $P<0.001$; **, $P<0.0001$; one-way ANOVA followed by Dunnett's post-test.
Figure 7G:
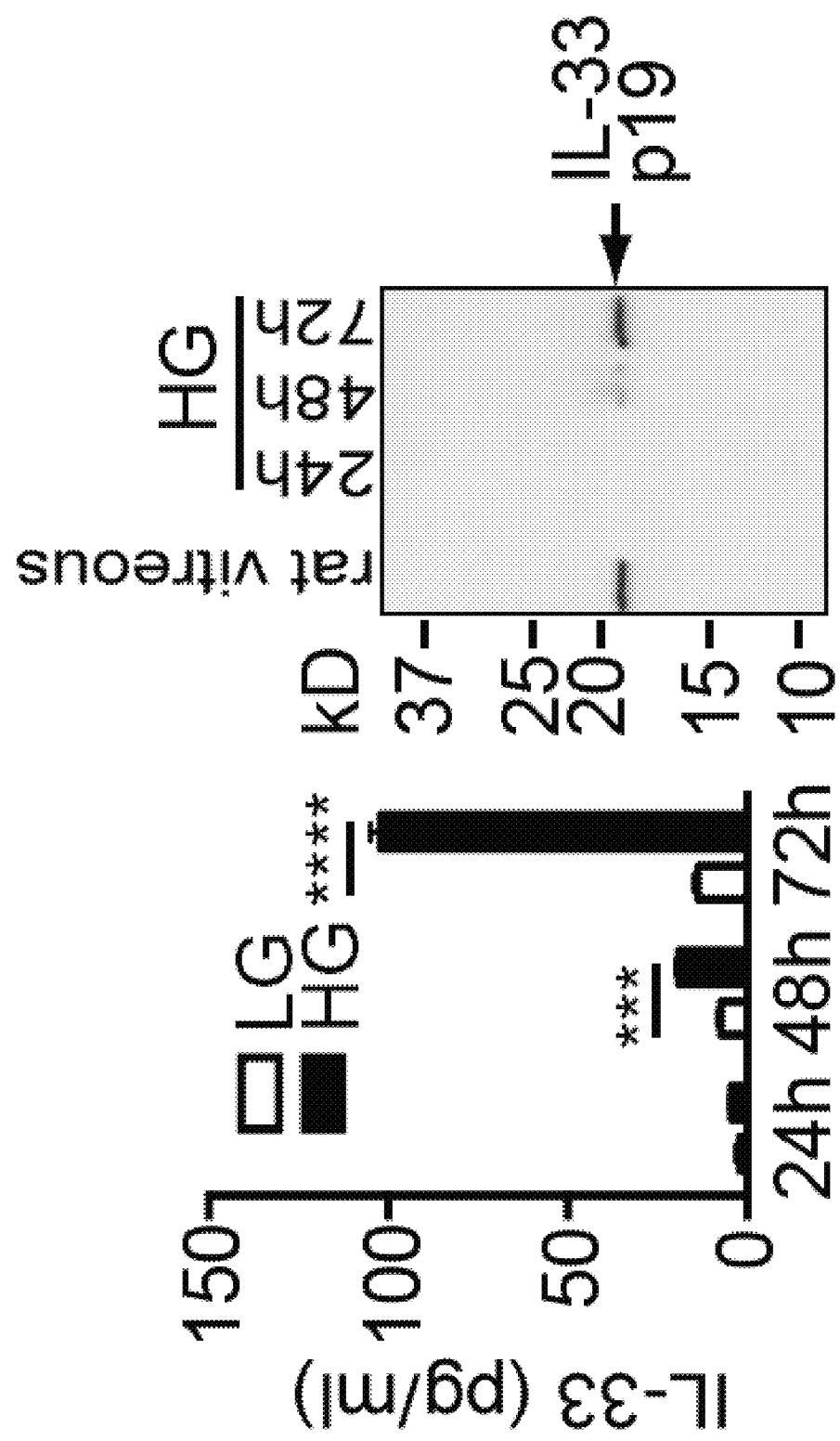
FIG. 7G shows ELISA (left panel) and Western blot (right panel) analysis of IL-33 secretion in rMC-1 cells cultured in high-glucose (HG) and low-glucose (LG)-containing medium. IL-33p19 was present in both rat vitreous and rMC-1 culture supernatant. Data shown are mean±SEM of triplicate wells and represent three independent experiments. *, $P<0.001$; **, $P<0.0001$, two-way ANOVA with Bonferroni's post-test. The data represent at least two experiments with similar results.
Figure 7H:
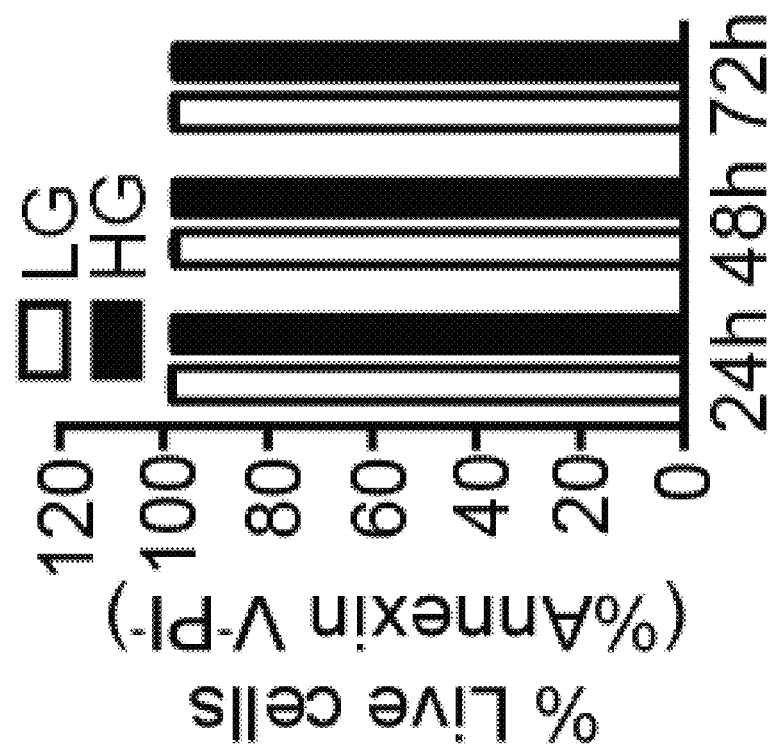
FIG. 7H is a graph showing that increased IL-33p19 secretion in rMC-1 cells cultured in HG medium (see FIG. 7G) was not associated with increased cell death. Cell viability was assessed by flow cytometry analysis of annexin V and propidium iodide (PI) staining. Live cells were gated as annexin V⁻ PI⁻. Data shown are mean±SEM of triplicate wells. The data represent at least two experiments with similar results.

B. IL-33 is Processed and Released from Müller Cells In Vitro and In Vivo Following Phototoxic Stress In the rat retina, IL-33 was primarily expressed in vimentin-positive Müller cells of the central and peripheral retina (FIG. 7A), as previously described for the mouse retina (FIG. 7B). In contrast to the IL-33 expression pattern in human eyes, IL-33 expression was very low in RPE or choroidal endothelial cells in normal rat and mouse eyes, and few IL-33$^+$ cells were observed in the RPE or choroid (FIGS. 7A and 7B). In the normal mouse eye, IL-33 mRNA and protein expression was orders of magnitude higher compared to other IL-1 family members (IL-1α, IL-1β, and IL-18) (FIG. 7C). rMC-1 cells, a Müller cell line obtained from rats exposed to bright light (Sarthy et al. *Invest. Ophthalmol. Vis. Sci.* 39:212-216, 1998), were used to study the regulation of IL-33 release in vitro. The rMC-1 Müller cells in culture displayed an activated phenotype as shown by expression of GFAP (FIG. 7D) (see also Sarthy et al. supra). Subcellular fractionation of rMC-1 Müller cells identified 30 kDa pro-IL-33 (IL-33p30) and ~24 kDa and ~19 kDa (IL-33p19) C-terminal peptides in the nuclear fraction, while IL-33p19 was the primary species expressed in the cytoplasm (FIG. 7E). Exposure of rMC-1 cells to high-glucose (25 mM) medium, which activates the Müller cells (FIG. 7F; see also Sarthy et al., supra), significantly increased IL-33 secretion compared to cells cultured in low-glucose (5.5 mM) medium (FIG. 7G). Western blot analysis of the culture supernatant demonstrated IL-33p19 as the only IL-33 species (FIG. 7G). High-glucose stimulation (up to 72 h) did not induce cell permeability or annexin V staining on rMC-1 cells (FIG. 7H), indicating that increased IL-33p19 secretion in high-glucose medium was not associated with increased cell death. These data demonstrated that IL-33 is expressed in both human and rodent Müller cells with predominant localization to the nucleus, and that IL-33p19 can be released from activated live rat Müller cells in culture.

Figure 7I:
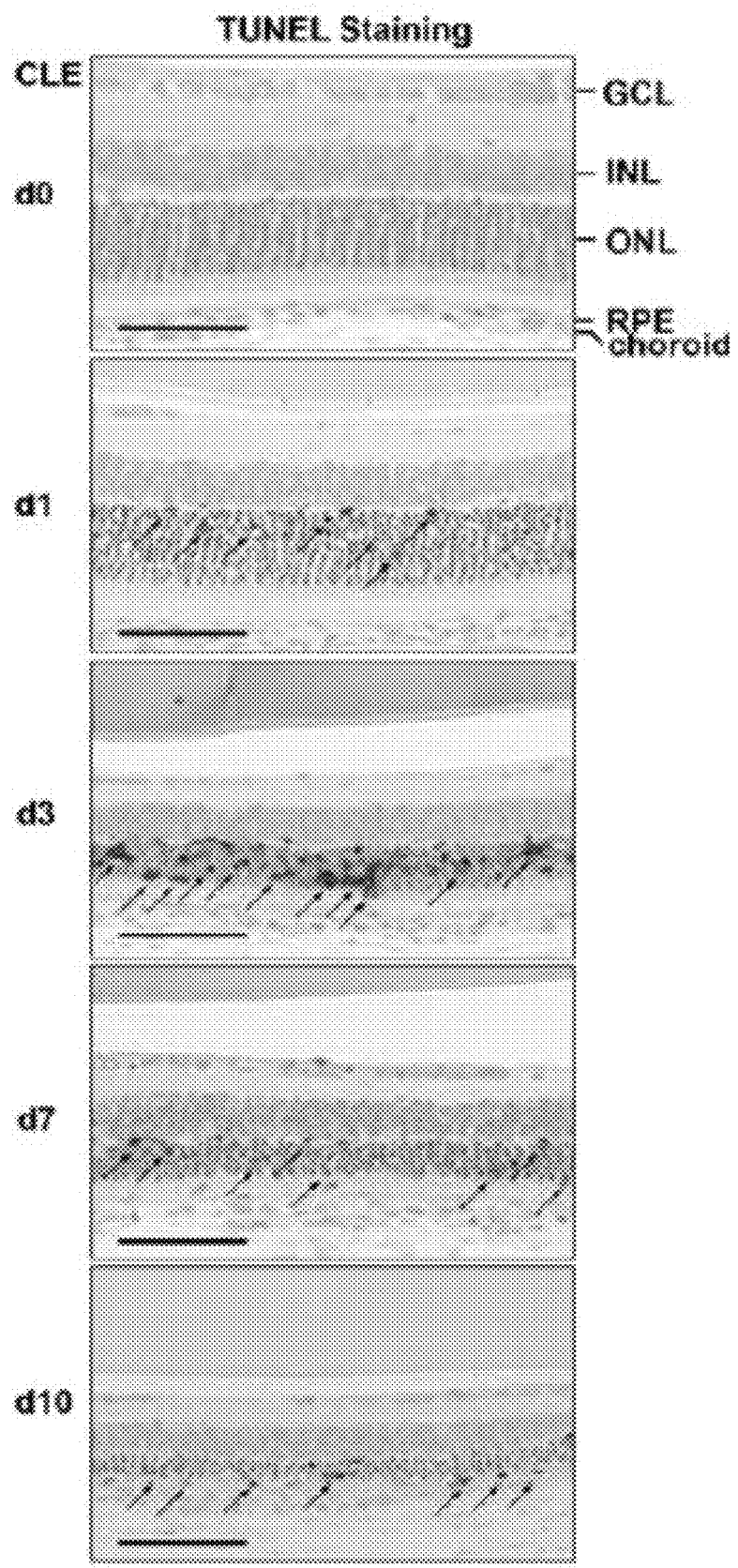
FIG. 7I is a series of images showing terminal deoxynucleotidyl transferase dUTP nick end labeling (TUNEL) staining (brown) of retina sections to detect photoreceptor cell death. Sprague-Dawley (SD) rats were exposed to light (1200 lux) for days as indicated. Arrows indicate TUNEL+ photoreceptors. Bars, 50 µm.
Figure 7J:
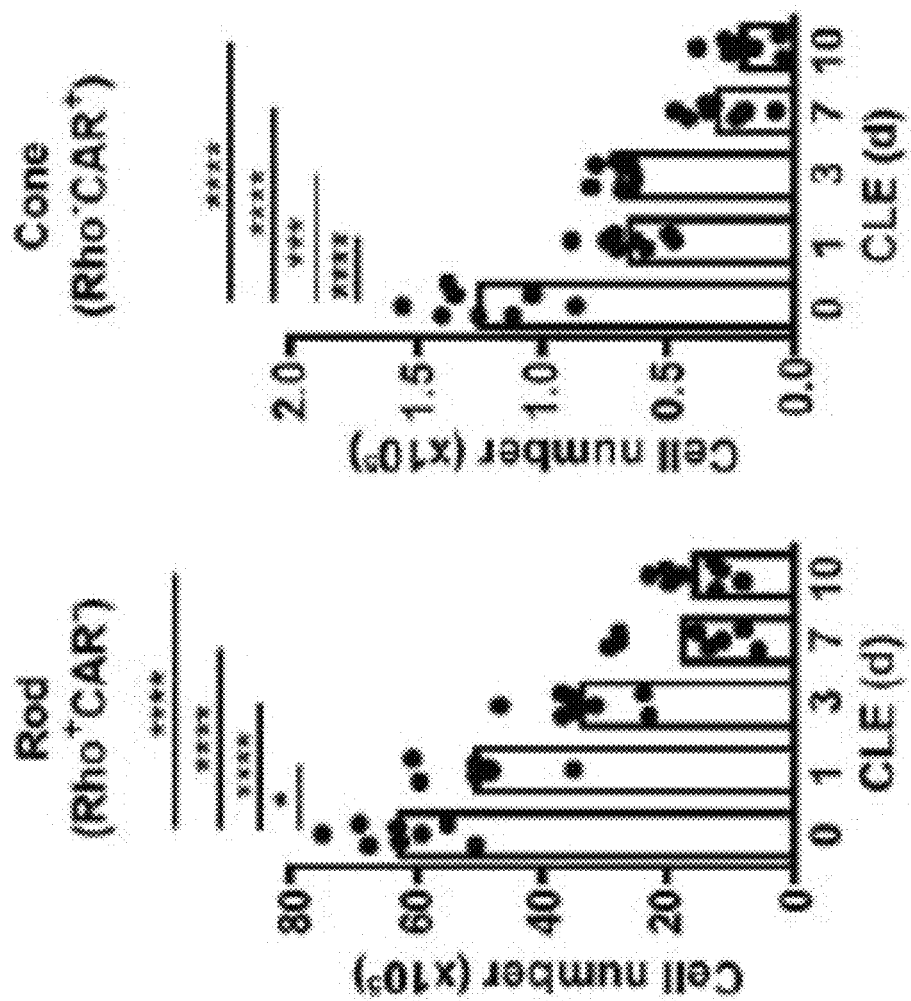
FIG. 7J is a series of graphs showing quantification of rods (left panel) and cones (right panel) by flow cytometry. Each data point represents an individual rat (n=8/time point). *, $P<0.05$; *, $P<0.001$; **, $P<0.0001$.

Next, an analysis of whether IL-33 is secreted from Müller cells following Müller cell activation in vivo was performed. Constant exposure of rodents to bright (1200 lux) light for several days resulted in progressive loss of rods and cones in parallel with increased activation of Müller cells, microglia, and macrophages (LaVail et al. *Proc. Natl. Acad. Sci. USA* 89:11249-11253, 1992). Following constant light exposure (CLE), an increased number of terminal dUTP nick end labelling (TUNEL)-positive cells was observed in the outer nuclear layer (ONL) (FIG. 7I), with subsequent loss of rods and cones (FIG. 7J). Rare TUNEL-positive cells were observed in the inner nuclear layer (INL) where the Müller cells reside.

Figure 7K:
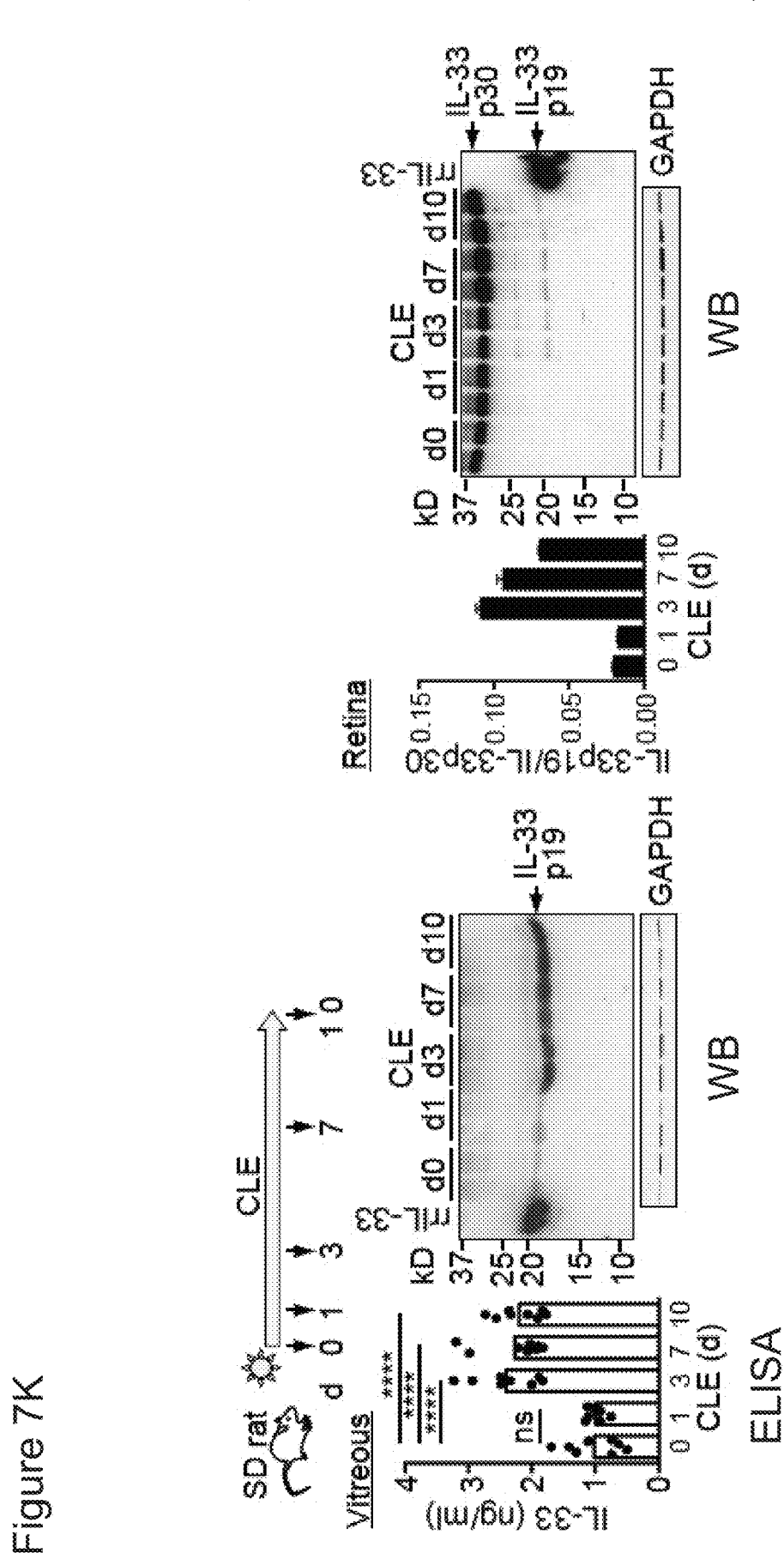
FIG. 7K shows that CLE increases expression and secretion of IL-33p19 in rat vitreous (left panels) and retina (right panels). SD rats were exposed to bright light for up to 10 days (see schematic diagram). IL-33 expression in the vitreous and retina was analyzed by ELISA and Western blot (WB). The ratio of IL-33p19 to IL-33p30 in the retina was quantitated with ImageJ software. A recombinant rat IL-33 protein (rrIL-33) (a.a. 109-264; approximately 18 kDa) was used as the positive control for the detection antibody. Each data point in ELISA represents an individual rat (n=8/time point) from one of two independent experiments. ****, $P<0.0001$; ns, non-significant; one-way ANOVA with Dunnett's post-test. The data represent at least two experiments with similar results.
Figure 7L:
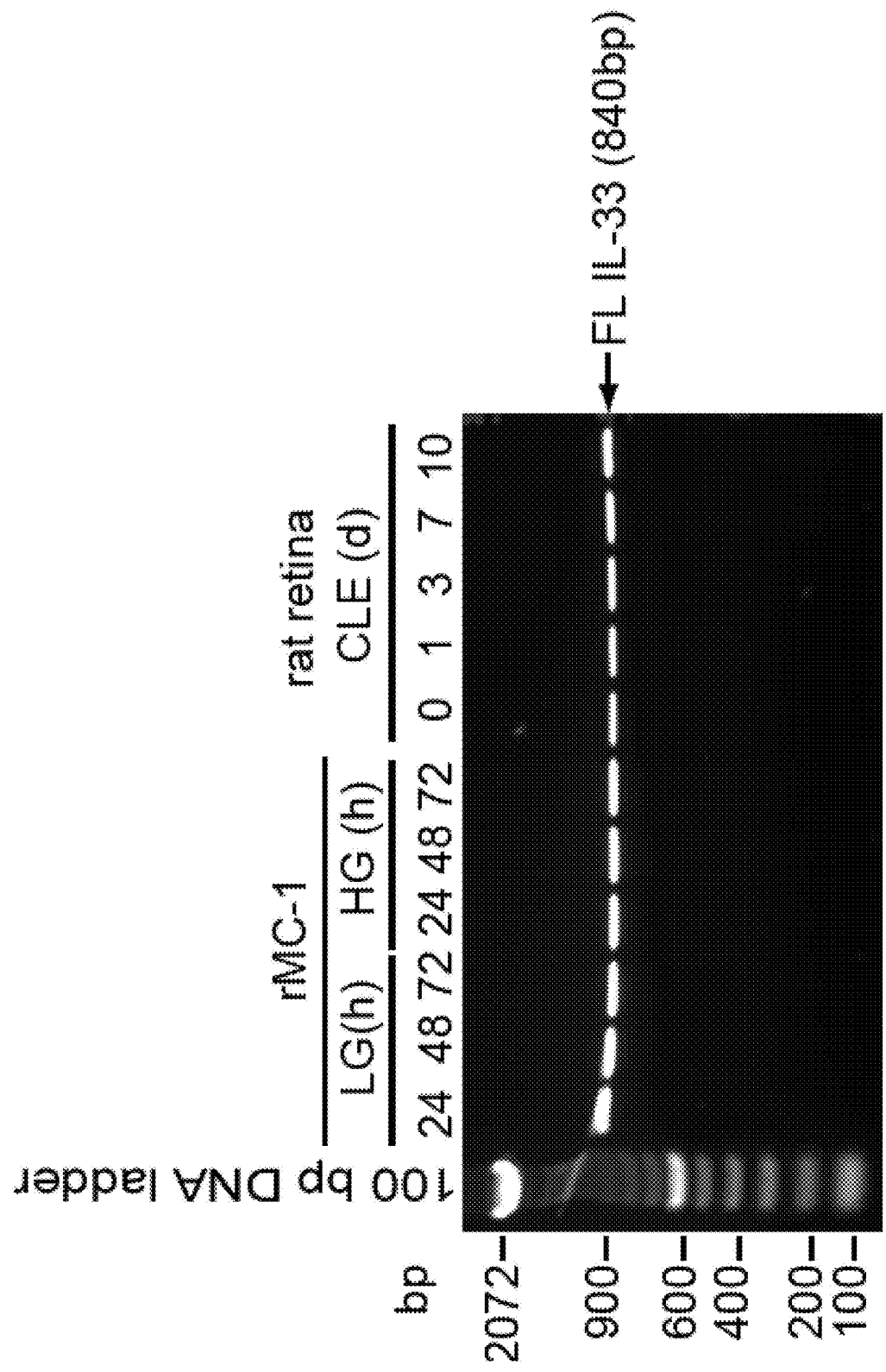
FIG. 7L is an image showing RT-PCR analysis of IL-33 transcripts in activated rMC-1 cells and light-injured retina (CLE). FL, full-length.

To determine whether IL-33 is released by cells in vivo, vitreous was collected at various time points following CLE. IL-33 levels in normal rat vitreous were approximately 1 ng/ml. IL-33 concentration increased two-fold in light-activated eyes, reaching a plateau at day 3 (FIG. 7K), indicative of release of IL-33 following light-induced retina stress. Western blot analysis confirmed that the processed C-terminal 19 kDa protein (IL-33p19), identical in size to the IL-33 fragment released from rMC-1 cells in culture (FIG. 7G), was the predominant IL-33 species present in vitreous before and after CLE (FIG. 7K). Full-length IL-33p30 was the primary species in the retina with an increased presence of the processed IL-33p19 species starting at day 3 following light exposure (FIG. 7K) with a time course similar to IL-33p19 expression in vitreous. To determine whether the increased presence of IL-33p19 in the light-injured retina and rMC-1 cells cultured in high glucose medium was due to the presence of an alternative IL-33 transcript variant, RT-PCR was performed using PCR primers spanning the 5' untranslated region (5'-UTR) (exon 1) to the stop codon (exon 9) of IL-33. Only the full-length IL-33 transcript was detected in both cases (FIG. 7L). Without wishing to be bound by theory, this suggests that IL-33p19 was generated by proteolysis rather than by alternative splicing. The protease responsible for IL-33 processing has yet to be identified and is the focus of ongoing studies.

Figure 7M:
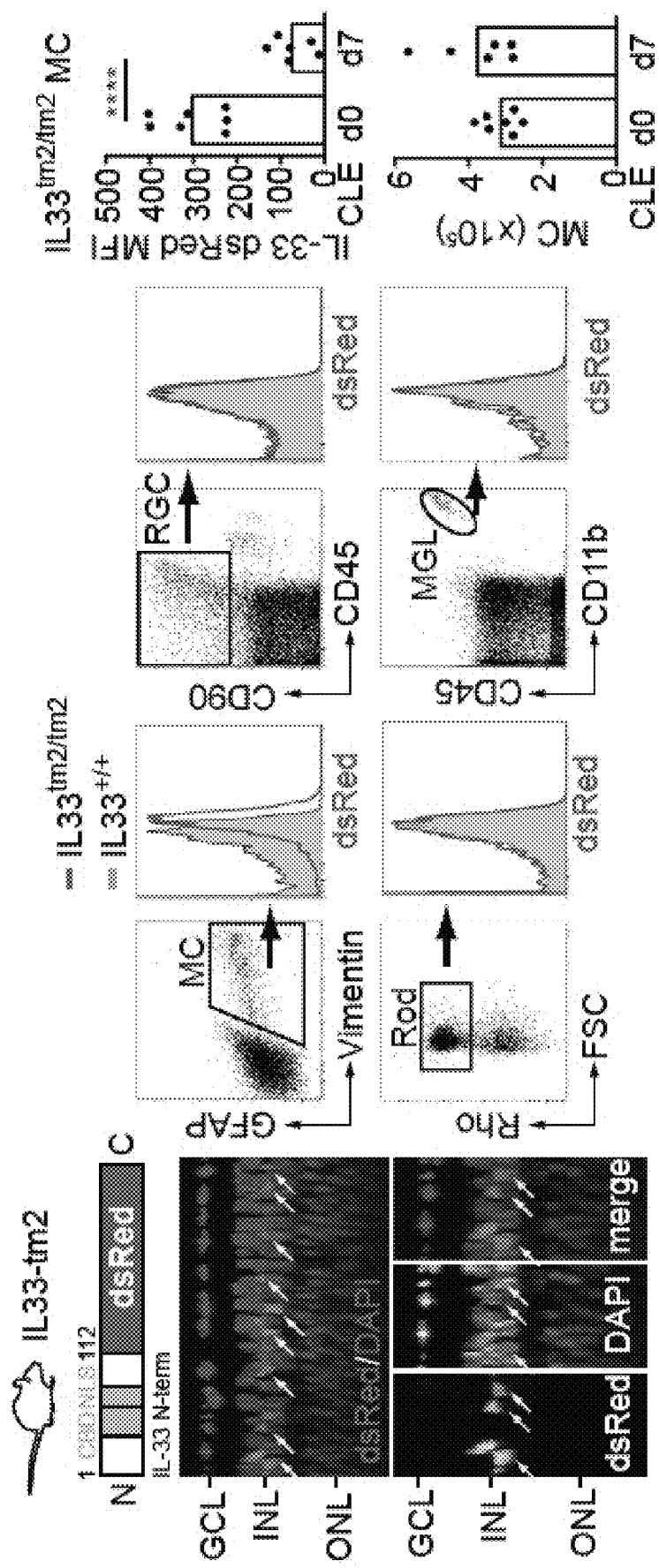
FIG. 7M shows that IL33$^{tm2/tm2}$ mice with the IL-33 cytokine domain replaced by dsRed and an intact nuclear localization sequence (NLS) and chromatin binding domain (CBD) show localization of IL-33 N-term-dsRed in nuclei of Müller cells in the INL. Images (left panel) are Z-section views of confocal microscopic imaging of IL33$^{tm2/tm2}$ retina flat-mount. dsRed signal is shown in red; DAPI signal is shown in blue. Arrows indicate IL-33⁺ Müller cells. Flow cytometry analysis of IL33$^{tm2/tm2}$ retina (middle panels) confirmed the expression of IL-33 in Müller cells (MC) but not in rods, ganglion cells (RGC), or microglia (MGL). IL-33 N-term-dsRed was processed after CLE. dsRed mean fluorescent intensity (MFI) of IL33$^{tm2/tm2}$ Müller cells as well as cell numbers at d0 and d7 of CLE were measured by flow cytometry (right panel). Data represent the MFI of dsRed in IL33$^{tm2/tm2}$ mice normalized by that of IL33$^{+/+}$ mice. Each data point represents an individual mouse (n=6-7/group) pooled from two experiments. Rho, rhodopsin; FCS, forward scatter. ****, $P<0.0001$; unpaired two-tailed Student's t test. The data represent at least two experiments with similar results.

Following CLE, a loss of native IL-33 from rat Müller cells was observed. Genetically-engineered IL33$^{tm2/tm2}$ mice (Bessa et al. *J. Autoimmunity* 55: 33-41, 2014), in which the N-terminal 112 amino acids of IL-33, containing the nuclear localization signal and the chromatin binding domain, is fused to a dsRed reporter, were analyzed to determine the regulation of IL-33 protein expression in Müller cells in vivo. In retina from IL33$^{tm2/tm2}$a mice, IL-33 N-term-dsRed localized primarily to the nucleus of Müller cells located in the INL of the retina (FIG. 7M), similar to the localization of native, full-length IL-33 (FIG. 7B). Flow cytometry analysis of the IL33$^{tm2/tm2}$ retina confirmed the selective expression of IL-33-N-term-dsRed in Müller cells (FIG. 7M). A significant loss of IL-33-dsRed from live Müller cells was observed following CLE without loss of Müller cells (FIG. 7M), which reflects the release of the IL-33 C-terminus from Müller cells in the absence of cell death. This finding is consistent with the observed loss of native IL-33 from rat Müller cells following light exposure. Therefore, these data demonstrate that C-terminal processed forms of IL-33 are released from Müller cells following cell activation in response to phototoxicity.

Figure 8A:
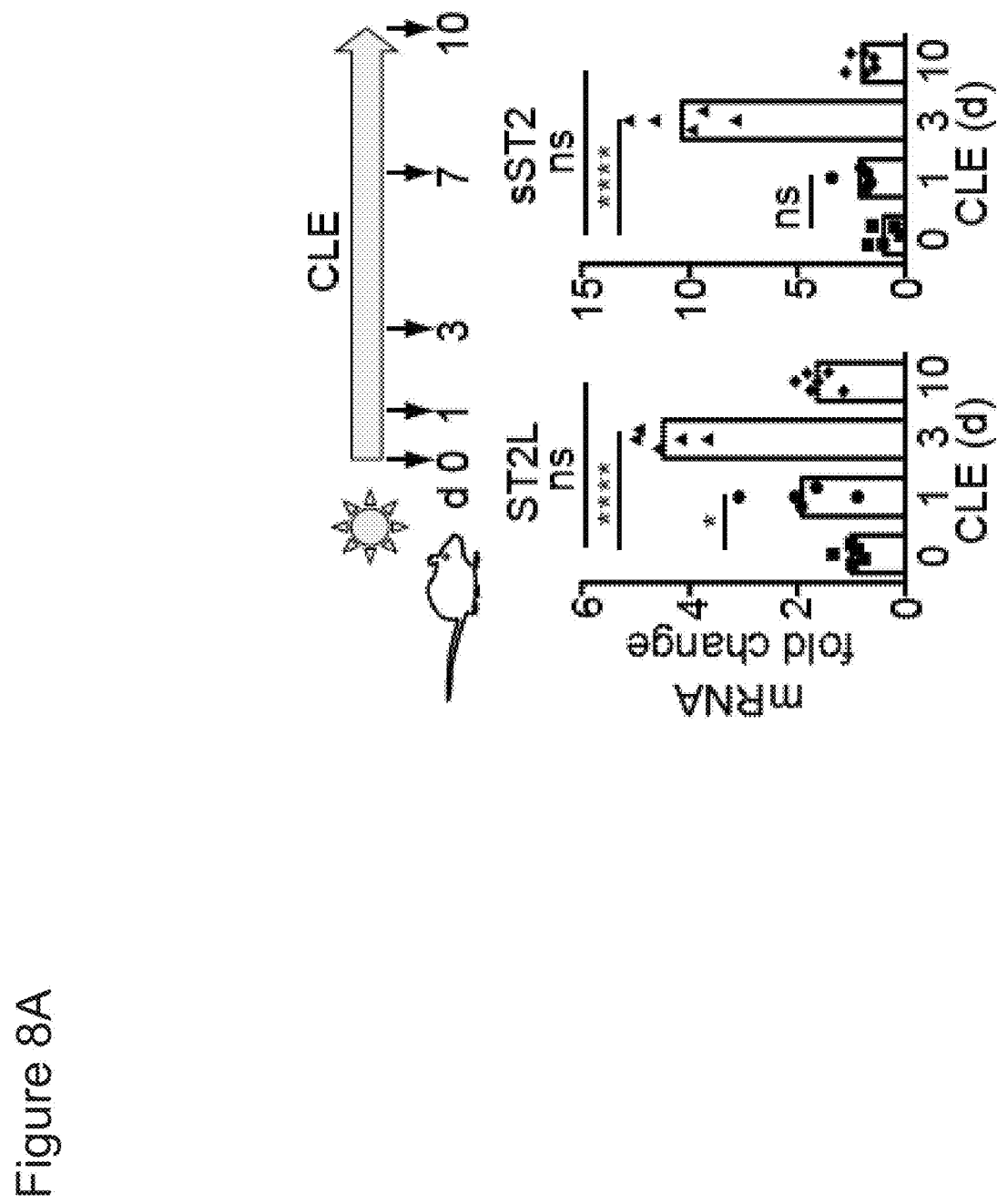
FIG. 8A is a series of graphs showing increased expression of membrane-bound (ST2L, left panel) and soluble ST2 (sST2, right panel) following CLE. Retinal RNA from BALB/c mice exposed to light for various days was analyzed by qPCR using probes specific for ST2L and sST2, and normalized by 18s rRNA expression. The fold change of ST2 expression is shown relative to ST2 expression in non-exposed mice (d0). Each data point represents an individual mouse (n=5-6/time point). Data represent two independent experiments. *, $P<0.05$; ****, $P<0.0001$; ns, non-significant; one-way ANOVA with Dunnett's post-test.
Figure 8B:
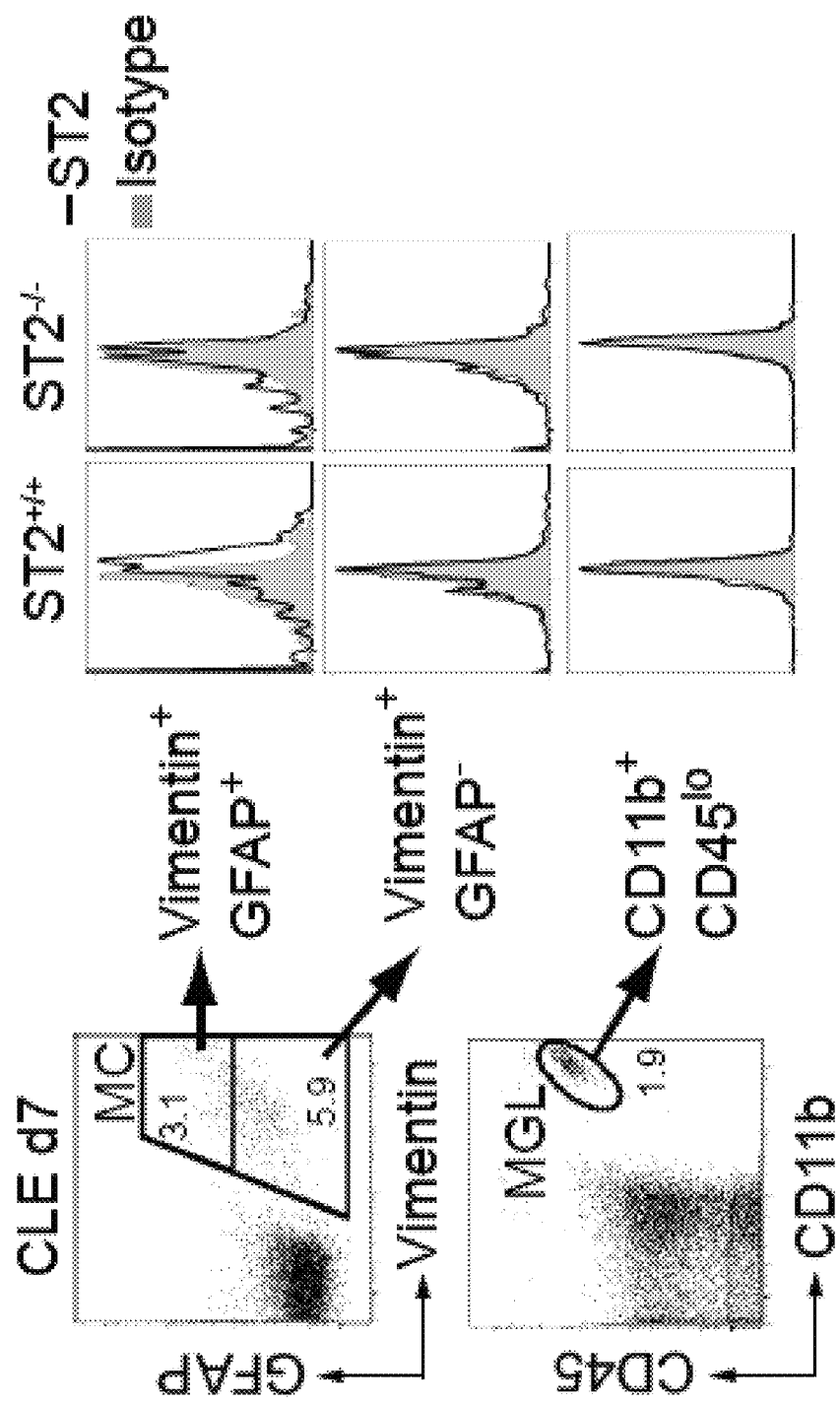
FIG. 8B is a series of graphs showing flow cytometry analysis of ST2 expression on various retinal cell populations. The results indicated exclusive expression of ST2 on activated Müller cells (MC) following 7 days light exposure. ST2 was only expressed on activated Müller cells (GFAP⁺ vimentin⁺ MC), but not on resting Müller cells (GFAP⁻ vimentin⁺ MC), microglia (CD11b⁺ CD45$^{lo}$ MGL), or photoreceptor cells. ST2$^{-/-}$ mice were used as the negative control in addition to an isotype control antibody.

C. ST2 is Expressed on Activated Müller Cells and Contributes to Photoreceptor Loss IL-33 triggers MyD88-mediated signalling following binding to its hetero-dimeric receptor, ST2/IL1RAcP (see, e.g., Schmitz et al. *Immunity* 23: 479-490, 2005). Retina transcripts encoding trans-membrane ST2 (ST2L) and a splice variant of ST2 that lacks the trans-membrane domain (sST2) increased 4- to 10-fold following CLE, peaking at day 3 (FIG. 8A). Flow cytometry analysis in parallel samples identified activated (GFAP$^+$) Müller cells as the primary source of trans-membrane ST2 in the light-exposed retina (FIG. 8B), while ST2 was not detectable on Müller cells before light exposure. ST2 was not detected on CD11b$^+$ CD45$^{lo}$ microglia (FIG. 8B), RGCs, or photoreceptors.

Figure 8C:
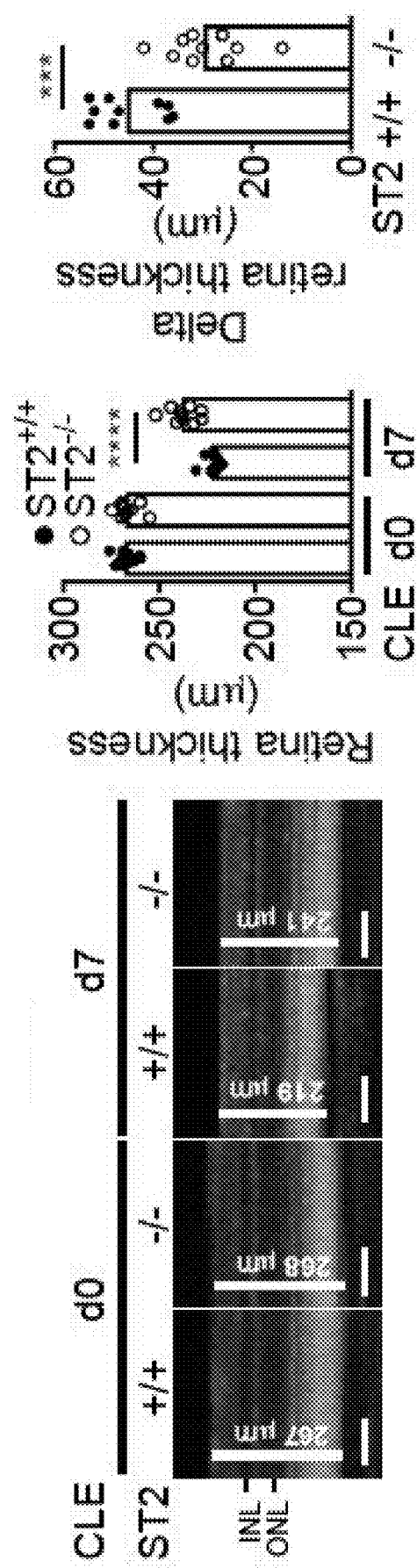
FIG. 8C shows optical coherence tomography (OCT) analysis of retina thickness at baseline (d0) and after 7 days exposure to light in ST2$^{+/+}$ and ST2$^{-/-}$ mice. Representative cross-sectional OCT images are shown. Change (delta) in retina thickness was calculated by subtracting retina thickness of d0 by that of d7 for each mouse (n=10/genotype). Data shown represent three independent experiments. Bars, 100 µm. *, $P<0.001$; **, $P<0.0001$; unpaired two-tailed Student's t test.
Figure 8D:
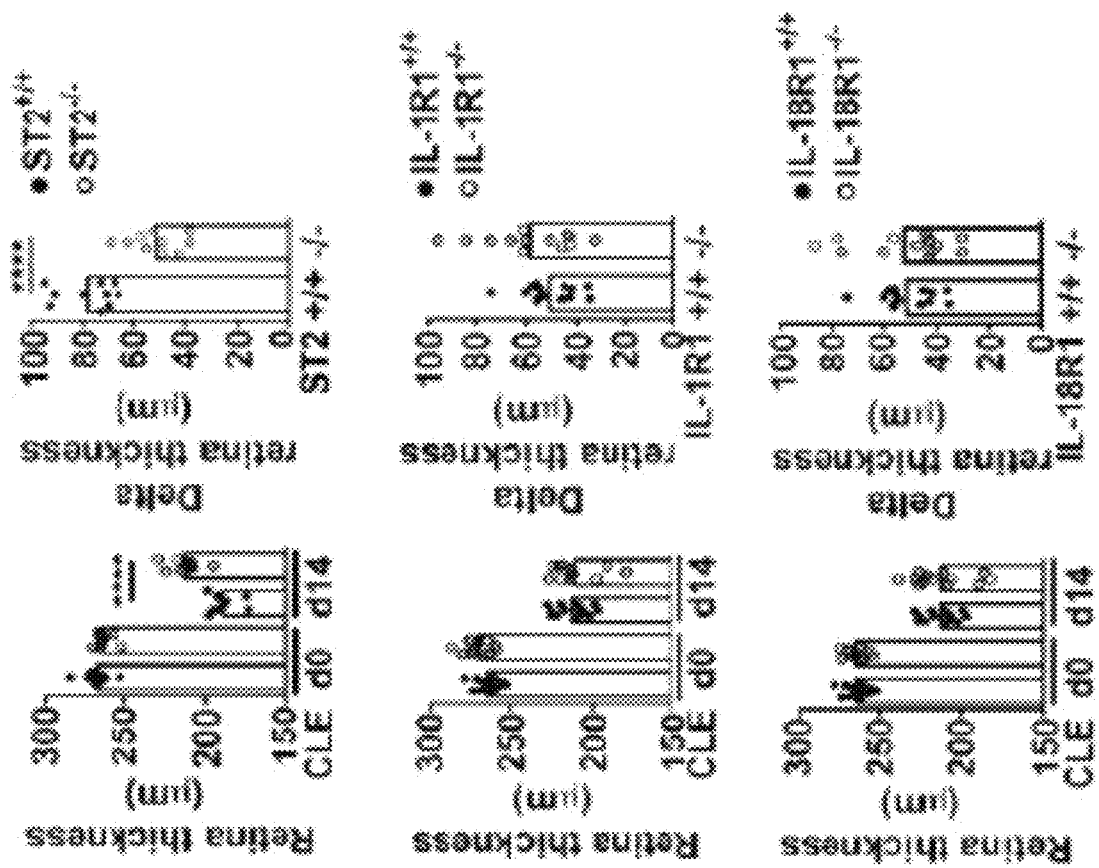
FIG. 8D is a series of graphs showing lack of retina protection in IL-1R1$^{-/-}$ and IL-18R1$^{-/-}$ mice following CLE. ST2$^{-/-}$, IL-1R1$^{-/-}$, and IL-18R1$^{-/-}$ mice as well as the corresponding wild-type (+/+) mice were exposed to light for 14 days. Retina thickness was measured by OCT. Delta retina thickness was calculated by subtracting retina thickness of d0 by that of d14 for individual mouse. Each data point represents an individual mouse (n=10-15/genotype). ****, $P<0.0001$.
Figure 8E:
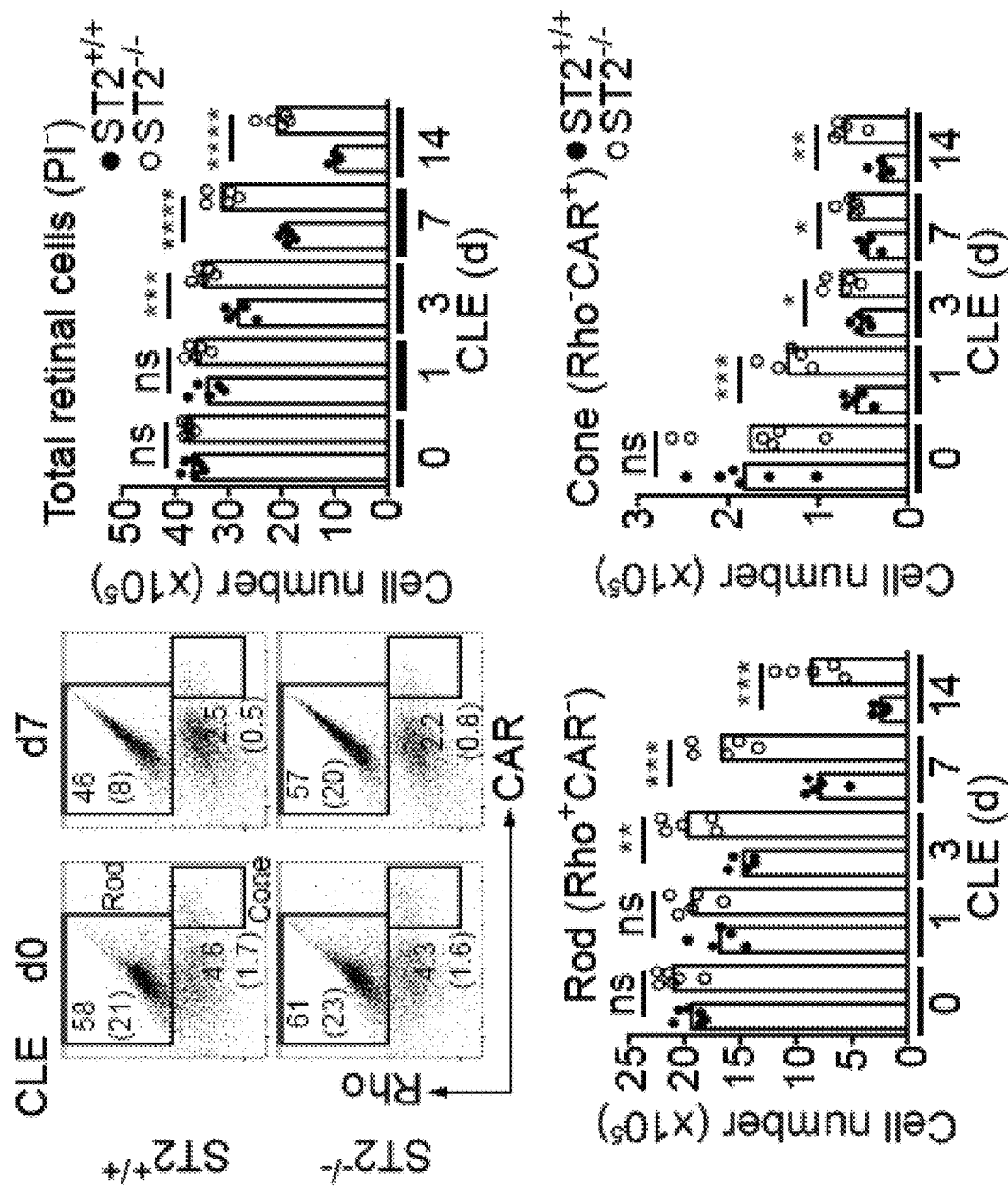
FIG. 8E is a series of graphs showing that rods and cones are protected in ST2$^{-/-}$ mice. Retinal cells in ST2$^{+/+}$ and ST2$^{-/-}$ mice at baseline (d0) and at various time points following CLE were quantified by flow cytometry. Flow cytometry plots (top left panel) indicate the gating strategy and percentage as well as absolute numbers (between parentheses) of rods and cones (×10⁵) in ST2$^{+/+}$ and ST2$^{-/-}$ mice at baseline and CLE d7. Each data point in the graphs in the lower panel represents an individual mouse (n=5-6/genotype). Data represent two independent experiments with similar results. Rho, rhodopsin; CAR, cone arrestin. *, $P<0.05$; , $P<0.01$; *, $P<0.001$; ****, $P<0.0001$; ns, non-significant; unpaired two-tailed Student's t test.
Figure 8F:
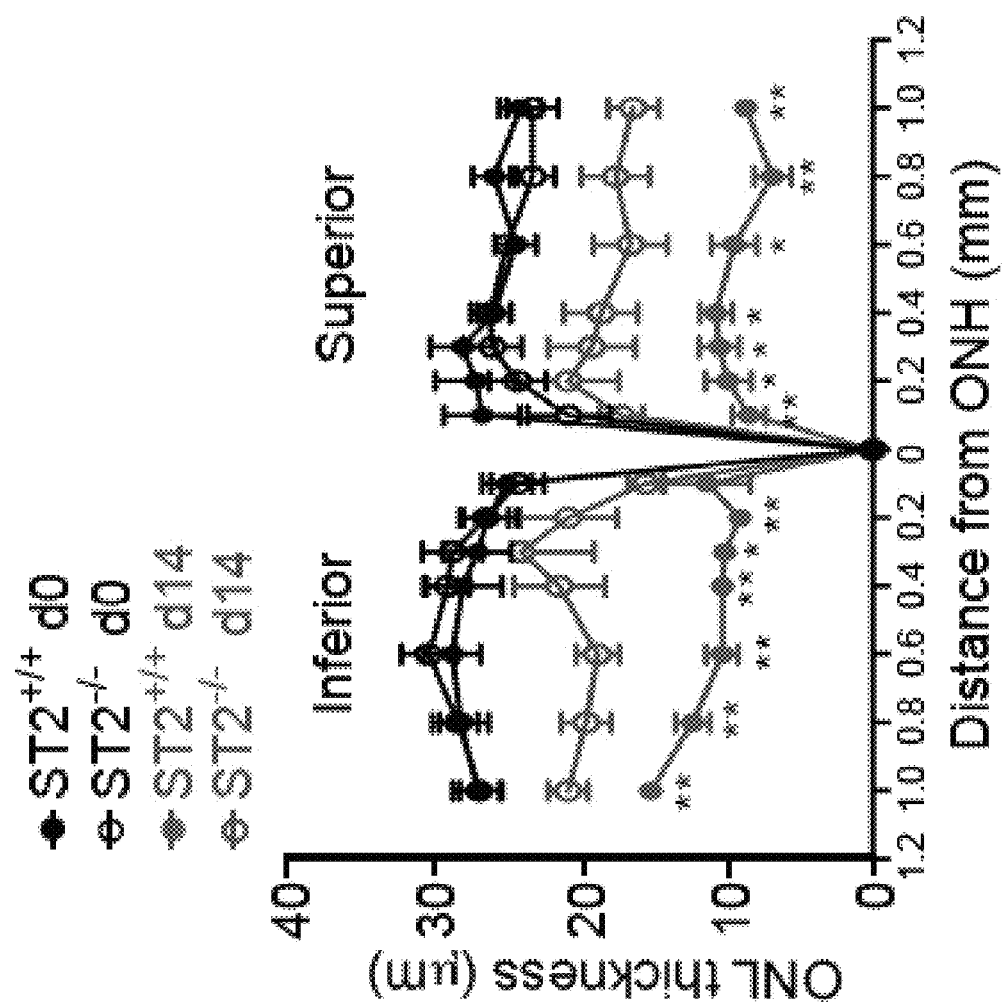
FIG. 8F is a graph showing morphometric analysis of ONL thickness of ST2$^{+/+}$ and ST2$^{-/-}$ mice at baseline (d0) and after 14 days exposure to light plotted as a function of distance from the optic nerve head (ONH). Significant protection of retina ONL in ST2$^{-/-}$ mice was observed in both superior and inferior quadrants. Data shown are means±SEM (n=5-7/genotype). *, $P<0.05$; **, $P<0.01$; two-way ANOVA with Tukey's post-test.
Figure 8G:
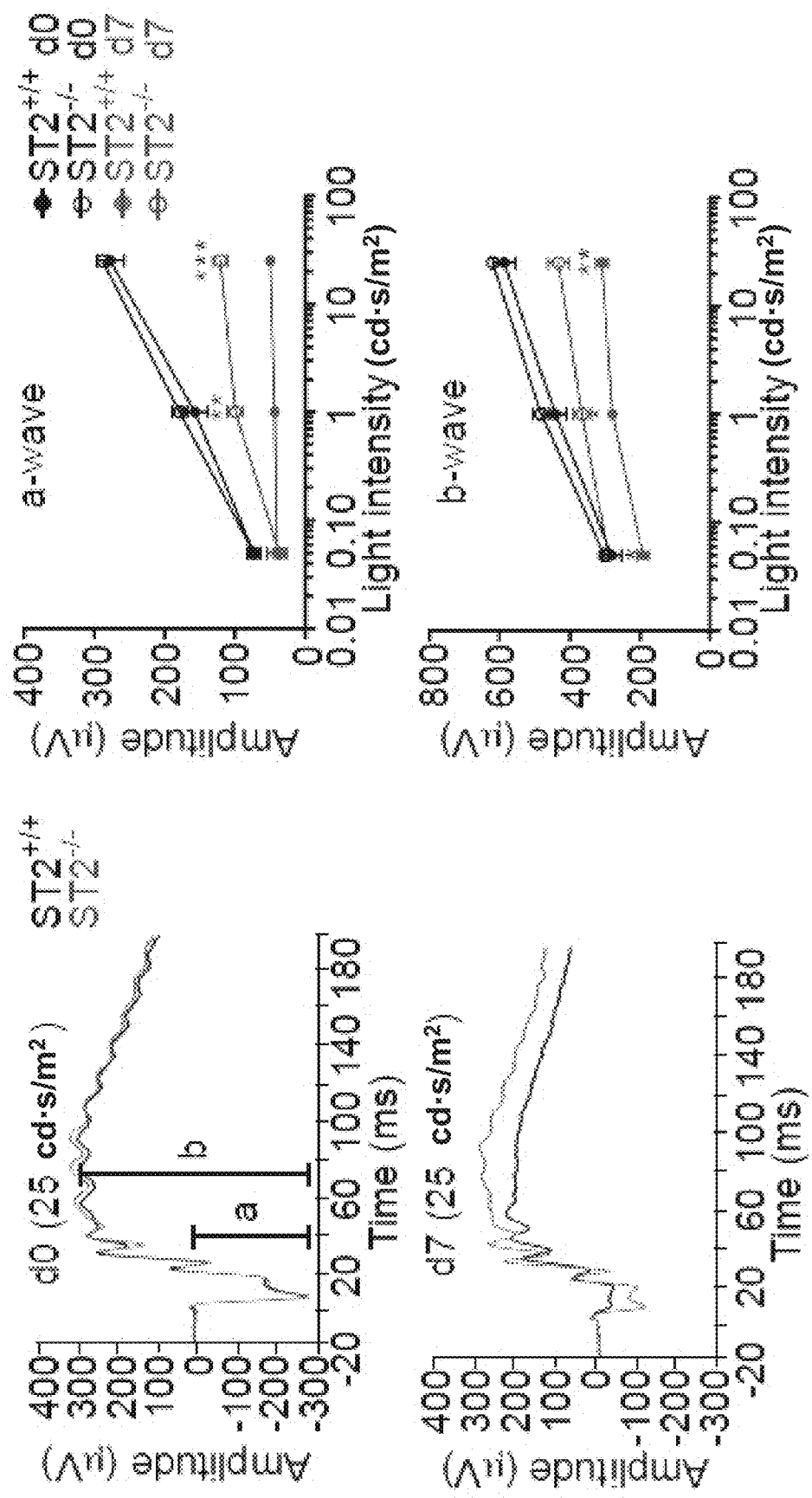
FIG. 8G is a series of graphs showing electroretinography (ERG) analysis of ST2$^{+/+}$ and ST2$^{-/-}$ mice at baseline (d0) and after 7 days CLE. Representative ERG recordings at 25 cd·s/m² flash intensity of baseline and after 7 days CLE are shown. Mean dark-adapted a- and b-wave amplitudes at flash intensities of 1 and 25 cd·s/m² were significantly greater in ST2$^{-/-}$ compared to ST2$^{+/+}$ mice after 7 days CLE. Data shown are means±SEM (n=10/genotype). *, $P<0.05$; , $P<0.01$; *, $P<0.001$; two-way ANOVA with Tukey's post-test.

An analysis was performed to determine whether IL-33 binding to ST2 impacts photoreceptor survival following CLE. Spectral Domain Optical Coherence Tomography (SD-OCT) demonstrated sparing of retina in ST2$^{-/-}$ compared to ST2$^{+/+}$ mice following 7 days (FIG. 8C) and 14 days (FIG. 8D) of CLE. Flow cytometry of total retina further confirmed that rods, cones, and ganglion cells were protected in ST2$^{-/-}$ vs ST2$^{+/+}$ mice during CLE for 14 days (FIG. 8E). Morphometric analysis on sections through the eye showed significant protection of photoreceptors in ST2$^{-/-}$ mice after retinal phototoxic injury in both the superior and inferior halves of the retina (FIG. 8F). Electroretinograms (ERG) were recorded at day 7 following CLE and demonstrated that sparing of retina cells in ST2$^{-/-}$ compared to ST2$^{+/+}$ mice translated to improved a- and b-wave responses, reflecting improvement of retina function (FIG. 8G). In contrast to retinas of ST2$^{-/-}$ mice, retinas of IL-1R1$^{-/-}$ and IL-18R1$^{-/-}$ mice that lack the receptors for IL-1α, IL1-β, and IL-18, respectively, were not protected compared with wild-type littermates following CLE (FIG. 8D).

Figure 9A:
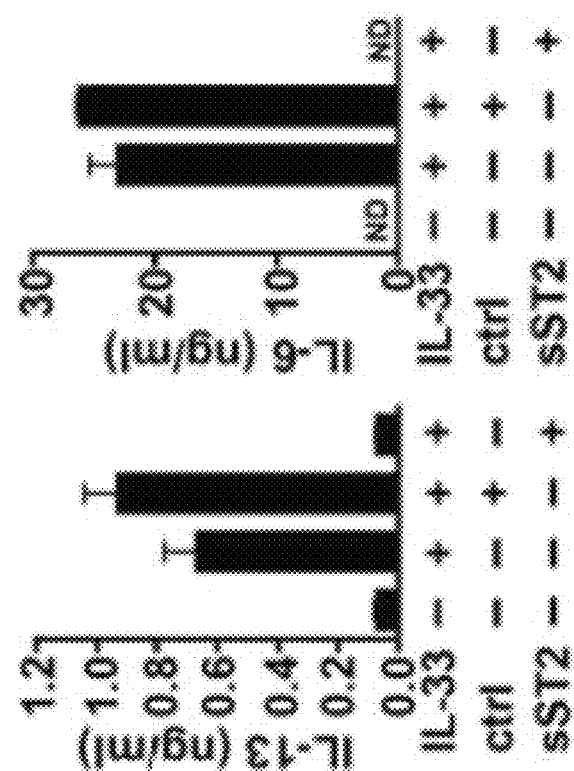
FIG. 9A is a series of graphs showing in vitro activity of soluble ST2. Bone marrow derived mast cells (BMMCs) were stimulated with 1 ng/ml recombinant mouse IL-33 in the absence or presence of 20 µg/ml of soluble ST2-His (sST2) or a control His-tagged protein for 24 h. IL-13 and IL-6 secretion in the supernatant were quantified by ELISA. Data represent means±SEM of triplicate experiments from two independent experiments.
Figure 9B:
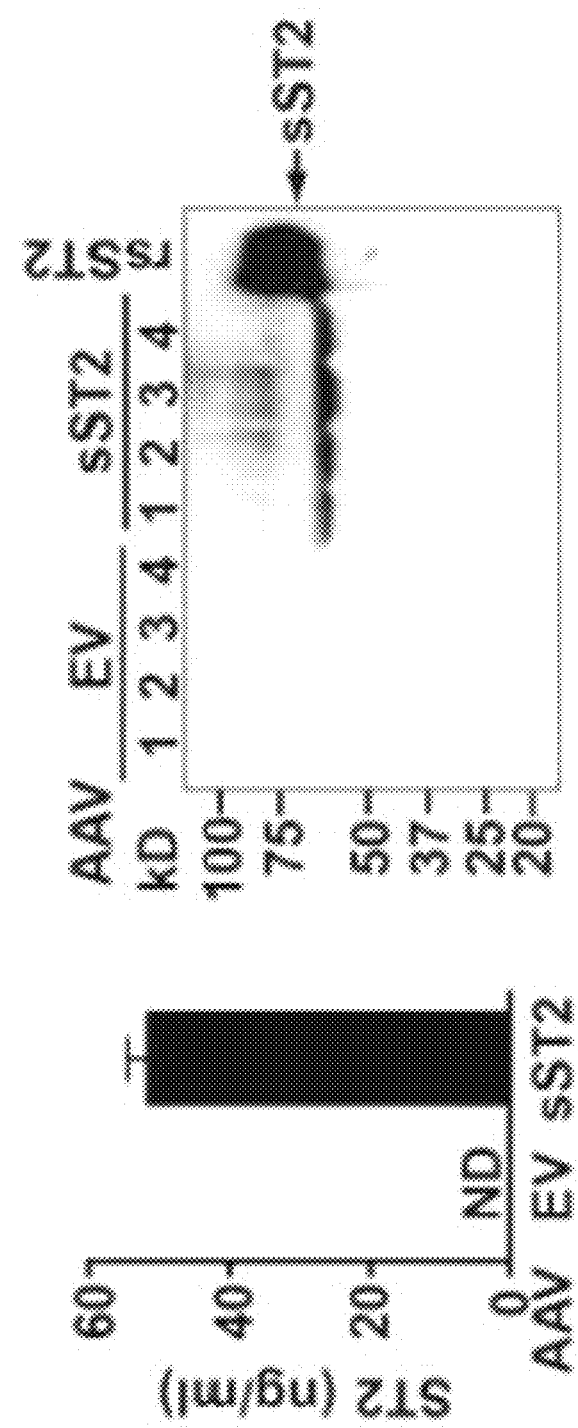
FIG. 9B shows expression of AAV-sST2. HEK293 cells were infected with an AAV vector expressing sST2-His (sST2) or empty vector (EV). Six days after infection, sST2 expression in the culture supernatant was determined by ELISA (left panel) and Western blot (right panel). Data represents means±SEM (n=8) of two experiments. ND, not detected; rsST2, recombinant soluble ST2-His.
Figure 9C:
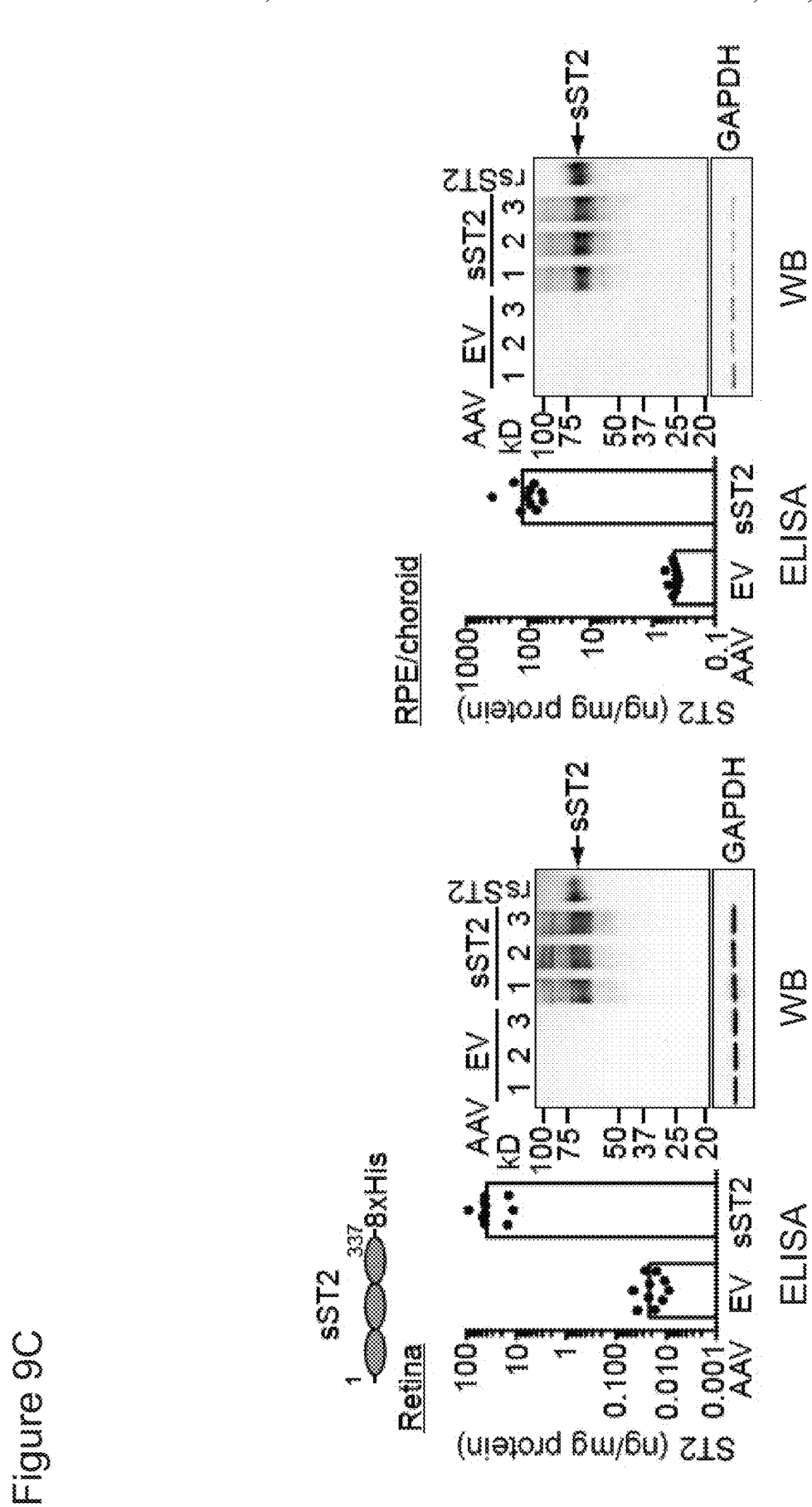
FIG. 9C shows expression of AAV-sST2. BALB/c mice were injected subretinally with an AAV expressing soluble ST2 (AAV-sST2) or AAV empty vector (AAV-EV), which served as a negative control. Expression of sST2 in the retina (left panel) and RPE/choroid (right panel) was analyzed three weeks post-infection by ELISA and Western blotting (WB). Western blotting of ST2 and GAPDH was performed on 10 μg of retina lysates and 3 μg of RPE/choroid lysates. rsST2, recombinant soluble ST2-His.
Figure 10:
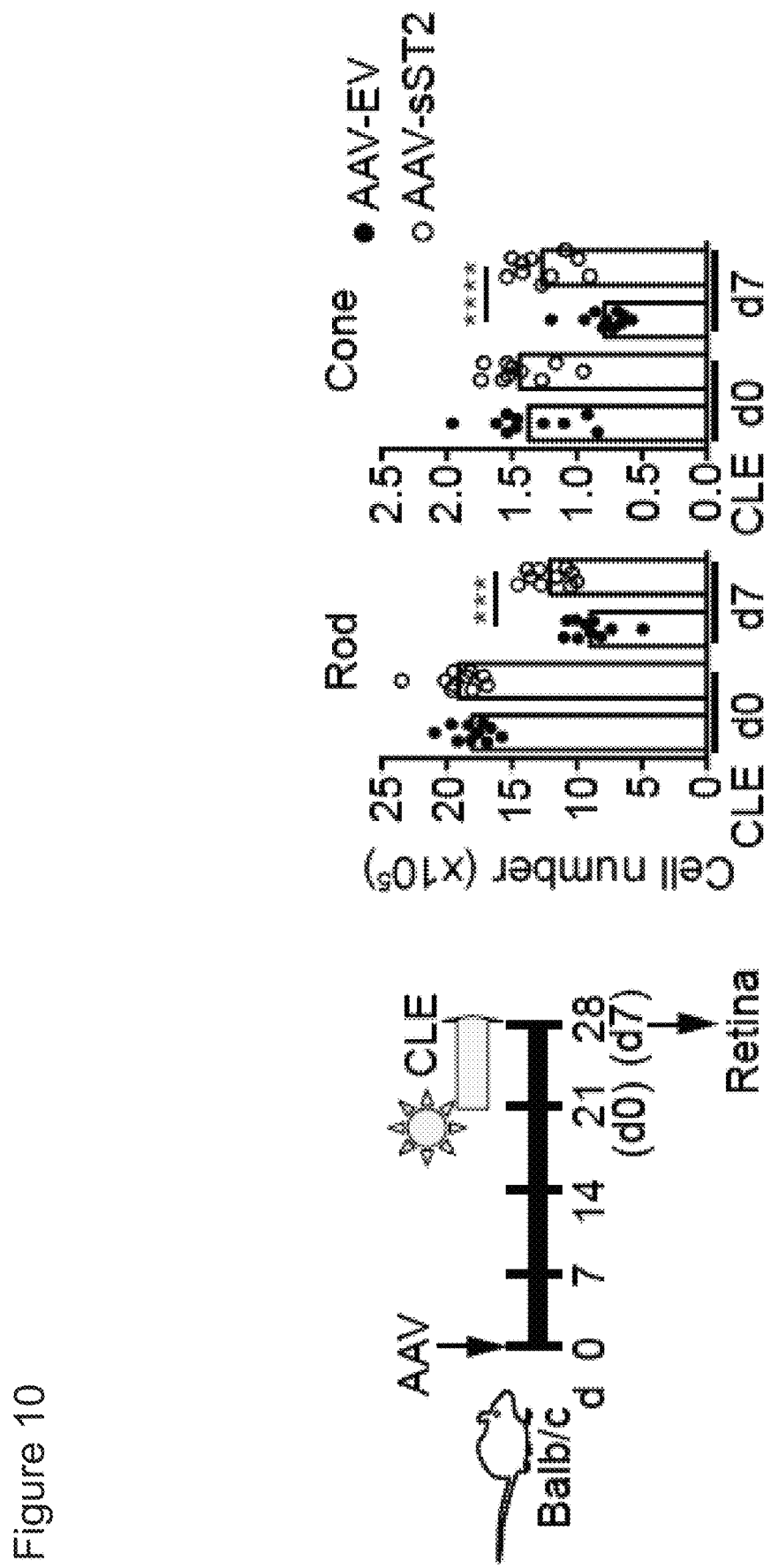
FIG. 10 is a series of graphs showing that administration of soluble ST2 protects photoreceptors from phototoxic stress. Mice were injected subretinally with an AAV expressing soluble ST2 (AAV-sST2) and exposed to light 21 days post-infection (schematic in top panel). Mice injected with AAV empty vector (AAV-EV) served as controls. Rods and cones were quantified by flow cytometry before (d0) and after 7 days (d7) light exposure. Each data point represents an individual mouse (n=10/group). *, P<0.001; **, P<0.0001; unpaired two-tailed Student's t tests. Data represent two independent experiments with similar results.

To further determine whether pharmacological blockade of the ST2/IL-33 interaction protects photoreceptors, mice were treated with a recombinant adeno-associated virus (AAV) expressing soluble ST2 (AAV-sST2) followed by CLE. Blocking activity of sST2 was verified in IL-33-stimulated bone marrow-derived mast cells (BMMC) (FIG. 9A). ELISA and Western blot analysis confirmed the expression of sST2 in AAV infected HEK293 cells (FIG. 9B). Subretinal injection of AAV-sST2 led to high level expression of sST2 in the retina and RPE (FIG. 9C). Light-exposed mice treated with AAV-sST2, but not control vector, showed protection of rods, cones, and ganglion cells (FIG. 10). These results demonstrate that IL-33 binding to its signalling receptor ST2/IL1RAcP results in a pathogenic response that leads to photoreceptor loss in the light-exposed retina.

D. IL-33 Increases Recruitment of Myeloid Cells to the Photoreceptor Layer

Figure 11A:
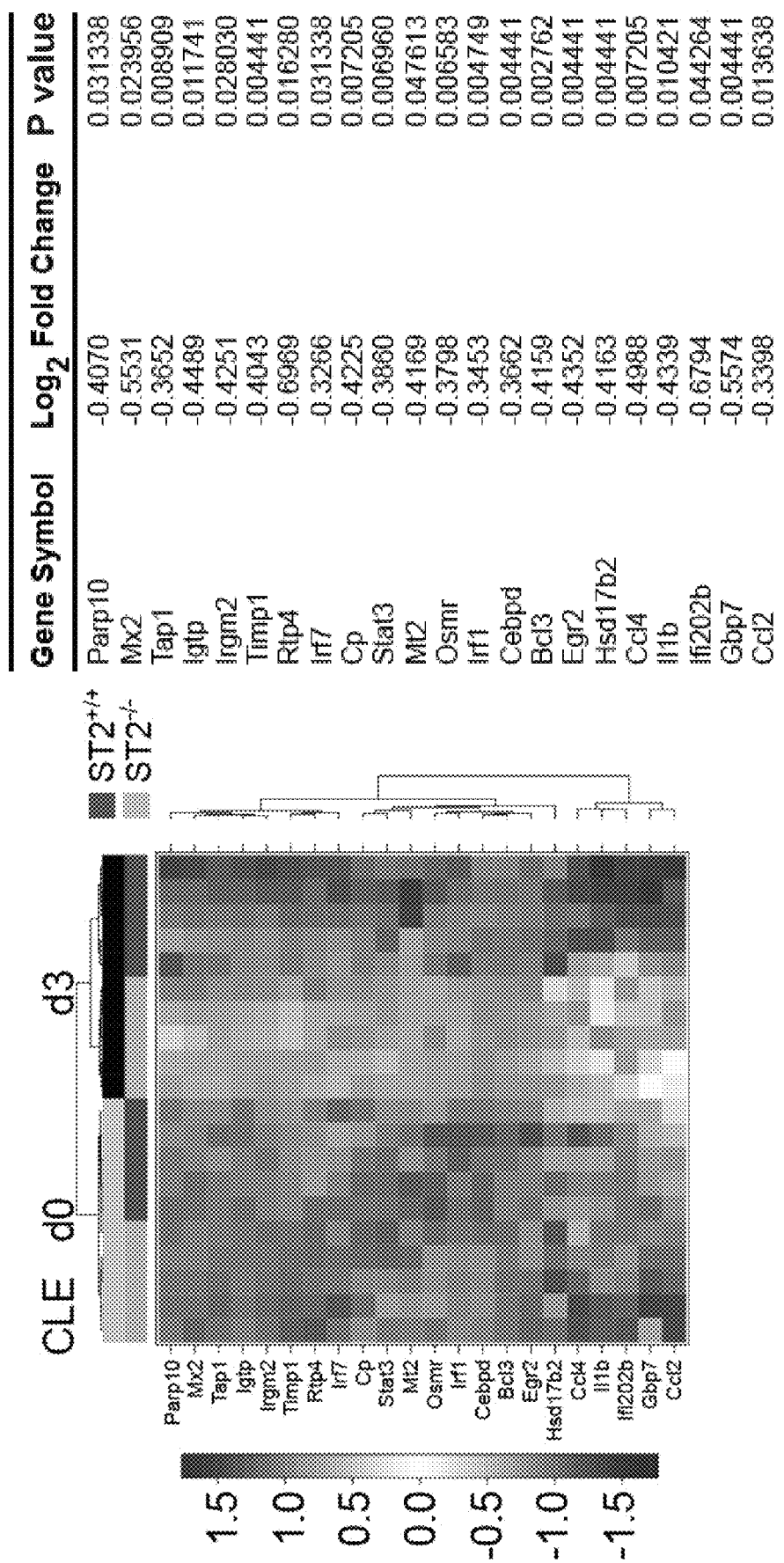
FIG. 11A shows the top 22 light exposure-inducible genes that were decreased in $ST2^{-/-}$ mice compared to $ST2^{+/+}$ mice following CLE for 3 days. The left panel is a heatmap showing the results of gene expression in the retina before (d0) and after (d3) CLE as analyzed by microarray. N=5. The right panel is a table showing the gene symbol, the log 2 fold change in expression, and the P value.
Figure 11C:
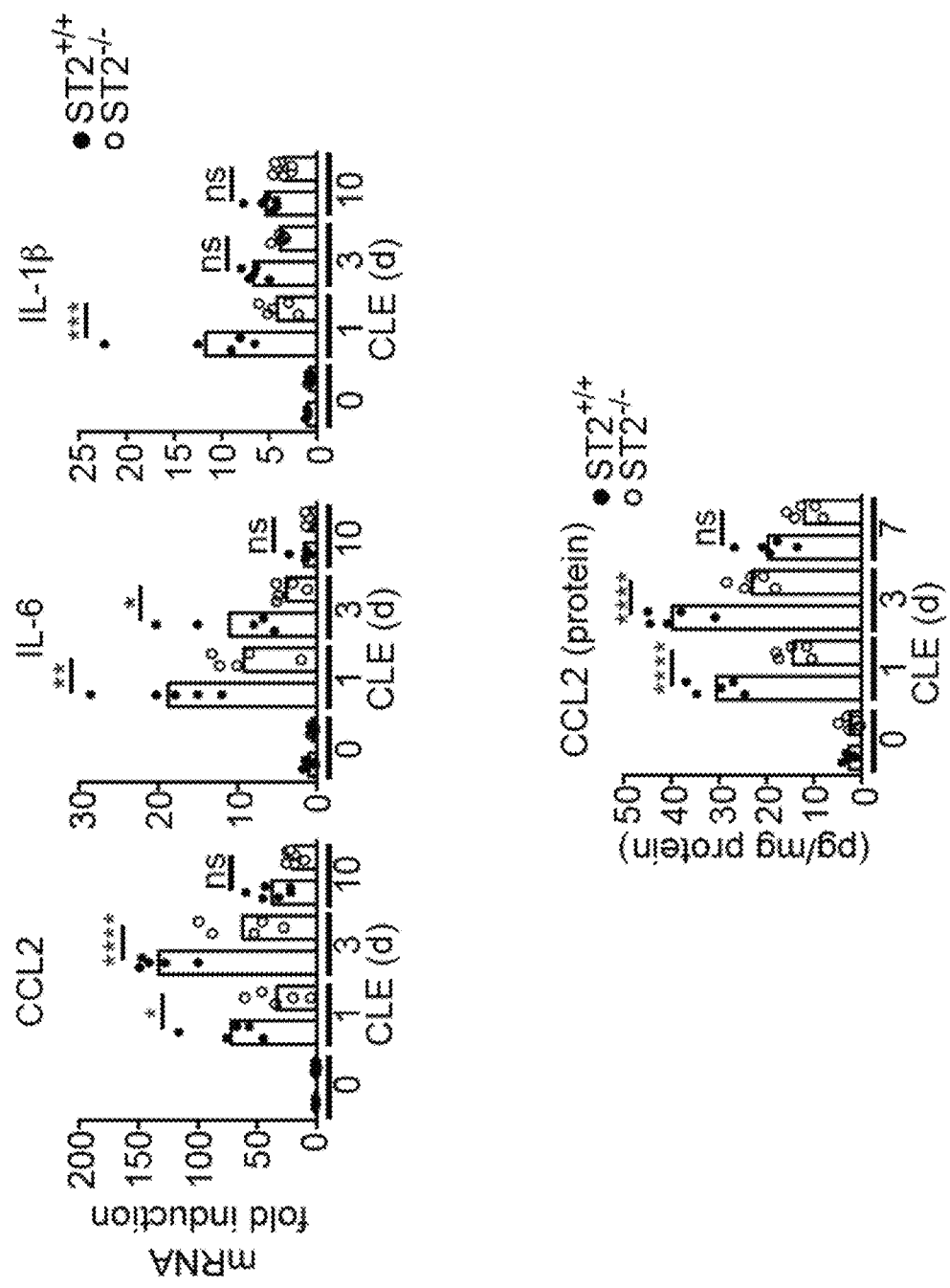
FIG. 11C is a series of graphs showing expression of CCL2, IL-6, and IL-1=. The top panel shows a time course qPCR analysis of CCL2, IL-6, and IL-13 expression in the retina following CLE. The results showed reduced expression in $ST2^{-/-}$ compared to $ST2^{+/+}$ mice (n=5-6/genotype). Gene expression in d0 $ST2^{+/+}$ mice was set as 1. CCL2 protein expression in the retina was measured by ELISA (bottom panel). Data represent two independent experiments with similar results. *, P<0.05; , P<0.01; *, P<0.001; ****, P<0.0001; one-way ANOVA with Tukey's post-test.

To determine which pathways downstream of ST2/IL1RAcP signaling cause photoreceptor loss, micro-array analysis of retinas of ST2$^{+/+}$ and ST2$^{-/-}$ mice exposed to constant light for 3 days was performed. Following CLE, the retinas of ST2$^{+/+}$ mice displayed an overall increase in signatures of inflammation compared to ST2$^{-/-}$ mice, including CCL2, IL-1β, IL-6, IRF1, IRF7, and STAT3 (FIGS. 11A and 11B). Real-time PCR confirmed increased expression of CCL2, IL-1P, and IL-6, with significantly lower expression in ST2$^{-/-}$ mice compared to ST2$^{+/+}$ mice (FIG. 11C). Consistent with the mRNA expression data, CCL2 protein expression in the retina was reduced in ST2$^{-/-}$ compared with ST2$^{+/+}$ mice following CLE (FIG. 11C).

Figure 11D:
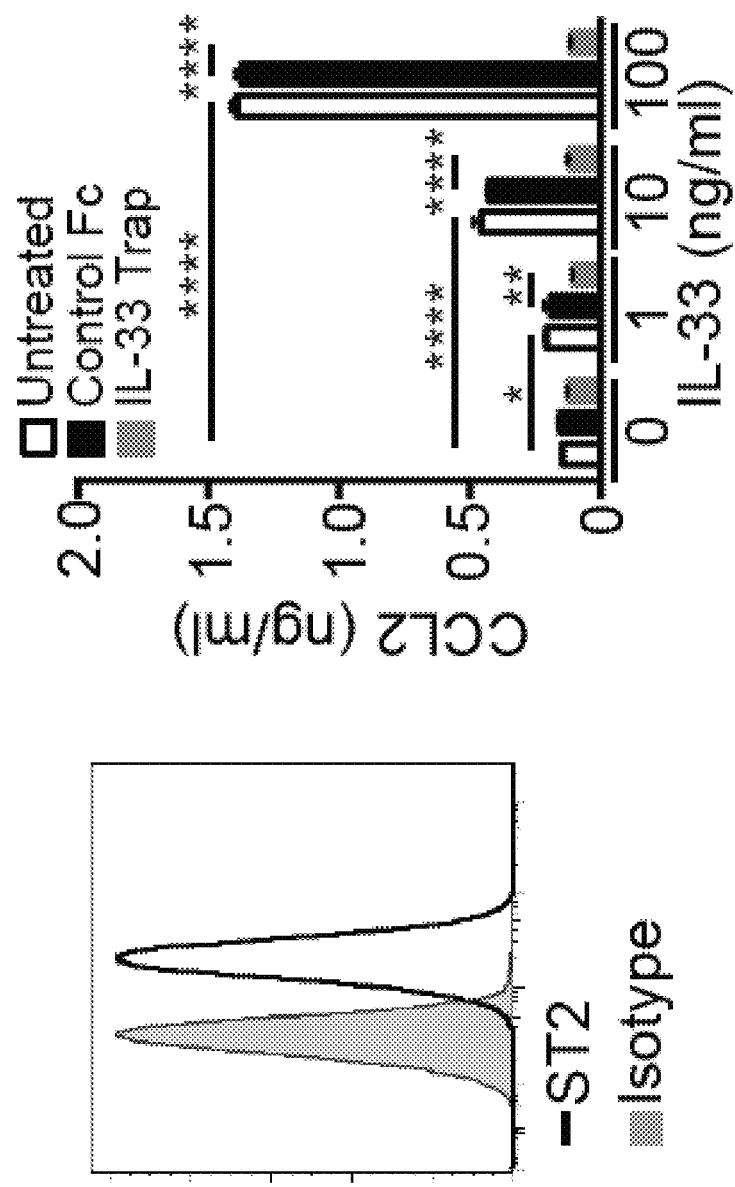
FIG. 11D is a series of graphs showing that addition of IL-33 induced CCL2 secretion from rMC-1 cells. ST2 expression on the surface of rMC-1 cells was detected by flow cytometry (left panel). Stimulation of rMC-1 cells with IL-33 induced CCL2 secretion in a dose-dependent manner, and stimulation was abrogated in the presence of IL-33 TRAP but not a control protein (right panel). CCL2 levels in 24 h culture supernatants were measured by ELISA. Data shown are means±SEM of triplicate wells and represent two independent experiments with similar results. *, P<0.05; , P<0.01; **, P<0.0001; two-way ANOVA with Tukey's post-test.
Figure 11E:
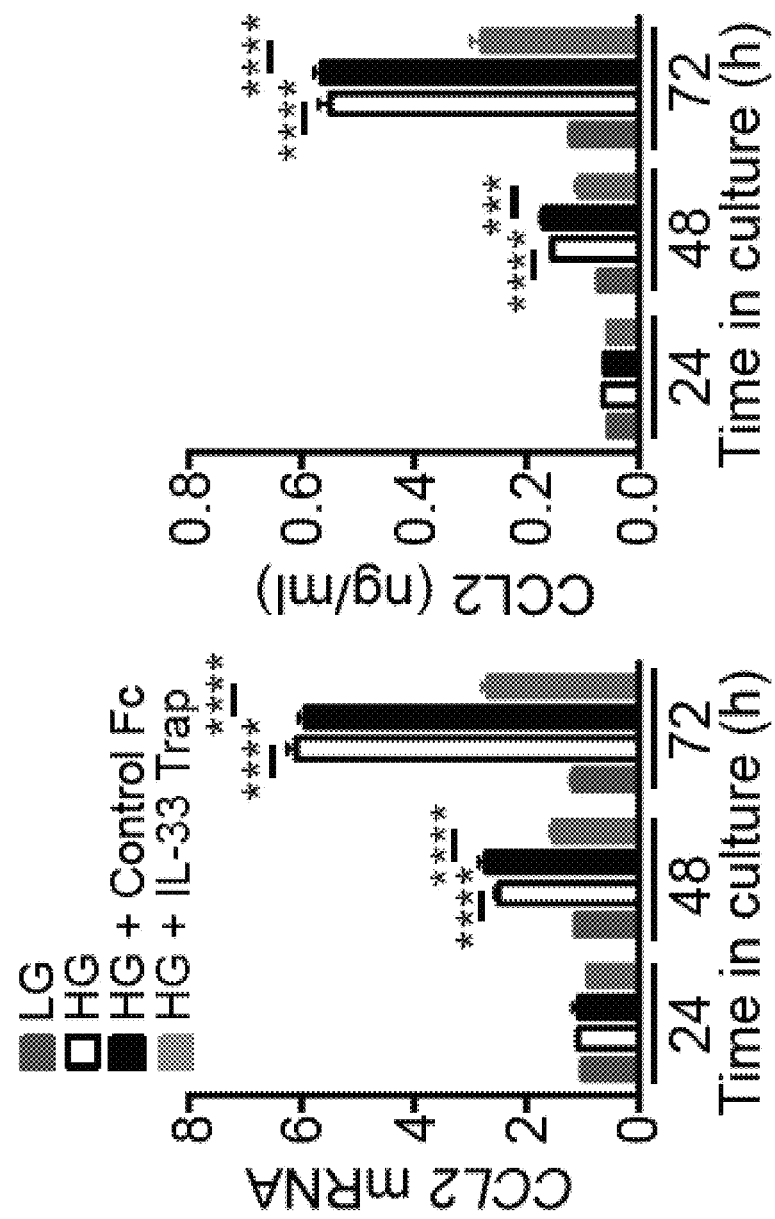
FIG. 11E is a series of graphs showing that autocrine induction and release of CCL2 from rMC-1 cells was blocked by addition of IL-33 TRAP. rMC-1 cells were cultured in HG containing medium in the presence of IL-33 TRAP or a control protein for up to 72 h. CCL2 mRNA expression (left panel) and secretion (right panel) were measured by qPCR and ELISA, respectively. Data shown are mean±SEM of triplicate experiments. *, P<0.001; **, P<0.0001; two-way ANOVA with Tukey's post-test.

An analysis was performed to determine whether IL-33 induces CCL2 expression in Müller cells. Consistent with the in vivo results described above, rMC-1 cells expressing the Müller cell activation marker GFAP expressed transmembrane, surface-exposed ST2 (FIG. 11D). When stimulated with recombinant IL-33, rMC-1 cells showed a dose-dependent increase in CCL2 expression, which was blocked by addition of IL-33 TRAP, confirming that IL-33 signals through ST2 on Müller cells (FIG. 11D). In addition to IL-33, rMC-1 cells expressed and secreted CCL2 over time when cultured in high-glucose medium (FIG. 11E). Neutralizing IL-33 secreted by Müller cells by addition of IL-33 TRAP to the culture medium significantly reduced CCL2 expression compared to rMC-1 cells cultured in the presence of vehicle (FIG. 11E). These results demonstrate that Müller cells in culture release bioactive IL-33 that in turn can induce CCL2 through autocrine activation.

Figure 12A:
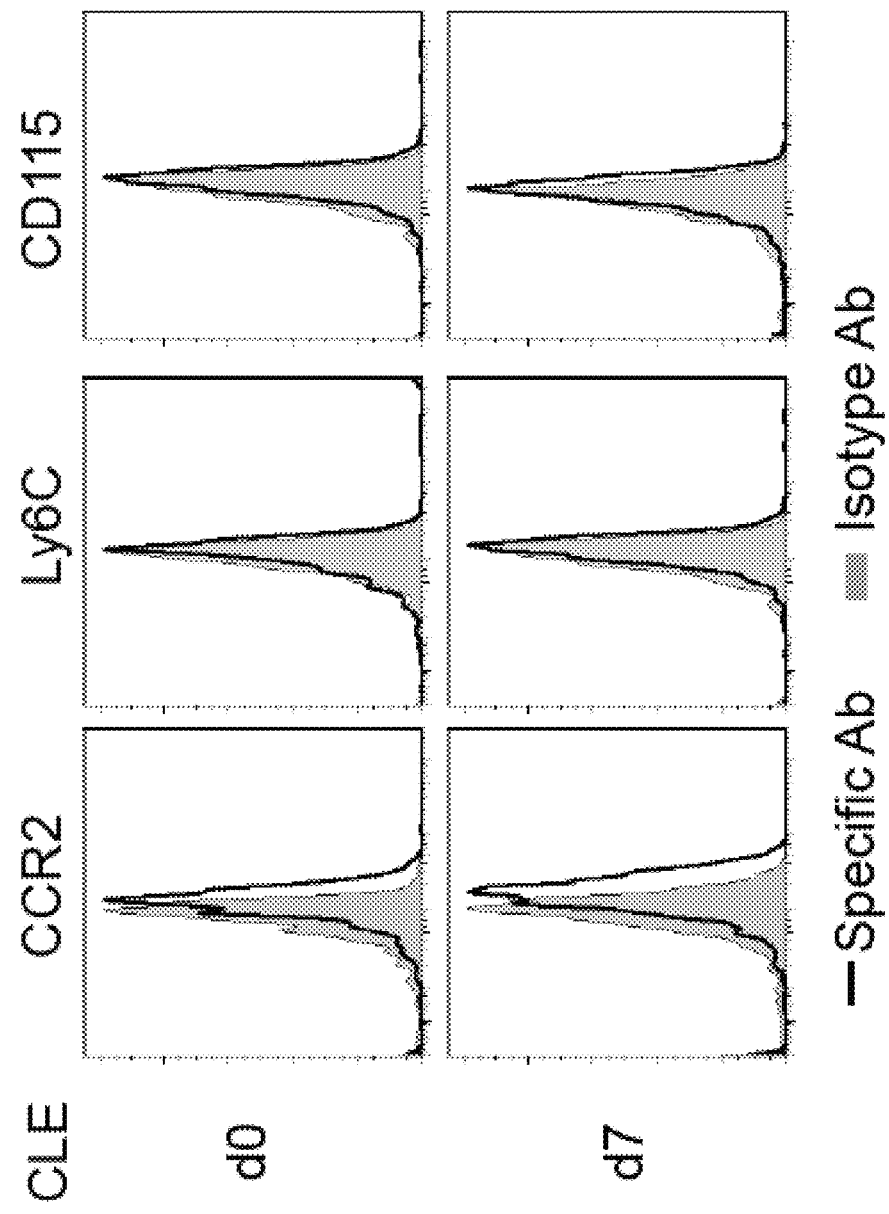
FIG. 12A is a series of graphs showing CCR2, Ly6C, and CD115 expression on retinal $CD11b^+CD45^{lo}$ myeloid cells before (d0) and after CLE (d7) as determined by flow cytometry. The data represent at least two independent experiments with similar results.
Figure 12B:
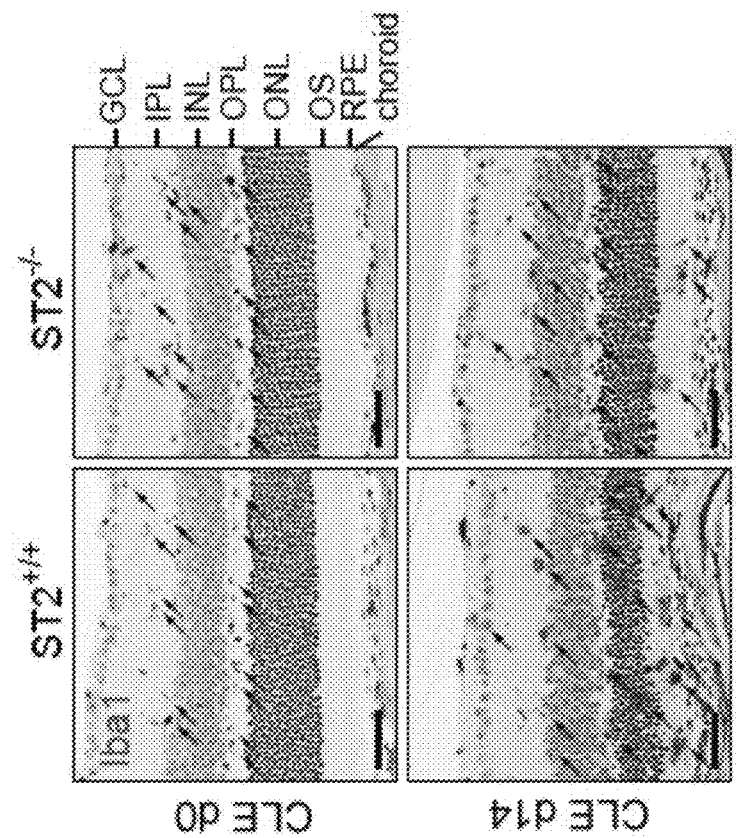
FIGS. 12B and 12C show reduced Iba1+ cells in ONL, OS, and GCL in $ST2^{-/-}$ mice compared with $ST2^{+/+}$ mice upon light exposure. Images (FIG. 12B) show representative immunohistochemistry of Iba1 staining (red). Total $Iba1^+$ cells (arrows) within each retinal layer of the entire superior and inferior retina before (d0) and after CLE (d14) were quantified. The results of the quantification are shown in FIG. 12C. Each data point represents an individual mouse (n=10/genotype). Bars, 40 μm. *, P<0.05; , P<0.01; **, P<0.0001; one-way ANOVA with Tukey's post-test.
Figure 12C:
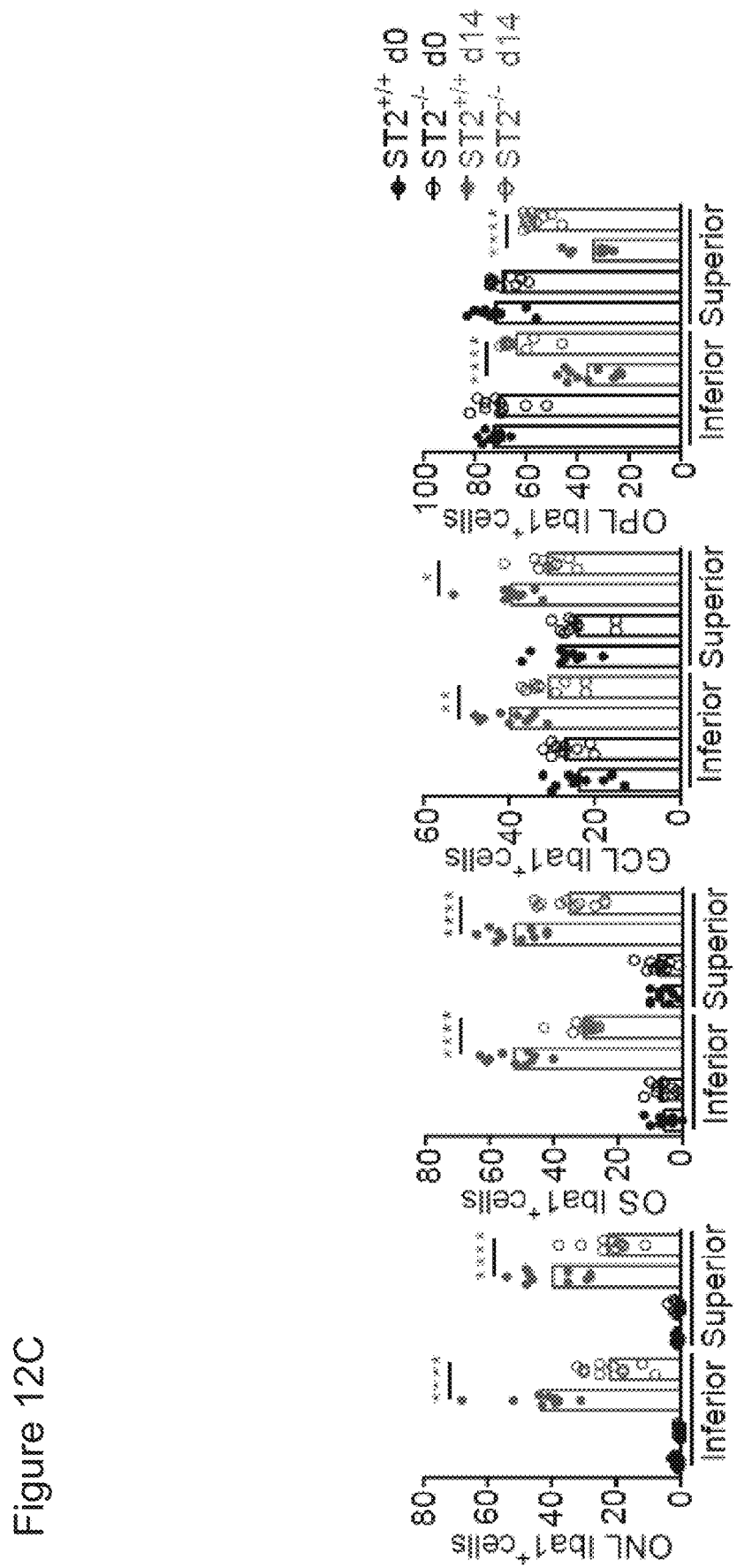

Both $CD11b^+CD45^{lo}$ (FIG. 12A and FIG. 13D) and $CD11b^+CD45^{hi}$ (FIG. 13D) cells in the retina express CCR2, the receptor for CCL2 (FIG. 12A). To determine whether IL-33 had any effect on myeloid cell distribution in the retina, $Iba1^+$ myeloid cells in each retinal layer were quantified before and after CLE in $ST2^{+/+}$ and $ST2^{-/-}$ mice. Before light exposure, $Iba1^+$ cells populated the inner plexiform layer (IPL) and outer plexiform layer (OPL), with very few cells in the ONL, outer segment (OS), and retinal ganglion cell layer (GCL) (FIG. 12B). After CLE for 14 days, $Iba1^+$ cells accumulated in the ONL, OS, and GCL, with a concomitant reduction of $Iba1^+$ cells in the OPL and IPL in $ST2^{+/+}$ mice. $ST2^{-/-}$ mice showed a 40-50% reduction of $Iba1^+$ cells in the ONL and OS, and a 50% increase in $Iba1^+$ cells in the OPL compared to $ST2^{+/+}$ mice (FIG. 12C). Therefore, following CLE, ST2/IL1RAcP signaling promoted CCL2 expression, increased presence of $Iba1^+$ myeloid cells in the outer retina layers, and loss of photoreceptor rods and cones. These results expand on a previously proposed role for Müller cell-secreted CCL2 in promoting myeloid cell presence in the ONL and induction of photoreceptor death following light-injury or retina detachment.

Figure 12D:
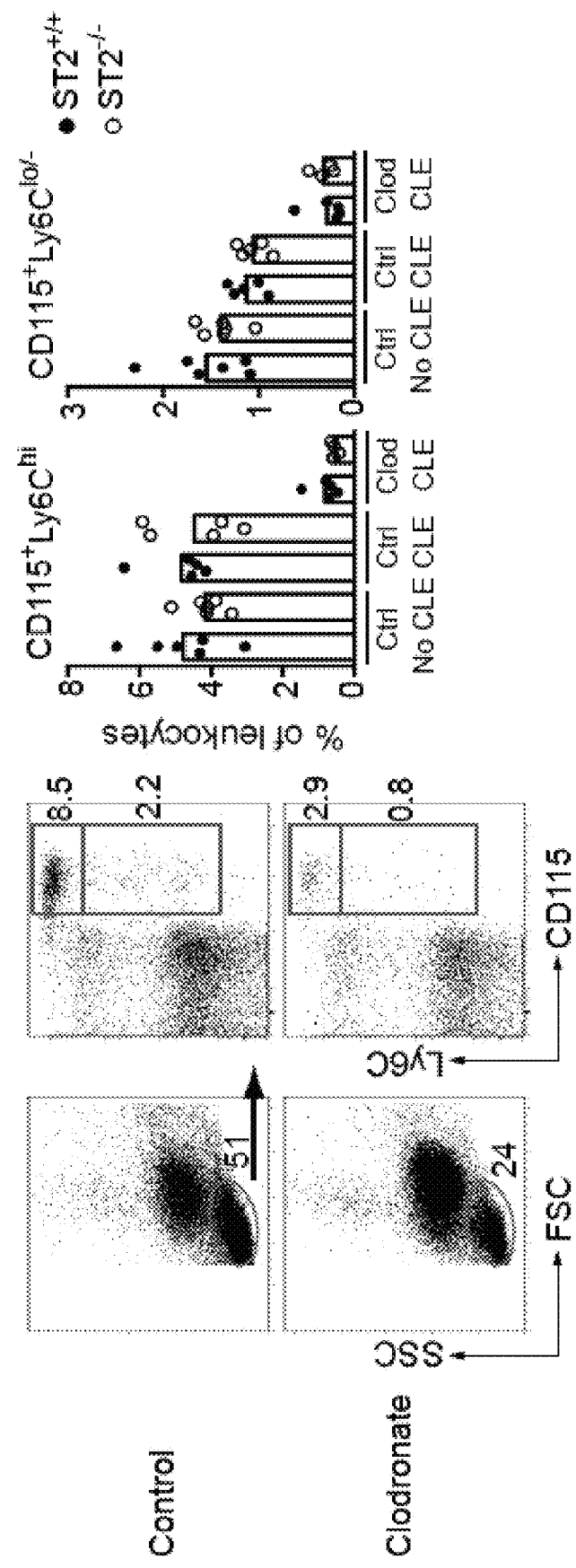
FIG. 12D shows flow cytometry gating strategy to quantify blood monocyte subsets in clodronate depletion during CLE treatment. $ST2^{+/+}$ and $ST2^{-/-}$ mice were treated with clodronate-liposomes (Clod) or control liposomes (Ctrl) daily during CLE. Seven days after CLE, peripheral blood monocytes were quantified by flow cytometry. Representative flow cytometry plots to identify $CD115^+Ly6C^{hi}$ monocytes and $CD115^+Ly6C^{lo/-}$ monocytes are shown (left panel). The results are shown in the graphs in the right panel. n=4-6/group.
Figure 12E:
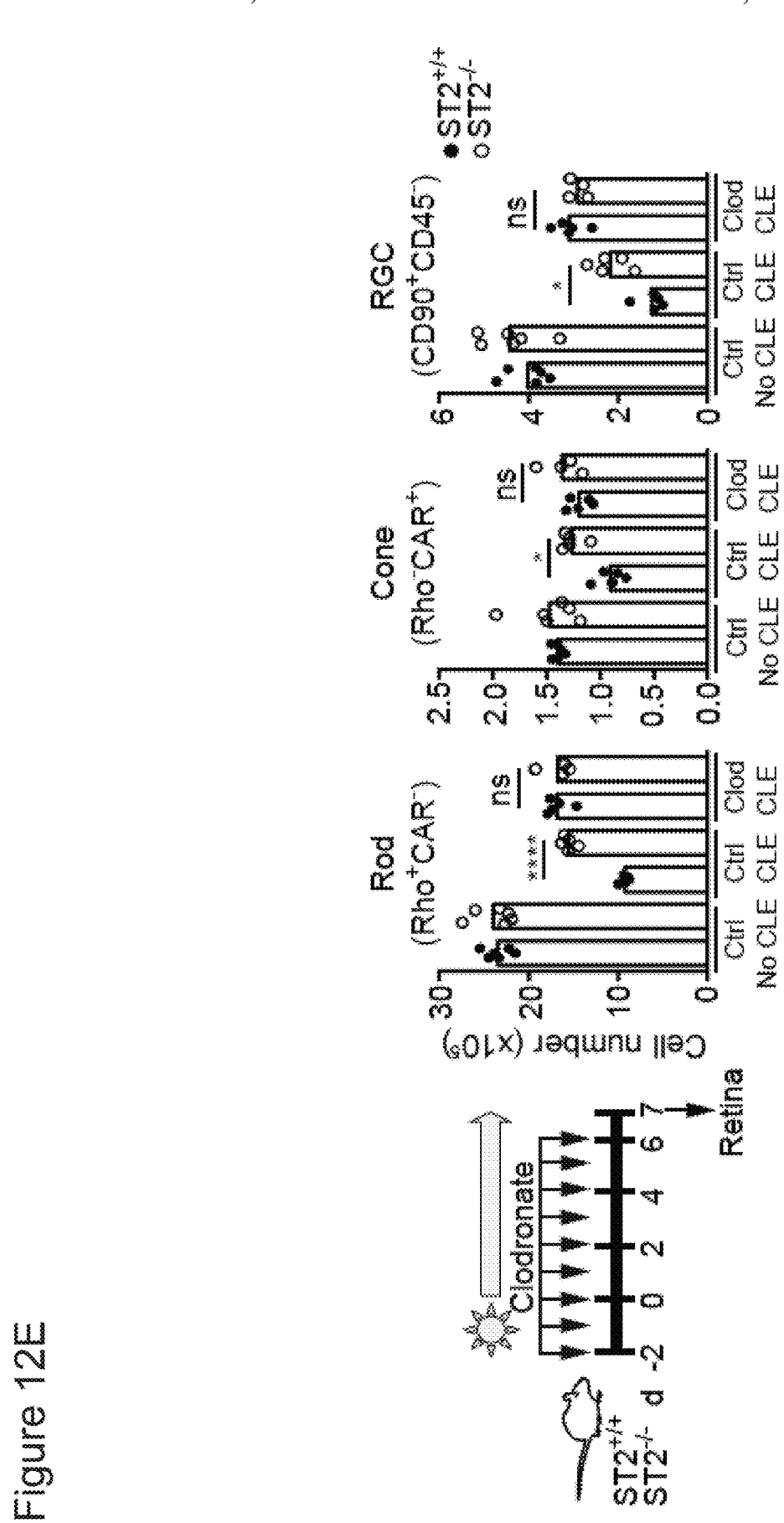
FIG. 12E shows IL-33/ST2-mediated photoreceptor cell loss in CLE is dependent on circulating monocytes. $ST2^{+/+}$ and $ST2^{-/-}$ mice were treated intravenously with clodronate-liposomes (Clod) daily starting 2 days prior to CLE as shown in the diagram in the left panel. Treatment with control liposomes (Ctrl) served as a control. Retinal cells were quantified by flow cytometry 7 days after CLE (see FIG. 12D). n=4-6/group. *, P<0.05; ****, P<0.0001; ns, non-significant; one-way ANOVA with Tukey's post-test. Data represent at least two independent experiments with similar results.

To determine whether IL-33/ST2-induced photoreceptor loss upon light exposure is mediated by infiltrating myeloid cells, we depleted peripheral monocytes in $ST2^{+/+}$ and $ST2^{-/-}$ mice with clodronate and quantified the number of photoreceptors and ganglion cells after 7 days of CLE. Clodronate treatment depleted $Ly6C^{hi}CD115^+$ and $Ly6C^{lo/-}CD115^+$ peripheral monocytes by greater than 80% and 70%, respectively (FIG. 12D). Monocyte depletion resulted in protection of rods, cones, and RGC following CLE in $ST2^{+/+}$ mice (FIG. 12E). However, ST2 deficiency did not provide further protection for photoreceptors when monocytes were depleted, indicating that infiltrating myeloid cells mediate IL-33/ST2-induced photoreceptor loss.

Figure 12F:
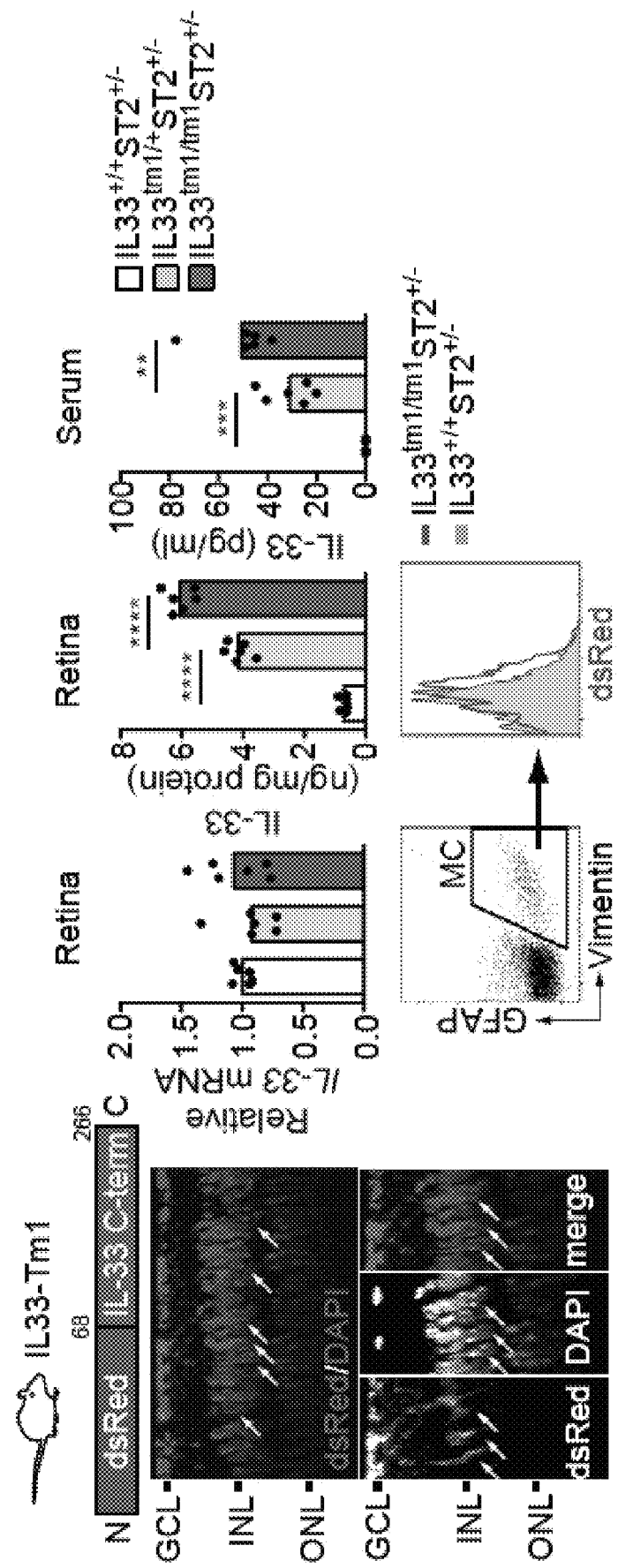
FIG. 12F shows that $IL33^{tm1/tm1}$ mice in which the N-terminal nuclear localization sequence and chromatin binding domain are replaced with dsRed (shown in diagram in left panel) but retaining the C-terminal cytokine domain showed localization of dsRed-IL-33-C-term in the cytoplasm of Müller cells. Images (left panel) are Z-section views of confocal microscopic imaging of $IL33^{tm1/tm1}$ retina flatmount. dsRed signal is shown in red; DAPI signal is shown in blue. Arrows indicate IL-33+ Müller cells. Expression of dsRed-IL-33-C-term in Müller cells was verified by flow cytometry (bottom right panel). While IL-33 mRNA measured by qPCR in $IL33^{tm1/-}$ and $IL33^{tm1/tm1}$ retina was comparable to wild-type (WT) retina, IL-33 protein levels measured by ELISA in the retina and serum in $IL33^{tm1/-}$ and $IL33^{tm1/tm1}$ mice were significantly higher than those in WT mice, indicating that IL-33 lacking the N-terminus was released from cells. Each data point represents an individual mouse (n=6/genotype). Data are representative of two independent experiments with similar results. , P<0.01; *, P<0.001; ****, P<0.0001; one way ANOVA with Tukey's post-test.
Figure 12G:
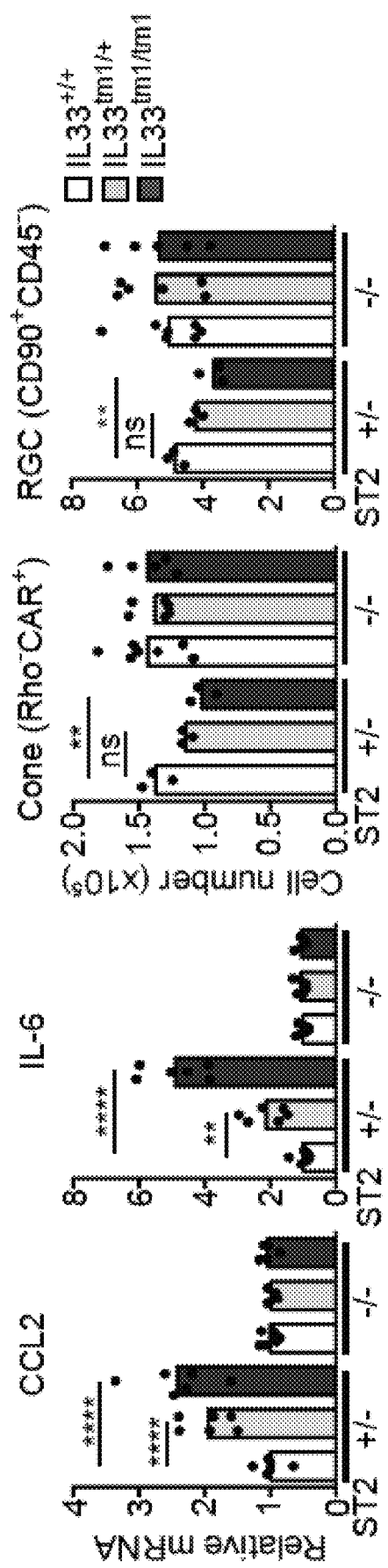
FIG. 12G is a series of graphs showing an ST2-dependent increase of CCL2 and IL-6 expression and loss of cones and RGC in $IL33^{tm1/tm1}$ mice. Retinas from $IL33^{+/+}$, $IL33^{tm1/+}$, and $IL33^{tm1/tm1}$ mice bred on either a $ST2^{+/-}$ or $ST2^{-/-}$ background were analyzed by qPCR and flow cytometry. A significant increase of CCL2 and IL-6 expression, as well as loss of cones and RGC, were observed in $IL33^{tm1/+}$ and $IL33^{tm1/tm1}$ mice in the $ST2^{+/-}$ background, but not in the $ST2^{-/-}$ background compared to $IL33^{+/+}$ control mice. Each data point represents an individual mouse (n=3-7/genotype). Data represent two independent experiments with similar results. , P<0.01; *, P<0.001; ****, P<0.0001; ns, non-significant; one-way ANOVA with Tukey's post-test.

To further determine whether IL-33 released from Müller cells has a pathogenic role, a genetically modified mouse in which the N-terminal nuclear localization signal and chromatin binding domain of IL-33 are replaced with dsRed ($IL33^{tm1/tm1}$ mice) was analyzed (Bessa et al. *J. Autoimmunity* 55: 33-41, 2014) (FIG. 12F). Similar to $IL33^{tm2/tm2}$ mice, the $IL33^{tm1/tm1}$ mice showed dsRed staining selectively in Müller cells of the neural retina. However, in contrast to $IL33^{tm2/tm2}$ mice, where dsRed is anchored to the nucleus via the IL-33 N-terminus, replacing the IL-33 N-terminus with dsRed in $IL33^{tm1/tm1}$ mice prevented IL-33 anchoring to the nucleus, resulting in release of dsRed-IL-33-C-term into the cytoplasm of Müller cell processes spanning the inner nuclear layer (FIG. 12F). Compatible with IL-33 transcription remaining under control of the endogenous promoter (Bessa et al., supra), IL-33 mRNA in the retina was unaltered in $IL33^{tm1/+}$ and $IL33^{tm1/tm1}$ mice compared to $IL33^{+/+}$ littermate mice, while IL-33 protein in serum and retina was elevated (FIG. 12F) due to spontaneous release of IL-33 lacking the N-terminus. In further agreement with a pathogenic role of the IL-33 axis, retina from the $IL33^{tm1/+}$ and $IL33^{tm1/tm1}$ mice showed increased CCL2 and IL-6 expression and loss of photoreceptor cones and ganglion cells when the mice expressed the ST2 receptor chain ($ST2^{+/-}$ background) (FIG. 12G). CCL2 and IL-6 expression and retinal cell loss were restored to control values in $IL33^{tm1/+}$ and $IL33^{tm1/tm1}$ mice lacking ST2 (FIG. 12G). These results indicate that IL-33, when deprived of its capacity to localize to the nucleus, is released from the cell and induces ST2-dependent cytokine and chemokine release, along with death of retinal cells.

E. Circulating Monocytes Homing to the Retina are Required for IL-33/ST2-Induced Photoreceptor Cell Loss Following Retinal Pigment Epithelium Disruption The retinal pigment epithelium (RPE) performs an important role in photoreceptor homeostasis through ingestion and recycling of photoreceptor outer segments, inactivating toxic visual cycle products, and fulfilling the metabolic demand of the retina. The RPE also maintains the outer blood-retina barrier integrity (see, e.g., Strauss, "The Retinal Pigment Epithelium." In *Webvision: The Organization of the Retina and Visual System* (Kolb et al., eds.) 1995). Loss of RPE cells has been proposed to be causal to photoreceptor loss in both wet and dry forms of AMD (see, e.g., Bhutto et al. *Molecular Aspects of Medicine* 33:295-317, 2012). Sodium iodate ($NaIO_3$) is an oxidizing compound that irreversibly affects RPE cell survival upon systemic administration (Carido et al. *Invest. Ophthalmol. Vis. Sci.* 55:5431-5444, 2014), allowing investigation of the role of retinal pathways important in photoreceptor loss secondary to RPE cell death.

Figure 13A:
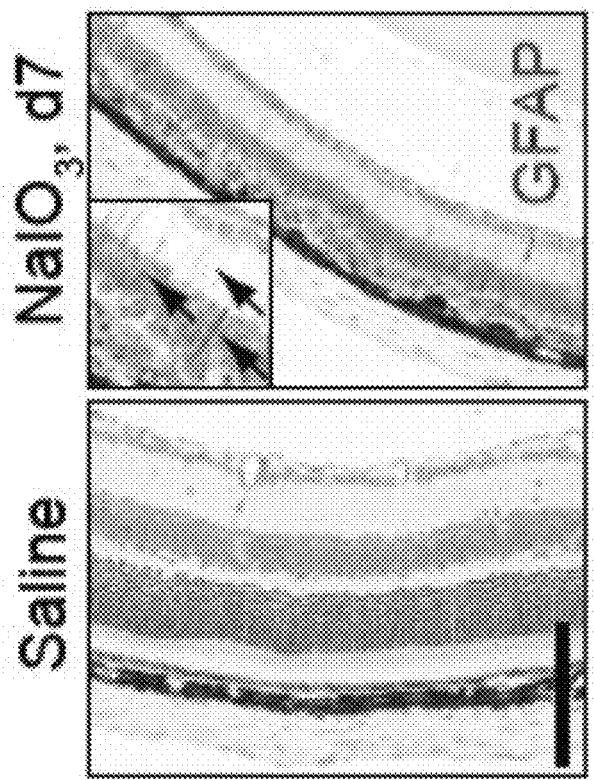
FIG. 13A is a series of images showing Müller cell activation in mice treated with NaIO$_3$. Immunohistochemistry of GFAP expression (red) in mice treated with NaIO$_3$ showed increased GFAP$^+$ Müller cells (arrows) compared to saline treated mice. Bar, 100 μm.
Figure 13B:
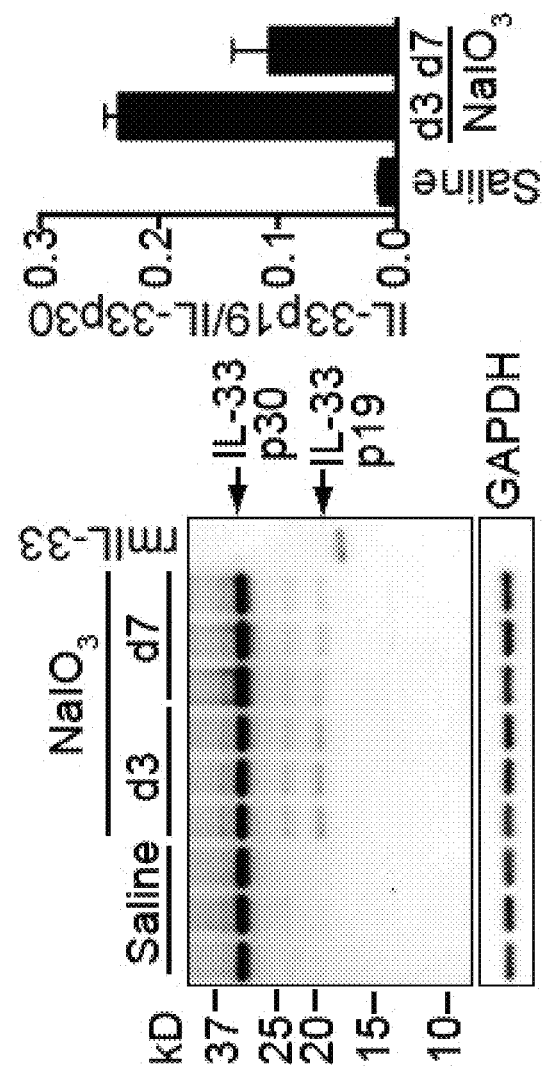
FIG. 13B shows increased IL-33 processing in the retina of mice treated with NaIO$_3$. IL-33 expression in the retina was analyzed by Western blotting (left panel). The ratio of IL-33p19 to IL-33p30 was quantitated with ImageJ software (right panel). The 19-kDa processed form of IL-33 peaked at day 3 following NaIO$_3$ treatment. Data represent two independent experiments.
Figure 13C:
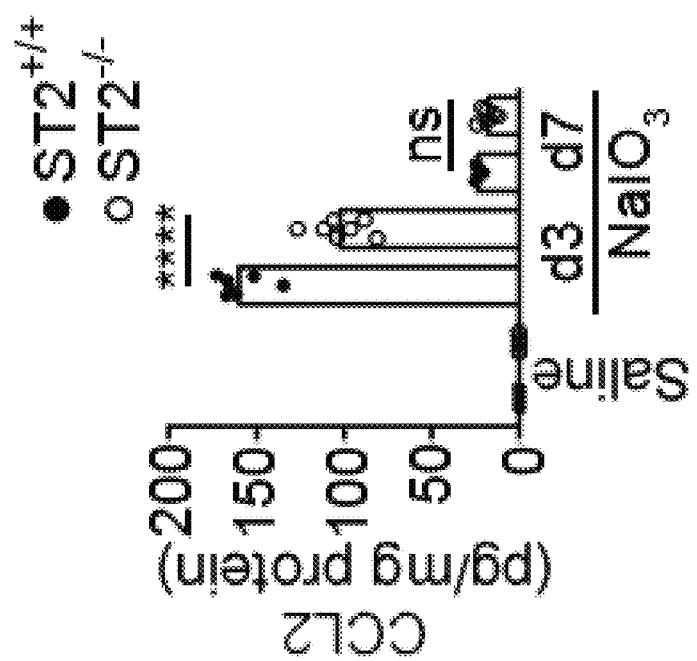
FIG. 13C is a graph showing reduced CCL2 induction in the retina in NaIO$_3$-treated ST2$^{-/-}$ mice compared with ST2$^{+/+}$ mice. CCL2 expression in the retina was determined by ELISA. n=5-7/genotype. ****, P<0.0001; ns, non-significant; one-way ANOVA with Tukey's post-test.
Figure 13D:
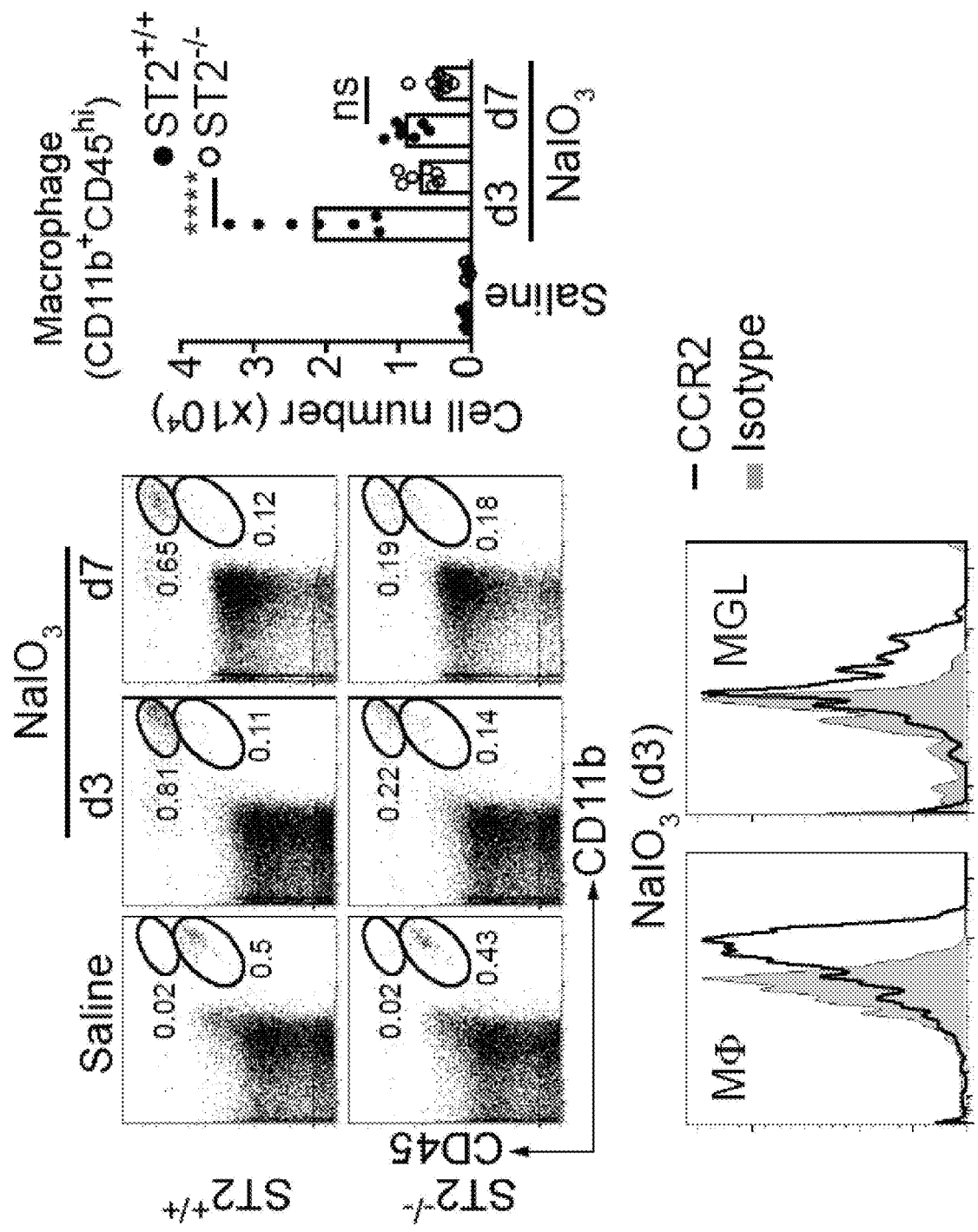
FIG. 13D is a series of graphs showing reduced macrophage infiltration in the retina in NaIO$_3$-treated ST2$^{-/-}$ mice compared with ST2$^{+/+}$ mice. Macrophages (CD11b$^+$CD45$^{hi}$) in the retina were quantified by flow cytometry (top left panel). Retina macrophages express higher level of CCR2 compared to microglia (CD11b$^+$CD45$^{lo}$) (bottom left panel) n=6-7/genotype. Data represent three independent experiments. Mϕ, macrophage; MGL, microglia. ****, P<0.0001; ns, non-significant; one-way ANOVA with Tukey's post-test.
Figure 13E:
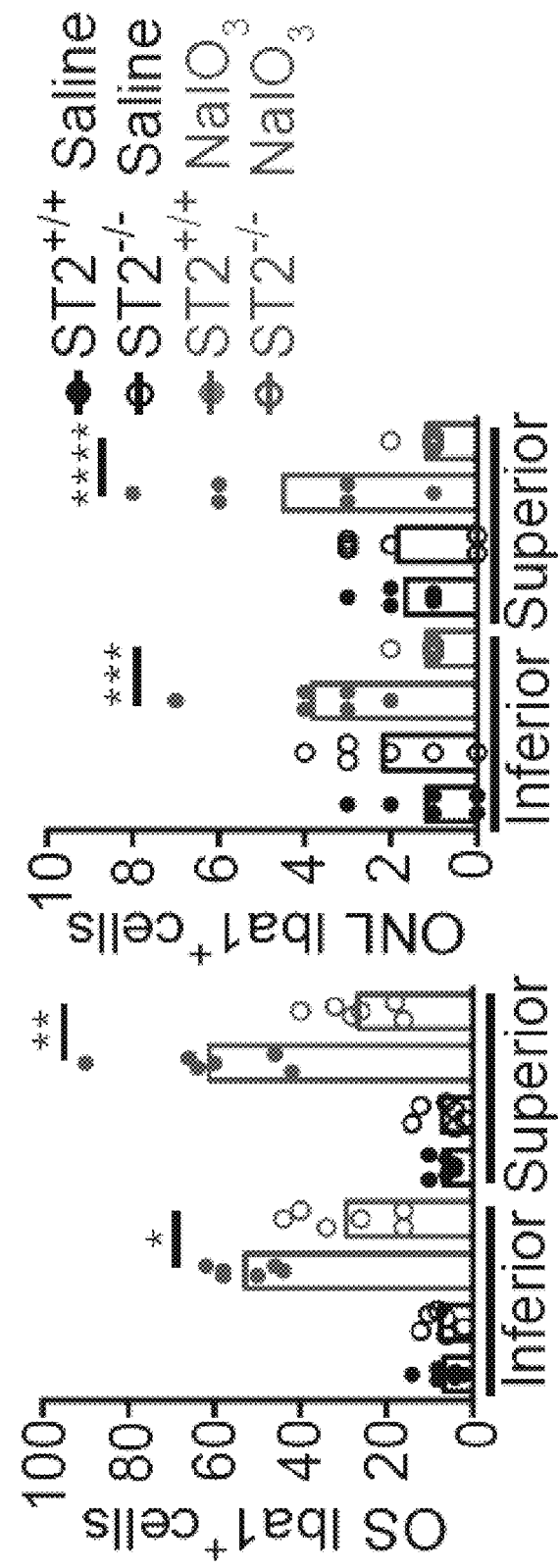
FIG. 13E is a series of graphs showing reduced Iba1$^+$ cells in OS and ONL in NaIO$_3$-treated ST2$^{-/-}$ mice compared with ST2$^{+/+}$ mice. Retina sections were stained for Iba1 by immunohistochemistry. Iba1$^+$ cells in OS and ONL of the entire superior and inferior retina in saline- or NaIO$_3$-treated mice (d3) were quantified. n=6/genotype. *, P<0.05; , P<0.01; *, P<0.001; ****, P<0.0001; one way ANOVA with Tukey's post-test.
Figure 13F:
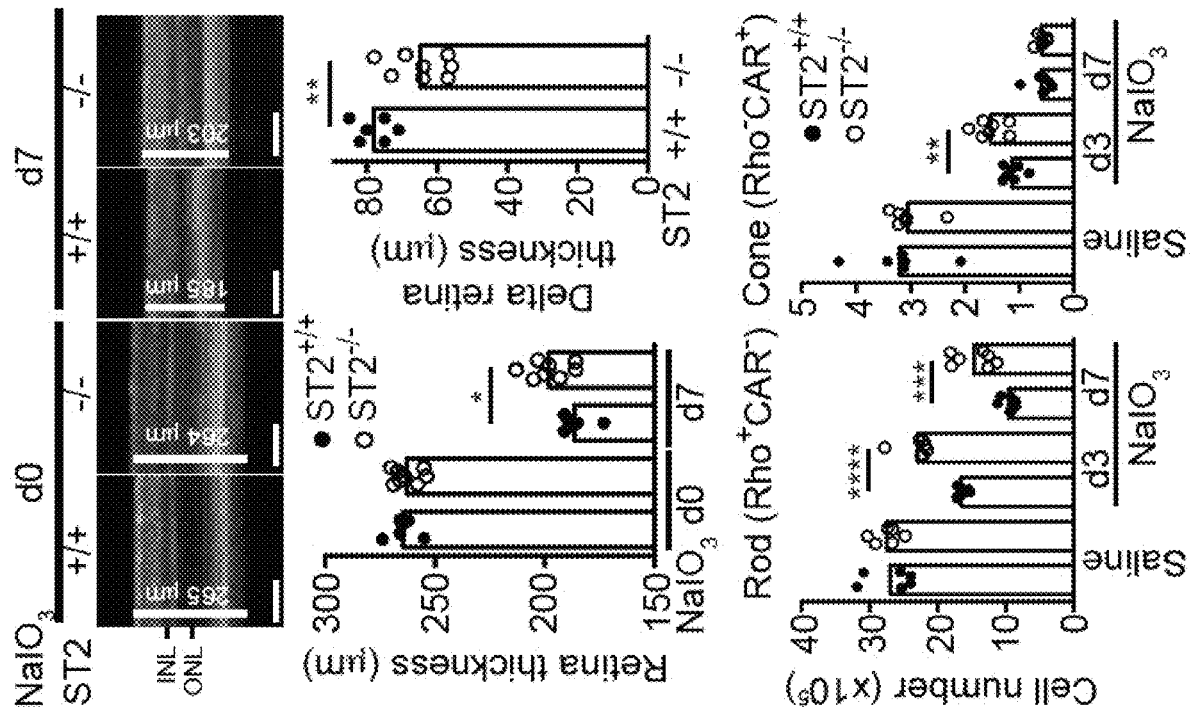
FIG. 13F shows protection of photoreceptors in ST2$^{-/-}$ mice. Retina thickness of ST2$^{+/+}$ and ST2$^{-/-}$ mice before (d0) and after NaIO$_3$ treatment (d7) was measured by OCT (middle panel). Representative cross-sectional OCT images are shown (top panel). Delta retina thickness was calculated by subtracting retina thickness of d0 by that of d7 for individual mouse. Bars, 100 μm. Retinal cells of ST2$^{+/+}$ and ST2$^{-/-}$ mice treated with saline or NaIO$_3$ (d3 and d7) were quantified by flow cytometry (bottom panel). Each data point represents an individual mouse (n=6-8/genotype). Data represent at least two independent experiments with similar results. *, P<0.05; , P<0.01; *, P<0.001; ****, P<0.0001; unpaired two-tailed Student's t test.
Figure 13G:
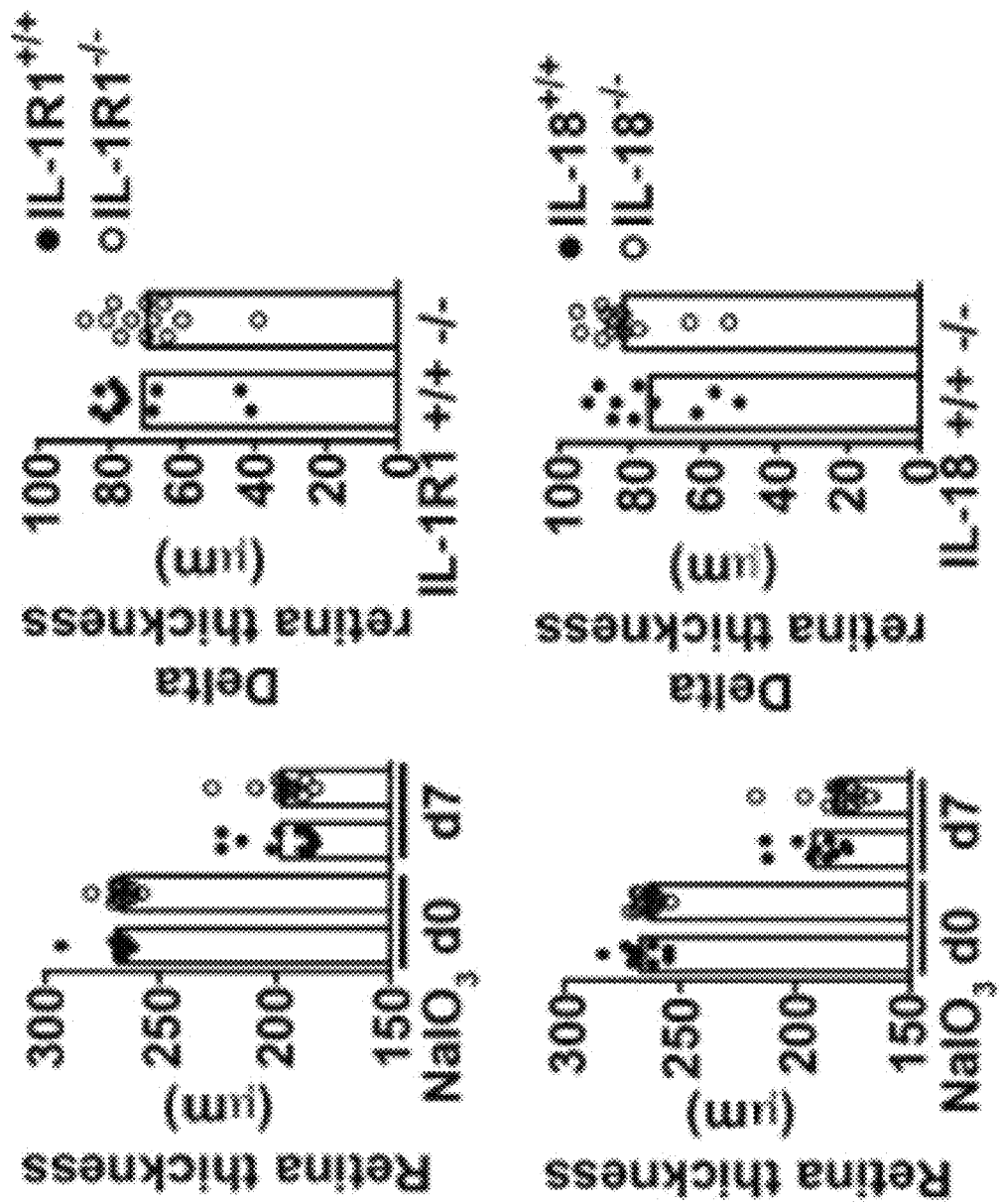
FIG. 13G is a series of graphs showing the lack of retinal protection in IL-1R1$^{-/-}$ and IL-18$^{-/-}$ mice in RPE damage-induced retinal degeneration. IL-1R1$^{-/-}$ and IL-18$^{-/-}$ mice were treated with 20 mg NaIO$_3$. Retina thickness at baseline (d0) and d7 was measured by OCT. Delta retina thickness was calculated by subtracting retina thickness of d0 by that of d7 for individual mouse. Each data point represents an individual mouse (n=10-13/genotype).

Systemic administration of $NaIO_3$ resulted in elimination of the majority of RPE cells in the central retina by day 3. This was accompanied by loss of photoreceptor outer nuclear cells, activation of Müller cells (FIG. 13A), and by the increased presence of 19-kDa processed form of IL-33 (IL-33p19) in the neural retina, peaking at day 3 following treatment (FIG. 13B). Treatment with $NaIO_3$ also resulted in a >1500-fold increase in CCL2 (FIG. 13C). The increase in CCL2 protein levels due to $NaIO_3$ administration was attenuated by approximately 35% in mice lacking ST2 (FIG. 13C). Given that IL-33 stimulation of Müller cells induced CCL2, a chemo-attractant for myeloid cells, an analysis was performed to determine whether blockade of IL-33 affected the number of myeloid cells in the retina. Treatment of $ST2^{+/+}$ mice with $NaIO_3$ resulted in a >20-fold increase in the number of $CD45^{hi}CD11b^+CCR2^+$ myeloid cells present in the retina, peaking at day 3. $ST2^4$ mice showed a ~70% and ~50% attenuated increase in $CD45^{hi}CD11b^+CCR2^+$ myeloid cell numbers at day 3 and day 7, respectively, following $NaIO_3$ treatment compared to $ST2^{+/+}$ mice (FIG. 13D). In contrast, the numbers of $CD45^{low}CD11b^+CCR2^+$ microglia dropped over 5-fold in both $ST2^{+/+}$ and $ST2^{-/-}$ mice at day 3 following $NaIO_3$ treatment and did not recover at day 7. Immunohistochemistry analysis of $Iba1^+$ cells showed approximately 50-60% reduction of infiltrating $Iba1^+$ myeloid cells in OS and ONL in $ST2^{-/-}$ mice compared to $ST2^{+/+}$ mice at day 3 after $NaIO_3$ treatment (FIG. 13E). The neural retina of $ST2^{-/-}$ mice was protected following $NaIO_3$ treatment, as shown by significantly thicker retina in $ST2^{-/-}$ mice compared to $ST2^{+/+}$ mice at day 7 following $NaIO_3$ treatment (FIG. 13F). Significant sparing of rods, cones, and retinal ganglion cells was further demonstrated by FACS analysis. In contrast to $ST2^{-/-}$ mice, the retina of IL-1R1$^{-/-}$ or IL-18$^{-/-}$ mice was not protected compared to WT mice at day 7 following NaIO$_3$ treatment (FIG. 13G).

Figure 13H:
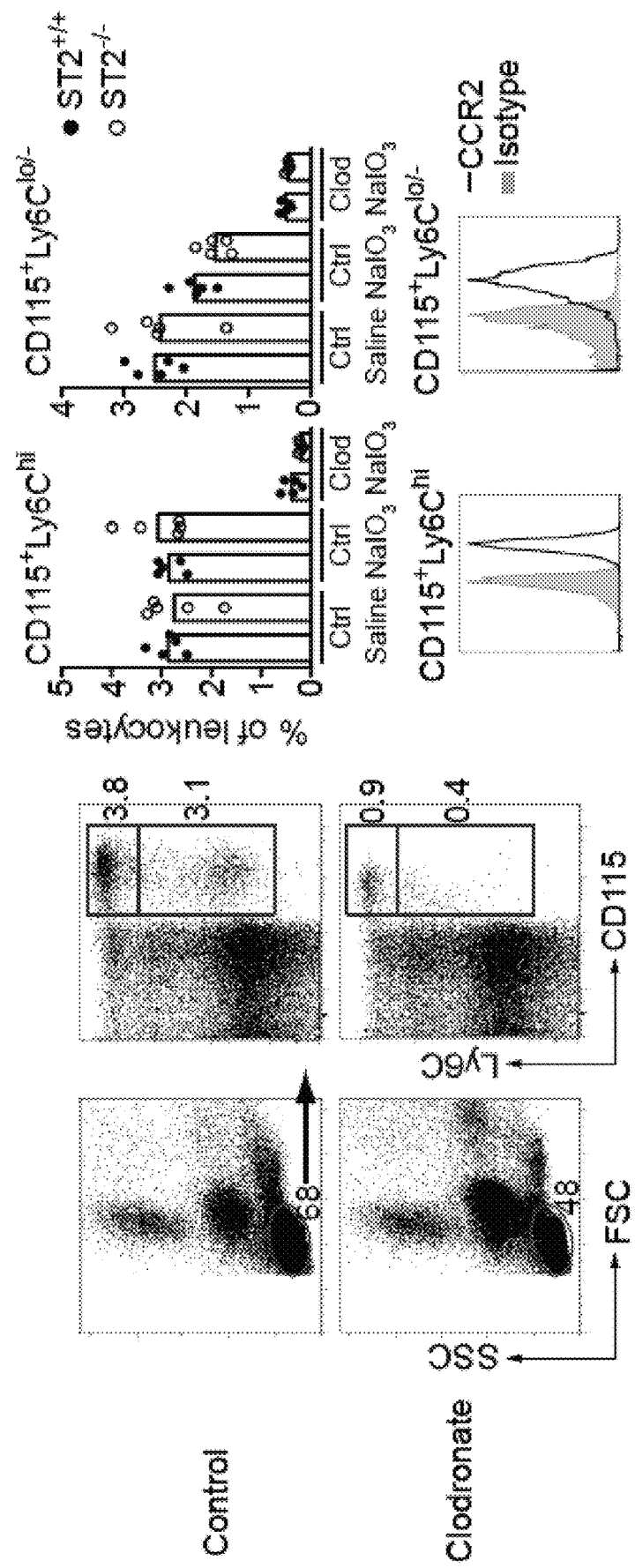
FIG. 13H is a series of graphs showing clodronate depletion of blood monocytes. ST2$^{+/+}$ and ST2$^{-/-}$ mice were treated with clodronate-liposomes ("Clod") or control liposomes ("Ctrl") daily starting 1 day prior to NaIO$_3$ treatment. Three days after NaIO$_3$ treatment, when the mice were euthanized for retinal cell quantification, peripheral blood monocytes were quantified by flow cytometry. Representative flow cytometry plots to identify CD115$^+$Ly6C$^{hi}$ monocytes and CD115$^+$Ly6C$^{lo/-}$ monocytes are shown. Each data point represents an individual mouse (n=5/group).
Figure 13I:
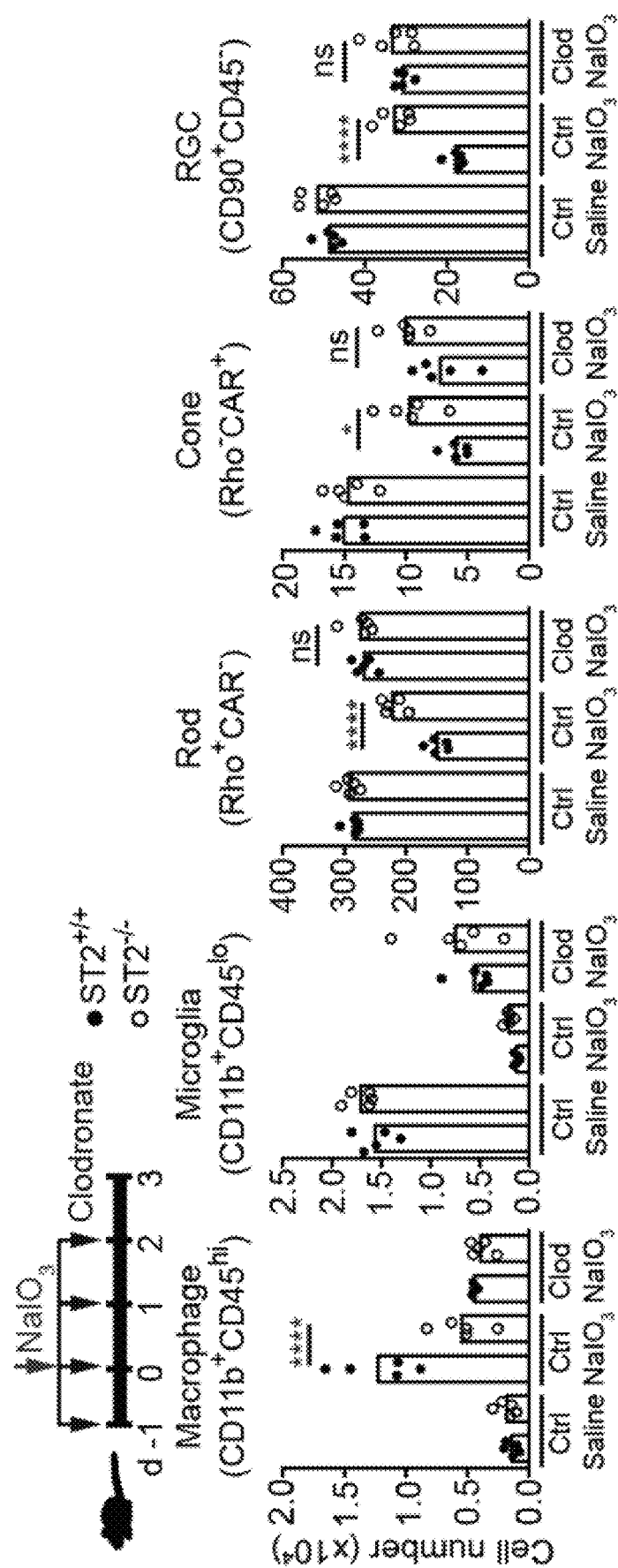
FIG. 13I is a series of graphs showing that IL-33/ST2-mediated photoreceptor cell loss is dependent on circulating monocytes. ST2$^{+/+}$ and ST2$^{-/-}$ mice were treated intravenously with clodronate-liposomes (Clod) daily starting 1 day prior to NaIO$_3$ treatment as shown in the schematic diagram. Treatment with control liposomes (Ctrl) served as a control. Retinal cells were quantified by flow cytometry 3 days after saline or NaIO$_3$ treatment. Each data point represents individual mouse (n=5/group). *, P<0.05; ****, P<0.0001; ns, non-significant; one way ANOVA with Tukey's post-test.

To determine whether infiltrating myeloid cells were required for IL-33-induced photoreceptor loss, peripheral myeloid cells in ST2$^{+/+}$ and ST2$^{-/-}$ mice were depleted with clodronate prior to NaIO$_3$ treatment, and the number of photoreceptors and ganglion cells at day 3 was quantified. Successful depletion of Ly6C$^{hi}$CD11b$^+$CCR2$^+$ and Ly6C$^{lo/-}$CD115$^+$CDR2$^+$ peripheral monocytes and CD45$^{hi}$CD11b$^+$CCR2$^+$ retina macrophages was confirmed by flow cytometry (FIGS. 13H and 13I). Clodronate-mediated myeloid cell depletion resulted in protection of the neural retina following NaIO$_3$-induced RPE cell loss (FIG. 13I). Similar to the results from monocyte depletion experiments in CLE, loss of ST2 did not result in further protection when myeloid cells were depleted, indicating that infiltrating macrophages were required for IL-33/ST2-induced photoreceptor loss when the RPE is disrupted.

In sum, using genetic and pharmacological approaches, these results demonstrated that IL-33 contributes to myeloid cell recruitment to the photoreceptor layer and retina cell loss. In both a light-induced injury model (CLE) and an RPE disruption model, IL-33 axis signaling promoted accumulation of myeloid cells in the ONL and OS layers of the retina. In a model of RPE cell loss, IL-33 axis signaling promoted the accumulation of myeloid cells in the retina. In both rodent models of retina injury and in human AMD, accumulation of myeloid cells in the injured retina was anatomically associated with photoreceptor cell loss.

F. Materials and Methods

Mice

ST2 knock-out (ST2$^{-/-}$) BALB/c mice (eight generations) were obtained from MRC Laboratory of Molecular Biology, Cambridge, UK (see Townsend et al. *J. Exp. Med.* 191:1069-1076, 2000). ST2$^{-/-}$ mice were backcrossed to the C57BL/6 background for ten generations to generate ST2$^{-/-}$ C57Bl/6 mice. IL33$^{tm1/+}$ and IL33$^{tm2/tm2}$ BALB/c mice were obtained from F. Hoffmann-La Roche Ltd., Basel, Switzerland (see Bessa et al. *J. Autoimmunity* 55: 33-41, 2014). Due to significant morbidity and mortality of IL33$^{tm1/+}$ mice, IL33$^{tm1/+}$ mice were crossed with ST2$^{-/-}$ BALB/c mice and maintained on the ST2$^{-/-}$ background. IL33$^{tm1/tm1}$ST2$^{+/-}$ mice were generated by breeding female IL33$^{tm1/+}$ST2$^{-/-}$ mice with male IL33$^{tm1/+}$ST2$^{+/+}$ mice. IL-1R1$^{-/-}$ (Il1r1$^{tm1\backslash mx}$), IL-18R1$^{-/-}$ (Il18r1$^{tm1Aki}$) and IL-18$^{-/-}$ (Il18$^{tm1Aki}$) C57Bl/6 mice were purchased from The Jackson Laboratory. IL-1R1$^{-/-}$ and IL-18R1$^{-/-}$ mice were backcrossed to the BALB/c background by speed congenics to generate IL-1R1$^{-/-}$ and IL-18R1$^{-/-}$ BALB/c mice (nine generations), respectively. Sprague-Dawley rats were purchased from The Charles River Laboratories. All animals were housed in a pathogen-free animal facility with a 12/12 h light/dark cycle at Genentech, Inc, and littermates were used in experiments. Animal experiments were conducted in accordance with protocols approved by the Genentech Institutional Animal Care and Use Committee and with the Association for Research in Vision and Ophthalmology (ARVO) Statement for the Use of Animals in Ophthalmic and Vision Research.

Recombinant Proteins

Recombinant mouse IL-33 (a.a. 109-266) was purchased from R&D Systems. Recombinant rat IL-33 (a.a. 109-264) was generated by subcloning a rat cDNA fragment encoding amino acids 109-264 of IL-33 into a pET28 vector (Novagen). The protein was expressed in *E. coli* and purified by Ni-NTA chromatography followed by gel filtration. Recombinant sST2 was generated by subcloning of mouse soluble ST2 (a.a. 1-337) into a pRK5 expression vector with a 8×-histidine (His) tag at the C-terminus. The fusion protein expressed in CHO cells was purified by Ni-NTA chromatography followed by SUPERDEX® 200 gel filtration. The neutralizing activity of sST2 was verified by blockade of cytokine production from IL-33-stimulated bone marrow-derived mast cell (BMMC). BMMCs were generated and stimulated with IL-33 as described (Moulin et al. *Cytokine* 40:216-225, 2007). Briefly, 10$^5$ cells were stimulated with 1 ng/ml IL-33 in the presence of 20 µg/ml sST2 or a control His-tagged protein in 200 µl RPMI-1640 culture medium in 96-well plates for 24 h. Culture supernatant was collected for measurement of IL-6 and IL-13 by ELISA (R&D Systems). Recombinant IL-33 TRAP in which the extracellular domain (ECD) of ST2 was heterodimerized with the ECD of IL1RAcP was generated using knobs-in-hole technology (see, e.g., U.S. Pat. No. 5,731,168 and Merchant et al. *Nature Biotechnology* 16:677-681, 1998). A pRK5 expression vector encoding the ECD of mouse ST2 (a.a. 26-328) with a C-terminal mIgG2a Fc fragment containing "knob" mutations was co-transfected into CHO cells with a pRK5 expression vector encoding the ECD of mouse IL1RAcP (a.a. 21-350) with a C-terminal mIgG2a Fc fragment containing "hole" mutations. The fusion protein was purified by MabSURE SELECT column (GE Healthcare) and SUPERDEX® 200 gel filtration.

Constant Light Exposure (CLE)

Male BALB/c mice aged 8-12 weeks or Sprague-Dawley rats aged 6-8 weeks were kept in normal housing with light intensity of <100 lux (used as baseline, d0). For light exposure, animals were housed singly in slightly modified normal cages covered with only a flat wire rack with no filter lid. To avoid disruption of light entering the cages, food pellets were placed on the bottom of cages and water was provided through a water bottle attached to the side of the cages. Retinal degeneration was induced by placing the cages on the shelves of a Metro rack outfitted with 48" fluorescent cool white lights above each shelf. The rack was also enclosed in hanging white panels to reflect light evenly back to shelves. Shelf height was adjusted in relation to light source so that light intensity on each shelf was ~1200 lux as measured by a luminometer. Cages were rotated within each shelf and between shelves during CLE to ensure equal light exposure. Animals were exposed to light for various days as indicated before evaluation.

RPE Damage-Induced Retinal Degeneration

Male C57Bl/6 mice aged 6-8 weeks were intravenously injected with 20 mg/kg body weight of sodium iodate (NaIO$_3$) (Sigma). The dosage of NaIO$_3$ was chosen based on previous dose titration experiments assessing RPE damage by fundus imaging and retina thickness change by OCT. Retinas were evaluated 3 or 7 days after NaIO$_3$ injection as indicated. Mice injected with equal volume of saline served as controls.

Spectral Domain Optical Coherence Tomography (SD-OCT)

After CLE, retinal thickness was measured by SD-OCT using the SPECTRALIS® HRA+OCT system (Heidelberg Engineering). To adjust for rodent optics, the system was modified according to the manufacturer's recommendations with a 55° wide field lens placed in front of the camera. Mice were anesthetized by intraperitoneal injection of ketamine (70-80 mg/kg body weight) and xylazine (15 mg/kg body weight). Pupils were dilated with drops of Tropicamide Ophthalmic Solution USP 1% (Bausch & Lomb). Drops of artificial tear were applied bilaterally to prevent corneal dehydration during the procedure. Horizontal volume scans through the region dorsal-temporal from the optic nerve (superior quadrant) were used to evaluate the retina thickness. Total retina thickness was defined as the width from the inner limiting membrane (ILM) to the RPE/choroid layer on the cross-sectional images, and measured using custom automated image segmentation routines in MATLAB® (MathWorks).

Electroretinography (ERG)

ERG recordings were performed with the ESPION²™ electrophysiology system (Diagnosys). Mice were dark-adapted overnight before ERG recording, and all procedures were performed under dim red light. Mice were anesthetized and their pupils dilated as described above. Body temperature was maintained using a homeothermic plate and held at 37° C. A reference electrode was inserted subcutaneously through the forehead and a ground electrode was inserted subcutaneously in the lumbar region. A gold-ring electrode (mouse electrode 1.5 mmø3.2 mm) (LKC Technologies) was placed on the corneal surface of each eye. A drop of GONIOVISC™ Hypromellose Ophthalmic Demulcent Solution 2.5% (HUB Pharmaceuticals) was applied on the cornea to establish an electrical contact between the cornea and the electrode, and to maintain corneal moisture during the procedure. The mice were placed in a platform covered with a COLORDOME™ light stimulator. Eyes were stimulated with white light of three flash intensities (0.05, 1, and 25 cd·s/m²) in five flashes per intensity. Maximum rod recovery between consecutive flashes was allowed by introducing an inter-stimulus interval ranging from 15 s at the lowest stimulus intensity to 1 min at the highest stimulus intensity. Signals were bandpass-filtered at 0.15-1000 Hz and sampled at 2 kHz. Between animals, electrodes were cleaned using ethanol wipes followed by rinsing in sterile PBS. After ERG, ophthalmic ointment was topically applied on the cornea to prevent desiccation. All of the recorded data points were analyzed using custom MATLAB® software (Mathworks) with a-wave amplitude measured from the baseline to the trough of the a-wave while b-wave amplitude from the trough of the a-wave to the peak of the b-wave. Responses to 3-5 flashes of light stimulation were averaged.

Clodronate Depletion of Monocytes/Macrophages

To deplete monocytes/macrophages, a dose of 1 mg in 200 µl volume of liposome-encapsulated clodronate (Encapsula Nano Sciences) was administered intravenously daily starting 2 days or 1 day prior to CLE or $NaIO_3$ treatment, respectively. Control mice received the same volume of control liposomes. To monitor systemic monocyte depletion, blood was collected by cardiac puncture under anesthesia with isoflurane. Erythrocytes were removed from whole blood samples with ACK (Ammonium-Chloride-Potassium) Lysing Buffer (Life Technologies). The cells were then resuspended in flow cytometry buffer, Fc blocked, stained with allophycocyanin (APC)-conjugated anti-CD115 (clone AFS98, eBioscience), fluorescein isothiocyanate (FITC)-conjugated anti-Ly6C (clone AL-21, BD Biosciences) and phycoerythrin (PE)-conjugated anti-CCR2 (R&D systems), and analyzed by flow cytometry.

Subretinal Injection of AAV Vectors

The AAV2/5 vector encoding mouse sST2 (a.a. 1-337)-8×His (SEQ ID NO: 332) under the control of the ubiquitous CAG promoter was custom-made by Vector Biosystems. The amino acid sequence of mouse sST2 (a.a. 1-337)-8×His is provided in SEQ ID NO: 333. Viral activity was verified by infection of HEK293 cells with multiplicity of infection (MOI) of $10^5$ genome copies (GC)/cell. Culture supernatant was harvested 6 days post-infection and analyzed for sST2 secretion by ELISA (R&D Systems) and Western blotting using the goat anti-mouse ST2 Ab (AF1004, R&D Systems). Infection with an AAV empty vector was used as a negative control. For subretinal injection of AAV, mice were anesthetized with ketamine/xylazine and pupils dilated as described above. Under a dissecting microscope, a small incision was made with a 30-gauge needle in the sclera near the junction with the cornea. 1 µl of AAV suspension containing $10^{12}$ GC/ml was injected into the subretinal space of the right eye through the incision using a blunt 33-gauge Hamilton needle and an auto-injection device. After injection, a triple antibiotic (neomycin, polymyxin B, and Bacitracin) ophthalmic ointment was applied topically to prevent infection and drying of the eye prior to recovery from anesthesia.

Vitreous and Retina Tissue Collection

To collect vitreous from rat eyes, rats were euthanized by $CO_2$ asphyxiation and enucleated. After removal of the cornea, the anterior chamber fluid was absorbed with a SUGI® wedge-shaped absorbent swab (Kettenbach Medical). The lens with the vitreous body attached was carefully pulled out from the posterior chamber using an angled microsurgical forceps. The lens-vitreous tissue was placed into a filtered centrifugation tube (Costar) containing 20 µl of protease inhibitor cocktail (Roche) dissolved in PBS and centrifuged at 14,000×G for 5 min at 4° C. The vitreous was collected as the eluent from the lower chamber. The retina was separated from the sclera and pigment epithelium and rinsed in PBS. The retina was either dissociated for flow cytometry analysis or homogenized for ELISA and Western blotting. Retina was homogenized in the cell lysis buffer (Cell Signaling) using a tissue homogenizer (IKA). The retina and RPE/choroid homogenate was centrifuged at 14,000×G for 10 min at 4° C. and the supernatant was collected. The vitreous and retina tissue lysates were stored at −80° C. until analysis.

Flow Cytometry

Retina was isolated as described above and digested with Earle's balanced salt solution (EBSS) containing 20 IU/ml papain and 200 IU/ml DNase (Worthington Biochemicals) for 30 min at 37° C. Tissue was dissociated by gentle pipetting. Papain digestion was terminated by resuspending the retinal cells in EBSS containing the ovomucoid protease inhibitor (Worthington Biochemicals). Total retinal cells were quantified by mixing an aliquot of single cell suspension 1:1 with a standard concentration of 6 µm FLUORES-BRITE® YG microspheres (Polysciences) followed by counting on an LSRFORTESSA™ flow cytometer (BD Biosciences). Live cells were gated on propidium iodide-negative (PI⁻) cells. Primary retinal cells were resuspended in flow cytometry buffer (PBS containing 0.5% bovine serum albumin and 2 mM EDTA, pH 8) and incubated with anti-CD16/CD32 (BD Biosciences) for 30 min to block non-specific staining. Mouse retinal cells were stained with PE-CY7-conjugated anti-CD11b (clone M1/70, BD Biosciences), APC-conjugated anti-CD90.2 (clone 53-2.1, BD Biosciences), ALEXA FLUOR® 700-conjugated anti-CD45 (clone 30-F11, BioLegend), FITC-conjugated anti-ST2 (clone DJ8, MD Bioproducts), PE-conjugated anti-CCR2 (R&D systems), and FITC-conjugated anti-Ly6C and PE-conjugated anti-CD115 (clone AFS98, eBioscience). Rat retinal cells were stained with PE-CY7®-conjugated anti-CD11b/c (clone OX-42, BD Biosciences), APC-conjugated anti-CD90 (clone OX-7, BD Biosciences), and/or ALEXA FLUOR® 700-conjugated anti-CD45 (clone OX-1, BioLegend).

To detect intracellular markers for both mouse and rat, the following fluorophore-conjugated antibodies were generated using the antibody conjugation kits (Abcam) according to manufacturer's instructions: PE-conjugated anti-cone arrestin (CAR) (EMD Millipore), PE-CY7®-conjugated anti-rhodopsin (Rho) (clone 1D4, EMD Millipore), PerCP-CY5.5®-conjugated anti-glial fibrillary acidic protein (GFAP) (clone GA5, Thermo Scientific). ALEXA FLUOR® 647-conjugated anti-vimentin (clone D21H3) was purchased from Cell Signaling Technology. Cells were stained with violet fixable viability dye (Life Technologies), fixed and permeabilized by using INTRAPREP™ permeabilization reagent (Beckman Coulter) according to the manufacturer's instructions. Cells were then stained with the antibody cocktail for 30 min and washed and analyzed on the LSR-FORTESSA™ flow cytometer. Staining of ST2, vimentin, and GFAP in rMC-1 cells was performed in the same way as described for the primary retinal cells. All data was acquired with BD FACSDIVA™ software and analyzed with FLOWJO® software (FlowJo). Total numbers of rods (Rho$^+$ CAR$^-$), cones (Rho$^-$ CAR$^+$), ganglion cells (CD90$^+$CD45$^-$), microglia (CD11b$^+$CD45$^{lo}$), and macrophages (CD11b$^+$ CD45$^{hi}$) were calculated by multiplying the percentage of each cell type with total live retinal cells.

rMC-1 Stimulation rMC-1 cells (Kerafast) were maintained in low glucose (5.5 mM) in Dulbecco's modified Eagle's medium (LG-DMEM) with 10% heat-inactivated fetal bovine serum (FBS), 100 U/ml penicillin, and 100 µg/ml streptomycin. For high-glucose stimulation, 5×10$^5$ cells were cultured in 2 ml of LG-DMEM with 2% FBS in a 6-well plate at 37° C. overnight. The medium was replaced by either LG-DMEM or high-glucose (25 mM)-containing DMEM (HG-DMEM) with 2% FBS and cultured for up to 72 h. Cell viability was determined by staining the cells with annexin V and propidium iodide (PI) using the FITC Annexin V Apoptosis Detection Kit (BD Biosciences) according to the manufacturer's instructions. Culture supernatant was harvested and IL-33 expression was analyzed by ELISA and Western blotting. For IL-33 stimulation of rMC-1 cells, 2×10$^5$ cells were cultured in 1 ml of LG-DMEM with 10% FBS in a 12-well plate and stimulated with rat IL-33 (1, 10, or 100 ng/ml) for 24 h. ST2-dependent activity of IL-33 on rMC-1 cells was determined by stimulating the cells with IL-33 in the presence of 10 µg/ml IL-33 TRAP or a control Fc protein. CCL2 levels in the culture supernatant were measured by ELISA. To determine autocrine activity of IL-33 in rMC-1 cells, cells were stimulated with high-glucose medium as described above in the presence of 10 µg/ml IL-33 TRAP or a control Fc protein for various time as indicated. RNA and culture supernatant were collected for CCL2 expression by qPCR and ELISA respectively.

ELISA

IL-33 concentrations in the vitreous, retina lysate, serum, and rMC-1 culture supernatant were measured using the mouse/rat IL-33 QUANTIKINE® ELISA kit (R&D Systems). CCL2, IL-1α, IL-1β, ST2, IL-6, and IL-13 were quantified with QUANTIKINE® ELISA kits (R&D Systems). IL-18 was measured with mouse IL-18 ELISA kit (MBL International). Cytokine concentrations in the retina lysate were normalized to total protein content measured by BCA assay (Pierce Biotechnology). To assess IL-33 levels in the vitreous of AMD patients, patients diagnosed with AMD (1 male and 5 females, age 68-91, median age 79) and patients undergoing surgery for macular pucker (3 males and 9 females, age 56-79, median age 72) and macular hole (5 males and 16 females, age 46-75, median age 65) were acquired from Midwest Eye Institute, with approval from Western Institutional Review Board (WIRB) and written patient informed consent. Eye dissection and vitreous collection were performed as previously described (Loyet et al. Invest. Ophthalmol. Vis. Sci. 53:6628-6637, 2012). Transconjunctival pars plana vitrectomy was performed under local anesthesia using a 25-gauge cannula (Alcon). IL-33 levels in the vitreous were measured using the human IL-33 QUANTIKINE® ELISA kit (R&D Systems).

Quantitative RT-PCR

Total RNA was isolated from retina and rMC-1 cells using the RNEASY® Plus Mini kit (Qiagen). First-strand cDNA was synthesized using the High-Capacity cDNA Reverse Transcription kit (Applied Biosystems). Quantitative PCR (qPCR) of IL-33, CCL2, ST2L, sST2, IL-6, IL-1α, IL-1β, IL-18, and GFAP was performed using the TAQMAN® Gene Expression Assay with verified primer and probe sets (Applied Biosystems) and the levels were normalized by expression of 18s rRNA (mouse) or β-actin (rat). To examine potential alternative splice variants of IL-33 in rMC-1 cells and rat retina, RT-PCR was performed using PCR primers spanning the 5' untranslated region (5'-UTR) (exon 1) to the stop codon (exon 9) of the full-length IL-33 mRNA using the following primers: 5'-TTAAGACCAGCTATCTC-CCATCA-3' (SEQ ID NO: 342) and 5'-ACGTTACATCT-TAGAGAGCTTAAACA-3' (SEQ ID NO: 343). PCR was performed using the EXPAND™ High Fidelity PCR System (Roche) according to the manufacturer's instructions. The resulting PCR products were analyzed by electrophoresis on 1% agarose gel.

Western Blotting

Vitreous, retina lysates, or rMC-1 culture supernatants were separated by electrophoresis on NOVEX® SDS 4-20% Tris-Glycine polyacrylamide gels (Life Technologies) and transferred to nitrocellulose membranes using the IBLOT® system (Invitrogen). After blocking, the membranes were probed with goat anti-mouse C-terminal IL-33 (AF3626, R&D Systems) that cross-reacts to rat IL-33, or rabbit anti-GAPDH (Cell Signaling), followed by probing with appropriate HRP-conjugated secondary antibodies (Jackson ImmunoResearch). Blots were processed by using ECL Plus Western blot detection reagents (GE Healthcare). Nuclear and cytoplasmic fractions of rMC-1 cells were prepared using the NE-PER® Nuclear and Cytoplasmic Extraction reagent (Thermo Scientific) according to the manufacturer's instructions. Protein concentration was quantitated by the BCA protein assay. Equal amounts of protein were analyzed for IL-33 expression by Western blotting as described above. Subcellular fractionation of nucleus and cytoplasm was verified by probing the blot with mouse anti-HDAC2 and anti-HSP90 (EMD Millipore), respectively.

Microarray Analysis

Total RNA was converted to double-stranded cDNA and then to CY® dye-labeled cRNA using an Agilent Fluorescent Linear Amplification kit. CY® dye-labeled cRNA was fragmented and hybridized to Agilent's whole mouse genome array as described in Agilent's In Situ Hybridization Kit Plus. All samples were labeled with CY5® dye and hybridized against CY3® dye-labeled universal mouse reference. Following hybridization, the arrays were washed, dried, and scanned on Agilent's DNA microarray scanner. Array imaging data was analyzed using Agilent's Feature Extraction software 8.5. Raw feature extracted data were processed as previously described (Vander Lugt et al. Nature Immunology 15:161-167, 2014). Microarray data were filtered to include only a single probe per gene, selecting the probe with the highest variance when multiple probes were present for a given gene (Bourgon et al. *Proc. Natl. Acad. Sci. USA* 107:9546-9551, 2010). Differential expression analysis was performed using the limma software package (Smyth, *Statistical Applications in Genetics and Molecular Biology* 3: Article 3, 2004). To identify genes differentially regulated in the ST2$^{-/-}$ mice, probes up-regulated by CLE in ST2$^{+/+}$ mice were identified, selecting probes that showed >1.5-fold change at a Benjamini-Hochberg adjusted P value of <0.01 (see, e.g., Hochberg et al. *Statistics in Medicine* 9:811-818, 1990). These probes were further filtered to those that showed >1.25-fold difference at a Benjamini-Hochberg adjusted P value of <0.05 between ST2$^{+/+}$ and ST2$^{-/-}$ mice.

Gene Ontology Analysis

Genes identified as differentially expressed were subjected to Gene Ontology analysis using the GOstats R package (Falcon et al. *Bioinformatics* 23:257-258, 2007). The set of genes differentially regulated by ST2$^{+/+}$ and ST2$^{-/-}$ mice was used as a test set, and the set of genes differentially regulated by CLE as the universe of genes to consider. The search was restricted to the biological process ontology, using a conditional test of significance. Gene Ontology terms that showed significant enrichment at a nominal (unadjusted) P value of 0.01 were selected.

RNA-seq

For RNA-seq analysis of human retina, post-mortem healthy donor eyes with no history of ocular diseases were acquired from the Lions Eye Institute with written donor informed consent. Donor eyes were enucleated 4 h or less post-mortem and preserved in RNALATER® immediately after collection. The macula is fully contained within the boundaries of superior and inferior temporal vascular arcades and is easily visualized. After the macula was dissected out from the peripheral fundus using dissecting scissors, the macular retina was separated from the RPE and choroid underneath the retina. Total RNA was isolated from the retina using RNEASY® Mini kit (Qiagen). RNA concentration was determined using a NANODROP™ 8000 Spectrophotometer. Samples preserved in RNALATER® usually yield high quality as assessed with an Agilent 2100 Bioanalyzer (Agilent Technologies). RNA-seq libraries were prepared using the TRUSEQ® RNA Sample Preparation kit (Illumina) according to the manufacturer's instructions and then sequenced by an Illumina HISEQ® 2000 system (Illumina). Sequencing data analysis was performed as previously described (Durinck et al. *Nature Genetics* 47:13-21, 2015). Sequencing reads were mapped to the reference human genome (GRCh37), using the GSNAP short read aligner (Wu et al. *Bioinformatics* 26:873-881, 2010). Expression was measured in reads per kilobase per million total reads (RPKM) by normalizing the number of reads aligning to coding sequence in a given gene to the total length of the coding sequence and the total number of reads.

Histology and Immunohistochemistry

For morphometric analysis of the outer nuclear layer (ONL) thickness, eyes were fixed in Davidson's fixative (Electron Microscopy Sciences) for 24 h. Paraffin-embedded 5 µm sections covering the entire retina including the optic nerve were cut along the vertical meridian of the globe and stained with hematoxylin and eosin (H&E). After mounting of the sections, slides were scanned using an Olympus NANOZOOMER® 2.0 HT digital slide scanner (Hamamatsu) running NDP Scan software with an Olympus Uplan SApo 0.75 NA 20× objective lens. Images were analyzed using custom automated image segmentation routines in MATLAB® (MathWorks).

Only sections cut through optic nerves were analyzed. The ONL thickness was measured at a distance of 0.1, 0.2, 0.3, 0.4, 0.6, 0.8, and 1.0 mm starting from either side of the optic nerve head. For imaging of IL33$^{tm2/tm2}$ and IL33$^{tm1/tm1}$ flat-mount retina, eyes were fixed in 4% paraformaldehyde for 2 h and rinsed in PBS. Retina tissues were dissected intact from the globe and stained with 1 µg/ml DAPI (Invitrogen) in PBST buffer (1×PBS, 0.5% TWEEN®-20) for 2 h followed by five times of wash in PBST buffer and rinse in PBS. The retina was flat-mounted and imaged with a Nikon A1R confocal microscope using a 40× objective lens. Images in FIG. 7M and FIG. 12F were optimized by making minor adjustments to brightness and contrast using PHOTOSHOP® (Adobe). For IL-33 and vimentin co-staining of rat eyes, eyes were fixed in Davidson's fixative for 24 h, immersed in 70% ethanol, and processed for paraffin-embedding and sectioning. IHC staining of sections was performed on a Dako Autostainer platform (Dako). After rehydration, sections were treated in Dako Target Retrieval Solution (Dako). Sections were incubated with 5 µg/ml of a mouse monoclonal antibody (mAb) mAb to IL-33 (clone Nessy 1, Enzo Life Sciences) and 0.18 µg/ml rabbit mAb to vimentin (Cell Signaling Technologies) or negative control antibodies in blocking buffer for 1 h. After washing, the sections were incubated with PowerVision Poly-HRP anti-mouse IgG and Poly-AP anti-rabbit IgG (Leica Biosystems) for 30 min followed by detection with diaminobenzidine (DAB) and Fast Red/Naphthol Phosphate reagent (ScyTek). After counterstaining with hematoxylin, the sections were imaged with bright field microscopy. IL-33. GFAP, and Iba1 staining of mouse eyes were performed in the same way with a rabbit polyclonal antibody to GFAP (DAKO) at 1:500 and a rabbit polyclonal antibody to Iba1 (Wako Chemicals) (0.5 µg/ml). Microglia quantification was performed by manually counting the Iba1$^+$ cells in each retinal layer along the full length of retinal sections cut in the vertical meridian including the optic disc. TUNEL staining of rat eye sections was performed with the APOTAG® Peroxidase In Situ Apoptosis Detection Kit (Chemicon) according to manufacturer's instructions.

For IHC analysis of human eyes, eyes from 7 normal donors (5 males and 2 females) with age range of 67-89 years and 7 AMD patients (2 males and 5 females) with age range of 82-92 years were obtained from the Lions Eye Institute with consent of the donors or donor families. Eyes were fixed and sectioned as described above. Fluorescent IHC co-staining of IL-33, vimentin, GFAP, Iba1, and PLVAP were performed using the antibodies to IL-33, vimentin, GFAP, and Iba1 as described above and an in-house mouse monoclonal antibody to PLVAP followed by staining with appropriate fluorescent dye-labeled secondary antibodies or fluorescent dye-TSA (tyramide signal amplification) and counterstaining with DAPI. Slides were scanned with the slide scanner as described above. Brightness was slightly adjusted for images in FIGS. 5A-5C, 5E, and 6A-6B using NDP view 2 software (Hamamatsu) to better visualize the signal, but all images within a panel were similarly modified. IL-33$^+$ and Iba1$^+$ cell quantification were performed by manually counting IL-33$^+$ and Iba1$^+$ cells along an approximately 500 µm-long region in the central and peripheral area of normal eyes or lesion and non-lesion area of AMD eyes.

Statistical Analysis

All data unless otherwise indicated were analyzed and graphed using Prism 6 software (GraphPad). Statistical analysis was performed using an unpaired two-tailed Student's t-test or ANOVA as indicated for comparison between groups. A P value of <0.05 was considered significant.

Example 4. Blockade of Both the IL-33 Pathway and the IL-13 Pathway Leads to a Greater Inhibition of Type 2 Inflammation in the Lung Compared to Blockade of Either Pathway Alone A. *Nippostrongylus brasiliensis* Model of Type 2 (Th2) Inflammation The cytokines IL-33 and IL-13 promote inflammation in Type 2 immune responses, with the majority of data supporting a role for IL-33 in regulating expression of IL-13. It is appreciated that the loss of either the IL-33 pathway or the IL-13 pathway attenuates Type 2 inflammatory responses, revealing non-redundant roles for the individual cytokines in vivo. However, it has been unclear whether the absence of the IL-33 signal impacts Type 2 immunity solely due to a reduction in IL-13, or due to inhibition of additional inflammatory pathways.

Figure 14A:
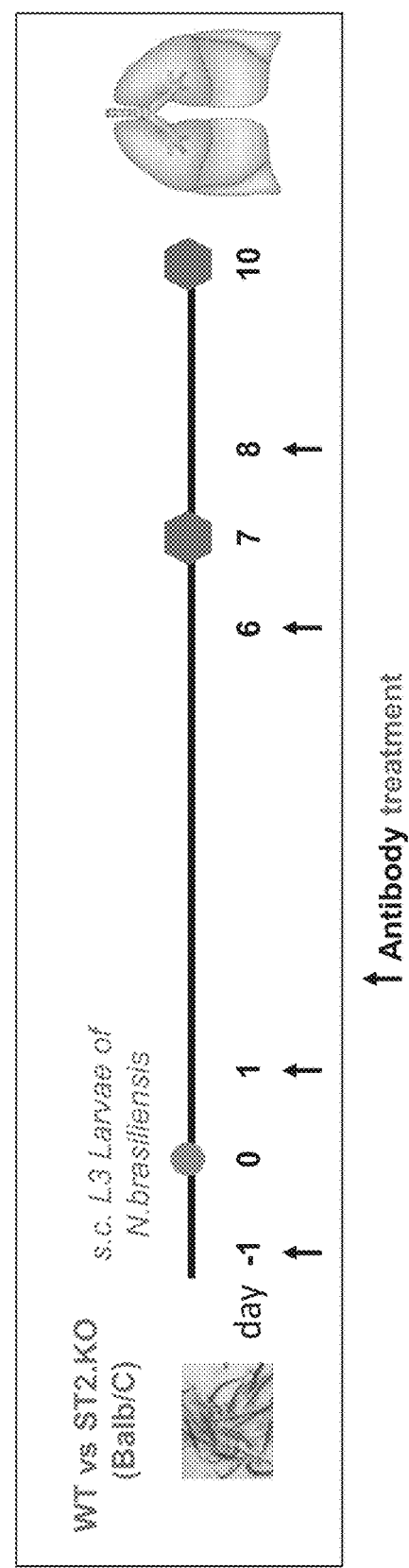
FIG. 14A shows a schematic diagram of the *Nippostrongylus brasiliensis* infection model of Type 2 (Th2) lung inflammation.
Figure 14B:
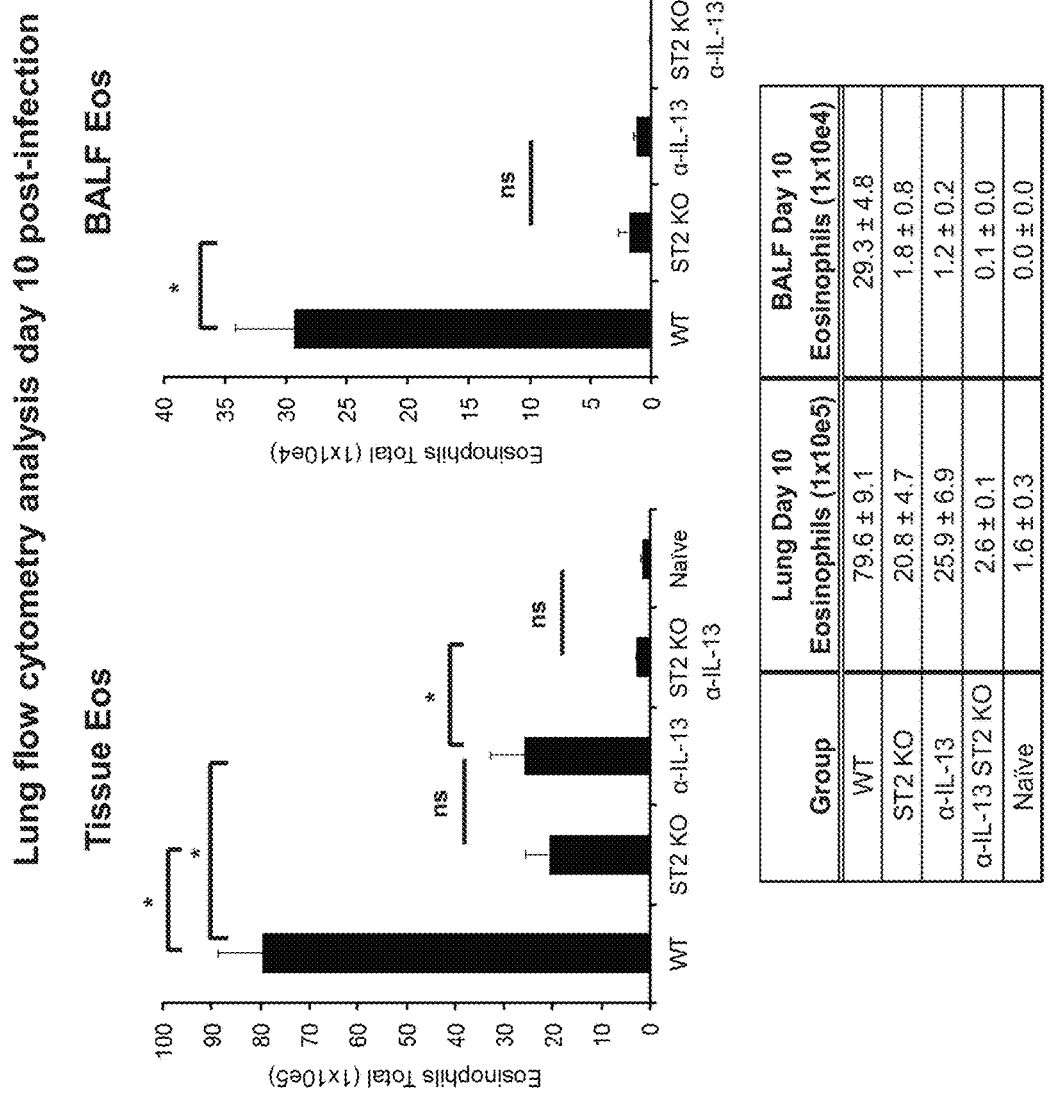
FIG. 14B shows eosinophil (eos) numbers in lung tissue (left panel) and BALF (right panel) derived from ST2$^{+/+}$ and ST2$^{-/-}$ (ST2 KO) mice following infection with *N. brasiliensis*. Mice having the indicated genotypes were treated with control anti-ragweed or anti-IL-13 (α-IL-13) antibodies as described in Section A of Example 4. Naïve ST2$^{+/+}$ mice served as a control. The bottom panel is a table showing the raw data from the study. *, P<0.05; ns, non-significant.
Figure 14C:
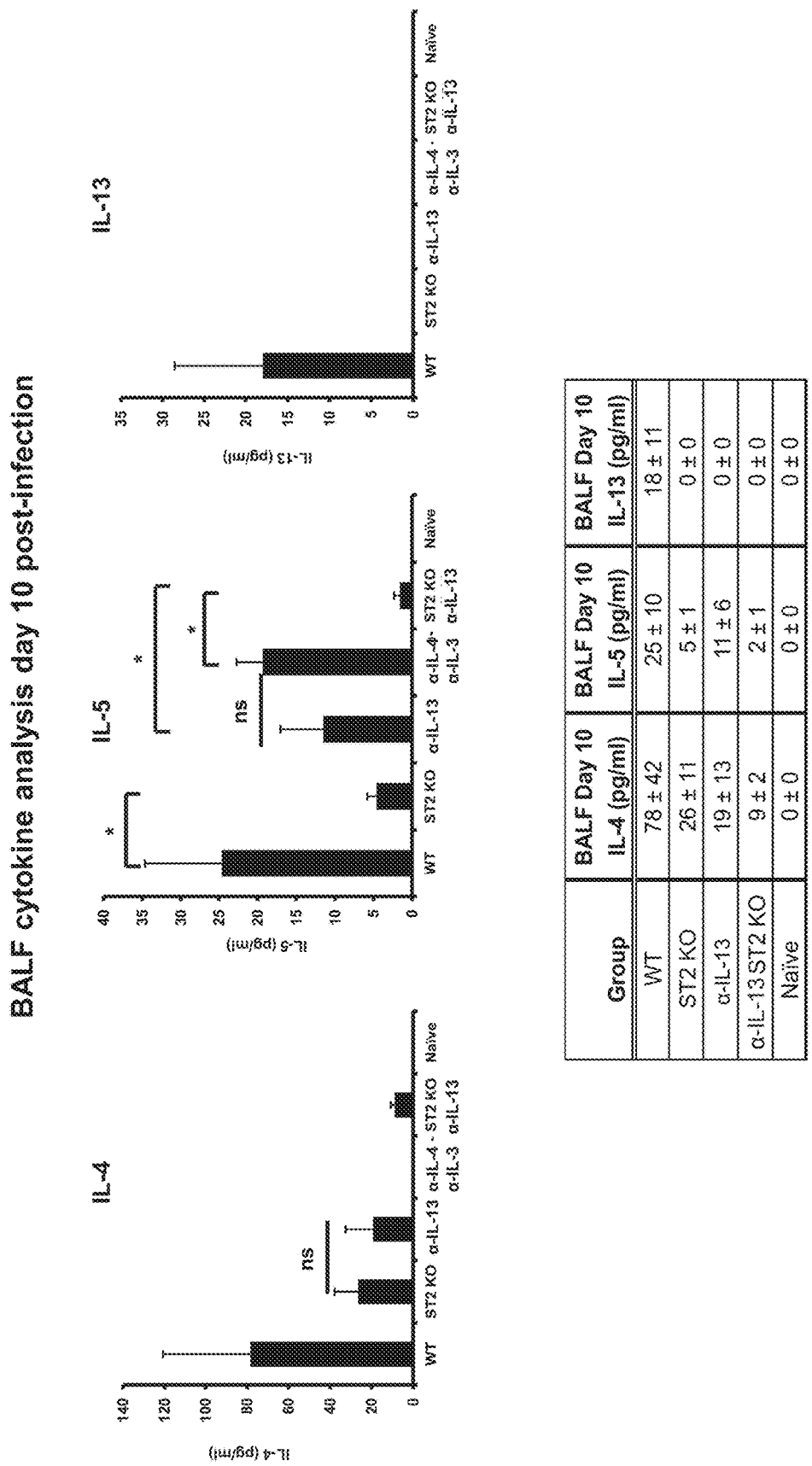
FIG. 14C shows the results of BALF cytokine analysis from the *N. brasiliensis* infection model of Th2 lung inflammation described in Example 4. The levels of IL-4, IL-5, and IL-13 are shown for mice having the indicated genotypes treated with control anti-ragweed, anti-IL-13 (α-IL-13), and/or anti-IL-4 (α-IL-4) antibodies as described in Section A of Example 4. Naïve mice served as a control. The bottom panel is a table showing the raw data from the study. *, P<0.05; ns, non-significant.

To address this question, $ST2^{+/+}$ and $ST2^{-/-}$ mice were challenged with agents that cause Type 2 inflammation in vivo, in the presence or absence of a neutralizing antibody to murine IL-13. The helminth *N. brasiliensis* causes an acute Type 2 inflammatory response in the lung and intestine, characterized by eosinophil mobilization into the tissues and Th2 cytokine production (IL-4, IL-5, IL-13) (see, e.g., *Frontiers in Immunology* 4(74):1, 2013). Both innate and adaptive immune pathways are required for anti-helminthic immunity. $ST2^{+/+}$ mice were treated with anti-IL-13 or control anti-ragweed antibodies to evaluate the role of IL-13 in Type 2 lung inflammation (FIG. 14A). Likewise, $ST2^{-/-}$ mice were treated with control or anti-IL-13 antibodies to assess the contribution of IL-33, and the combined contribution of IL-13 and IL-33 in vivo. Consistent with previous reports (see, e.g., *Nature* 464:1367), *N. brasiliensis* infection caused robust eosinophilic inflammation in both the BALF and lung tissue of $ST2^{-/-}$ mice, which was significantly diminished in the absence of ST2 (i.e., as shown in $ST2^{-/-}$ mice). Similarly, treatment with a neutralizing antibody to IL-13 resulted in a significant reduction in BALF and tissue eosinophils. Surprisingly, the combined blockade of both IL-33 signaling and IL-13 led to a greater inhibition of eosinophil mobilization into the lung, with levels comparable to the naïve controls (FIG. 14B). Furthermore, IL-13 was not detected in the BALF of the $ST2^{-/-}$ mice, consistent with the role for IL-33 in IL-13 induction. In addition, combined blockade of both pathways led to a greater reduction IL-4 and IL-5 in BALF over blockade of either pathway alone (FIG. 14C).

Material and Methods

Female $ST2^{+/+}$ and $ST2^{-/-}$ Balb/C mice aged 7-9 weeks were infected with 500 *Nippostrongylus brasiliensis* (*N. brasiliensis*) L3 larvae suspended in 200 µl of saline via subcutaneous injection on the flank on day 0. After infection, animals were placed on polymixin b- and neomycin-medicated water for five days. Antibodies (200 µg/mouse in 200 µl of PBS) were administered via intraperitoneal (i.p.) injection on days −1, 1, 3, 6, and 8 post-infection (see FIG. 14A). Animals were sacrificed on day 10 post-infection for analysis of lung inflammation. Bronchial lavage fluid (BALF) and perfused lung tissues were collected for flow cytometry and protein analysis. Naïve ST2 and $ST2^{-/-}$ mice were used as controls.

For lung tissue processing, perfused lungs were digested in 2 mg/ml Collagenase D (Roche) for 1 h at 37° C. and dissociated using GENTLEMACS™ C tubes (Miltenyi) according to the manufacturer's instructions. Single-cell suspensions were incubated for 15 min with Fc Receptor Block (2.4G2; BD Pharmingen) before being stained with antibody for 30 min on ice. Eosinophils, neutrophils, and macrophages were analyzed with the following antibodies: biotinylated anti-CD45 (30-F11; eBioscience), allophycocyanin/Cy7-anti-CD11b (M1/70; BD Pharmingen), phycoerythrin/Cy7-anti-CD11c (HL3; BD Pharmingen), phycoerythrin-anti-Siglec-F (E50-2440; BD Pharmingen), allophycocyanin-anti-F4/80 (BM8; eBioscience), fluorescein isothiocyanate-anti-Gr-1 (RB6-8C5; BD Pharmingen), and followed by streptavidin PACIFIC ORANGE™ (S32365; Molecular Probes). BALF cytokines were measured by ELISA.

B. TNP-OVA Study

The *N. Brasiliensis* infection model described above in Section A of this Example is an acute response to a pathogen, and is considered to not reflect the antigen-induced responses seen in chronic allergic inflammation. The question of redundancy between the IL-33 pathway and the IL-13 pathway in allergic inflammation was addressed using the well-characterized TNP-OVA sensitization/challenge model of airway inflammation. In this model, an adaptive immune response against the TNP-OVA antigen is mounted, characterized by eosinophil mobilization into the tissues, and T cell IL-5 and IL-13 cytokine production.

Figure 15A:
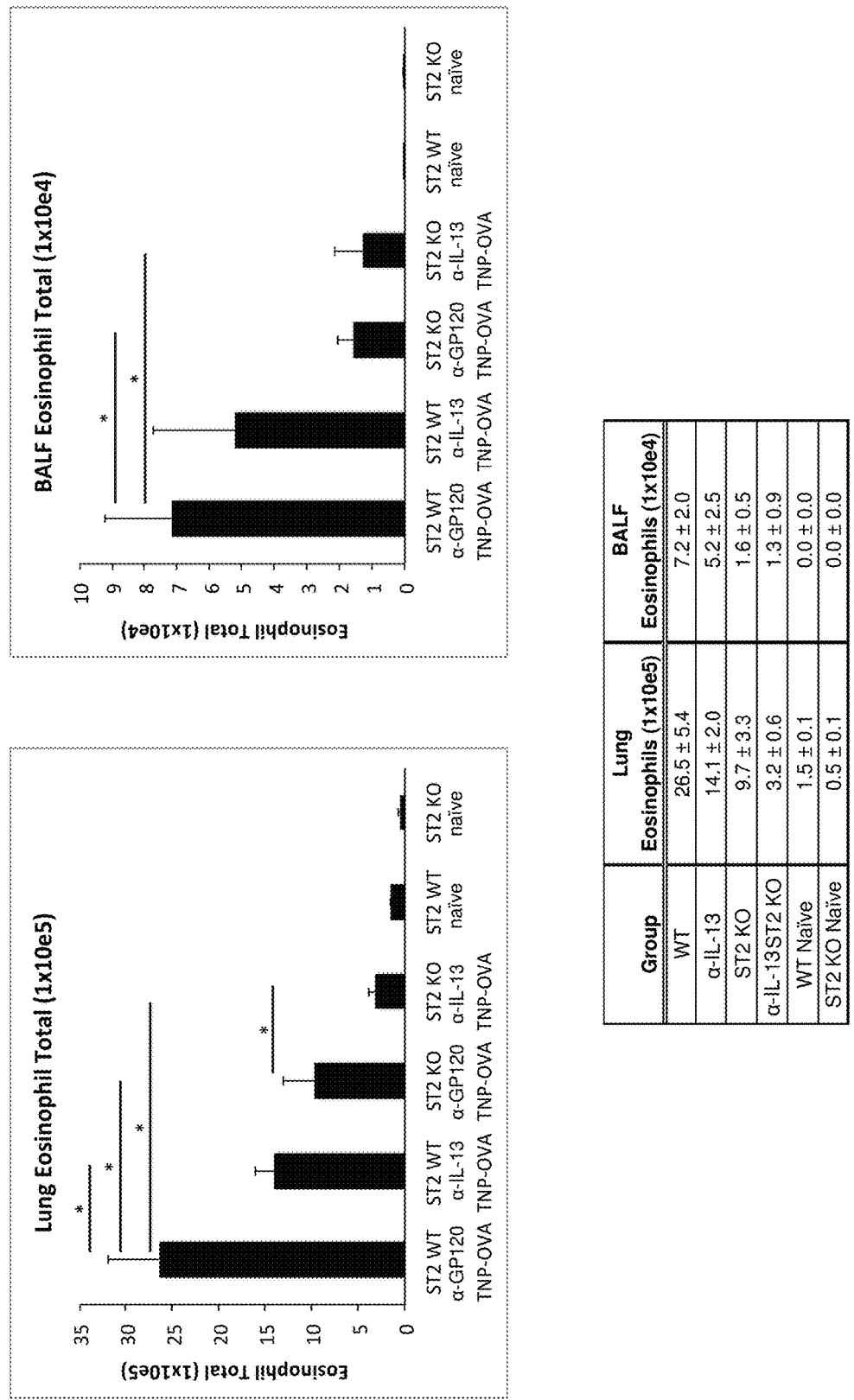
FIG. 15A shows eosinophil numbers in lung tissue (top left panel) and BALF (top right panel) derived from ST2$^{+/+}$ and ST2$^{-/-}$ mice following sensitization/challenge with TNP-OVA antigen. The table in the bottom panel shows the raw data from the study. Mice having the indicated genotypes were treated with control anti-ragweed or anti-IL-13 (α-IL-13) antibodies as described in Section B of Example 4. Naïve mice served as a control. *, P<0.05.
Figure 15B:
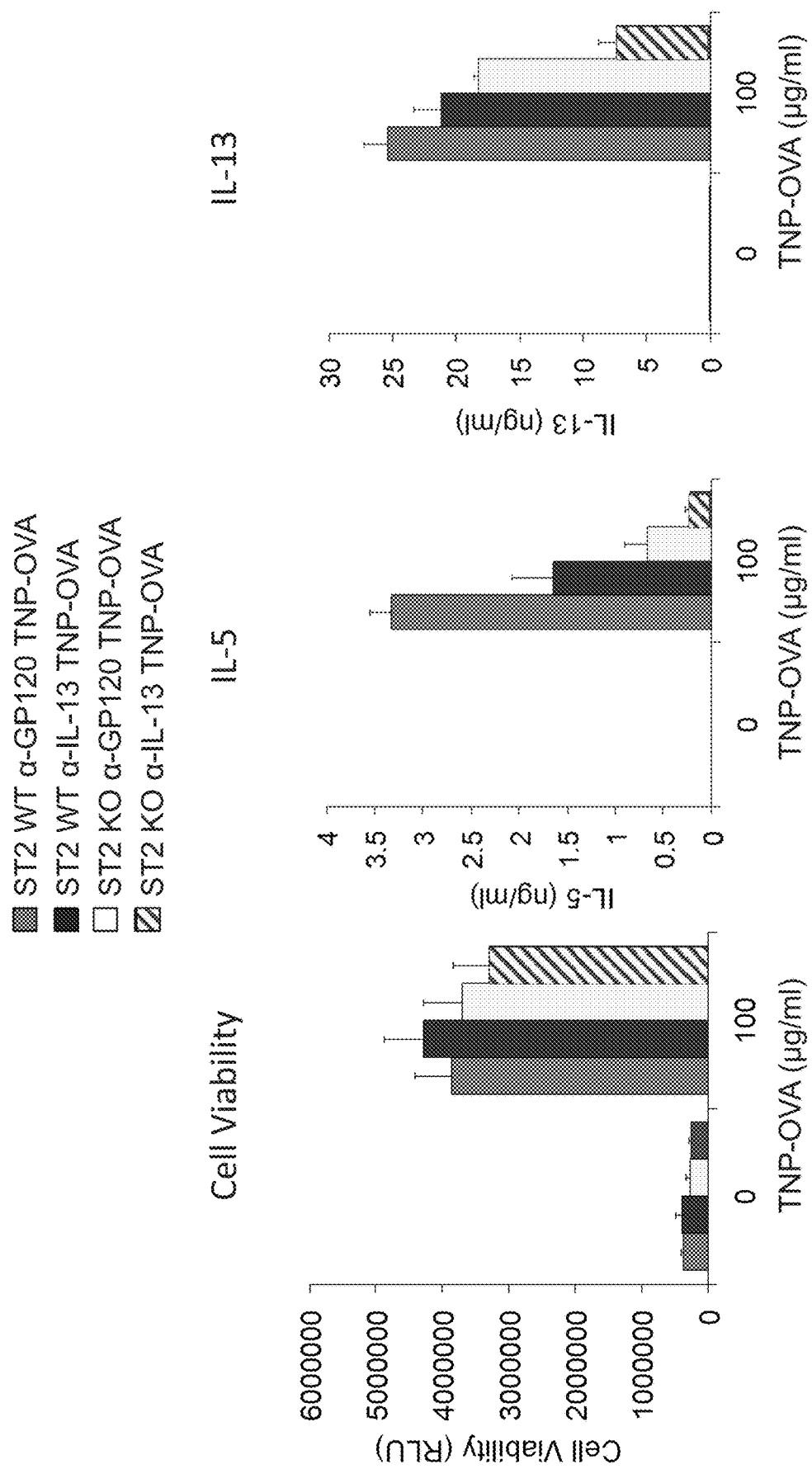
FIG. 15B is a series of graphs showing the cell viability (left panel) and cytokine secretion in an antigen recall assay (IL-5, middle panel; IL-13, right panel) from the TNP-OVA model described in Section B of Example 4. An anti-GP120 (α-GP120) antibody served as a control.

$ST2^{+/+}$ and $ST24^{-/-}$ mice were sensitized with TNP-OVA/Alum and challenged with TNP-OVA in the presence or absence of an anti-IL-13 blocking antibody. Consistent with studies using neutralizing reagents to IL-33 or ST2, the robust eosinophilic inflammation seen in $ST2^{+/+}$ mice following TNP-OVA sensitization/challenge was significantly diminished in the $ST2^{-/-}$ strain (see, e.g., *Exp. Lung Research* 40(2):66, 2014). As previously demonstrated, inhibition of IL-13 also attenuated accumulation of lung tissue eosinophils (Taube et al., *J. Immunol.* 169(11):6482, 2002). In agreement with the *N. brasiliensis* infection study described above in Section A of this Example, the combined blockade of both IL-33 signaling and IL-13 reduced eosinophil influx into the lung to levels seen in naïve mice (FIG. 15A). Analysis of T cell responses to TNP-OVA antigen again revealed the absence of both pathways had a greater effect on IL-13 and IL-5 production over inhibition of each pathway alone (FIG. 15B).

The in vivo studies described in this section and in Section A of this Example demonstrate that blocking both IL-33 and IL-13 had a greater effect on Type 2 lung inflammation compared to blocking either of the pathways individually, and highlight the non-overlapping functions of IL-33 and IL-13. The *N. brasiliensis* helminth infection leads to activation of innate and adaptive immune components, while the TNP-OVA study is a classic model of the adaptive immune response to antigen. Although the models reflect different aspects of Type 2 inflammation, both stress the roles of IL-13 and IL-33 in mediating eosinophilic inflammation, with inhibition of both pathways completely abrogating this response. These data emphasize the additional functions of IL-33 that contribute to inflammation, and the additional benefit that blocking both IL-33 and IL-13 will bring to Type 2 immune disorders including IL-33-mediated disorders such as asthma.

Materials and Methods

Female $ST2^{+/+}$ and $ST2^{-/-}$ Balb/C mice aged 7-8 weeks were sensitized via intraperitoneal (i.p.) injection of 50 µg TNP-OVA and 2 mg alum in 100 µl PBS, on day 0 (Biosearch Technologies). Seven mice were used per group. Starting on day 35 post-sensitization, mice were challenged for 7 consecutive days with aerosol 1% TNP-OVA in PBS via a nebulizer. Anti-gp120 IgG1 or anti-mouse IL-13 IgG1 (100 µg/mouse in 200 µl of PBS) were administered i.p. on days 35-41 post-sensitization. Animals were sacrificed on day 42 for analysis of lung inflammation. BALF and perfused lung tissues were collected for flow cytometry and protein analysis. Mediastinal lymph nodes were collected for T cell recall assays. Naïve ST2$^{+/+}$ and ST2$^{+/+}$ mice were used as controls. BALF cytokines levels were measured by ELISA. Perfused lungs were digested in 2 mg/ml Collagenase D (Roche) for 1 hour at 37° C. and dissociated using GENTLEMACS™ C tubes (Miltenyi) according to the manufacturer's instructions. Single-cell suspensions were incubated for 15 min with Fc Receptor Block (2.4G2; BD Pharmingen) before being stained with antibody for 30 min on ice. Eosinophils, neutrophils, and macrophages were analyzed with the following antibodies: biotinylated anti-CD45 (30-F11; eBioscience), allophycocyanin/Cy7-anti-CD11b (M1/70; BD Pharmingen), phycoerythrin/Cy7-anti-CD11c (HL3; BD Pharmingen), phycoerythrin-anti-Siglec-F (E50-2440; BD Pharmingen), allophycocyanin-anti-F4/80 (BM8; eBioscience), fluorescein isothiocyanate-anti-Gr-1 (RB6-8C5; BD Pharmingen), and followed by streptavidin PACIFIC ORANGE™ (S32365; Molecular Probes).

For the in vitro T cell recall assay, single-cell suspensions from mediastinal lymph nodes (3×10$^5$ cells per well) were cultured for 6 days in the presence or absence of 100 µg/ml TNP-OVA (Biosearch Technologies) in RPMI 1640 media containing 10% FBS and supplemented with L-glutamine and penicillin/streptomycin. After 6 days, cell proliferation was measured by CELLTITER-GLO® Luminescent Cell Viability Assay (Promega) and supernatants were collected for cytokine level analysis via ELISA.

Example 5. Regulation of Mast Cell Degranulation and Cytokine Secretion by IL-33

A. IL-33 Augments Antigen-Induced Mast Cell Degranulation In Vitro and In Vivo

Stimulation of mast cells with antigen-IgE complexes results in the rapid release of vasoactive and proinflammatory mediators from preformed granules. These mediators, which include histamines, proteases, and proteoglycans, serve as a first-line defense against invading pathogens. To determine whether IL-33 augments this response, mast cells were sensitized with IgE for 24 h, and stimulated with anti-IgE in the presence or absence of IL-33 for 1 h. While IL-33 did not induce degranulation by itself, it significantly augmented degranulation of β-hexosaminidase, tryptase, and histamine (FIG. 16A).

To confirm IL-33-dependent augmentation of mast cell activation and degranulation in vivo, a model of passive systemic anaphylaxis was utilized. Following sensitization with anti-dinitrophenyl (anti-DNP) IgE for 28 h, ST2$^{+/+}$ and ST2$^{-/-}$ mice were challenged with DNP-HSA with or without IL-33. The anaphylactic response was measured as a decrease in body temperature over the course of 1 h (FIG. 16B). Similar to the in vitro studies described above, in the absence of antigen, IL-33 did not promote the anaphylactic response (FIG. 16C). Likewise, ST2$^{+/+}$ and ST2$^{-/-}$ displayed similar changes in body temperature following FcεRI (Fc epsilon RI) activation (FIG. 16D). However, in agreement with the in vitro studies, the addition of IL-33 augmented the mast cell response, as demonstrated by the greater drop in body temperature compared to the control group (FIG. 16E).

B. IL-33 Amplifies Antigen-Induced Mast Cell Cytokine Secretion

In addition to degranulation, mast cells contribute to host defense through secretion of cytokines and chemokines. To evaluate the role of IL-33 in mast cell cytokine release, mast cells were sensitized with IgE for 24 hours, and stimulated with anti-IgE in the presence of absence of IL-33 for 72 h. Antigen stimulation resulted in IL-8 secretion, which was augmented by the addition of IL-33 (FIG. 16F). FcεRI crosslinking alone did not result in secretion of IL-5 or IL-13 (FIG. 16F). As reported earlier, IL-33 stimulated the release of IL-5 and IL-13, which was significantly increased with the addition of FcεRI stimulation. In addition, IL-33-mediated release of TNF-α and IL-10 from mast cells was observed (Figure FIG. 16G). Microarray analysis revealed that IL-33 induced a number of chemokines, cytokines, and growth factors (FIG. 16H) (see, e.g., Nagarkar et al. *J. Allergy Clin. Immunol.* 136(1): 202-205, 2015). These results highlight the role of IL-33 in promoting mast cell responses and defense mechanisms.

C. Materials and Methods

In Vitro Mast Cell Assays

Mast cells were isolated as previously described (see, e.g., Nagarkar et al. *J. Allergy Clin. Immunol.* 136(1): 202-205, 2015). Peripheral blood-derived CD34$^+$ cells derived from 10 donors were purchased from Stemcell Technologies (Vancouver, BC, Canada) and were differentiated into primary cultured in vitro CD34 cell-derived human mast cells for a period of 12 weeks in the presence of IL-6 and SCF as described previously. At 0 weeks, the cells were suspended in serum-free Iscove's methylcellulose medium (METHOCULT™ SFBIT H4236, Stemcell Technologies) containing 200 ng/ml SCF, 50 ng/ml IL-6, 5 ng/ml IL-3, 11 µM 2-mercaptoethanol (2-ME, Invitrogen (Carlsbad, Calif.)), 100 U/ml penicillin, and 100 µg/ml streptomycin (Invitrogen), and then incubated at 37° C. in 5% CO$_2$. At 2 weeks of culture, fresh methylcellulose medium containing 200 ng/ml SCF, 50 ng/ml IL-6, 11 µM 2-ME, 100 U/ml penicillin, and 100 µg/ml streptomycin was layered over the methylcellulose cultures. At 4 weeks of culture, a 1 ml aliquot of Iscove's Modified Dulbecco's Medium (IMDM), supplemented with 200 ng/ml SCF, 50 ng/ml IL-6, insulin-transferrin-selenium (Invitrogen), 55 µM 2-ME, 100 U/ml penicillin, and 100 µg/ml streptomycin was layered over the methylcellulose cultures. At 6 weeks of culture, all cells were retrieved after dissolving the methylcellulose medium with PBS. The cells were then suspended and cultured in IMDM supplemented with 100 ng/ml SCF, 50 ng/ml IL-6, 0.1% BSA, insulin-transferrin-selenium, 55 µM 2-ME, 100 U/ml penicillin, and 100 µg/ml streptomycin, and the culture medium was replaced a week later. After an additional week of culture, the culture medium was switched to IMDM supplemented with 100 ng/ml SCF, 50 ng/ml IL-6, 5% FBS (Invitrogen), 55 µM 2-ME, 100 U/ml penicillin, and 100 µg/ml streptomycin. The culture medium was changed weekly thereafter, and the cells were incubated for an additional 5-7 weeks. By the end of 12 weeks, the majority of non-mast cells were expected to undergo attrition. The final purity of the mast cells was determined by measuring FcεRI expression using flow cytometry after 12 weeks of culture following 48 hours treatment with 1 µg/ml myeloma IgE (EMD Millipore, Billerica, Mass.). The final purity of mast cells was 90%. Mast cells from 10 independent donors were generated in this manner.

For microarray analysis of IL-33-stimulated mast cells, mast cells from two donors (1×10 cells/ml) were stimulated with 10 ng/ml IL-33 in duplicate for a period of 24 h. RNA was then collected for microarray analysis. For determining IL-33 responses, mast cells were stimulated with IL-33 as indicated (FIG. 16A) for 48 h. Cell-free supernatants were collected for analysis of IL-5, IL-13, IL-4, IL-10, and TNF-α levels using Meso Scale Discovery Th1/Th2 10-plex panel (MSD, Rockville, Md.) according to the manufacturer's instructions. For IL-33 and IgE crosslinking co-stimulation experiments, IgE-sensitized mast cells ($0.5\times10^6$ cells/ml) were stimulated with IL-33 as indicated in the presence or absence of 10 μg/ml anti-IgE (411520; EMD Millipore) and cell-free supernatants were collected after 72 h. Released cytokine levels were analyzed with ELISA kits for IL-8 (DY208; R&D systems), IL-5 (88-7056; eBioscience) and IL-13 (88-7439; eBioscience).

Degranulation

Human mast cell degranulation was measured as the percentage of β-hexaminodase, tryptase, and histamine released over the total cellular content. The calcium ionophore A23187 (C7522; Sigma Aldrich) was used a positive control at 10 μM. Mast cells were sensitized with 2 μg/ml purified human IgE (AG30P; EMD Millipore) for 24 hours. Sensitized mast cells were washed and resuspended at $6.25\times10^8$ cells/ml in Tyrode's buffer (10 mM HEPES, 130 mM NaCl, 6.2 mM D-glucose, 3.0 mM KCl, 1.4 mM $CaCl_2$, 1.0 mM $MgCl_2$, and 0.1% BSA). Mast cells ($6.25\times10^4$/well) were plated in triplicate in 96-well v-bottom plates and stimulated with 10 μg/ml anti-IgE (411520; EMD Millipore) in the presence or absence of 100 ng/ml human IL-33 for 1 hour, in a final volume of 20 μl. Cell supernatants were collected and cell pellets were lysed with 20 μl of 0.5% TRITON™ X-100 in Tyrode's buffer. β-hexosaminidase release was assayed by using a fluorometric assay. Supernatants and cell lysates (10 μl) were incubated for 1 hour with 50 μl 4 mM p-nitrophenyl-N-acetyl-β-D-glucosaminide (N9376, Sigma Aldrich) in 0.1 M citrate buffer, pH 4.5, and 150 μl 0.2 M glycine was added to stop the reaction. Absorbance was measured at 405 nm in an ELISA reader. Tryptase levels and activity in supernatants and cell lysates were calculated using the Mast Cell Degranulation Assay Kit (IMM001; EMD Millipore) according to the manufacturer's instructions. Histamine levels in supernatants and cell lysates were assayed using a Histamine ELISA kit and following the manufacturer's instructions (409010; Neogen).

Passive Systemic Anaphylaxis

Female $ST2^{+/+}$ and $ST2^{-/-}$ Balb/C mice aged 7-8 weeks were sensitized with 200 μg of DNP-mouse IgE (Biosearch Technologies) in 200 μl of saline via intravenous injection (i.v.) on day 0. Five mice were used per group. After 28 hours, mice were challenged i.v. with 100 μg DNP-HAS (Biosearch Technologies), 2 μg murine IL-33 (R&D Systems), or the combination in 200 μl of saline. Body temperature was measured by scanning an implanted chip with a scanner at 5 minute intervals for 1 h post-challenge.

Gene Expression Analysis

RNA extraction and PCR were performed as previously described (see, e.g., Nagarkar et al. *J. Allergy Clin. Immunol.* 136(1): 202-205, 2015). Total RNA was extracted from mast cells using the Qiagen RNEASY® Kit (Germantown, Md.). cDNA was generated from total RNA using ISCRIPT™ Reverse Transcription Supermix from Bio-Rad (Hercules, Calif.). Amplification of cDNA was performed using TAQ-MAN® Gene Expression Assays (Applied Biosystems, Foster City, Calif.). Fold changes in gene expression, unless otherwise indicated, were compared to respective medium control. For microarray analysis, RNA from mast cell samples was submitted for Agilent single-round amplification.

Microarray Analysis and Statistics

Microarray and statistics were performed as described (see, e.g., Nagarkar et al. *J. Allergy Clin. Immunol.* 136(1): 202-205, 2015). The quantity and quality of total RNA samples were determined, respectively, using an ND-1000 spectrophotometer (Thermo Scientific. Wilmington, Del., USA) and Bioanalyzer 2100 (Agilent Technologies. Santa Clara, Calif., USA). A CY® dye-labeled cRNA preparation and array hybridization were prepared according to the manufacturer's instructions (Agilent Technologies).

Briefly, total RNA sample was converted to double-stranded cDNA and then to CY® dye-labeled cRNA using an Agilent Quick Amp Labeling kit. The labeled cRNA was purified using an RNEASY® Mini kit (Qiagen). cRNA yield and CY® dye incorporation were determined using the ND-1000 spectrophotometer (Thermo Scientific). 750 ng of the labeled cRNA was fragmented and hybridized to Agilent Whole Human Genome 4 44K v2 arrays. All samples were labeled with CY®5 dye and hybridized against a CY®3 dye-labeled universal human reference (Stratagene, La Jolla, Calif. USA). Samples were hybridized for 17 h at 65° C. Following hybridization, the arrays were washed, dried, and scanned using an Agilent scanner. The Agilent Feature Extraction software version 11.5 was used to analyze the acquired array images. All statistical calculations were performed using the R Project software package, version 2.15.1. Array quality control was assessed using arrayQualityMetrics package for R. Microarrays were normalized and probe intensities transformed using the vsn package of Bioconductor. Independent filtering of microarray data was conducted using the genefilter package to increase statistical power to detect true positives while maintaining type I error control.

As array features that are invariant or do not correspond to an Entrez gene transcripts are typically uninformative for differential gene expression analysis, filtering on the basis of annotation and expression variability was conducted. Briefly, filtering was conducted as follows: 1) only array features representing Entrez or CCGf genes were retained; 2) multiple array features corresponding to a single Entrez gene were reduced to a single array feature on the basis of highest inter-quartile range (IQR); and 3) linear model test statistics of gene expression microarray data was performed with the limma package of Bioconductor. In brief, this method utilizes an empirical Bayes approach equivalent to shrinkage of the estimated sample variances towards a pooled estimate, resulting in far more stable inference when the number of arrays is limited. Differential expression test statistics were estimated as a linear contrast of a model including treatment as a factor. Adjusted P-values to account for multiple hypothesis testing was addressed utilizing the method of Benjamini and Hochberg.

Example 6. Pro-Inflammatory Role for the IL-33 Axis in the K/BxN Serum Transfer Arthritis Model A. Loss of IL33 or ST2 Ameliorates Arthritic Disease.

K/BxN serum contains autoantibodies to glucose-6-phosphate isomerase (GPI), which form immune complexes. Administration of these immune complexes to naïve immunocompetent mice induces pathology similar to rheumatoid arthritis, such as joint swelling, bone erosion, immune cell infiltration, and increase in cytokines and chemokines. This reaction is dependent on the innate immune system, including the alternative complement pathway, mast cells, and neutrophils. The non-redundant role of mast cells, in particular during disease initiation, was previously demonstrated (see, e.g., Lee et al. *Science* 297:1689-1692, 2002).

Given the role for IL-33 in mast cell activation (as demonstrated in Example 6), disease activity was examined in IL33$^{-/-}$ (FIG. 17A) and ST2$^{-/-}$ (FIGS. 17B-17D) mice. Consistent with previous reports, deficiency in ST2 resulted in reduced arthritis. A similar observation was seen in the IL33$^{-/-}$ mice. These data expand on cellular studies demonstrating that IL-33 can affect multiple aspects of mast cell function, including pro-inflammatory cytokine secretion, survival, and degranulation.

B. Materials and Methods

Female ST2$^{+/+}$ and ST2$^{-/-}$ C57Bl/6 mice were generated by backcrossing the ST2$^{+/+}$ and ST2$^{-/-}$ Balb/C strain 10 generations. Mice aged 7-8 weeks were administered 20 µl of arthrogenic K/BxN serum on day 0 intravenously (i.v.). Ten mice were used per group. Serum was first tested to determine the optimal amount needed to induce arthritis in ST2$^{+/+}$ mice. Paws were checked daily for evidence of arthritis. The extent of disease was scored by visual observation using the following metric:

0=No evidence of erythema and swelling

1=Erythema and mild swelling confined to the mid-foot (tarsal) or ankle

2=Erythema and mild swelling extending from the ankle to the mid-foot

3=Erythema and moderate swelling extending from the ankle to the metatarsal joints 4=Erythema and severe swelling encompass the ankle, foot and digits Data were plotted as the mean score, which is the sum of the 4 paw scores. Disease severity was determined using the following metric:

Mild (mean score 0-3)

Moderate (mean score 4-8)

Severe disease (mean score 9-above).

The mean score reflects the number of joints involved.

Female IL33$^{+/+}$ and IL33$^{-/-}$ C57Bl/6 mice aged 7-8 weeks were administered 70 µl of arthrogenic K/BxN serum on day 0 intravenously (i.v.). Five mice were used per group. Serum was again tested to determine the optimal amount needed to induce arthritis in the IL33$^{+/+}$ strain. Scoring of disease activity was performed as indicated above.

Example 7. IL-33 Induced Macrophage Recruitment into the Lung is Independent of IL-4, IL-5, and IL-13

The in vivo studies described herein exemplify the non-redundant role for IL-33 in promoting Type 2 inflammation, including, for example, eosinophil recruitment to tissues. However, IL-33 also induces other components of host defense that are not exclusively linked to Type 2 immunity. Macrophages, in particular, contribute to multiple aspects of anti-microbial responses and tissue homeostasis, including phagocytosis, cytokine and growth factor secretion, and wound repair. Central to their function is recruitment to the site of infection, which is mediated in part by cytokines such as IL-33.

To address whether IL-33-induced mobilization of macrophages into the lung is independent of Type 2 cytokines, and therefore indicative of a broader aspect of IL-33 function in immunity, mice were treated with IL-33 in the presence or absence of neutralizing antibodies to IL-4, IL-5, and IL-13 (FIGS. 18A-18C). Given the role for these cytokines in lung inflammation. BALF cellularity was analyzed. Consistent with the roles for these cytokines in eosinophil mobilization, IL-33-induced eosinophil infiltration into BALF was completely abrogated upon blockade of IL-4, IL-5, and IL-13 (FIG. 18C). However, macrophage infiltration into the lung was not perturbed by this treatment (FIG. 18B), emphasizing the unique properties of IL-33 beyond induction of IL-4, IL-5, and IL-13. Given the roles for macrophages in host defense, these data suggest alternative functions for IL-33 in vivo beyond the traditional Type 2 immune responses.

Materials and Methods

Female C57BL/6 mice aged 7-8 weeks were purchased from the Jackson Laboratory. Five mice were used per group. Recombinant mouse IL-33 (a.a. 109-266) was purchased from R&D Systems. A control group of animals received only saline treatments. From days 0-7, mice were injected intraperitoneally (i.p.) daily with either 100 µg of control antibodies or with neutralizing antibodies to IL-4, IL-5, and IL-13 (anti-IL-4 and anti-IL-5 were from R&D Systems, anti-IL13 was generated in-house) (FIG. 18A). On days 1 through day 7, mice were i.p. injected daily with 0.5 µg of recombinant murine IL-33. Mice were euthanized on day 8 and Bronchial Lavage Fluid (BALF) was collected. Cell counts were assessed by flow cytometry analysis. BALF cells were incubated for 15 min with Fc Receptor Block (2.4G2; BD Pharmingen) before being stained with antibody for 30 min on ice. Eosinophils, neutrophils, and macrophages were analyzed with the following antibodies: biotinylated anti-CD45 (30-F11; eBioscience), allophycocyanin/Cy7-anti-CD11b (M1/70; BD Pharmingen), phycoerythrin/Cy7-anti-CD11c (HL3; BD Pharmingen), phycoerythrin-anti-Siglec-F (E50-2440; BD Pharmingen), allophycocyanin-anti-F4/80 (BM8; eBioscience), fluorescein isothiocyanate-anti-Gr-1 (RB6-8C5; BD Pharmingen), and followed by streptavidin PACIFIC ORANGE™ (S32365; Molecular Probes).

Example 8. Characterization of Anti-IL-33 Monospecific and Anti-IL-33/Anti-IL-13 Bispecific Antibodies We previously established a technology to generate human IgG1 bispecific antibodies with two different light chains in *E. coli* (Yu et al., 2011, *Sci Transl Med* 3, 84ra44). The method utilizes knobs-into-holes technology (see, e.g., U.S. Pat. No. 5,731,168, Ridgway et al., 1996, *Protein Eng.* 9, 617-621; Atwell et al., 1997, *J Mol Biol* 270, 26-35, which are incorporated herein by reference in its entirety) to promote hetero-dimerization of immunoglobulin heavy chains. To enable the use of two different light chains without light chain mispairing, we cultured each arm as half antibodies in separate *E. coli* cells. We applied this approach to generate the anti-IL-13/IL-33 bispecific antibody by subcloning the anti-IL-33 and anti-IL-13 parental antibodies into vectors allowing the expression of the anti-IL-33 arm as a human IgG4 hole and of the anti-IL-13 arm as a human IgG4 knob.

A bispecific anti-IL-33/anti-IL-13 antibody referred to as 10C12.38.H6.87Y.58I/IL-13 IgG4 was generated using knob-in-hole (KIH) technology. The anti-IL-33 arm of 10C12.38.H6.87Y.58I/IL-13 IgG4 has a VH amino acid sequence of SEQ ID NO: 36 and a VL amino acid sequence of SEQ ID NO: 37, corresponding to antibody 10C12.38.H6.87Y.58I. The anti-IL-33 arm of 10C12.38.H6.87Y.58I/IL-13 IgG4 has a VH amino acid sequence of SEQ ID NO: 302 and a VL amino acid sequence of SEQ ID NO: 303. The anti-IL-33 arm of 10C12.38.H6.87Y.58I/IL-13 IgG4 has a heavy chain amino acid sequence of SEQ ID NO: 306 and a light chain amino acid sequence of SEQ ID NO: 307, and the anti-IL-13 arm of 10C12.38.H6.87Y.58V1/IL-13 IgG4 has a heavy chain amino acid sequence of SEQ ID NO: 304 and a light chain amino acid sequence of SEQ ID NO: 305.

We based the anti-IL-13 CDRs of the bispecific antibody on lebrikizumab, which has been previously generated and characterized. See, e.g., PCT Publication No. WO 2005/062967. For the bispecific antibody, the anti-IL-13 antibody had two deviations in the FR region as compared to lebrikizumab: Q1E on heavy chain and M4L on the light chain.

For antibody expression, E. coli strain 64B4 was used. An overnight culture was grown at 30° C. in LB (100 µg/ml carbenicillin), diluted 1:100 into 5 ml CRAP media (100 µg/ml carbenicillin) (Simmons et al., 2002, J. Immunol. Methods, 263: 133-147) and grown for 24 hours at 30° C.

For scale-up to 10 L fermenters, initial starter cultures (500 ml) were grown into stationary phase and used to inoculate 10 L fermentations (Simmons et al., 2002, J. Immunol. Methods, 263: 133-147). 10 L fed-batch cultures were grown and whole broths were harvested via microfluidics. The lysed cells were then treated overnight at 4° C. with a final concentration of 0.4% PEI (v/v). Each mixture was subsequently centrifuged at 15,000×g for 20 minutes followed by filtration through a 0.22 µm filter. The IL-33 antibody was then captured at 4° C. on a 400 mL MabSURE SELECT column (GE Healthcare Life Sciences). The column was washed to baseline with 25 mM TRIS pH 7.5, 150 mM NaCl, 2 mM NaN3 (TBS) followed by washes with TBS containing 0.1% Triton X-114 overnight, 0.4M KPO4, 5 mM EDTA, 0.2% Polysorbate 20, 1 mM sodium azide, pH 7.0 and finally washing to baseline with TBS. The IL-33 arm was then eluted with 0.1 M Acetic acid pH 2.7 and the eluted pool titrated to pH 5.0 using 1M Arginine/Succinate pH 9.0.

The identity of the IL-33 and the IL-13 half antibodies were confirmed by liquid chromatography electrospray ionization with time-of-flight (LC-ESI/TOF) analysis. Purity was analyzed by 4-20% gradient Tris-Glycine SDS PAGE gel and aggregate levels were determined by SEC.

Following the assembly reaction with the two half antibodies, the bispecific antibody was purified by hydrophobic interaction, cation exchange and gel filtration chromatography. Specifically, for the assembly, the half antibodies were combined at a 1:1 molar ratio at pH 8.5 in arginine succinate with a 200 molar excess of GSH for 4 days at room temperature and followed by the addition of 5 mM DHAA for 16 hours at 4° C. This material was fractionated on a hydrophobic chromatography column (Thermo ProPac HIC-10) using an ammonium sulfate gradient containing 25% isopropanol at pH 6.5. The pool containing the IL-13/IL-33 bispecific antibody was then dialyzed into 20 mM Histidine, pH 5.5 (H buffer) and loaded onto a cation exchange column (SPFF, GE Healthcare Life Sciences), washed with H buffer containing 0.1% Triton X114, 0.1% Triton X100 overnight, washed to baseline with H buffer and then eluted with 300 mM Arginine succinate pH 5.5. The bispecific antibody fractions were pooled and loaded onto a size exclusion chromatography column (S200, GE Healthcare Life Sciences). The fractions containing the purified anti-IL-13/IL-33 bispecific were pooled, dialyzed and vialed.

The potency of a monospecific anti-IL-33 antibody (10C12.38.H6.87Y.58I IgG4) and the bispecific anti-IL-33/anti-IL-13 bispecific antibody 10C12.38.H6.87Y.58I/IL-13 IgG4 (also referred to herein as "10C12-IL-13 KIH IgG4") as inhibitors of human IL-33 cellular activity was examined using both a cell-based blocking assay using a reporter cell line and in primary human cells. The monospecific anti-IL-33 IgG4 and the bispecific anti-IL-33/anti-IL-13 IgG4 formats were tested against the cellular potency of a decoy receptor, ST2-LZ.

Stimulation of HEK-BLUE™ IL-33 cells with IL-33 results in robust NF-kB and AP-1 activation, which was measured by NF-κB/AP-1-driven SEAP reporter activity. Activity was not perturbed by the addition of the control IgG4 antibody. Both the monospecific anti-IL-33 antibody 10C12.38.H6.87Y.58I IgG4 and the bispecific antibody 10C12-IL-13 KIH IgG4 displayed potent dose-dependent inhibition of IL33 activity, with $IC_{90}$ values of 102.1 and 204.7 pM, respectively (FIG. 19A). As expected, the $IC_{90}$ value for the bispecific antibody activity was approximately half of the value obtained for the monospecific counterpart. Both clones displayed greater inhibition over the decoy receptor, ST2-LZ (see Example 2).

In addition to the cell-based blocking assay using HEK-BLUE™ cells, the monospecific anti-IL-33 antibody 10C12.38.H6.87Y.58I IgG4 and the bispecific antibody 10C12-IL-13 KIH IgG4 were tested for inhibition of IL-33 activity in primary cells. Addition of IL-33 to human basophils results in rapid phosphorylation of the signaling molecule p38, which can be measured by flow cytometry using intracellular staining methods (FIG. 19B). By adding the CD123 marker, basophil activity can be examined within the bulk peripheral blood monocyte (PBMC) population, obviating the need for cell isolation (FIG. 19B). Using this flow cytometry-based methodology, the monoclonal and bispecific antibody clones were examined for blockade of IL-33 induction of phosphorylated p38 (phospho-p38) in basophils (FIG. 19C). Consistent with the reporter cell data described above, addition of either the monospecific anti-IL-33 antibody 10C12.38.H6.87Y.58I IgG4 or the bispecific antibody 10C12-IL-13 KIH IgG4 caused a dose-dependent inhibition in IL-33-induced phospho-p38 levels in basophils (FIG. 19D). The control IgG4 antibody did not affect the IL-33 signal (FIG. 19D).

The binding kinetics of the bispecific antibody 10C12-IL-13 KIH IgG4 to human IL-33, cyno IL-33, and human IL-13 was assessed using BIACORE® 3000 SPR (FIG. 20). The average $K_D$ of this antibody across three experiments using different antibody preparations is shown in Table 4.

TABLE 4

$K_D$ of bispecific antibody 10C12-IL-13 KIH IgG4 to IL-33 and IL-13

| $K_D$ (nM) Human IL-33 | $K_D$ (nM) Cyno IL-33 | $K_D$ (nM) Human IL-13 |
|---|---|---|
| 0.025 | 0.076 | <0.010 |

Materials and Methods

HEK-BLUE™ IL-33/1 IL-13 reporter cells were purchased from Invivogen (Catalog # hkb-iI33). 300 µg/ml IL-33 ligand (IL-33 N-His, SEQ ID NO: 314) and pre-diluted anti-IL-33 antibodies: control IgG4, anti-1L33 10C12.38.H6.87Y.58I IgG4, 10C12-IL13 KIH IgG4, or ST2 LZ (SEQ ID NO: 319), were mixed and incubated for 1 hour at room temperature. The antibody and ligand mixture were transferred to HEK-BLUE™ IL-33/IL-1β cells, seeded at 50,000 cells per well. After incubation at 37° C. for 20 hours in a $CO_2$ incubator, the SEAP activities in cell culture supernatants were measured by recording the optical density (OD) values at 630 nm after incubating with the substrate of alkaline phosphatase (QUANTI-BLUE™, InvivoGen).

Human PBMCs were stimulated for 30 minutes with 10 ng/ml of recombinant human IL33. Prior to stimulation, cells were treated with increasing concentrations of control IgG4, anti-1L33 10C12.38.H6.87Y.58I IgG4, or 10C12-IL-13 KIH IgG4 for 1 hour. Cells were fixed for FACS analysis. Basophils were identified using the fluorescein isothiocyanate-anti-CD123 (11-1239-42: eBioscience). IL-33 activity was analyzed by intracellular staining with phycoerythrin-anti-phospho-p38 MAPK (Thr180/Tyr182) (6908S; Cell Signaling) according to the manufacturer's protocol. Data is shown as the mean fluorescence intensity (MFI) of the phospho-p38 signal within the gated CD123$^+$ basophil population.

The binding kinetics of the bispecific antibody 10C12-IL13 KIH IgG4 to human IL-33, cyno IL-33, and human IL-13 was assessed using SPR on a BIACORE® 3000 (GE Healthcare). Anti-human Fab (GE Healthcare) was immobilized on a CM5 sensor chip via amine-based coupling according to the manufacturer's protocol. The bispecific antibody was captured and binding was measured to human IL-33 (Genentech), cyno IL-33 (Genentech), and human IL-13 (Peprotech). Two-fold concentration series of cytokine with a range of 1.56 to 25 nM was used for the experiments. Sensograms for binding of cytokine were recorded using an injection time of 2 min with a flow rate of 30 µl/min, at a temperature of 25° C., and with a running buffer of 10 mM HEPES, pH 7.4, 150 mM NaCl, 3 mM EDTA, and 0.005% TWEEN®-20. After injection, disassociation of the ligand from the antibody was monitored for 600 sec in running buffer. The surface was regenerated between binding cycles with a 40 µl injection of 10 mM Glycine-HCl pH 2.1. After subtraction of a blank which contained running buffer only, sensograms observed for cytokine binding to the bispecific antibody were analyzed using a 1:1 Langmuir binding model with software supplied by the manufacturer to calculate the kinetics and binding constants, including the dissociation constant ($K_D$).

Example 9. Comparison of Inhibitory Activity and Binding Kinetics of the Anti-IL-33 Antibody 10C12.38.H6.87Y.58I IgG4 with Other Anti-IL-33 Antibodies A. Introduction The blocking activity and binding kinetics of the anti-IL-33 antibody 10C12.38.H6.87Y.58I IgG4 were directly compared with the blocking activities and binding kinetics of twenty anti-IL-33 antibodies (referred to herein as RG1-RG20) described in International Patent Application Publication No. WO 2014/164959. The anti-IL-33 antibodies from WO 2014/164959 that were compared to 10C12.38.H6.87Y.58I IgG4 are shown in Table 5, which indicates the antibody name from WO 2014/164959, the abbreviated name used herein, the constant region (IgG1 or IgG4), and the amino acid and nucleotide sequences SEQ ID NOs for the VH and VL of each antibody.

TABLE 5

Anti-IL-33 antibodies from WO 2014/164959

| Antibody Name from WO 2014/164959 | Abbreviated Name | Constant Region | Amino Acid Sequence SEQ ID NO VH | Amino Acid Sequence SEQ ID NO VL | Nucleotide Sequence SEQ ID NO VH | Nucleotide Sequence SEQ ID NO VL |
|---|---|---|---|---|---|---|
| H1M9559N | RG1 | IgG1 | 344 | 345 | 346 | 347 |
| H1M9566N | RG2 | IgG1 | 348 | 349 | 350 | 351 |
| H1M9568N | RG3 | IgG1 | 352 | 353 | 354 | 355 |
| H4H9629P | RG4 | IgG4 | 356 | 357 | 358 | 359 |
| H4H9633P | RG5 | IgG4 | 360 | 361 | 362 | 363 |
| H4H9640P | RG6 | IgG4 | 364 | 365 | 366 | 367 |
| H4H9659P | RG7 | IgG4 | 368 | 369 | 370 | 371 |
| H4H9660P | RG8 | IgG4 | 372 | 373 | 374 | 375 |
| H4H9662P | RG9 | IgG4 | 376 | 377 | 378 | 379 |
| H4H9663P | RG10 | IgG4 | 380 | 381 | 382 | 383 |
| H4H9664P | RG11 | IgG4 | 384 | 385 | 386 | 387 |
| H4H9665P | RG12 | IgG4 | 388 | 389 | 390 | 391 |
| H4H9666P | RG13 | IgG4 | 392 | 393 | 394 | 395 |
| H4H9667P | RG14 | IgG4 | 396 | 397 | 398 | 399 |
| H4H9670P | RG15 | IgG4 | 400 | 401 | 402 | 403 |
| H4H9671P | RG16 | IgG4 | 404 | 405 | 406 | 407 |
| H4H9672P | RG17 | IgG4 | 408 | 409 | 410 | 411 |
| H4H9675P | RG18 | IgG4 | 412 | 413 | 414 | 415 |
| H4H9676P | RG19 | IgG4 | 416 | 417 | 418 | 419 |
| H1M9565N | RG20 | IgG1 | 420 | 421 | 422 | 423 |

B. Cell-Based IL-33 Blocking Assay Using a Reporter Cell Line

The potency of the anti-IL-33 antibody 10C12.38.H6.87Y.58I IgG4 and each anti-IL-33 antibody listed in Table 5 (RG1-RG20) as an inhibitor of human IL-33 cellular activity was examined using a cell-based IL-33 blocking assay using a HEK-BLUE™ reporter cell line (FIG. 21A). A natural inhibitor of IL-33 activity, sST2 (sST2-LZ), served as a positive control. Stimulation of HEK-BLUE™ IL-33/IL-1β cells with human IL-33 resulted in robust NF-κB and AP-1 activation, which was measured by NF-κB/AP-1-driven SEAP reporter activity (FIG. 21B). IL-33 activity was not perturbed by the addition of the control IgG4 antibody (FIG. 21A). Most anti-IL-33 antibodies tested displayed dose-dependent inhibition of human IL-33 activity (FIG. 21A), with IC$_{50}$ values listed in FIG. 21C. Only two antibodies displayed greater inhibition over the decoy receptor, sST2-LZ (IC$_{50}$=27 pM). 10C12.38.H6.87Y.58I IgG4 displayed the highest blocking activity (IC$_{50}$=2.4 pM), followed by the RG18 antibody (IC50=11 pM). The five RG antibodies with the highest blocking activity (RG3, RG4, RG7, RG8, and RG18) are displayed in FIG. 21D, along with sST2-LZ and 10C12.38.H6.87Y.58I IgG4.

Similarly, the potency of each antibody as an inhibitor of cynomolgus monkey IL-33 cellular activity was examined using a cell-based blocking assay using a HEK-BLUE™ M reporter cell line (FIG. 22A). Stimulation of HEK-BLUE™ IL-33/IL-1 cells with cyno IL-33 resulted in robust NF-κB and AP-1 activation, which was measured by NF-κB/AP-1-driven SEAP reporter activity (FIG. 22B). In general, the anti-IL-33 antibodies tested displayed weaker dose-dependent inhibition of cynomolgus monkey IL-33 activity compared to the blocking activities against human IL-33, with $IC_{50}$ values listed in FIG. 21C. The decoy receptor sST2-LZ displayed the highest blocking activity (IC50=30 pM) and was followed by 10C12.38.H6.87Y.58I IgG4 ($IC_{50}$=4.2 nM) and then the RG20 antibody ($IC_{50}$=6.1 nM). The five RG antibodies with the highest blocking activity (RG3, RG9, RG10, RG12, and RG20) are displayed in FIG. 22C, along with sST2-LZ and 10C12.38.H6.87Y.58I IgG4. Of note, the RG18 antibody that displayed high blocking activity against human IL-33, displayed 14-fold weaker blocking activity for cynomolgus monkey IL-33 relative to 10C12.38.H6.87Y.58I IgG4. FIG. 22D shows the dose-response curves of the RG antibodies that were non-blocking in this assay.

Materials and Methods

IL-33 pathway activity in HEK-BLUE™ IL-33/IL-1β reporter cells (InvivoGen, hkb-il33) was measured using a colorimetric assay performed according to the manufacturer's instructions. HEK-BLUE™ IL-33/IL-1β reporter cells were plated at 50,000 cells per well in 96-well plates in DMEM 4.5 g/l glucose, supplemented with 2 mM L-Glutamine, 10% FBS, 50 U/ml penicillin, 50 µg/mL streptomycin, 100 µg/mL NORMOCIN™ (InvivoGen, ant-nr-1). The cells were incubated with a 5-fold serial dilution ranging from 139 nM to 0.003 pM of human IL-33 (hIL-33; R&D Systems, #3625-IL-010/CF) or in-house generated cynomolgus monkey N-terminal 6-His-tagged and C-terminal Avi-tagged IL-33 (S112-T270) (see Example 2). For blocking experiments, the cells were incubated with 10 pM of human IL-33 or 5 pM cyno IL-33 in combination with 3-fold serial dilutions of antibodies or sST2-LZ (sST2 (M1-F328) C-terminal leucine zipper (LZ)-Flag-His) ranging from 90 nM to 0.51 pM. The antibodies or sST2-LZ were pre-incubated with IL-33 for 30 minutes at 37° C. prior to addition to the cells. Each reaction had at a final volume of 200 µL per well and each condition was tested in triplicate. The cells were incubated at 37° C. in a humidified incubator with 5% $CO_2$ and supernatants were collected after 20 h. SEAP reporter activity was detected using QUANTI-BLUE™ M assay (InvivoGen, rep-qb1). 20 µl of supernatants were added to 80 µl of dissolved and filtered QUANTI-BLUE™ M reagent in flat 96-well plates and incubated for 1 h at 37° C. SEAP levels were determined using a spectrophotometer at 620 nm.

C. Natural Killer (NK) Primary Cell Assay for IL-33 Activity

In addition to the reporter cell assay described above, the anti-IL-33 antibody 10C12.38.H6.87Y.58I IgG4 and each anti-IL-33 antibody listed in Table 5 (RG1-RG20) were also tested for inhibition of IL-33 activity in primary human natural killer (NK) cells (FIGS. 23A-23D). IL-33 and IL-12 cannot activate NK cells by themselves, but together they can synergize to induce IFN-γ from NK cells (see, e.g., Smithgall et al. Int. Immunol. 20(8): 1019-1030, 2008). The inhibitory activity of the anti-IL-33 antibody 10C12.38.H6.87Y.58I IgG4 and the anti-IL-33 antibodies RG1-RG20 were compared to a natural inhibitor, sST2 (sST2-LZ). Stimulation of freshly-purified NK cells (FIG. 23A) with increasing concentrations of human IL-33 in the presence of IL-12 resulted in robust IFN-γ secretion after 24 h, as measured by ELISA (FIG. 23B). Most anti-IL-33 antibodies tested displayed dose-dependent inhibition of human IL-33 activity (FIG. 23C), with $IC_{50}$ values listed in FIG. 23D. Similar to the reporter cell line results described above in Section B, only two antibodies displayed greater inhibition over the decoy receptor, sST2-LZ ($IC_{50}$=150 pM). 10C12.38.H6.87Y.58I IgG4 displayed the highest blocking activity ($IC_{50}$=30 pM), followed by the RG18 antibody ($IC_{50}$=97 pM). The five RG antibodies with the highest blocking activity (RG7, RG8, RG9, RG18, and RG19) are displayed in FIG. 23E, along with sST2-LZ and 10C12.38.H6.87Y.58I IgG4. FIGS. 23F-23I compare the $IC_{50}$ curves between groups of five RG antibodies, 10C12.38.H6.87Y.58I IgG4, and sST2-LZ.

Materials and Methods

PBMCs were isolated from fresh whole blood by density gradient centrifugation. Whole blood was diluted two-fold in PBS, layered over FICOLL®-Paque (GE Healthcare, #17-1440-03) in LEUCOSEP™ tubes (Greiner Bio One, #227290), and centrifuged at 2,000 RPM for 20 min at room temperature. The interphase layer containing the PBMCs was aspirated and transferred to a new tube, and washed twice with PBS. NK cells were isolated using the NK Cell Isolation Kit (Miltenyi Biotec, 130-092-657) according to the manufacturer's instructions. The purity of the cells was analyzed by flow cytometry with CD56-APC (BD Pharmingen, 555518) and CD3-FITC (BD Pharmingen, 561807) staining. Isolated NK cells (>90% purity) were plated in flat-bottom 96-well plates at a final concentration of $5 \times 10^5$ cells/ml in RPMI 1640 supplemented with 10% FBS, 2 mM L-glutamine, 100 U/ml penicillin, and 100 µg/mL streptomycin. The cells were incubated with 1 ng/ml of human IL-12 (hIL-12; R&D Systems, #219-IL-025/CF) and a 5-fold serial dilution of human IL-33 (huIL-33; R&D Systems, #3625-IL-010/CF) alone from 139 nM to 0.003 pM, or with 260 pM of huIL-33 in combination with 3-fold serial dilutions of antibodies or sST2-LZ from 100 nM to 0.56 pM. The antibodies or sST2-LZ were pre-incubated with IL-33 for 30 min at 37° C. prior addition to the cells. Each reaction was at a final volume of 200 µl per well and each condition was tested in triplicate. The cells were incubated overnight at 37° C. in a humidified incubator with 5% $CO_2$. Supernatants were collected after 24 h. The levels of human IFN-γ in the culture supernatant were measured by ELISA (R&D Systems, #DY285) according to the manufacturer's instructions. For each plate, % IL-33 activity was calculated as follows:

$$\% \text{ IL-33 activity} = 100 \times (OD450_{sample} - OD450_{no\ IL\text{-}33}) / (OD450_{no\ antibody} - OD450_{no\ IL\text{-}33}).$$

D. IL-33-Induced p38 MAPK (Thr180/Tyr182) Phosphorylation in Human Basophils

The anti-IL-33 antibody 10C12.38.H6.87Y.58I IgG4 and each anti-IL-33 antibody listed in Table 5 (RG1-RG20) were also tested for inhibition of IL-33 activity in primary human basophils. Addition of IL-33 to human basophils resulted in rapid phosphorylation of the signaling molecule p38 MAPK (Thr180/Tyr82), which can be measured by flow cytometry using intracellular staining methods. By adding the CD123 marker, basophil activity can be examined within the bulk PBMC population, obviating the need for cell isolation.

Using this flow cytometry-based methodology, the anti-IL-33 antibodies were examined for blockade of IL-33-mediated induction of phospho-p38 in basophils (FIG. 24A). Addition of IL-33 to PBMCs resulted in a dose-dependent increase in p38 MAPK (Thr180/Tyr182) phosphorylation (phospho-p38) in the basophil population (FIG. 24B). Consistent with the reporter cell line and NK cell data described above, addition of anti-IL-33 antibodies caused a dose-dependent inhibition in IL-33-induced phospho-p38 in basophils (FIG. 24C), with $IC_{50}$ values listed in FIG. 24D. The antibodies with highest blocking activity as determined using the $IC_{50}$ curves were RG11 ($IC_{50}$=0.14 pM), 10C12.38.H6.87Y.58I IgG4 ($IC_{50}$=0.15 pM), followed by the RG18 antibody ($IC_{50}$=0.38 pM). The five RG antibodies with the highest blocking activity (RG3. RG4, RG8, RG11, and RG18) are displayed in FIG. 24E, along with sST2-LZ and 10C12.38.H6.87Y.58I IgG4. FIGS. 24F-24I compare the $IC_{50}$ curves between groups of five RG antibodies, 10C12.38.H6.87Y.58I IgG4, and sST2-LZ.

Since the $IC_{50}$ curves were made from only six points, the results described above were analyzed at specific antibody concentrations (FIGS. 24J-24K). The mean fluorescence intensity (MFI) obtained at either 0.4 nM (FIG. 24J) or 2 nM (FIG. 24K) anti-IL-33 antibody or sST2-LZ concentration was plotted. The plots in FIGS. 24J and 24K display the antibodies sorted from highest to lowest blocking activity. At both concentrations, 10C12.38.H6.87Y.58I IgG4 displayed the highest blocking activity, and hence the lowest MFI value. Consistent with the reporter cell line and NK primary cell data, the RG18 antibody was among the top three antibodies in terms of blocking activity against human IL-33.

Materials and Methods

PBMCs were isolated from fresh whole blood by density gradient centrifugation. Whole blood was diluted two-fold in PBS, layered over FICOLL®-Paque (GE Healthcare, #17-1440-03) in LEUCOSEP™ tubes (Greiner Bio One, #227290), and centrifuged at 2000 RPM for 20 min at room temperature. The interphase layer containing the PBMCs was aspirated and transferred to a new tube, and washed twice with PBS. The isolated PBMCs were plated in v-bottom 96-well plates at 1 million cells/well in 50 µl of PBS. 5-fold serial dilutions (ranging from 10 nM to 3.2 pM) of anti-IL-33 antibodies, sST2-LZ, or an isotype control antibody were pre-incubated with 500 pM (final concentration) of human IL-33 (R&D Systems, #6325-IL/CF) for 30 min at 37° C. 50 µl of the mix were added to the PBMCs for a final volume of 100 µl per well. The cells were incubated for 20 min at 37° C. in a humidified incubator with 5% $CO_2$. The reactions were stopped by addition of 100 µl of pre-warmed BD PHOSFLOW™ fix buffer (BD Biosciences, 557870) and incubated for 10 min at 37° C. The cells were pelleted by centrifugation at 1500 RPM for 5 min and the supernatants were decanted. The cell pellets were washed with 200 µl flow cytometry buffer (1×PBS, 0.5% BSA, 0.05% sodium azide). The cells were permeabilized by slowly adding 100 µl cold BD PHOSFLOW™ Perm Buffer II (BD Biosciences, 558052) and incubated on ice for 30 min. The cell pellets were washed twice in flow cytometry buffer. IL-33 dependent phosphorylation of p38 in basophils was analyzed by staining each sample with anti-Phospho-p38 MAPK (Thr180/Tyr182)-PE (used at 1:50, Cell Signaling Technology, 6908S) and anti-CD123-FITC (used at 1:10, eBiosciences, 11-1239-42). The samples were incubated at room temperature for 1 h in the dark. The cells were pelleted and washed twice with flow cytometry buffer. The cells were analyzed on a BD FACSCALIBUR™ to determine the mean fluorescence intensity (MFI) levels of phospho-p38 MAPK (Thr180/Tyr182) in $CD123^+$ basophils.

E. Anti-IL-33 Antibody Binding to IL-33 as Determined by Surface Plasmon Resonance The binding kinetics of the anti-IL-33 antibody 10C12.38.H6.87Y.58I IgG4 and each anti-IL-33 antibody listed in Table 5 (RG1-RG20) to IL-33 were measured using surface plasmon resonance (SPR) on a BIACORE® T200 instrument (GE Healthcare). Anti-human Fc or anti-murine Fc (GE Healthcare, #BR-1008-39 or BR-1008-38, respectively) was immobilized on a CM5 sensor chip via amine-based coupling according to the manufacturer's protocol. Surfaces were used to capture monoclonal human IgG4 and monoclonal murine IgGs for kinetic studies. Antibody binding was measured to human IL-33 (R&D systems, #3625-IL-010/CF) and cyno IL-33 N-His (SEQ ID NO: 317) (Genentech, Inc.). A three-fold concentration series of cytokine with a range of 3.7 to 100 nM was used for the experiments. Sensograms for binding of IL-33 were recorded using an injection time of 4 min with a flow rate of 30 µl/minute with a running buffer of 0.01 M N-(2-Acetamido)iminodiacetic acid (ADA) pH 7.4, 0.15 M NaCl, 3 mM EDTA, and 0.05% TWEEN®-20. After injection, disassociation of the ligand from the antibody was monitored for 10 min in running buffer. The surface was regenerated in between cycles with an injection of 3 M magnesium chloride or Glycine-HCl pH 1.7. All binding experiments were performed at a temperature of 25'C and 37° C. After subtraction of a blank which contained running buffer only, sensograms observed for IL-33 binding to anti-IL-33 antibodies were analyzed using a 1:1 Langmuir binding model with software supplied by the manufacturer to calculate the kinetics and binding constants, including the dissociation constant ($K_D$). Dissociative half-lives ($t_{1/2}$) were calculated from the kinetic rate constants. $K_D$ (M)=$k_{off}/k_{on}$ and $t_{1/2}$ (min)=$\ln(2)/(60*k_{off})$. Table 6 shows the results of the binding kinetics for binding to human IL-33 at 25° C. Table 7 shows the results of the binding kinetics for binding to human IL-33 at 37° C. Table 8 shows the results of the binding kinetics for binding to cyno IL-33 at 25° C. Table 9 shows the results of the binding kinetics for binding to cyno IL-33 at 37° C. In Tables 6-9, *IC indicates the result is inconclusive due to weak capture of antibody was observed, leading to poor binding data.

In each condition, the anti-IL-33 antibody 10C12.38.H6.87Y.58I IgG4 had the highest affinity to human or cyno IL-33, as measured by $K_D$, compared to the anti-IL-33 antibodies RG1-RG20 (Tables 6-9). 10C12.38.H6.87Y.58I IgG4 had approximately 2-4 fold improved affinity compared to the RG antibody with the highest affinity for human IL-33, which was RG18 (Tables 6 and 7). 10C12.38.H6.87Y.58I IgG4 also had had approximately 2-4 fold improved affinity compared to the RG antibody with the highest affinity for cyno IL-33, which was RG2 at 25° C. and RG10 at 37° C.

TABLE 6

Binding kinetics of anti-IL-33 antibodies for binding to human IL33 at 25° C.

| Antibody | $k_{on}$ (1/Ms) | $k_{off}$ (1/s) | $K_D$ (M) | $t_{1/2}$ (min) |
|---|---|---|---|---|
| RG1 | 226000 | 0.000184 | 8.11E−10 | 63 |
| RG2 | 96900 | 0.0000773 | 7.98E−10 | 149 |
| RG3 | IC* | IC* | IC* | IC* |
| RG4 | 1130000 | 0.000632 | 5.59E−10 | 18 |
| RG5 | 491000 | 0.000462 | 9.41E−10 | 25 |
| RG6 | 797000 | 0.000438 | 5.49E−10 | 26 |
| RG7 | 456000 | 0.000499 | 1.09E−09 | 23 |

TABLE 6-continued

Binding kinetics of anti-IL-33 antibodies for binding to human IL33 at 25° C.

| Antibody | $k_{on}$ (1/Ms) | $k_{off}$ (1/s) | $K_D$ (M) | $t_{1/2}$ (min) |
|---|---|---|---|---|
| RG8 | 581000 | 0.00039 | 6.7E−10 | 30 |
| RG9 | 871000 | 0.000459 | 5.27E−10 | 25 |
| RG10 | 1680000 | 0.000937 | 5.58E−10 | 12 |
| RG11 | 339000 | 0.000445 | 1.31E−09 | 26 |
| RG12 | 931000 | 0.00116 | 1.25E−09 | 10 |
| RG13 | 665000 | 0.00115 | 1.74E−09 | 10 |
| RG14 | 626000 | 0.000328 | 5.25E−10 | 35 |
| RG15 | 680000 | 0.000517 | 7.61E−10 | 22 |
| RG16 | 1310000 | 0.000963 | 7.36E−10 | 12 |
| RG17 | 960000 | 0.000806 | 8.39E−10 | 14 |
| RG18 | 1630000 | 0.000637 | 3.91E−10 | 18 |
| RG19 | 1790000 | 0.001 | 5.6E−10 | 12 |
| RG20 | 84400 | 0.000238 | 2.82E−09 | 49 |
| 10C12.38.H6.87Y.58I IgG4 | 4600000 | 0.000613 | 1.33E−10 | 19 |

TABLE 7

Binding kinetics of anti-IL-33 antibodies for binding to human IL-33 at 37° C.

| Antibody | $k_{on}$ (1/Ms) | $k_{off}$ (1/s) | $K_D$ (M) | $t_{1/2}$ (min) |
|---|---|---|---|---|
| RG1 | 374000 | 0.000888 | 2.37E−09 | 13 |
| RG2 | 129000 | 0.000522 | 4.04E−09 | 22 |
| RG3 | IC* | IC* | IC* | IC* |
| RG4 | 2820000 | 0.000738 | 2.61E−10 | 16 |
| RG5 | 1160000 | 0.000845 | 7.26E−10 | 14 |
| RG6 | 1740000 | 0.000626 | 3.59E−10 | 18 |
| RG7 | 1080000 | 0.000498 | 4.62E−10 | 23 |
| RG8 | 1370000 | 0.000413 | 3.02E−10 | 28 |
| RG9 | 2340000 | 0.000566 | 2.42E−10 | 20 |
| RG10 | 3110000 | 0.00161 | 5.17E−10 | 7 |
| RG11 | 789000 | 0.000531 | 6.74E−10 | 22 |
| RG12 | 2350000 | 0.00235 | 1E−09 | 5 |
| RG13 | 1690000 | 0.00158 | 9.34E−10 | 7 |
| RG14 | 1210000 | 0.000497 | 4.11E−10 | 23 |
| RG15 | 1280000 | 0.000663 | 5.19E−10 | 17 |
| RG16 | 3680000 | 0.00203 | 5.52E−10 | 6 |
| RG17 | 2390000 | 0.00127 | 5.31E−10 | 9 |
| RG18 | 4060000 | 0.000779 | 1.92E−10 | 15 |
| RG19 | 3470000 | 0.00158 | 4.57E−10 | 7 |
| RG20 | 218000 | 0.000162 | 7.42E−10 | 71 |
| 10C12.38.H6.87Y.58I IgG4 | 6160000 | 0.000547 | 8.89E−11 | 21 |

TABLE 8

Binding kinetics of anti-IL-33 antibodies for binding to cyno IL33 at 25° C.

| Antibody | $k_{on}$ (1/Ms) | $k_{off}$ (1/s) | $K_D$ (M) | $t_{1/2}$ (min) |
|---|---|---|---|---|
| RG1 | 122000 | 0.000458 | 3.76E−09 | 25 |
| RG2 | 117000 | 0.0000766 | 6.56E−10 | 151 |
| RG3 | IC* | IC* | IC* | IC* |
| RG4 | 379000 | 0.0204 | 5.4E−08 | 1 |
| RG5 | 227000 | 0.00337 | 1.49E−08 | 3 |
| RG6 | 244000 | 0.000528 | 2.17E−09 | 22 |
| RG7 | 183000 | 0.000479 | 2.61E−09 | 24 |
| RG8 | 238000 | 0.00064 | 2.69E−09 | 18 |
| RG9 | 245000 | 0.000313 | 1.28E−09 | 37 |
| RG10 | 511000 | 0.000545 | 1.07E−09 | 21 |
| RG11 | 99000 | 0.000556 | 5.62E−09 | 21 |
| RG12 | 437000 | 0.000426 | 9.76E−10 | 27 |
| RG13 | 164000 | 0.00625 | 3.8E−08 | 2 |
| RG14 | 208000 | 0.00059 | 2.83E−09 | 20 |
| RG15 | 212000 | 0.000557 | 2.63E−09 | 21 |
| RG16 | 533000 | 0.000915 | 1.72E−09 | 13 |
| RG17 | 331000 | 0.0019 | 5.74E−09 | 6 |
| RG18 | 362000 | 0.000988 | 2.73E−09 | 12 |
| RG19 | 787000 | 0.00248 | 3.15E−09 | 5 |
| RG20 | 203000 | 0.000606 | 2.98E−09 | 19 |
| 10C12.38.H6.87Y.58I IgG4 | 1050000 | 0.000278 | 2.65E−10 | 42 |

TABLE 9

Binding kinetics of anti-IL-33 antibodies for binding to cyno IL33 at 37° C.

| Antibody | $k_{on}$ (1/Ms) | $k_{off}$ (1/s) | $K_D$ (M) | $t_{1/2}$ (min) |
|---|---|---|---|---|
| RG1 | 232000 | 0.00193 | 8.33E−09 | 6 |
| RG2 | 185000 | 0.000469 | 2.54E−09 | 25 |
| RG3 | IC* | IC* | IC* | IC* |
| RG4 | 916 | 0.000502 | 5.47E−07 | 23 |
| RG5 | 265000 | 0.0113 | 4.27E−08 | 1 |
| RG6 | 9340000 | 0.0392 | 4.2E−09 | 0 |
| RG7 | 277000 | 0.00114 | 4.13E−09 | 10 |
| RG8 | 385000 | 0.00305 | 7.93E−09 | 4 |
| RG9 | 484000 | 0.00112 | 2.31E−09 | 10 |
| RG10 | 1960000 | 0.00202 | 1.03E−09 | 6 |
| RG11 | 205000 | 0.00213 | 1.04E−08 | 5 |
| RG12 | 727000 | 0.00142 | 1.96E−09 | 8 |
| RG13 | 293000 | 0.0139 | 4.74E−08 | 1 |
| RG14 | 398000 | 0.00214 | 5.38E−09 | 5 |
| RG15 | 380000 | 0.00221 | 5.82E−09 | 5 |
| RG16 | 890000 | 0.00326 | 3.66E−09 | 4 |
| RG17 | 584000 | 0.00757 | 1.3E−08 | 2 |
| RG18 | 751000 | 0.00505 | 6.72E−09 | 2 |
| RG19 | 1600000 | 0.0111 | 6.93E−09 | 1 |
| RG20 | IC* | IC* | IC* | IC* |
| 10C12.38.H6.87Y.58I IgG4 | 1690000 | 0.000804 | 4.76E−10 | 14 |

F. Competitive Binding ELISA to Measure Blocking Activity of Anti-IL-33 Antibodies Materials Recombinant human ST2-Fc chimera protein and human IL-33 protein were obtained from R&D Systems (Minneapolis, Minn.). Recombinant cynomolgus monkey IL-33 protein was made at Genentech. Both human and cyno IL-33 proteins were biotin-labeled using EZ-LINK® NHS-PEG4-Biotin (Thermo Scientific; Rockford, Ill.) according to the manufacturer's protocol.

Experimental Method

The ability of the anti-IL-33 antibody 10C12.38.H6.87Y.58I IgG4 and each anti-IL-33 antibody listed in Table 5 (RG1-RG20) to block either human IL-33 or cyno IL-33 binding to human ST2 receptor was tested in a competitive binding ELISA. Briefly, 1 μg/ml of recombinant human ST2-Fc chimera protein prepared in coating buffer (50 mM sodium carbonate, pH 9.6) was coated on a 384-well MAXISORP® plate (Nalgene Nunc International; Rochester, N.Y.) and incubated overnight at 4° C. On the next day, non-specific binding was blocked with PBS containing 0.5% (w/v) solution of bovine serum albumin (BSA). Fixed concentrations of biotinylated human or cyno IL-33 prepared in assay buffer (25 mM PBS, pH 7.2, 0.1% BSA, 0.05% TWEEN®-20) were mixed with an equal volume of serially-diluted anti-IL-33 antibodies or assay buffer alone and incubated for 1 h at room temperature. The final assay concentrations of biotinylated human IL-33 or cyno IL-33 were 20 pM and 45 pM, respectively, and the final assay concentration of each antibody ranged from 0-300 nM. The pre-mixed solutions were added to the ST2-Fc coated plate and incubated for 1 h at room temperature. The binding of biotinylated IL-33 to coated ST2-Fc was detected by the sequential addition of Streptavidin Poly-HRP80 (Fitzgerald; Buckinghamshire, UK) and 3,3',5,5'-tetramethyl benzidine (TMB) Microwell Peroxidase Substrate System (KPL; Gaithersburg, Md.). The absorbance (450 nm) was recorded using a MULTISKAN ASCENT® plate reader (Thermo Scientific; Rockford, Ill.). The binding activity (%) of biotin-IL-33 to ST2 in the presence of anti-IL-33 was plotted as a function of antibody concentration. The data generated were fitted to a four-parameter equation to determine $IC_{50}$ values for each antibody (FIGS. 25A and 25B) using Prism software (Graphpad Software; La Jolla, Calif.). The maximum blocking (%) of each antibody was calculated as the ratio of the reduction in signal measured in the presence of antibody relative to the difference between the signal with IL-33 alone and background measurements. The $IC_{50}$ and maximum blocking activity for each antibody are summarized in Table 10. Results show the average data of three independent experiments.

As shown in Table 10, 10C12.38.H6.87Y.58I IgG4 was the most efficient blocker of any of the antibodies tested, with lower IC50 values and higher maximum blocking compared to all of the antibodies from WO 2014/164959.

TABLE 10

Blocking of biotin-huIL-33 or biotin-cyIL-33 binding to huST2 by anti-IL-33 antibodies

| Antibody | Blocking 20 pM biotin-huIL-33 to hST2-Fc, $IC_{50}$ (M) | Maximum Blocking | Blocking 40 pM biotin-cyIL-33 to hST2-Fc, $IC_{50}$ (M) | Maximum Blocking |
|---|---|---|---|---|
| 10C12.38.H6.87Y.58I IgG4 | 2.1E−11 | 92% | 4.3E−10 | 87% |
| H1M9559N | 4.1E−09 | 75% | NA | NB |
| H1M9566N | 9.9E−11 | 27% | NA | NB |
| H1M9565N | 5.4E−08 | 81% | 1.9E−08 | 85% |
| H1M9568N | 1.9E−10 | 85% | 7.7E−08 | 45% |
| H4H9629P | 9.2E−11 | 82% | NA | NB |
| H4H9633P | 1.1E−09 | 68% | NA | NB |
| H4H9640P | 1.9E−10 | 80% | 4.5E−08 | 25% |
| H4H9659P | 2.3E−10 | 88% | 4.7E−08 | 42% |
| H4H9660P | 9.2E−11 | 78% | 1.2E−07 | 18% |
| H4H9662P | 2.5E−10 | 85% | 6.6E−08 | 47% |
| H4H9663P | 4.4E−10 | 82% | 2.6E−08 | 61% |
| H4H9664P | 1.9E−10 | 87% | NA | 10% |
| H4H9665P | 7.0E−10 | 63% | 1.9E−08 | 53% |
| H4H9666P | 2.1E−10 | 81% | NA | NB |
| H4H9667P | 4.1E−10 | 77% | NA | 7% |
| H4H9670P | 4.2E−10 | 80% | 1.5E−07 | 27% |
| H4H9671P | 9.6E−11 | 77% | 7.0E−08 | 40% |
| H4H9672P | 2.2E−10 | 77% | NA | NB |
| H4H9675P | 6.3E−11 | 84% | NA | NB |
| H4H9676P | 9.7E−10 | 73% | NA | NB |

NA = Not applicable
NB = Non-blocker

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated nucleic acid encoding an antibody that specifically binds IL-33, wherein the antibody comprises a binding domain comprising the following six HVRs:
 (a) an HVR-H1 comprising the amino acid sequence of SFSX$_1$S (SEQ ID NO: 62), wherein X$_1$ is Met, Leu, or Val;
 (b) an HVR-H2 comprising the amino acid sequence of TISGGKTFTDYVDX$_1$VKG (SEQ ID NO: 63), wherein X$_1$ is Ser or Ala;
 (c) an HVR-H3 comprising the amino acid sequence of ANYGX$_1$X$_2$FFEV (SEQ ID NO: 64), wherein X$_1$ is Asn or Asp, and X$_2$ is Trp or Phe;
 (d) an HVR-L1 comprising the amino acid sequence of RASESVAKYGLSLLN (SEQ ID NO: 4);
 (e) an HVR-L2 comprising the amino acid sequence of AASNRGS (SEQ ID NO: 5); and
 (f) an HVR-L3 comprising the amino acid sequence of QQSKEVPFT (SEQ ID NO: 6).

2. The nucleic acid of claim 1, wherein the binding domain comprises the following six HVRs:
 (a) an HVR-H1 comprising the amino acid sequence of SFSMS (SEQ ID NO: 1);
 (b) an HVR-H2 comprising the amino acid sequence of TISGGKTFTDYVDSVKG (SEQ ID NO: 2);
 (c) an HVR-H3 comprising the amino acid sequence of ANYGNWFFEV (SEQ ID NO: 3);
 (d) an HVR-L1 comprising the amino acid sequence of RASESVAKYGLSLLN (SEQ ID NO: 4);
 (e) an HVR-L2 comprising the amino acid sequence of AASNRGS (SEQ ID NO: 5); and
 (f) an HVR-L3 comprising the amino acid sequence of QQSKEVPFT (SEQ ID NO: 6).

3. The nucleic acid of claim 2, wherein the antibody is monoclonal, human, humanized, or chimeric.

4. The nucleic acid of claim 2, wherein the antibody is an antibody fragment that binds IL-33.

5. The nucleic acid of claim 4, wherein the antibody fragment is selected from the group consisting of Fab, Fab'-SH, Fv, scFv, and (Fab')$_2$ fragments.

6. The nucleic acid of claim 5, wherein the antibody fragment is an Fab fragment.

7. The nucleic acid of claim 2, wherein the antibody is a full-length antibody.

8. The nucleic acid of claim 1, wherein the antibody specifically binds human or cynomolgus monkey (cyno) IL-33.

9. The nucleic acid of claim 8, wherein the antibody specifically binds both human and cyno IL-33.

10. The nucleic acid of claim 9, wherein the antibody specifically binds both human and cyno IL-33 with a $K_D$ of about 1 nM or lower.

11. The nucleic acid of claim 10, wherein the antibody specifically binds human IL-33 with a $K_D$ between about 1 pM and about 500 pM.

12. The nucleic acid of claim 11, wherein the antibody specifically binds human IL-33 with a $K_D$ between about 15 pM and about 140 pM.

13. The nucleic acid of claim 10, wherein the antibody specifically binds cyno IL-33 with a $K_D$ between about 1 pM and about 500 pM.

14. The nucleic acid of claim 13, wherein the antibody specifically binds cyno IL-33 with a $K_D$ between about 125 pM and about 500 pM.

15. The nucleic acid of claim 10, wherein the antibody specifically binds both human and cyno IL-33 with a $K_D$ of between about 1 pM and about 500 pM.

16. The nucleic acid of claim 15, wherein the antibody specifically binds human IL-33 with a $K_D$ of between about 1 pM and about 200 pM.

17. The nucleic acid of claim 1, wherein the antibody is capable of inhibiting the binding of IL-33 to an IL-33 receptor.

18. The nucleic acid of claim 17, wherein the inhibiting is measured using a cell-based blocking assay.

19. The nucleic acid of claim 18, wherein the antibody inhibits the binding of human IL-33 to an IL-33 receptor with a 90% inhibitory concentration (1090) of between about 0.001 µg/ml and about 0.5 µg/ml.

20. The nucleic acid of claim 19, wherein the 1090 is between about 0.002 µg/ml and about 0.25 µg/ml.

21. The nucleic acid of claim 20, wherein the 1090 is about 0.004 µg/ml.

22. The nucleic acid of claim 1, wherein the antibody inhibits binding of human IL-33 to an IL-33 receptor with an 1050 of between about 800 fM and about 10 pM.

23. The nucleic acid of claim 22, wherein the 1050 is between about 1 pM and about 5 pM.

24. The nucleic acid of claim 23, wherein the 1050 is about 2.5 pM.

25. The nucleic acid of claim 1, wherein the antibody inhibits binding of cyno IL-33 to an IL-33 receptor with an 1050 of between about 1 nM and about 5 nM.

26. The nucleic acid of claim 25, wherein the 1050 is about 4 nM.

27. The nucleic acid of claim 1, wherein the antibody comprises an aglycosylation site mutation.

28. The nucleic acid of claim 1, wherein the antibody is monoclonal, human, humanized, or chimeric.

29. The nucleic acid of claim 1, wherein the antibody is an antibody fragment that binds IL-33.

30. The nucleic acid of claim 29, wherein the antibody fragment is selected from the group consisting of Fab, Fab'-SH, Fv, scFv, and (Fab')$_2$ fragments.

31. The nucleic acid of claim 30, wherein the antibody fragment is an Fab fragment.

32. The nucleic acid of claim 1, wherein the antibody is a full-length antibody.

33. The nucleic acid of claim 32, wherein the antibody is an IgG antibody.

34. The nucleic acid of claim 33, wherein the IgG antibody is an IgG1 antibody.

35. The nucleic acid of claim 33, wherein the IgG antibody is an IgG4 antibody.

36. The nucleic acid of claim 35, wherein the IgG4 antibody comprises a mutation in the hinge region.

37. The nucleic acid of claim 36, wherein the mutation is a substitution mutation.

38. The nucleic acid of claim 37, wherein the substitution mutation is at amino acid residue S228 (EU numbering).

39. The nucleic acid of claim 38, wherein the substitution mutation is an S228P mutation.

40. The nucleic acid of claim 1, wherein the antibody is a monospecific antibody.

41. The nucleic acid of claim 1, wherein the antibody is a multispecific antibody.

42. The nucleic acid of claim 41, wherein the antibody is a bispecific antibody.

43. The nucleic acid of claim 42, wherein the bispecific antibody comprises a second binding domain that binds to a second biological molecule, wherein the second biological molecule is selected from the group consisting of interleukin-13 (IL-13), interleukin-4 (IL-4), interleukin-5 (IL-5), interleukin-17 (IL-17), Factor D, HtrA1, VEGF, and a VEGF receptor.

44. The nucleic acid of claim 43, wherein the second biological molecule is IL-13.

45. The nucleic acid of claim 44, wherein the second binding domain comprises the following six HVRs:
 (a) an HVR-H1 comprising the amino acid sequence of AYSVN (SEQ ID NO: 296);
 (b) an HVR-H2 comprising the amino acid sequence of MIWGDGKIVYNSALKS (SEQ ID NO: 297);
 (c) an HVR-H3 comprising the amino acid sequence of DGYYPYAMDN (SEQ ID NO: 298);
 (d) an HVR-L1 comprising the amino acid sequence of RASKSVDSYGNSFMH (SEQ ID NO: 299);
 (e) an HVR-L2 comprising the amino acid sequence of LASNLES (SEQ ID NO: 300); and
 (f) an HVR-L3 comprising the amino acid sequence of QQNNEDPRT (SEQ ID NO: 301).

46. An isolated nucleic acid encoding an antibody that specifically binds both IL-33 and IL-13, wherein the antibody comprises a first binding domain that specifically binds IL-33 comprising the following six HVRs:
 (a) an HVR-H1 comprising the amino acid sequence of SFSMS (SEQ ID NO: 1);
 (b) an HVR-H2 comprising the amino acid sequence of TISGGKTFTDYVDSVKG (SEQ ID NO: 2);
 (c) an HVR-H3 comprising the amino acid sequence of ANYGNWFFEV (SEQ ID NO: 3);
 (d) an HVR-L1 comprising the amino acid sequence of RASESVAKYGLSLLN (SEQ ID NO: 4);
 (e) an HVR-L2 comprising the amino acid sequence of AASNRGS (SEQ ID NO: 5); and
 (f) an HVR-L3 comprising the amino acid sequence of QQSKEVPFT (SEQ ID NO: 6); and a second binding domain that specifically binds IL-13 comprising the following six HVRs:
 (a) an HVR-H1 comprising the amino acid sequence of AYSVN (SEQ ID NO: 296);

(b) an HVR-H2 comprising the amino acid sequence of MIWGDGKIVYNSALKS (SEQ ID NO: 297);
(c) an HVR-H3 comprising the amino acid sequence of DGYYPYAMDN (SEQ ID NO: 298);
(d) an HVR-L1 comprising the amino acid sequence of RASKSVDSYGNSFMH (SEQ ID NO: 299);
(e) an HVR-L2 comprising the amino acid sequence of LASNLES (SEQ ID NO: 300); and
(f) an HVR-L3 comprising the amino acid sequence of QQNNEDPRT (SEQ ID NO: 301).

47. An isolated nucleic acid encoding an antibody that specifically binds IL-33, wherein the antibody comprises a binding domain comprising (a) a heavy chain variable (VH) domain comprising an amino acid sequence having at least 95% sequence identity to the amino acid sequence of SEQ ID NO: 36 and (b) a light chain variable (VL) domain comprising an amino acid sequence having at least 95% sequence identity to the amino acid sequence of SEQ ID NO: 37.

48. The nucleic acid of claim 47, wherein the VH domain further comprises:
(a) an FR-H1 comprising the amino acid sequence of EVQLVESGGGLVQPGGSLRLSCAASGFTFS (SEQ ID NO: 12);
(b) an FR-H2 comprising the amino acid sequence of WVRQAPGKGLEWVA (SEQ ID NO: 13);
(c) an FR-H3 comprising the amino acid sequence of RFTISRDDSKNTLYLQMNSLRAEDTAVYYCTR (SEQ ID NO: 14); and
(d) an FR-H4 comprising the amino acid sequence of WGQGTLVTVSS (SEQ ID NO: 15).

49. The nucleic acid of claim 48, wherein the VH domain comprises the amino acid sequence of SEQ ID NO: 36.

50. The nucleic acid of claim 47, wherein the VL domain further comprises:
(a) an FR-L1 comprising the amino acid sequence of EIVLTQSPATLSLSPGERATLSC (SEQ ID NO: 25);
(b) an FR-L2 comprising the amino acid sequence of WFQQKPGQPPRLLIF (SEQ ID NO: 26);
(c) an FR-L3 comprising the amino acid sequence of GIPARFSGSGSGTDFTLTISSLEPEDFAVYYC (SEQ ID NO: 27); and
(d) an FR-L4 comprising the amino acid sequence of FGQGTKVEIK (SEQ ID NO: 28).

51. The nucleic acid of claim 50, wherein the VL domain comprises the amino acid sequence of SEQ ID NO: 37.

52. The nucleic acid of claim 47, wherein the VH domain comprises the amino acid sequence of SEQ ID NO: 36 and the VL domain comprises the amino acid sequence of SEQ ID NO: 37.

53. An isolated nucleic acid encoding an antibody that specifically binds IL-33, wherein the antibody comprises a binding domain comprising (a) a VH domain comprising an amino acid sequence having at least 99% sequence identity to the amino acid sequence of SEQ ID NO: 36 and (b) a VL domain comprising an amino acid sequence having at least 99% sequence identity to the amino acid sequence of SEQ ID NO: 37.

54. An isolated nucleic acid encoding an antibody that specifically binds IL-33, wherein the antibody comprises (a) a heavy chain comprising an amino acid sequence having at least 99% sequence identity to the amino acid sequence of SEQ ID NO: 288 and (b) a light chain comprising an amino acid sequence having at least 99% sequence identity to the amino acid sequence of SEQ ID NO: 289.

55. An isolated nucleic acid encoding an antibody that specifically binds IL-33, wherein the antibody comprises (a) a heavy chain comprising an amino acid sequence having at least 99% sequence identity to the amino acid sequence of SEQ ID NO: 290 and (b) a light chain comprising an amino acid sequence having at least 99% sequence identity to the amino acid sequence of SEQ ID NO: 291.

56. A vector comprising the isolated nucleic acid of claim 1, 2, 31, 6, 47, or 52.

57. An isolated host cell comprising the vector of claim 56.

58. The host cell of claim 57, wherein the host cell is a mammalian cell.

59. The host cell of claim 58, wherein the mammalian cell is a Chinese hamster ovary (CHO) cell.

60. The host cell of claim 57, wherein the host cell is a prokaryotic cell.

61. The host cell of claim 60, wherein the prokaryotic cell is *E. coli*.

62. A method of producing an antibody that specifically binds IL-33, the method comprising culturing the host cell of claim 57 in a culture medium.

63. The method of claim 62, wherein the method further comprises recovering the antibody from the host cell or the culture medium.

64. The method of claim 62, wherein the host cell is a mammalian cell.

65. The method of claim 64, wherein the mammalian cell is a CHO cell.

66. The method of claim 62, wherein the host cell is a prokaryotic cell.

67. The method of claim 66, wherein the prokaryotic cell is *E. coli*.

* * * * *

UNITED STATES PATENT AND TRADEMARK OFFICE
CERTIFICATE OF CORRECTION

PATENT NO. : 10,723,795 B2
APPLICATION NO. : 16/119667
DATED : July 28, 2020
INVENTOR(S) : Philip E. Hass et al.

It is certified that error appears in the above-identified patent and that said Letters Patent is hereby corrected as shown below:

In the Specification

Column 3, Lines 14-15, replace "DIVLTQSPGFLWSLGQRATISC" with --DIVLTQSPGFLVVSLGQRATISC--.

Column 4, Line 3, replace "WGQGTIVTVSS" with --WGQGTTVTVSS--.

Column 5, Line 19, replace "DIVLTQSPGFLWSLGQRATISC" with --DIVLTQSPGFLVVSLGQRATISC--.

Column 10, Line 28, replace "(t)" with --(f)--.

Column 16, Line 6, replace "HVR-H11" with --HVR-H1--.
    Line 14, replace "(t)" with --(f)--.

Column 31, Line 35, replace "IL-1=" with --IL-1β--.
    Line 36, replace "IL-13" with --IL-1β--.

Column 35, Line 67, replace "10C12-1L13" with --10C12-IL13--.

Column 39, Line 6, replace "cynomoigus" with --cynomolgus--.
    Line 17, replace "IL-33$_{190\text{-}270}$" with --IL-33$_{109\text{-}270}$--.

Column 42, Line 16, replace "IgG2, IgG3, IgG4," with --IgG$_2$, IgG$_3$, IgG$_4$,--.

Column 44, Line 51, replace "monocional" with --monoclonal--.

Column 48, Line 19, replace "aitretamine" with --altretamine--.
    Lines 34-35, replace "chlomaphazine" with --chlornaphazine--.
    Line 53, replace "HC1" with --HCl--.

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,723,795 B2

Line 65, replace "6-mercaptopuine" with --6-mercaptopurine--.

Column 49, Line 34, replace "difluoromethylomithine" with --difluoromethylornithine--.
Line 55, replace "tipifamib" with --tipifarnib--.
Line 59, replace "famesyitransferase" with --farnesyltransferase--.
Line 60, replace "lonafamib" with --lonafarnib--.

Column 53, Lines 33-34, replace "hypemociception" with --hypernociception--.
Line 34, replace "hypemociception" with --hypernociception--.

Column 62, Line 2, replace "3-lactam-containing" with --β-lactam-containing--.

Column 71, Line 30, replace "Thr80" with --Thr180--.

Column 72, Line 5, replace "Thr80" with --Thr180--.

Column 76, Line 21, replace "DIVLTQSPGFLWSLGQRATISC" with --DIVLTQSPGFLVVSLGQRATISC--.

Column 81, Line 21, replace "(t)" with --(f)--.

Column 89, Line 17, replace "106" with --$10^{-6}$--.
Line 18, replace "10." with --$10^{-6}$--.

Column 101, Line 51, replace "lie" with --Ile--.
Line 52, replace "Gin" with --Gln--.

Column 104, Line 30, replace "*Poc.*" with --*Proc.*--.

Column 109, Line 46, replace "Chad" with --Chari--.

Column 125, Line 52, replace "retrobulbary" with --retrobulbarly--.

Column 128, Line 26, replace "cynomoigus" with --cynomolgus--.
Line 62, replace "cynomogus" with --cynomolgus--.

Column 129, Line 9, replace "cynomoigus" with --cynomolgus--.
Line 11, replace "cynomogus" with --cynomolgus--.
Line 27, replace "MAXISORPP" with --MAXISORP®--.
Line 28, replace "Intemational" with --International--.
Line 46, replace "Biomedicals." with --Biomedicals,--.

Column 130, Line 2, replace "IL-10" with --IL-1β--.
Line 10, replace "pUNO1-hIl01 RL1a" with --pUNO1-hIl01RL1a--.
Line 47, replace "oligonudeotide" with --oligonucleotide--.

CERTIFICATE OF CORRECTION (continued)
U.S. Pat. No. 10,723,795 B2

Column 136, Line 59, replace "IL-1P" with --IL-1β--.

Column 138, Line 51, replace "ST2$^4$" with --ST2$^{-/-}$--.

Column 147, Line 35, replace "ST2$^{-/-}$" with --ST2$^{+/+}$--.
    Line 60, replace "ST2" with --ST2$^{+/+}$--.

Column 148, Line 24, replace "ST24$^{-/-}$" with --ST2$^{-/-}$--.

Column 149, Line 5, replace "ST2$^{+/+}$" with --ST2$^{-/-}$--.

Column 150, Line 27, replace "CD34" with --CD34$^+$--.
    Line 64, replace "1×10" with --1×1$^6$--.

Column 151, Line 22, replace "10$^8$" with --10$^6$--.

Column 155, Line 1, replace "10C12.38.H6.87Y.58V1/IL-13" with --10C12.38.H6.87Y.58I/IL-13--.

Column 156, Line 54, replace "IL-13" with --IL-1β--.
    Line 55, replace "μg/ml" with --pg/ml--.

Column 157, Line 4, replace "anti-1L33" with --anti-IL33--.

Column 158, Line 64, replace "IC50" with --IC$_{50}$--.

Column 159, Line 5, replace "IL-1" with --IL-1β--.
    Line 12, replace "IC50" with --IC$_{50}$--.
    Line 48, replace "M assay" with --assay--.
    Line 50, replace "M reagent" with --reagent--.

Column 165, Line 27, replace "IC50" with --IC$_{50}$--.

In the Claims

Column 399, Claim 19, Line 41, replace "1090" with --IC90--.
    Claim 20, Line 43, replace "1090" with --IC90--.
    Claim 21, Line 45, replace "1090" with --IC90--.
    Claim 23, Line 50, replace "1050" with --IC50--.
    Claim 24, Line 52, replace "1050" with --IC50--.
    Claim 26, Line 57, replace "1050" with --IC50--.